(12) United States Patent
Goldberg et al.

(10) Patent No.: US 10,975,037 B2
(45) Date of Patent: Apr. 13, 2021

(54) PHENYL SUBSTITUTED PYRAZOLES AS MODULATORS OF RORγT

(71) Applicant: Janssen Pharmaceutica NV, Beerse (BE)

(72) Inventors: Steven Goldberg, Carlsbad, CA (US); Connor L. Martin, San Diego, CA (US); Elizabeth G. Fennema, La Mesa, CA (US); David A. Kummer, San Diego, CA (US); Rachel T. Nishimura, San Diego, CA (US); Craig R. Woods, San Diego, CA (US); Ronald L. Wolin, San Diego, CA (US); William M. Jones, Jenkintown, PA (US); Anne M. Fourie, San Diego, CA (US); Xiaohua Xue, San Diego, CA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 16/442,837

(22) Filed: Jun. 17, 2019

(65) Prior Publication Data
US 2019/0382349 A1     Dec. 19, 2019

Related U.S. Application Data

(60) Provisional application No. 62/686,308, filed on Jun. 18, 2018.

(51) Int. Cl.
| C07D 231/14 | (2006.01) |
| C07D 401/12 | (2006.01) |
| C07D 403/10 | (2006.01) |
| C07D 405/12 | (2006.01) |

(52) U.S. Cl.
CPC ......... *C07D 231/14* (2013.01); *C07D 401/12* (2013.01); *C07D 403/10* (2013.01); *C07D 405/12* (2013.01)

(58) Field of Classification Search
None
See application file for complete search history.

(56) References Cited

U.S. PATENT DOCUMENTS

| 5,342,835 | A   | 8/1994  | Pepin et al. |
| 8,809,547 | B2  | 8/2014  | Bretschneider et al. |
| 9,458,104 | B2* | 10/2016 | Gege ............ A61P 11/06 |
| 10,369,146 | B2 | 8/2019  | Leonard et al. |
| 2005/0014805 | A1 | 1/2005 | Zhang et al. |
| 2012/0245137 | A1 | 9/2012 | Pajouhesh |
| 2014/0163001 | A1 | 6/2014 | Yamamoto |
| 2015/0038350 | A1 | 2/2015 | Nishinaga et al. |
| 2015/0072890 | A1 | 3/2015 | James |
| 2015/0111870 | A1 | 4/2015 | Leonard |
| 2015/0266824 | A1 | 9/2015 | Beck |
| 2016/0120850 | A1 | 5/2016 | Goldberg et al. |
| 2016/0122326 | A1 | 5/2016 | Goldberg et al. |
| 2016/0122335 | A1 | 5/2016 | Goldberg et al. |
| 2016/0122336 | A1 | 5/2016 | Goldberg et al. |
| 2016/0304476 | A1 | 10/2016 | Aicher |
| 2016/0304505 | A1 | 10/2016 | Aicher |
| 2017/0253591 | A1 | 9/2017 | Yamamoto |
| 2017/0313691 | A1 | 11/2017 | Goldberg |
| 2019/0269134 | A1 | 9/2019 | Fublein et al. |
| 2019/0382349 | A1 | 12/2019 | Goldberg et al. |
| 2019/0382350 | A1 | 12/2019 | Goldberg et al. |
| 2019/0382354 | A1 | 12/2019 | Goldberg et al. |
| 2019/0382373 | A1 | 12/2019 | Goldberg et al. |

FOREIGN PATENT DOCUMENTS

| CL | 201102650 | 10/2011 |
| CL | 201200534 | 2/2012 |
| CL | 201803050 | 10/2018 |
| CL | 201901343 | 5/2019 |

(Continued)

OTHER PUBLICATIONS

Angew. Chem. Int. Ed. Engl. 1982, 21, 567-583.
(Continued)

*Primary Examiner* — Kamal A Saeed
(74) *Attorney, Agent, or Firm* — Yuriy P. Stercho

(57) ABSTRACT

The present invention comprises compounds of Formula I.

Formula I

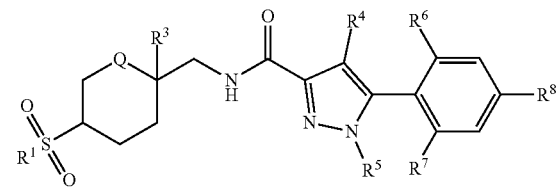

wherein:
$R^1$, $R^3$, $R^4$, $R^5$, $R^6$, $R^7$, $R^8$, and Q are defined in the specification.

The invention also comprises a method of treating or ameliorating a ROR-γ-t mediated syndrome, disorder or disease, including wherein the syndrome, disorder or disease is selected from the group consisting of rheumatoid arthritis, psoriatic arthritis, and psoriasis. The invention also comprises a method of modulating RORγt activity in a mammal by administration of a therapeutically effective amount of at least one compound of Formula I.

28 Claims, No Drawings
Specification includes a Sequence Listing.

(56) References Cited

FOREIGN PATENT DOCUMENTS

| | | |
|---|---|---|
| CN | 103833672 | 6/2014 |
| EP | 360701 A1 | 3/1990 |
| EP | 2738170 | 6/2014 |
| JP | 2005507932 | 3/2005 |
| WO | WO 1996003392 A1 | 2/1996 |
| WO | WO 2002083111 A2 | 10/2002 |
| WO | WO 2003015776 A1 | 2/2003 |
| WO | WO 2006087355 | 8/2006 |
| WO | WO 2006124687 A1 | 11/2006 |
| WO | WO 2007087427 A2 | 8/2007 |
| WO | WO 2008064317 A1 | 5/2008 |
| WO | WO 2008064318 A2 | 5/2008 |
| WO | WO 2009011850 | 1/2009 |
| WO | WO 2010006713 | 1/2010 |
| WO | WO 2011053948 A1 | 5/2011 |
| WO | WO 2011112263 A1 | 9/2011 |
| WO | WO 2011112264 A1 | 9/2011 |
| WO | WO 2011115892 A1 | 9/2011 |
| WO | WO 2012027965 | 3/2012 |
| WO | WO 2012074547 A2 | 6/2012 |
| WO | WO 2012129491 | 9/2012 |
| WO | WO 2012158784 A2 | 11/2012 |
| WO | WO 2012174362 | 12/2012 |
| WO | WO 2013029338 | 3/2013 |
| WO | WO 2013036912 A2 | 3/2013 |
| WO | WO 2013079223 A | 6/2013 |
| WO | WO 2013092939 A1 | 6/2013 |
| WO | WO 2013171729 | 11/2013 |
| WO | WO 2013178362 A1 | 12/2013 |
| WO | WO 2014023367 | 2/2014 |
| WO | WO 2014093191 | 6/2014 |
| WO | WO 2015035278 A1 | 3/2015 |
| WO | WO 2015042212 A1 | 3/2015 |
| WO | WO 2015082533 A1 | 6/2015 |
| WO | WO 2015103507 A1 | 7/2015 |
| WO | WO 2015103508 A1 | 7/2015 |
| WO | WO 2015103509 A1 | 7/2015 |
| WO | WO 2015103510 A1 | 7/2015 |
| WO | WO 2015145371 A1 | 10/2015 |
| WO | WO 2016069974 | 5/2016 |
| WO | WO 2018123918 | 7/2018 |
| WO | WO 2018185236 | 10/2018 |

OTHER PUBLICATIONS

Barczyk, A., W. Pierzchala, et al. (2003). "Interleukin-17 in sputum correlates with airway hyperresponsiveness to methacholine." Respir Med 97(6): 726-33.

Beurel, E., Harrington, L. E., Jope, R. S. (2013) "Inflammatory T helper 17 cells promote depression-like behavior in mice." Biol Psychiatry 73(7): 622-30.

Bimekizumab demonstrates impressive joint and skin responses for psoriatic arthritis patients. Dec. 20, 2017. https://www.ucb.com/stories-media/Press-Releases/article/Bimekizumab-demonstrates-impressive-joint-and-skin-responses-for-psoriatic-arthritis-patients-nbsp.

Bowes, J. and A. Barton "The genetics of psoriatic arthritis: lessons from genome-wide association studies." Discov Med 10(52): 177-83 (2010).

Chang M, "Pharmacologic Repression of Retinoic Acid Receptor—Related Orphan Nuclear Receptor □ Is Therapeutic in the Collagen-Induced Arthritis Experimental Model", Arthritis & Rheumatology (2014), 66(3), 579-588.

Chang, M. R. et al. (2015) "Antiobesity Effect of a Small Molecule Repressor of RORγ." Mol Pharmacol. 88(1): 48-56.

Chen, Y., et al. (2011). "Emerging tendency towards autoimmune process in major depressive patients: A novel insight from Th17 cells." Psychiatry Research 188(2): 224-230.

Cheng, Chia-Chung et al., The Friedlander synthesis of quinolines, Organic Reactions, 1982, 28, pp. 37-201.

Cua, D. J., J. Sherlock, et al. (2003). "Interleukin-23 rather than interleukin-12 is the critical cytokine for autoimmune inflammation of the brain." Nature 421(6924): 744-8.

De Wit et al., , RORγt inhibitors suppress TH17 responses in inflammatory arthritis and inflammatory bowel disease. Journal of Allergy and Clinical Immunology, vol. 137 , Issue 3, (2016), 960-963.

Dolff S et al., Disturbed Th1, Th2, Th17 and T-reg balance in patients with systemic lupus erythematosus, Clinical Immunology 141(2):197-204 • Aug. 2011.

Dong, C. (2006). "Diversification of T-helper-cell lineages: finding the family root of IL-17-producing cells." Nat Rev Immunol 6(4): 329-33.

Fauber et al., J. Med. Chem. 2014, 57, 5871-5892.

Feagan BG, et al. Ustekinumab as induction and maintenance therapy for Crohn's disease. N Engl J Med. 2016;375(20):1946-60.

Fitzpatrick, Leo Robert. Ror-gamma T inhibition as a Pharmacological Approach for Inflammatory Bowel Disease. Medical Research Archives, [S.l.], v. 2, n. 2, Aug. 2015.

Fujino, S., A. Andoh, et al. (2003). "Increased expression of interleukin 17 in inflammatory bowel disease." Gut 52(1): 65-70.

Garber K. (2011). "Psoriasis: from bed to bench and back" Nat Biotech 29, 563-566.

Gazouli, M., I. Pachoula, et al. "NOD2/CARD15, ATG16L1 and IL23R gene polymorphisms and childhood-onset of Crohn's disease." World J Gastroenterol 16(14): 1753-8 (2010).

Hodgson et al., Ustekinumab for Treating Moderately to Severely Active Crohn's Disease after Prior Therapy: An Evidence Review Group Perspective of a NICE Single Technology Appraisal. PharmacoEconomics (2018) 36:4, 387-398.

Hueber, W., Patel, D.D., Dryja, T., Wright, A.M., Koroleva, I., Bruin, G., Antoni, C., Draelos, Z., Gold, M.H., Durez, P., Tak, P.P., Gomez-Reino, J.J., Foster, C.S., Kim, R.Y., Samson, C.M., Falk, N.S., Chu, D.S., Callanan, D., Nguyen, Q.D., Rose, K., Haider, A., Di Padova, F. (2010) Effects of AIN457, a fully human antibody to interleukin-17A, on psoriasis, rheumatoid arthritis, and uveitis. Sci Transl Med 2, 5272.

Innovimmune: ROR Gamma Inhibitor (INV-17) Tested in Lupus Model. 2015 Eular Congress News. https://static1.squarespace.com/static/577aff0015d5db17f97d2d57/t/584f44f9725e254d6b032644/1481590043630/150611_INV-17+Lupus+Thursday_EULAR_2015+small+size.pdf.

Ivanov, II, B. S. McKenzie, et al. (2006). "The orphan nuclear receptor RORgammat directs the differentiation program of proinflammatory IL-17+T helper cells." Cell 126(6): 1121-33.

Jethwa H at al., The interleukin (IL)-23/IL-17 axis in ankylosing spondylitis: new advances and potentials for treatment, Clinical and Experimental Immunology, 2015, 183: 30-36.

Kochi, Y., Y. Okada, et al. (2010) "A regulatory variant in CCR6 is associated with rheumatoid arthritis susceptibility." Nat Genet 42(6): 515-9.

Kolls, J. K. and A. Linden (2004). "Interleukin-17 family members and inflammation." Immunity 21(4): 467-76.

Korn, T., E. Bettelli, et al. (2009). "IL-17 and Th17 Cells." Annu Rev Immunol 27: 485-517.

Krueger, J. G., S. Fretzin, et al. "IL-17A is essential for cell activation and inflammatory gene circuits in subjects with psoriasis." J Allergy Clin Immunol 130(1):145-154 e9 (2012).

Kumar N, "The Benzenesulfoamide T0901317 [N-(2,2,2-Trifluoroethyl)-N-[4-[2,2,2-trifluoro-1-hydroxy-1-(trifluoromethyl)ethyl]phenyl]-benzenesulfonamide] Is a Novel Retinoic Acid Receptor-Related Orphan Receptor-□/□ Inverse Agonist", Molecular Pharmacology (2010), 77(2), 228-236.

Langrish, C. L., Y. Chen, et al. (2005). "IL-23 drives a pathogenic T cell population that induces autoimmune inflammation." J Exp Med 201(2): 233-40.

Leonardi, C., R. Matheson, et al. "Anti-interleukin-17 monoclonal antibody ixekizumab in chronic plaque psoriasis." N Engl J Med 366(13): 1190-9 (2012).

Liegault, et al., "Establishment of Broadly Applicable reaction condisions for the Palladium-Catalyzed Direct Arylation of Heteroatom-Containing Aromatic Compounds", The Journal of Organic Chemistry, (2009), vol. 74, No. 5, 6, pp. 1826-1834.

(56) References Cited

OTHER PUBLICATIONS

Lock, C., G. Hermans, et al. (2002). "Gene-microarray analysis of multiple sclerosis lesions yields new targets validated in autoimmune encephalomyelitis." Nat Med 8(5): 500-8.
Matulis, D., Kranz, J. K., Salemme, F. R., and Todd, M. J. (2005) Thermodynamic stability of carbonic anhydrase: measurements of binding affinity and stoichiometry using ThermoFluor. *Biochemistry* 44, 5258-66.
McGinley et al., (2018) Th17 cells, γδ T cells and their interplay in EAE and multiple sclerosis. *Journal of Autoimmunity* 87, 97-108.
McKenzie, B. S., R. A. Kastelein, et al. (2006). "Understanding the IL-23-IL-17 immune pathway." Trends Immunol 27(1): 17-23.
Mease, P. J. et al. Brodalumab, an anti-IL17RA monoclonal antibody, in psoriatic arthritis, The New England Journal of Medicine 370, 2295-2306 (2014).
Meissburger, B. et al. (2011) "Adipogenesis and insulin sensitivity in obesity are regulated by retinoid-related orphan receptor gamma." EMBO Mol Med. 3(11): 637-651.
Nunez, C., B. Dema, et al. (2008). "IL23R: a susceptibility locus for celiac disease and multiple sclerosis?" Genes Immun 9(4): 289-93.
Pantoliano, M. W., Petrella, E. C., Kwasnoski, J. D., Lobanov, V. S., Myslik, J., Graf, E., Carver, T., Asel, E., Springer, B. A., Lane, P., and Salemme, F. R. (2001) High-density miniaturized thermal shift assays as a general strategy for drug discovery. *J Biomol Screen* 6, 429-40.
Papp, K. A., "Brodalumab, an anti-interleukin-17-receptor antibody for psoriasis." N Engl J Med 2012 366(13): 1181-9.
Poddhubnyy et al., Ann Rheum Dis 2014;0:1-7.
Pure & Appl. Chem. 45, 1976, 11-30.
Qian et al., Clin. Invest. (2012) 2(4), 417-421.
Registry(STN)[online], [Search Date: May 13, 2019]CAS Registration No. 791058-42-9,263386-02-3.
Sandborn WJ et al. Ustekinumab Induction and Maintenance Therapy in Refractory Crohn's Disease N Engl J Med 2012; 367:1519-1528.
Silva MJ et al, Glucocorticoid Resistant Asthma: The Potential Contribution of IL-17. Biomark J. 2016, 1:6.
Stamp, L. K., M. J. James, et al. (2004). "Interleukin-17: the missing link between T-cell accumulation and effector cell actions in rheumatoid arthritis" Immunol Cell Biol 82(1): 1-9.
Tonel, G., C. Conrad, et al. "Cutting edge: A critical functional role for IL-23 in psoriasis." J Immunol 185(10): 5688-91 (2010).
Wang X, Wei Y, Xiao H, et al. A novel IL-23p19/Ebi3 (IL-39) cytokine mediates inflammation in Lupus-like mice. Eur J Immunol. 2016;46(6):1343-1350.
Weitz JE et al., Ustekinumab: Targeting the IL-17 Pathway to Improve Outcomes in Psoriatic Arthritis. Expert Opin Biol Ther 2104 14, 515-526.
Withers DR, et al. Transient inhibition of ROR-γt therapeutically limits intestinal inflammation by reducing TH17 cells and preserving group 3 innate lymphoid cells Nature Medicine 2016, 22, 319.
Yang et al., Trends in Pharmacological Sciences, Oct. 2014, vol. 35, No. 10, 493-500.
Yang X et al. Does IL-17 Respond to the Disordered Lung Microbiome and Contribute to the Neutrophilic Phenotype in Asthma? Mediators of Inflammation. vol. 2016 (2016), Article ID 6470364, pp. 1-7.
Yao, et al, "Preparation Method of N-butyl-5-phenylthiazole-4-Formamide Derivative Via Coupling Reaction Under Catalysis of Copper Catalyst", Database accession No. 2014:924023.
Yen, D., J. Cheung, et al. (2006). "IL-23 is essential for T cell-mediated colitis and promotes inflammation via IL-17 and IL-6." J Clin Invest 116(5): 1310-6.
Zhang, et al., "Decarboxylative Cross-Coupling of Azoyl Carboxylic Acids with Aryl Halides", Organic Letters, (2010) vol. 12, No. 21, pp. 4745-47457.
PCT/US2015/058193, Written Opinion dated Jan. 26, 2016.
PCT/US2015/058198, Written Opinion dated Jan. 21, 2016.
PCT/US2015/058200, Written Opinion dated Jan. 27, 2016.
PCT/US2015/058193, International Search Report, dated Jan. 26, 2016.
PCT/US2015/058198, International Search Report, dated Jan. 21, 2016.
PCT/US2015/058200, International Search Report, dated Jan. 27, 2016.
PCT/US2017/029531, International Search Report, dated Sep. 15, 2017.
PCT/US2017/029531, International Preliminary Report on Patentability, dated Oct. 30, 2018.
PCT/IB2019/055043, International Search Report, dated Sep. 30, 2019.
PCT/IB2019/055045, International Search Report, dated Sep. 30, 2019.
PCT/IB2019/055046, International Search Report, dated Oct. 4, 2019.
PCT/IB2019/055048, International Search Report, dated Sep. 27, 2019.
Eastman; Oncotarget. 2017, 8, 8854-8866. DOI: 10.18632/oncotarget.12673 (Year: 2017).
Guendisch; PLoS ONE 2017, 12, e0188391. DOI: 10.1371/journal.pone.0188391 (Year: 2017).
Huh; Eur. J. Immunol. 2012. 42, 2232-2237. DOI: 10.1002/eji.201242740 (Year: 2012).
Isono; Drug Discovery Today, 2014, 19, 1205-1211. DOI: 10.1016/j.drudis.2014.04.012 (Year: 2014).
Kiaei; Basic Clin Neurosci. 2013, 4, 3-4. URL: http://bcn.iums.ac.ir/article-1-307-en.html (Year: 2013).
Xue; Scientific Reports 2016, 6, Article No. 37977. DOI: 10.1038/srep37977 (Year: 2016).

* cited by examiner

PHENYL SUBSTITUTED PYRAZOLES AS MODULATORS OF RORγT

CROSS REFERENCE TO RELATED APPLICATIONS

This application claims priority from U.S. Provisional Application 62/686,308, filed on Jun. 18, 2018, which is incorporated by reference herein in its entirety.

SEQUENCE LISTING

The instant application contains a Sequence Listing which has been filed electronically in ASCII format and is hereby incorporated by reference in its entirety. Said ASCII copy, created on Jun. 11, 2019, is named PRD3477USNP.txt and is 8,209 bytes in size.

FIELD OF THE INVENTION

The invention is directed to substituted pyrazole compounds, which are modulators of the nuclear receptor RORγt, pharmaceutical compositions, and methods for use thereof. More particularly, the RORγt modulators are useful for preventing, treating or ameliorating an RORγt mediated inflammatory syndrome, disorder or disease.

BACKGROUND OF THE INVENTION

Retinoic acid-related nuclear receptor gamma t (RORγt) is a nuclear receptor, exclusively expressed in cells of the immune system, and a key transcription factor driving Th17 cell differentiation. Th17 cells are a subset of CD4+ T cells, expressing CCR6 on their surface to mediate their migration to sites of inflammation, and dependent on IL-23 stimulation, through the IL-23 receptor, for their maintenance and expansion. Th17 cells produce several proinflammatory cytokines including IL-17A, IL-17F, IL-21, and IL-22 (Korn, T., E. Bettelli, et al. (2009). "IL-17 and Th17 Cells." Annu Rev Immunol 27: 485-517), which stimulate tissue cells to produce a panel of inflammatory chemokines, cytokines and metalloproteases, and promote recruitment of granulocytes (Kolls, J. K. and A. Linden (2004). "Interleukin-17 family members and inflammation." Immunity 21(4): 467-76; Stamp, L. K., M. J. James, et al. (2004). "Interleukin-17: the missing link between T-cell accumulation and effector cell actions in rheumatoid arthritis" Immunol Cell Biol 82(1): 1-9). Th17 cells have been shown to be the major pathogenic population in several models of autoimmune inflammation, including collagen-induced arthritis (CIA) and experimental autoimmune encephalomyelitis (EAE) (Dong, C. (2006). "Diversification of T-helper-cell lineages: finding the family root of IL-17-producing cells." Nat Rev Immunol 6(4): 329-33; McKenzie, B. S., R. A. Kastelein, et al. (2006). "Understanding the IL-23-IL-17 immune pathway." Trends Immunol 27(1): 17-23). RORγt-deficient mice are healthy and reproduce normally, but have shown impaired Th17 cell differentiation in vitro, a significantly reduced Th17 cell population in vivo, and decreased susceptibility to EAE (Ivanov, II, B. S. McKenzie, et al. (2006). "The orphan nuclear receptor RORgammat directs the differentiation program of proinflammatory IL-17+T helper cells." Cell 126(6): 1121-33). Mice deficient for IL-23, a cytokine required for Th17 cell survival, fail to produce Th17 cells and are resistant to EAE, CIA, and inflammatory bowel disease (IBD) (Cua, D. J., J. Sherlock, et al. (2003). "Interleukin-23 rather than interleukin-12 is the critical cytokine for autoimmune inflammation of the brain." Nature 421(6924): 744-8; Langrish, C. L., Y. Chen, et al. (2005). "IL-23 drives a pathogenic T cell population that induces autoimmune inflammation." J Exp Med 201(2): 233-40; Yen, D., J. Cheung, et al. (2006). "IL-23 is essential for T cell-mediated colitis and promotes inflammation via IL-17 and IL-6." J Clin Invest 116(5): 1310-6). Consistent with these findings, an anti-IL23-specific monoclonal antibody blocks development of psoriasis-like inflammation in a murine disease model (Tonel, G., C. Conrad, et al. "Cutting edge: A critical functional role for IL-23 in psoriasis." J Immunol 185(10): 5688-91).

RORγT deficient mice exhibited resistance to learned helplessness. Treatment with the RORγT inhibitor SR1001, or anti-interleukin-17A antibodies reduced Th17-dependent learned helplessness (Beurel, E., Harrington, L. E., Jope, R. S. (2013) "Inflammatory T helper 17 cells promote depression-like behavior in mice." Biol Psychiatry 73(7): 622-30). In human patients with major depressive disorder, both peripheral blood lymphocyte RORγT mRNA expression and peripheral Th17 cells were found to be elevated relative to the control group (Chen, Y., et al. (2011). "Emerging tendency towards autoimmune process in major depressive patients: A novel insight from Th17 cells." Psychiatry Research 188(2): 224-230).

Administration of RORγ inverse agonist SR1555 to obese diabetic mice resulted in a modest reduction in food intake accompanied with significant reduction in fat mass, resulting in reduced body weight and improved insulin sensitivity (Chang, M. R. et al. (2015) "Antiobesity Effect of a Small Molecule Repressor of RORγ." Mol Pharmacol. 88(1): 48-56). In addition, Rorγ–/– mice are protected from hyperglycemia and insulin resistance in the state of obesity (Meissburger, B. et al. (2011) "Adipogenesis and insulin sensitivity in obesity are regulated by retinoid-related orphan receptor gamma." EMBO Mol Med. 3(11): 637-651).

In humans, a number of observations support the role of the IL-23/Th17 pathway in the pathogenesis of inflammatory diseases. IL-17, the key cytokine produced by Th17 cells, is expressed at elevated levels in a variety of allergic and autoimmune diseases (Barczyk, A., W. Pierzchala, et al. (2003). "Interleukin-17 in sputum correlates with airway hyperresponsiveness to methacholine." Respir Med 97(6): 726-33; Fujino, S., A. Andoh, et al. (2003). "Increased expression of interleukin 17 in inflammatory bowel disease." Gut 52(1): 65-70; Lock, C., G. Hermans, et al. (2002). "Gene-microarray analysis of multiple sclerosis lesions yields new targets validated in autoimmune encephalomyelitis." Nat Med 8(5): 500-8; Krueger, J. G., S. Fretzin, et al. "IL-17A is essential for cell activation and inflammatory gene circuits in subjects with psoriasis." J Allergy Clin Immunol 130(1): 145-154 e9). Furthermore, human genetic studies have shown association of polymorphisms in the genes for Th17 cell-surface receptors, IL-23R and CCR6, with susceptibility to IBD, multiple sclerosis (MS), rheumatoid arthritis (RA) and psoriasis (Gazouli, M., I. Pachoula, et al. "NOD2/CARD15, ATG16L1 and IL23R gene polymorphisms and childhood-onset of Crohn's disease." World J Gastroenterol 16(14): 1753-8., Nunez, C., B. Dema, et al. (2008). "IL23R: a susceptibility locus for celiac disease and multiple sclerosis?" Genes Immun 9(4): 289-93; Bowes, J. and A. Barton "The genetics of psoriatic arthritis: lessons from genome-wide association studies." Discov Med 10(52): 177-83; Kochi, Y., Y. Okada, et al. "A regulatory variant in CCR6 is associated with rheumatoid arthritis susceptibility." Nat Genet 42(6): 515-9).

Ustekinumab (Stelara®), an anti-p40 monoclonal antibody blocking both IL-12 and IL-23, is approved for the treatment of adult patients (18 years or older), with moderate to severe plaque psoriasis, who are candidates for phototherapy or systemic therapy. Currently, monoclonal antibodies specifically targeting only IL-23, to more selectively inhibit the Th17 subset, are also in clinical development for psoriasis (Garber K. (2011). "Psoriasis: from bed to bench and back" Nat Biotech 29, 563-566), further implicating the important role of the IL-23- and RORγt-driven Th17 pathway in this disease. Results from recent phase II clinical studies strongly support this hypothesis, as anti-IL-17 receptor and anti-IL-17 therapeutic antibodies both demonstrated high levels of efficacy in patients with chronic psoriasis (Papp, K. A., "Brodalumab, an anti-interleukin-17-receptor antibody for psoriasis." N Engl J Med 2012 366(13): 1181-9; Leonardi, C., R. Matheson, et al. "Anti-interleukin-17 monoclonal antibody ixekizumab in chronic plaque psoriasis." N Engl J Med 366(13): 1190-9). Anti-IL-17 antibodies have also demonstrated clinically relevant responses in early trials in RA and uveitis (Hueber, W., Patel, D. D., Dryja, T., Wright, A. M., Koroleva, I., Bruin, G., Antoni, C., Draelos, Z., Gold, M. H., Durez, P., Tak, P. P., Gomez-Reino, J. J., Foster, C. S., Kim, R. Y., Samson, C. M., Falk, N. S., Chu, D. S., Callanan, D., Nguyen, Q. D., Rose, K., Haider, A., Di Padova, F. (2010) Effects of AIN457, a fully human antibody to interleukin-17A, on psoriasis, rheumatoid arthritis, and uveitis. Sci Transl Med 2, 5272).

All the above evidence supports inhibition of the Th17 pathway by modulating RORγt activity as an effective strategy for the treatment of immune-mediated inflammatory diseases.

SUMMARY OF THE INVENTION

The present invention comprises a compound of Formula I:

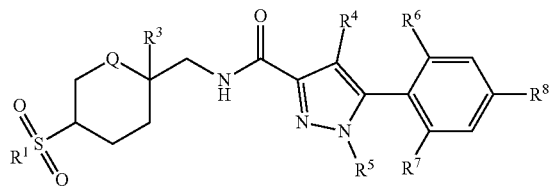

Formula I wherein
$R^1$ is —$C_{(1-4)}$alkyl, —$NH_2$, —$NHC_{(1-4)}$alkyl, —NHC(O) H, —NHC(O)$NH_2$, —NHC(O)NH$C_{(1-4)}$alkyl, —NHC(O) $C_{(1-4)}$alkyl, or —N($C_{(1-4)}$alkyl)$_2$;
Q is NC(O)$C_{(1-3)}$alkyl, NCH$_2$C(O)$C_{(1-3)}$alkyl, NCH$_2$CO$_2$NH$_2$, NH, O, or CHR$^2$;
$R^2$ is —H, —$NH_2$, —OH, —CN, or —C(O)$NH_2$;
$R^3$ is —H, —OH, —CN, —$NH_2$, —CONH$_2$, —CO$_2$H, —CO$_2$$C_{(1-4)}$alkyl, —CH$_2$OH, —CH$_2$NH$_2$, —CH$_2$CN, —NHC$_{(1-4)}$alkyl, or —CONHC$_{(1-4)}$alkyl;
$R^4$ is —Cl, —$C_{(1-4)}$alkyl, —F, —CN, —C(O)$NH_2$,

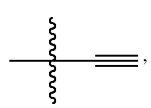 [SMILES: *C#C]

or —H; wherein said —$C_{(1-4)}$alkyl is optionally substituted with up to six fluorine atoms;
$R^5$ is —$C_{(1-4)}$alkyl, wherein said —$C_{(1-4)}$alkyl is optionally substituted with —CN, —OH, —OCH$_3$, —OCF$_3$, or up to six fluorine atoms;
$R^6$ is H, —Cl, —F, —$C_{(1-3)}$alkyl, —O$C_{(1-3)}$alkyl, —OCD$_3$, or —CN, wherein said —$C_{(1-3)}$alkyl and said —O$C_{(1-3)}$alkyl are optionally substituted with up to three fluorine atoms;
$R^7$ is H, —F, —OCH$_3$, —CH$_3$, —CF$_3$, —OCF$_3$, or —Cl;
$R^8$ is

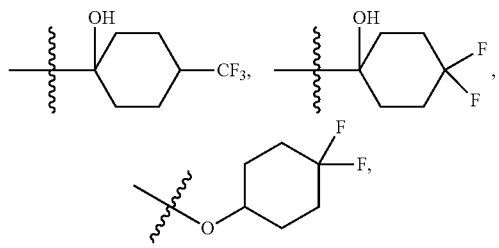

—$C_{(1-6)}$alkyl, —O$C_{(1-6)}$alkyl, or —NA$^1$A$^2$; wherein said —$C_{(1-6)}$alkyl is optionally substituted with —OH, or oxo, and the —$C_{(1-6)}$alkyl may additionally be substituted with up to six fluorine atoms or —$C_{(3-6)}$cycloalkyl, wherein said cycloalkyl is optionally substituted with —CF$_3$, —CH$_3$, or up to four fluorine atoms, and said —O$C_{(1-6)}$alkyl is optionally substituted with up to three fluorine atoms, and the —O$C_{(1-6)}$alkyl may additionally be substituted with —$C_{(3-6)}$cycloalkyl, wherein said cycloalkyl is optionally substituted with —CF$_3$, —CH$_3$, or up to four fluorine atoms;
$A^1$ is —$C_{(1-3)}$alkyl, wherein said —$C_{(1-3)}$alkyl is optionally substituted with up to six fluorine atoms;
$A^2$ is —H, or —$C_{(1-3)}$alkyl, wherein said —$C_{(1-3)}$alkyl is optionally substituted with up to six fluorine atoms; or $A^1$ and $A^2$ are taken together with their attached nitrogen to form

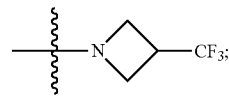 [SMILES: *N1CC(C(F)(F)F)C1]

and pharmaceutically acceptable salts thereof.

DETAILED DESCRIPTION OF THE INVENTION

The present invention comprises a compound of Formula I:

Formula I

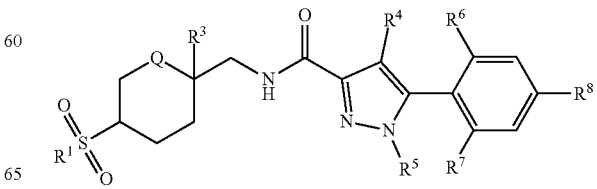

wherein

R¹ is —C$_{(1-4)}$alkyl, —NH$_2$, —NHC$_{(1-4)}$alkyl, —NHC(O)H, —NHC(O)NH$_2$, —NHC(O)NHC$_{(1-4)}$alkyl, —NHC(O)C$_{(1-4)}$alkyl, or —N(C$_{(1-4)}$alkyl)$_2$;

Q is NC(O)C$_{(1-3)}$alkyl, NCH$_2$C(O)C$_{(1-3)}$alkyl, NCH$_2$CO$_2$NH$_2$, NH, O, or CHR²;

R² is —H, —NH$_2$, —OH, —CN, or —C(O)NH$_2$;

R³ is —H, —OH, —CN, —NH$_2$, —CONH$_2$, —CO$_2$H, —CO$_2$C$_{(1-4)}$alkyl, —CH$_2$OH, —CH$_2$NH$_2$, —CH$_2$CN, —NHC$_{(1-4)}$alkyl, or —CONHC$_{(1-4)}$alkyl;

R⁴ is —Cl, —C$_{(1-4)}$alkyl, —F, —CN, —C(O)NH$_2$,

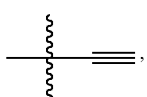

or —H; wherein said —C$_{(1-4)}$alkyl is optionally substituted with up to six fluorine atoms;

R⁵ is —C$_{(1-4)}$alkyl, wherein said —C$_{(1-4)}$alkyl is optionally substituted with —CN, —OH, —OCH$_3$, —OCF$_3$, or up to six fluorine atoms;

R⁶ is H, —Cl, —F, —C$_{(1-3)}$alkyl, —OC$_{(1-3)}$alkyl, —OCD$_3$, or —CN, wherein said —C$_{(1-3)}$alkyl and said —OC$_{(1-3)}$alkyl are optionally substituted with up to three fluorine atoms;

R⁷ is H, —F, —OCH$_3$, —CH$_3$, —CF$_3$, —OCF$_3$, or —Cl;

R⁸ is

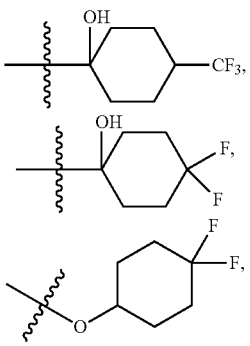

—C$_{(1-6)}$alkyl, —OC$_{(1-6)}$alkyl, or —NA¹A²; wherein said —C$_{(1-6)}$alkyl is optionally substituted with —OH, or oxo, and the —C$_{(1-6)}$alkyl may additionally be substituted with up to six fluorine atoms or —C$_{(3-6)}$cycloalkyl, wherein said cycloalkyl is optionally substituted with —CF$_3$, (including

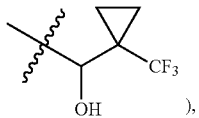 [SMILES: *C(O)C1(C(F)(F)F)CC1]

—CH$_3$, or up to four fluorine atoms, and said —OC$_{(1-6)}$alkyl is optionally substituted with up to three fluorine atoms, and the —OC$_{(1-6)}$alkyl may additionally be substituted with —C$_{(3-6)}$cycloalkyl, wherein said cycloalkyl is optionally substituted with —CF$_3$, —CH$_3$ (including

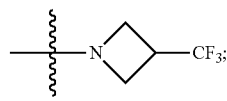 [SMILES: *N1CC(C(F)(F)F)C1]

or up to four fluorine atoms (including

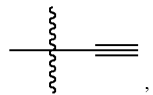 [SMILES: *C#C]

);

A¹ is —C$_{(1-3)}$alkyl, wherein said —C$_{(1-3)}$alkyl is optionally substituted with up to six fluorine atoms;

A² is —H, or —C$_{(1-3)}$alkyl, wherein said —C$_{(1-3)}$alkyl is optionally substituted with up to six fluorine atoms; or A¹ and A² are taken together with their attached nitrogen to form

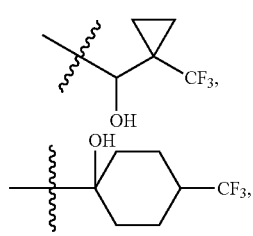

and pharmaceutically acceptable salts thereof.

In another embodiment of the invention:

R¹ is —C$_{(1-3)}$alkyl, —NH$_2$, —NHC$_{(1-2)}$alkyl, —NHC(O)H, —NHC(O)NH$_2$, —NHC(O)NHC$_{(1-2)}$alkyl, NHC(O)C$_{(1-3)}$alkyl, or —N(CH$_3$)$_2$;

Q is NC(O)CH$_3$, NCH$_2$C(O)CH$_3$, NCH$_2$CO$_2$NH$_2$, NH, O, or CHR²;

R² is —H, —NH$_2$, or —OH;

R³ is —H, —OH, —CN, —NH$_2$, —CONH$_2$, —CO$_2$H, —CO$_2$CH$_2$CH$_3$, or —CH$_2$OH;

R⁴ is —Cl, —C$_{(1-4)}$alkyl, —F, —CN, —CF$_3$, —C(O)NH$_2$,

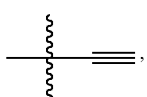

or —H;

R⁵ is —C$_{(1-4)}$alkyl, wherein said —C$_{(1-4)}$alkyl is optionally substituted with —CN, —OH, —OCH$_3$, or —OCF$_3$;

R⁶ is H, —Cl, —F, —C$_{(1-3)}$alkyl, —OC$_{(1-3)}$alkyl, —OCD$_3$, or —CN, wherein said —C$_{(1-3)}$alkyl and said —OC$_{(1-3)}$alkyl are optionally substituted with up to three fluorine atoms;

R⁷ is H, —F, —OCH$_3$, —CH$_3$, —CF$_3$, or —OCF$_3$;

R⁸ is

-continued

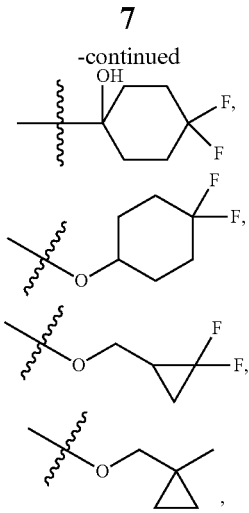

—C$_{(1-6)}$alkyl, —OC$_{(1-6)}$alkyl, or —NA$^1$A$^2$; wherein said —C$_{(1-6)}$alkyl is optionally substituted with —OH or oxo, and the —C$_{(1-6)}$alkyl may additionally be substituted with up to six fluorine atoms, and said —OC$_{(1-6)}$alkyl is optionally substituted with up to three fluorine atoms;

A$^1$ is —C$_{(1-3)}$alkyl, wherein said —C$_{(1-3)}$alkyl is optionally substituted with up to six fluorine atoms;

A$^2$ is —H, or —C$_{(1-3)}$alkyl, wherein said —C$_{(1-3)}$alkyl is optionally substituted with up to six fluorine atoms; or A$^1$ and A$^2$ are taken together with their attached nitrogen to form

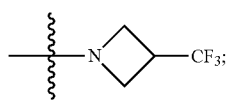 [SMILES: *N1CC(C(F)(F)F)C1]

and pharmaceutically acceptable salts thereof.

In another embodiment of the invention:

R$^1$ is —C$_{(1-3)}$alkyl, —NH$_2$, —NHC$_{(1-2)}$alkyl, —NHC(O)H, —NHC(O)NH$_2$, —NHC(O)NHC$_{(1-2)}$alkyl, or NHC(O)C$_{(1-3)}$alkyl;

Q is NC(O)CH$_3$, NCH$_2$C(O)CH$_3$, NCH$_2$CO$_2$NH$_2$, NH, O, or CHR$^2$;

R$^2$ is —H, —NH$_2$, or —OH;

R$^3$ is —H, —OH, —CN, —NH$_2$, —CONH$_2$, —CO$_2$H, —CO$_2$CH$_2$CH$_3$, or —CH$_2$OH;

R$^4$ is —Cl, —C$_{(1-4)}$alkyl, —F, —CN, —CF$_3$, —C(O)NH$_2$, or

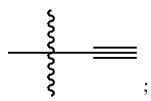

R$^5$ is —C$_{(1-4)}$alkyl, wherein said —C$_{(1-4)}$alkyl is optionally substituted with —CN, —OH, or —OCH$_3$;

R$^6$ is H, —Cl, —F, —C$_{(1-3)}$alkyl, —OC$_{(1-3)}$alkyl, —OCD$_3$, or —CN, wherein said —C$_{(1-3)}$alkyl and said —OC$_{(1-3)}$alkyl are optionally substituted with up to three fluorine atoms;

R$^7$ is H, —F, —OCH$_3$, or —CH$_3$;

R$^8$ is

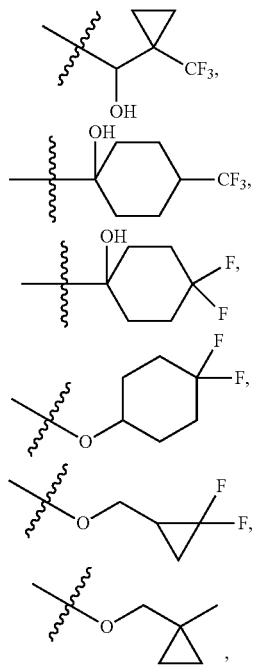

—C$_{(1-6)}$alkyl, —OC$_{(1-6)}$alkyl, or —NA$^1$A$^2$; wherein said —C$_{(1-6)}$alkyl is optionally substituted with —OH or oxo, and the —C$_{(1-6)}$alkyl may additionally be substituted with up to six fluorine atoms, and said —OC$_{(1-6)}$alkyl is optionally substituted with up to three fluorine atoms;

A$^1$ is —C$_{(1-3)}$alkyl, wherein said —C$_{(1-3)}$alkyl is optionally substituted with up to six fluorine atoms;

A$^2$ is —H, —CH$_3$, —CF$_3$, or A$^1$ and A$^2$ are taken together with their attached nitrogen to form

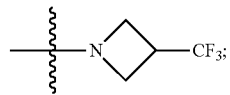

and pharmaceutically acceptable salts thereof.

In another embodiment of the invention:

R$^1$ is —C$_{(1-2)}$alkyl, —NH$_2$, —NHC$_{(1-2)}$alkyl, —NHC(O)H, —NHC(O)NH$_2$, —NHC(O)NHC$_{(1-2)}$alkyl, or —NHC(O)C$_{(1-2)}$alkyl;

Q is NC(O)CH$_3$, NCH$_2$C(O)CH$_3$, NCH$_2$CO$_2$NH$_2$, NH, O, or CHR$^2$;

R$^2$ is —H, —NH$_2$, or —OH;

R$^3$ is —H, —OH, —CN, —NH$_2$, —CONH$_2$, —CO$_2$H, —CO$_2$CH$_2$CH$_3$, or —CH$_2$OH;

R$^4$ is —Cl, —C$_{(1-4)}$alkyl, —F, —CN, or —CF$_3$;

R$^5$ is —C$_{(1-4)}$alkyl, wherein said —C$_{(1-4)}$alkyl is optionally substituted with —CN, —OH, or —OCH$_3$;

R$^6$ is H, —Cl, —F, —C$_{(1-3)}$alkyl, —OC$_{(1-3)}$alkyl, —OCD$_3$, or —CN, wherein said —C$_{(1-3)}$alkyl and said —OC$_{(1-3)}$alkyl are optionally substituted with up to three fluorine atoms;

R⁷ is H, —F, or —OCH₃;
R⁸ is

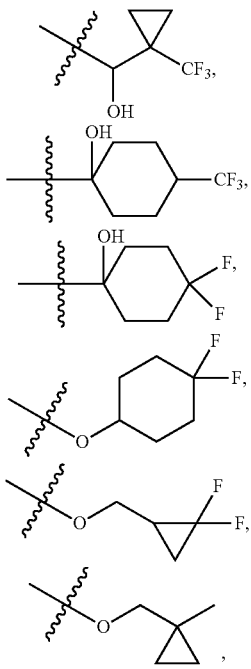

—$C_{(3-6)}$alkyl, —$OC_{(1-3)}$alkyl, or —$NA^1A^2$; wherein said —$C_{(3-6)}$alkyl is optionally substituted with —OH or oxo, and the —$C_{(3-6)}$alkyl may additionally be substituted with up to six fluorine atoms, and said —$OC_{(1-3)}$alkyl is optionally substituted with up to three fluorine atoms;

$A^1$ is —$C_{(1-3)}$alkyl, wherein said —$C_{(1-3)}$alkyl is optionally substituted with up to six fluorine atoms;

$A^2$ is —H, —CH₃, or $A^1$ and $A^2$ are taken together with their attached nitrogen to form

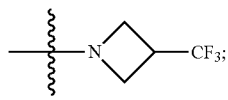 [SMILES: *N1CC(C(F)(F)F)C1]

and pharmaceutically acceptable salts thereof.

In another embodiment of the invention:

$R^1$ is —$C_{(1-2)}$alkyl, —NH₂, —NHCH₃, —NHC(O)H, —NHC(O)NH₂, —NHC(O)NHCH₃, or —NHC(O)$C_{(1-2)}$alkyl;

Q is NC(O)CH₃, NCH₂C(O)CH₃, NCH₂CO₂NH₂, NH, O, or CHR²;

$R^2$ is —H, —NH₂, or —OH;

$R^3$ is —H, —OH, —CN, —NH₂, —CONH₂, —CO₂H, —CO₂CH₂CH₃, or —CH₂OH;

$R^4$ is —Cl, —$C_{(1-3)}$alkyl, —F, —CN, or —CF₃;

$R^5$ is —$C_{(1-4)}$alkyl, wherein said —$C_{(1-4)}$alkyl is optionally substituted with —CN, —OH, or —OCH₃;

$R^6$ is H, —Cl, —F, —$C_{(1-3)}$alkyl, —$OC_{(1-3)}$alkyl, —OCD₃, or —CN, wherein said —$C_{(1-3)}$alkyl and said —$OC_{(1-3)}$alkyl are optionally substituted with up to three fluorine atoms;

R⁷ is H, or —F;
R⁸ is

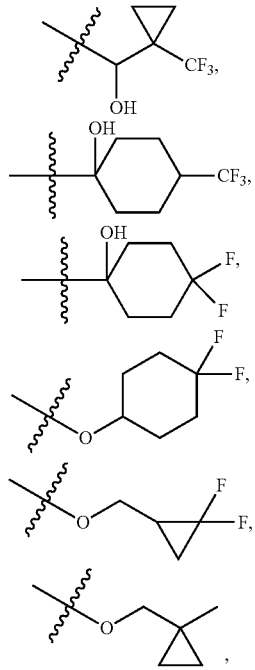

—$C_{(3-6)}$alkyl, —$OC_{(1-3)}$alkyl, or —$NA^1A^2$; wherein said —$C_{(3-6)}$alkyl is optionally substituted with —OH or oxo, and the —$C_{(3-6)}$alkyl may additionally be substituted with up to six fluorine atoms, and said —$OC_{(1-3)}$alkyl is optionally substituted with up to three fluorine atoms;

$A^1$ is —$C_{(2-3)}$alkyl, wherein said —$C_{(2-3)}$alkyl is optionally substituted with up to six fluorine atoms;

$A^2$ is H, or $A^1$ and $A^2$ are taken together with their attached nitrogen to form

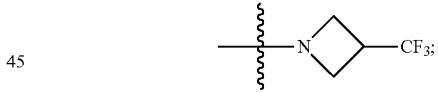

and pharmaceutically acceptable salts thereof.

Another embodiment of the invention is a compound selected from the group consisting of:

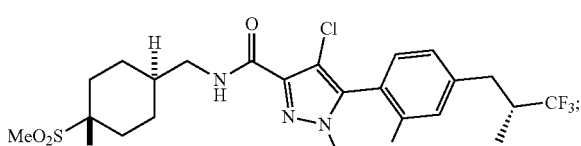

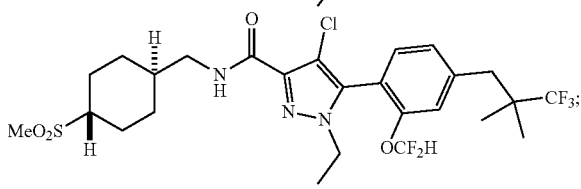

11
-continued
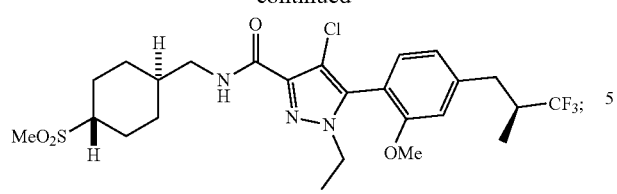
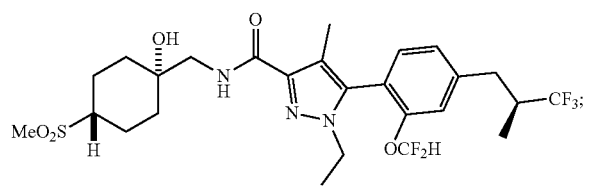
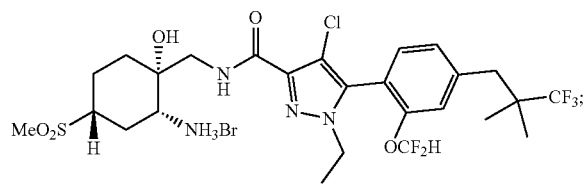
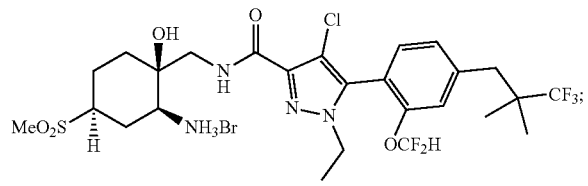
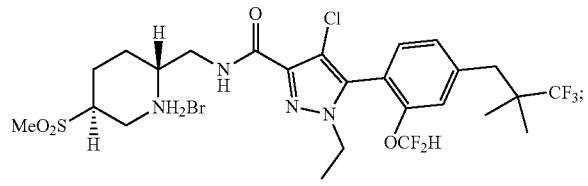
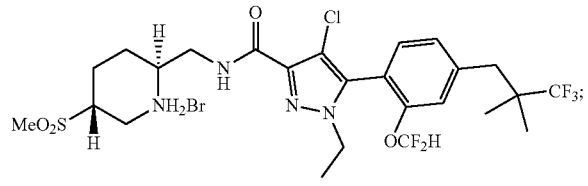
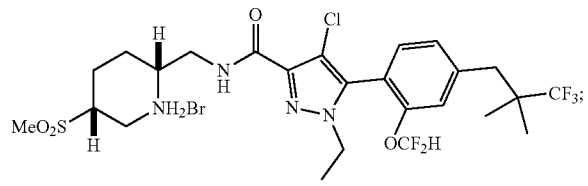
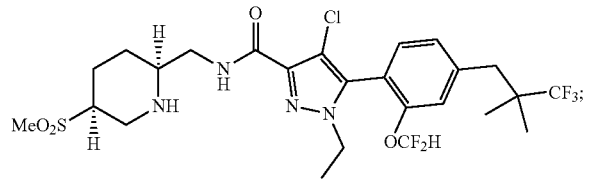
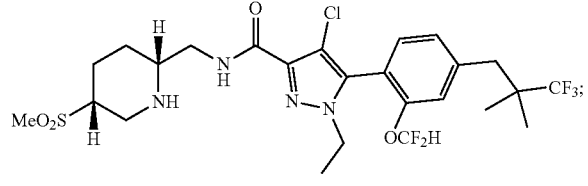
12
-continued
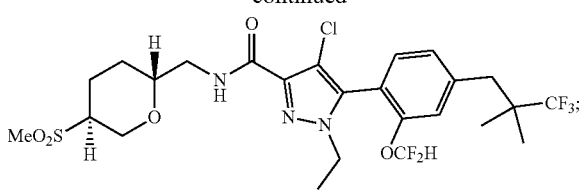
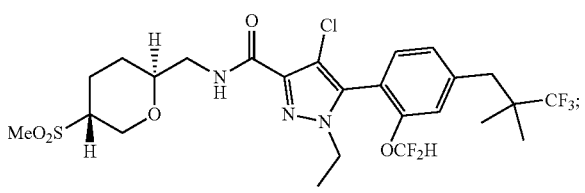
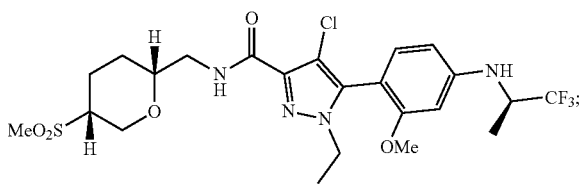
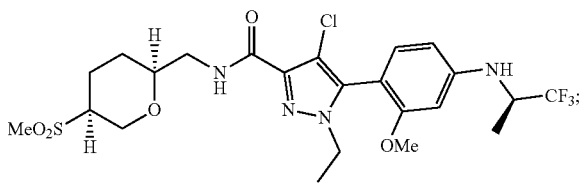
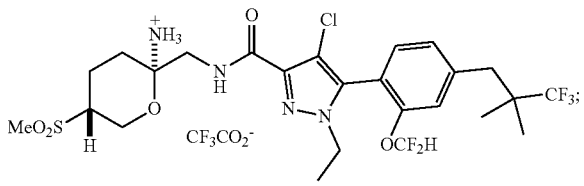
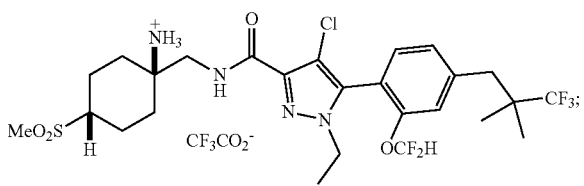
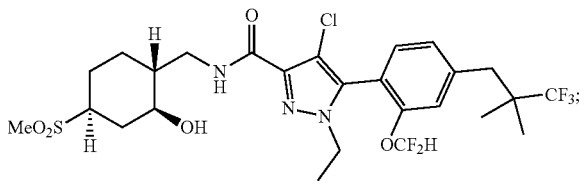
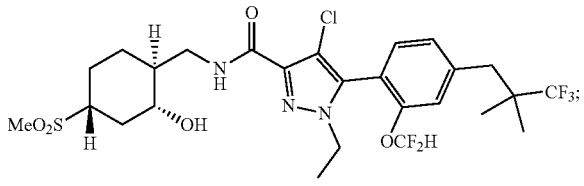
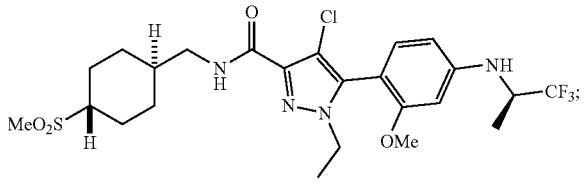

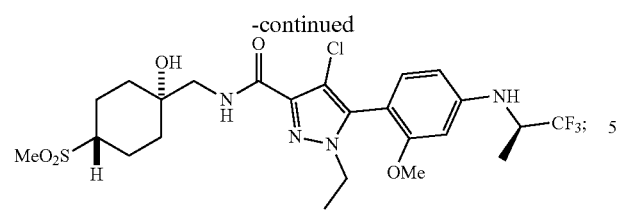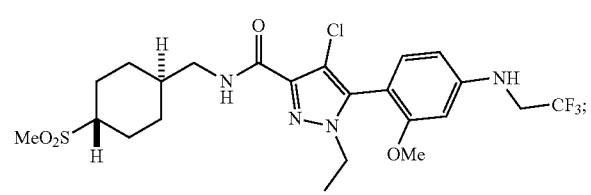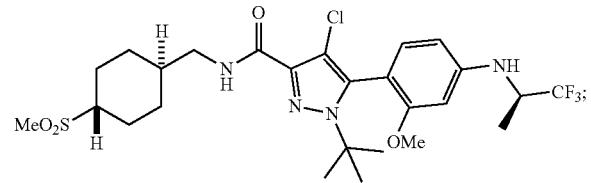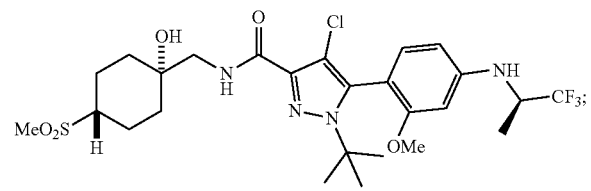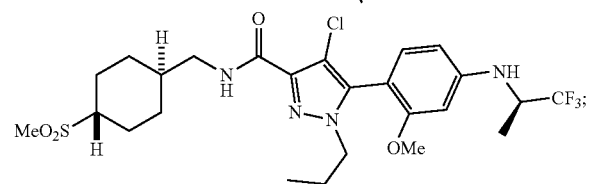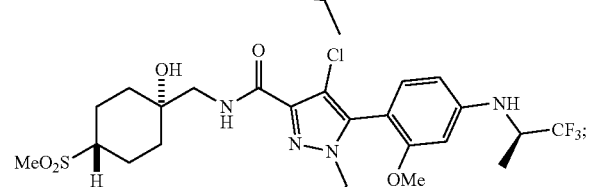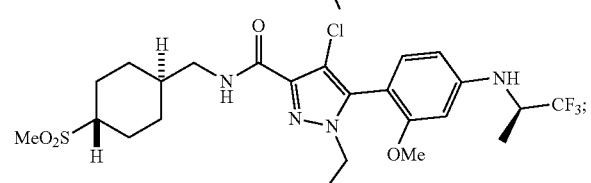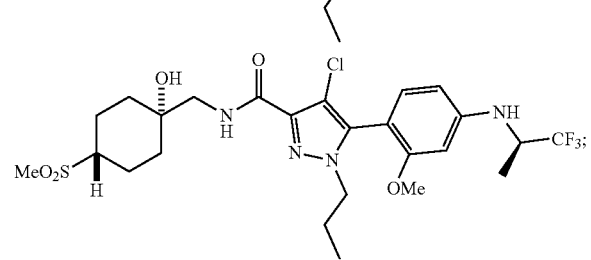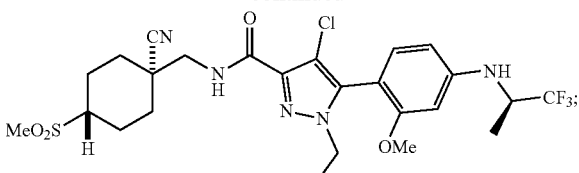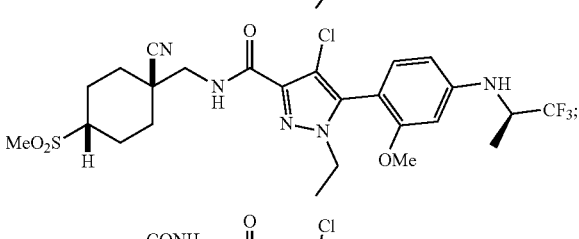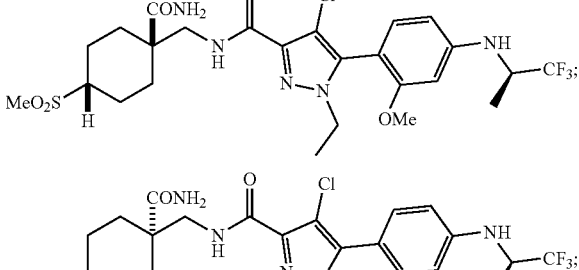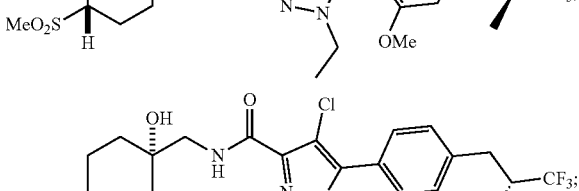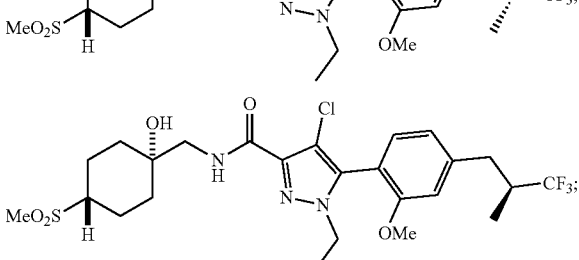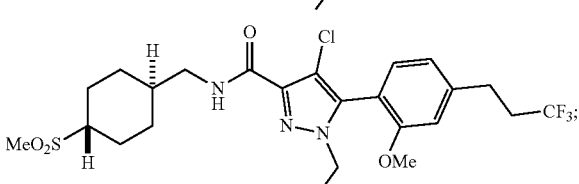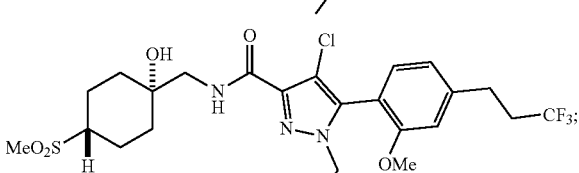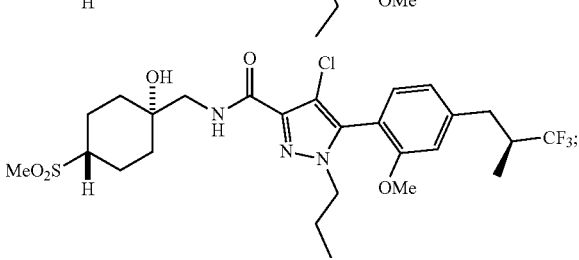

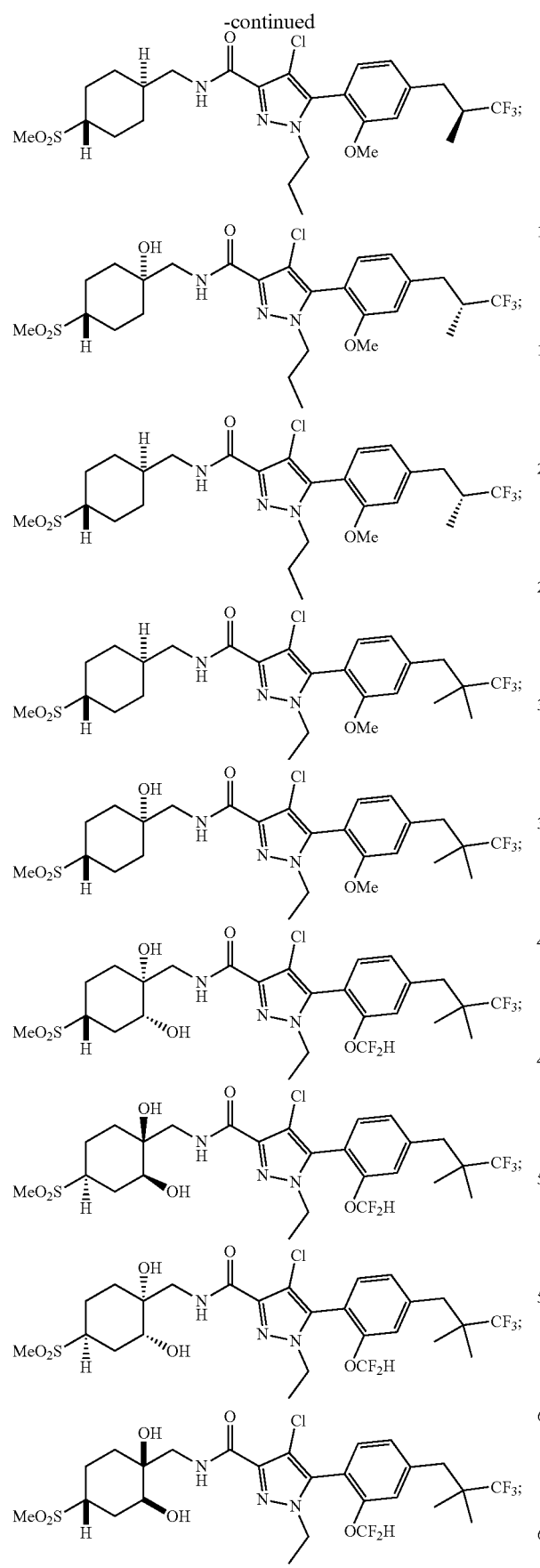
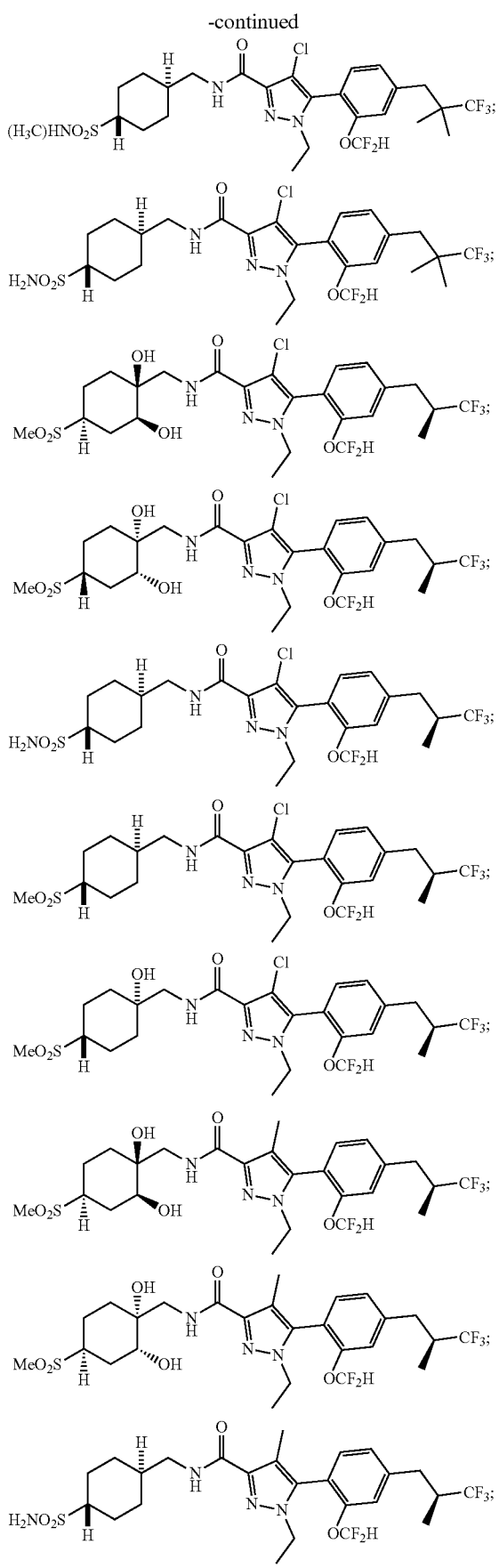

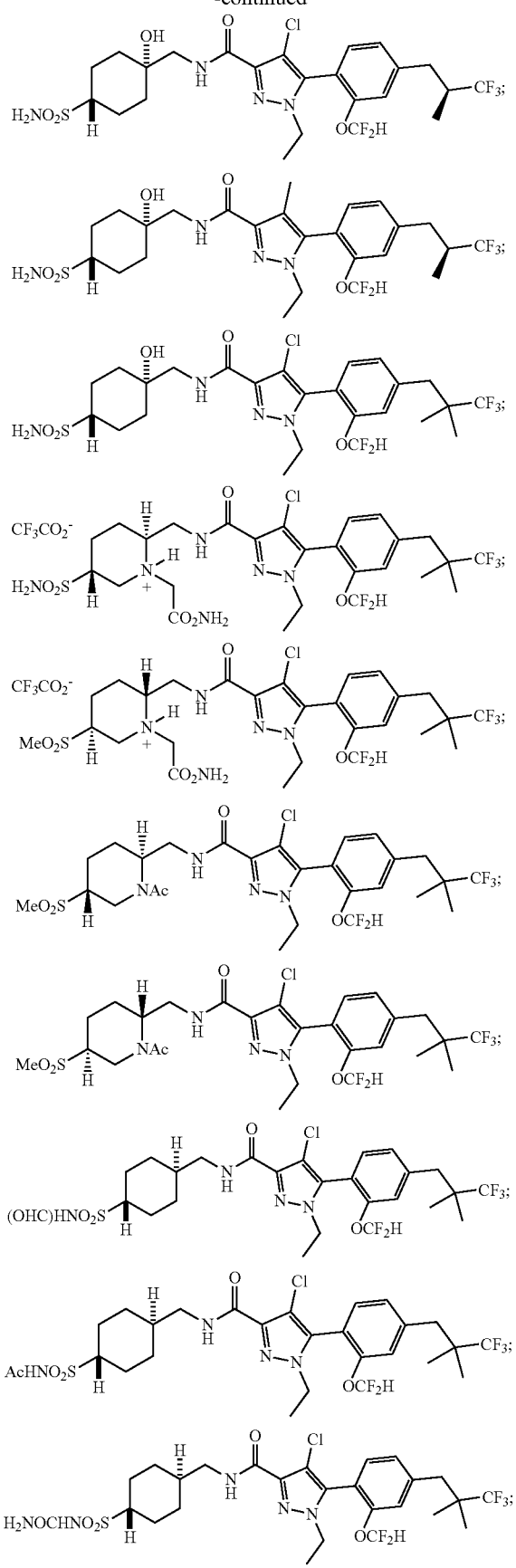
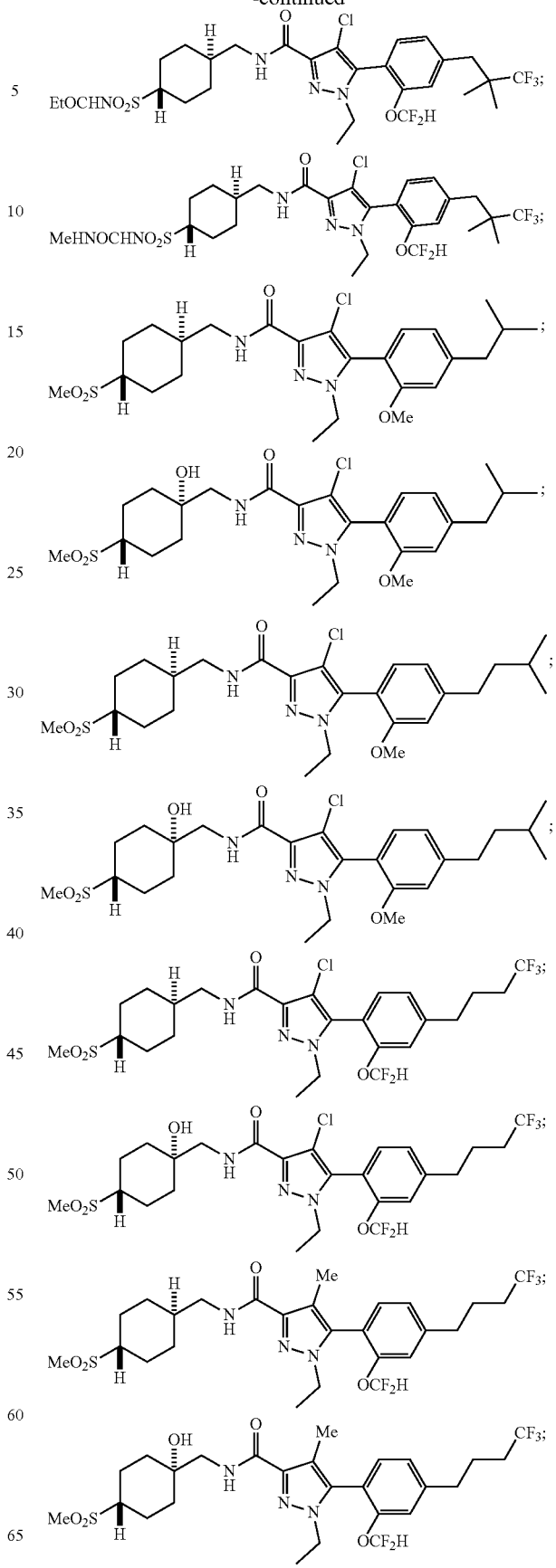

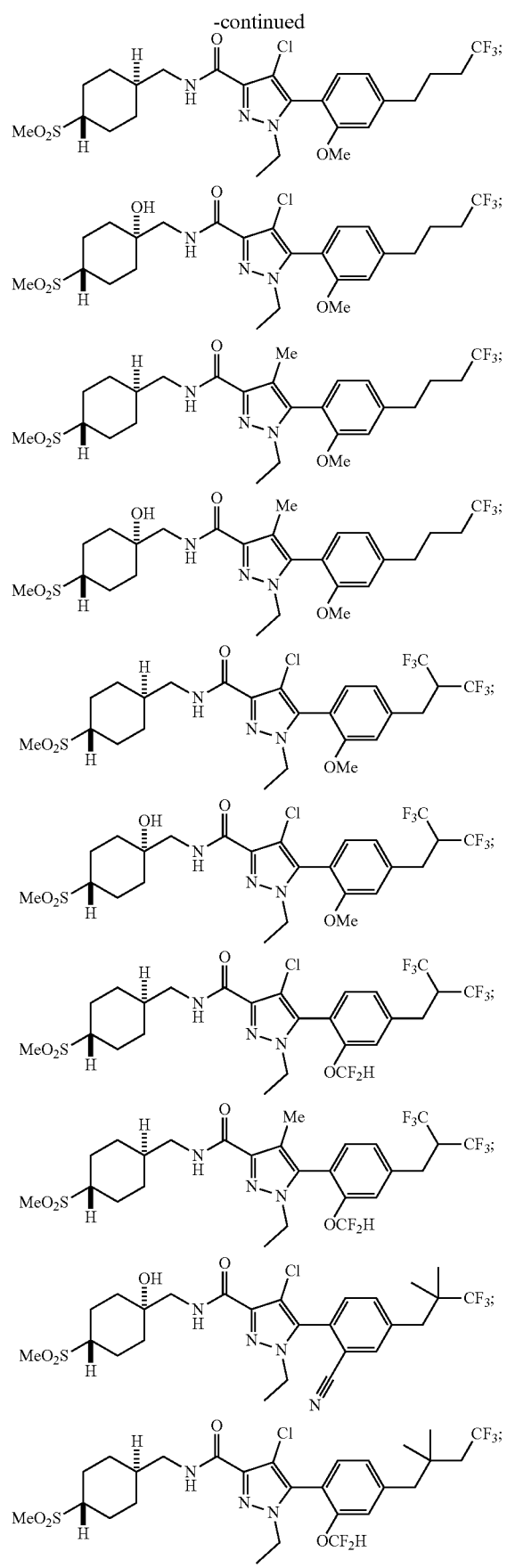
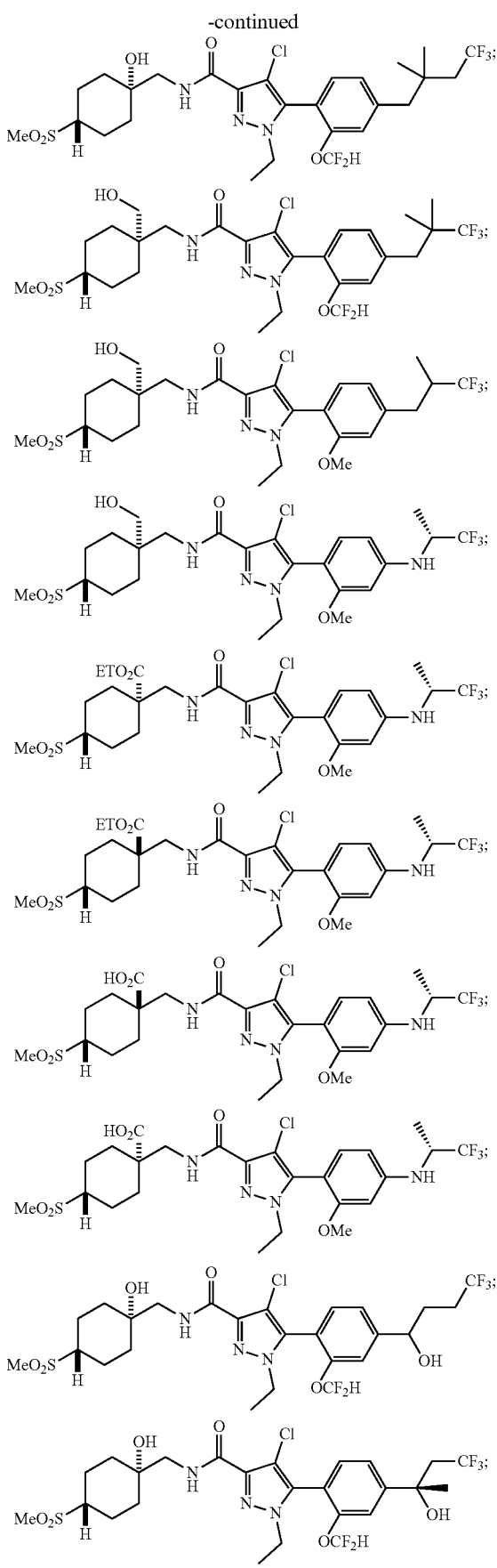

21
-continued
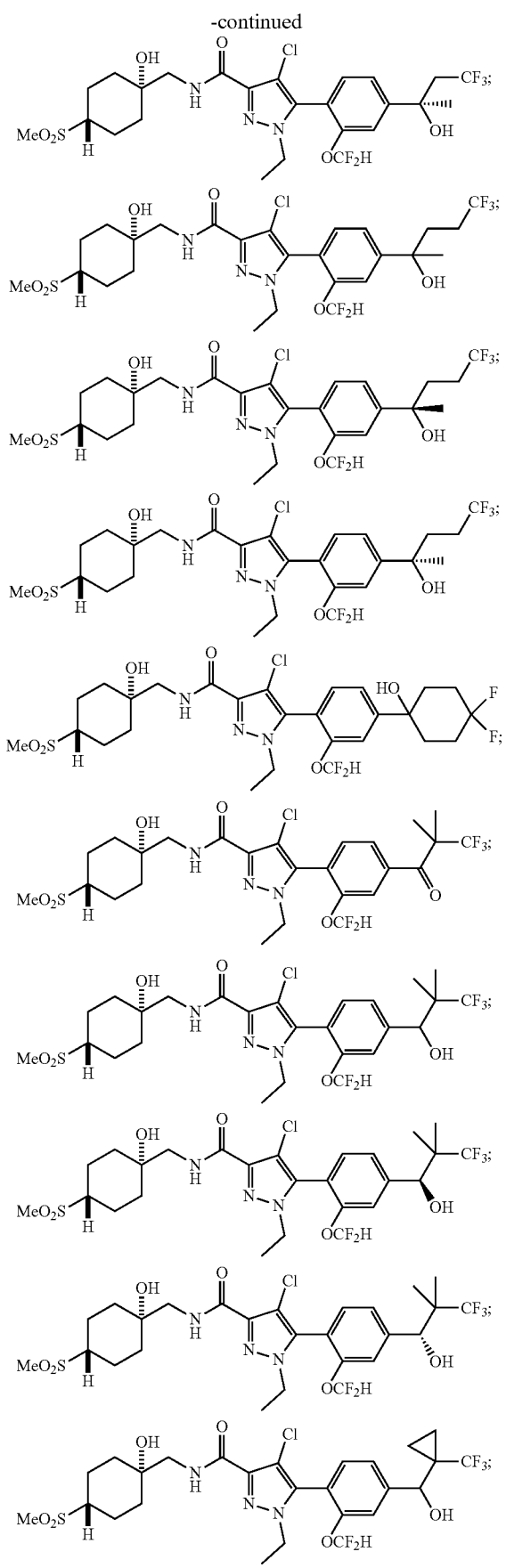
22
-continued
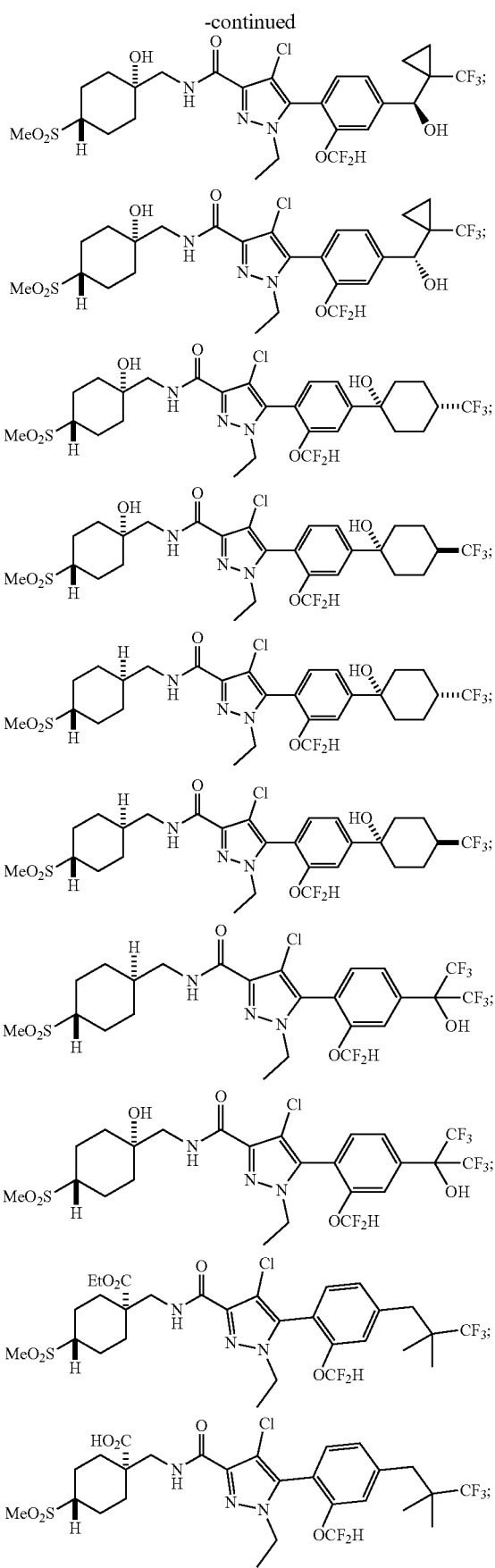

-continued
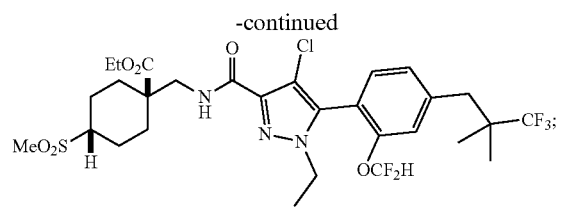
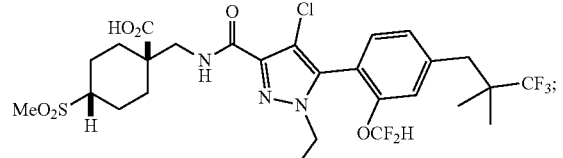
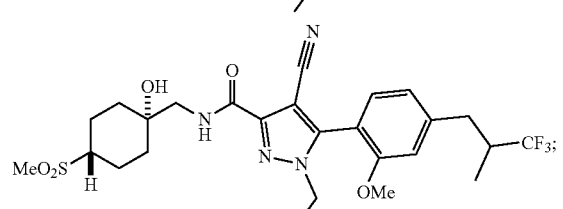
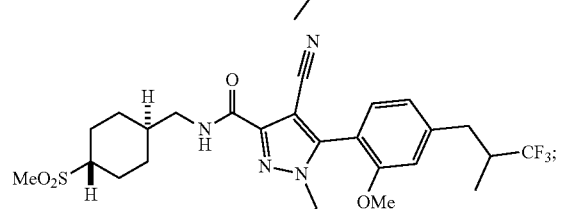
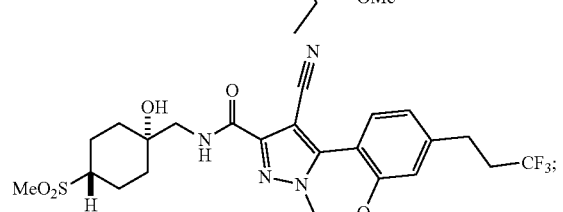

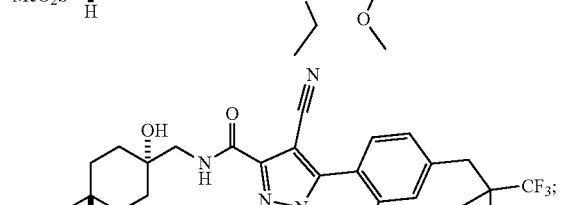
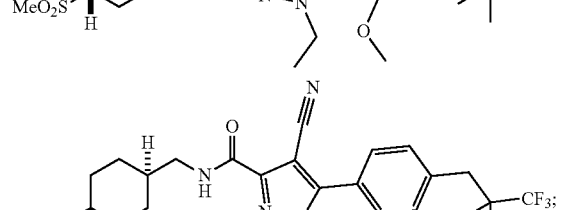
-continued
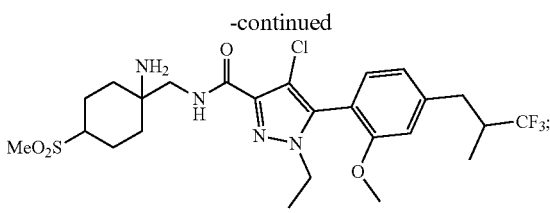
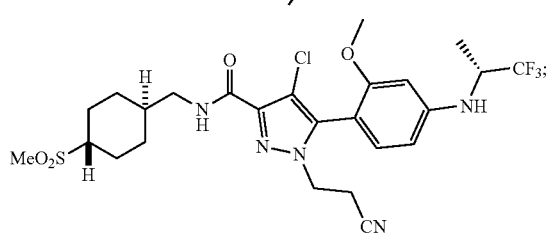
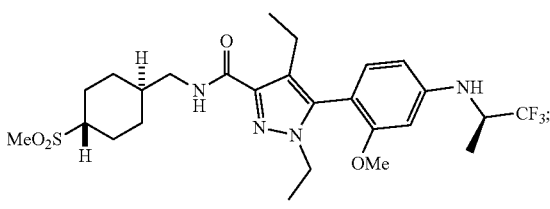
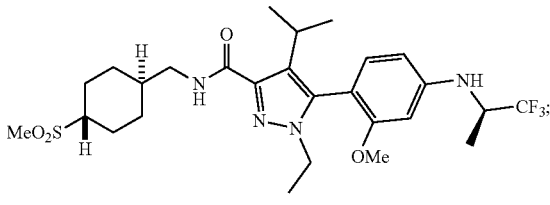
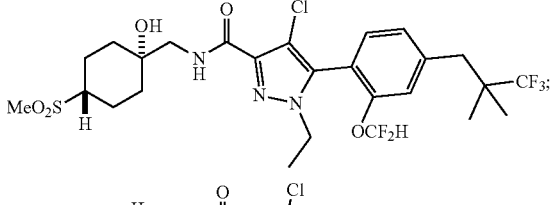
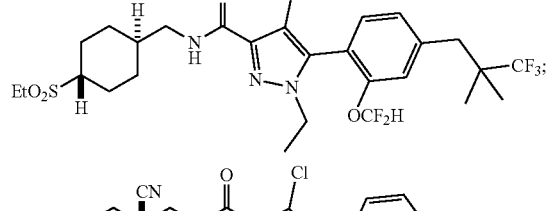
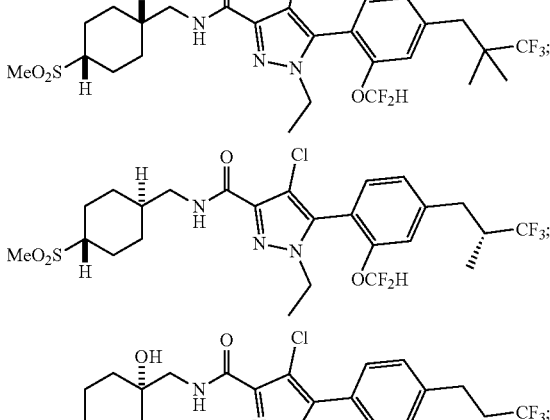

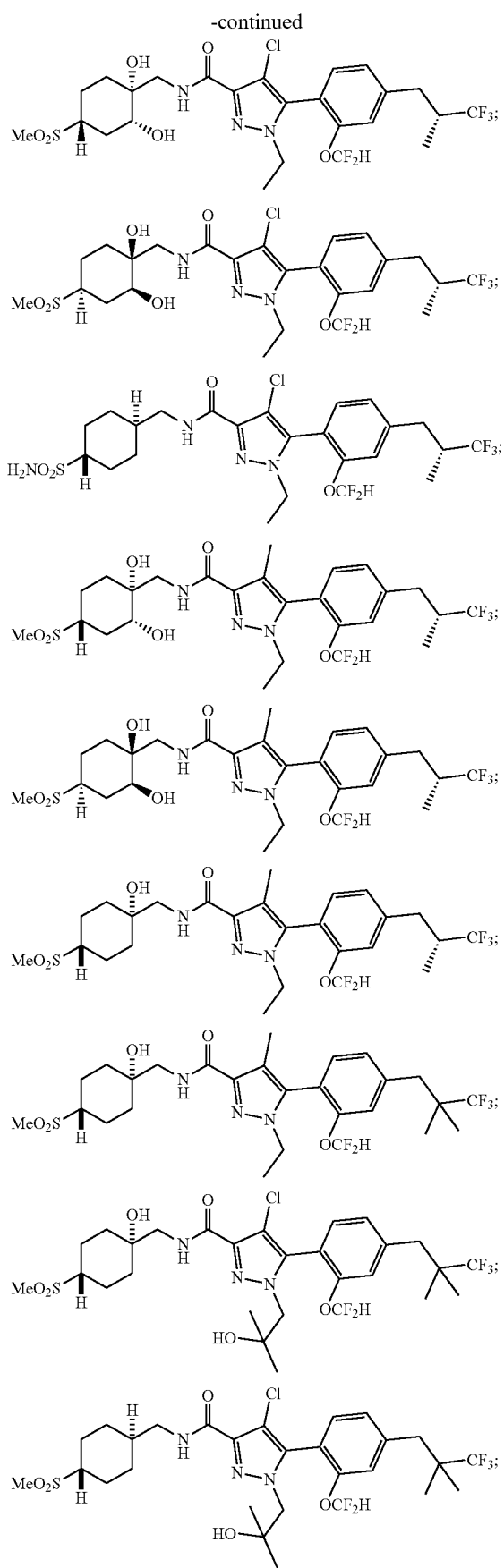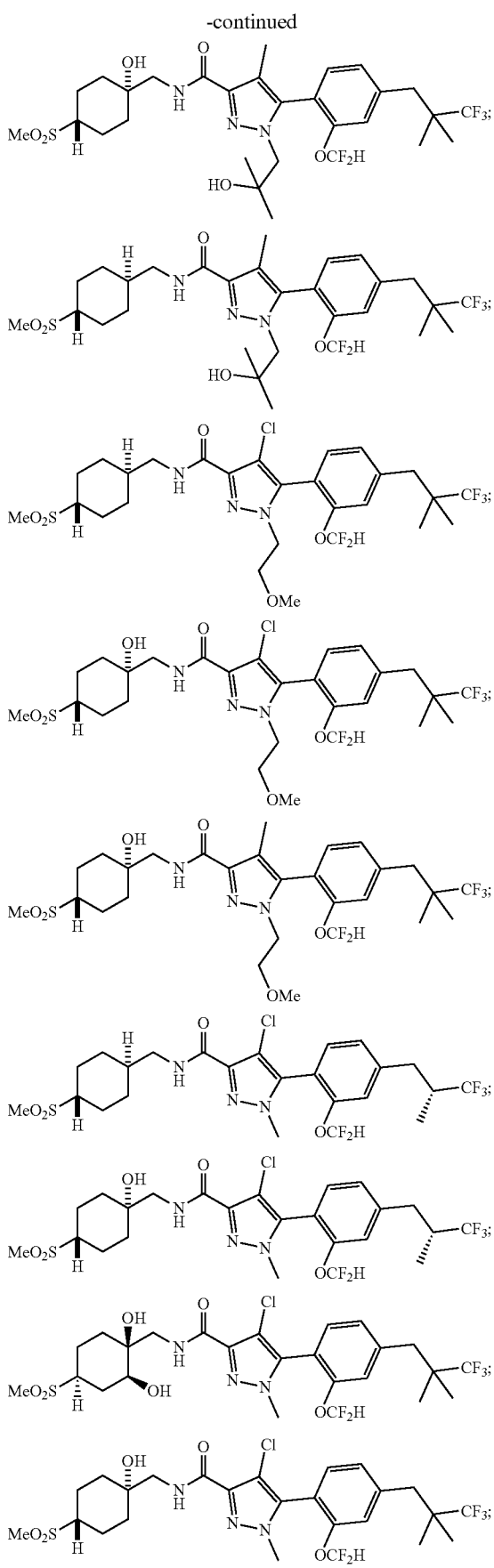

-continued
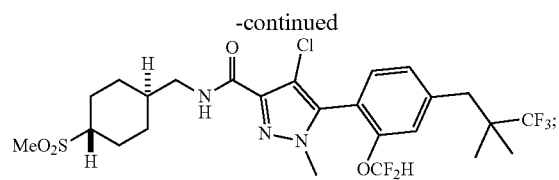
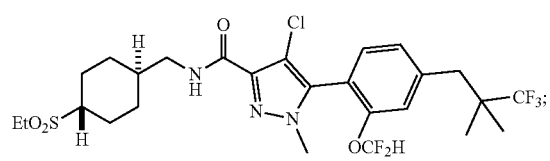
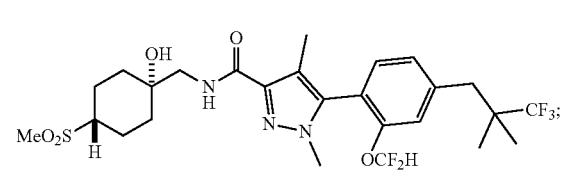
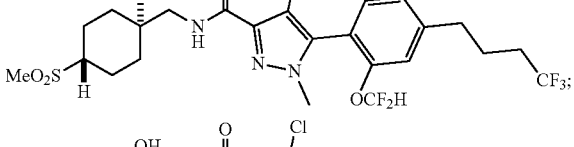
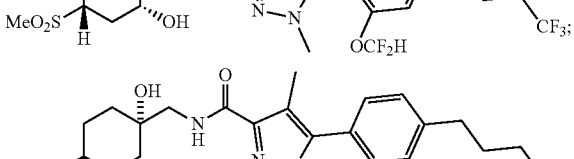
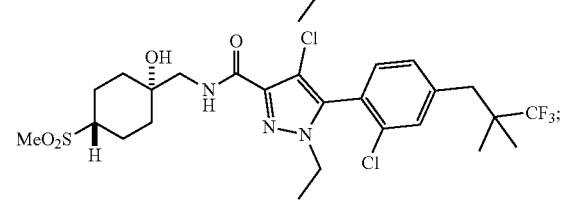
-continued
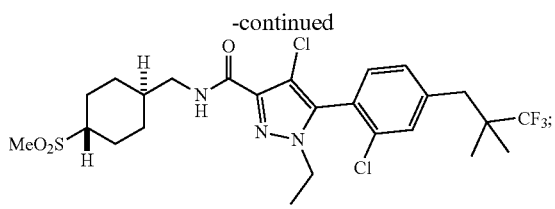
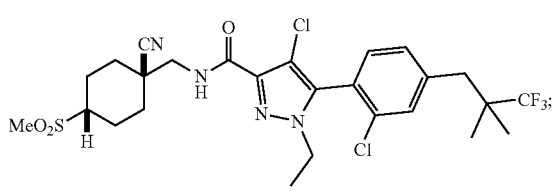
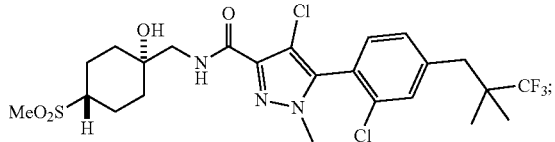
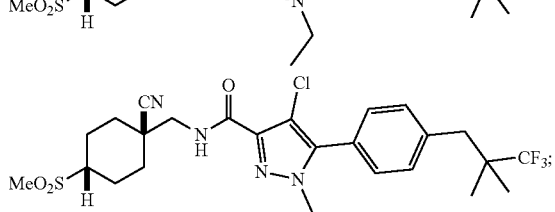
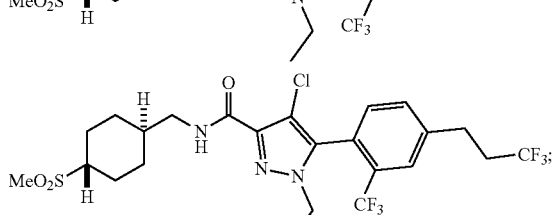
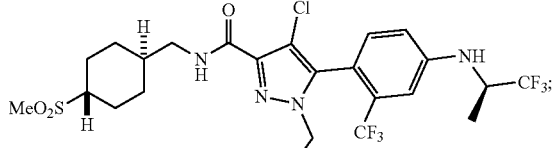
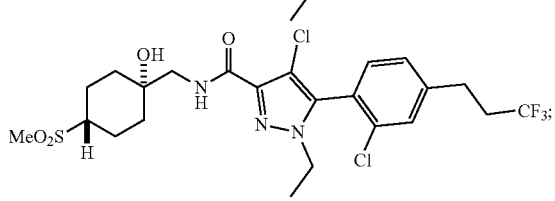

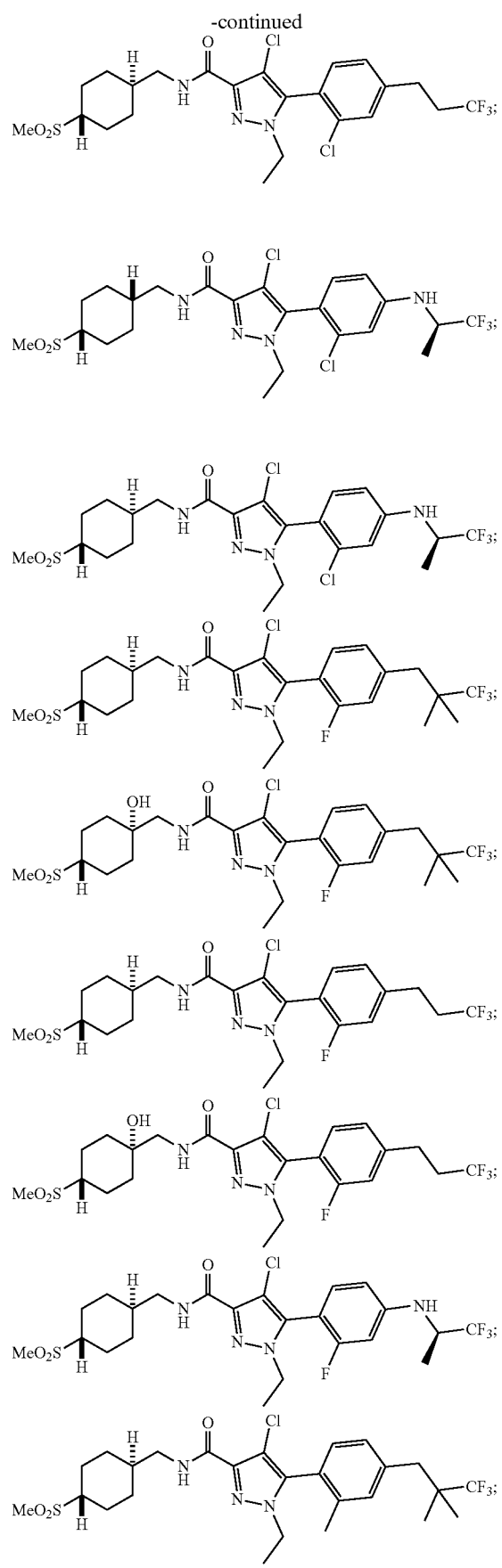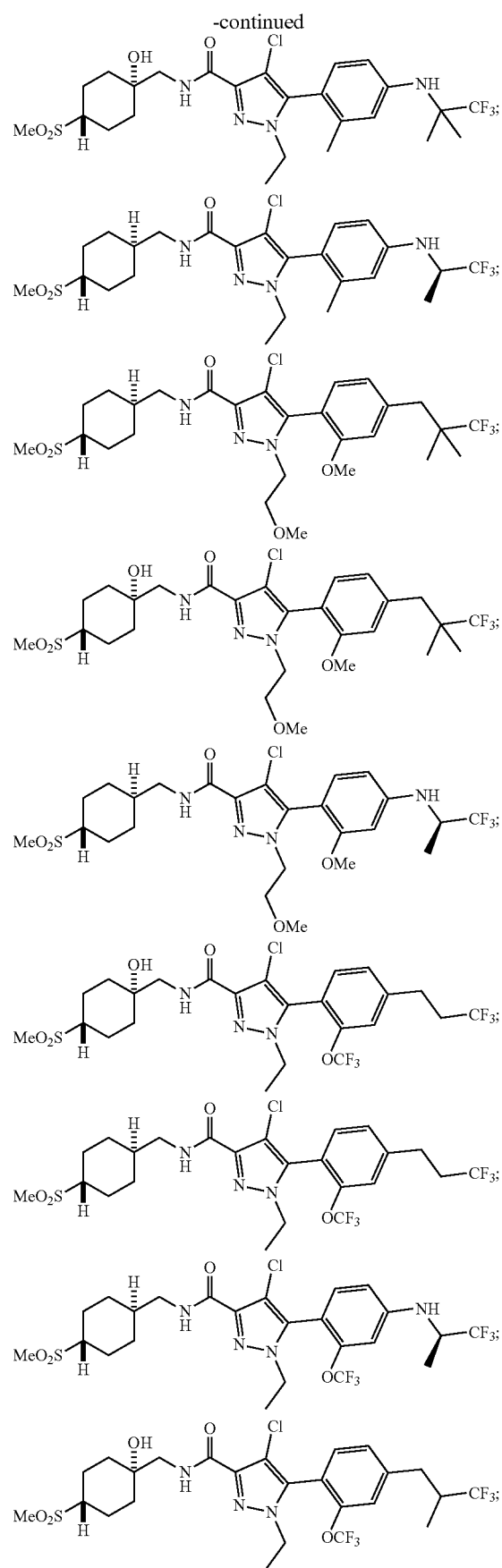

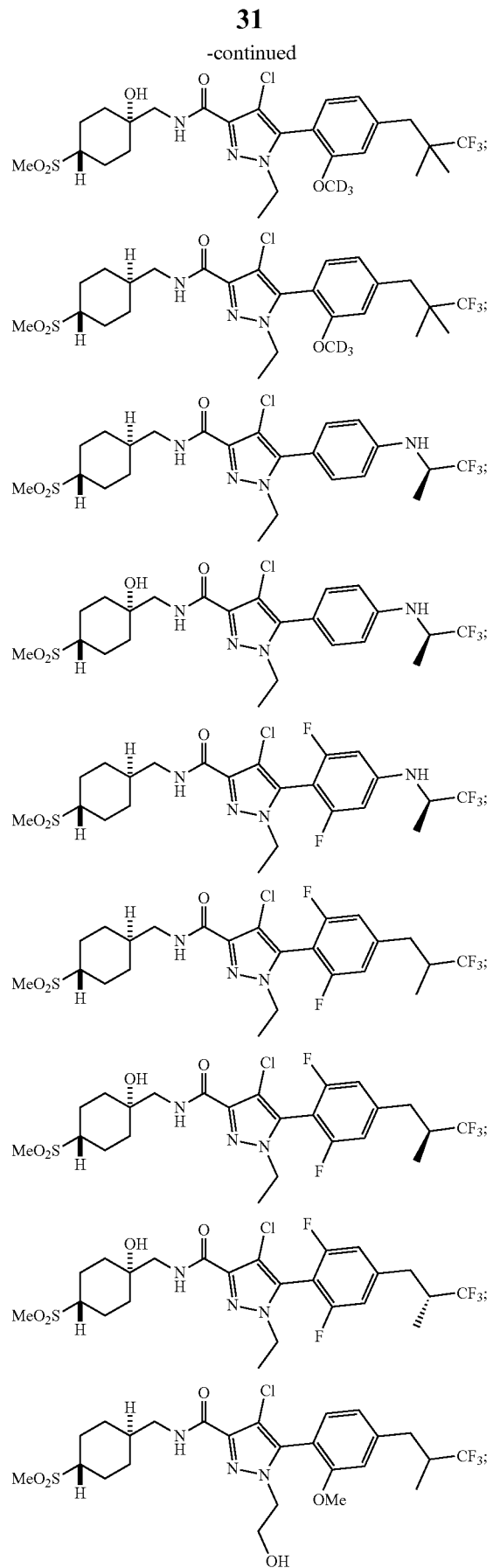
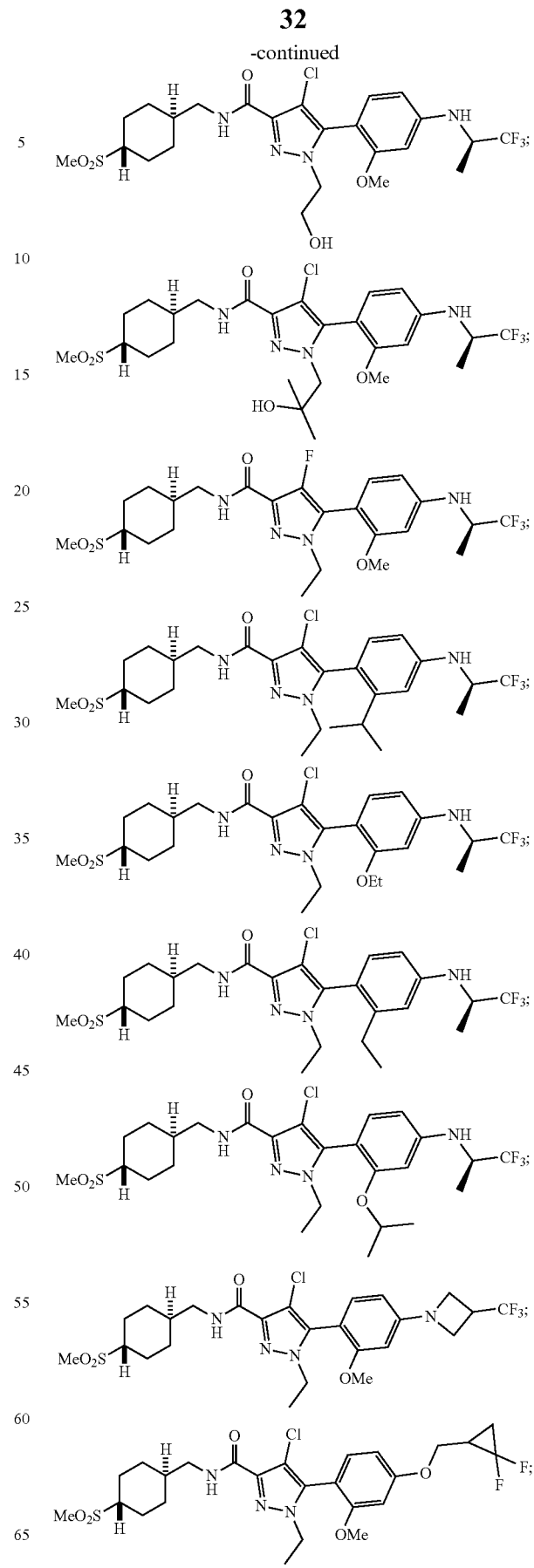

33
-continued
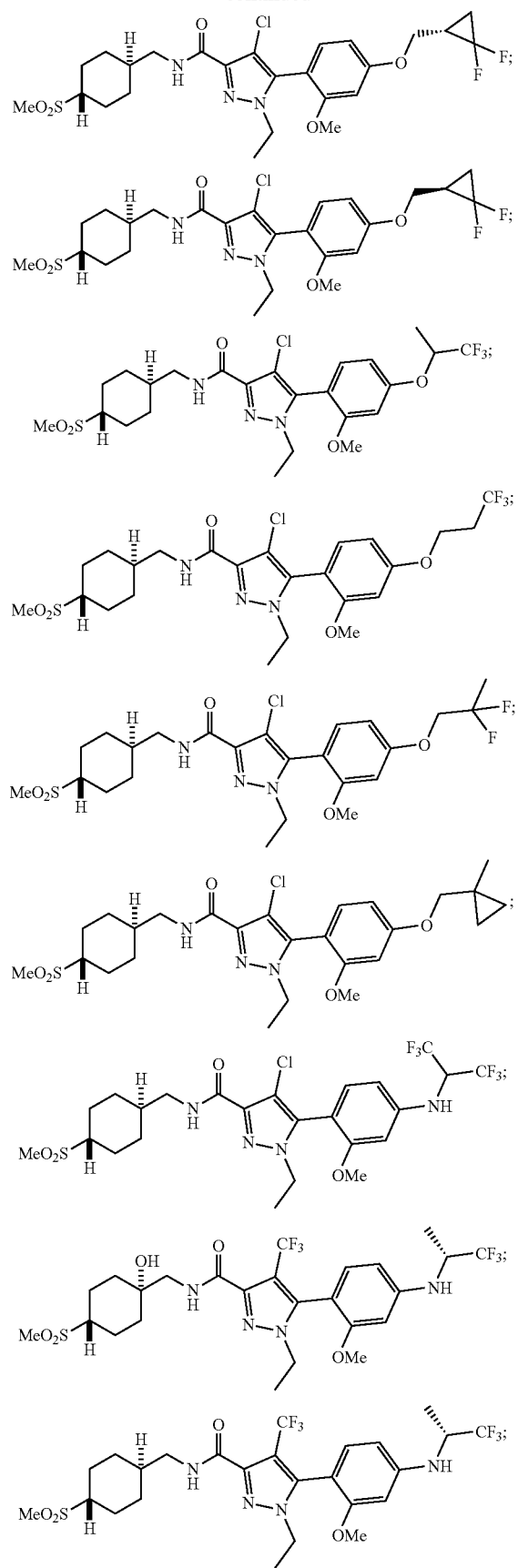
34
-continued
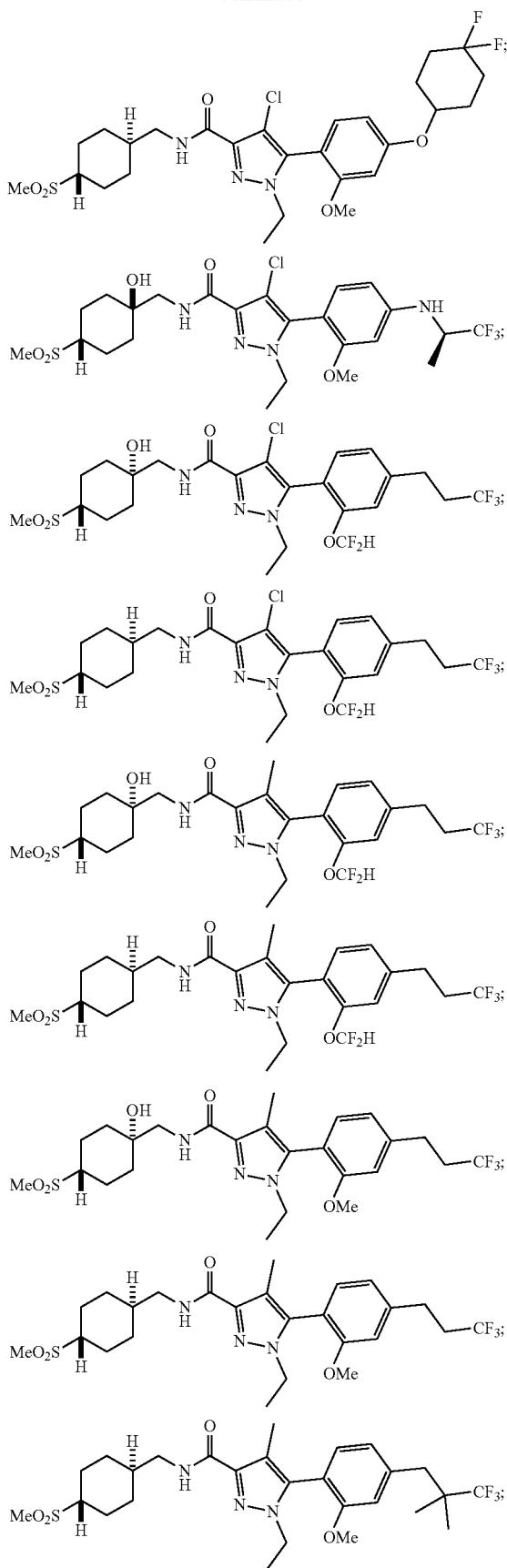

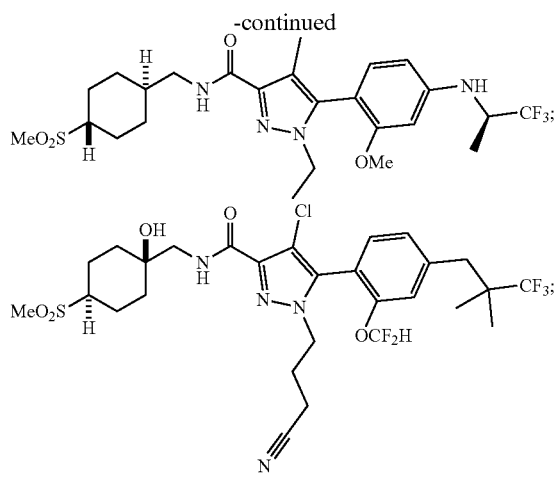

and pharmaceutically acceptable salts thereof.

Another embodiment of the invention comprises a compound of Formula I and a pharmaceutically acceptable carrier.

The present invention also provides a method for preventing, treating or ameliorating an RORγt mediated inflammatory syndrome, disorder or disease comprising administering to a subject in need thereof an effective amount of a compound of Formula I or a form, composition or medicament thereof.

The present invention provides a method of preventing, treating or ameliorating a syndrome, disorder or disease, wherein said syndrome, disorder or disease is selected from the group consisting of: ophthalmic disorders, uveitis, atherosclerosis, rheumatoid arthritis, psoriasis, psoriatic arthritis, atopic dermatitis, multiple sclerosis, Crohn's Disease, ulcerative colitis, ankylosing spondylitis, nephritis, organ allograft rejection, fibroid lung, systic fibrosis, renal insufficiency, diabetes and diabetic complications, diabetic nephropathy, diabetic retinopathy, diabetic retinitis, diabetic microangiopathy, tuberculosis, chronic obstructive pulmonary disease, sarcoidosis, invasive staphylococcia, inflammation after cataract surgery, allergic rhinitis, allergic conjunctivitis, chronic urticaria, systemic lupus erythematosus, asthma, allergic asthma, steroid resistant asthma, neutrophilic asthma, periodontal diseases, periodonitis, gingivitis, gum disease, diastolic cardiomyopathies, cardiac infarction, myocarditis, chronic heart failure, angiostenosis, restenosis, reperfusion disorders, glomerulonephritis, solid tumors and cancers, chronic lymphocytic leukemia, chronic myelocytic leukemia, multiple myeloma, malignant myeloma, Hodgkin's disease, carcinomas of the bladder, breast, cervix, colon, lung, prostate, or stomach, depression and metabolic syndrome comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: rheumatoid arthritis, psoriasis, chronic obstructive pulmonary disorder, psoriatic arthritis, ankylosing spondylitis, Crohn's disease, and ulcerative colitis.

The present invention provides a method of treating or ameliorating a syndrome, disorder or disease, wherein said syndrome, disorder or disease is selected from the group consisting of: depression and metabolic syndrome.

The present invention provides a method of treating or ameliorating a syndrome, disorder or disease, wherein said syndrome, disorder or disease is selected from the group consisting of: rheumatoid arthritis, psoriasis, chronic obstructive pulmonary disorder, psoriatic arthritis, ankylosing spondylitis, Crohn's disease, and ulcerative colitis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: inflammatory bowel diseases, rheumatoid arthritis, psoriasis, chronic obstructive pulmonary disorder, psoriatic arthritis, ankylosing spondylitis, neutrophilic asthma, steroid resistant asthma, multiple sclerosis, and systemic lupus erythematosus comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: inflammatory bowel diseases, rheumatoid arthritis, psoriasis, chronic obstructive pulmonary disorder, psoriatic arthritis, ankylosing spondylitis, neutrophilic asthma, steroid resistant asthma, multiple sclerosis, systemic lupus erythematosus, depression and metabolic syndrome comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: rheumatoid arthritis, and psoriasis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: psoriatic arthritis and psoriasis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: depression and metabolic syndrome comprising administering to a subject in need thereof an effective amount of a compound of Formula I or a form, composition or medicament thereof.

The present invention provides a method of treating or ameliorating a syndrome, disorder or disease, in a subject in need thereof comprising administering to the subject an effective amount of the compound of Formula I or composition or medicament thereof in a combination therapy with one or more anti-inflammatory agents, or immunosuppressive agents, wherein said syndrome, disorder or disease is selected from the group consisting of: rheumatoid arthritis, and psoriasis.

The present invention provides a method of treating or ameliorating a syndrome, disorder or disease, in a subject in need thereof comprising administering to the subject an effective amount of the compound of Formula I or composition or medicament thereof in a combination therapy with one or more anti-inflammatory agents, or immunosuppressive agents, wherein said syndrome, disorder or disease is selected from the group consisting of: psoriatic arthritis and psoriasis.

The present invention provides a method of treating or ameliorating a syndrome, disorder or disease, in a subject in need thereof comprising administering to the subject an effective amount of the compound of Formula I or composition or medicament thereof in a combination therapy with one or more anti-inflammatory agents, or immunosuppressive agents, wherein said syndrome, disorder or disease is selected from the group consisting of: depression and metabolic syndrome.

The present invention provides a method of treating or ameliorating a syndrome, disorder or disease, wherein said syndrome, disorder or disease is rheumatoid arthritis, comprising administering to a subject in need thereof an effective amount of a compound of Formula I or a form, composition or medicament thereof.

The present invention provides a method of treating or ameliorating a syndrome, disorder or disease, wherein said syndrome, disorder or disease is psoriasis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is chronic obstructive pulmonary disorder comprising administering to a subject in need thereof an effective amount of a compound of Formula I or a form, composition or medicament thereof.

The present invention provides a method of treating or ameliorating a syndrome, disorder or disease, wherein said syndrome, disorder or disease is psoriatic arthritis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is ankylosing spondylitis comprising administering to a subject in need thereof an effective amount of a compound of Formula I or a form, composition or medicament thereof.

The present invention provides a method of treating or ameliorating an inflammatory bowel disease, wherein said inflammatory bowel disease is Crohn's disease comprising administering to a subject in need thereof an effective amount of a compound of Formula I or a form, composition or medicament thereof.

The present invention provides a method of treating or ameliorating an inflammatory bowel disease, wherein said inflammatory bowel disease is ulcerative colitis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is neutrophilic asthma comprising administering to a subject in need thereof an effective amount of a compound of Formula I or a form, composition or medicament thereof.

The present invention provides a method of treating or ameliorating a syndrome, disorder or disease, wherein said syndrome, disorder or disease is steroid resistant asthma comprising administering to a subject in need thereof an effective amount of a compound of Formula I or a form, composition or medicament thereof.

The present invention provides a method of treating or ameliorating a syndrome, disorder or disease, wherein said syndrome, disorder or disease is multiple sclerosis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is systemic lupus erythematosus comprising administering to a subject in need thereof an effective amount of a compound of Formula I or a form, composition or medicament thereof.

The present invention provides a method of treating or ameliorating a syndrome, disorder or disease, wherein said syndrome, disorder or disease is depression comprising administering to a subject in need thereof an effective amount of a compound of Formula I or a form, composition or medicament thereof.

The present invention provides a method of treating or ameliorating a syndrome, disorder or disease, wherein said syndrome, disorder or disease is metabolic syndrome comprising administering to a subject in need thereof an effective amount of a compound of Formula I or a form, composition or medicament thereof.

The invention also relates to methods of modulating RORγt activity in a mammal by administration of an effective amount of at least one compound of Formula I.

Another embodiment of the invention is a method of inhibiting production of interleukin-17, comprising administering to a subject in need thereof an effective amount of a compound of Formula I.

Definitions

The term "administering" with respect to the methods of the invention, means a method for therapeutically or prophylactically preventing, treating or ameliorating a syndrome, disorder or disease as described herein by using a compound of Formula I or a form, composition or medicament thereof. Such methods include administering an effective amount of said compound, compound form, composition or medicament at different times during the course of a therapy or concurrently in a combination form. The methods of the invention are to be understood as embracing all known therapeutic treatment regimens.

The term "subject" refers to a patient, which may be an animal, typically a mammal, typically a human, which has been the object of treatment, observation or experiment and is at risk of (or susceptible to) developing a syndrome, disorder or disease that is associated with aberrant RORγt expression or RORγt overexpression, or a patient with an inflammatory condition that accompanies syndromes, disorders or diseases associated with aberrant RORγt expression or RORγt overexpression.

The term "effective amount" means that amount of active compound or pharmaceutical agent that elicits the biological or medicinal response in a tissue system, animal or human, that is being sought by a researcher, veterinarian, medical doctor, or other clinician, which includes preventing, treating or ameliorating the symptoms of a syndrome, disorder or disease being treated.

As used herein, the term "composition" is intended to encompass a product comprising the specified ingredients in the specified amounts, as well as any product which results, directly or indirectly, from combinations of the specified ingredients in the specified amounts.

The term "alkyl" refers to both linear and branched chain radicals of up to 12 carbon atoms, preferably up to 6 carbon atoms, unless otherwise indicated, and includes, but is not limited to, methyl, ethyl, propyl, isopropyl, butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl. Any alkyl group may be optionally substituted with one $OCH_3$, one OH, or up to two fluorine atoms. The term "$C_{(a-b)}$" (where a and b are integers referring to a designated number of carbon atoms) refers to an alkyl, alkenyl, alkynyl, alkoxy or cycloalkyl radical or to the alkyl portion of a radical in which alkyl appears as the prefix root containing from a to b carbon atoms inclusive. For example, $C_{(1-4)}$ denotes a radical containing 1, 2, 3 or 4 carbon atoms.

The term "oxo" refers to a substituent on an alkyl group, wherein two hydrogen atoms on the same carbon atom have been replaced with a single oxygen atom. Said oxygen atom is double bonded to said carbon atom, replacing the pair of single bonds to hydrogen atoms.

Pharmaceutically Acceptable Salts

Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid. Pharmaceutically acceptable basic/cationic salts include, and are not limited to aluminum, 2-amino-2-hydroxymethyl-propane-1,3-diol (also known as tris(hydroxymethyl)aminomethane, tromethane or "TRIS"), ammonia, benzathine, t-butylamine, calcium, calcium gluconate, calcium hydroxide, chloroprocaine, choline, choline bicarbonate, choline chloride, cyclohexylamine, diethanolamine, ethylenediamine, lithium, LiOMe, L-lysine, magnesium, meglumine, $NH_3$, $NH_4OH$, N-methyl-D-glucamine, piperidine, potassium, potassium-t-butoxide, potassium hydroxide (aqueous), procaine, quinine, sodium, sodium carbonate, sodium-2-ethylhexanoate, sodium hydroxide, triethanolamine, or zinc.

Methods of Use

The present invention is directed to a method for preventing, treating or ameliorating a RORγt mediated inflammatory syndrome, disorder or disease comprising administering to a subject in need thereof an effective amount of a compound of Formula I or a form, composition or medicament thereof.

Since RORγt is an N-terminal isoform of RORγ, it is recognized that compounds of the present invention which are modulators of RORγt are likely to be modulators of RORγ as well.

Therefore the mechanistic description "RORγt modulators" is intended to encompass RORγ modulators as well.

When employed as RORγt modulators, the compounds of the invention may be administered in an effective amount within the dosage range of about 0.5 mg to about 10 g, preferably between about 0.5 mg to about 5 g, in single or divided daily doses. The dosage administered will be affected by factors such as the route of administration, the health, weight and age of the recipient, the frequency of the treatment and the presence of concurrent and unrelated treatments.

It is also apparent to one skilled in the art that the therapeutically effective dose for compounds of the present invention or a pharmaceutical composition thereof will vary according to the desired effect. Therefore, optimal dosages to be administered may be readily determined by one skilled in the art and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

The compounds of Formula I may be formulated into pharmaceutical compositions comprising any known pharmaceutically acceptable carriers. Exemplary carriers include, but are not limited to, any suitable solvents, dispersion media, coatings, antibacterial and antifungal agents and isotonic agents. Exemplary excipients that may also be components of the formulation include fillers, binders, disintegrating agents and lubricants.

The pharmaceutically-acceptable salts of the compounds of Formula I include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamino salts and salts with amino acids such as arginine. Also, the basic nitrogen-containing groups may be quaternized with, for example, alkyl halides.

The pharmaceutical compositions of the invention may be administered by any means that accomplish their intended purpose. Examples include administration by parenteral, subcutaneous, intravenous, intramuscular, intraperitoneal, transdermal, buccal or ocular routes. Alternatively or concurrently, administration may be by the oral route. Suitable formulations for parenteral administration include aqueous solutions of the active compounds in water-soluble form, for example, water-soluble salts, acidic solutions, alkaline solutions, dextrose-water solutions, isotonic carbohydrate solutions and cyclodextrin inclusion complexes.

The present invention also encompasses a method of making a pharmaceutical composition comprising mixing a pharmaceutically acceptable carrier with any of the compounds of the present invention. Additionally, the present invention includes pharmaceutical compositions made by mixing a pharmaceutically acceptable carrier with any of the compounds of the present invention.

Polymorphs and Solvates

Furthermore, the compounds of the present invention may have one or more polymorph or amorphous crystalline forms and as such are intended to be included in the scope of the invention. In addition, the compounds may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include ethanolates, methanolates, and the like.

It is intended that the present invention include within its scope polymorphs and solvates of the compounds of the present invention. Thus, in the methods of treatment of the present invention, the term "administering" shall encompass the means for treating, ameliorating or preventing a syndrome, disorder or disease described herein with the compounds of the present invention or a polymorph or solvate thereof, which would obviously be included within the scope of the invention albeit not specifically disclosed.

In another embodiment, the invention relates to a compound as described in Formula I for use as a medicament.

In another embodiment, the invention relates to the use of a compound as described in Formula I for the preparation of a medicament for the treatment of a disease associated with an elevated or aberrant RORγt activity.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", Ed. H. Bundgaard, Elsevier, 1985.

Furthermore, it is intended that within the scope of the present invention, any element, in particular when mentioned in relation to a compound of Formula I, shall comprise all isotopes and isotopic mixtures of said element, either naturally occurring or synthetically produced, either with natural abundance or in an isotopically enriched form. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$. The isotopes may be radioactive or non-radioactive. Radiolabelled compounds of Formula I may comprise a radioactive isotope selected from the group of $^3H$, $^{11}C$, $^{18}F$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^3H$, $^{11}C$ and $^{18}F$.

Some compounds of the present invention may exist as atropisomers. Atropisomers are stereoisomers resulting from hindered rotation about single bonds where the steric strain barrier to rotation is high enough to allow for the isolation of the conformers. It is to be understood that all such conformers and mixtures thereof are encompassed within the scope of the present invention.

Where the compounds according to this invention have at least one stereo center, they may accordingly exist as enantiomers or diastereomers. It is to be understood that all such isomers and mixtures thereof are encompassed within the scope of the present invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral column vial HPLC or SFC. In some instances rotamers of compounds may exist which are observable by 1H NMR leading to complex multiplets and peak integration in the 1H NMR spectrum.

Chiral centers, of which the absolute configurations are known, are labelled by prefixes R and S, assigned by the standard sequence-rule procedure, and preceded when necessary by the appropriate locants. Chiral centers, of which the relative but not the absolute configurations are known, are labelled arbitrarily by prefixes R* and S*, preceded when necessary by the appropriate locants. These prefixes are assigned by the standard sequence-rule procedure on the arbitrary assumption that the center of chirality with the lowest locant has chirality R. When a compound contains chiral centers with known absolute configurations and a sterically unrelated set of chiral centers with known relative configurations but unknown absolute configurations, then R* and S* are used to designate the latter. (Pure & Appl. Chem. 45, 1976, 11-30). Racemates containing a single chiral center are labelled RS or are not labelled. For racemates with more than one chiral center, the chiral center with the lowest locant is labelled RS and the others are labelled RS or SR according to whether they are R or S when the chiral center with the lowest locant is R. Pseudoasymmetric stereogenic centers are treated in the same way as chiral centers, but are given lower-case symbols, r or s (Angew. Chem. Int. Ed. Engl. 1982, 21, 567-583).

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

Abbreviations

Herein and throughout the application, the following abbreviations may be used.
Ac acetyl
AIBN 2,2'-azobis(2-methylpropionitrile)
9-BBN 9-borabicyclo[3.3.1]nonane
Boc tert-butyloxycarbonyl
br broad
Bu butyl
CAN ceric ammonium nitrate
Cbz carboxybenzyl δ NMR chemical shift in parts per million downfield from a standard
CSA 10-camphorsulfonic acid
d doublet
DABSO 1,4-diazabicyclo[2.2.2]octane bis(sulfur dioxide) adduct
DAST (diethylamino)sulfur trifluoride
dba dibenzylideneacetone
DBU 1,8-diazabicyclo[5.4.0]undec-7-ene
DCE dichloroethane
DCM dichloromethane
Deoxo-Fluor® bis(2-methoxyethyl)aminosulfur trifluoride
DIAD diisopropyl azodicarboxylate
DIPEA N,N-diisopropylethylamine (Hünig's base)
DMA N,N-dimethylacetamide
DME 1,2-dimethoxyethane
DMEN N,N-dimethylethylenediamine
DMF N,N-dimethylformamide
DMSO dimethyl sulfoxide
dppf 1,1'-bis(diphenylphosphino)ferrocene
EDCI 1-ethyl-3-(3-dimethylaminopropyl) carbodiimide hydrochloride
ESI electrospray ionization
esp α,α,α',α'-tetramethyl-1,3-benzenedipropionic acid
Et ethyl
g grams(s)
h hour(s)
HATU O-(7-azabenzotriazol-1-yl)-N,N,N',N'-tetramethyluronium hexafluorophosphate
HOBt 1-hydroxybenzotriazole
HPLC high pressure liquid chromatography
Hz Hertz
i iso
IPA isopropanol
J coupling constant (NMR spectroscopy)
L liter(s)
LiHMDS lithium bis(trimethylsilyl)amide
LAH lithium aluminum hydride
LC liquid chromatography
m milli or multiplet
m/z mass-to-charge ratio
M+ parent molecular ion
M molar (moles/liter) or mega
mCPBA 3-chloroperbenzoic acid
Me methyl
MeCN acetonitrile
min minute(s)
μ micro
MS mass spectrometry
MTBE tert-butyl methyl ether
NBS N-bromosuccinimide
NCS N-chlorosuccinimide
NIS N-iodosuccinimide
n normal
n nano
N normal (equivalent concentration)
NMO 4-methylmorpholine N-oxide
NMR nuclear magnetic resonance
Pd/C palladium on carbon
PEPPSI-IPr [1,3-bis(2,6-diisopropylphenyl)imidazol-2-ylidene](3-chloropyridyl)palladium(II) dichloride
Ph phenyl
Pr propyl
Pt/C platinum on carbon
q quartet
rt room temperature
RuPhos 2-Dicyclohexylphosphino-2',6'-diisopropoxybiphenyl
RuPhos G1 chloro-(2-dicyclohexylphosphino-2',6'-diisopropoxy-1,1'-biphenyl) [2-(2-aminoethyl)phenyl]palladium(II)
s singlet
Selectfluor® 1-chloromethyl-4-fluoro-1,4-diazoniabicyclo[2.2.2]octane bis(tetrafluoroborate)
SFC supercritical fluid chromatography
t tert
t triplet
TBAF tetrabutylammonium fluoride
TBS tert-butyldimethylsilyl
t-Bu-XPhos 2-di-tert-butylphosphino-2',4',6'-triisopropylbiphenyl
TEA triethylamine
TFA trifluoroacetic acid
THF tetrahydrofuran
TMP 2,2,6,6-tetramethylpiperidine
TMS trimethylsilyl
TosMIC p-toluenesulfonylmethyl isocyanide
Ts p-toluenesulfonyl
T3P propanephosphonic acid anhydride
XPhos 2-dicyclohexylphosphino-2',4',6'-triisopropylbiphenyl
v/v volume-to-volume ratio
wt % weight percent
w/w weight-to-weigh ratio General Schemes:

The compounds of Formula I in the present invention can be prepared according to Scheme 1. Palladium-catalyzed cross coupling reaction between bromophenylpyrazoles A-I and C-, N-, or O-nucleophiles (e.g., organoboron reagents, organozinc reagents, amines, alcohols) can give phenylpyrazoles A-II. Ester hydrolysis using aqueous hydroxide solution and a cosolvent such as 1,4-dioxane or THF can give carboxylic acids A-III. Amides of Formula I can be formed by reaction of A-III with amines or amine salts promoted by a reagent such as HATU or EDCI and a base such as DIPEA in a solvent such as DMF, MeCN, or DCM. The reaction sequence can be altered such that bromophenylpyrazoles A-I can undergo ester hydrolysis and then amide bond formation to give bromophenylpyrazole amides A-IV. Palladium-catalyzed cross-coupling reaction between A-IV and nucleophiles can give amides of Formula I. Amides of Formula I ($R^4$=Cl) can undergo Suzuki cross-coupling reaction with organoboron reagents such as trimethylboroxine using a palladium precatalyst and ligand combination such as RuPhos G1/RuPhos and a carbonate base such as $K_2CO_3$ in a solvent such as 1,4-dioxane to give amides of Formula I ($R^4$=alkyl). Amides of Formula I ($R^1$=$NH_2$) can undergo reaction with electrophiles such as formate esters, carboxylic acid anhydrides, or isocyanates promoted by reagents such as Lewis acids, alkoxide bases, or carbonate bases to give amides of Formula I ($R^1$=$NHR^9$; $R^9$=formyl, acyl, or carbamoyl).

Scheme 1

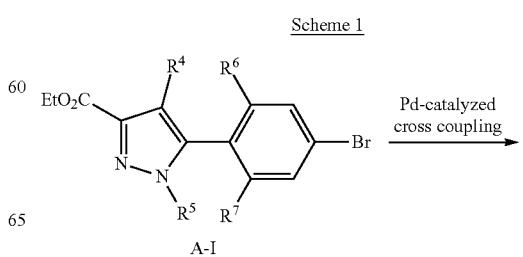

A-I

Pd-catalyzed cross coupling

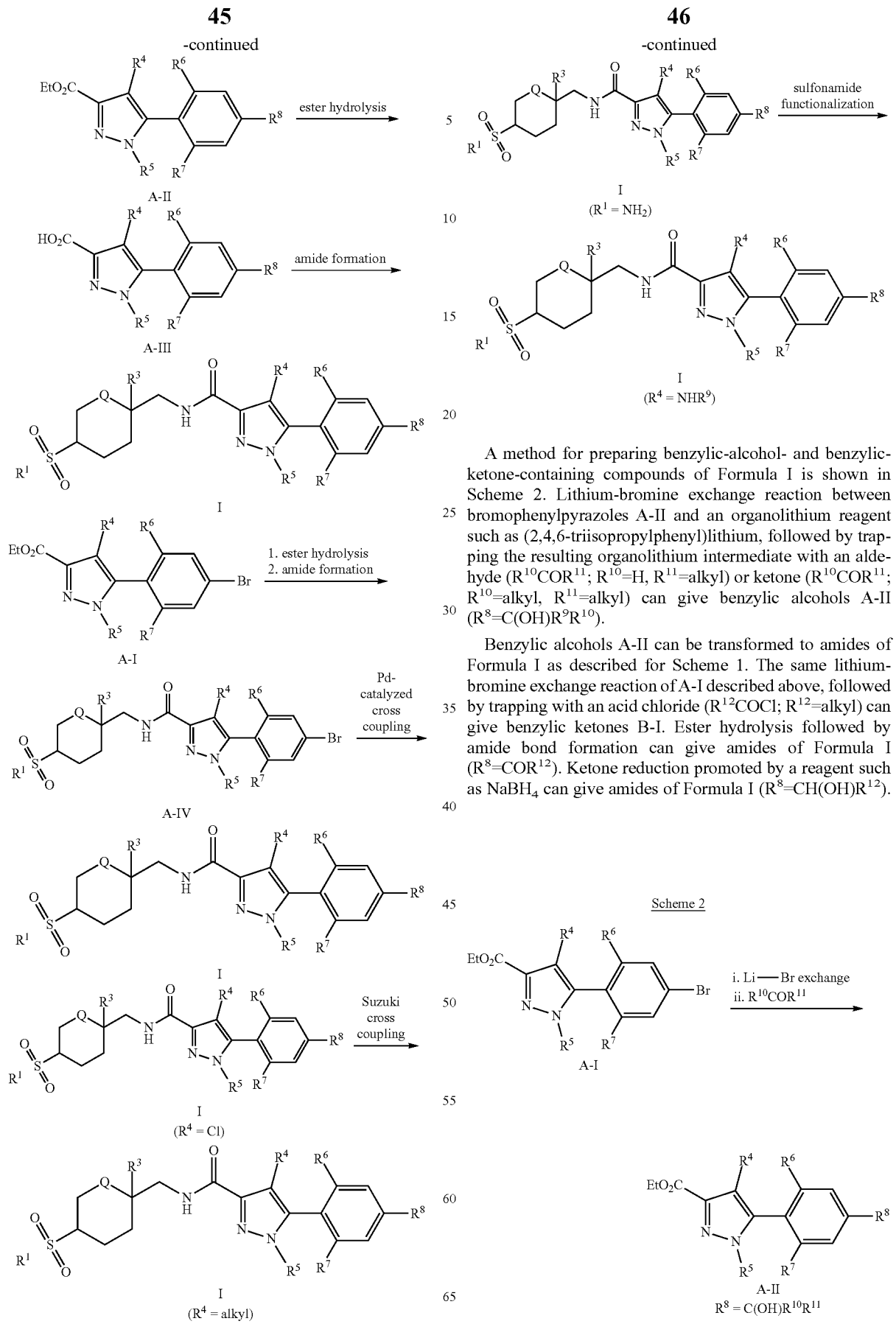

A method for preparing benzylic-alcohol- and benzylic-ketone-containing compounds of Formula I is shown in Scheme 2. Lithium-bromine exchange reaction between bromophenylpyrazoles A-II and an organolithium reagent such as (2,4,6-triisopropylphenyl)lithium, followed by trapping the resulting organolithium intermediate with an aldehyde ($R^{10}COR^{11}$; $R^{10}$=H, $R^{11}$=alkyl) or ketone ($R^{10}COR^{11}$; $R^{10}$=alkyl, $R^{11}$=alkyl) can give benzylic alcohols A-II ($R^8$=C(OH)$R^9R^{10}$).

Benzylic alcohols A-II can be transformed to amides of Formula I as described for Scheme 1. The same lithium-bromine exchange reaction of A-I described above, followed by trapping with an acid chloride ($R^{12}COCl$; $R^{12}$=alkyl) can give benzylic ketones B-I. Ester hydrolysis followed by amide bond formation can give amides of Formula I ($R^8$=$COR^{12}$). Ketone reduction promoted by a reagent such as $NaBH_4$ can give amides of Formula I ($R^8$=CH(OH)$R^{12}$).

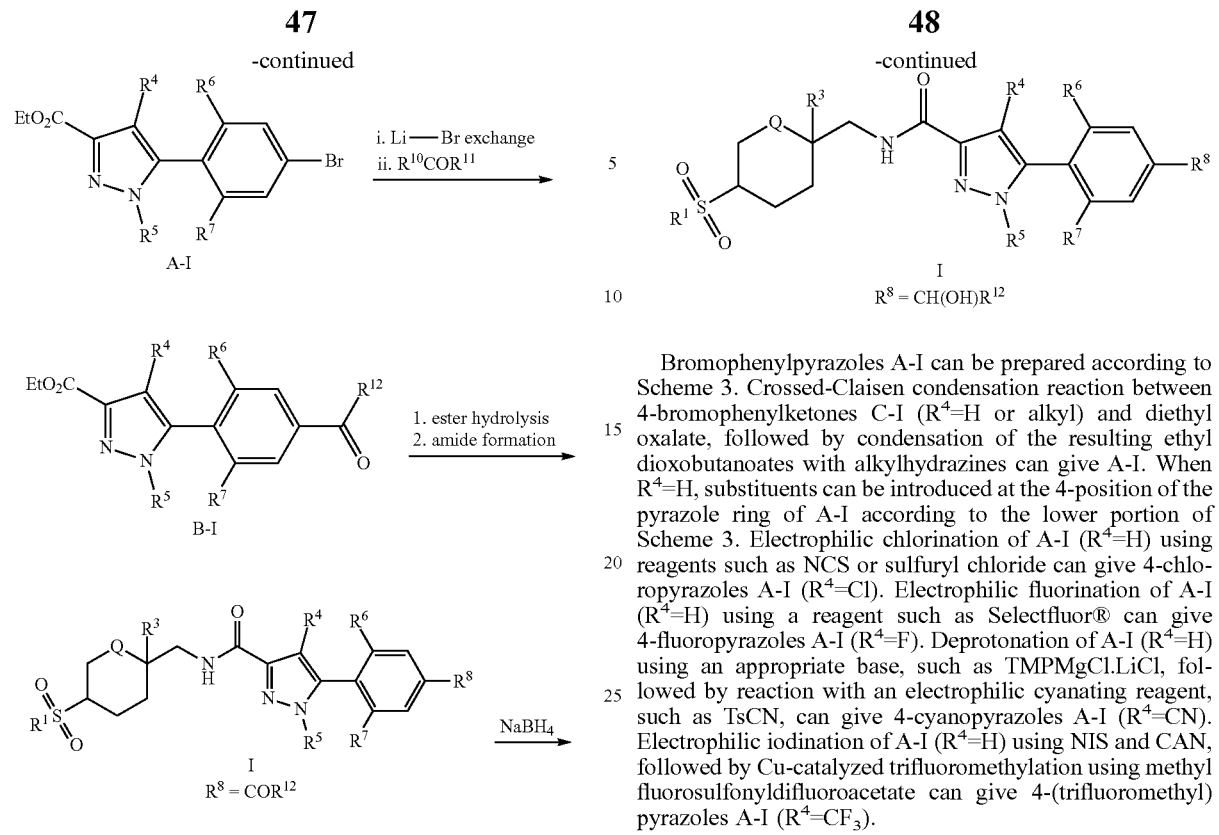

Bromophenylpyrazoles A-I can be prepared according to Scheme 3. Crossed-Claisen condensation reaction between 4-bromophenylketones C-I ($R^4$=H or alkyl) and diethyl oxalate, followed by condensation of the resulting ethyl dioxobutanoates with alkylhydrazines can give A-I. When $R^4$=H, substituents can be introduced at the 4-position of the pyrazole ring of A-I according to the lower portion of Scheme 3. Electrophilic chlorination of A-I ($R^4$=H) using reagents such as NCS or sulfuryl chloride can give 4-chloropyrazoles A-I ($R^4$=Cl). Electrophilic fluorination of A-I ($R^4$=H) using a reagent such as Selectfluor® can give 4-fluoropyrazoles A-I ($R^4$=F). Deprotonation of A-I ($R^4$=H) using an appropriate base, such as TMPMgCl.LiCl, followed by reaction with an electrophilic cyanating reagent, such as TsCN, can give 4-cyanopyrazoles A-I ($R^4$=CN). Electrophilic iodination of A-I ($R^4$=H) using NIS and CAN, followed by Cu-catalyzed trifluoromethylation using methyl fluorosulfonyldifluoroacetate can give 4-(trifluoromethyl)pyrazoles A-I ($R^4$=CF$_3$).

Scheme 3

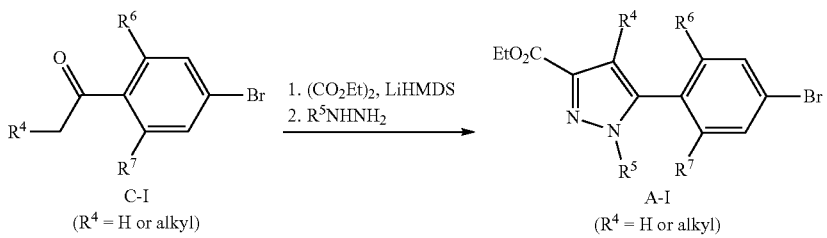

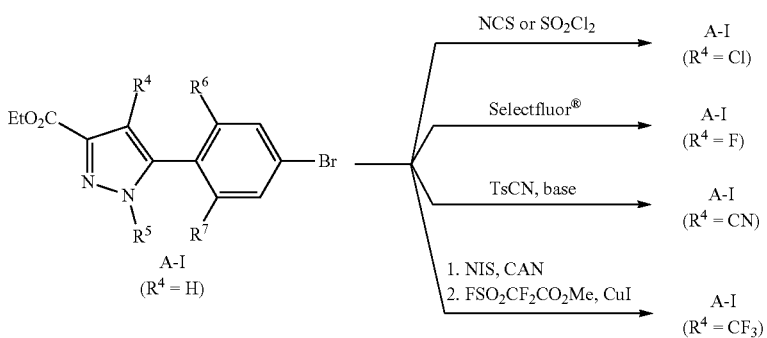

An alternative sequence for the preparation of phenylpyrazoles A-II containing alkyl substituents at the 4-position of the pyrazole ring is shown in Scheme 4. Palladium-catalyzed cross coupling reaction between A-I ($R^4$=Cl) and nucleophiles can give A-II ($R^4$=Cl). These pyrazoles A-II ($R^4$=Cl) can undergo Suzuki cross-coupling reaction with organoboron reagents such as trimethylboroxine using a palladium precatalyst and ligand combination such as RuPhos G1/RuPhos and a carbonate base such as $K_2CO_3$ in a solvent such as 1,4-dioxane to give A-II ($R^4$=alkyl).

N-Cyanoalkylpyrazoles A-I ($R^5$=$(CH_2)_2CH_2CN$) can be prepared according to Scheme 6. N-hydroxyalkylpyrazoles A-I ($R^5$=$(CH_2)_2CH_2OH$) can be prepared according to the upper portion of Scheme 3, using hydroxyalkyl hydrazines. O-Mesylation of A-I ($R^5$=$(CH_2)_2CH_2OH$) using MsCl and TEA can give mesylates A-I ($R^5$=$(CH_2)_2CH_2OMs$). Reaction of A-I ($R^5$=$(CH_2)_2CH_2OMs$) with a cyanide salt such as KCN in a polar aprotic solvent such as DMSO can give A-I ($R^5$=$(CH_2)_2CH_2CN$).

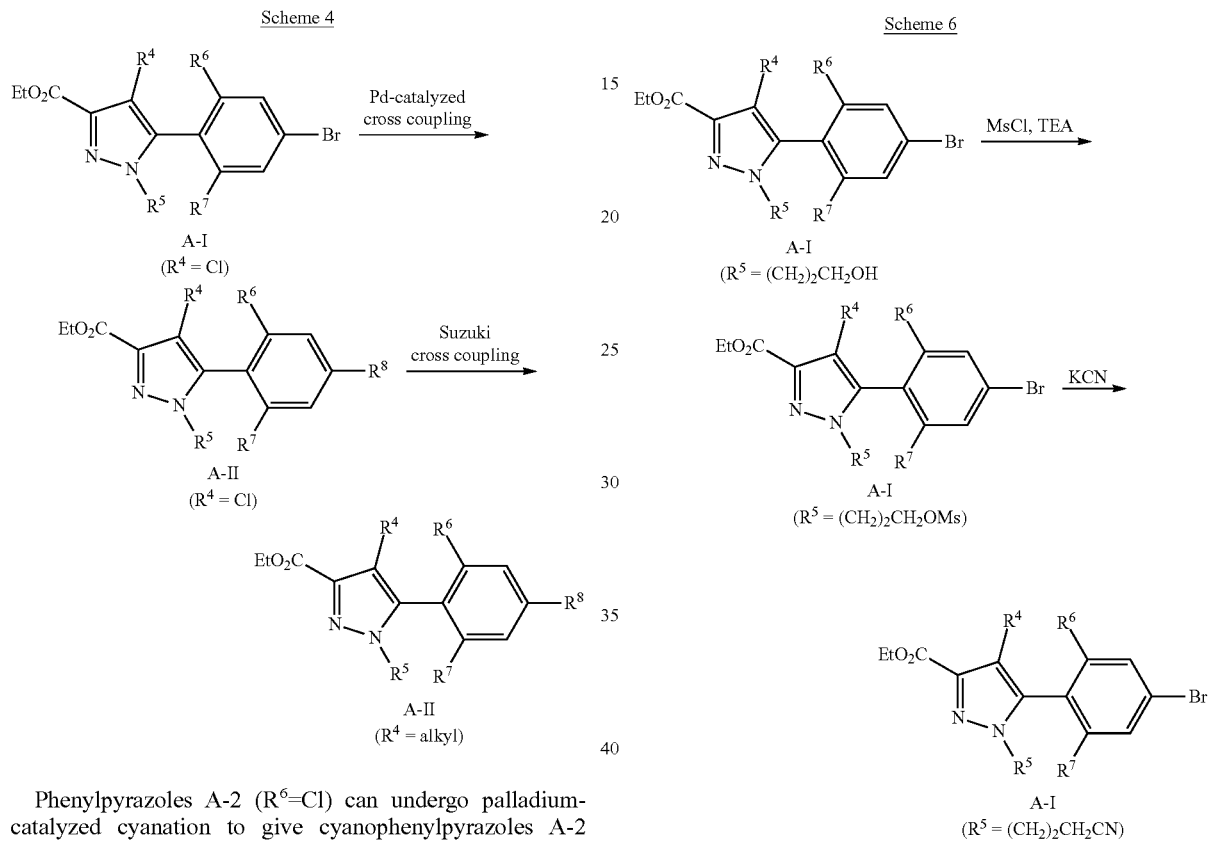

Phenylpyrazoles A-2 ($R^6$=Cl) can undergo palladium-catalyzed cyanation to give cyanophenylpyrazoles A-2 ($R^6$=CN) as shown in Scheme 5.

4-Bromophenylketones C-I can be prepared according to Scheme 7. Benzoic acids D-I can be converted to the corresponding Weinreb amides, D-II, using N,O-dimethylhydroxylamine hydrochloride, a peptide coupling reagent such as HATU, and a base such as DIPEA. These amides, D-II, can undergo reaction with organolithium or Grignard reagents to give C-I. 4-Bromophenylketones C-I ($R^6$=OH) can undergo O-alkylation with reagents such as alkyl halides or difluoromethylating reagents in the presence of carbonate or hydroxide bases to give C-I ($R^6$=alkoxy).

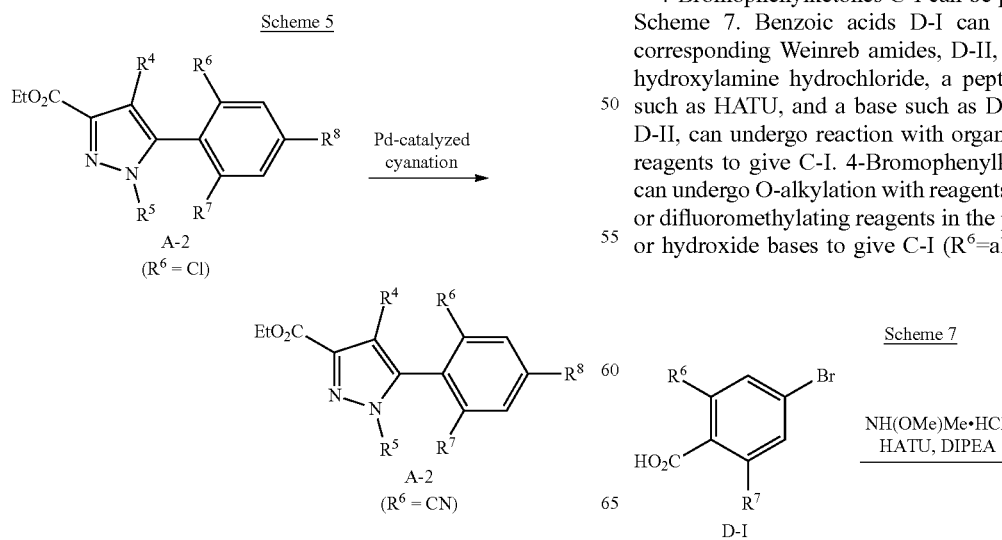

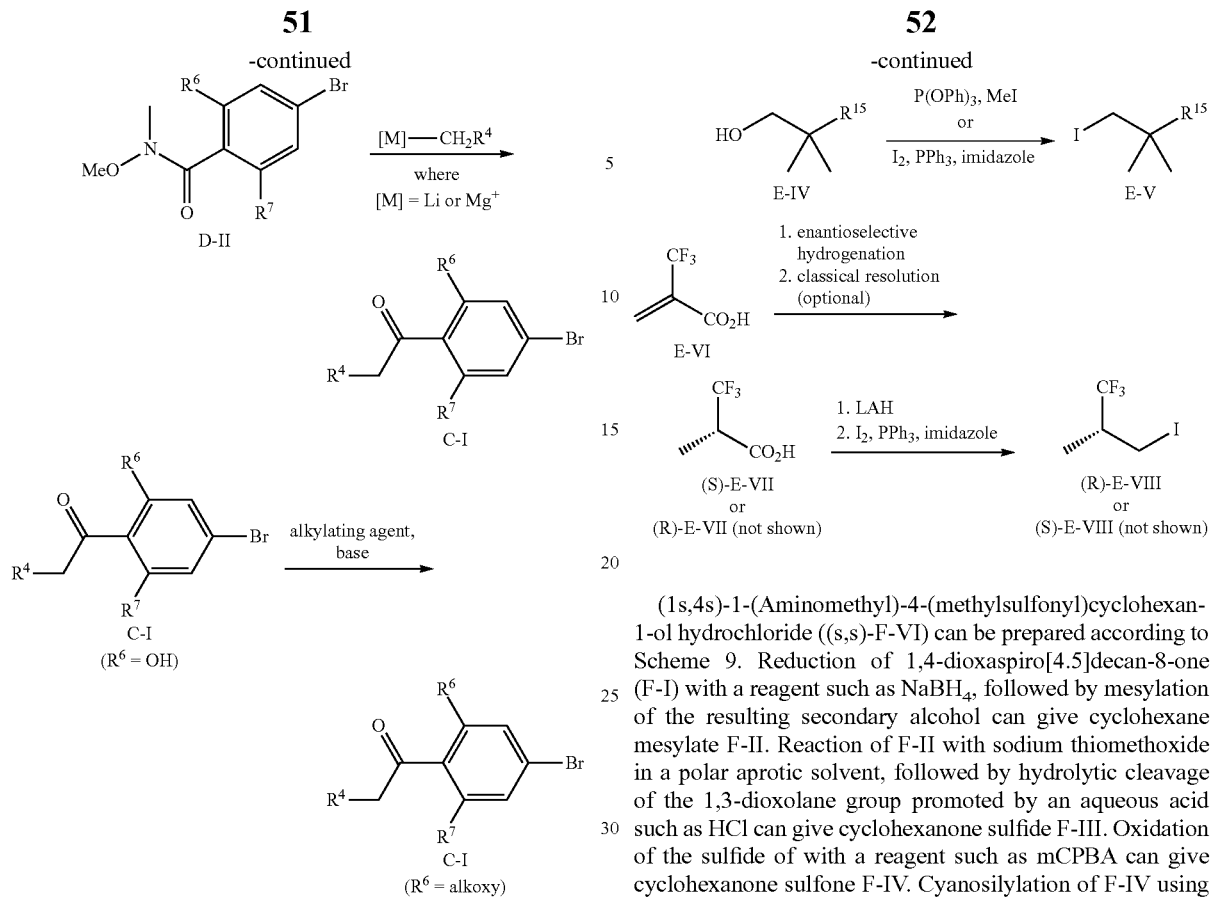

Reagents, or precursors to reagents, for use in palladium-catalyzed cross-coupling reactions can be prepared according to Scheme 8. Alkenes E-I ($R^{13}$=alkyl, $R^{14}$=alkyl) can undergo hydroboration reaction with 9-BBN to give borane reagents E-II. Carboxylic acids E-III ($R^{15}$=alkyl) can undergo reduction promoted by LAH in an ethereal solvent to give primary alcohols E-IV. These alcohols can be converted to iodides E-V by heating them with triphenyl phosphite and iodomethane or by heating them with a combination of reagents such as iodine, triphenylphosphine, and imidazole in a solvent such as NMP. Chiral, enantioenriched iodides can be prepared by enantioselective hydrogenation of acrylate E-VI, optionally followed by classical resolution of the resulting carboxylic acids E-VII. Reduction of E-VII with LAH in an ethereal solvent followed by treatment of the resulting alcohol intermediates with combination of reagents such as iodine, triphenylphosphine, and imidazole can give enantioenriched iodides E-VIII.

(1s,4s)-1-(Aminomethyl)-4-(methylsulfonyl)cyclohexan-1-ol hydrochloride ((s,s)-F-VI) can be prepared according to Scheme 9. Reduction of 1,4-dioxaspiro[4.5]decan-8-one (F-I) with a reagent such as $NaBH_4$, followed by mesylation of the resulting secondary alcohol can give cyclohexane mesylate F-II. Reaction of F-II with sodium thiomethoxide in a polar aprotic solvent, followed by hydrolytic cleavage of the 1,3-dioxolane group promoted by an aqueous acid such as HCl can give cyclohexanone sulfide F-III. Oxidation of the sulfide of with a reagent such as mCPBA can give cyclohexanone sulfone F-IV. Cyanosilylation of F-IV using TMSCN and TEA can give nitrile F-V. Reduction of F-V with borane followed by quenching with HCl can give a diastereomeric mixture of amino alcohol HCl salts, F-VI. Equilibration of the isomeric mixture can be promoted by heating with an alkoxide base, such as t-BuONa, in THF/t-BuOH to enrich the mixture in the s,s isomer. Once the thermodynamic ratio is reached, the mixture can undergo reaction with $Boc_2O$, and the resulting product can be triturated with EtOAc/n-heptane to provide the stereochemically pure hydroxy carbamate (s,s)-F-VII. Removal of the Boc group under acidic conditions, such as ethanolic HCl, can give amine salt (s,s)-F-VI.

Scheme 8

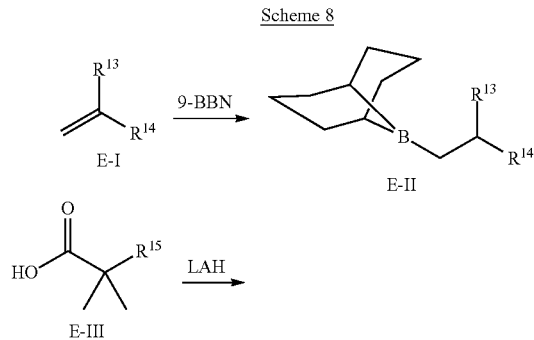

Scheme 9

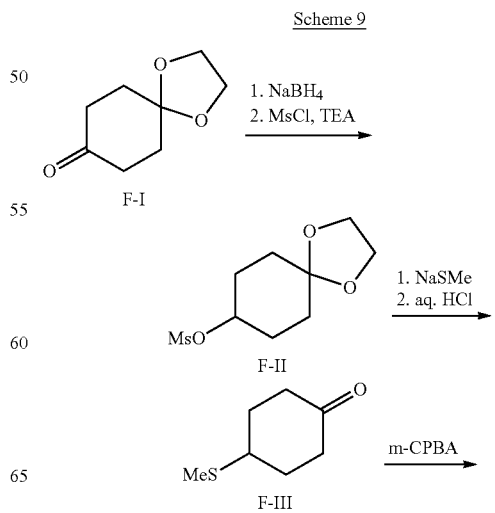

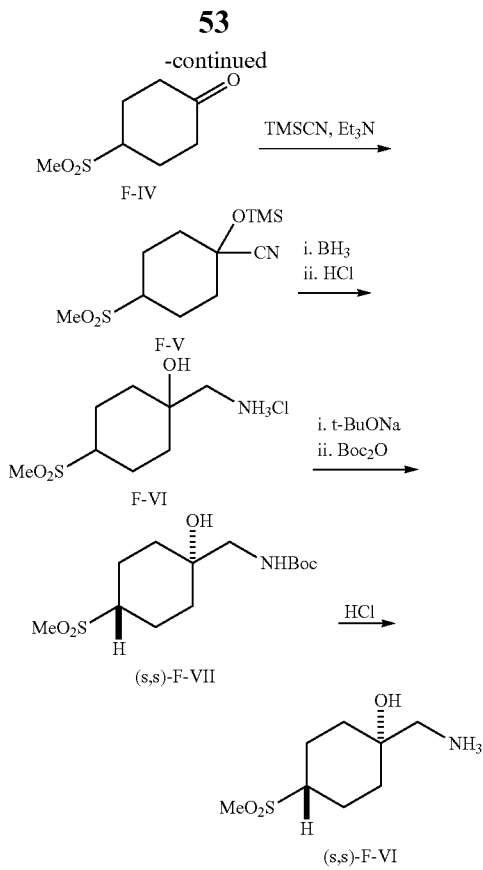

(1r,4r)-1-(Aminomethyl)-4-(methylsulfonyl)cyclohexan-1-ol hydrochloride ((r,r)-F-VI) can be prepared according to Scheme 10. Ketone cyanation of cyclohexanone sulfone F-IV using a reagent combination such as benzoyl cyanide and DBU can give nitrile G-I. Reduction of G-I using LAH in an ethereal solvent can give an amino alcohol intermediate. Reaction of this intermediate with Boc₂O, followed chromatographic separation of the hydroxy carbamate product diastereomers gives (r,r)-F-VII. Removal of the Boc group under acidic conditions, such as those of TFA in DCM, followed by salt metathesis using HCl gives amino alcohol salt (r,r)-F-VI.

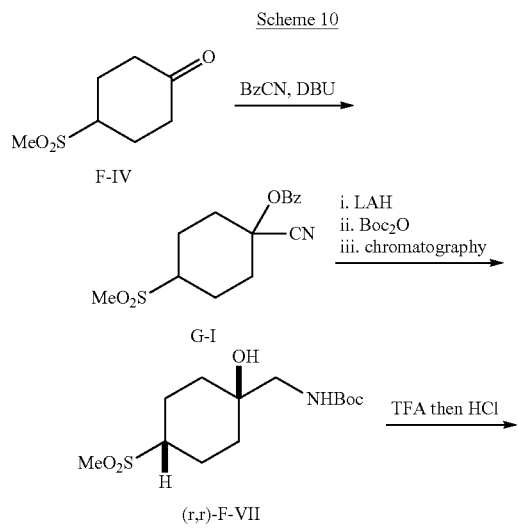

((1r,4r)-4-(Methylsulfonyl)cyclohexyl)methanamine hydrochloride (trans-H-III HCl) can be prepared according to Scheme 11. Reductive cyanation of cyclohexanone sulfide F-III using TosMIC with an alkoxide base, such as t-BuONa, in an ethereal solvent can give cyanocyclohexane sulfide H-I. Oxidation of H-I with a reagent system such as Oxone® in acetone/water can give cyanocyclohexane sulfone H-II. Reduction of H-II with LAH in an ethereal solvent can give amine H-III as a mixture of cis and trans isomers. The corresponding Boc carbamate intermediate, H-IV, can be prepared if H-III is not isolated, but instead Boc₂O is added to the solution generated after quenching and filtering the LAH reduction reaction mixture. Isolation of H-IV followed by sequential triturations using IPA/n-heptanes and then EtOAc/n-heptanes can provide stereochemically pure trans-H-IV. Removal of the Boc group under acidic conditions, such as ethanolic HCl, can give amine salt trans-H-III·HCl.

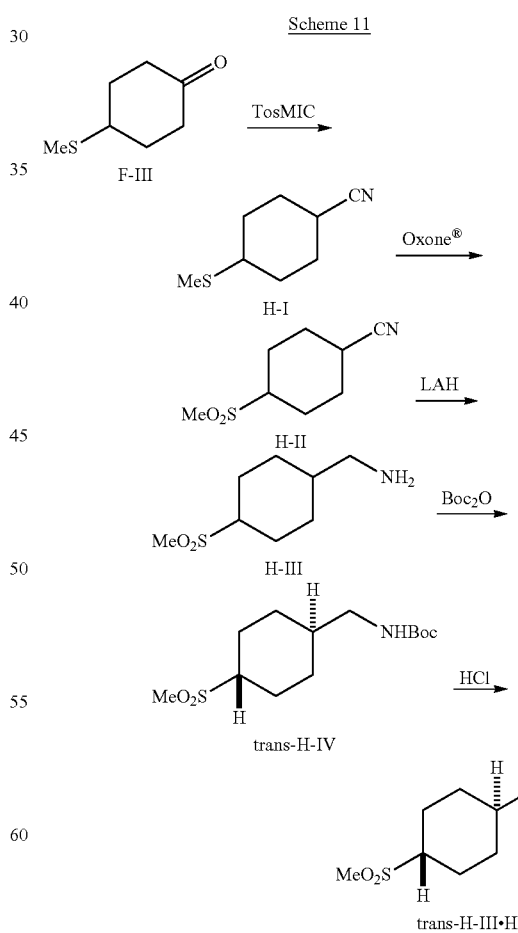

(1R*,2R*,4R*)-1-(Aminomethyl)-4-(methylsulfonyl)cyclohexane-1,2-diol hydrochloride ((1R*,2R*,4R*)—I—III)

and (1S*,2S*,4S*)-1-(aminomethyl)-4-(methylsulfonyl)cyclohexane-1,2-diol hydrochloride ((1S*,2S*,4S*)-I-III) can be prepared according to Scheme 12. Reaction between cyclohexanone sulfone F-IV and nitromethane catalyzed by DMEN can give nitro cyclohexene I-I. Reduction of I-I using zinc metal in AcOH, followed by reaction of the resulting amine salt intermediate with Boc$_2$O in a solvent mixture containing THF and aqueous NaHCO$_3$ can give cyclohexene carbamate I-II. Dihydroxylation of I-II using a catalyst such as K$_2$OsO$_4$.2H$_2$O and a terminal reductant such as NMO in acetone/water can give a diol intermediate, which can undergo TFA-promoted cleavage of the Boc group, followed by treatment with HCl to give amino diol HCl salt (1RS,2RS)-I-III as a mixture of C4 epimers. Equilibration of the isomeric mixture can be promoted by heating with an alkoxide base, such as t-BuOK, in t-BuOH to enrich the mixture in the 1RS,2RS,4RS isomer. Reaction of this equilibrated mixture with CbzCl in aqueous NaHCO$_3$ solution, followed by trituration of the product with EtOAc/hexanes can give (1RS,2RS,4RS)-I-IV as a single diastereomer. Resolution of (1RS,2RS,4RS)-I-IV by SFC using a chiral stationary phase can give (1R*,2R*,4R*)-I-IV and (1S*,2S*,4S*)-I-IV in stereochemically pure form. Hydrogenolysis of the Cbz carbamates with hydrogen gas using a catalyst such as Pd/C, followed by treatment of the resulting amines with HCl can give amino diol salts (1R*,2R*,4R*)-I-III and (1S*,2S*,4S*)-I-III.

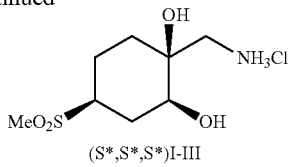

(S*,S*,S*)-I-III (1s,4s)-4-(Aminomethyl)-4-hydroxycyclohexane-1-sulfonamide hydrochloride ((s,s)-J-VIII) can be prepared according to Scheme 13. Treatment of cyclohexanol J-I with iodine, PPh3, and imidazole can give iodocyclohexane J-II. Treatment of J-II with Rieke® zinc, followed by reaction of the resulting organozinc intermediate with DABSO can give zinc sulfinate J-III. Treatment of a DCM suspension of J-III with NCS, followed by addition of tert-butylamine can give t-butylsulfonamide J-IV. Hydrolytic cleavage of the 1,3-dioxolane group of J-IV under weakly acidic conditions, such as those of a AcOH/water/1,4-dioxane solvent mixture, and heating can give cyclohexanone sulfonamide J-V. Cyanosilylation of J-V using TMSCN and a catalytic amount of ZnI$_2$ can give nitrile J-VI. Reduction of J-VI using an ethereal solution of LAH, followed by treatment of the ensuing amine intermediate with TFA can give a primary sulfonamide amine salt intermediate. This salt can be converted to the corresponding free base, which can then undergo reaction with Boc$_2$O to give hydroxy carbamate J-VII. After chromatographic separation of the diastereomers, the s,s isomer can be treated with TFA and then HCl to afford amino alcohol sulfonamide (s,s)-J-VIII.

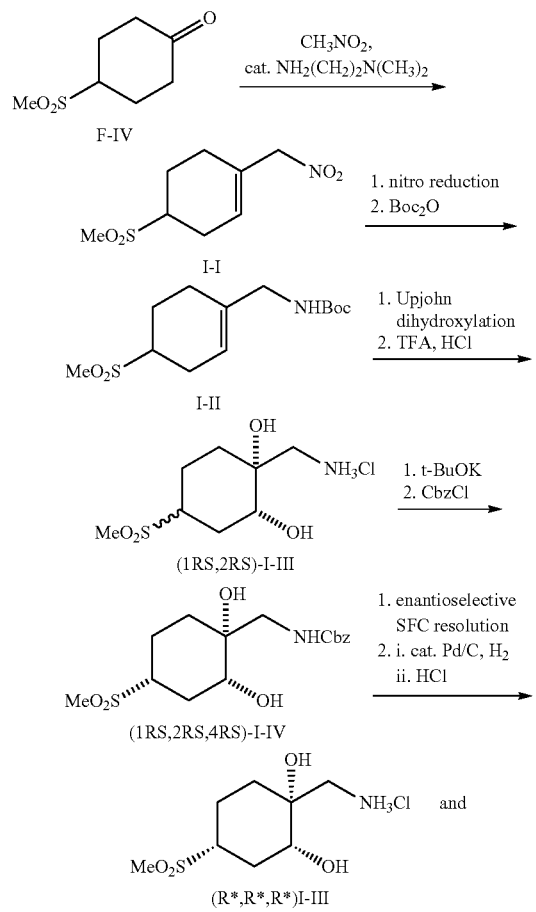

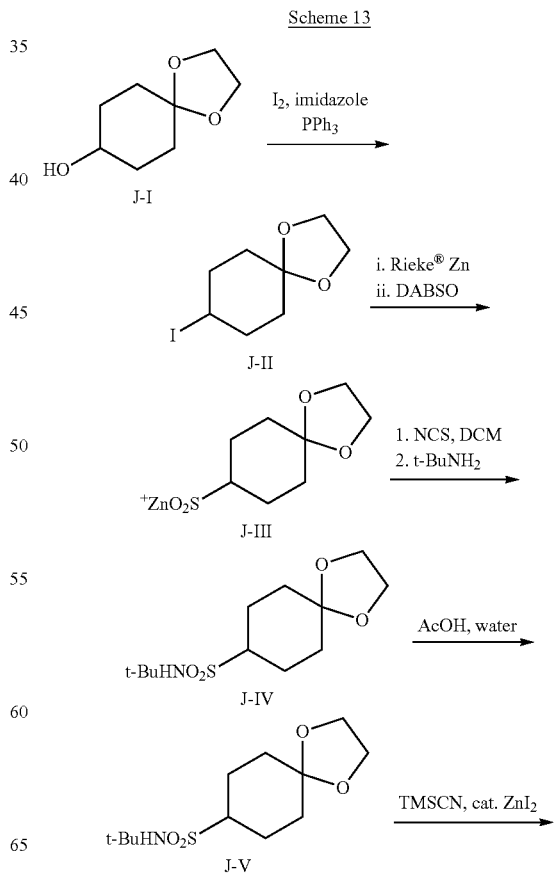

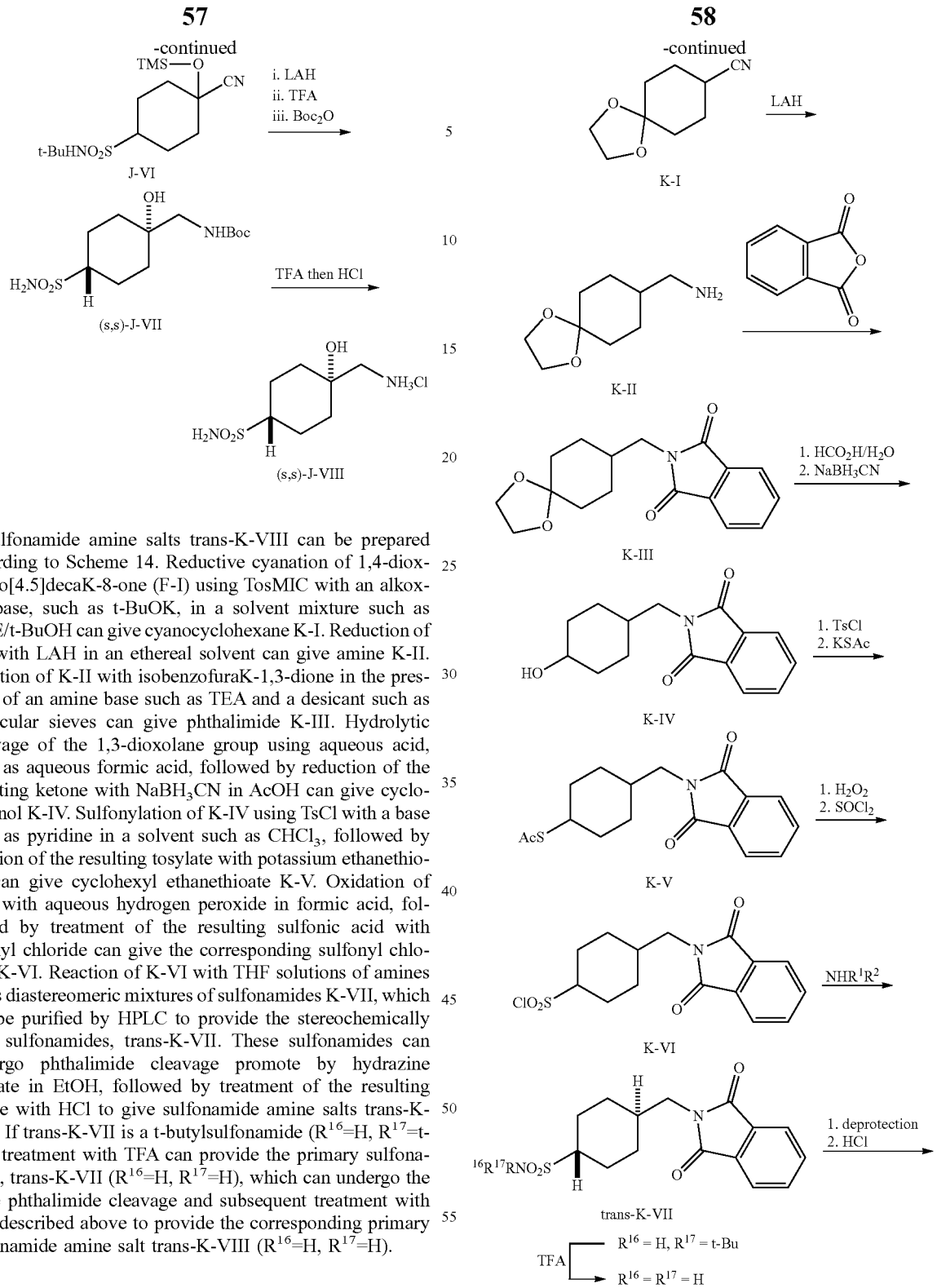

Sulfonamide amine salts trans-K-VIII can be prepared according to Scheme 14. Reductive cyanation of 1,4-dioxaspiro[4.5]decaK-8-one (F-I) using TosMIC with an alkoxide base, such as t-BuOK, in a solvent mixture such as DME/t-BuOH can give cyanocyclohexane K-I. Reduction of K-I with LAH in an ethereal solvent can give amine K-II. Reaction of K-II with isobenzofuraK-1,3-dione in the presence of an amine base such as TEA and a desiccant such as molecular sieves can give phthalimide K-III. Hydrolytic cleavage of the 1,3-dioxolane group using aqueous acid, such as aqueous formic acid, followed by reduction of the resulting ketone with NaBH$_3$CN in AcOH can give cyclohexanol K-IV. Sulfonylation of K-IV using TsCl with a base such as pyridine in a solvent such as CHCl$_3$, followed by reaction of the resulting tosylate with potassium ethanethioate can give cyclohexyl ethanethioate K-V. Oxidation of K-V with aqueous hydrogen peroxide in formic acid, followed by treatment of the resulting sulfonic acid with thionyl chloride can give the corresponding sulfonyl chloride K-VI. Reaction of K-VI with THF solutions of amines gives diastereomeric mixtures of sulfonamides K-VII, which can be purified by HPLC to provide the stereochemically pure sulfonamides, trans-K-VII. These sulfonamides can undergo phthalimide cleavage promote by hydrazine hydrate in EtOH, followed by treatment of the resulting amine with HCl to give sulfonamide amine salts trans-K-VIII. If trans-K-VII is a t-butylsulfonamide ($R^{16}$=H, $R^{17}$=t-Bu), treatment with TFA can provide the primary sulfonamide, trans-K-VII ($R^{16}$=H, $R^{17}$=H), which can undergo the same phthalimide cleavage and subsequent treatment with HCl described above to provide the corresponding primary sulfonamide amine salt trans-K-VIII ($R^{16}$=H, $R^{17}$=H).

Scheme 14

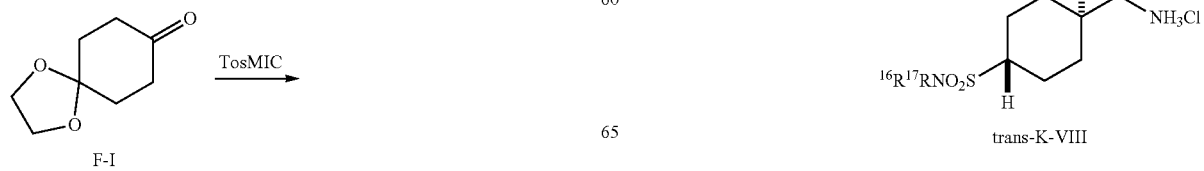

5-(Methylsulfonyl)tetrahydro-2H-pyran-2-yl)methanamine hydrochlorides (L-L_VI) can be prepared according to Scheme 15. Dihydropyran amine L-I can undergo reaction with Boc₂O to give dihydropyrane carbamate L-II. Sequential hydroboration and oxidation of this vinyl ether in THF using first BH₃.THF complex and then aqueous hydrogen peroxide and sodium hydroxide can give alcohol cis-L-III after chromatographic separation of the product diastereomers. Mitsunobu reaction of cis-L-III with thioacetic acid using an azodicarboxylate reagent such as DIAD and triphenylphosphine in an ethereal solvent can give cyclohexyl ethanethioate trans-L-IV. One-pot hydrolysis of this thioester using aqueous hydroxide, followed by methylation of the resulting thiol with iodomethane can give thioether trans-L-V. Oxidation of trans-L-V with an oxidant such as mCPBA, followed by treatment of the resulting sulfone with TFA and then HCl gives tetrahydropyran amine salt trans-L-VI. The cis diastereomer, cis-L-VI, can be prepared by reaction of L-II with thioacetic acid promoted by a radical initiator such as AIBN to give cis-L-IV. The same hydrolysis/methylation/oxidation/Boc-cleavage sequence described above for transforming trans-L-IV to trans-L-VI can be used to transform cis-L-IV to cis-L-VI.

Scheme 15

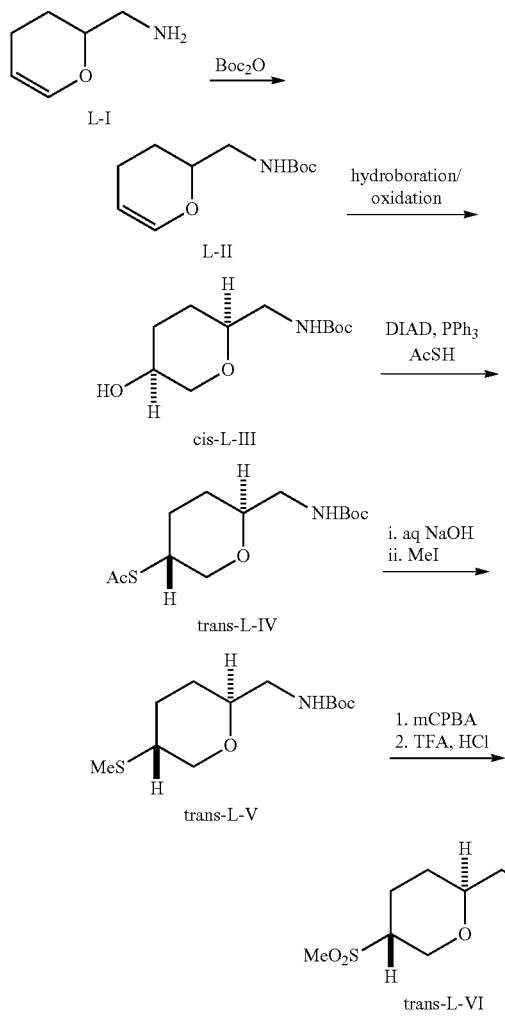

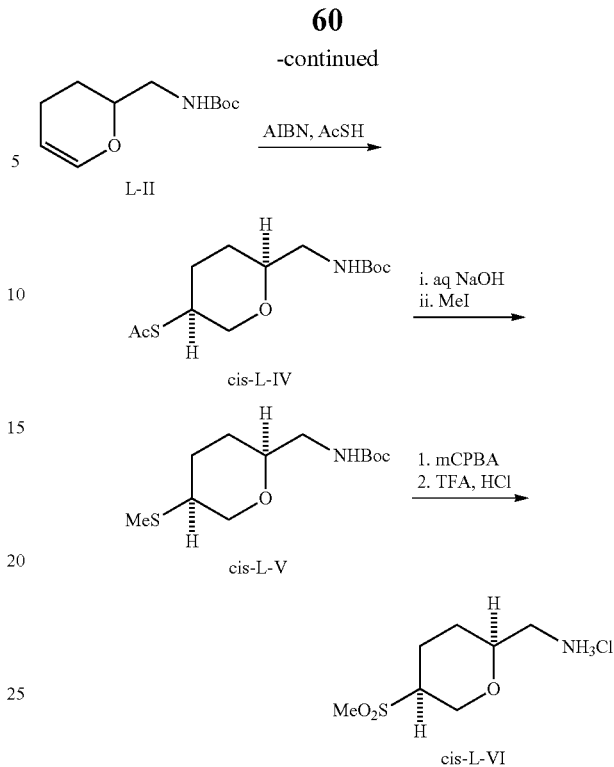

1-(Aminomethyl)-4-(methylsulfonyl)cyclohexane-1-carbonitrile hydrochlorides M-VII can be prepared according Scheme 16. Conjugate addition of sodium methanesulfinate to 5,6-dihydro-2h-pyran-2-one (M-I) promoted by an organic acid, such as AcOH, in MeCN can give lactone sulfone M-II. Reduction of this lactone with LAH in an ethereal solvent, followed by transformation of the resulting diol to the corresponding dibromide using PBr₃ can give M-III. Reaction of M-III with a cyanoacetate promoted by a carbonate base, such as Cs₂CO₃, in DMF can give cyclohexane M-IV (R=alkyl). Treatment of M-IV with LAH in an ethereal solvent, followed by reaction of the resulting amino alcohol with Boc₂O can give carbamate alcohol M-V. Swern oxidation of this alcohol, followed by separation of the diastereomers by silica gel chromatography can give both aldehydes, (r*,r*)-M-VI and (s*,s*)-M-VI. Conversion of the aldehydes to the corresponding nitriles by treatment with a combination of reagents such as hydroxylamine*HCl, TEA, and T3P in DMF, followed by treatment of the nitrile intermediates with TFA and then HCl can give amino nitriles (r*,r*)-M-VII and (s*,s*)-M-VII.

Scheme 16

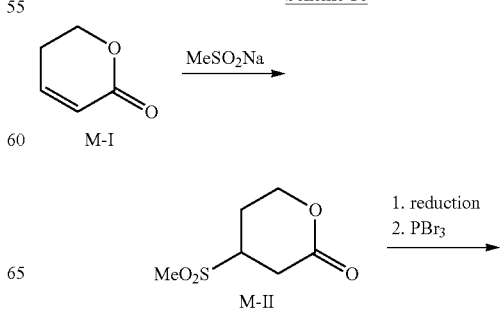

Scheme 17

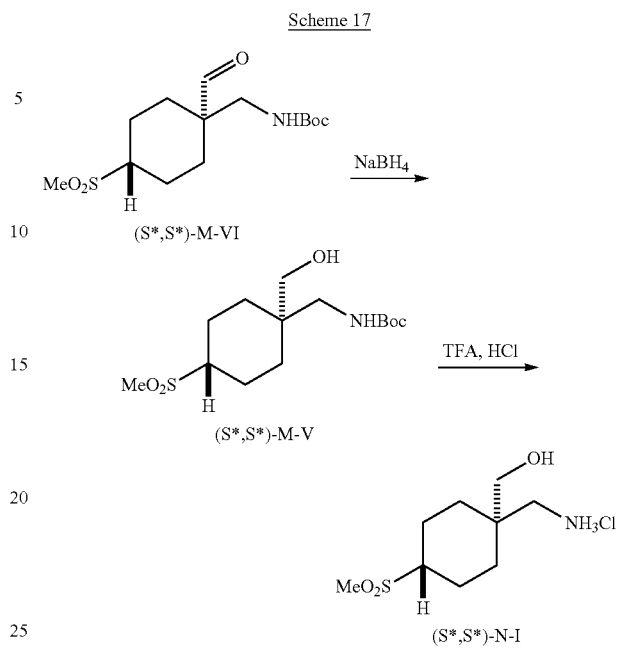

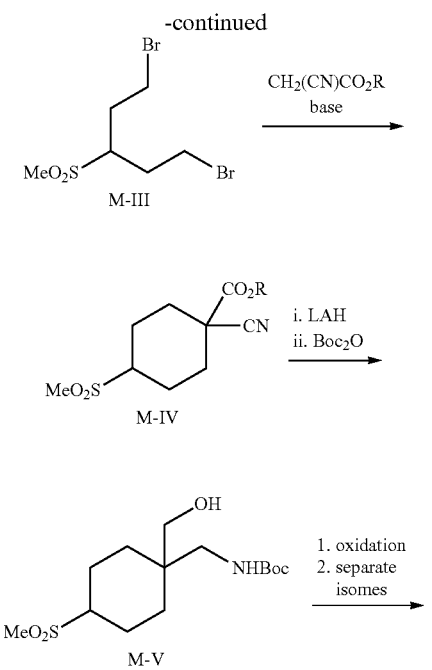

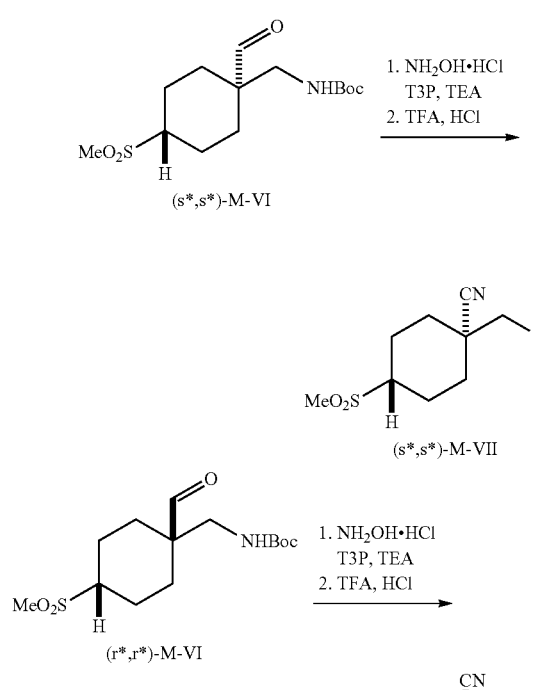

((1s*,4s*)-1-(Aminomethyl)-4-(methylsulfonyl)cyclohexyl)methanol hydrochloride ((s*,s*)-N-I) can be prepared according Scheme 17. Aldehyde (s*,s*)-M-VI can be reduced with NaBH₄ in MeOH to give carbamate alcohol (s*,s*)-M-V. Treatment of (s*,s*)-M-V with TFA and then HCl gives amino alcohol salt (s*,s*)-N-I.

(1RS,2SR,5RS)-2-(Aminomethyl)-5-(methylsulfonyl)cyclohexan-1-ol hydrochloride (O-II) can be prepared according Scheme 18. Sequential hydroboration and oxidation of cyclohexene carbamate I-II in THF using first BH3.THF complex and then aqueous hydrogen peroxide and sodium hydroxide can give secondary alcohol O-I after chromatographic separation of the product diastereomers. Treatment of O-I with TFA and then HCl can give amino alcohol salt O-II.

Scheme 18

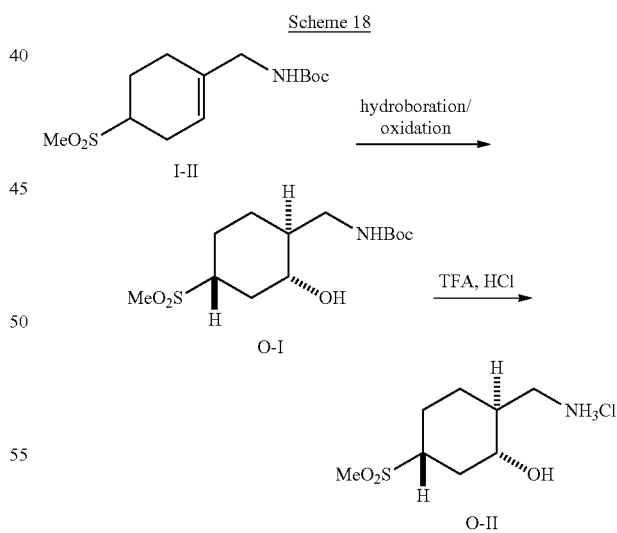

((1r,4r)-4-(Ethylsulfonyl)cyclohexyl)methanamine hydrochloride (P-P-VI) can be prepared according Scheme 19. Cyclohexane mesylate F-II can undergo reaction with sodium ethanethiolate in DMF to give thioether P-I. Hydrolytic cleavage of the 1,3-dioxolane group of P-I promoted by acid, such as HCl or TsOH, in aqueous medium gives cyclohexanone sulfide P-II. Reductive cyanation of P-II using TosMIC with a base such as t-BuONa or t-BuOK in ethereal solvent can give trans cyanocyclohexane sulfide P-III after separation of the product diastereomers by silica gel chromatography. Oxidation of P-III using a reagent system such as Oxone® in acetone/water can give cyanocyclohexane sulfone P-IV. Reduction of P-IV with nickel boride in MeOH and trapping the resulting amine intermediate in situ with Boc₂O can give carbamate P-V. Treatment of P-V with ethanolic HCl can give cyclohexylsulfone amine salt P-VI.

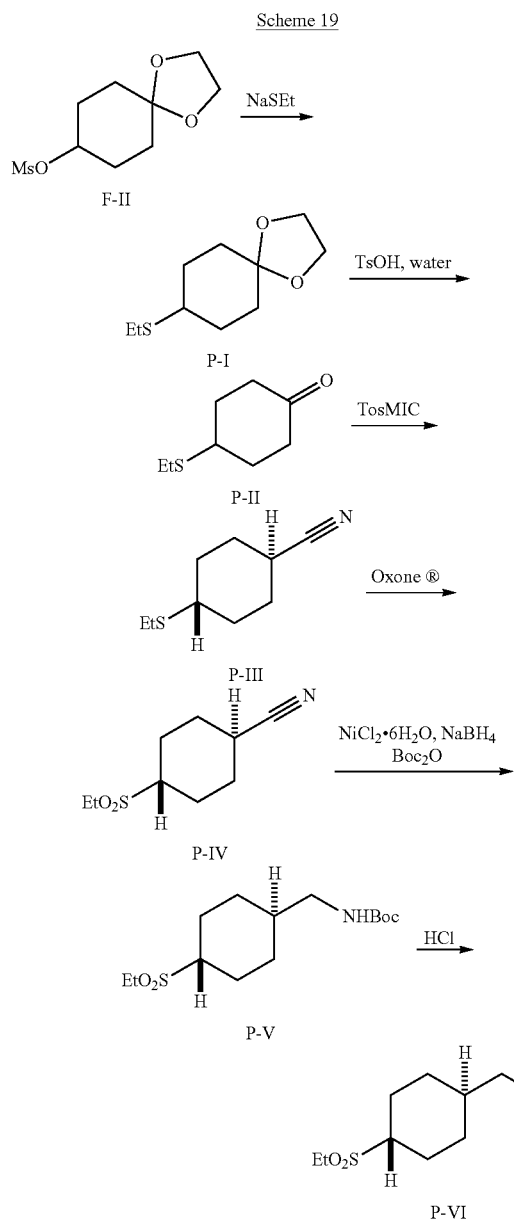

(S)-N-(1-(Aminomethyl)-4-(methylsulfonyl)cyclohexyl)-2-methylpropane-2-sulfinamides (Q-Q-IV) can be prepared according Scheme 20. Condensation of (S)-tert-butylsulfinamide with cyclohexanone sulfone F-IV promoted by a dehydrating agent such as Ti(Oi-Pr)₄ can give sulfinimine Q-I. Cyanation of Q-I with a reagent such as Et₂AlCN can give cyano sulfinamide Q-II. Reduction of Q-II with alane, followed by reaction of the resulting amine with CbzCl in a biphasic toluene/aqueous NaOH mixture can give carbamate Q-III as a mixture of diastereomers. The s,R and r,S isomers can be separated by silica gel chromatography. Hydrogenolysis of each Q-III diastereomer in an alcoholic solvent using hydrogen gas and a catalyst such as Pd/C can give (s,R)-Q-IV and (r,S)-Q-IV.

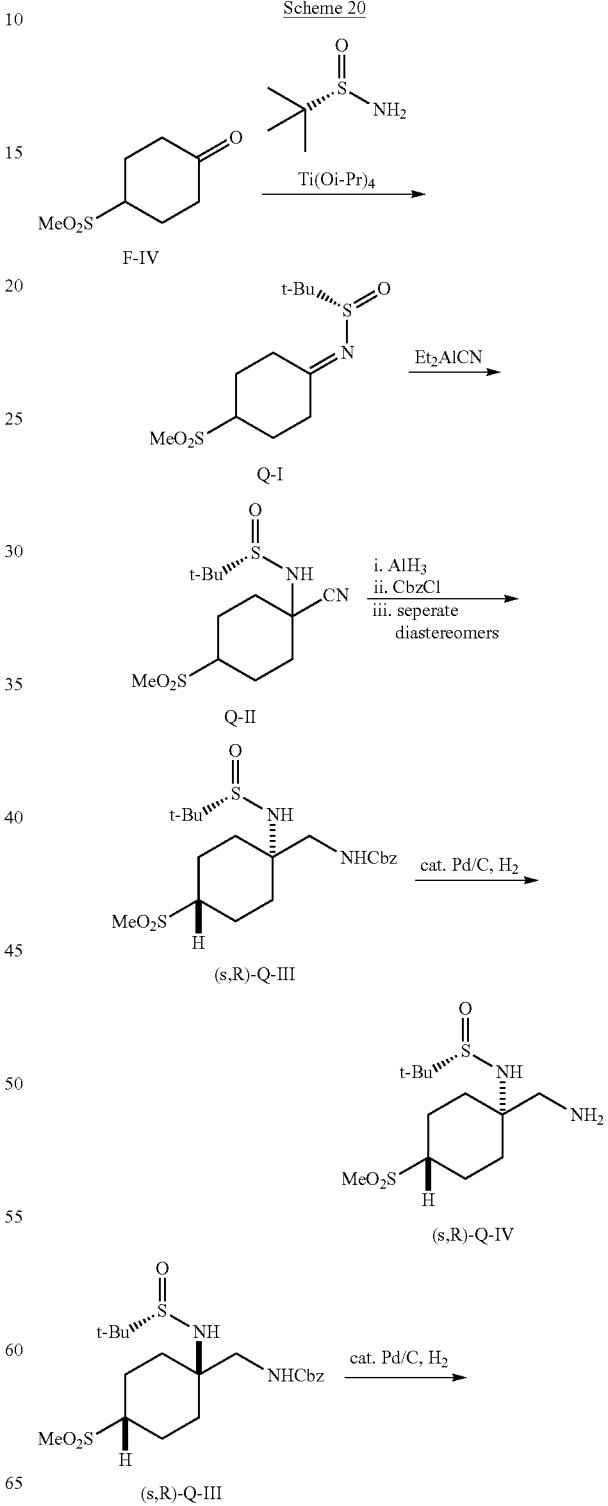

-continued

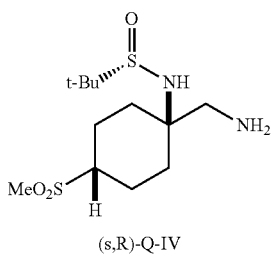

(s,R)-Q-IV

Benzyl ((1RS,2RS, 5RS)-2-(aminomethyl)-2-hydroxy-5-(methylsulfonyl)cyclohexyl)carbamate hydrochloride (R-II) can be prepared according to Scheme 21. Sharpless aminohydroxylation of cyclohexene carbamate I-II can be carried out using benzyl carbamate, t-BuOCl, and a catalytic amount of $K_2OsO_4 \cdot 2H_2O$ in t-BuOH/water to give dicarbamate alcohol R-I as a single diastereomer after silica gel chromatography. Treatment of R-I with TFA and then HCl can give amino alcohol salt R-II.

Scheme 21

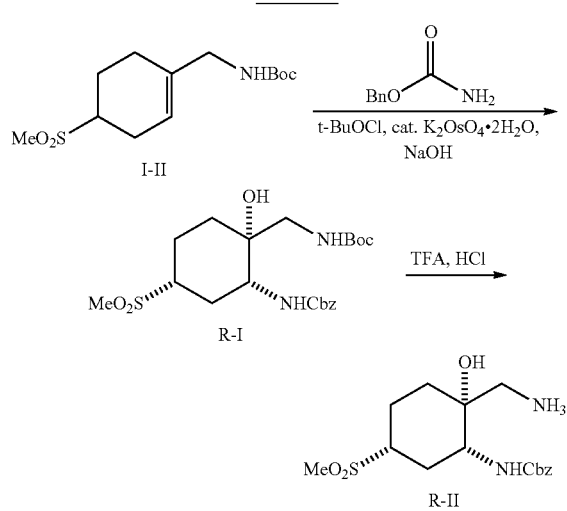

The compounds of Formula I in the present invention can be prepared according to Scheme 22. Flow hydrogenation of pyridine carbamate S-I can be accomplished by passing an EtOH solution of S-I over a Pt/C catalyst bed under pressure of hydrogen gas. Reaction of the resulting piperidine intermediate with CbzCl in a biphasic toluene/aqueous NaOH mixture can give piperidine dicarbamate S-II, which can be isolated as the trans diastereomer after silica gel chromatography. Treatment of S-II with TFA and then HCl can give piperidine methylamine salt S-II. Amide coupling reaction between amine salt S-III and carboxylic acids A-III promoted by a reagent such as HATU or EDCI and a base such as DIPEA can give amides of Formula I ($R^1$=Me, $R^3$=H, Q=NCbz). Resolution of these isomers by SFC on a chiral stationary phase, followed by cleavage of the Cbz group using HBr in AcOH can give amides of Formula I ($R^1$=Me, $R^3$=H, Q=$NH_2Br$). Reaction of these amine salts with electrophiles such as acid anhydrides or alkyl halides can give amides of Formula I ($R^1$=Me, $R^3$=H, Q=$NR^{18}$; $R^{18}$=alkyl or acyl).

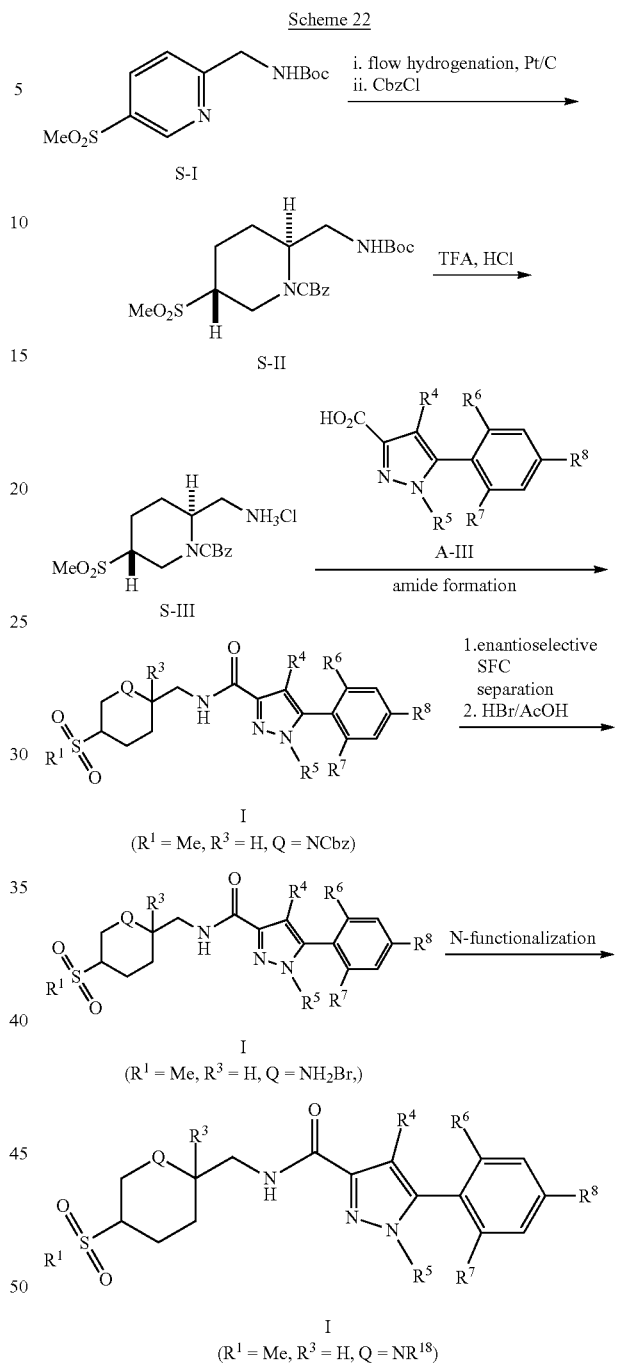

The compounds of Formula I in the present invention can be prepared according to Scheme 23. The diastereomeric mixture of nitrile esters T-I can be separated by silica gel chromatography to give (r,r)-T-I and (s,s)-T-I, which can each be elaborated separately. Raney® nickel-promoted hydrogenation of T-I using hydrogen gas and alcoholic solvent can give amine T-II. Amide coupling reaction between amine T-II and carboxylic acids A-III promoted by a reagent such as HATU or EDCI and a base such as DIPEA can give amides of Formula I ($R^1$=Me, $R^3$=$CO_2Et$, Q=$CH_2$). Hydrolysis of the ester can give amide of Formula I ($R^1$=Me, $R^3$=$CO_2H$, Q=$CH_2$).

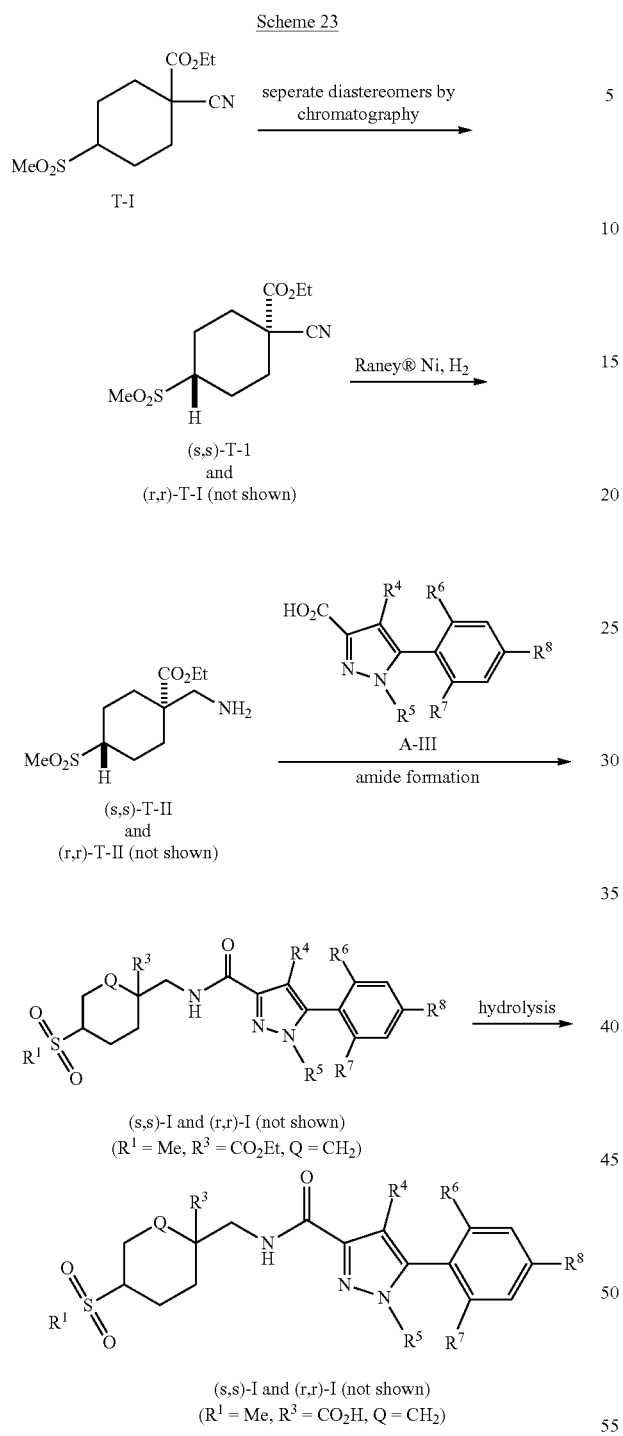

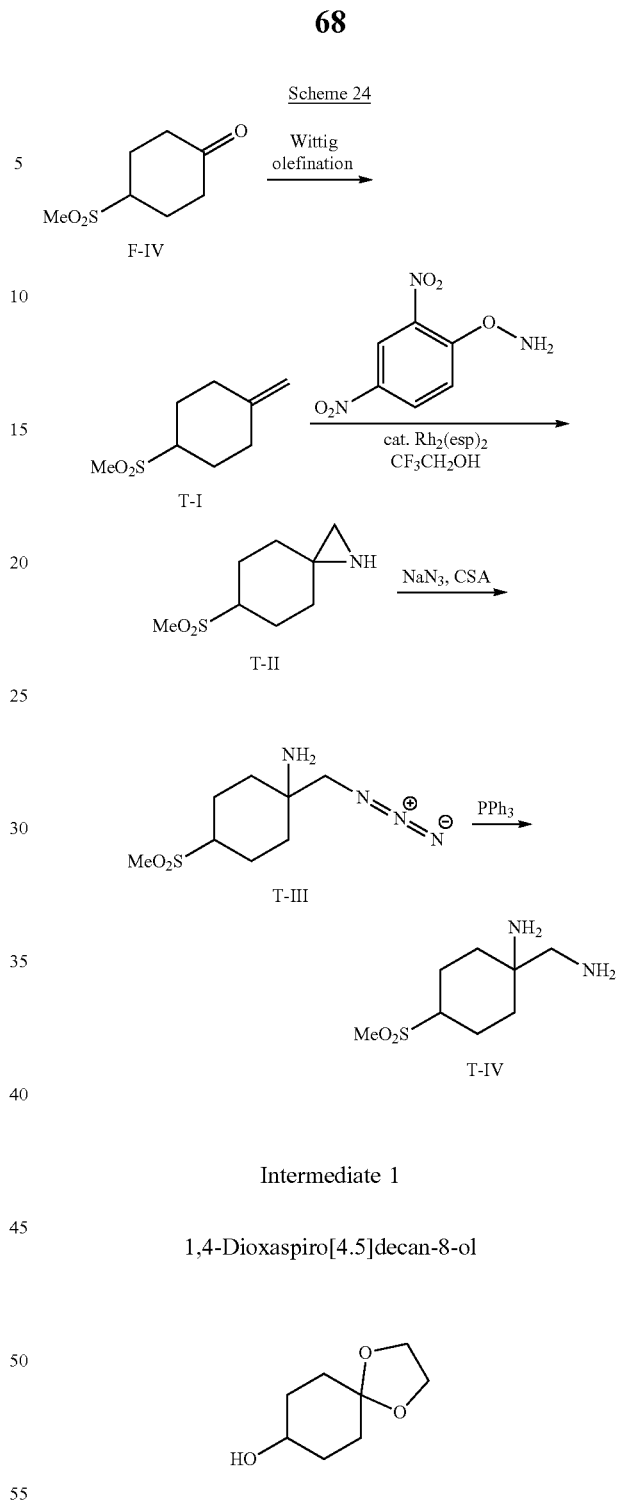

Intermediate 1

1,4-Dioxaspiro[4.5]decan-8-ol 1-(Aminomethyl)-4-(methylsulfonyl)cyclohexan-1-amine (T-IV) can be prepared according to Scheme 24. Cyclohexanone sulfone F-IV can undergo Wittig olefination using methyltriphenylphosphonium bromide and an alkoxide base such as KOt-Bu in an ethereal solvent to give methylidene T-I. Rhodium-catalyzed aziridination of T-I using O-(2,4-dinitrophenyl)hydroxylamine in trifluoroethanol can give aziridine T-II. Reaction of T-II and sodium azide promoted by CSA can give amino azide T-III. Reduction of T-III with triphenylphosphine can give diamine T-IV.

Sodium borohydride (83.4 g, 2.21 mol) was added in portions over 2 h to a stirring 0-5° C. solution of 1,4-dioxaspiro[4.5]decan-8-one (1150 g, 7.372 mol) and MeOH (7.0 L) at a rate that maintained the internal temperature below 5° C. After the reaction went to completion, water was added, and the mixture was concentrated. The residue was then diluted with DCM and water, the layers were separated, and the aqueous layer was extracted twice with DCM. The organic layers were combined, washed with brine, dried with anhydrous $Na_2SO_4$, filtered, and then concentrated to afford the title compound as a colorless liquid (65.9% w/w).

Intermediate 2

1,4-Dioxaspiro[4.5]decan-8-yl Methanesulfonate

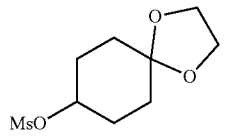

Methanesulfonyl chloride (1000 g, 8.790 mol) was added dropwise to a stirring solution of 1,4-dioxaspiro[4.5]decan-8-ol (1722 g, 65.9% w/w, 7.17 mol, Intermediate 1) and TEA (2178 g, 21.52 mol) in DCM (10 L) at a rate that maintained the internal temperature between 10 and 20° C. After the reaction went to completion, it was combined with another mixture prepared in a similar way. The combined mixture was washed with water and then concentrated. The residue was slurried in n-heptane and EtOH (10:1 v/v) at room temperature, and the suspension was filtered. The filter cake was dried under vacuum to afford the title compound as a yellow solid.

Intermediate 3

8-(Methylthio)-1,4-dioxaspiro[4.5]decane

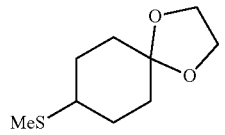 [SMILES: CSC1CCC2(CC1)OCCO2]

Sodium thiomethoxide (249 g, 3.56 mol) was added in five portions to a stirring 0-5° C. solution of 1,4-dioxaspiro[4.5]decan-8-yl methanesulfonate (800 g, 3.39 mol, Intermediate 2) in DMF (4.8 L), and the reaction mixture was allowed to warm to 15-20° C. over 24 h. An additional portion of NaSMe (23.7 g, 0.339 mol) was then added, and stirring was continued until the reaction went to completion. Water and MTBE were then added, and the layers were separated. The organic layer was washed three times with water, concentrated, and then dried under vacuum to afford the title compound as a yellow oil.

Intermediate 4

4-(Methylthio)cyclohexan-1-one

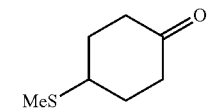

A mixture of 8-(methylthio)-1,4-dioxaspiro[4.5]decane (680 g, 3.61 mol, Intermediate 3), i-PrOAc (6.8 L), and 3 N aqueous HCl (680 mL) was stirred at 20-25° C. for 30 min. After this time, the layers were separated. The organic layer was treated with a 3 N aqueous HCl (680 mL) as described in the process above eight additional times. During the final washing, the mixture was stirred for 1 h. The organic layer was then concentrated to afford the title compound as a yellow oil.

Intermediate 5

4-(Methylsulfonyl)cyclohexan-1-one

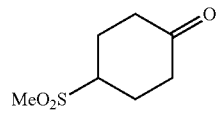

m-Chloroperbenzoic acid (1151 g, 85% w/w, 5.668 mol) was added in portions to a stirring −5 to 5° C. solution of 4-(methylthio)cyclohexan-1-one (545 g, 3.78 mol, Intermediate 4) in DCM (11 L) at a rate that maintained the internal temperature below 5° C. After the addition was complete, stirring was continued for 45 min before an additional portion of mCPBA (231 g, 85% w/w, 1.13 mol) was added, and stirring was continued for 30 min. A third portion of mCPBA (76.9 g, 85% w/w, 0.378 mol) was added, and stirring was continued at −5 to 5° C. for 30 min. The reaction mixture was then filtered. The filter cake was rinsed with DCM, and the filtrate and rinse were combined and then concentrated. The concentrate was then diluted with MTBE and stirred at 50° C. for 1 h before it was allowed to cool to rt and stir for 16 h. The slurry was then filtered, and the filter cake was rinsed with MTBE and dried under vacuum to afford the title compound as a colorless solid.

Intermediate 6

4-(Methylsulfonyl)-1-((trimethylsilyl)oxy)cyclohexane-1-carbonitrile

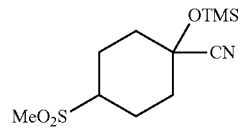

Trimethylsilyl cyanide (410 g, 4.13 mol) was added dropwise to a stirring solution of 4-(methylsulfonyl)cyclohexan-1-one (560 g, 3.18 mol, Intermediate 5) and TEA (113 g, 1.11 mol) in DCM (5.6 L) at a rate that maintained an internal temperature of 25-30° C., and the resulting mixture was stirred for 30 min. After this time, a saturated aqueous NaHCO₃ solution was added, and the layers were separated. The organic layer was washed with brine and then concentrated. The residual DCM was then removed by two cycles of sequential dilution with n-heptane and concentration. The concentrate was then stirred as a slurry in n-heptane at rt for 16 h before it was filtered. The filter cake was rinsed with n-heptane and then dried under vacuum to afford the title compound as a colorless solid.

Intermediate 7

1-(Aminomethyl)-4-(methylsulfonyl)cyclohexan-1-ol Hydrochloride

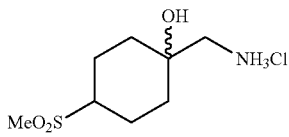

Borane (1.74 L, 1.0 M in THF, 1.74 mol) was added dropwise to a stirring 60° C. solution of 4-(methylsulfonyl)-1-((trimethylsilyl)oxy)cyclohexane-1-carbonitrile (400 g, 1.45 mol, Intermediate 6) in THF (1.6 L), and the solution was stirred until the reaction went to completion. The solution was then cooled in an ice-water bath and quenched by carefully adding MeOH. After the quench was completed, the mixture was acidified with 33% ethanolic HCl solution (200 mL) and stirred for 30 min. The mixture was then filtered, and the filter cake was rinsed with MTBE and then dried under vacuum to afford the title compound as a colorless solid.

Intermediate 8 tert-Butyl (((1s,4s)-1-hydroxy-4-(methylsulfonyl)cyclohexyl)methyl)carbamate

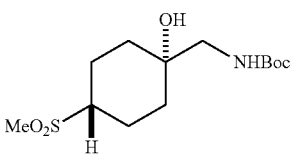 [SMILES: CC(C)(C)OC(=O)NC[C@]1(O)CC[C@@H](S(C)(=O)=O)CC1]

Sodium tert-butoxide (118 g, 1.05 mol) was added in portions to a stirring solution of 1-(aminomethyl)-4-(methylsulfonyl)cyclohexan-1-ol hydrochloride (170 g, 0.70 mol, Intermediate 7) in t-BuOH (850 mL) and THF (850 mL) at rt. The resulting mixture was then heated to 60° C. and stirred until the cis and trans isomers reached equilibrium as judged by HPLC analysis. The reaction mixture was then allowed to cool to rt before 3 N aqueous HCl (70 mL, 0.21 mol) was added. A solution of Boc₂O (159 g, 0.728 mol) in THF (510 mL) was then added dropwise at rt, and the mixture was stirred until the reaction went to completion. The resulting mixture was combined with another mixture prepared in a similar way on a similar scale. The combined mixture was filtered, and the filter cake was washed with DCM. The filtrate and wash were combined and then concentrated to afford an off-white solid, which was stirred as a slurry in EtOAc/n-heptane (0.8 L, 1:1 v/v) at 60° C. for 1 h. The suspension was allowed to cool and then filtered. The filter cake was rinsed with EtOAc/n-heptane (1:1 v/v) and then dried under vacuum to afford the title compound as a colorless solid.

Intermediate 9

(1s,4s)-1-(Aminomethyl)-4-(methylsulfonyl)cyclohexan-1-ol Hydrochloride

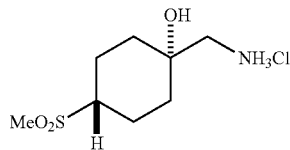

Ethanolic HCl (0.9 L, 33 wt %) was added dropwise to a solution of tert-butyl (((1s,4s)-1-hydroxy-4-(methylsulfonyl)cyclohexyl)methyl)carbamate (290 g, 0.94 mol, Intermediate 8) in EtOH (0.9 L), and the mixture was stirred at rt. After the reaction went to completion, the suspension was filtered, and the filter cake was rinsed with EtOH. The filter cake was then stirred as a slurry in EtOH at reflux temperature for 2 h before it was allowed to cool to rt. The suspension was then filtered, and the filter cake was washed three times with EtOH. The filter cake was then dried at under vacuum at 50° C. the title compound as a colorless solid.

Intermediate 10

4-(Methylthio)cyclohexane-1-carbonitrile

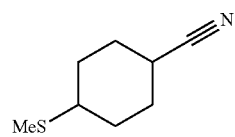

Sodium tert-butoxide (655 g, 5.82 mol) was added in portions to a stirring −38° C. mixture of 4-(methylthio)cyclohexan-1-one (350 g, 2.43 mol, Intermediate 4), TosMIC (616 g, 3.15 mol) and EtOH (263 mL, 4.50 mol) in MTBE (7.0 L) at a rate that maintained the internal temperature between −40 and −35° C., and the resulting mixture was stirred for 1 h. After this time, the mixture was allowed to warm to 3° C., and then it was filtered. The filter cake was washed with water, and the layers of the filtrate were separated. The filter cake was then suspended in aqueous layer, and the resulting mixture was filtered. The filter cake was washed with MTBE. Then the layers of the combined filtrate and wash were separated, and the aqueous layer was extracted with MTBE. The organic layers were combined, washed with water, washed with brine, and then concentrated. The concentrate was purified by vacuum distillation to afford the title compound as a light yellow oil.

Intermediate 11

4-(Methylsulfonyl)cyclohexane-1-carbonitrile

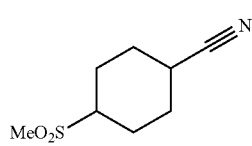 [SMILES: CS(=O)(=O)C1CCC(C#N)CC1]

Oxone (2238 g, 3.640 mol) was added to a stirring −10° C. mixture of 4-(methylthio)cyclohexane-1-carbonitrile (255 g, 1.64 mol, Intermediate 10), acetone (2.5 L), and water (2.5 L) over 45 min at a rate that maintained the internal temperature below 2° C., and the resulting mixture was stirred for 40 min. The reaction mixture was then filtered, and the filter cake was washed with acetone. The filtrate was concentrated to remove most of acetone, and the residue was extracted with five times with EtOAc. The organic layers were combined, dried over anhydrous Na₂SO₄, filtered, and concentrated to afford a colorless solid. This solid was stirred as a slurry in n-heptane at rt overnight, and then the suspension was filtered. The filter cake was dried under vacuum to afford the title compound as a colorless solid.

Intermediate 12 tert-Butyl (((1r,4r)-4-(methylsulfonyl)cyclohexyl)methyl)carbamate

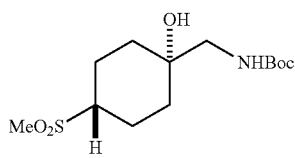 [SMILES: CC(C)(C)OC(=O)NC[C@]1(O)CC[C@@H](S(C)(=O)=O)CC1]

A solution of 4-(methylsulfonyl)cyclohexane-1-carbonitrile (200 g, 1.07 mol, Intermediate 11) in THF (3.0 L) was added dropwise to a stirring −10 to −5° C. suspension of LAH (123 g, 3.24 mol) in THF (1.0 L) over 3 h at a rate that maintained an internal temperature of −10 to 10° C., and the resulting mixture stirred for 2 h. After the reaction went to completion, a solution of THF and water (246 g, 1:1 w/w), 15% aqueous NaOH (123 g), and water (369 g) were sequentially added. The mixture was then filtered, and the filter cake was rinsed with THF. Di-tert-butyl dicarbonate (245 g, 3.40 mol) was then added to the combined filtrate and rinse, and the mixture was stirred at rt overnight. The mixture was then concentrated. The residue was diluted with water, and the mixture was extracted three times with EtOAc. The organic layers were combined, washed with brine, dried with anhydrous Na₂SO₄, filtered, and then concentrated. This concentrate was combined with an additional concentrate prepared in a similar way on a similar scale, diluted with i-PrOH (0.6 L), and stirred at 85° C. for 30 min. n-Heptane (1.2 L) was added dropwise, and the resulting mixture was stirred for 30 min. The mixture was allowed to cool to 25° C., and stirring was continued for 2 h. The mixture was then filtered, and the filter cake was washed with n-heptane and dried under vacuum at 45° C. to give a colorless solid. This solid was combined with another batch prepared in a similar way but on one-fourth scale, dissolved in EtOAc (0.6 L), and stirred at 60° C. for about 2 h. n-Heptane (2.4 L) was then added dropwise over 2 h, and stirring was continued at 60° C. for 1 h. The resulting mixture was then allowed to cool to 25° C. and was stirred for 2 h. The mixture was then filtered, and the filter cake was washed with n-heptane and dried under vacuum at 40° C. to afford the title compound as a colorless solid.

Intermediate 13

((1r,4r)-4-(Methylsulfonyl)cyclohexyl)methanamine Hydrochloride

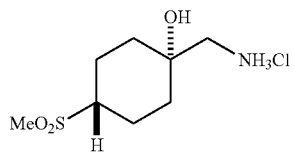

Ethanolic HCl (684 g, 33 wt %, 6.27 mol) was added dropwise to a solution of tert-butyl (((1r,4r)-4-(methylsulfonyl)cyclohexyl)methyl)carbamate (180 g, 0.62 mol, Intermediate 12) in EtOH (0.6 L), and the resulting mixture was stirred at rt. After the reaction went to completion, MTBE (2.5 L) was added, and the suspension was filtered. The filter cake was rinsed with MTBE and then dried under vacuum at 50° C. to afford the title compound as a colorless solid.

Intermediate 14

(4-(Methylsulfonyl)cyclohexyl)methanamine

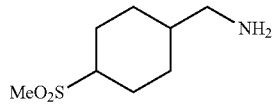

4-(Methylsulfonyl)cyclohexane-1-carbonitrile (5.29 g, 97% w/w, 27.3 mmol, Intermediate 11) was added in portions over 5 min to a 0-5° C. solution of LAH (82 mL, 1.0 M in THF, 82 mmol), and the residual solid on the walls of the nitrile-containing flask was washed into the reaction solution with THF (20 mL). The resulting solution was stirred at 0-5° C. for 10 min before it was allowed to warm to rt over 16 h. After this time, the resulting heterogeneous mixture was diluted with THF (100 mL) and cooled in an ice bath. Water (3.3 mL), 15% aqueous NaOH (3.3 mL), and more water (9.9 mL) were sequentially added at a rate that maintained the internal temperature below 30° C., and then the mixture was allowed to warm to rt with stirring over 20 min. Celite® was added, and the mixture was filtered and then concentrated to afford the title compound as a colorless oil that eventually solidified (trans:cis=7.7:1.0).

Intermediate 15

4-(Methylsulfonyl)-1-(nitromethyl)cyclohex-1-ene

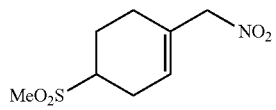 [SMILES: CS(=O)(=O)C1CC=C(C[N+](=O)[O-])CC1]

A solution of 4-(methylsulfonyl)cyclohexanone (15.27 g, 86.65 mmol, Intermediate 5), nitromethane (15 mL, 350 mmol), and DMEN (2.8 mL, 26 mmol) in benzene (220 mL) was stirred at reflux temperature for 16 h in a reactor fitted with a Dean-Stark trap. After this time, the solution was allowed to cool and then diluted with 1 N aqueous HCl (200 mL). The layers of the resulting mixture were mixed then separated, and the aqueous layer was extracted EtOAc. The organic layers were combined, washed with brine, dried with anhydrous MgSO$_4$, filtered, and then concentrated to afford the title compound as a colorless solid.

Intermediate 16

(4-(Methylsulfonyl)cyclohex-1-en-1-yl)methanamine Hydrochloride

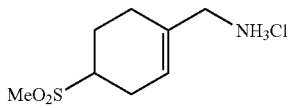

A warm solution of 4-(methylsulfonyl)-1-(nitromethyl)cyclohex-1-ene (15.52 g, 70.78 mmol, Intermediate 15) in AcOH (80 mL) was added dropwise over 1.5 h to a stirring suspension of zinc (50 g, 760 mmol) in AcOH (100 mL), which was submerged in a 70° C. bath. The drip rate was periodically adjusted to maintain the internal reaction temperature below 85° C. After the addition was complete, stirring was continued at 70° C. for 4 h before the reaction mixture was allowed to cool. The mixture was then diluted with an equal volume of EtOAc and filtered through Celite®. The filtrate was concentrated, diluted with IPA (300 mL), and filtered. The filtrate was then concentrated to half its original volume before a 1,4-dioxane solution of HCl (18 mL, 4.0 M, 72 mmol) was added. The resulting mixture was concentrated, diluted with MeOH (200 mL), and stirred until the solids were well-dispersed. The resulting suspension was concentrated to half the original volume, diluted with an equal volume of EtOAc, and then filtered. The filter cake was dried by aspiration to afford the title compound as a colorless solid.

Intermediate 17 tert-Butyl ((4-(methylsulfonyl)cyclohex-1-en-1-yl)methyl)carbamate

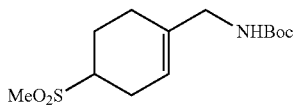 [SMILES: CC(C)(C)OC(=O)NCC1=CCC(S(C)(=O)=O)CC1]

A solution of (4-(methylsulfonyl)cyclohex-1-en-1-yl)methanamine hydrochloride (22.0 g, 97.5 mmol, Intermediate 16) in THF (100 mL) was diluted with a saturated aqueous NaHCO$_3$ solution, Boc$_2$O (20.9 mL, 97.5 mmol) was added, and then the mixture was stirred at rt for 16 h. After this time, the mixture was diluted with EtOAc and filtered. The layers were separated, and the aqueous layer was extracted with EtOAc. The organic layers were combined, washed with brine, dried with anhydrous MgSO$_4$, filtered, and then concentrated to afford the title compound as a tan solid.

Intermediate 18 tert-Butyl (((1RS,2RS)-1,2-dihydroxy-4-(methylsulfonyl)cyclohexyl)methyl)carbamate

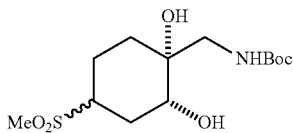

Potassium osmate(VI) dihydrate (470 mg, 1.3 mmol) was added to a solution of tert-butyl ((4-(methylsulfonyl)cyclohex-1-en-1-yl)methyl)carbamate (17.55 g, 94% w/w, 57.01 mmol, Intermediate 17) and NMO monohydrate (8.7 g, 61 mmol) in acetone/water (250 mL, 4:1 v/v), and the mixture was stirred at rt for 20 h. After this time, a solution of Na$_2$S$_2$O$_4$ (3.1 g, 15 mmol) in water (15 mL) was added, and the mixture was stirred for 30 min. After this time, the mixture was concentrated to one-third its original volume. The concentrate was diluted with EtOAc and enough hexanes to make the mixture biphasic. The pH of the aqueous layer was adjusted to pH<4 with 10 M aqueous H$_2$SO$_4$, and the layers were mixed and then separated. The aqueous layer was extracted four times with EtOAc, and then the organic layers were combined, dried with anhydrous MgSO$_4$, filtered, and concentrated to afford the title compound as a pale-purple gum.

Intermediate 19

(1RS,2RS)-1-(Aminomethyl)-4-(methylsulfonyl)cyclohexane-1,2-diol Hydrochloride

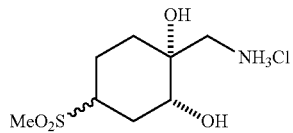

Trifluoroacetic acid (48 mL, 0.63 mol) was added to a solution of tert-butyl (((1RS,2RS)-1,2-dihydroxy-4-(methylsulfonyl)cyclohexyl)methyl)carbamate (17.77 g, 94% w/w, 51.65 mmol, Intermediate 18) in DCM (180 mL), and the resulting solution was maintained at rt for 2 h. After this time, the solution was concentrated, MeOH was added, and the solution was concentrated again. The concentrate was dissolved in MeOH (50 mL), a solution of HCl in 1,4-dioxane (14.2 mL, 4 M, 56.8 mmol) was added, and the solution was concentrated to give a brown oil. This oil was dissolved in MeOH (50 mL) and then EtOAc (200 mL) was added over 30 min to induce crystallization. The resulting slurry was filtered, and the solids were washed with EtOAc and then dried by aspiration to afford the title compound as a tan solid (dr=1.6:1.0 according to NMR analysis).

Intermediate 20

(1RS,2RS,4RS)-1-(Aminomethyl)-4-(methylsulfonyl)cyclohexane-1,2-diol Hydrochloride

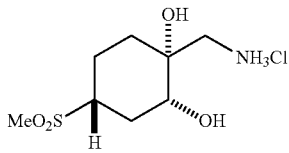

Potassium tert-butoxide (7.7 g, 68 mmol) was added to a suspension of (1RS,2RS)-1-(aminomethyl)-4-(methylsulfonyl)cyclohexane-1,2-diol hydrochloride (11.84 g, 45.58 mmol, Intermediate 19) in t-BuOH (120 mL), and the resulting thick, heterogeneous mixture was stirred at 60° C. for 65 h. After this time, the mixture was allowed to cool, and then a solution of HCl in 1,4-dioxane (18.2 mL, 4 M, 72.9 mmol) was added. The mixture was then concentrated to afford the title compound as a tan solid (dr=10:1.0 according to NMR analysis).

Intermediate 21

Benzyl (((1RS,2RS,4RS)-1,2-dihydroxy-4-(methylsulfonyl)cyclohexyl)methyl)carbamate

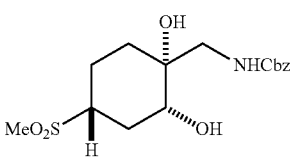 [SMILES: CS(=O)(=O)[C@@H]1CC[C@@](O)(CNC(=O)OCc2ccccc2)[C@H](O)C1]

Benzyl chloroformate (16.6 mL, 112 mmol) was added to a 0-5° C. mixture of (1RS,2RS,4RS)-1-(aminomethyl)-4-(methylsulfonyl)cyclohexane-1,2-diol hydrochloride (19.81 g, 56.05 mmol, Intermediate 20) and NaHCO$_3$ (14.1 g, 168 mmol) in water (160 mL), and the resulting mixture was stirred vigorously and allowed to gradually warm to rt over 24 h. After this time, the resulting suspension was filtered, and the filter cake was washed with water and then dried by aspiration. The solids were diluted with hexanes and EtOAc (100 mL, 3:1 v/v) and stirred for 3 h. The slurry was filtered, and the filter cake was washed with hexanes and then dried by aspiration to afford the title compound as a light-tan solid (dr>100:1 according to NMR analysis).

Intermediate 22

Benzyl (((1S*,2S*,4S*)-1,2-dihydroxy-4-(methylsulfonyl)cyclohexyl)methyl)carbamate

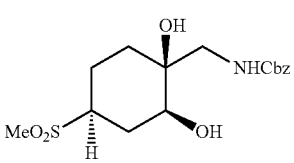 [SMILES: CS(=O)(=O)[C@H]1CC[C@](O)(CNC(=O)OCc2ccccc2)[C@@H](O)C1]

Intermediate 23

Benzyl (((1R*,2R*,4R*)-1,2-dihydroxy-4-(methylsulfonyl)cyclohexyl)methyl)carbamate

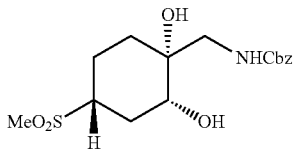 [SMILES: CS(=O)(=O)[C@@H]1CC[C@@](O)(CNC(=O)OCc2ccccc2)[C@H](O)C1]

Intermediate 21 was purified by SFC using a chiral stationary phase (Chiralpak IA, 60% CO$_2$, 40% EtOH/i-PrOH (1:1 v/v)) to give a pair of enantiomers. The first-eluting enantiomer was Intermediate 22, and the second-eluting enantiomer was Intermediate 23.

Intermediate 24

(1R*,2R*,4R*)-1-(Aminomethyl)-4-(methylsulfonyl)cyclohexane-1,2-diol Hydrochloride

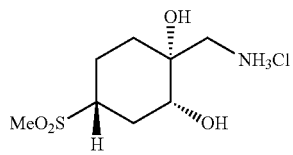

A vessel containing benzyl (((1R*,2R*,4R*)-1,2-dihydroxy-4-(methylsulfonyl)cyclohexyl)methyl)carbamate (4.22 g, 11.8 mmol, Intermediate 23) and Pd/C (10% Pd, 50% water, Degussa E101 NE/W) (2.5 g, 1.2 mmol Pd) was evacuated and backfilled three times with nitrogen before EtOH (130 mL) was added, and the mixture was stirred under an atmosphere of hydrogen at rt for 16 h. After this time, the suspension was diluted with enough water to dissolve the newly-formed precipitate, filtered through Celite®, and then concentrated. This concentrate was dissolved in MeOH and water (30 mL, 1:1 v/v) before a solution of HCl in 1,4-dioxane (3.0 mL, 4 M, 12 mmol) was added, and the resulting mixture was concentrated. The oily residue was diluted with EtOH and concentrated again to afford a colorless solid. This solid was suspended in EtOAc and then isolated by filtration. The moist filter cake was dried under vacuum to afford the title compound as a colorless solid. $[\alpha]_{589}^{20}$+1.9, $[\alpha]_{436}^{20}$+5.2, $[\alpha]_{365}^{20}$+10 (c 1.1, MeOH).

Intermediate 25

(1S*,2S*,4S*)-1-(Aminomethyl)-4-(methylsulfonyl)cyclohexane-1,2-diol Hydrochloride

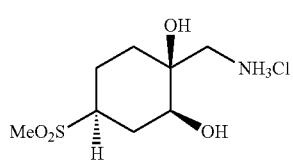

The title compound was prepared as described for the synthesis of Intermediate 24 using benzyl Intermediate 24(((1S*,2S*,4S*)-1,2-dihydroxy-4-(methylsulfonyl)cyclohexyl)methyl)carbamate (Intermediate 22) in place of benzyl (((1R*,2R*,4R*)-1,2-dihydroxy-4-(methylsulfonyl)cyclohexyl) methyl)carbamate. $[\alpha]_{589}^{20}$ –1.7, $[\alpha]_{436}^{20}$ –5.1, $[\alpha]_{365}^{20}$ –10 (c 1.7, MeOH).

Intermediate 26

4-(Methylsulfonyl)tetrahydro-2H-pyran-2-one

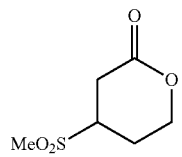

Acetic acid (11.2 mL, 196 mmol) and then 5,6-dihydro-2h-pyran-2-one (15.0 mL, 157 mmol) were added to a suspension of sodium methanesulfinate (23.1 g, 204 mmol) in MeCN (200 mL), and the resulting suspension was stirred at 70° C. for 48 h. After this time, the warm mixture was filtered. The filter cake was rinsed with MeCN, and the combined filtrate and rinse were concentrated to afford an off-white solid. This solid was briefly triturated with 20 mL of boiling DCM, cooled to 0° C. for 1 h, and then filtered. The filter cake was washed with DCM and then dried under vacuum to afford the title compound as an off-white solid.

Intermediate 27

3-(Methylsulfonyl)pentane-1,5-diol

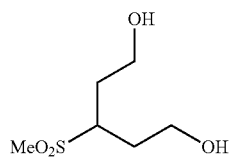

4-(Methylsulfonyl)tetrahydro-2H-pyran-2-one (10 g, 0.056 mol, Intermediate 26) was added portionwise over 5 min to a 0-5° C. suspension of LAH (6.4 g, 0.17 mol) in THF (170 mL) at a rate that maintained the internal temperature below 20° C. The resulting mixture was allowed to warm to rt and was stirred over 16 h. After this time, the mixture was diluted with THF (170 mL) and cooled in an ice bath. Water (6.4 mL), 15% aqueous NaOH (6.4 mL), and then more water (19 mL) were added dropwise, and the resulting mixture was allowed to warm to rt over 15 min. Celite® and anhydrous MgSO$_4$ were then added, and the mixture was filtered and then concentrated to afford the title compound as a colorless oil.

Intermediate 28

1,5-Dibromo-3-(methylsulfonyl)pentane

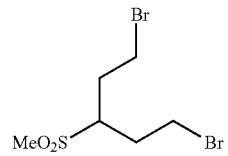

Phosphorus tribromide (6.8 mL, 72 mmol) was added to mixture of 3-(methylsulfonyl)pentane-1,5-diol (6.25 g, 34.3 mmol, Intermediate 27) in benzene (11 mL), and the resulting mixture was stirred at 60° C. for 20 h. After this time, the mixture was allowed to cool and then poured into a stirring DCM and ice mixture. The layers were mixed and then separated, and the aqueous layer was extracted with DCM. The organic layers were combined, washed with brine, dried with anhydrous MgSO$_4$, filtered, and then concentrated to afford the title compound as a colorless solid.

Intermediate 29

Methyl 1-cyano-4-(methylsulfonyl)cyclohexane-1-carboxylate

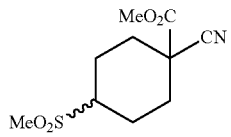

Methyl cyanoacetate (14 g, 0.14 mol) and then 1,5-dibromo-3-(methylsulfonyl)pentane (36 g, 0.12 mol, Intermediate 28) were added to a suspension of Cs$_2$CO$_3$ (115 g, 353 mmol) in DMF (800 mL), and the resulting mixture was stirred at rt for 20 h. After this time, the mixture was filtered, and the filter cake was rinsed with DMF. The combined filtrate and rinse were then concentrated to afford an oily solid. This residue was diluted with DCM, triturated, and then filtered. The filtrate was concentrated to afford the title compound a yellow solid.

Intermediate 30

Methyl (1s*,4s*)-1-cyano-4-(methylsulfonyl)cyclohexane-1-carboxylate

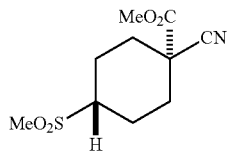

The diastereomeric mixture, Intermediate 29, was purified by silica chromatography (60-80% EtOAc/hexanes) to afford the title compound, which was the major diastereomer.

Intermediate 31 tert-Butyl ((1-(hydroxymethyl)-4-(methylsulfonyl)cyclohexyl)methyl)carbamate

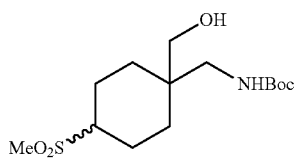

Methyl 1-cyano-4-(methylsulfonyl)cyclohexanecarboxylate (86 g, 0.35 mol, Intermediate 29) in THF (200 mL) was added to a 0° C. suspension of LAH (53.2 g, 1.40 mol) in THF (800 mL), and the resulting suspension was allowed to warm to rt over 16 h. After this time, mixture was cooled in an ice bath and diluted with THF (500 mL). Water (53 mL), 15% aqueous NaOH (53 mL), and then more water (160 mL) were added dropwise, and the mixture was stirred for 20 min. The mixture was then filtered through Celite®, Boc$_2$O (76.5 g, 351 mmol) was added to the filtrate, and the resulting mixture was stirred overnight. The layers were then separated, and the aqueous layer was extracted twice with EtOAc. The organic layers were combined, dried with anhydrous MgSO$_4$, filtered, and then concentrated to afford the title compound as a colorless solid.

Intermediate 32 tert-Butyl (((1r*,4r*)-1-formyl-4-(methylsulfonyl)cyclohexyl)methyl)carbamate

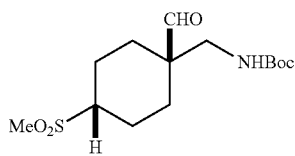 [SMILES: CC(C)(C)OC(=O)NC[C@]1(C=O)CC[C@H](S(C)(=O)=O)CC1]

Intermediate 33 tert-Butyl (((1s*,4s*)-1-formyl-4-(methylsulfonyl)cyclohexyl)methyl)carbamate

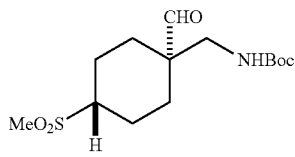 [SMILES: CC(C)(C)OC(=O)NC[C@]1(C=O)CC[C@@H](S(C)(=O)=O)CC1]

A solution of DMSO (2.2 mL, 31 mmol) in DCM (5 mL) was added dropwise to a −78° C. solution of oxalyl chloride (1.3 mL, 15 mmol) in DCM (25 mL), and this solution was maintained at −78° C. for 15 min. After this time, a solution of tert-butyl ((1-(hydroxymethyl)-4-(methylsulfonyl)cyclohexyl)methyl)carbamate (3.95 g, 12.3 mmol, Intermediate 31) in DCM (10 mL) was added, and the resulting opaque mixture was stirred for an additional 15 min. After this time, TEA (8.5 mL, 61 mmol) was added, and the mixture was allowed to warm to rt over 30 min with stirring. The suspension was then diluted with DCM, washed with a 1 N aqueous HCl solution, dried with anhydrous MgSO$_4$, filtered, and then concentrated. The residue was purified by silica gel chromatography (50-100% EtOAc/hexanes) to give a separable pair of diastereomers.

The major diastereomer was Intermediate 32: $^1$H NMR (500 MHz, CDCl$_3$) δ 9.54 (s, 1H), 4.63 (t, J=6.5 Hz, 1H), 3.21 (d, J=6.7 Hz, 2H), 2.82-2.73 (m, 1H), 2.79 (s, 3H), 2.38-2.28 (m, 2H), 2.24-2.16 (m, 2H), 1.57 (qd, J=13.0, 3.7 Hz, 2H), 1.42 (s, 9H), 1.32 (td, J=14.0, 4.2 Hz, 2H).

The minor diastereomer was Intermediate 33: $^1$H NMR (500 MHz, CDCl$_3$) δ 9.36 (s, 1H), 4.85 (t, J=6.6 Hz, 1H), 3.41 (d, J=6.7 Hz, 2H), 2.90-2.78 (m, 1H), 2.86 (s, 3H), 2.23-2.14 (m, 2H), 1.90 (qd, J=12.5, 3.8 Hz, 2H), 1.85-1.77 (m, 2H), 1.62 (td, J=13.4, 4.1 Hz, 2H), 1.41 (s, 9H).

Intermediate 34 tert-Butyl (((1s*,4s*)-1-cyano-4-(methylsulfonyl)cyclohexyl)methyl)carbamate

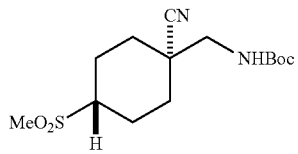

Triethylamine (1.5 mL, 11 mmol) was added to a mixture of tert-butyl (((1s*,4s*)-1-formyl-4-(methylsulfonyl)cyclohexyl)methyl)carbamate (1.06 g, 3.32 mmol, Intermediate 32) and hydroxylamine hydrochloride (254 mg, 3.65 mmol) in DMF (5.3 mL), and the mixture was stirred for 5 min. After this time, T3P (2.2 mL, 3.7 mmol) was added and the mixture was stirred at 100° C. for 4 h. Additional T3P (1.0 mL, 1.7 mmol) was then added, and stirring was continued for 20 h. After this time, the mixture was cooled to 0° C. and then filtered. The filter cake was rinsed with EtOAc, and the combined filtrate and rinse was concentrated. The concentrate was diluted with EtOAc and a saturated aqueous NaHCO$_3$ solution, and the layers were mixed and then separated. The aqueous layer was extracted with EtOAc, and the organic layers combined, washed with brine, dried with MgSO$_4$, filtered, and then concentrated. The residue was purified by silica gel chromatography (50-100% EtOAc/hexanes) to afford the title compound as a colorless solid.

Intermediate 35

(1s*,4s*)-1-(Aminomethyl)-4-(methylsulfonyl)cyclohexane-1-carbonitrile Hydrochloride

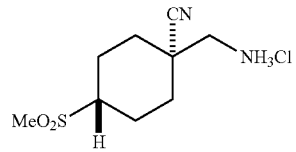

A solution of tert-butyl (((1s*,4s*)-1-cyano-4-(methylsulfonyl)cyclohexyl)methyl)carbamate (150 mg, 0.474 mmol, Intermediate 34) in DCM (1.6 mL) and TFA (0.41 mL, 5.4 mmol) was maintained at rt for 2 h. After this time, the solution was concentrated and then dissolved in enough DCM and MeOH (1:1 v/v) to make a solution. A 1,4-dioxane solution of HCl (0.13 mL, 4 M, 0.52 mmol) was then added, and the resulting suspension was concentrated. The solid residue was suspended in EtOAc, filtered, rinsed with additional EtOAc, and then dried under vacuum to afford the title compound as a colorless solid.

Intermediate 36

(1r*,4r*)-1-(Aminomethyl)-4-(methylsulfonyl)cyclohexane-1-carbonitrile Hydrochloride

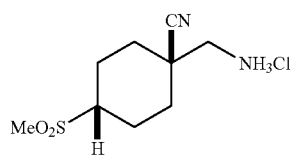

The title compound was prepared as described for the synthesis of Intermediate 35, using tert-butyl (((1r*,4r*)-1-formyl-4-(methylsulfonyl)cyclohexyl)methyl)carbamate (Intermediate 33) in place of tert-butyl (((1s*,4s*)-1-formyl-4-(methylsulfonyl)cyclohexyl)methyl)carbamate.

Intermediate 37

(1r,4r)-4-(Ethylthio)cyclohexane-1-carbonitrile

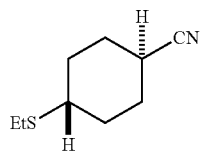

The title compound was prepared as described for the synthesis of Intermediate 10, using sodium ethanethiolate in place of sodium thiomethoxide. Instead of vacuum distillation, the title compound was isolated by silica gel chromatography (0-10% EtOAc/hexanes) at the end of the sequence.

Intermediate 38

(1r,4r)-4-(Ethylsulfonyl)cyclohexane-1-carbonitrile

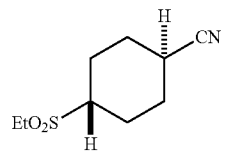

The title compound was prepared as described for the synthesis of Intermediate 11, using (1r,4r)-4-(ethylthio)cyclohexane-1-carbonitrile (Intermediate 37) in place of 4-(methylthio)cyclohexane-1-carbonitrile.

Intermediate 39 tert-Butyl (((1r,4r)-4-(ethylsulfonyl)cyclohexyl)methyl)carbamate

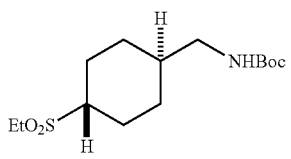

Sodium borohydride (79.4 g, 2.08 mol) was added in portions to a 0-5° C. solution of (1r,4r)-4-(ethylsulfonyl)cyclohexane-1-carbonitrile (35 g, 0.17 mol, Intermediate 38), Boc$_2$O (152 g, 0.696 mol), and NiCl$_2$.6H$_2$O (41 g, 0.17 mol) in methanol (400 mL), and the resulting mixture was stirred at 0° C. briefly before it was allowed to warm to rt over 4 h. After this time, ice water was added, and the mixture was filtered through Celite®. The filter cake was washed with EtOAc, and the filtrate and wash were combined, washed with water, dried with anhydrous Na$_2$SO$_4$, filtered and concentrated. The concentrate was purified by silica gel chromatography (0→30% EtOAc/hexanes) to afford the title compound as a colorless solid.

Intermediate 40

((1r,4r)-4-(Ethylsulfonyl)cyclohexyl)methanamine Hydrochloride

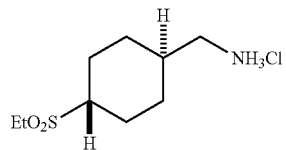

The title compound was prepared as described for the synthesis of Intermediate 13, using tert-butyl (((1r,4r)-4-(ethylsulfonyl)cyclohexyl)methyl)carbamate (Intermediate 39) in place of tert-butyl (((1r,4r)-4-(methylsulfonyl)cyclohexyl)methyl)carbamate and 4.0 M HCl in 1,4-dioxane in place of ethanolic HCl.

Intermediate 41

8-Iodo-1,4-dioxaspiro[4.5]decane

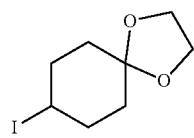

A solution of iodine (31.6 g, 125 mmol) in THF (75 mL) was added dropwise over 1 h to a stirring 0-5° C. solution of 1,4-dioxaspiro[4.5]decan-8-ol (16.4 g, 104 mmol, Intermediate 1), imidazole (8.5 g, 130 mmol), and triphenylphosphine (32.7 g, 125 mmol) in THF (115 mL), and the resulting mixture was allowed to warm to rt over 16 h. After this time, the reaction mixture was filtered, concentrated, and then diluted with DCM. The resulting solution was washed with water, dried with anhydrous MgSO₄, filtered, and concentrated. Hexane was added, and the resulting mixture agitated for 30 min at 32° C. The mixture was then filtered, and the filtrate was concentrated. The concentrate was purified by silica gel chromatography (5→15% EtOAc/hexanes) to afford the title compound as a pale-yellow oil.

Intermediate 42

N-(tert-Butyl)-1,4-dioxaspiro[4.5]decane-8-sulfonamide

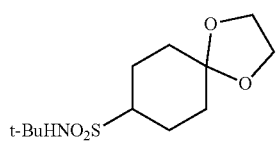

8-Iodo-1,4-dioxaspiro[4.5]decane (21.5 g, 98% w/w, 78.6 mmol, Intermediate 41) was added to a suspension of Rieke® zinc in THF (113 mL, 0.05 g/mL, 86.5 mmol) over 5 min, and 10 mL of THF was used to wash the residue in the transfer vessel into the reaction mixture. The mixture was stirred at 65° C. for 3 h. After this time, the suspension was allowed to cool and then DABSO (11.3 g, 47.2 mmol) was added, and the mixture was stirred at rt for 16 h. After this time, the mixture was filtered through Celite®, and the filter cake was washed with THF. The filtrate and wash were combined and then concentrated to afford the crude zinc sulfinate as a beige foam. N-Chlorosuccinimide (7.4 g, 56 mmol) was added to a suspension of the crude zinc sulfinate described above (29.9 g, 74% w/w, 55.7 mmol) in DCM (280 mL), and the resulting mixture was stirred at rt for 1 h. After his time, Celite® was added and the mixture was filtered. The filter cake was washed with DCM, and then the filtrate and wash were combined and concentrated. The concentrate was diluted with THF (115 mL), and the solution was cooled to 0-5° C. tert-Butylamine (23 mL, 220 mmol) was then added in one portion, and the resulting mixture was stirred and allowed to warm to rt over 18 h. After this time, the mixture was diluted with water and EtOAc. The layers were mixed and then separated, and the aqueous layer was extracted three times with EtOAc. The organic layers were combined, washed with brine, dried with anhydrous MgSO₄, filtered, and then concentrated. The concentrate was then purified by silica gel chromatography (20→60% EtOAc/hexanes) to afford the title compound as a colorless solid.

Intermediate 43

N-(tert-Butyl)-4-oxocyclohexane-1-sulfonamide

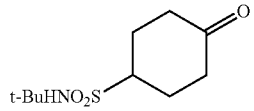

N-(tert-Butyl)-1,4-dioxaspiro[4.5]decane-8-sulfonamide (8.2 g, 30 mmol, Intermediate 42) was dissolved in a mixture of AcOH, 1,4-dioxane, and water (175 mL, 2:2:1 v/v/v), and the solution was maintained at 105° C. for 18 h. After this time, the solution was allowed to cool and then concentrated to afford an off-white solid. This solid was crystallized from a hot toluene/heptane solution to afford the title compound as a colorless solid.

Intermediate 44

N-(tert-Butyl)-4-cyano-4-hydroxycyclohexane-1-sulfonamide

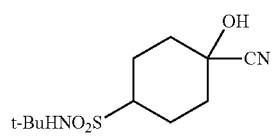

Trimethylsilyl cyanide (0.77 mL, 6.1 mmol) was added to a mixture of N-(tert-butyl)-4-oxocyclohexane-1-sulfonamide (1.1 g, 4.7 mmol, Intermediate 43) and zinc iodide (30 mg, 0.094 mmol) in DCM (9.5 mL), and the mixture was stirred at rt for 72 h. After this time, the reaction mixture was diluted with a saturated aqueous NaHCO₃ solution and filtered. The layers of the filtrate were separated, and the aqueous layer was extracted with DCM. The combined organic layers were dried with MgSO₄, filtered, and then concentrated. The concentrate was dissolved in DCM (9 mL), and then trimethylsilyl cyanide (0.77 mL, 6.1 mmol) and zinc iodide (30 mg, 0.094 mmol) were added, and the mixture was stirred at rt for 20 h. The mixture was then diluted with hexanes, filtered, and concentrated to afford the title compound as a tan solid.

Intermediate 45 tert-Butyl (((1s,4s)-1-hydroxy-4-sulfamoylcyclohexyl)methyl)carbamate

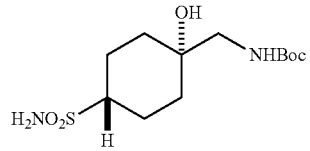

N-(tert-Butyl)-4-cyano-4-hydroxycyclohexane-1-sulfonamide (1.28 g, 3.85 mmol, Intermediate 44) was added portionwise to a 0-5° C. solution of LAH in THF (12.3 mL, 1.0 M, 12.3 mmol), and the resulting solution was allowed to warm to rt over 3 h. The solution was then cooled to 0-5° C. before water (0.50 mL), 15% aqueous NaOH (0.50 mL), and more water (1.5 mL) were sequentially added. The mixture was then allowed to warm to rt over 15 min before anhydrous MgSO₄ was added, and the mixture was filtered through Celite®. The filter cake was washed with THF, and the filtrate and wash were combined and concentrated. The concentrate was then diluted with 6 mL of TFA, and the solution was maintained at rt for 15 h. After this time, the solution was concentrated and then diluted with THF (12 mL) and a saturated aqueous NaHCO₃ solution (5 mL).

Di-tert-butyl dicarbonate (0.83 mL, 3.9 mmol) was added, and the mixture was stirred at rt for 40 h. After this time, the mixture was diluted with EtOAc and water, the layers were separated, and the aqueous layer was extracted twice with EtOAc. The organic layers were combined, washed with brine, dried with anhydrous MgSO$_4$, filtered, and then concentrated to give the crude product as a mixture of diastereomers. The concentrate was purified by silica gel chromatography (80→100% EtOAc/hexanes) to afford a fraction enriched in the first-eluting diastereomer as a colorless film. This residue was diluted with CHCl$_3$, and the resulting solution was stirred overnight at rt. After this time, a suspension had formed. The mixture was filtered, and the filter cake was washed with cold CHCl$_3$ and then dried by aspiration to afford the title compound as a colorless solid.

Intermediate 46

(1s,4s)-4-(Aminomethyl)-4-hydroxycyclohexane-1-sulfonamide Hydrochloride

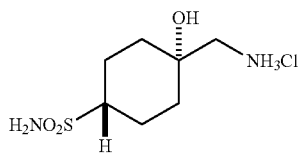

The title compound was prepared as described for the synthesis of Intermediate 35, using tert-butyl (((1s,4s)-1-hydroxy-4-sulfamoylcyclohexyl)methyl)carbamate (Intermediate 45) in place of tert-butyl (((1s*,4s*)-1-cyano-4-(methylsulfonyl)cyclohexyl)methyl)carbamate.

Intermediate 47

1,4-Dioxaspiro[4.5]decane-8-carbonitrile

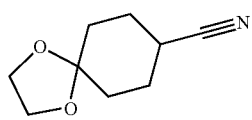 [SMILES: N#CC1CCC2(CC1)OCCO2]

A solution of t-BuOK (147 g, 1.31 mol) in t-BuOH and DME (2.0 L, 1:1 v/v) was added dropwise to a 0-5° C. solution of 1,4-dioxaspiro[4.5]decan-8-one (100 g, 640 mmol) and TosMIC (131 g, 672 mmol) in DME (2.0 L), and the resulting mixture was stirred at 0-5° C. for 1 h before it was allowed to warm to rt over 12 h. After this time, the mixture was poured into water and then extracted three timed with MTBE. The organic layers were combined, washed with brine, dried with anhydrous Na$_2$SO$_4$, filtered, and then concentrated to afford the title compound, which was used in the next step without further purification.

Intermediate 48

(1,4-dioxaspiro[4.5]decan-8-yl)methanamine

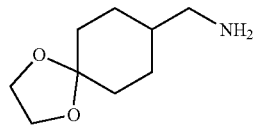

A solution of 1,4-dioxaspiro[4.5]decane-8-carbonitrile (130 g, 0.777 mol, Intermediate 47) in THF (500 mL) was added dropwise to a 0-5° C. suspension of LAH (44.3 g, 1.17 mol) in THF (2.0 L), and the resulting mixture was stirred at 65° C. for 12 h. After this time, the mixture was allowed to cool to rt and stirred for another 12 h. The mixture was then cooled to 0-5° C. before water (45 mL) and 15% aqueous NaOH (135 mL) were sequentially added dropwise. The resulting mixture was allowed to warm to rt over 1 h with stirring before anhydrous MgSO$_4$ was added, and the suspension was stirred for another 1 h at rt. The mixture was then filtered through a pad of Celite®, and the pad was washed with EtOAc. The filtrate and wash were combined, concentrated, and then purified by distillation to afford the title compound as a colorless oil.

Intermediate 49

2-(1,4-Dioxaspiro[4.5]decan-8-ylmethyl)isoindoline-1,3-dione

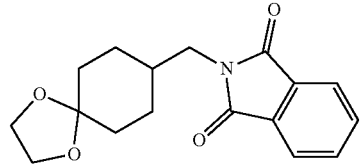 [SMILES: O=C1c2ccccc2C(=O)N1CC1CCC2(CC1)OCCO2]

A mixture of isobenzofuran-1,3-dione (64.2 g, 433 mmol), 1,4-dioxaspiro[4.5]decan-8-ylmethanamine (90.0 g, 433 mmol, Intermediate 48), TEA (52.6 g, 0.519 mol), and 4 Å molecular sieves (90 g) in toluene and DMF (990 mL, 10:1 v/v) was stirred at 110° C. for 12 h. After this time, the suspension was allowed to cool to rt and then filtered through a pad of Celite®. The pad was washed with EtOAc, and the filtrate and wash were combined, concentrated, and then purified by silica gel chromatography (10-50% EtOAc/petroleum ether) to afford the title compound as a colorless solid.

Intermediate 50

2-((4-Oxocyclohexyl)methyl)isoindoline-1,3-dione

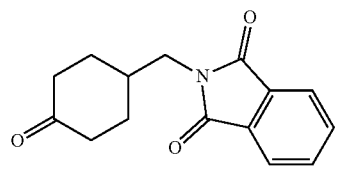 [SMILES: O=C1CCC(CN2C(=O)c3ccccc3C2=O)CC1]

Water (11.0 mL, 611 mmol) was added to a solution of 2-(1,4-dioxaspiro[4.5]decan-8-ylmethyl)isoindoline-1,3-dione (122 g, 405 mmol, Intermediate 49) in formic acid (900 mL), and the resulting solution was maintained at rt for 16 h. After this time, the solution was concentrated and then diluted with EtOAc. The resulting solution washed twice with a saturated aqueous NaHCO₃ solution, dried with anhydrous Na₂SO₄, filtered, and then concentrated to afford the title compound as a colorless solid.

Intermediate 51

2-((4-Hydroxycyclohexyl)methyl)isoindoline-1,3-dione

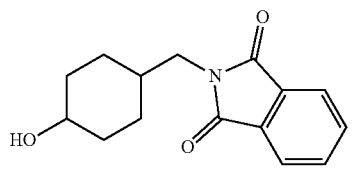 [SMILES: O=C1c2ccccc2C(=O)N1CC1CCC(O)CC1]

Sodium cyanoborohydride (48.5 g, 772 mmol) was added portionwise to a solution of 2-((4-oxocyclohexyl)methyl)isoindoline-1,3-dione (100 g, 389 mmol, Intermediate 50) in AcOH (1.0 L), and the resulting mixture was stirred at rt for 16 h. After this time, the mixture was concentrated, and the concentrate was dissolved in EtOAc. The resulting solution washed twice with a saturated aqueous NaHCO₃ solution, dried with anhydrous Na₂SO₄, filtered, and concentrated to afford the title compound as a colorless solid, which was used in the next step without further purification.

Intermediate 52

4-((1,3-Dioxoisoindolin-2-yl)methyl)cyclohexyl 4-methylbenzenesulfonate

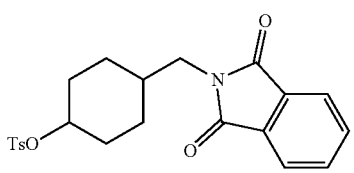 [SMILES: Cc1ccc(S(=O)(=O)OC2CCC(CN3C(=O)c4ccccc4C3=O)CC2)cc1]

4-Methylbenzene-1-sulfonyl chloride (199 g, 1.04 mol) was added to a 0-5° C. solution of 2-((4-hydroxycyclohexyl)-methyl)isoindoline-1,3-dione (135 g, 0.521 mol, Intermediate 51), and pyridine (165 g, 2.08 mol) in CHCl₃ (800 mL), and the resulting mixture was allowed to warm to rt over 12 h with stirring. After this time, the mixture was concentrated, and the concentrate was dissolved in EtOAc, washed with 2 N aqueous HCl, dried with anhydrous Na₂SO₄, filtered, and then concentrated. The concentrate was purified by silica gel chromatography (5→25% EtOAc/petroleum ether) to afford the title compound as a colorless solid.

Intermediate 53

S-(4-((1,3-dioxoisoindolin-2-yl)methyl)cyclohexyl) ethanethioate

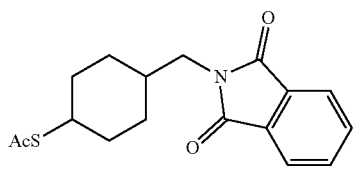

Potassium ethanethioate (27.6 g, 242 mmol) was added to a solution of 4-((1,3-dioxoisoindolin-2-yl)methyl)cyclohexyl 4-methylbenzenesulfonate (40.0 g, 96.7 mmol, Intermediate 52) in DMF (600 mL), and the resulting mixture was stirred at 75° C. for 12 h. After this time, the mixture was allowed to cool to rt and then concentrated. The concentrate was dissolved in EtOAc, washed with brine, dried with anhydrous Na₂SO₄, filtered, and then concentrated. The concentrate was purified by silica gel chromatography (5→25% EtOAc/petroleum ether) to afford the title compound as a yellow solid.

Intermediate 54

4-((1,3-Dioxoisoindolin-2-yl)methyl)cyclohexane-1-sulfonic Acid

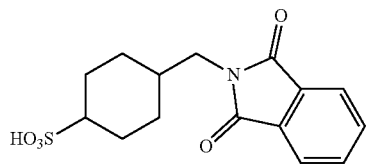 [SMILES: O=C1c2ccccc2C(=O)N1CC1CCC(S(=O)(=O)O)CC1]

A solution of H₂O₂ in water (20 mL, 30-34% w/w, 19 mmol) was added to formic acid (200 mL) at 0-5° C., and the solution was maintained at 0-5° C. for 1 h. A solution of S-(4-((1,3-dioxoisoindolin-2-yl)methyl)cyclohexyl) ethanethioate (10.0 g, 31.5 mmol, Intermediate 53) in formic acid and DCM (100 mL, 1:1 v/v) was then added, the mixture was allowed to warm to rt over 12 h with stirring. After this time, the mixture was cooled to 0-5° C. before solid Na₂SO₃ was added. The resulting mixture was filtered, concentrated, and then purified by silica gel chromatography (5-25% MeOH/DCM) to afford the title compound as a colorless solid.

Intermediate 55

4-((1,3-Dioxoisoindolin-2-yl)methyl)cyclohexane-1-sulfonyl chloride

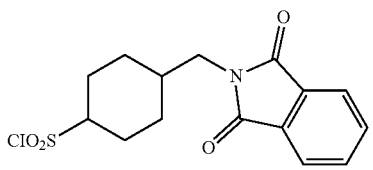

Thionyl chloride (44.2 g, 371 mmol) and DMF (1.0 mL, 13 mmol) were added to a solution of 4-((1,3-dioxoisoindolin-2-yl)methyl)cyclohexane-1-sulfonic acid (24.0 g, 74.2 mmol, Intermediate 54) in CHCl₃ (300 mL), and the resulting mixture was stirred at 75° C. for 12 h. After this time, the mixture was allowed to cool to rt, and then it was concentrated. The concentrate underwent two cycles of sequential dilution with toluene and concentration to afford the title compound as a colorless solid.

Intermediate 56

4-((1,3-Dioxoisoindolin-2-yl)methyl)-N-methylcyclohexane-1-sulfonamide

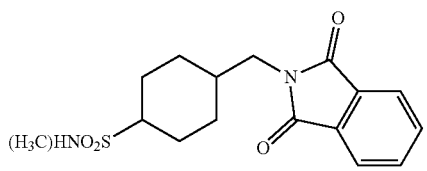

Methylamine (205 mL, 2.0 M in THF, 410 mmol) was added to a 0-5° C. mixture of 4-((1,3-dioxoisoindolin-2-yl)methyl)cyclohexane-1-sulfonyl chloride (11 g, 32 mmol, Intermediate 55) and 4 Å molecular sieves (70 g) in THF (300 mL), and the resulting mixture was allowed to warm to rt over 48 h with stirring. After this time, the mixture was filtered through Celite®, concentrated, and then purified by silica gel chromatography (3→25% MeOH/DCM). The product was repurified by preparative HPLC (Phenomenex Synergi Max-RP, 20→60% MeCN/H₂O, 10 mM NH₄HCO₃) to afford the title compound as a colorless solid.

Intermediate 57

(1r,4r)-4-((1,3-Dioxoisoindolin-2-yl)methyl)-N-methylcyclohexane-1-sulfonamide

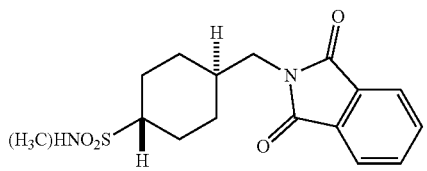

Intermediate 56 was purified by SFC (Chiralpak IA, 70% CO₂, 30% MeOH) to give the title compound as a colorless solid.

Intermediate 58

(1r,4r)-4-(Aminomethyl)-N-methylcyclohexane-1-sulfonamide

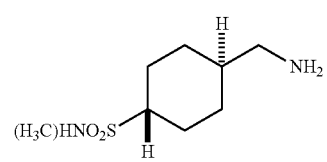

(1r,4r)-4-((1,3-Dioxoisoindolin-2-yl)methyl)-N-methylcyclohexane-1-sulfonamide (200 mg, 0.595 mmol, Intermediate 57) and hydrazine hydrate (0.089 mL, 65% w/w, 1.2 mmol) were combined in EtOH (4.8 mL), and the resulting thick mixture was stirred at 80° C. for 14 h. After this time, the hot mixture was filtered, and the filter cake was washed with boiling EtOH. The filtrate and wash were combined, allowed to cool, and re-filtered. The filter cake was washed with EtOH, and the filtrate and wash were combined and then concentrated to afford the title compound as a colorless solid.

Intermediate 59

N-(tert-Butyl)-4-((1,3-dioxoisoindolin-2-yl)methyl)cyclohexane-1-sulfonamide

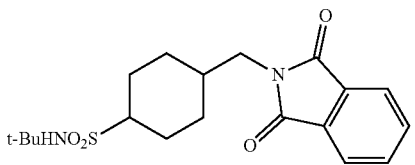

The title compound was prepared as described for the synthesis of Intermediate 56, using neat tert-butylamine in place of methanamine solution.

Intermediate 60

4-((1,3-Dioxoisoindolin-2-yl)methyl)cyclohexane-1-sulfonamide

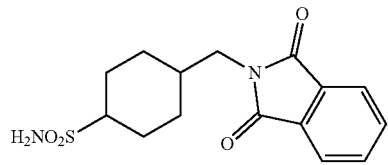 [SMILES: NS(=O)(=O)C1CCC(CN2C(=O)c3ccccc3C2=O)CC1]

Trifluoroacetic acid (10 mL, 130 mmol) was added dropwise to a 0-5° C. solution of N-(tert-butyl)-4-((1,3-dioxoisoindolin-2-yl)methyl)cyclohexane-1-sulfonamide (2.0 g, 5.3 mmol, Intermediate 59) in DCM (10 mL), and the resulting mixture was stirred at 0-5° C. for 12 h before it was concentrated. The concentrate was purified by preparative HPLC (Phenomenex Synergi Max-RP, 12-52% MeCN/H₂O, 10 mM NH₄HCO₃) to afford the title compound as a colorless solid.

Intermediate 61

(1r,4r)-4-((1,3-Dioxoisoindolin-2-yl)methyl)cyclohexane-1-sulfonamide

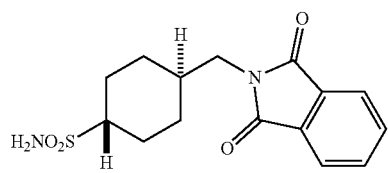 [SMILES: NS(=O)(=O)[C@H]1CC[C@H](CN2C(=O)c3ccccc3C2=O)CC1]

Intermediate 60 was purified by SFC (Chiralcel OJ-H, 80% CO₂, 20% MeOH) to give the title compound as a colorless solid.

Intermediate 62

(1r,4r)-4-(Aminomethyl)cyclohexane-1-sulfonamide Hydrochloride

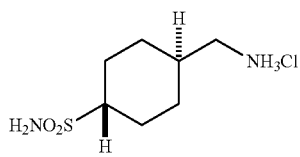

(1r,4r)-4-((1,3-Dioxoisoindolin-2-yl)methyl)cyclohexane-1-sulfonamide (1.1 g, 3.4 mmol, Intermediate 61) was suspended in EtOH (20 mL), hydrazine hydrate (0.51 mL, 65% w/w, 6.9 mmol) was added, and the resulting mixture was stirred at 80° C. for 16 h. After this time, the thick suspension was allowed to cool to rt and then was concentrated to afford a colorless solid. This solid was suspended in THF (20 mL), Boc₂O (3.7 mL, 17 mmol) and enough water to dissolve the solids were added, and the mixture was stirred at rt overnight. The mixture was then concentrated to afford a colorless solid. This solid was diluted with acetone (15 mL), mixed, and then filtered. The filter cake was discarded. The filtrate was diluted with enough hexanes to promote formation of a precipitate, and the resulting suspension was stirred for 10 min and then filtered. The filter cake was washed with hexanes and dried by aspiration to afford tert-butyl (((1r,4r)-4-sulfamoylcyclohexyl)methyl)carbamate as a colorless solid. This solid was diluted with DCM (10 mL), TFA (2.6 mL, 34 mmol) was added, and the resulting solution was maintained at rt for 2 h. After this time, the solution was concentrated to afford a colorless solid. This solid was dissolved in MeOH, a dioxane solution of HCl (0.77 mL, 4.0 M, 3.1 mmol) was added, and then the solution was concentrated. The resulting solid residue was suspended in EtOAc, and the solids were collected by filtration, washed with EtOAc, and dried by aspiration to afford the title compound as a colorless solid.

Intermediate 63

Tert-Butyl (((1RS,2RS,4RS)-2-(((benzyloxy)carbonyl)amino)-1-hydroxy-4-(methylsulfonyl) cyclohexyl)methyl)carbamate

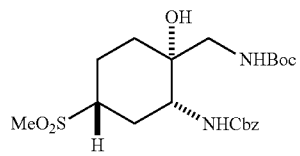

tert-Butyl hypochlorite (750 mg, 6.91 mmol) in t-BuOH (4.0 mL) was added dropwise to a rapidly stirring suspension of benzyl carbamate (1.57 g, 10.4 mmol) in aqueous NaOH (7.0 mL, 1.0 M, 7.0 mmol), and the resulting solution was maintained at rt for 2.5 h. After this time, potassium osmate(VI) dihydrate (64 mg, 0.17 mmol) was added, and the resulting mixture was stirred for 15 min, at which point the mixture became homogeneous. tert-Butyl ((4-(methylsulfonyl)cyclohex-1-en-1-yl)methyl)carbamate (1.0 g, 3.5 mmol, Intermediate 17) and additional t-BuOH (3 mL) were then added, and the resulting suspension was stirred at rt for 1.5 h. After this time, the reaction mixture was diluted with EtOAc and water, the layers were separated, and the aqueous layer was extracted twice with EtOAc. The organic layers were combined, washed with an aqueous Na₂S₂O₃ solution, washed with brine, dried with anhydrous MgSO₄, filtered, and then concentrated. The residue was purified by silica gel chromatography (60-100% EtOAc/hexanes) to afford the title compound as a colorless solid.

Intermediate 64

Benzyl ((1RS,2RS,5RS)-2-(aminomethyl)-2-hydroxy-5-(methylsulfonyl)cyclohexyl) carbamate Hydrochloride

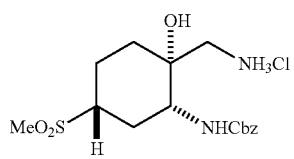

The title compound was prepared as described for the synthesis of Intermediate 35, using tert-butyl (((1RS,2RS,4RS)-2-(((benzyloxy)carbonyl)amino)-1-hydroxy-4-(methylsulfonyl)cyclohexyl) methyl)carbamate (Intermediate 63) in place of tert-butyl (((1s*,4s*)-1-cyano-4-(methyl sulfonyl)cyclohexyl)methyl)carbamate.

Intermediate 65

Tert-Butyl ((5-(methylsulfonyl)pyridin-2-yl)methyl)carbamate

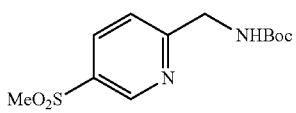

Di-tert-butyl dicarbonate (0.87 mL, 4.1 mmol) was added to a mixture of (5-(methylsulfonyl)pyridin-2-yl)methanamine (740 mg, 3.97 mmol) in THF and saturated aqueous NaHCO₃ solution (12 mL, 2:1 v/v), and the mixture was stirred at rt for 20 h. After this time, the mixture was diluted with EtOAc, the layers were separated, and the aqueous layer was extracted twice with EtOAc. The organic layers were combined, washed with brine, dried with anhydrous MgSO₄, filtered, and then concentrated to give a yellow solid. This residue was purified by silica gel chromatography (EtOAc/hexanes) to afford the title compound as a colorless solid.

Intermediate 66

Benzyl (2RS,5SR)-2-(((tert-butoxycarbonyl)amino)methyl)-5-(methylsulfonyl)piperidine-1-carboxylate

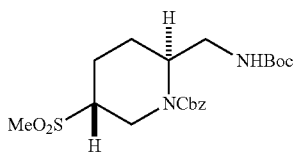 [SMILES: CC(C)(C)OC(=O)NC[C@@H]1CC[C@@H](S(C)(=O)=O)CN1C(=O)OCc1ccccc1]

Intermediate 67

Benzyl (2RS,5RS)-2-(((tert-butoxycarbonyl)amino)methyl)-5-(methylsulfonyl)piperidine-1-carboxylate

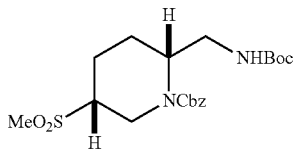 [SMILES: CC(C)(C)OC(=O)NC[C@H]1CC[C@@H](S(C)(=O)=O)CN1C(=O)OCc1ccccc1]

A solution of HCl in 1,4-dioxane (0.50 mL, 4.0 M, 2.0 mmol) was added to a solution of tert-butyl ((5-(methylsulfonyl)pyridin-2-yl)methyl)carbamate (570 mg, 1.99 mmol, Intermediate 65) in EtOH (20 mL), and a few drops of water were added to make the salt mixture homogeneous. The solution was then flowed at 1 mL/min through a 10% Pt/C cartridge heated at 50° C. under 80 bar of hydrogen using an H-cube flow reactor for 25 h of continuous cycling. After this time, the solution was concentrated and then diluted with toluene and 1 N aqueous NaOH (20 mL, 1:1 v/v). Benzyl chloroformate (0.34 mL, 2.4 mmol) was added, and the mixture was stirred at rt for 2 h. After this time, the layers of the reaction mixture were separated, and the aqueous layer was extracted twice with EtOAc. The organic layers were combined, washed with brine, dried with MgSO$_4$, filtered, and then concentrated. The residue was purified by silica gel chromatography (70→80% EtOAc/hexanes) to give a pair of diastereomers, both as colorless films.

The minor diastereomer was Intermediate 66: $^1$H NMR (400 MHz, CDCl$_3$) δ 7.41-7.29 (m, 5H), 5.19 (d, J=12.2 Hz, 1H), 5.11 (d, J=12.2 Hz, 1H), 4.76 (br s, 1H), 4.57 (appar d, J=15.6 Hz, 1H), 4.31-4.22 (m, 1H), 3.61-3.47 (m, 2H), 3.16 (dt, J=14.0, 5.5 Hz, 1H), 3.06-2.98 (m, 1H), 2.83 (s, 3H), 2.26-2.07 (m, 3H), 1.54-1.37 (m, 10H).

The major diastereomer was Intermediate 67: $^1$H NMR (400 MHz, CDCl$_3$) δ 7.40-7.29 (m, 5H), 5.20-5.01 (m, 2H), 4.84-4.30 (m, 3H), 3.44 (br s, 1H), 3.30-3.08 (m, 2H), 3.05-2.78 (m, 4H), 2.20-2.08 (m, 1H), 2.00-1.61 (m, 3H), 1.54-1.32 (m, 9H).

Intermediate 68

Benzyl (2RS,5SR)-2-(aminomethyl)-5-(methylsulfonyl)piperidine-1-carboxylate Hydrochloride

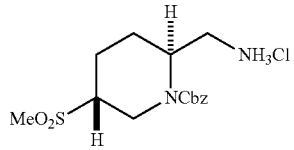

The title compound was prepared as described for the synthesis of Intermediate 35, using benzyl (2RS, 5SR)-2-(((tert-butoxycarbonyl)amino)methyl)-5-(methyl sulfonyl)piperidine-1-carboxylate (Intermediate 66) in place of tert-butyl (((1s*,4s*)-1-cyano-4-(methyl sulfonyl)cyclohexyl)methyl)carbamate.

Intermediate 69 tert-Butyl ((3,4-dihydro-2H-pyran-2-yl)methyl)carbamate

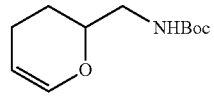

Di-tert-butyl dicarbonate (3.4 mL, 16 mmol) was added to a solution of (3,4-dihydro-2H-pyran-2-yl)methanamine (1.8 g, 16 mmol) in THF (20 mL) before a saturated aqueous NaHCO$_3$ solution (10 mL) was added, and the resulting mixture was stirred at rt for 16 h. After this time, the mixture was diluted with EtOAc and water, the layers were separated, and then the aqueous layer was extracted twice with EtOAc. The organic layers were combined, washed with brine, dried with anhydrous MgSO$_4$, filtered, and then concentrated to afford the title compound as a colorless oil.

Intermediate 70 tert-Butyl (((2RS,5RS)-5-hydroxytetrahydro-2H-pyran-2-yl)methyl)carbamate

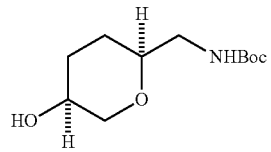 [SMILES: CC(C)(C)OC(=O)NC[C@@H]1CC[C@H](O)CO1]

A solution of tert-butyl ((3,4-dihydro-2H-pyran-2-yl)methyl)carbamate (3.10 g, 14.5 mmol, Intermediate 69) in THF (6.0 mL) was added to a 0-5° C. solution of BH$_3$.THF in THF (30 mL, 1.0 M, 30 mmol), and the resulting solution was allowed to warm to rt over 2 h. After this time, the solution was cooled to 0-5° C., and then water (12 mL), aqueous NaOH (5 mL, 10 M, 50 mmol), and H$_2$O$_2$ (3.9 mL, 50% w/w, 68 mmol) were added slowly in sequence. The resulting mixture was stirred at 50° C. for 3 h before it was cooled to 0-5° C. and then diluted with a saturated aqueous Na$_2$S$_2$O$_3$ solution. The mixture was then concentrated to remove most of the THF. A scoop of K$_2$CO$_3$ was then added to the aqueous mixture, and then it was extracted three times with EtOAc. The organic layers were combined, washed with brine, dried with anhydrous MgSO$_4$, filtered, and then concentrated to afford a colorless oil. This residue was purified by silica gel chromatography (50→100% EtOAc/hexanes) to give a pair of diastereomers (dr=3:1), both as colorless films. The title compound was the second-eluting, minor diastereomer.

Intermediate 71

S-((3RS,6SR)-6-(((tert-Butoxycarbonyl)amino)methyl)tetrahydro-2H-pyran-3-yl) ethanethioate

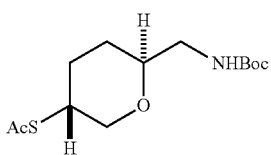

Diisopropyl azodicarboxylate (0.48 mL, 2.4 mmol) was added to a 0-5° C. solution of PPh$_3$ (621 mg, 2.37 mmol) in THF (6 mL), and the resulting solution was maintained at 0-5° C. for 30 min. After this time, a solution of tert-butyl (((2RS,5RS)-5-hydroxytetrahydro-2H-pyran-2-yl)methyl)carbamate (274 mg, 1.19 mmol, Intermediate 70) and thioacetic acid (0.19 mL, 2.7 mmol) in THF (3 mL) was added dropwise, and the resulting mixture was stirred at 0-5° C. for 30 min before it was allowed to warm to rt over 2 h. After this time, the resulting solution was concentrated and then purified by silica gel chromatography (0→60% EtOAc/hexanes) to afford the title compound as a pale-yellow film.

Intermediate 72 tert-Butyl (((2RS,5SR)-5-(methylthio)tetrahydro-2H-pyran-2-yl)methyl)carbamate

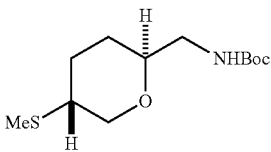

An aqueous NaOH solution (0.4 mL, 15% w/w, 1.8 mmol) was added to a solution of S-((3RS,6SR)-6-(((tert-butoxycarbonyl)amino)methyl)tetrahydro-2H-pyran-3-yl) ethanethioate (129 mg, 0.446 mmol, Intermediate 71) in 0.4 mL of MeOH, and the resulting solution was maintained at 70° C. for 1 h. After this time, MeI (0.031 mL, 0.49 mmol) was added and the resulting biphasic mixture was stirred at 70° C. for an additional 1 h. After this time, the mixture was allowed to cool, diluted with water, and then extracted three times with EtOAc. The organic layers were combined, washed with brine, dried with anhydrous MgSO$_4$, filtered, and then concentrated to afford the title compound as a pale-yellow oil.

Intermediate 73

Tert-Butyl (((2RS,5SR)-5-(methylsulfonyl)tetrahydro-2H-pyran-2-yl)methyl)carbamate

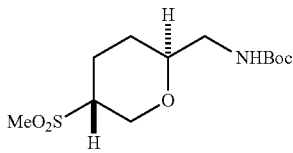

m-Chloroperbenzoic acid (196 mg, 77% w/w, 0.876 mmol) was added to a 0-5° C. solution of tert-butyl (((2RS,5SR)-5-(methylthio)tetrahydro-2H-pyran-2-yl)methyl)carbamate (109 mg, 0.417 mmol, Intermediate 72) in DCM and MeOH (1.8 mL, 5:1 v/v), and the resulting mixture was allowed to warm to rt over 2 h. After this time, an aqueous Na$_2$S$_2$O$_3$ solution was added. The layers were mixed then separated, and the aqueous layer was extracted with DCM and then with EtOAc. The organic layers were combined, washed with brine, dried with anhydrous MgSO$_4$, filtered, and then concentrated. The residue was purified by silica gel chromatography (50-100% EtOAc/hexanes) to afford the title compound as a colorless film.

Intermediate 74

((2RS,5SR)-5-(Methylsulfonyl)tetrahydro-2H-pyran-2-yl)methanamine Hydrochloride

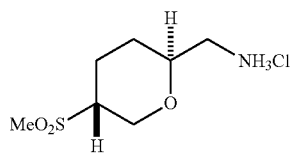

The title compound was prepared as described for the synthesis of Intermediate 35, using tert-butyl (((2RS,5SR)-5-(methylsulfonyl)tetrahydro-2H-pyran-2-yl)methyl)carbamate (Intermediate 73) in place of tert-butyl (((1s*,4s*)-1-cyano-4-(methylsulfonyl)cyclohexyl)methyl)carbamate.

Intermediate 75

S-((3RS,6RS)-6-(((tert-Butoxycarbonyl)amino)methyl)tetrahydro-2H-pyran-3-yl) ethanethioate

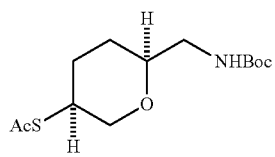

2,2'-Azobis(2-methylpropionitrile) (62 mg, 0.375 mmol) was added to a solution of tert-butyl ((3,4-dihydro-2H-pyran-2-yl)methyl)carbamate (800 mg, 3.75 mmol, Intermediate 69) and thioacetic acid (0.30 mL, 4.1 mmol), and the resulting solution was maintained at rt for 17 h. After this time, the mixture was concentrated and then purified by silica gel chromatography (0-40% EtOAc/hexanes) to afford the title compound as a colorless oil.

Intermediate 76

((2RS,5RS)-5-(Methylsulfonyl)tetrahydro-2H-pyran-2-yl)methanamine Hydrochloride

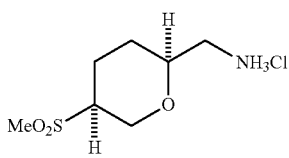

The title compound was prepared as described for the synthesis of Intermediate 74, using S-((3RS,6RS)-6-(((tert-butoxycarbonyl)amino)methyl)tetrahydro-2H-pyran-3-yl) ethanethioate (Intermediate 75) in place of S-((3RS,6SR)-6-(((tert-butoxycarbonyl)amino)methyl)tetrahydro-2H-pyran-3-yl) ethanethioate.

Intermediate 77

(S)-2-Methyl-N-(4-(methylsulfonyl)cyclohexylidene)propane-2-sulfinamide

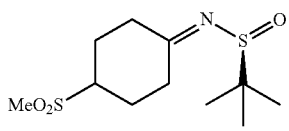

Titanium isopropoxide (7.0 mL, 24 mmol) and then (S)-2-methyl-2-propanesulfinamide (1.45 g, 12.0 mmol) were added to a solution of 4-(methylsulfonyl)cyclohexan-1-one (2.11 g, 12.0 mmol, Intermediate 5) in THF (24 mL), and the resulting solution was maintained at rt for 65 h. An equal volume of saturated aqueous NaHCO₃ solution was then added, and the mixture was filtered through Celite®. The filter cake was washed with THF, and then the filtrate and wash were combined and filtered again through Celite®. The layers of the filtrate were separated, and the aqueous layer was extracted with EtOAc. The organic layers were combined, dried with anhydrous MgSO₄, filtered, and then concentrated to afford a tan residue. This residue was purified by silica gel chromatography twice (first: 30→80% acetone/hexanes; second: 100% EtOAc) to afford the title compound as a colorless solid.

Intermediate 78

(S)-N-(1-Cyano-4-(methylsulfonyl)cyclohexyl)-2-methylpropane-2-sulfinamide

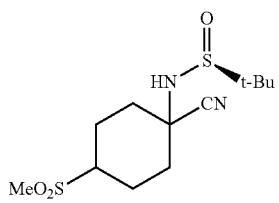 [SMILES: CC(C)(C)[S@](=O)NC1(C#N)CCC(S(C)(=O)=O)CC1]

A solution of Et₂AlCN (6.7 mL, 1.0 M in toluene, 6.7 mmol) was added to a 0-5° C. solution of (S)-2-methyl-N-(4-(methylsulfonyl)cyclohexylidene)propane-2-sulfinamide (930 mg, 3.33 mmol, Intermediate 77) in THF (15 mL), and the resulting solution was maintained at 0-5° C. for 10 min before it was allowed to warm to rt over 15 h. After this time, a saturated aqueous NH₄Cl solution was added, and the resulting mixture was diluted with EtOAc. The layers were mixed and then separated, and the aqueous layer was extracted twice with EtOAc. The organic layers were combined, dried with anhydrous MgSO₄, filtered, and then concentrated to afford the title compound as a yellow foam (dr=3:1).

Intermediate 79

Benzyl (((1s*,4R*)-1-(((S)-tert-butylsulfinyl)amino)-4-(methylsulfonyl)cyclohexyl)methyl) carbamate

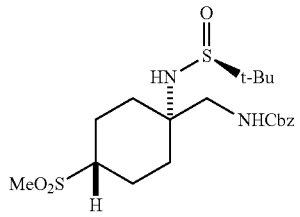 [SMILES: CC(C)(C)[S@](=O)N[C@]1(CNC(=O)OCc2ccccc2)CC[C@H](S(C)(=O)=O)CC1]

Intermediate 80

Benzyl (((1r*,4S*)-1-(((S)-tert-butylsulufinyl)amino)-4-(methysulfony)cyclo hexyl)methyl) carbamate

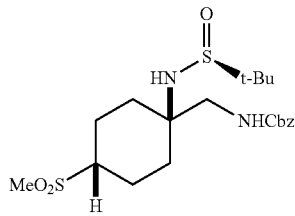 [SMILES: CC(C)(C)[S@](=O)N[C@]1(CNC(=O)OCc2ccccc2)CC[C@@H](S(C)(=O)=O)CC1]

A solution of AlH₃ (6.0 mL, 1.0 M in THF, 6.0 mmol) was added to a 0-5° C. reactor containing solid (S)-N-(1-cyano-4-(methylsulfonyl)cyclohexyl)-2-methylpropane-2-sulfinamide (737 mg, 2.41 mmol, Intermediate 78), and the resulting solution was allowed to warm to rt over 2 h. After this time, the solution was diluted with THF (15 mL), and then water (0.23 mL), 15% aqueous NaOH (0.23 mL), and more water (0.75 mL) were sequentially added. The resulting mixture was stirred for 20 min before Celite® was added, and the mixture was filtered then concentrated. The concentrate was diluted with toluene and a 1.0 N aqueous NaOH solution (6 mL, 1:1 v/v), and then CbzCl (0.35 mL, 2.4 mmol) was added, and the resulting mixture was stirred at rt for 16 h. After this time, EtOAc and water were added, and the layers were mixed then separated. The aqueous layer was extracted with EtOAc, and the organic layers were combined, washed with brine, dried with anhydrous MgSO₄, filtered, and then concentrated to afford a yellow film. This residue was purified by silica gel chromatography (100% EtOAc) to afford a pair of diastereomers, both as colorless films. The first-eluting diastereomer was Intermediate 79, and the second-eluting diastereomer was Intermediate 80.

Intermediate 81

(S)-N-((1s*,4R*)-1-(Aminomethyl)-4-(methylsulfonyl)cyclohexyl)-2-methylpropane-2-sulfinamide

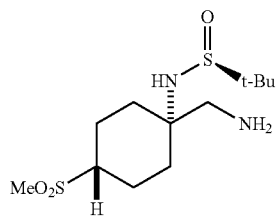 [SMILES: CC(C)(C)[S@](=O)N[C@]1(CN)CC[C@H](S(C)(=O)=O)CC1]

Benzyl (((1s*,4R*)-1-(((S)-tert-butylsulfinyl)amino)-4-(methylsulfonyl)cyclohexyl)methyl) carbamate (105 mg, 0.236 mmol, Intermediate 79) and Pd/C (250 mg, 0.12 mmol, 10% Pd dry basis, 50% water w/w, Degussa type E101 NE/W) were combined in a vessel, and the vessel was evacuated and then backfilled three times with nitrogen. Ethanol (2.6 mL) was added, and then the mixture was stirred under an atmosphere of hydrogen for 16 h. After this time, the mixture was filtered through Celite®, and the filter cake was washed with EtOH. The filtrate and wash were combined and then concentrated to afford the title compound as a colorless film.

Intermediate 82 tert-Butyl (((1RS,2SR,4SR)-2-hydroxy-4-(methylsulfonyl)cyclohexyl)methyl)carbamate

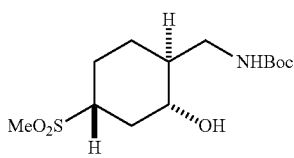

A solution of BH₃.THF in THF (30 mL, 1.0 M, 30 mmol) was added to a 0-5° C. solution of tert-butyl ((4-(methylsulfonyl)cyclohex-1-en-1-yl)methyl)carbamate (2.9 g, 10 mmol, Intermediate 17) in THF (30 mL), and the resulting solution was allowed to warm to rt over 16 h with stirring. After this time, the resulting mixture was cooled to 0-5° C. and then quenched with drops of water. When the bubbling ceased, 10% aqueous NaOH (8.0 mL, 22 mmol) and then H₂O₂ (2.5 mL, 50% w/w, 43 mmol) were added, and the mixture was stirred at rt for 5 h. After this time, the mixture was diluted with brine, and the layers were mixed then separated. The aqueous layer was extracted twice with EtOAc, and the combined organic layers were dried with anhydrous MgSO₄, filtered, and then concentrated to afford a colorless gum. This residue was purified by silica gel chromatography (75-100% EtOAc/hexanes) to afford the first-eluting diastereomer as a colorless solid. This solid was purified further by crystallizing it from boiling i-PrOAc (12 mL) to afford the title compound as a colorless solid.

Intermediate 83

(1RS,2SR,5RS)-2-(Aminomethyl)-5-(methylsulfonyl)cyclohexan-1-ol Hydrochloride

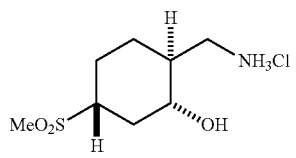

The title compound was prepared as described for the synthesis of Intermediate 35, using tert-butyl (((1RS,2SR,4SR)-2-hydroxy-4-(methylsulfonyl)cyclohexyl)methyl)carbamate (Intermediate 82) in place of tert-butyl (((1s*,4s*)-1-cyano-4-(methylsulfonyl)cyclohexyl)methyl)carbamate.

Intermediate 84

Tert-Butyl (((1RS,2RS,4RS)-1,2-dihydroxy-4-(methylsulfonyl)cyclohexyl)methyl)carbamate

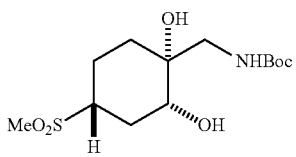

Intermediate 85

Tert-Butyl (((1RS,2RS,4SR)-1,2-dihydroxy-4-(methylsulfonyl)cyclohexyl)methyl)carbamate

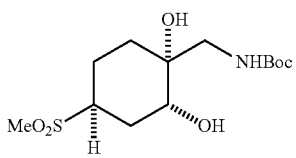

Intermediate 18 was purified by silica gel chromatography (80-100% EtOAc/hexanes) to give a pair of diastereomers. The first-eluting diastereomer was Intermediate 84, and the second-eluting diastereomer was Intermediate 85.

Intermediate 86

(1RS,2RS,4RS)-1-(Aminomethyl)-4-(methylsulfonyl)cyclohexane-1,2-diol Hydrochloride

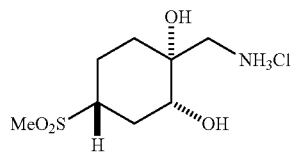

The title compound was prepared as described for the synthesis of Intermediate 35, using tert-butyl (((1RS,2RS,4RS)-1,2-dihydroxy-4-(methylsulfonyl)cyclohexyl)methyl)carbamate (Intermediate 84) in place of tert-butyl (((1s*,4s*)-1-cyano-4-(methylsulfonyl)cyclohexyl)methyl)carbamate.

Intermediate 87

(1RS,2RS,4SR)-1-(Aminomethyl)-4-(methylsulfonyl)cyclohexane-1,2-diol Hydrochloride

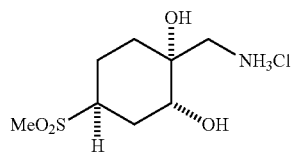

The title compound was prepared as described for the synthesis of Intermediate 35, using tert-butyl (((1RS,2RS,4SR)-1,2-dihydroxy-4-(methylsulfonyl)cyclohexyl)methyl)carbamate (Intermediate 85) in place of tert-butyl (((1s*,4s*)-1-cyano-4-(methylsulfonyl)cyclohexyl)methyl)carbamate.

Intermediate 88

(S*)-3,3,3-Trifluoro-2-methylpropanoic Acid

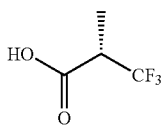

A solution of 2-(trifluoromethyl)acrylic acid (60.0 g, 0.429 mol), dicyclohexylamine (77.6 g, 0.428 mol), and (R)-RuCl[(p-cymene(BINAP)]Cl (3.96 g, 4.26 mmol) in MeOH (1.2 L) was stirred under an atmosphere of hydrogen (4-5 MPa) at 35-40° C. for 48 h. After this time, the mixture was filtered, and then the filtrate was concentrated. The concentrate was diluted with MTBE and EtOAc (600 mL, 1:1 v/v), and the solution was washed with a 10% aqueous Na$_2$CO$_3$ solution (300 mL×3). The aqueous phases were combined, and the pH was adjusted to pH 2-4 with aqueous HCl. The resulting mixture was filtered, and the filtrate was extracted with three times with MTBE. The organic layers were combined, dried with anhydrous Na$_2$SO$_4$, filtered, and then concentrated to give a yellow liquid (82.6% ee).

(S)-(+)-1,2,3,4-Tetrahydronaphthalen-1-amine (14.6 g, 99.2 mmol) was added dropwise to a 30° C. solution of (S*)-3,3,3-trifluoro-2-methylpropanoic acid from the previous step (17.6 g, 0.124 mol) in MTBE (210 mL), and then the mixture was cooled to 20° C. and stirred for 16 h. After this time, the suspension was filtered and the filter cake was dried to give (S)-1,2,3,4-tetrahydronaphthalen-1-amine (S*)-3,3,3-trifluoro-2-methylpropanoic acid salt as a colorless solid (dr=97.4:2.6).

A 5% aqueous KHSO$_4$ solution (400 mL) was added to a suspension of (S)-1,2,3,4-tetrahydronaphthalen-1-amine (S*)-3,3,3-trifluoro-2-methylpropanoic acid salt (26.7 g, 92.4 mmol) from the previous step in MTBE (260 mL), and the mixture was stirred until the solids dissolved. The layers were then separated, and the aqueous layer was extracted three times with MTBE. The organic layers were combined, washed twice with a 5% aqueous KHSO$_4$ solution, washed with water, and then concentrated to afford the title compound as yellow liquid (95.0% ee).

Intermediate 89

(S*)-3,3,3-Trifluoro-2-methylpropan-1-ol

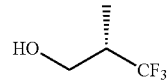

Lithium aluminum hydride (15.0 g, 0.369 mol) was added in portions to a stirring solution of (S*)-3,3,3-trifluoro-2-methylpropanoic acid (34.6 g, 0.244 mol, Intermediate 88) in Et$_2$O (350 mL), which was cooled in an ice bath, at a rate that maintained the internal temperature below 15° C. The mixture was then allowed to warm to 20° C., and stirring was continued for 2 h. After this time, water (25 mL) was carefully added, and then the mixture was dried with anhydrous Na$_2$SO$_4$, filtered, and then concentrated under atmospheric pressure to give the title compound as a colorless liquid (95.8% ee).

Intermediate 90

(R*)-1,1,1-Trifluoro-3-iodo-2-methylpropane

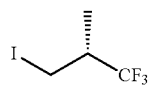

Iodine (44.58 g, 175.6 mmol) was added in five portions to a stirring solution of (S*)-3,3,3-trifluoro-2-methylpropan-1-ol (15.0 g, 117 mmol, Intermediate 89), PPh$_3$ (46.07 g, 175.6 mmol) and imidazole (11.96 g, 175.7 mmol) in NMP (75 mL) at a rate that maintained the internal temperature between 40 and 50° C. The mixture was then warmed to 55-60° C. and stirred until the reaction went to completion.

Intermediate 91

(S*)-1,1,1-Trifluoro-3-iodo-2-methylpropane

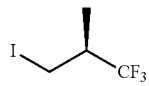

The title compound was prepared as described for the synthesis of Intermediate 90, using (S)-RuCl[(p-cymene(BINAP)]Cl and (S)-(−)-phenylethylamine in place of (R)-RuCl[(p-cymene(BINAP)]Cl and (S)-(+)-1,2,3,4-tetrahydronaphthalen-1-amine, respectively.

Intermediate 92

3,3,3-Trifluoro-2,2-dimethylpropan-1-ol

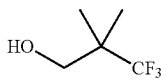

A solution of 3,3,3-trifluoro-2,2-dimethylpropanoic acid (340 g, 2.18 mol) in Et$_2$O (340 mL) was added dropwise to a −15 to −5° C. suspension of LAH (108 g, 2.83 mol) in Et$_2$O (3.1 L), and the mixture was stirred for 15 min. After this time, water (108 mL), 15% aqueous NaOH (108 mL), and more water (324 mL) were added at a rate that maintained the internal temperature at 0-10° C. Anhydrous MgSO$_4$ was then added, and the mixture was stirred for 30 min. The mixture was then filtered, and the filter cake was washed with Et$_2$O. The filtrate and wash were combined and then concentrated to afford the title compound as a pale-yellow liquid.

Intermediate 93

1,1,1-Trifluoro-3-iodo-2,2-dimethylpropane

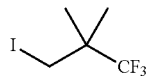

Iodine (536 g, 2.11 mol) was added in five portions to a stirring solution of PPh$_3$ (554 g, 2.11 mol), 3,3,3-trifluoro-2,2-dimethylpropan-1-ol (200 g, 1.41 mol, Intermediate 92), and imidazole (144 g, 2.11 mol) in NMP (1.0 L) at a rate that maintained the internal temperature between 45 and 50° C. The mixture was then warmed to 95-100° C. and stirred until the reaction went to completion. The reaction mixture was then allowed to cool to 50-65° C. and purified by distillation to give the title compound as a solution in NMP (58% w/w, bp 50-65° C. at 1-2 mmHg).

Intermediate 94

9-(3,3,3-Trifluoro-2-methylpropyl)-9-borabicyclo[3.3.1]nonane (0.5 M in THF)

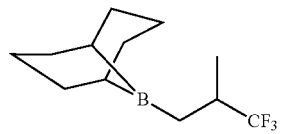

The 3,3,3-trifluoro-2-methylprop-1-ene (6.5 g, 59 mmol) was condensed into a pressure vessel at −78° C. before a solution of 9-BBN in THF (100 mL, 0.5 M, 50 mmol) was slowly added. The vessel was then sealed and the suspension was allowed to warm to rt over 2 h. The resulting solution was then maintained at 65° C. for 18 h before it was allowed to cool to rt, sparged with argon, and then transferred to a Schlenk flask for storage.

Intermediate 95

9-(3,3,3-Trifluoropropyl)-9-borabicyclo[3.3.1]nonane (0.5 M in THF)

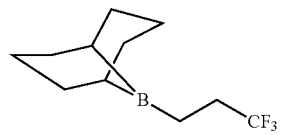

The title compound was prepared as described for the synthesis of Intermediate 94, using 3,3,3-trifluoroprop-1-ene in place of 3,3,3-trifluoro-2-methylprop-1-ene.

Intermediate 96

1-(4-Bromo-2-methoxyphenyl)ethan-1-one

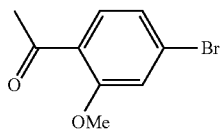

Iodomethane (150 mL, 2.20 mol) was added dropwise to a mixture of 1-(4-bromo-2-hydroxyphenyl)ethanone (318 g, 1.48 mol) and K$_2$CO$_3$ (407 g, 2.95 mol) in DMF (1.0 L), and the reaction mixture was stirred at rt for 14 h. After this time, the reaction mixture was diluted with water, and the resulting mixture was extracted three times with EtOAc. The combined organic layers were washed with brine, dried with anhydrous Na$_2$SO$_4$, filtered, and concentrated to afford 320 g of a yellow solid. This solid was suspended in petroleum ether and EtOAc (500 mL, 10:1 v/v), stirred for 30 min, filtered, and then dried to afford the title compound as a colorless solid.

Intermediate 97, Step a

Ethyl 4-(4-bromo-2-methoxyphenyl)-2,4-dioxobutanoate

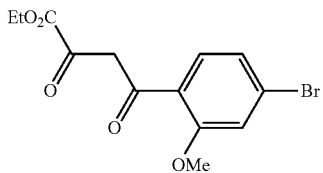

Lithium bis(trimethylsilyl)amide (301 mL, 1 M in THF, 301 mmol) was added dropwise to a −78° C. solution of 1-(4-bromo-2-methoxyphenyl)ethan-1-one (60.0 g, 262 mmol, Intermediate 96) in anhydrous THF (1 L) under nitrogen, and the resulting mixture was stirred at −78° C. for an additional 30 min. A solution of diethyl oxalate (38.2 g, 262 mmol) in THF (200 mL) was then added dropwise to the resulting thick suspension. After the addition was complete, the stirring reaction mixture was allowed to warm to rt over 18 h. After this time, the reaction mixture was poured into a concentrated aqueous HCl solution and ice water (500 mL, 1:10 v/v), and the resulting mixture was extracted three times with EtOAc. The combined organic layers were washed with brine, dried with anhydrous $Na_2SO_4$, filtered, and then concentrated to afford a yellow solid.

The procedure above was carried out three additional times. The crude solids from each run were combined, suspended in petroleum ether and EtOAc (1 L, 5:1 v/v), stirred for 30 min, filtered, and then dried to give the title compound as a yellow solid.

Intermediate 97, Step b

Ethyl 5-(4-bromo-2-methoxyphenyl)-1-ethyl-1H-pyrazole-3-carboxylate

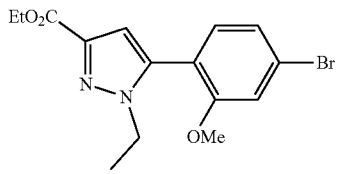 [SMILES: CCOC(=O)c1cc(-c2ccc(Br)cc2OC)n(CC)n1]

A mixture of ethyl 4-(4-bromo-2-methoxyphenyl)-2,4-dioxobutanoate (120 g, 364 mmol, Intermediate 97, Step a) and ethylhydrazine hydrochloride (34.9 g, 364 mmol) in EtOH (800 mL) was heated at reflux temperature for 3 h. After this time, the reaction mixture was allowed to cool to rt and then concentrated. The concentrate was purified by silica gel chromatography (5:1 EtOAc/petroleum ether) to afford the title compound as an orange solid.

Intermediate 97, Step c

Ethyl 5-(4-bromo-2-methoxyphenyl)-4-chloro-1-ethyl-1H-pyrazole-3-carboxylate

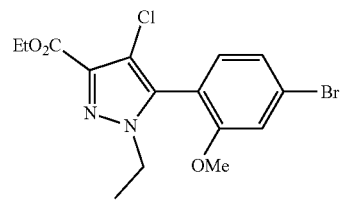 [SMILES: CCOC(=O)c1nn(CC)c(-c2ccc(Br)cc2OC)c1Cl]

N-Chlorosuccinimide (34.8 g, 260 mmol) was added to a solution of ethyl 5-(4-bromo-2-methoxyphenyl)-1-ethyl-1H-pyrazole-3-carboxylate (92.0 g, 260 mmol, Intermediate 97, Step b) and TFA (20 mL, 260 mmol) in MeCN (550 mL), and the reaction mixture was stirred at 60° C. for 3 h. An additional portion of NCS (3.48 g, 26.0 mmol) was then added, and stirring was continued for 1 h. After this time, the reaction mixture was allowed to cool, concentrated, and then purified by silica gel chromatography (5:1 EtOAc/petroleum ether) to afford the title compound as a colorless solid.

Intermediate 98

Ethyl 4-chloro-1-ethyl-5-(2-methoxy-4-(3,3,3-trifluoro-2-methylpropyl)phenyl)-1H-pyrazole-3-carboxylate

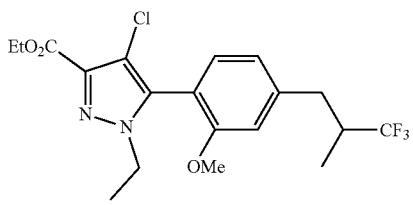

Ethyl 5-(4-bromo-2-methoxyphenyl)-4-chloro-1-ethyl-1H-pyrazole-3-carboxylate (510 mg, 1.32 mmol, Intermediate 97, Step c), $K_2CO_3$ (360 mg, 2.63 mmol), and Pd(dppf)Cl$_2$.DCM (53 mg, 65 mmol) were combined in a vessel, and the vessel was evacuated and backfilled with nitrogen three times. A solution of 9-(3,3,3-trifluoro-2-methylpropyl)-9-borabicyclo[3.3.1]nonane (3.2 mL, 0.5 M in THF, 1.6 mmol, Intermediate 94) and DMF (3.2 mL) were then added, and the resulting mixture was stirred at 65° C. for 2 h. After this time, the mixture was allowed to cool, and then it was diluted with EtOAc and water. The layers were separated, and the organic layer was washed with water, washed with brine, dried with anhydrous $MgSO_4$, filtered, and then concentrated. The residue was purified by silica gel chromatography (10-40% EtOAc/hexanes) to afford the title compound as a yellow oil.

Intermediate 99

Ethyl (R*)-4-chloro-1-ethyl-5-(2-methoxy-4-(3,3,3-trifluoro-2-methylpropyl)phenyl)-1H-pyrazole-3-carboxylate

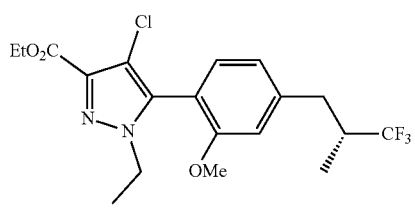 [SMILES: CCOC(=O)c1nn(CC)c(-c2ccc(C[C@@H](C)C(F)(F)F)cc2OC)c1Cl]

Intermediate 100

Ethyl (S*)-4-chloro-1-ethyl-5-(2-methoxy-4-(3,3,3-trifluoro-2-methylpropyl)phenyl)-1H-pyrazole-3-carboxylate

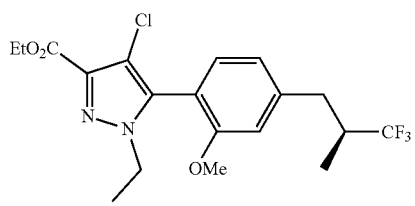 [SMILES: CCOC(=O)c1nn(CC)c(-c2ccc(C[C@H](C)C(F)(F)F)cc2OC)c1Cl]

Intermediate 98 was purified by SFC using a chiral stationary phase (Chiralpak AD-H, 98.24% $CO_2$, 1.76% i-PrOH) to give a pair of enantiomers. The first-eluting enantiomer was Intermediate 99, and the second-eluting enantiomer was Intermediate 100.

Intermediate 101

1-(4-Bromo-2-(difluoromethoxy)phenyl)ethan-1-one

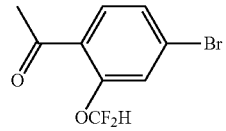

A solution of 1-(4-bromo-2-hydroxyphenyl)ethanone (152 g, 0.707 mol) in MeCN (3.0 L) was added dropwise to a stirring −10° C. solution of KOH (793 g, 14.1 mol) in water (3.0 L). The mixture was then cooled to −30° C. before diethyl (bromodifluoromethyl)phosphonate (377 g, 1.41 mol) was added one portion, and the resulting mixture was stirred at −30° C. for 20 min. The mixture was then allowed to warm to 10° C. and stirred for 1 h. After this time, the reaction mixture was extracted twice with MTBE. The organic layers were combined, dried over anhydrous $Na_2SO_4$, filtered, and then concentrated. The concentrate was slurried in n-heptane and then filtered. The filter cake was washed with n-heptane and then dried to afford the title compound as a colorless solid.

Intermediate 102, Step a

Ethyl 4-(4-bromo-2-(difluoromethoxy)phenyl)-2,4-dioxobutanoate

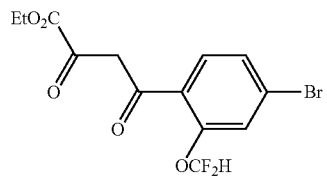

A solution of LiHMDS in THF (484 mL, 1.0 M, 484 mmol) was diluted with THF (1100 mL) and cooled to −60° C. 1-(4-Bromo-2-(difluoromethoxy)phenyl)ethan-1-one (110 g, 0.415 mol, Intermediate 101) in THF (550 mL) was then added dropwise at a rate that maintained the internal temperature at −60° C. The mixture was then cooled to −70 to −78° C. and stirred for 1h. After this time, a solution of diethyloxalate (71 g, 490 mmol) in THF (110 mL) was added, and the reaction mixture was allowed to warm to 10° C. with stirring over 30 min. The reaction mixture was then diluted with a saturated aqueous $NH_4Cl$ solution and EtOAc. The layers were mixed and then separated, and the aqueous layer was extracted with EtOAc. The combined organic layers were washed with 1 N aqueous HCl dried with anhydrous $Na_2SO_4$, filtered, and then concentrated. The concentrate was slurried with n-heptane/EtOAc (6:1 v/v) at 15° C. for 0.5 h. After this time, the mixture was filtered, and the filter cake was washed with n-heptane/EtOAc (6:1 v/v) and then dried to afford the title compound.

Intermediate 102, Step b

Ethyl 5-(4-bromo-2-(difluoromethoxy)phenyl)-1-ethyl-1H-pyrazole-3-carboxylate

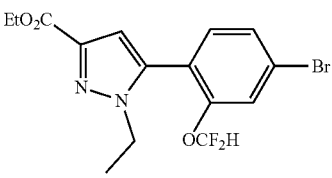

Concentrated aqueous HCl (1.1 mL, 37% w/w, 13 mmol) was added to a solution of ethyl 4-(4-bromo-2-(difluoromethoxy)phenyl)-2,4-dioxobutanoate (50 g, 140 mmol, Intermediate 102, Step a) and ethyl hydrazine oxalate (22.6 g, 151 mmol) in EtOH (500 mL), and the reaction mixture was stirred at 60° C. for 2h. After this time, the mixture was concentrate and then diluted with DCM and water. The layers were mixed and then separated, and the aqueous layer was extracted with DCM. The combined organic layers were then dried with anhydrous $Na_2SO_4$, filtered, and then concentrated. The concentrate was combined another batch prepared in a similar way and then purified by silica gel chromatography (EtOAc/DCM, 100:1 v/v) to afford the title compound.

111

Intermediate 102, Step c

Ethyl 5-(4-bromo-2-(difluoromethoxy)phenyl)-4-chloro-1-ethyl-1H-pyrazole-3-carboxylate

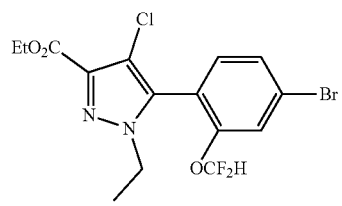

Sulfuryl chloride (40.4 g, 299 mmol) was added to a stirring 0° C. solution of ethyl 5-(4-bromo-2-(difluoromethoxy)phenyl)-1-ethyl-1H-pyrazole-3-carboxylate (106 g, 0.272 mol, Intermediate 102, Step b) in DCM (1.1 L), and then the mixture was allowed to warm to 20° C. over 16 h. After this time, the mixture was concentrate and then diluted with EtOAc and a 10% aqueous $K_2CO_3$ solution. The layers were mixed and then separated, and the aqueous layer was extracted with EtOAc. The combined organic layers were dried with anhydrous $Na_2SO_4$, filtered, and then concentrated to afford the title compound.

Intermediate 103

Ethyl 4-chloro-5-(2-(difluoromethoxy)-4-(3,3,3-trifluoro-2,2-dimethylpropyl)phenyl)-1-ethyl-1H-pyrazole-3-carboxylate

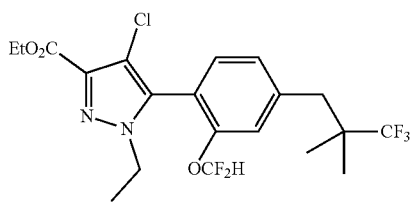

1,1,1-Trifluoro-3-iodo-2,2-dimethylpropane (0.14 mL, 1.71 g/mL, 0.94 mmol, Intermediate 93) was added to a suspension of Rieke® zinc in THF (1.2 mL, 0.05 g/mL, 0.89 mmol), and the resulting suspension was stirred at 65° C. for 1 h. Ethyl 5-(4-bromo-2-(difluoromethoxy)phenyl)-4-chloro-1-ethyl-1H-pyrazole-3-carboxylate (250 mg, 0.590 mmol, Intermediate 102, Step c), $Pd(OAc)_2$ (7 mg, 0.03 mmol), and X-Phos (28 mg, 0.059 mmol) were combined in a separate vessel, and the vessel was evacuated and backfilled with nitrogen three times. The organozinc suspension was added to the vessel containing the aryl bromide via cannula transfer, and the resulting suspension was stirred at 65° C. for 30 min. After this time, the mixture was allowed to cool and then it was diluted with a saturated aqueous $NH_4Cl$ solution and EtOAc. Water was added, the layers were separated, and the aqueous layer was extracted twice with EtOAc. The combined organic layers were washed with brine, dried with anhydrous $MgSO_4$, filtered, and then concentrated. The residue was purified by silica gel chromatography (10-30% EtOAc/hexanes) to afford the title compound as a pale yellow film.

112

Intermediate 104

Ethyl (S*)-4-chloro-5-(2-(difluoromethoxy)-4-(3,3,3-trifluoro-2-methylpropyl)phenyl)-1-ethyl-1H-pyrazole-3-carboxylate

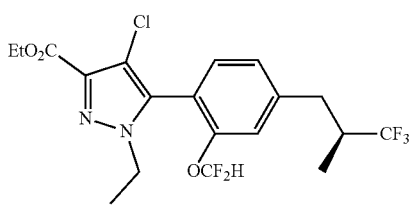

A suspension of Rieke® zinc in THF (39 mL, 0.05 g/mL, 30 mmol) was added to (R*)-1,1,1-trifluoro-3-iodo-2-methylpropane (12.8 g, 50.5% w/w in NMP, 27.1 mmol, Intermediate 90), and the resulting mixture was stirred at 60-65° C. for 1 h. After this time, the mixture was allowed to cool to rt, and then LiBr (3.02 g, 34.8 mmol), PEPPSI-IPr (0.37 g, 5.5 mmol), and ethyl 5-(4-bromo-2-(difluoromethoxy) phenyl)-4-chloro-1-ethyl-1H-pyrazole-3-carboxylate (4.60 g, 0.109 mol, Intermediate 102, Step c) were added. The resulting mixture was stirred at 25-30° C. for 16 h. After this time, the mixture was poured into a 5% aqueous citric acid solution. The resulting mixture was diluted with MTBE and then filtered. The filter cake was washed with MTBE. The layers of the combined filtrate and wash were mixed and then separated, and the aqueous layer was extracted with MTBE. The organic layers were combined, washed with water, and then concentrated. The concentrate was purified by silica gel chromatography (15→30% EtOAc/hexanes) to afford the title compound as a light-yellow solid.

Intermediate 105

Ethyl (S*)-5-(2-(difluoromethoxy)-4-(3,3,3-trifluoro-2-methylpropyl)phenyl)-1-ethyl-4-methyl-1H-pyrazole-3-carboxylate

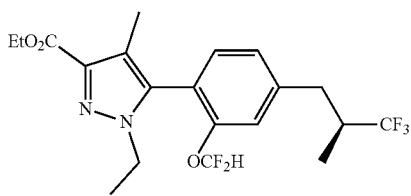

Ethyl (S*)-4-chloro-5-(2-(difluoromethoxy)-4-(3,3,3-trifluoro-2-methylpropyl)phenyl)-1-ethyl-1H-pyrazole-3-carboxylate (732 mg, 1.60 mmol, Intermediate 104), RuPhos G1 precatalyst (65 mg, 0.079 mmol), RuPhos (37 mg, 0.079 mmol), and $K_2CO_3$ (872 mg, 6.31 mmol) were combined in a vessel, and the vessel was evacuated and backfilled with nitrogen three times. 1,4-Dioxane (9 mL) and then 2,4,6-trimethyl-1,3,5,2,4,6-trioxatriborinane (0.44 mL, 3.2 mmol) were added, and the mixture was stirred at 100° C. for 14 h. After this time, the mixture was allowed to cool and then diluted with EtOAc and water. The layers were separated, and the aqueous layer was extracted with EtOAc. The combined organic layers were dried with anhydrous $MgSO_4$, filtered, and then concentrated. The residue was purified by silica gel chromatography (15-30% EtOAc/hexanes) to afford the title compound as a colorless oil.

Intermediate 106

Ethyl (R)-4-chloro-1-ethyl-5-(2-methoxy-4-((1,1,1-trifluoropropan-2-yl)amino)phenyl)-1H-pyrazole-3-carboxylate

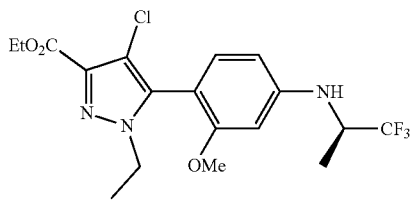 [SMILES: CCOC(=O)c1nn(CC)c(-c2ccc(N[C@H](C)C(F)(F)F)cc2OC)c1Cl]

Ethyl 5-(4-bromo-2-methoxyphenyl)-4-chloro-1-ethyl-1H-pyrazole-3-carboxylate (1.69 g, 4.36 mmol, Intermediate 97, Step c), RuPhos G1 precatalyst (178 mg, 0.218 mmol), RuPhos (102 mg, 0.218 mmol), and $Cs_2CO_3$ (4.26 g, 13.0 mmol) were combined in a vessel, and the vessel was evacuated and backfilled with nitrogen three times. (R)-1,1,1-Trifluoro-2-propylamine (0.62 mL, 17 mmol) and 1,4-dioxane (8.8 mL) were then added, and the mixture was stirred at 110° C. for 1 h. After this time, the reaction mixture was allowed to cool to rt and then was diluted with EtOAc and water. The layers were mixed and then separated, and the aqueous layer was extracted twice with EtOAc. The combined organic layers were dried with anhydrous $MgSO_4$, filtered, and then concentrated. The residue was purified by silica gel chromatography (15→50% EtOAc/hexanes) to afford the title compound as a colorless foam.

Intermediate 107

4-Bromo-N,2-dimethoxy-N-methylbenzamide

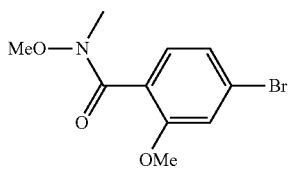

N-(3-Dimethylaminopropyl)-N'-ethylcarbodiimide hydrochloride (13.9 g, 72.7 mmol) and then TEA (12.2 g, 121 mmol) were added to a 0° C. solution of 4-bromo-2-methoxybenzoic acid (14.0 g, 60.6 mmol) and N,O-dimethylhydroxylamine hydrochloride (6.5 g, 67 mmol) in DCM (300 mL), and the resulting mixture was stirred at rt for 14 h. After this time, the reaction mixture was washed with water, washed with a saturated aqueous $NH_4Cl$ solution, washed brine, dried with anhydrous $Na_2SO_4$, filtered, and then concentrated to afford the title compound as yellow oil.

Intermediate 108

1-(4-Bromo-2-methoxyphenyl)propan-1-one

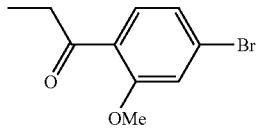

Ethylmagnesium chloride in $Et_2O$ (3.3 mL, 3.0 M, 10 mmol) was added to a 0° C. solution of 4-bromo-N,2-dimethoxy-N-methylbenzamide (1.37 g, 5.00 mmol, Intermediate 107) in THF (20 mL), and the reaction mixture was allowed to warm to rt over 3 h with stirring. After this time, a saturated aqueous $NH_4Cl$ solution was added, and then the mixture was extracted three times with EtOAc. The combined organic layers were washed with brine, dried with anhydrous $Na_2SO_4$, filtered, and then concentrated to afford the title compound as light-yellow oil.

Intermediate 109

Ethyl 5-(4-bromo-2-methoxyphenyl)-1-ethyl-4-methyl-1H-pyrazole-3-carboxylate

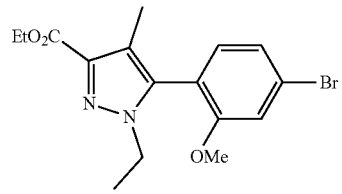 [SMILES: CCOC(=O)c1nn(CC)c(-c2ccc(Br)cc2OC)c1C]

The title compound was prepared as described for the synthesis of Intermediate 97, Step b, using in step a 1-(4-bromo-2-methoxyphenyl)propan-1-one (Intermediate 108) in place of 1-(4-bromo-2-methoxyphenyl)ethan-1-one.

Intermediate 110

Ethyl (R)-4-chloro-5-(2-methoxy-4-((1,1,1-trifluoropropan-2-yl)amino)phenyl)-1-propyl-1H-pyrazole-3-carboxylate

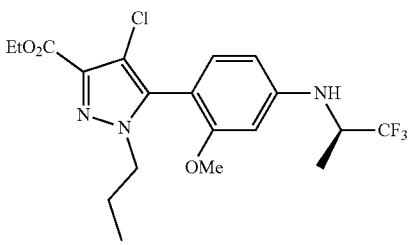 [SMILES: CCCn1nc(C(=O)OCC)c(Cl)c1-c1ccc(N[C@H](C)C(F)(F)F)cc1OC]

The title compound was prepared as described for the synthesis of Intermediate 106, using propylhydrazine hydrochloride in place of ethylhydrazine hydrochloride.

Intermediate 111

Ethyl 4-chloro-5-(2-methoxy-4-(3,3,3-trifluoro-2-methylpropyl)phenyl)-1-propyl-1H-pyrazole-3-carboxylate

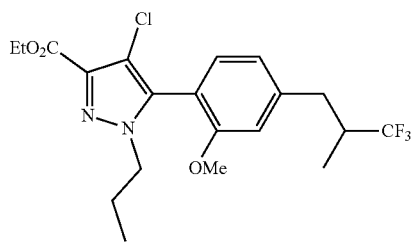 [SMILES: CCCn1nc(C(=O)OCC)c(Cl)c1-c1ccc(CC(C)C(F)(F)F)cc1OC]

The title compound was prepared as described for the synthesis of Intermediate 98, using propylhydrazine hydrochloride in place of ethylhydrazine hydrochloride.

Intermediate 112

Ethyl (R*)-4-chloro-5-(2-methoxy-4-(3,3,3-trifluoro-2-methylpropyl)phenyl)-1-propyl-1H-pyrazole-3-carboxylate

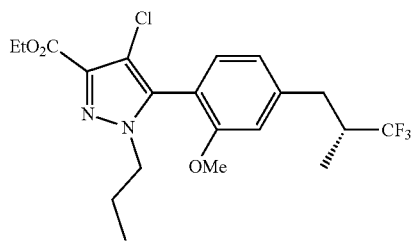 [SMILES: CCCn1nc(C(=O)OCC)c(Cl)c1-c1ccc(C[C@@H](C)C(F)(F)F)cc1OC]

Intermediate 113

Ethyl (S*)-4-chloro-5-(2-methoxy-4-(3,3,3-trifluoro-2-methylpropyl)phenyl)-1-propyl-1H-pyrazole-3-carboxylate

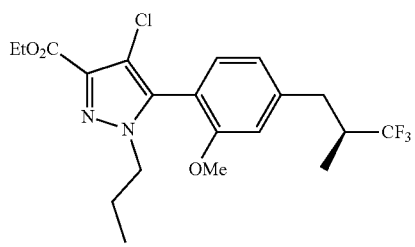 [SMILES: CCCn1nc(C(=O)OCC)c(Cl)c1-c1ccc(C[C@H](C)C(F)(F)F)cc1OC]

Intermediate 111 was purified by SFC using a chiral stationary phase (Chiralpak AD-H, 98.5% $CO_2$, 1.5% i-PrOH with 0.3% i-PrNH$_2$) to give a pair of enantiomers. The first-eluting enantiomer was Intermediate 112, and the second-eluting enantiomer was Intermediate 113.

Intermediate 114

Ethyl (R)-4-chloro-1-isobutyl-5-(2-methoxy-4-((1,1,1-trifluoropropan-2-yl)amino)phenyl)-1H-pyrazole-3-carboxylate

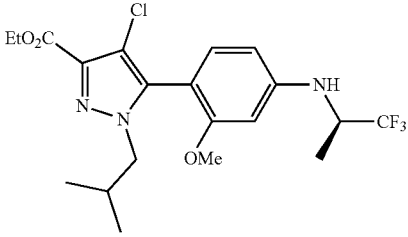 [SMILES: CCOC(=O)c1nn(CC(C)C)c(-c2ccc(N[C@H](C)C(F)(F)F)cc2OC)c1Cl]

The title compound was prepared as described for the synthesis of Intermediate 106, using isobutylhydrazine hydrochloride in place of ethylhydrazine hydrochloride.

Intermediate 115

Ethyl (R)-1-(tert-butyl)-4-chloro-5-(2-methoxy-4-((1,1,1-trifluoropropan-2-butyl)-4-chloro-5-yl)amino)phenyl)-1H-pyrazole-3-carboxylate

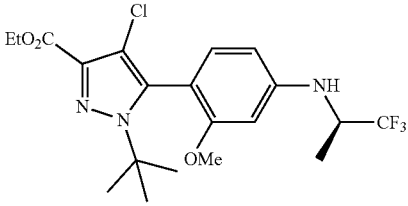 [SMILES: CCOC(=O)c1nn(C(C)(C)C)c(-c2ccc(N[C@H](C)C(F)(F)F)cc2OC)c1Cl]

The title compound was prepared as described for the synthesis of Intermediate 106, using tert-butylhydrazine hydrochloride in place of ethylhydrazine hydrochloride.

Intermediate 116

Ethyl (R)-4-chloro-5-(2-(difluoromethoxy)-4-(3,3,3-trifluoro-2-methylpropyl)phenyl)-1-ethyl-1H-pyrazole-3-carboxylate

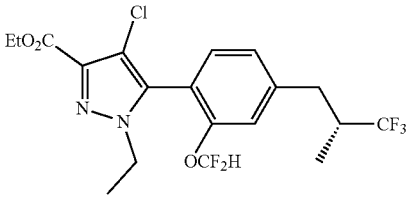

(S*)-1,1,1-Trifluoro-3-iodo-2-methylpropane (0.67 g, 2.8 mmol, Intermediate 91) was added to a suspension of Rieke® zinc in THF (3.7 mL, 0.05 g/mL, 2.8 mmol), and the resulting suspension was stirred at 60° C. for 2 h. Ethyl 5-(4-bromo-2-(difluoromethoxy)phenyl)-4-chloro-1-ethyl-1H-pyrazole-3-carboxylate (1.00 g, 2.36 mmol, Intermediate 102, Step c) and Pd(t-Bu$_3$P)$_2$ (60 mg, 0.12 mmol) were combined in a separate vessel, and the vessel was evacuated and backfilled with nitrogen three times. The organozinc suspension was then added to the vessel containing the aryl bromide by cannula transfer, and the resulting suspension was stirred at 65° C. for 30 min before it was allowed to cool to rt. The mixture was then diluted with EtOAc and a saturated aqueous NH₄Cl solution and filtered through a pad of Celite®. The pad was washed with EtOAc and water, and the layers of the combined filtrate and wash were separated. The aqueous layer was extracted with EtOAc, and the combined organic layers were washed with brine, dried with anhydrous MgSO₄, filtered, and then concentrated. The residue was purified by silica gel chromatography (15→30% EtOAc/hexanes) to afford the title compound as a colorless oil.

Intermediate 117

Ethyl 4-chloro-1-ethyl-5-(2-methoxy-4-(3,3,3-trifluoro-2,2-dimethylpropyl)phenyl)-1H-pyrazole-3-carboxylate

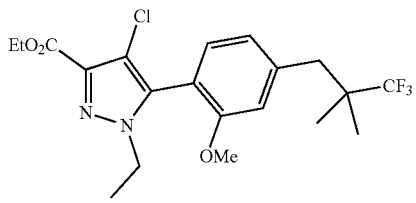 [SMILES: CCOC(=O)c1nn(CC)c(-c2ccc(CC(C)(C)C(F)(F)F)cc2OC)c1Cl]

The title compound was prepared as described for the synthesis of Intermediate 116, using ethyl 5-(4-bromo-2-methoxyphenyl)-4-chloro-1-ethyl-1H-pyrazole-3-carboxylate (Intermediate 97, Step c) and 1,1,1-trifluoro-3-iodo-2,2-dimethylpropane (Intermediate 93) in place of ethyl 5-(4-bromo-2-(difluoromethoxy)phenyl)-4-chloro-1-ethyl-1H-pyrazole-3-carboxylate and (S*)-1,1,1-trifluoro-3-iodo-2-methylpropane.

Intermediate 118

Ethyl 5-(4-bromo-2-(methoxy-d₃)phenyl)-4-chloro-1-ethyl-1H-pyrazole-3-carboxylate

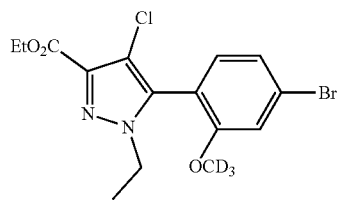

The title compound was prepared as described for the synthesis of Intermediate 97, Step c, using iodomethane-d₃ in place of iodomethane.

Intermediate 119

Ethyl 4-chloro-1-ethyl-5-(2-(methoxy-d₃)-4-(3,3,3-trifluoro-2,2-dimethylpropyl)phenyl)-1H-pyrazole-3-carboxylate

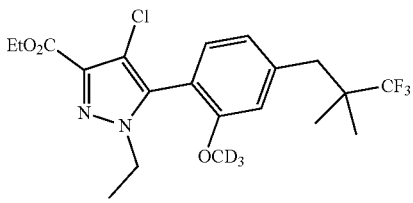

The title compound was prepared as described for the synthesis of Intermediate 116, using ethyl 5-(4-bromo-2-(methoxy-d₃)phenyl)-4-chloro-1-ethyl-1H-pyrazole-3-carboxylate (Intermediate 118) in place of ethyl 5-(4-bromo-2-(difluoromethoxy)phenyl)-4-chloro-1-ethyl-1H-pyrazole-3-carboxylate.

Intermediate 120 tert-Butyl (((1s*,4s*)-1-(hydroxymethyl)-4-(methylsulfonyl)cyclohexyl)methyl)carbamate

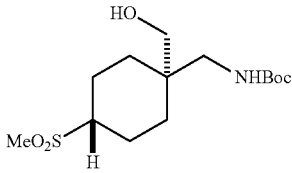

Sodium borohydride was added to a stirring solution of tert-butyl (((1s*,4s*)-1-formyl-4-(methylsulfonyl)cyclohexyl)methyl)carbamate (220 mg, 0.69 mmol, Intermediate 33) in MeOH (4.5 mL) at 0° C. After 30 minutes, the mixture was removed from the cooling bath and allowed to warm to rt. After 1 h, methanol was added, and then the mixture was concentrated. The residue was diluted with THF and filtered through silica gel with THF washing. The filtrate and wash were combined and concentrated to afford the title compound.

Intermediate 121

((1s*,4s*)-1-(Aminomethyl)-4-(methylsulfonyl)cyclohexyl)methanol Hydrochloride

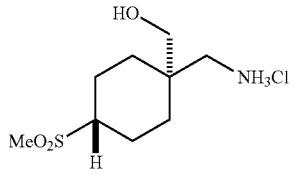

A mixture containing tert-butyl (((1s*,4s*)-1-(hydroxymethyl)-4-(methylsulfonyl)cyclohexyl)methyl)carbamate (197 mg, 0.613 mmol, Intermediate 120), TFA (0.56 mL, 7.3 mmol), 4 M HCl solution in dioxane (0.18 mL, 0.72 mmol) and DCM (3 mL) was stirred at rt. After 10 h, the mixture was concentrated. Heptanes was added to the residue and the mixture was concentrated to furnish the title compound as an oil.

An alternative procedure for the synthesis of ((1s*,4s*)-1-(aminomethyl)-4-(methylsulfonyl)cyclohexyl)methanol (free base):

A solution of LAH in THF (2.8 mL, 1.0 M, 2.8 mmol) was added to a stirring suspension of methyl (1s*,4s*)-1-cyano-4-(methylsulfonyl)cyclohexane-1-carboxylate (205 mg, 0.836 mmol, Intermediate 30) in THF (0.9 mL) at 0° C. The mixture was then allowed to warm to rt. After 1 h, the mixture was cooled to 0° C. and water (0.1 mL), 15% aqueous NaOH (0.1 mL), and then more water (0.3 mL) were sequentially added. The slurry was stirred for 15 minutes, then Celite® was added. After 10 minutes, the mixture was filtered and then concentrated to afford the title compound as the corresponding free base.

Intermediate 122

Ethyl (1s*,4s*)-1-cyano-4-(methylsulfonyl)cyclohexane-1-carboxylate

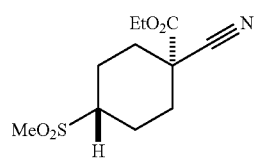 [SMILES: CCOC(=O)[C@]1(C#N)CC[C@H](S(C)(=O)=O)CC1]

Intermediate 123

Ethyl (1r*,4r*)-1-cyano-4-(methylsulfonyl)cyclohexane-1-carboxylate

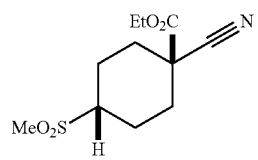 [SMILES: CCOC(=O)[C@]1(C#N)CC[C@@H](S(C)(=O)=O)CC1]

A mixture containing 1,5-dibromo-3-(methylsulfonyl)pentane (10 g, 32 mmol, Intermediate 28), ethyl cyanoacetate (4.5 g, 40 mmol), and Cs$_2$CO$_3$ (26.5 g, 81.3 mmol) in DMF (25 mL) was stirred at rt. After 24 h, the mixture was filtered and the filtrate was concentrated under reduced pressure. Dichloromethane was added to the concentrate, and the mixture was triturated, filtered, and then concentrated. Purification by silica gel chromatography (0-80% EtOAc/petroleum ether) afforded the title compounds, Intermediate 122 and Intermediate 123, as colorless solids.

Intermediate 124

Ethyl (1s*,4s*)-1-(aminomethyl)-4-(methylsulfonyl)cyclohexane-1-carboxylate

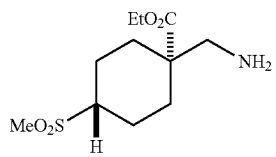 [SMILES: CCOC(=O)[C@]1(CN)CC[C@H](S(C)(=O)=O)CC1]

A mixture of ethyl (1s*,4s*)-1-cyano-4-(methylsulfonyl)cyclohexane-1-carboxylate (900 mg, Intermediate 122) and Raney®-nickel (200 mg) in ethanol (50 mL) was refluxed under an atmosphere of hydrogen gas. After 24 h, the mixture was allowed to cool to rt, filtered, and then concentrated. Purification by silica gel chromatography (DCM/methanol) furnished the titled compound as a yellow gum.

Intermediate 125

Ethyl (1r*,4r*)-1-(aminomethyl)-4-(methylsulfonyl)cyclohexane-1-carboxylate

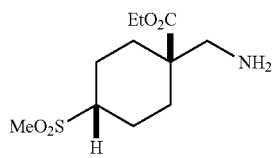 [SMILES: CCOC(=O)[C@]1(CN)CC[C@@H](S(C)(=O)=O)CC1]

The title compound was prepared as described for Intermediate 124, using ethyl (1r*,4r*)-1-cyano-4-(methylsulfonyl)cyclohexane-1-carboxylate (Intermediate 123) in place of ethyl (1s*,4s*)-1-cyano-4-(methyl sulfonyl)cyclohexane-1-carboxylate.

Intermediate 126

4,4,4-Trifluoro-2,2-dimethylbutan-1-ol

A solution of LAH in ether (29 mL, 1.0 M, 29 mmol) was added dropwise to a stirring solution of ethyl 4,4,4-trifluoro-2,2-dimethylbutanoate (2.78 g, 14.0 mmol) in ether (50 mL) at 0° C. The mixture was allowed to warm to rt over 2 h and then cooled back to 0° C. Water (1.1 mL), 15 wt % aqueous NaOH solution (1.1 mL), and water (3 mL) were added dropwise in sequence. The resulting suspension was stirred at rt for 30 minutes. Anhydrous MgSO$_4$ was added, the mixture filtered through Celite®, and the filtrate concentrated (20 mmHg, rt) to afford the title compound as a colorless liquid.

Intermediate 127

1,1,1-Trifluoro-4-iodo-3,3-dimethylbutane

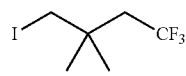

A mixture containing 4,4,4-trifluoro-2,2-dimethylbutan-1-ol (1.43 g, 9.16 mmol, Intermediate 126), methyl iodide (1.1 mL, 18 mmol), and triphenyl phosphite (2.9 mL, 11 mmol) was warmed to 80° C. in a sealed vessel. After 50 h, the vessel was allowed to cool to rt, the solution diluted with pentane, and then the mixture was washed with 1 M aqueous NaOH solution. The organic layer was dried over anhydrous $MgSO_4$, filtered, and concentrated (200 mmHg, rt). The concentrate was further purified by distillation under vacuum (300 mmHg at 50° C. then 20 mmHg at 95° C.) to provide the title compound as a colorless liquid.

Intermediate 128

9-(4,4,4-Trifluorobutyl)-9-borabicyclo[3.3.1]nonane (0.5 M in THF)

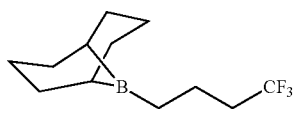 [SMILES: FC(F)(F)CCCB1C2CCCC1CCC2]

The title compound was prepared as described for Intermediate 94, using 4,4,4-trifluorobut-1-ene in place of 3,3,3-trifluoro-2-methylprop-1-ene.

Intermediate 129, Step a

4-Bromo-2,6-difluoro-N-methoxy-N-methylbenzamide

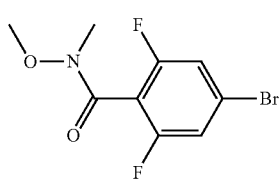

A mixture of 4-bromo-2,6-difluorobenzoic acid (5.0 g, 21 mmol), HATU (9.63 g, 25.3 mmol), N,O-dimethylhydroxylamine hydrochloride (2.06 g, 21.1 mmol), and DIPEA (5.45 g, 42.2 mmol) in DMF (30 mL) was stirred at rt for 16 h. After this time, a saturated aqueous $NH_4Cl$ solution was added, and the resulting mixture was extracted three times with EtOAc. The combined organic layers were washed with brine, dried over anhydrous $Na_2SO_4$, filtered, and concentrated. The residue was purified by silica gel chromatography (petroleum ether:EtOAc=2:1) to give the title compound as colorless gum.

Intermediate 129, Step b 1-(4-Bromo-2,6-difluorophenyl)ethan-1-one

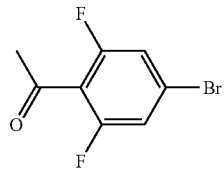

A solution of methylmagnesium bromide in ether (12 mL, 3.0 M, 36 mmol) was added dropwise to a stirring 0° C. solution of 4-bromo-2,6-difluoro-N-methoxy-N-methylbenzamide (5.0 g, 18 mmol, Intermediate 129, Step a) in THF (50 mL). The reaction mixture was allowed to warm to rt and stirred for 18 h. After this time, a saturated aqueous $NH_4Cl$ solution was added. The layers were separated, and the aqueous layer was extracted three times with EtOAc. The combined organic layers were washed with brine, dried with anhydrous $Na_2SO_4$, filtered, concentrated, and purified by silica gel chromatography (petroleum ether:EtOAc=10:1) to give the title compound as colorless gum.

Intermediate 130

Ethyl 5-(4-bromo-2,6-difluorophenyl)-4-chloro-1-ethyl-1H-pyrazole-3-carboxylate

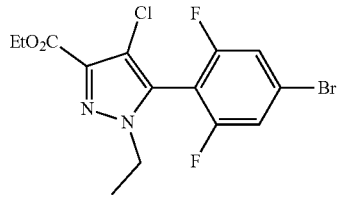 [SMILES: CCOC(=O)c1nn(CC)c(-c2c(F)cc(Br)cc2F)c1Cl]

The title compound was prepared as described for the synthesis of Intermediate 97, using in step a 1-(4-bromo-2,6-difluorophenyl)ethan-1-one (Intermediate 129, Step b) in place of 1-(4-bromo-2-methoxyphenyl)ethan-1-one, and using acetic acid as an additive in step b.

Intermediate 131

1-(4-Bromo-2-methylphenyl)ethan-1-one

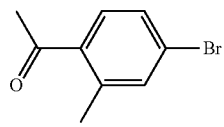

The title compound was prepared as described for the synthesis of Intermediate 129, using in step a 4-bromo-2-methylbenzoic acid in place of 4-bromo-2,6-difluorobenzoic acid.

Intermediate 132

Ethyl 5-(4-bromo-2-methylphenyl)-4-chloro-1-ethyl-1H-pyrazole-3-carboxylate

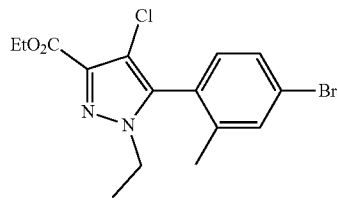 [SMILES: CCOC(=O)c1nn(CC)c(-c2ccc(Br)cc2C)c1Cl]

The title compound was prepared as described for the synthesis of Intermediate 97, using in step a 1-(4-bromo-2-methylphenyl)ethan-1-one (Intermediate 131) in place of 1-(4-bromo-2-methoxyphenyl)ethan-1-one, and using acetic acid in place of ethanol as the solvent in step b.

Intermediate 133

Ethyl 5-(4-bromo-2-fluorophenyl)-4-chloro-1-ethyl-1H-pyrazole-3-carboxylate

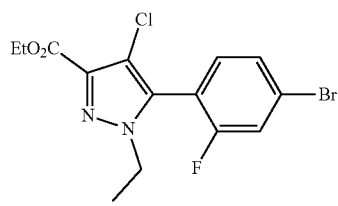

The title compound was prepared as described for the synthesis of Intermediate 97, using in step a 1-(4-bromo-2-fluorophenyl)ethan-1-one in place of 1-(4-bromo-2-methoxyphenyl)ethan-1-one, and using acetic acid as an additive in step b.

Intermediate 134

Ethyl 4-chloro-1-ethyl-5-(4-isobutyl-2-methoxyphenyl)-1H-pyrazole-3-carboxylate

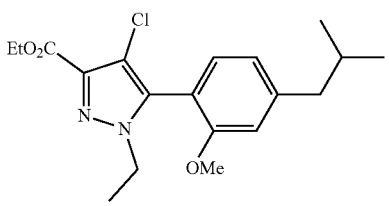 [SMILES: CCOC(=O)c1nn(CC)c(-c2ccc(CC(C)C)cc2OC)c1Cl]

A mixture containing ethyl 5-(4-bromo-2-methoxyphenyl)-4-chloro-1-ethyl-1H-pyrazole-3-carboxylate (700 mg, 1.80 mmol, Intermediate 97, Step c), isobutylboronic acid (385 mg, 3.78 mmol), $K_2CO_3$ (859 mg, 6.22 mmol), and Pd(dppf)Cl$_2$·DCM (155 mg, 0.19 mmol) in toluene (6 mL) was warmed to 100° C. in a sealed tube. After 1 h, the mixture was allowed to cool to rt, EtOAc was added, and the mixture was filtered through a plug of Celite®. The filtrate was absorbed onto Celite® and then purified by silica gel chromatography (hexanes/EtOAc) to provide the title compound as a colorless oil.

Intermediate 135

Ethyl 4-chloro-1-ethyl-5-(4-isopentyl-2-methoxyphenyl)-1H-pyrazole-3-carboxylate

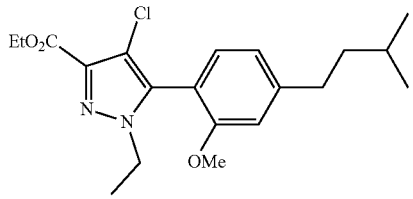 [SMILES: CCOC(=O)c1nn(CC)c(-c2ccc(CCC(C)C)cc2OC)c1Cl]

The title compound was prepared as described for Intermediate 134, using 3-methyl-1-butylboronic acid in place of isobutylboronic acid.

Intermediate 136

Ethyl 4-chloro-5-(2-(difluoromethoxy)-4-(4,4,4-trifluorobutyl)phenyl)-1-ethyl-1H-pyrazole-3-carboxylate

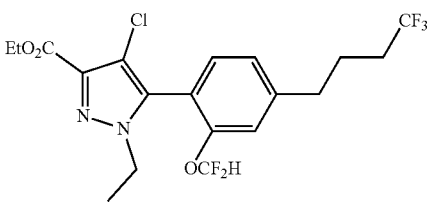

The title compound was prepared as describe for the synthesis of Intermediate 98, using ethyl 5-(4-bromo-2-(difluoromethoxy)phenyl)-4-chloro-1-ethyl-1H-pyrazole-3-carboxylate (Intermediate 102, Step c) in place of ethyl 5-(4-bromo-2-methoxyphenyl)-4-chloro-1-ethyl-1H-pyrazole-3-carboxylate and 9-(4,4,4-trifluorobutyl)-9-borabicyclo[3.3.1]nonane (Intermediate 128) in place of (3,3,3-trifluoro-2-methylpropyl)-9-borabicyclo[3.3.1]nonane.

Intermediate 137

Ethyl 4-chloro-1-ethyl-5-(2-methoxy-4-(4,4,4-trifluorobutyl)phenyl)-1H-pyrazole-3-carboxylate

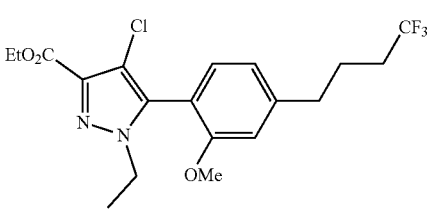 [SMILES: CCOC(=O)c1nn(CC)c(-c2ccc(CCCC(F)(F)F)cc2OC)c1Cl]

The title compound was prepared as describe for the synthesis of Intermediate 98, using 9-(4,4,4-trifluorobutyl)-9-borabicyclo[3.3.1]nonane (Intermediate 128) in place of (3,3,3-trifluoro-2-methylpropyl)-9-borabicyclo[3.3.1]nonane.

Intermediate 138

Ethyl 1-ethyl-5-(2-methoxy-4-(4,4,4-trifluorobutyl)phenyl)-4-methyl-1H-pyrazole-3-carboxylate

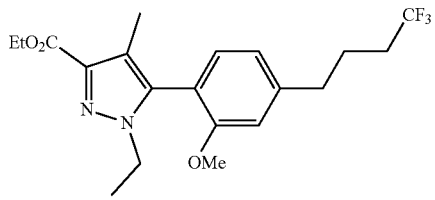 [SMILES: CCOC(=O)c1nn(CC)c(-c2ccc(CCCC(F)(F)F)cc2OC)c1C]

1,4-Dioxane was degassed by bubbling nitrogen through for 20 minutes. A microwave tube was charged with RuPhos G1 (31 mg, 0.038 mmol), RuPhos (19 mg, 0.041 mmol), and $K_2CO_3$ (402 mg, 2.91 mmol) and the headspace was purged with nitrogen gas. A solution of ethyl 4-chloro-1-ethyl-5-(2-methoxy-4-(4,4,4-trifluorobutyl)phenyl)-1H-pyrazole-3-carboxylate (0.300 g, 0.716 mmol, Intermediate 137) and trimethylboroxine (0.20 mL, 1.4 mmol) in degassed 1,4-dioxane (4 mL) was then added. The tube was sealed and warmed to 110° C. in a metal heating block. After 1 h, the mixture was allowed to cool to rt and then partitioned between half-saturated aqueous NaCl solution and a solution of EtOAc and hexanes (6:1 v/v). The layers were separated. The aqueous layer was extracted with EtOAc. The organic layers were combined, dried over $MgSO_4$, filtered, and then absorbed onto Celite®. Purification by silica gel chromatography (EtOAc/hexanes) provided the title compound as an oil.

Intermediate 139

Ethyl 5-(2-chloro-4-(3,3,3-trifluoro-2,2-dimethylpropyl)phenyl)-1-ethyl-1H-pyrazole-3-carboxylate

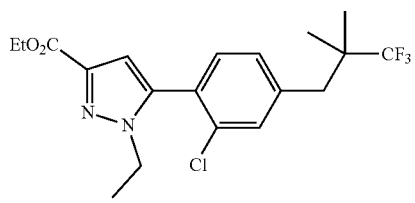 [SMILES: CCOC(=O)c1cc(-c2ccc(CC(C)(C)C(F)(F)F)cc2Cl)n(CC)n1]

1,1,1-Trifluoro-3-iodo-2,2-dimethylpropane (0.3 mL, 2 mmol, Intermediate 93) was added dropwise to a stirring suspension of Rieke® zinc in THF (2.5 mL, 0.05 g/mL, 1.9 mmol) at rt. The suspension was warmed to 60° C. After 30 minutes, the mixture was allowed to cool to rt and then added to a mixture of ethyl 5-(4-bromo-2-chlorophenyl)-1-ethyl-1H-pyrazole-3-carboxylate (0.5 g, 1.3 mmol, Intermediate 162, Step b), $Pd(OAc)_2$ (17 mg, 0.076 mmol), and XPhos (60 mg, 0.13 mmol). The resulting mixture was stirred at 60° C. After 1 h, the solution was allowed to cool to rt and then diluted with EtOAc. The mixture was filtered through Celite®. The filtrate was absorbed onto Celite® and purified by silica gel chromatography (EtOAc/hexanes) to afford the title compound.

Intermediate 140

Ethyl 5-(2-cyano-4-(3,3,3-trifluoro-2,2-dimethylpropyl)phenyl)-1-ethyl-1H-pyrazole-3-carboxylate

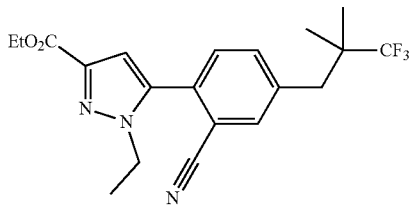 [SMILES: CCOC(=O)c1cc(-c2ccc(CC(C)(C)C(F)(F)F)cc2C#N)n(CC)n1]

DMA was degassed by bubbling nitrogen for 10 minutes. A glass tube was charged with ethyl 5-(2-chloro-4-(3,3,3-trifluoro-2,2-dimethylpropyl)phenyl)-1-ethyl-1H-pyrazole-3-carboxylate (300 mg, 0.7 mmol, Intermediate 139), $Zn(CN)_2$ (195 mg, 1.66 mmol), XPhos (115 mg, 0.241 mmol), $Pd_2(dba)_3$ (140 mg, 0.15 mmol), Zn dust (5 mg, 0.08 mmol) and the headspace purged with nitrogen gas. Degassed DMA (12 mL) was added and the tube capped. The mixture was warmed to 110° C. After 12 h, the mixture was allowed to cool to rt and then filtered through a plug of Celite®. The filtrate was partitioned between water and EtOAc. The layers were separated. The organic layer was dried with $Na_2SO_4$, filtered, and the filtrate was absorbed onto Celite®. Purification by silica gel chromatography (EtOAc/hexanes) provided the title compound as a pale-yellow oil.

Intermediate 141

Ethyl 4-chloro-5-(2-(difluoromethoxy)-4-(4,4,4-trifluoro-2,2-dimethylbutyl)phenyl)-1-ethyl-1H-pyrazole-3-carboxylate

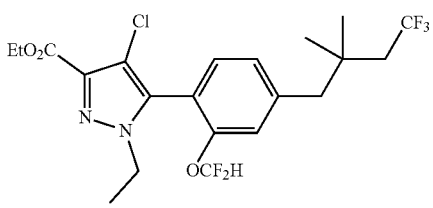

The title compound was prepared as described for the synthesis of Intermediate 103, using 1,1,1-trifluoro-4-iodo-3,3-dimethylbutane (Intermediate 127) in place of 1,1,1-trifluoro-3-iodo-2,2-dimethylpropane.

Intermediate 142

Ethyl 4-chloro-5-(2-(difluoromethoxy)-4-(2,2,2-trifluoroacetyl)phenyl)-1-ethyl-1H-pyrazole-3-carboxylate

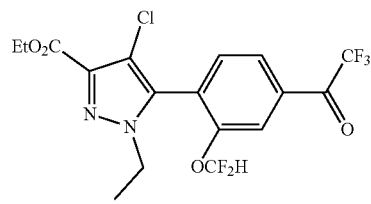

The title compound was prepared as described for the synthesis of Intermediate 255, using ethyl 2,2,2-trifluoroacetate in place of 4,4,4-trifluorobutanal.

Intermediate 143

Ethyl 4-chloro-5-(2-(difluoromethoxy)-4-(1,1,1,3,3,3-hexafluoro-2-hydroxypropan-2-yl)phenyl)-1-ethyl-1H-pyrazole-3-carboxylate

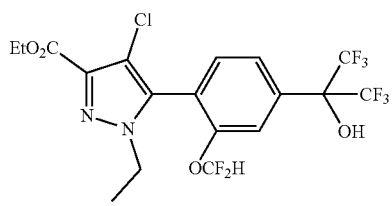

A solution of TBAF (0.725 mL, 1.0 M in THF, 0.725 mmol) was added dropwise to a stirring mixture of ethyl 4-chloro-5-(2-(difluoromethoxy)-4-(2,2,2-trifluoroacetyl)phenyl)-1-ethyl-1H-pyrazole-3-carboxylate (218 mg, 0.475 mmol, Intermediate 142) and trimethyl(trifluoromethyl)silane (0.35 mL, 2.4 mmol) in THF (3 mL) at −30° C. The mixture was slowly allowed to warm to rt over 15 minutes, then a half-saturated aqueous NaCl solution and EtOAc were added. The layers were separated. The organic layer was dried with anhydrous Na$_2$SO$_4$, filtered and adsorbed onto Celite®. Purification by silica gel chromatography afforded the title compound.

Intermediate 144

Ethyl 4-chloro-5-(2-(difluoromethoxy)-4-((1s*,4s*)-1-hydroxy-4-(trifluoromethyl)cyclohexyl)phenyl)-1-ethyl-1H-pyrazole-3-carboxylate

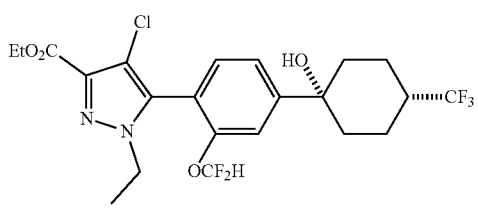

Intermediate 145

Ethyl 4-chloro-5-(2-(difluoromethoxy)-4-((1r*,4r*)-1-hydroxy-4-(trifluoromethyl)cyclohexyl)phenyl)-1-ethyl-1H-pyrazole-3-carboxylate

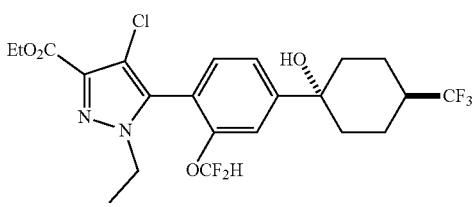

The title compounds were prepared as separable isomers as described for the synthesis of Intermediate 255, using 4-(trifluoromethyl)cyclohexanone in place of 4,4,4-trifluorobutanal. The diastereomers were separated by silica gel chromatography. The relative stereochemistry of the isomers was not established.

Intermediate 146

5-(4-Bromo-2-methoxyphenyl)-4-chloro-1-ethyl-N-(((1r,4r)-4-(methylsulfonyl)cyclohexyl)methyl)-1H-pyrazole-3-carboxamide

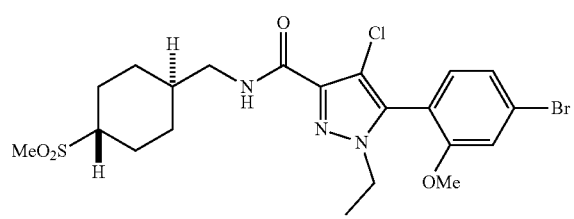 [SMILES: CCn1nc(C(=O)NC[C@H]2CC[C@H](S(C)(=O)=O)CC2)c(Cl)c1-c1ccc(Br)cc1OC]

The title compound was prepared as described for the synthesis of Example 2, using ethyl 5-(4-bromo-2-methoxyphenyl)-4-chloro-1-ethyl-1H-pyrazole-3-carboxylate (Intermediate 97, Step c) in place of ethyl 4-chloro-5-(2-(difluoromethoxy)-4-(3,3,3-trifluoro-2,2-dimethylpropyl)phenyl)-1-ethyl-1H-pyrazole-3-carboxylate and DCM in place of MeCN as solvent in the amide-bond-forming step.

Intermediate 147

5-(4-Bromo-2-methoxyphenyl)-4-chloro-1-ethyl-N-(((1s,4s)-1-hydroxy-4-(methylsulfonyl)cyclohexyl)methyl)-1H-pyrazole-3-carboxamide

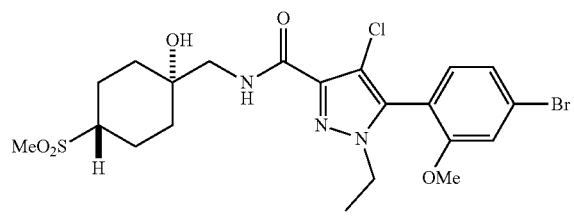 [SMILES: CCn1nc(C(=O)NC[C@]2(O)CC[C@@H](S(C)(=O)=O)CC2)c(Cl)c1-c1ccc(Br)cc1OC]

The title compound was prepared as described for the synthesis of Example 2, using ethyl 5-(4-bromo-2-methoxyphenyl)-4-chloro-1-ethyl-1H-pyrazole-3-carboxylate (Intermediate 97, Step c) and (1s,4s)-1-(aminomethyl)-4-(methylsulfonyl)cyclohexan-1-ol hydrochloride (Intermediate 9) in place of ethyl 4-chloro-5-(2-(difluoromethoxy)-4-(3,3,3-trifluoro-2,2-dimethylpropyl)phenyl)-1-ethyl-1H-pyrazole-3-carboxylate and ((1r,4r)-4-(methylsulfonyl)cyclohexyl)methanamine hydrochloride. Dichloromethane was used in place of MeCN as solvent in the amide-bond-forming step.

Intermediate 148

5-(4-Bromo-2-(difluoromethoxy)phenyl)-4-chloro-1-ethyl-N-(((1r,4r)-4-(methylsulfonyl)cyclohexyl)methyl)-1H-pyrazole-3-carboxamide

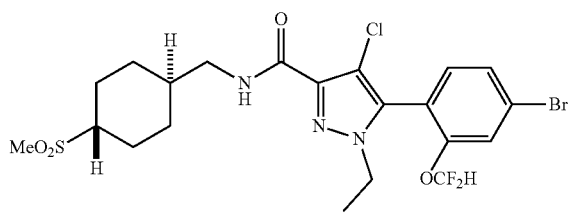

The title compound was prepared as described for the synthesis of Example 2, using ethyl 5-(4-bromo-2-(difluoromethoxy)phenyl)-4-chloro-1-ethyl-1H-pyrazole-3-carboxylate (Intermediate 103) in place of ethyl 4-chloro-5-(2-(difluoromethoxy)-4-(3,3,3-trifluoro-2,2-dimethylpropyl)phenyl)-1-ethyl-1H-pyrazole-3-carboxylate and DCM in place of MeCN as solvent in the amide-bond-forming step.

Intermediate 149

5-(2-Cyano-4-(3,3,3-trifluoro-2,2-dimethylpropyl)phenyl)-1-ethyl-N-(((1s,4s)-1-hydroxy-4-(methylsulfonyl)cyclohexyl)methyl)-1H-pyrazole-3-carboxamide

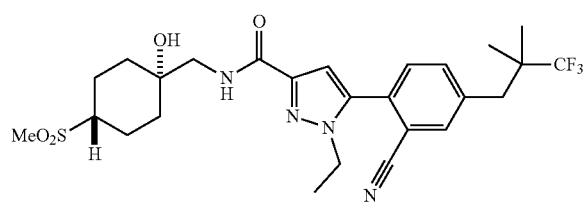 [SMILES: CCn1nc(C(=O)NC[C@]2(O)CC[C@@H](S(C)(=O)=O)CC2)cc1-c1ccc(CC(C)(C)C(F)(F)F)cc1C#N]

The title compound was prepared as described for the synthesis of Example 2, using ethyl 5-(2-cyano-4-(3,3,3-trifluoro-2,2-dimethylpropyl)phenyl)-1-ethyl-1H-pyrazole-3-carboxylic acid (Intermediate 140) and (1s,4s)-1-(aminomethyl)-4-(methylsulfonyl)cyclohexan-1-ol hydrochloride (Intermediate 9) in place of ethyl 4-chloro-5-(2-(difluoromethoxy)-4-(3,3,3-trifluoro-2,2-dimethylpropyl)phenyl)-1-ethyl-1H-pyrazole-3-carboxylate and ((1r,4r)-4-(methylsulfonyl)cyclohexyl)methanamine hydrochloride. Dichloromethane was used in place of MeCN as solvent in the amide-bond-forming step.

Intermediate 150, Step a

1-Methylene-4-(methylsulfonyl)cyclohexane

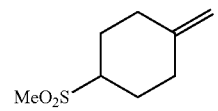

A solution of methyltriphenylphosphonium bromide (40.1 g, 112 mmol) and KOt-Bu (12.6 g, 112 mmol) in THF (548 mL) was stirred at rt for 1 h. A solution of 4-(methylsulfonyl)cyclohexan-1-one (9.88 g, 56.1 mmol, Intermediate 5) in THF (50 mL) was added to the reaction and the mixture was stirred overnight at rt. The reaction mixture was quenched with a saturated aqueous NH$_4$Cl solution, DCM was added, and the layers were separated. The aqueous layer was extracted with DCM. The combined organic layers were dried with anhydrous Na$_2$SO$_4$, filtered, and concentrated. The residue was purified by silica gel chromatography (25-75% EtOAc/hexanes) to afford the title compound.

Intermediate 150, Step b 6-(Methylsulfonyl)-1-azaspiro[2.5]octane

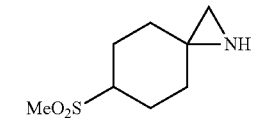

A mixture of 1-methylene-4-(methylsulfonyl)cyclohexane (3.52 g, 19.0 mmol, Intermediate 150, Step a), O-(2,4-dinitrophenyl)hydroxylamine (4.54 g, 22.8 mmol), and Rh$_2$(esp)$_2$ (147 mg, 0.193 mmol) in 2,2,2-trifluoroethanol (95 mL) was stirred at rt under an atmosphere of argon for 3 h. The reaction mixture was diluted with CHCl$_3$, and then 15 wt % aqueous NaHCO$_3$ was added. The layers were separated and the aqueous layer was extracted with chloroform. The combined organic layers were washed with brine, dried with anhydrous Na$_2$SO$_4$, filtered, and concentrated. The residue was purified by silica gel chromatography (0→5% MeOH/DCM) to afford the title compound.

Intermediate 150, Step c 1-(Azidomethyl)-4-(methylsulfonyl)cyclohexan-1-amine

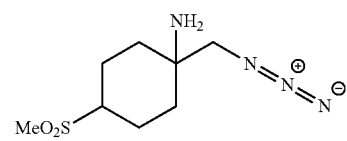

6-(Methylsulfonyl)-1-azaspiro[2.5]octane (0.941 g, 4.97 mmol, Intermediate 150, Step b) was dissolved in MeCN (50 mL) and cooled in an ice bath under an atmosphere of argon. (1S)-(+)-10-Camphorsulfonic acid (1.39 g, 5.96 mmol) was added to the solution, and the reaction was stirred for 35 min. After this time, sodium azide (0.983 g, 15.1 mmol) was added and the reaction mixture was heated to 50° C. for 5 h. The reaction mixture was then allowed to cool to rt and was diluted with DCM and water. A saturated aqueous NaHCO$_3$ solution was added to adjust the pH of the aqueous layer to pH 9. The layers were separated and the aqueous layer was extracted with DCM. The combined organic layers were washed with brine, dried with anhydrous Na$_2$SO$_4$, filtered, and concentrated. The residue was purified by silica gel chromatography (2-10% MeOH/DCM) to afford the title compound.

Intermediate 150, Step d 1-(Aminomethyl)-4-(methylsulfonyl)cyclohexan-1-amine

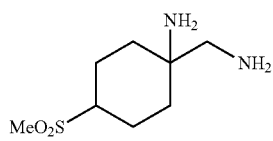

A solution of 1-(azidomethyl)-4-(methylsulfonyl)cyclohexan-1-amine (650 mg, 2.8 mmol, Intermediate 150, Step c) and triphenylphosphine (2.208 g, 8.419 mmol) in THF (2.8 mL) was stirred at rt for 3 h. Water (3.5 mL) was added and the resulting suspension was stirred at 50° C. overnight. The reaction mixture was concentrated under a stream of nitrogen and dissolved in EtOAc and water. The layers were separated and the organic layer was extracted with water twice. The combined aqueous layers were washed with EtOAc and then the aqueous layer was lyophilized to provide the title compound as an orange solid.

Intermediate 151

Ethyl 5-(4-bromo-2-methoxyphenyl)-4-cyano-1-ethyl-1H-pyrazole-3-carboxylate

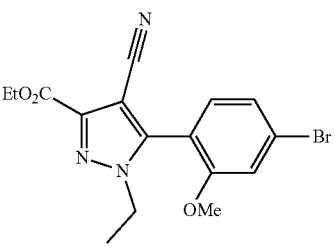 [SMILES: CCOC(=O)c1nn(CC)c(-c2ccc(Br)cc2OC)c1C#N]

A solution of TMPMgCl.LiCl (6.5 mL, 1.0 M in THF/toluene, 6.5 mmol) was added to a solution of ethyl 5-(4-bromo-2-methoxyphenyl)-1-ethyl-1H-pyrazole-3-carboxylate (1.50 g, 4.25 mmol Intermediate 97, Step b) in THF (14 mL) and cooled in an ice bath. The resulting solution was stirred for 6 h, then p-toluenesulfonyl cyanide (1.16 g, 6.39 mmol) was added and the stirring solution was allowed to warm to rt overnight. The reaction mixture was diluted with a saturated aqueous NH$_4$Cl solution and EtOAc. The layers were separated and the organic layer was dried over Na$_2$SO$_4$, filtered, and concentrated. The residue was purified by silica gel chromatography (0-20% EtOAc/hexanes) to provide the title compound as a colorless oil.

Intermediate 152

Ethyl 4-cyano-1-ethyl-5-(2-methoxy-4-(3,3,3-trifluoro-2-methylpropyl)phenyl)-1H-pyrazole-3-carboxylate

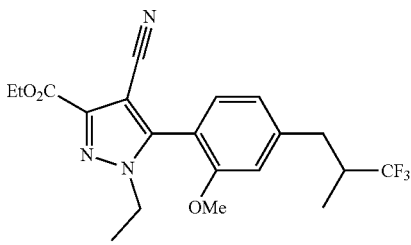 [SMILES: CCOC(=O)c1nn(CC)c(-c2ccc(CC(C)C(F)(F)F)cc2OC)c1C#N]

The title compound was prepared as described for the synthesis of Intermediate 98, using ethyl 5-(4-bromo-2-methoxyphenyl)-4-cyano-1-ethyl-1H-pyrazole-3-carboxylate (Intermediate 151) in place of ethyl 5-(4-bromo-2-methoxyphenyl)-4-chloro-1-ethyl-1H-pyrazole-3-carboxylate.

Intermediate 153

Ethyl 4-cyano-1-ethyl-5-(2-methoxy-4-(3,3,3-trifluoropropyl)phenyl)-1H-pyrazole-3-carboxylate

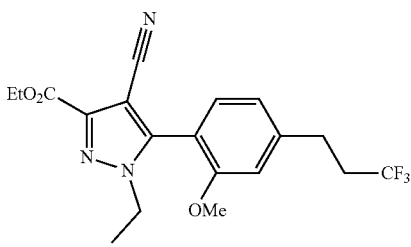 [SMILES: CCOC(=O)c1nn(CC)c(-c2ccc(CCC(F)(F)F)cc2OC)c1C#N]

The title compound was prepared as described for the synthesis of Intermediate 98, using ethyl 5-(4-bromo-2-methoxyphenyl)-4-cyano-1-ethyl-1H-pyrazole-3-carboxylate (Intermediate 151) in place of ethyl 5-(4-bromo-2-methoxyphenyl)-4-chloro-1-ethyl-1H-pyrazole-3-carboxylate and 9-(3,3,3-trifluoropropyl)-9-borabicyclo[3.3.1]nonane (Intermediate 95) in place of 9-(3,3,3-trifluoro-2-methylpropyl)-9-borabicyclo[3.3.1]nonane.

Intermediate 154

Ethyl 4-cyano-1-ethyl-5-(2-methoxy-4-(3,3,3-trifluoro-2,2-dimethylpropyl)phenyl)-1H-pyrazole-3-carboxylate

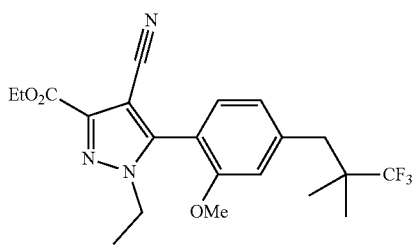 [SMILES: CCOC(=O)c1nn(CC)c(-c2ccc(CC(C)(C)C(F)(F)F)cc2OC)c1C#N]

The title compound was prepared as described for the synthesis of Intermediate 116, using ethyl 5-(4-bromo-2-methoxyphenyl)-4-cyano-1-ethyl-1H-pyrazole-3-carboxylate (Intermediate 151) in place of ethyl 5-(4-bromo-2-(difluoromethoxy)phenyl)-4-chloro-1-ethyl-1H-pyrazole-3-carboxylate and 1,1,1-trifluoro-3-iodo-2,2-dimethylpropane (Intermediate 93) in place of (S*)-1,1,1-trifluoro-3-iodo-2-methylpropane.

Intermediate 159

4-Bromo-N-methoxy-N-methyl-2-(trifluoromethoxy)benzamide

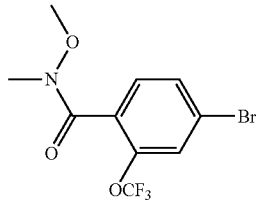 [SMILES: CON(C)C(=O)c1ccc(Br)cc1OC(F)(F)F]

The title compound was prepared as described for the synthesis of Intermediate 107, using 4-bromo-2-(trifluoromethoxy)benzoic acid in place of 4-bromo-2-methoxybenzoic acid and DMF as the solvent.

Intermediate 160

1-(4-Bromo-2-(trifluoromethoxy)phenyl)ethan-1-one

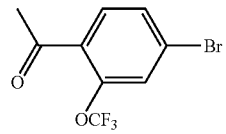

The title compound was prepared as described for the synthesis of Intermediate 108, using methylmagnesium bromide in place of ethylmagnesium chloride and 4-bromo-N-methoxy-N-methyl-2-(trifluoromethoxy)benzamide (Intermediate 159) in place of 4-bromo-N,2-dimethoxy-N-methylbenzamide.

Intermediate 161, Step a

Ethyl 4-(4-bromo-2-(trifluoromethoxy)phenyl)-2,4-dioxobutanoate

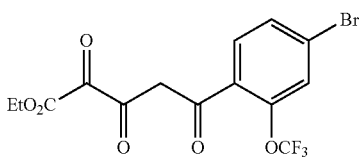

The title compound was prepared as described for the synthesis of Intermediate 97, Step a, using 1-(4-bromo-2-(trifluoromethoxy)phenyl)ethan-1-one (Intermediate 160) in place of 1-(4-bromo-2-methoxyphenyl)ethan-1-one.

Intermediate 161, Step b

Ethyl 5-(4-bromo-2-(trifluoromethoxy)phenyl)-1-ethyl-1H-pyrazole-3-carboxylate

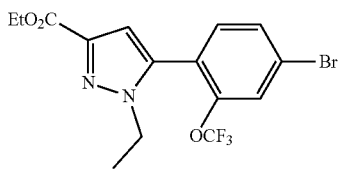 [SMILES: CCOC(=O)c1cc(-c2ccc(Br)cc2OC(F)(F)F)n(CC)n1]

A mixture of ethyl 4-(4-bromo-2-(trifluoromethoxy)phenyl)-2,4-dioxobutanoate (2.80 g, 7.31 mmol, Intermediate 161, Step a) and ethylhydrazine hydrochloride (1.28 g, 8.54 mmol) in AcOH (26.9 mL) was heated to 60° C. for 18 h. After this time, the reaction mixture was allowed to cool to rt and then concentrated. The concentrate was diluted with EtOAc and a saturated aqueous NaHCO$_3$ solution, and the layers were mixed and separated. The organic layer was dried with anhydrous MgSO$_4$, filtered, and then concentrated. The residue was purified by silica gel chromatography (10-25% EtOAc/hexanes) to afford the title compound.

Intermediate 161, Step c

Ethyl 5-(4-bromo-2-(trifluoromethoxy)phenyl)-4-chloro-1-ethyl-1H-pyrazole-3-carboxylate

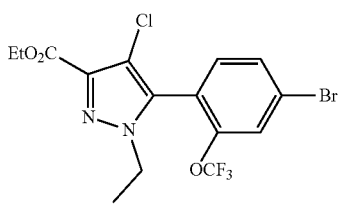 [SMILES: CCOC(=O)c1nn(CC)c(-c2ccc(Br)cc2OC(F)(F)F)c1Cl]

The title compound was prepared as described for the synthesis of Intermediate 102, Step c, using ethyl 5-(4-bromo-2-(trifluoromethoxy)phenyl)-1-ethyl-1H-pyrazole-3- carboxylate (Intermediate 161, Step b) in place of ethyl 5-(4-bromo-2-(difluoromethoxy)phenyl)-1-ethyl-1H-pyrazole-3-carboxylate.

Intermediate 162, Step a

Ethyl 5-(4-bromo-2-chlorophenyl)-2,3,5-trioxopentanoate

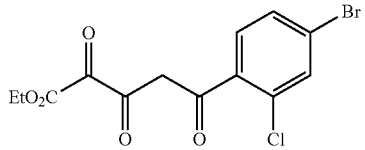 [SMILES: CCOC(=O)C(=O)C(=O)CC(=O)c1ccc(Br)cc1Cl]

The title compound was prepared as described for the synthesis of Intermediate 97, Step a, using 1-(4-bromo-2-chlorophenyl)ethan-1-one in place of 1-(4-bromo-2-methoxyphenyl)ethan-1-one.

Intermediate 162, Step b

Ethyl 5-(4-bromo-2-chlorophenyl)-1-ethyl-1H-pyrazole-3-carboxylate

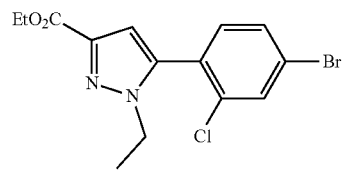

The title compound was prepared as described for the synthesis of Intermediate 161, Step b, using ethyl 5-(4-bromo-2-chlorophenyl)-2,3,5-trioxopentanoate (Intermediate 162, Step a) in place of ethyl 4-(4-bromo-2-(trifluoromethoxy)phenyl)-2,4-dioxobutanoate.

Intermediate 162, Step c

Ethyl 5-(4-bromo-2-chlorophenyl)-4-chloro-1-ethyl-1H-pyrazole-3-carboxylate

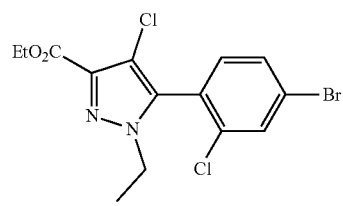 [SMILES: CCOC(=O)c1nn(CC)c(-c2ccc(Br)cc2Cl)c1Cl]

The title compound was prepared as described for the synthesis of Intermediate 102, Step c, using ethyl 5-(4-bromo-2-chlorophenyl)-1-ethyl-1H-pyrazole-3-carboxylate (Intermediate 162, Step b) in place of ethyl 5-(4-bromo-2-(difluoromethoxy)phenyl)-1-ethyl-1H-pyrazole-3-carboxylate.

Intermediate 163

4-Bromo-N-methoxy-N-methyl-2-(trifluoromethyl)benzamide

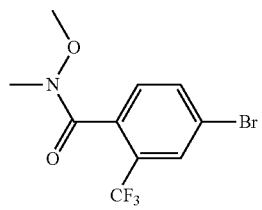

The title compound was prepared as described for the synthesis of Intermediate 107, using 4-bromo-2-(trifluoromethyl)benzoic acid in place of 4-bromo-2-methoxybenzoic acid and DMF as the solvent.

Intermediate 164

1-(4-Bromo-2-(trifluoromethyl)phenyl)ethan-1-one

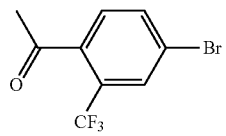

The title compound was prepared as described for the synthesis of Intermediate 108, using methylmagnesium bromide in place of ethylmagnesium chloride and 4-bromo-N-methoxy-N-methyl-2-(trifluoromethyl)benzamide (Intermediate 163) in place of 4-bromo-N,2-dimethoxy-N-methylbenzamide.

Intermediate 165, Step a

Ethyl 5-(4-bromo-2-(trifluoromethyl)phenyl)-2,3,5-trioxopentanoate

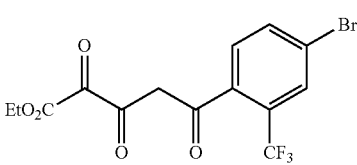 [SMILES: CCOC(=O)C(=O)C(=O)CC(=O)c1ccc(Br)cc1C(F)(F)F]

The title compound was prepared as described for the synthesis of Intermediate 97, Step a, using 1-(4-bromo-2-(trifluoromethyl)phenyl)ethan-1-one (Intermediate 164) in place of 1-(4-bromo-2-methoxyphenyl)ethan-1-one.

Intermediate 165, Step b

Ethyl 5-(4-bromo-2-(trifluoromethyl)phenyl)-1-ethyl-1H-pyrazole-3-carboxylate

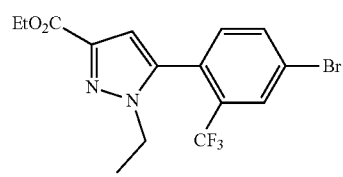

The title compound was prepared as described for the synthesis of Intermediate 161, Step b, using ethyl 5-(4-bromo-2-(trifluoromethyl)phenyl)-2,3,5-trioxopentanoate (Intermediate 165, Step a) in place of ethyl 4-(4-bromo-2-(trifluoromethoxy)phenyl)-2,4-dioxobutanoate.

Intermediate 165, Step c

Ethyl 5-(4-bromo-2-(trifluoromethyl)phenyl)-4-chloro-1-ethyl-1H-pyrazole-3-carboxylate

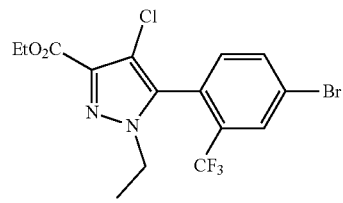 [SMILES: CCOC(=O)c1nn(CC)c(-c2ccc(Br)cc2C(F)(F)F)c1Cl]

The title compound was prepared as described for the synthesis of Intermediate 102, Step c, using ethyl 5-(4-bromo-2-(trifluoromethyl)phenyl)-1-ethyl-1H-pyrazole-3-carboxylate (Intermediate 165, Step b) in place of ethyl 5-(4-bromo-2-(difluoromethoxy)phenyl)-1-ethyl-1H-pyrazole-3-carboxylate.

Intermediate 166, Step a

Ethyl 5-(4-bromophenyl-2,3,5-trioxopentanoate

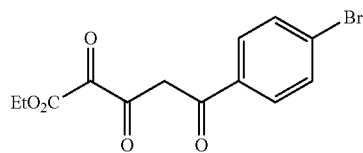 [SMILES: CCOC(=O)C(=O)C(=O)CC(=O)c1ccc(Br)cc1]

The title compound was prepared as described for the synthesis of Intermediate 97, Step a, using 1-(4-bromophenyl)ethanone in place of 1-(4-bromo-2-methoxyphenyl)ethan-1-one.

Intermediate 166, Step b

Ethyl 5-(4-bromophenyl)-1-ethyl-1H-pyrazole-3-carboxylate

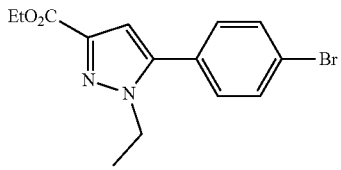

The title compound was prepared as described for the synthesis of Intermediate 97 Step b, using ethyl 5-(4-bromophenyl)-2,3,5-trioxopentanoate (Intermediate 166, Step a) in place of 1-(4-bromo-2-methoxyphenyl)ethan-1-one.

Intermediate 166, Step c

Ethyl 5-(4-bromophenyl)-4-chloro-1-ethyl-1H-pyrazole-3-carboxylate

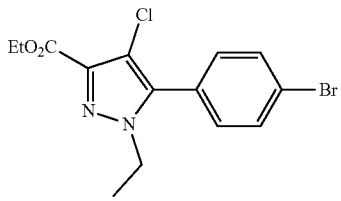 [SMILES: CCOC(=O)c1nn(CC)c(-c2ccc(Br)cc2)c1Cl]

The title compound was prepared as described for the synthesis of Intermediate 97, Step c, using ethyl 5-(4-bromophenyl)-1-ethyl-1H-pyrazole-3-carboxylate (Intermediate 166, Step b) in place of ethyl 5-(4-bromo-2-methoxyphenyl)-1-ethyl-1H-pyrazole-3-carboxylate.

Intermediate 167, Step a

Ethyl 5-(4-bromo-2-(difluoromethoxy)phenyl)-1-methyl-1H-pyrazole-3-carboxylate

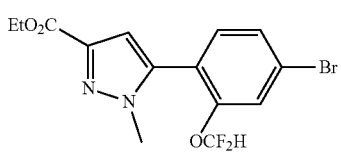

The title compound was prepared as described for the synthesis of Intermediate 102, Step b, using methyl hydrazine in place of ethyl hydrazine oxalate.

Intermediate 167, Step b

Ethyl 5-(4-bromo-2-(difluoromethoxy)phenyl)-4-chloro-1-methyl-1H-pyrazole-3-carboxylate

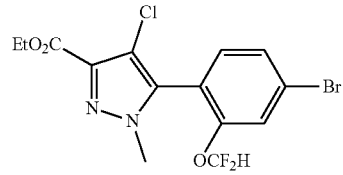

The title compound was prepared as described for the synthesis of Intermediate 97, Step c, using ethyl 5-(4-bromo-2-(difluoromethoxy)phenyl)-1-methyl-1H-pyrazole-3-carboxylate (Intermediate 167, Step a) in place of ethyl 5-(4-bromo-2-methoxyphenyl)-1-ethyl-1H-pyrazole-3-carboxylate.

Intermediate 168

1-(4-Bromo-2-methoxyphenyl)butan-1-one

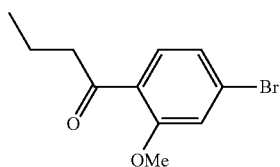

The title compound was prepared as described for the synthesis of Intermediate 108, using n-propylmagnesium bromide in place of ethylmagnesium chloride.

Intermediate 169, Step a

Ethyl 3-(4-bromo-2-methoxybenzoyl)-2-oxopentanoate

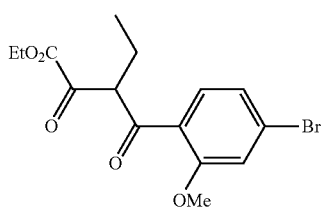 [SMILES: CCOC(=O)C(=O)C(CC)C(=O)c1ccc(Br)cc1OC]

The title compound was prepared as described for the synthesis of Intermediate 97, Step a using 1-(4-bromo-2-methoxyphenyl)butan-1-one (Intermediate 168) in place of 1-(4-bromo-2-methoxyphenyl)ethan-1-one.

Intermediate 169, Step b

Ethyl 5-(4-bromo-2-methoxyphenyl)-1,4-diethyl-1H-pyrazole-3-carboxylate

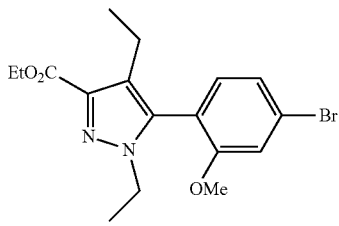 [SMILES: CCOC(=O)c1nn(CC)c(-c2ccc(Br)cc2OC)c1CC]

The title compound was prepared as described for the synthesis of Intermediate 97, Step b using ethyl 3-(4-bromo-2-methoxybenzoyl)-2-oxopentanoate (Intermediate 169, Step a) in place of ethyl 4-(4-bromo-2-methoxyphenyl)-2,4-dioxobutanoate.

Intermediate 170

Ethyl (R)-1,4-diethyl-5-(2-methoxy-4-((1,1,1-trifluoropropan-2-yl)amino)phenyl)-1H-pyrazole-3-carboxylate

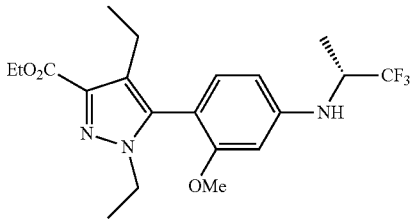 [SMILES: CCOC(=O)c1nn(CC)c(-c2ccc(N[C@H](C)C(F)(F)F)cc2OC)c1CC]

The title compound was prepared as described for the synthesis of Intermediate 106 using ethyl 5-(4-bromo-2-methoxyphenyl)-1,4-diethyl-1H-pyrazole-3-carboxylate (Intermediate 169, Step b) in place of ethyl 5-(4-bromo-2-methoxyphenyl)-4-chloro-1-ethyl-1H-pyrazole-3-carboxylate.

Intermediate 171

1-(4-Bromo-2-methoxyphenyl)-3-methylbutan-1-one

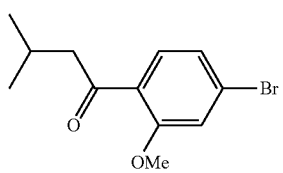

The title compound was prepared as described for the synthesis of Intermediate 108, using isopropylmagnesium bromide in place of ethylmagnesium chloride.

141

Intermediate 172, Step a

Ethyl 3-(4-bromo-2-methoxybenzoyl)-4-methyl-2-oxopentanoate

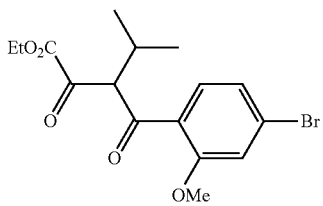 [SMILES: CCOC(=O)C(=O)C(C(=O)c1ccc(Br)cc1OC)C(C)C]

The title compound was prepared as described for the synthesis of Intermediate 97, Step a using 1-(4-bromo-2-methoxyphenyl)-3-methylbutan-1-one (Intermediate 171) in place of 1-(4-bromo-2-methoxyphenyl)ethan-1-one and LiOt-Bu in place of LiHMDS.

Intermediate 172, Step b

Ethyl 5-(4-bromo-2-methoxyphenyl)-1-ethyl-4-isopropyl-1H-pyrazole-3-carboxylate

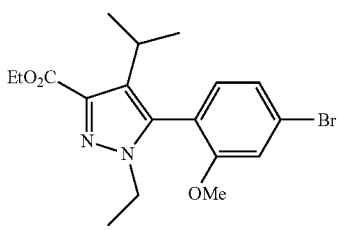 [SMILES: CCOC(=O)c1nn(CC)c(-c2ccc(Br)cc2OC)c1C(C)C]

The title compound was prepared as described for the synthesis of Intermediate 97, Step b using ethyl 3-(4-bromo-2-methoxybenzoyl)-4-methyl-2-oxopentanoate (Intermediate 172, Step a) in place of ethyl 4-(4-bromo-2-methoxyphenyl)-2,4-dioxobutanoate.

Intermediate 173

Ethyl (R)-1-ethyl-4-isopropyl-5-(2-methoxy-4-((1,1,1-trifluoropropan-2-yl)amino)phenyl)-1H-pyrazole-3-carboxylate

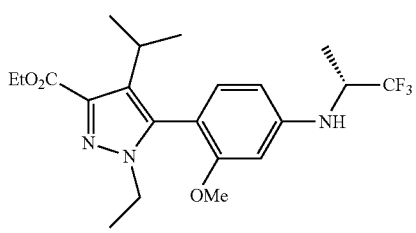 [SMILES: CCOC(=O)c1nn(CC)c(-c2ccc(N[C@H](C)C(F)(F)F)cc2OC)c1C(C)C]

142

The title compound was prepared as described for the synthesis of Intermediate 106 using ethyl 5-(4-bromo-2-methoxyphenyl)-1-ethyl-4-isopropyl-1H-pyrazole-3-carboxylate (Intermediate 172, Step b) in place of ethyl 5-(4-bromo-2-methoxyphenyl)-4-chloro-1-ethyl-1H-pyrazole-3-carboxylate.

Intermediate 174

Ethyl 5-(4-bromo-2-(difluoromethoxy)phenyl)-1-(2-hydroxy-2-methylpropyl)-1H-pyrazole-3-carboxylate

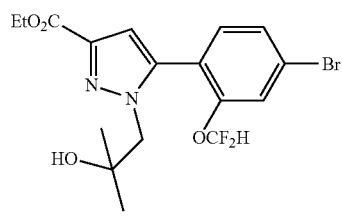

The title compound was prepared as described for the synthesis of Intermediate 161, Step b, using ethyl 4-(4-bromo-2-(difluoromethoxy)phenyl)-2,4-dioxobutanoate (Intermediate 102, Step a) in place of ethyl 4-(4-bromo-2-(trifluoromethoxy)phenyl)-2,4-dioxobutanoate and 1-hydrazinyl-2-methylpropan-2-ol in place of ethylhydrazine hydrochloride.

Intermediate 175

Ethyl 5-(4-bromo-2-(difluoromethoxy)phenyl)-4-chloro-1-(2-hydroxy-2-methylpropyl)-1H-pyrazole-3-carboxylate

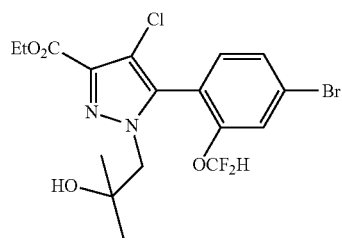

The title compound was prepared as described for the synthesis of Intermediate 97, Step c, using ethyl 5-(4-bromo-2-(difluoromethoxy)phenyl)-1-(2-hydroxy-2-methylpropyl)-1H-pyrazole-3-carboxylate (Intermediate 174) in place of ethyl 5-(4-bromo-2-methoxyphenyl)-1-ethyl-1H-pyrazole-3-carboxylate and without the use of TFA.

Intermediate 176

Ethyl 4-chloro-5-(2-(difluoromethoxy)-4-(3,3,3-trifluoro-2,2-dimethylpropyl)phenyl)-1-(2-hydroxy-2-methylpropyl)-1H-pyrazole-3-carboxylate

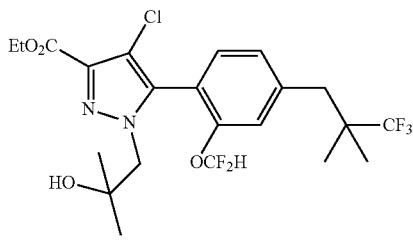

The title compound was prepared as described for the synthesis of Intermediate 116, using 1,1,1-trifluoro-3-iodo-2,2-dimethylpropane in place of (S*)-1,1,1-trifluoro-3-iodo-2-methylpropane and ethyl 5-(4-bromo-2-(difluoromethoxy)phenyl)-4-chloro-1-(2-hydroxy-2-methylpropyl)-1H-pyrazole-3-carboxylate (Intermediate 175) in place of ethyl 5-(4-bromo-2-(difluoromethoxy)phenyl)-4-chloro-1-ethyl-1H-pyrazole-3-carboxylate.

Intermediate 177, Step a

Ethyl 5-(4-bromo-2-methoxyphenyl)-1-(2-methoxyethyl)-1H-pyrazole-3-carboxylate

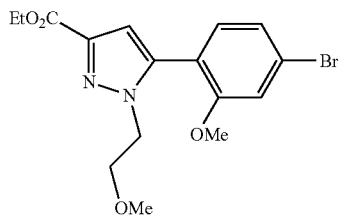 [SMILES: CCOC(=O)c1cc(-c2ccc(Br)cc2OC)n(CCOC)n1]

The title compound was prepared as described for the synthesis of Intermediate 161, Step b, using ethyl 4-(4-bromo-2-methoxyphenyl)-2,4-dioxobutanoate (Intermediate 97, Step a) in place of ethyl 4-(4-bromo-2-(trifluoromethoxy)phenyl)-2,4-dioxobutanoate and (2-methoxyethyl)hydrazine hydrochloride in place of ethylhydrazine hydrochloride.

Intermediate 177, Step b

Ethyl 5-(4-bromo-2-methoxyphenyl)-4-chloro-1-(2-methoxyethyl)-1H-pyrazole-3-carboxylate

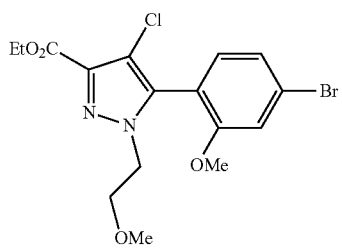 [SMILES: CCOC(=O)c1nn(CCOC)c(-c2ccc(Br)cc2OC)c1Cl]

The title compound was prepared as described for the synthesis of Intermediate 102, Step c, using ethyl 5-(4-bromo-2-methoxyphenyl)-1-(2-methoxyethyl)-1H-pyrazole-3-carboxylate (Intermediate 177, Step a) in place of ethyl 5-(4-bromo-2-(difluoromethoxy)phenyl)-1-ethyl-1H-pyrazole-3-carboxylate.

Intermediate 178

Ethyl 4-chloro-5-(2-methoxy-4-(3,3,3-trifluoro-2,2-dimethylpropyl)phenyl)-1-(2-methoxyethyl)-1H-pyrazole-3-carboxylate

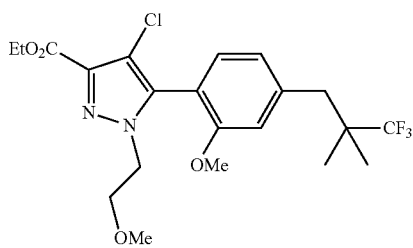 [SMILES: CCOC(=O)c1nn(CCOC)c(-c2ccc(CC(C)(C)C(F)(F)F)cc2OC)c1Cl]

The title compound was prepared as described for the synthesis of Intermediate 116, using 1,1,1-trifluoro-3-iodo-2,2-dimethylpropane in place of (S*)-1,1,1-trifluoro-3-iodo-2-methylpropane and ethyl 5-(4-bromo-2-methoxyphenyl)-4-chloro-1-(2-methoxyethyl)-1H-pyrazole-3-carboxylate (Intermediate 177, Step b) in place of ethyl 5-(4-bromo-2-(difluoromethoxy)phenyl)-4-chloro-1-ethyl-1H-pyrazole-3-carboxylate.

Intermediate 179, Step a

Ethyl 5-(4-bromo-2-methoxyphenyl)-1-(2-hydroxyethyl)-1H-pyrazole-3-carboxylate

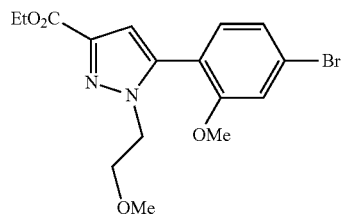 [SMILES: CCOC(=O)c1cc(-c2ccc(Br)cc2OC)n(CCOC)n1]

The title compound was prepared as described for the synthesis of Intermediate 161, Step b, using ethyl 4-(4-bromo-2-methoxyphenyl)-2,4-dioxobutanoate (Intermediate 97, Step a) in place of ethyl 4-(4-bromo-2-(trifluoromethoxy)phenyl)-2,4-dioxobutanoate and 2-hydrazinylethan-1-ol in place of ethylhydrazine hydrochloride.

Intermediate 179, Step b

Ethyl 5-(4-bromo-2-methoxyphenyl)-4-chloro-1-(2-hydroxyethyl)-1H-pyrazole-3-carboxylate

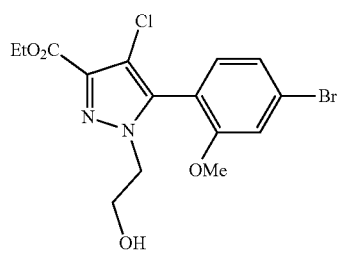 [SMILES: CCOC(=O)c1nn(CCO)c(-c2ccc(Br)cc2OC)c1Cl]

The title compound was prepared as described for the synthesis of Intermediate 97, Step c, using ethyl 5-(4-bromo-2-methoxyphenyl)-1-(2-hydroxyethyl)-1H-pyrazole-3-carboxylate (Intermediate 179, Step a) in place of ethyl 5-(4-bromo-2-methoxyphenyl)-1-ethyl-1H-pyrazole-3-carboxylate.

Intermediate 180

Ethyl (R*)-5-(2-(difluoromethoxy)-4-(3,3,3-trifluoro-2-methylpropyl)phenyl)-1-ethyl-4-methyl-1H-pyrazole-3-carboxylate

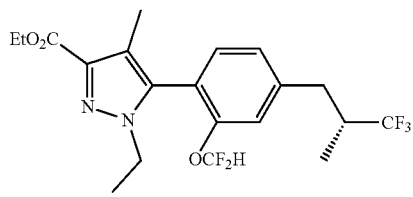

The title compound was prepared as described for the synthesis of Intermediate 105, using ethyl (R*)-4-chloro-5-(2-(difluoromethoxy)-4-(3,3,3-trifluoro-2-methylpropyl)phenyl)-1-ethyl-1H-pyrazole-3-carboxylate (Intermediate 116) in place of ethyl 4-chloro-5-(2-(difluoromethoxy)-4-((S*)-3,3,3-trifluoro-2-methylpropyl)phenyl)-1-ethyl-1H-pyrazole-3-carboxylate.

Intermediate 181

Ethyl 5-(2-(difluoromethoxy)-4-(3,3,3-trifluoro-2,2-dimethylpropyl)phenyl)-1-ethyl-4-methyl-1H-pyrazole-3-carboxylate

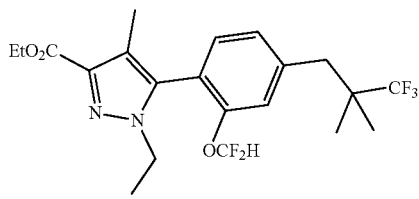

The title compound was prepared as described for the synthesis of Intermediate 105, using ethyl 4-chloro-5-(2-(difluoromethoxy)-4-(3,3,3-trifluoro-2,2-dimethylpropyl)phenyl)-1-ethyl-1H-pyrazole-3-carboxylate (Intermediate 103) in place of ethyl 4-chloro-5-(2-(difluoromethoxy)-4-((S*)-3,3,3-trifluoro-2-methylpropyl)phenyl)-1-ethyl-1H-pyrazole-3-carboxylate.

Intermediate 182

Ethyl 5-(2-(difluoromethoxy)-4-(3,3,3-trifluoro-2,2-dimethylpropyl)phenyl)-1-(2-hydroxy-2-methylpropyl)-4-methyl-1H-pyrazole-3-carboxylate

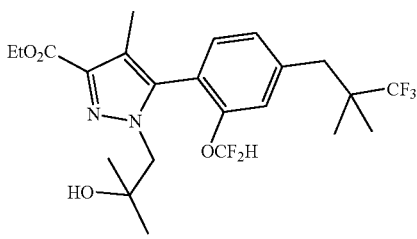

The title compound was prepared as described for the synthesis of Intermediate 105, using ethyl 4-chloro-5-(2-(difluoromethoxy)-4-(3,3,3-trifluoro-2,2-dimethylpropyl)phenyl)-1-(2-hydroxy-2-methylpropyl)-1H-pyrazole-3-carboxylate (Intermediate 176) in place of ethyl 4-chloro-5-(2-(difluoromethoxy)-4-((S*)-3,3,3-trifluoro-2-methylpropyl)phenyl)-1-ethyl-1H-pyrazole-3-carboxylate.

Intermediate 183

Ethyl 5-(2-methoxy-4-(3,3,3-trifluoro-2,2-dimethylpropyl)phenyl)-1-(2-methoxyethyl)-4-methyl-1H-pyrazole-3-carboxylate

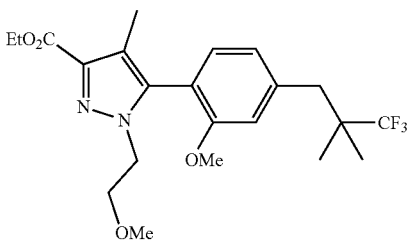 [SMILES: CCOC(=O)c1nn(CCOC)c(-c2ccc(CC(C)(C)C(F)(F)F)cc2OC)c1C]

The title compound was prepared as described for the synthesis of Intermediate 105, using ethyl 4-chloro-5-(2-methoxy-4-(3,3,3-trifluoro-2,2-dimethylpropyl)phenyl)-1-(2-methoxyethyl)-1H-pyrazole-3-carboxylate (Intermediate 178) in place of ethyl 4-chloro-5-(2-(difluoromethoxy)-4-((S*)-3,3,3-trifluoro-2-methylpropyl)phenyl)-1-ethyl-1H-pyrazole-3-carboxylate.

Intermediate 184

Ethyl (R*)-4-chloro-5-(2-(difluoromethoxy)-4-(3,3,3-trifluoro-2-methylpropyl)phenyl)-1-methyl-1H-pyrazole-3-carboxylate

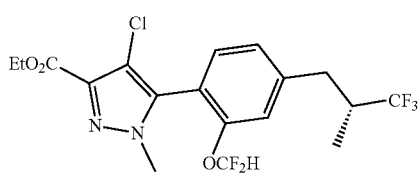

The title compound was prepared as described for the synthesis of Intermediate 116 using ethyl 5-(4-bromo-2-(difluoromethoxy)phenyl)-4-chloro-1-methyl-1H-pyrazole-3-carboxylate (Intermediate 167, Step b) in place of ethyl 5-(4-bromo-2-(difluoromethoxy)phenyl)-4-chloro-1-ethyl-1H-pyrazole-3-carboxylate.

Intermediate 185

Ethyl 4-chloro-5-(2-(difluoromethoxy)-4-(3,3,3-trifluoro-2,2-dimethylpropyl)phenyl)-1-methyl-1H-pyrazole-3-carboxylate

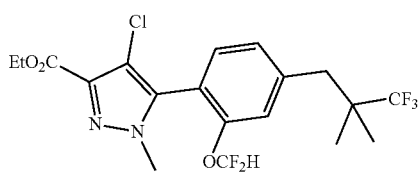

The title compound was prepared as described for the synthesis of Intermediate 116 using ethyl 5-(4-bromo-2-(difluoromethoxy)phenyl)-4-chloro-1-methyl-1H-pyrazole-3-carboxylate (Intermediate 167, Step b) in place of ethyl 5-(4-bromo-2-(difluoromethoxy)phenyl)-4-chloro-1-ethyl-1H-pyrazole-3-carboxylate and 1,1,1-trifluoro-3-iodo-2,2-dimethylpropane (Intermediate 93) in place of (S*)-1,1,1-trifluoro-3-iodo-2-methylpropane.

Intermediate 186

Ethyl 4-chloro-5-(2-(difluoromethoxy)-4-(4,4,4-trifluorobutyl)phenyl)-1-methyl-1H-pyrazole-3-carboxylate

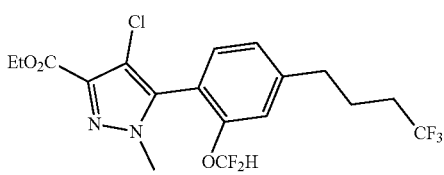

The title compound was prepared as described for the synthesis of Intermediate 98, using ethyl 5-(4-bromo-2-(difluoromethoxy)phenyl)-1-methyl-1H-pyrazole-3-carboxylate (Intermediate 167, Step b) in place of ethyl 5-(4-bromo-2-methoxyphenyl)-4-chloro-1-ethyl-1H-pyrazole-3-carboxylate and 9-(4,4,4-trifluorobutyl)-9-borabicyclo[3.3.1]nonane (Intermediate 128) in place of 9-(3,3,3-trifluoro-2-methylpropyl)-9-borabicyclo[3.3.1]nonane.

Intermediate 187

Ethyl 5-(2-(difluoromethoxy)-4-(4,4,4-trifluorobutyl)phenyl)-1,4-dimethyl-1H-pyrazole-3-carboxylate

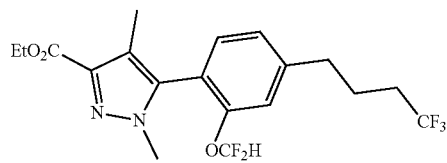

The title compound was prepared as described for the synthesis of Intermediate 105, using ethyl 4-chloro-5-(2-(difluoromethoxy)-4-(4,4,4-trifluorobutyl)phenyl)-1-methyl-1H-pyrazole-3-carboxylate (Intermediate 186) in place of ethyl 4-chloro-5-(2-(difluoromethoxy)-4-((S*)-3,3,3-trifluoro-2-methylpropyl)phenyl)-1-ethyl-1H-pyrazole-3-carboxylate.

Intermediate 188

Ethyl 4-chloro-1-ethyl-5-(4-(3,3,3-trifluoro-2,2-dimethylpropyl)-2-(trifluoromethyl)phenyl)-1H-pyrazole-3-carboxylate

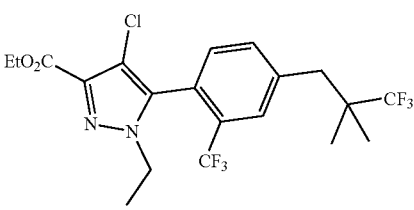 [SMILES: CCOC(=O)c1nn(CC)c(-c2ccc(CC(C)(C)C(F)(F)F)cc2C(F)(F)F)c1Cl]

The title compound was prepared as described for the synthesis of Intermediate 116, using ethyl 5-(4-bromo-2-(trifluoromethyl)phenyl)-4-chloro-1-ethyl-1H-pyrazole-3-carboxylate (Intermediate 165, Step c) in place of ethyl 5-(4-bromo-2-(difluoromethoxy)phenyl)-4-chloro-1-ethyl-1H-pyrazole-3-carboxylate and 1,1,1-trifluoro-3-iodo-2,2-dimethylpropane (Intermediate 93) in place of (S*)-1,1,1-trifluoro-3-iodo-2-methylpropane.

Intermediate 189

Ethyl 4-chloro-5-(2-chloro-4-(3,3,3-trifluoro-2,2-dimethylpropyl)phenyl)-1-ethyl-1H-pyrazole-3-carboxylate

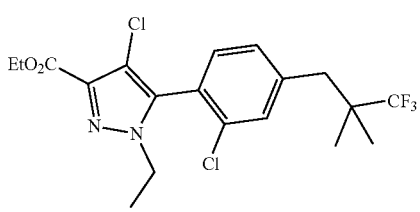 [SMILES: CCOC(=O)c1nn(CC)c(-c2ccc(CC(C)(C)C(F)(F)F)cc2Cl)c1Cl]

The title compound was prepared as described for the synthesis of Intermediate 116, using ethyl 5-(4-bromo-2-chlorophenyl)-4-chloro-1-ethyl-1H-pyrazole-3-carboxylate (Intermediate 162, Step c) in place of ethyl 5-(4-bromo-2-(difluoromethoxy)phenyl)-4-chloro-1-ethyl-1H-pyrazole-3-carboxylate and 1,1,1-trifluoro-3-iodo-2,2-dimethylpropane (Intermediate 93) in place of (S*)-1,1,1-trifluoro-3-iodo-2-methylpropane.

Intermediate 190

Ethyl 4-chloro-1-ethyl-5-(4-(3,3,3-trifluoro-2,2-dimethylpropyl)phenyl)-1H-pyrazole-3-carboxylate

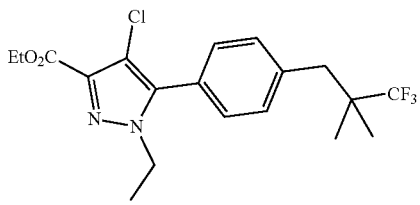 [SMILES: CCOC(=O)c1nn(CC)c(-c2ccc(CC(C)(C)C(F)(F)F)cc2)c1Cl]

The title compound was prepared as described for the synthesis of Intermediate 116, using ethyl 5-(4-bromophenyl)-4-chloro-1-ethyl-1H-pyrazole-3-carboxylate (Intermediate 166, Step c) in place of ethyl 5-(4-bromo-2-(difluoromethoxy)phenyl)-4-chloro-1-ethyl-1H-pyrazole-3-carboxylate and 1,1,1-trifluoro-3-iodo-2,2-dimethylpropane (Intermediate 93) in place of (S*)-1,1,1-trifluoro-3-iodo-2-methylpropane.

Intermediate 191

Ethyl 4-chloro-1-ethyl-5-(2-(trifluoromethyl)-4-(3,3,3-trifluoropropyl)phenyl)-1H-pyrazole-3-carboxylate

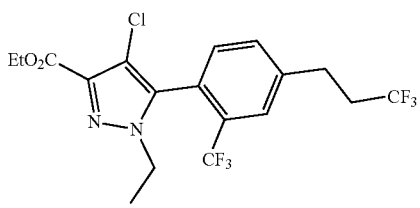

The title compound was prepared as described for the synthesis of Intermediate 98, using 9-(3,3,3-trifluoropropyl)-9-borabicyclo[3.3.1]nonane (Intermediate 95) in place of 9-(3,3,3-trifluoro-2-methylpropyl)-9-borabicyclo[3.3.1]nonane and ethyl 5-(4-bromo-2-(trifluoromethyl)phenyl)-4-chloro-1-ethyl-1H-pyrazole-3-carboxylate (Intermediate 165, Step c) in place of ethyl 5-(4-bromo-2-methoxyphenyl)-4-chloro-1-ethyl-1H-pyrazole-3-carboxylate.

Intermediate 192

Ethyl (R)-4-chloro-1-ethyl-5-(2-(trifluoromethyl)-4-(((1,1,1-trifluoropropan-2-yl)amino)phenyl)-1H-pyrazole-3-carboxylate

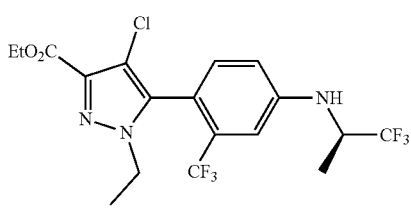 [SMILES: CCOC(=O)c1nn(CC)c(-c2ccc(N[C@H](C)C(F)(F)F)cc2C(F)(F)F)c1Cl]

The title compound was prepared as described for the synthesis of Intermediate 106, using ethyl 5-(4-bromo-2-(trifluoromethyl)phenyl)-4-chloro-1-ethyl-1H-pyrazole-3-carboxylate (Intermediate 165, Step c) in place of ethyl 5-(4-bromo-2-methoxyphenyl)-4-chloro-1-ethyl-1H-pyrazole-3-carboxylate.

Intermediate 193

Ethyl 4-chloro-5-(2-chloro-4-(3,3,3-trifluoropropyl)phenyl)-1-ethyl-1H-pyrazole-3-carboxylate

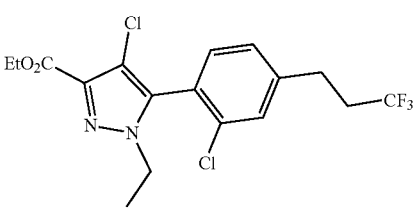 [SMILES: CCOC(=O)c1nn(CC)c(-c2ccc(CCC(F)(F)F)cc2Cl)c1Cl]

The title compound was prepared as described for the synthesis of Intermediate 98, using 9-(3,3,3-trifluoropropyl)-9-borabicyclo[3.3.1]nonane (Intermediate 95) in place of 9-(3,3,3-trifluoro-2-methylpropyl)-9-borabicyclo[3.3.1]nonane and ethyl 5-(4-bromo-2-chlorophenyl)-4-chloro-1-ethyl-1H-pyrazole-3-carboxylate (Intermediate 162, Step c) in place of ethyl 5-(4-bromo-2-methoxyphenyl)-4-chloro-1-ethyl-1H-pyrazole-3-carboxylate.

Intermediate 194

Ethyl (R)-4-chloro-5-(2-chloro-4-((1,1,1-trifluoropropan-2-yl)amino)phenyl)-1-ethyl-1H-pyrazole-3-carboxylate

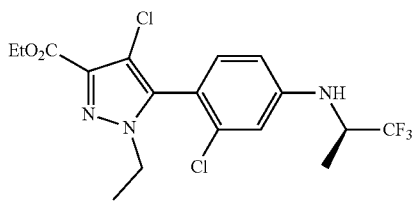 [SMILES: CCOC(=O)c1nn(CC)c(-c2ccc(N[C@H](C)C(F)(F)F)cc2Cl)c1Cl]

The title compound was prepared as described for the synthesis of Intermediate 106, using ethyl 5-(4-bromo-2-chlorophenyl)-4-chloro-1-ethyl-1H-pyrazole-3-carboxylate (Intermediate 162, Step c) in place of ethyl 5-(4-bromo-2-methoxyphenyl)-4-chloro-1-ethyl-1H-pyrazole-3-carboxylate.

Intermediate 195

Ethyl 4-chloro-1-ethyl-5-(2-fluoro-4-(3,3,3-trifluoro-2,2-dimethylpropyl)phenyl)-1H-pyrazole-3-carboxylate

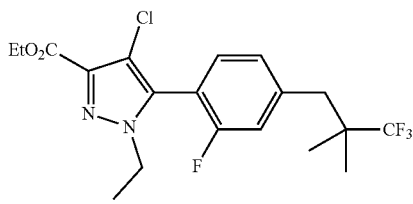 [SMILES: CCOC(=O)c1nn(CC)c(-c2ccc(CC(C)(C)C(F)(F)F)cc2F)c1Cl]

The title compound was prepared as described for the synthesis of Intermediate 116, using ethyl 5-(4-bromo-2-fluorophenyl)-4-chloro-1-ethyl-1H-pyrazole-3-carboxylate (Intermediate 133) in place of ethyl 5-(4-bromo-2-(difluoromethoxy)phenyl)-4-chloro-1-ethyl-1H-pyrazole-3-carboxylate and 1,1,1-trifluoro-3-iodo-2,2-dimethylpropane (Intermediate 93) in place of (S*)-1,1,1-trifluoro-3-iodo-2-methylpropane.

Intermediate 196

Ethyl 4-chloro-1-ethyl-5-(2-fluoro-4-(3,3,3-trifluoropropyl)phenyl)-1H-pyrazole-3-carboxylate

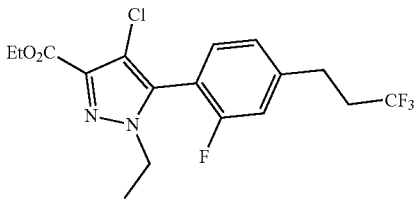 [SMILES: CCOC(=O)c1nn(CC)c(-c2ccc(CCC(F)(F)F)cc2F)c1Cl]

The title compound was prepared as described for the synthesis of Intermediate 98, using 9-(3,3,3-trifluoropropyl)-9-borabicyclo[3.3.1]nonane (Intermediate 95) in place of 9-(3,3,3-trifluoro-2-methylpropyl)-9-borabicyclo[3.3.1]nonane and ethyl 5-(4-bromo-2-fluorophenyl)-4-chloro-1-ethyl-1H-pyrazole-3-carboxylate (Intermediate 133) in place of ethyl 5-(4-bromo-2-methoxyphenyl)-4-chloro-1-ethyl-1H-pyrazole-3-carboxylate.

Intermediate 197

Ethyl (R)-4-chloro-1-ethyl-5-(2-fluoro-4-((1,1,1-trifluoropropan-2-yl)amino)phenyl)-H-pyrazole-3-carboxylate

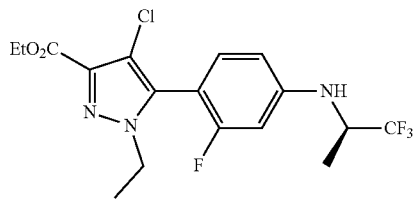 [SMILES: CCOC(=O)c1nn(CC)c(-c2ccc(N[C@H](C)C(F)(F)F)cc2F)c1Cl]

The title compound was prepared as described for the synthesis of Intermediate 106, using and ethyl 5-(4-bromo-2-fluorophenyl)-4-chloro-1-ethyl-1H-pyrazole-3-carboxylate (Intermediate 133) in place of ethyl 5-(4-bromo-2-methoxyphenyl)-4-chloro-1-ethyl-1H-pyrazole-3-carboxylate.

Intermediate 198

Ethyl 4-chloro-1-ethyl-5-(2-methyl-4-(3,3,3-trifluoro-2,2-dimethylpropyl)phenyl)-1H-pyrazole-3-carboxylate

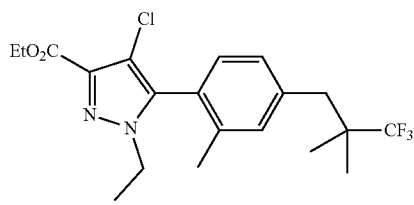 [SMILES: CCOC(=O)c1nn(CC)c(-c2ccc(CC(C)(C)C(F)(F)F)cc2C)c1Cl]

The title compound was prepared as described for the synthesis of Intermediate 116, using ethyl 5-(4-bromo-2-methylphenyl)-4-chloro-1-ethyl-1H-pyrazole-3-carboxylate (Intermediate 132) in place of ethyl 5-(4-bromo-2-(difluoromethoxy)phenyl)-4-chloro-1-ethyl-1H-pyrazole-3-carboxylate and 1,1,1-trifluoro-3-iodo-2,2-dimethylpropane (Intermediate 93) in place of (S*)-1,1,1-trifluoro-3-iodo-2-methylpropane.

Intermediate 199

Ethyl (R)-4-chloro-1-ethyl-5-(2-methyl-4-((1,1,1-trifluoropropan-2-yl)amino)phenyl)-1H-pyrazole-3-carboxylate

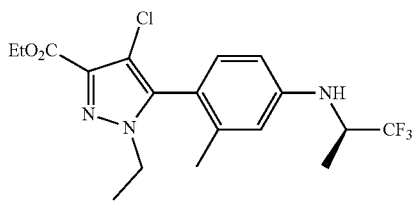 [SMILES: CCOC(=O)c1nn(CC)c(-c2ccc(N[C@H](C)C(F)(F)F)cc2C)c1Cl]

The title compound was prepared as described for the synthesis of Intermediate 106, using ethyl 5-(4-bromo-2-methylphenyl)-4-chloro-1-ethyl-1H-pyrazole-3-carboxylate (Intermediate 132) in place of ethyl 5-(4-bromo-2-methoxyphenyl)-4-chloro-1-ethyl-1H-pyrazole-3-carboxylate.

Intermediate 200, Step a

Ethyl 5-(4-bromo-2-(difluoromethoxy)phenyl)-1-(2-methoxyethyl)-1H-pyrazole-3-carboxylate

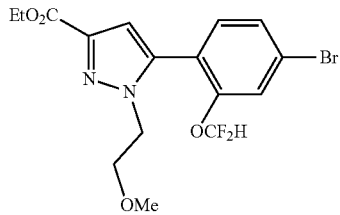

The title compound was prepared as described for the synthesis of Intermediate 161, Step b, using ethyl 4-(4-bromo-2-(difluoromethoxy)phenyl)-2,4-dioxobutanoate (Intermediate 102, Step a) in place of ethyl 4-(4-bromo-2-(trifluoromethoxy)phenyl)-2,4-dioxobutanoate and (2-methoxyethyl)hydrazine hydrochloride in place of ethylhydrazine hydrochloride.

Intermediate 200, Step b

Ethyl 5-(4-bromo-2-(difluoromethoxy)phenyl)-4-chloro-1-(2-methoxyethyl)-1H-pyrazole-3-carboxylate

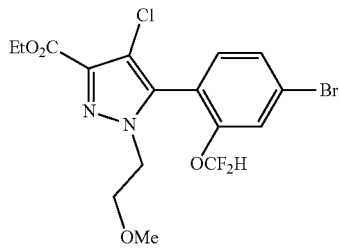

The title compound was prepared as described for the synthesis of Intermediate 102, Step c, using ethyl 5-(4-bromo-2-methoxyphenyl)-1-(2-methoxyethyl)-1H-pyrazole-3-carboxylate (Intermediate 200, Step a) in place of ethyl 5-(4-bromo-2-(difluoromethoxy)phenyl)-1-ethyl-1H-pyrazole-3-carboxylate.

Intermediate 201

Ethyl 4-chloro-5-(2-(difluoromethoxy)-4-(3,3,3-trifluoro-2,2-dimethylpropyl)phenyl)-1-(2-methoxyethyl)-1H-pyrazole-3-carboxylate

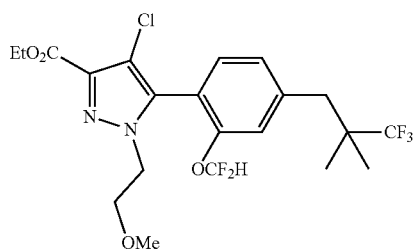

The title compound was prepared as described for the synthesis of Intermediate 116, using 1,1,1-trifluoro-3-iodo-2,2-dimethylpropane in place of (S*)-1,1,1-trifluoro-3-iodo-2-methylpropane and ethyl 5-(4-bromo-2-(difluoromethoxy)phenyl)-4-chloro-1-(2-methoxyethyl)-1H-pyrazole-3-carboxylate (Intermediate 200, Step b) in place of ethyl 5-(4-bromo-2-(difluoromethoxy)phenyl)-4-chloro-1-ethyl-1H-pyrazole-3-carboxylate.

Intermediate 202

Ethyl (R)-4-chloro-5-(2-methoxy-4-((1,1,1-trifluoropropan-2-yl)amino)phenyl)-1-(2-methoxyethyl)-1H-pyrazole-3-carboxylate

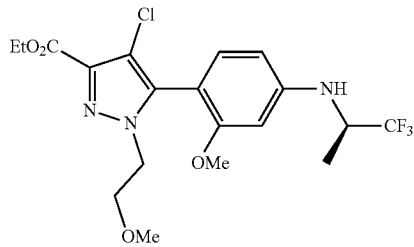 [SMILES: CCOC(=O)c1nn(CCOC)c(-c2ccc(N[C@H](C)C(F)(F)F)cc2OC)c1Cl]

The title compound was prepared as described for the synthesis of Intermediate 106, using ethyl 5-(4-bromo-2-methoxyphenyl)-4-chloro-1-(2-methoxyethyl)-1H-pyrazole-3-carboxylate (Intermediate 177, Step b) in place of ethyl 5-(4-bromo-2-methoxyphenyl)-4-chloro-1-ethyl-1H-pyrazole-3-carboxylate.

Intermediate 203

Ethyl 4-chloro-1-ethyl-5-(2-(trifluoromethoxy)-4-(3,3,3-trifluoropropyl)phenyl)-1H-pyrazole-3-carboxylate

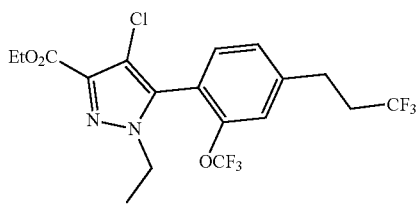 [SMILES: CCOC(=O)c1nn(CC)c(-c2ccc(CCC(F)(F)F)cc2OC(F)(F)F)c1Cl]

The title compound was prepared as described for the synthesis of Intermediate 98, using 9-(3,3,3-trifluoropropyl)-9-borabicyclo[3.3.1]nonane (Intermediate 95) in place of 9-(3,3,3-trifluoro-2-methylpropyl)-9-borabicyclo[3.3.1]nonane and ethyl 5-(4-bromo-2-(trifluoromethoxy)phenyl)-4-chloro-1-ethyl-1H-pyrazole-3-carboxylate (Intermediate 161, Step c) in place of ethyl 5-(4-bromo-2-methoxyphenyl)-4-chloro-1-ethyl-1H-pyrazole-3-carboxylate.

Intermediate 204

Ethyl (R)-4-chloro-1-ethyl-5-(2-(trifluoromethoxy)-4-((1,1,1-trifluoropropan-2-yl)amino)phenyl)-1H-pyrazole-3-carboxylate

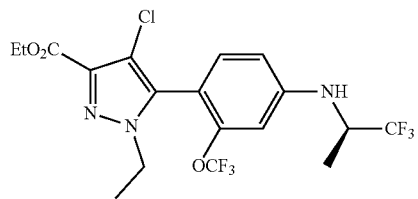 [SMILES: CCOC(=O)c1nn(CC)c(-c2ccc(N[C@H](C)C(F)(F)F)cc2OC(F)(F)F)c1Cl]

The title compound was prepared as described for the synthesis of Intermediate 106, using ethyl 5-(4-bromo-2-(trifluoromethoxy)phenyl)-4-chloro-1-ethyl-1H-pyrazole-3-carboxylate (Intermediate 161, Step c) in place of ethyl 5-(4-bromo-2-methoxyphenyl)-4-chloro-1-ethyl-1H-pyrazole-3-carboxylate (Intermediate 97, Step c).

Intermediate 205

Ethyl 4-chloro-1-ethyl-5-(4-(3,3,3-trifluoro-2-methylpropyl)-2-(trifluoromethoxy)phenyl)-1H-pyrazole-3-carboxylate

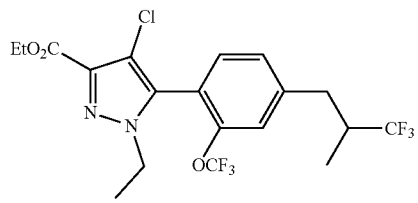 [SMILES: CCOC(=O)c1nn(CC)c(-c2ccc(CC(C)C(F)(F)F)cc2OC(F)(F)F)c1Cl]

The title compound was prepared as described for the synthesis of Intermediate 98, using ethyl 5-(4-bromo-2-(trifluoromethoxy)phenyl)-4-chloro-1-ethyl-1H-pyrazole-3-carboxylate (Intermediate 161, Step c) in place of ethyl 5-(4-bromo-2-methoxyphenyl)-4-chloro-1-ethyl-1H-pyrazole-3-carboxylate.

Intermediate 206

Ethyl (R)-4-chloro-1-ethyl-5-(4-((1,1,1-trifluoropropan-2-yl)amino)phenyl)-1H-pyrazole-3-carboxylate

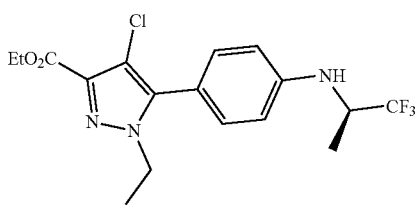 [SMILES: CCOC(=O)c1nn(CC)c(-c2ccc(N[C@H](C)C(F)(F)F)cc2)c1Cl]

The title compound was prepared as described for the synthesis of Intermediate 106, using ethyl 5-(4-bromophenyl)-4-chloro-1-ethyl-1H-pyrazole-3-carboxylate (Intermediate 166, Step c) in place of ethyl 5-(4-bromo-2-methoxyphenyl)-4-chloro-1-ethyl-1H-pyrazole-3-carboxylate (Intermediate 97, Step c).

Intermediate 207

Ethyl (R)-4-chloro-5-(2,6-difluoro-4-((1,1,1-trifluoropropan-2-yl)amino)phenyl)-1-ethyl-1H-pyrazole-3-carboxylate

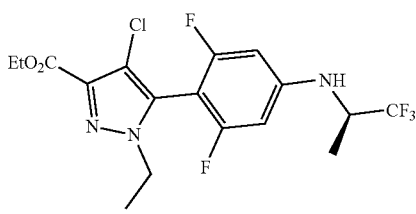 [SMILES: CCOC(=O)c1nn(CC)c(-c2c(F)cc(N[C@H](C)C(F)(F)F)cc2F)c1Cl]

The title compound was prepared as described for the synthesis of Intermediate 106, using ethyl 5-(4-bromo-2,6-difluorophenyl)-4-chloro-1-ethyl-1H-pyrazole-3-carboxylate (Intermediate 130) in place of ethyl 5-(4-bromo-2-methoxyphenyl)-4-chloro-1-ethyl-1H-pyrazole-3-carboxylate.

Intermediate 208

Ethyl 4-chloro-5-(2,6-difluoro-4-(3,3,3-trifluoro-2-methylpropyl)phenyl)-1-ethyl-1H-pyrazole-3-carboxylate

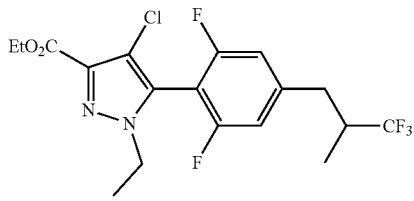 [SMILES: CCOC(=O)c1nn(CC)c(-c2c(F)cc(CC(C)C(F)(F)F)cc2F)c1Cl]

The title compound was prepared as described for the synthesis of Intermediate 98, using ethyl 5-(4-bromo-2,6-difluorophenyl)-4-chloro-1-ethyl-1H-pyrazole-3-carboxylate (Intermediate 130) in place of ethyl 5-(4-bromo-2-methoxyphenyl)-4-chloro-1-ethyl-1H-pyrazole-3-carboxylate.

Intermediate 209

Ethyl 4-chloro-1-(2-hydroxyethyl)-5-(2-methoxy-4-(3,3,3-trifluoro-2-methylpropyl)phenyl)-1H-pyrazole-3-carboxylate

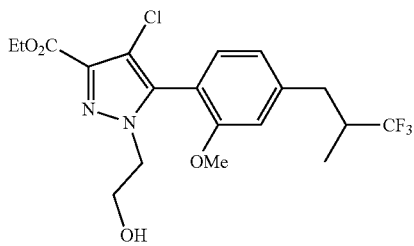 [SMILES: CCOC(=O)c1nn(CCO)c(-c2ccc(CC(C)C(F)(F)F)cc2OC)c1Cl]

The title compound was prepared as described for the synthesis of Intermediate 98, using ethyl 5-(4-bromo-2-methoxyphenyl)-4-chloro-1-(2-hydroxyethyl)-1H-pyrazole-3-carboxylate (Intermediate 179, Step b) in place of ethyl 5-(4-bromo-2-methoxyphenyl)-4-chloro-1-ethyl-1H-pyrazole-3-carboxylate.

Intermediate 210

Ethyl (R)-4-chloro-1-(2-hydroxyethyl)-5-(2-methoxy-4-((1,1,1-trifluoropropan-2-yl)amino)phenyl)-1H-pyrazole-3-carboxylate

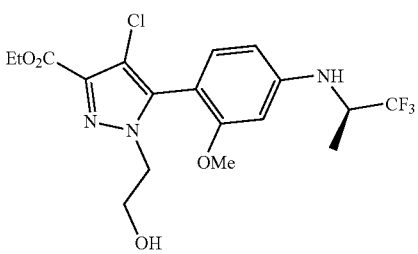 [SMILES: CCOC(=O)c1nn(CCO)c(-c2ccc(N[C@H](C)C(F)(F)F)cc2OC)c1Cl]

The title compound was prepared as described for the synthesis of Intermediate 106, using ethyl 5-(4-bromo-2-methoxyphenyl)-4-chloro-1-(2-hydroxyethyl)-1H-pyrazole-3-carboxylate (Intermediate 179, Step b) in place of ethyl 5-(4-bromo-2-methoxyphenyl)-4-chloro-1-ethyl-1H-pyrazole-3-carboxylate.

Intermediate 211, Step a

Ethyl 5-(4-bromo-2-methoxyphenyl)-1-(2-hydroxy-2-methylpropyl)-1H-pyrazole-3-carboxylate

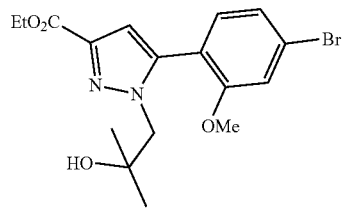 [SMILES: CCOC(=O)c1cc(-c2ccc(Br)cc2OC)n(CC(C)(C)O)n1]

The title compound was prepared as described for the synthesis of Intermediate 161, Step b, using ethyl 4-(4-bromo-2-methoxyphenyl)-2,4-dioxobutanoate (Intermediate 97, Step a) in place of ethyl 4-(4-bromo-2-(trifluoromethoxy)phenyl)-2,4-dioxobutanoate and 1-hydrazinyl-2-methylpropan-2-ol in place of ethylhydrazine hydrochloride.

Intermediate 211, Step b

Ethyl 5-(4-bromo-2-methoxyphenyl)-4-chloro-1-(2-hydroxy-2-methylpropyl)-1H-pyrazole-3-carboxylate

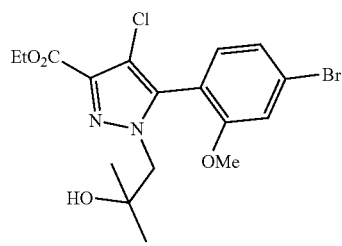 [SMILES: CCOC(=O)c1nn(CC(C)(C)O)c(-c2ccc(Br)cc2OC)c1Cl]

The title compound was prepared as described for the synthesis of Intermediate 97, Step c, using ethyl 5-(4-bromo-2-methoxyphenyl)-1-(2-hydroxy-2-methylpropyl)-1H-pyrazole-3-carboxylate (Intermediate 211, Step a) in place of ethyl 5-(4-bromo-2-methoxyphenyl)-1-ethyl-1H-pyrazole-3-carboxylate and without the use of TFA.

Intermediate 212

Ethyl (R)-4-chloro-1-(2-hydroxy-2-methylpropyl)-5-(2-methoxy-4-((1,1,1-trifluoropropan-2-yl)amino)phenyl)-1H-pyrazole-3-carboxylate

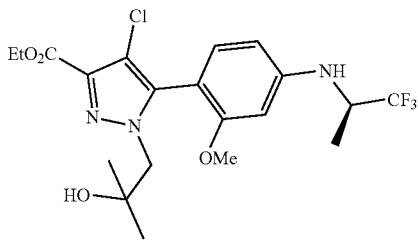 [SMILES: CCOC(=O)c1nn(CC(C)(C)O)c(-c2ccc(N[C@H](C)C(F)(F)F)cc2OC)c1Cl]

The title compound was prepared as described for the synthesis of Intermediate 106, using ethyl 5-(4-bromo-2-methoxyphenyl)-4-chloro-1-(2-hydroxy-2-methylpropyl)-1H-pyrazole-3-carboxylate (Intermediate 211, Step b) in place of ethyl 5-(4-bromo-2-methoxyphenyl)-4-chloro-1-ethyl-1H-pyrazole-3-carboxylate.

Intermediate 213

Ethyl 5-(4-bromo-2-methoxyphenyl)-1-ethyl-4-fluoro-1H-pyrazole-3-carboxylate

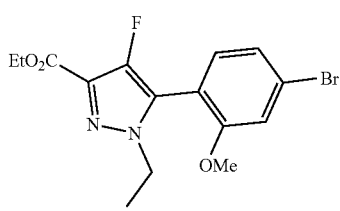 [SMILES: CCOC(=O)c1nn(CC)c(-c2ccc(Br)cc2OC)c1F]

Selectfluor® (535 mg, 1.51 mmol) was added to ethyl 5-(4-bromo-2-methoxyphenyl)-1-ethyl-1H-pyrazole-3-carboxylate (510 mg, 1.444 mmol, Intermediate 97, Step b) in MeCN (7.5 mL), and the mixture was stirred at 65° C. for 26 h. After this time, the mixture was allowed to cool, and then it was diluted with DCM and 1 N aqueous HCl. The layers were separated, and the organic layer was dried with anhydrous MgSO$_4$, filtered, and then concentrated. The residue was purified by silica gel chromatography (0-50% EtOAc/hexanes) and then by SFC (Lux Cellulose-5, 92% CO$_2$, 8% IPA, 0.2% i-PrNH$_2$) to give the title compound.

Intermediate 214

Ethyl (R)-1-ethyl-4-fluoro-5-(2-methoxy-4-((1,1,1-trifluoropropan-2-yl)amino)phenyl)-1H-pyrazole-3-carboxylate

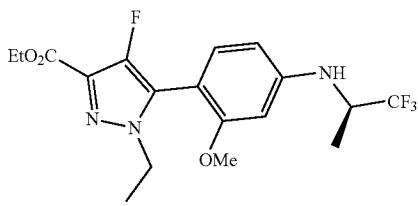 [SMILES: CCOC(=O)c1nn(CC)c(-c2ccc(N[C@H](C)C(F)(F)F)cc2OC)c1F]

The title compound was prepared as described for the synthesis of Intermediate 106, using ethyl 5-(4-bromo-2-methoxyphenyl)-1-ethyl-4-fluoro-1H-pyrazole-3-carboxylate (Intermediate 213) in place of ethyl 5-(4-bromo-2-methoxyphenyl)-4-chloro-1-ethyl-1H-pyrazole-3-carboxylate.

Intermediate 215

4-Bromo-2-isopropyl-N-methoxy-N-methylbenzamide

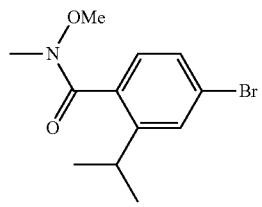 [SMILES: CON(C)C(=O)c1ccc(Br)cc1C(C)C]

The title compound was prepared as described for the synthesis of Intermediate 107, using 4-bromo-2-isopropylbenzoic acid in place of 4-bromo-2-methoxybenzoic acid and DMF as the solvent.

Intermediate 216

1-(4-Bromo-2-isopropylphenyl)ethan-1-one

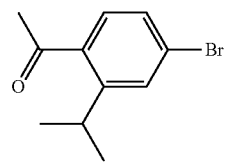

The title compound was prepared as described for the synthesis of Intermediate 108, using methylmagnesium bromide in place of ethylmagnesium chloride and 4-bromo-2-isopropyl-N-methoxy-N-methylbenzamide (Intermediate 205) in place of 4-bromo-N,2-dimethoxy-N-methylbenzamide.

Intermediate 217, Step a

Ethyl 5-(4-bromo-2-isopropylphenyl)-2,3,5-trioxopentanoate

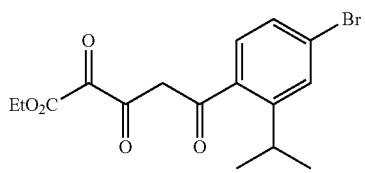 [SMILES: CCOC(=O)C(=O)C(=O)CC(=O)c1ccc(Br)cc1C(C)C]

The title compound was prepared as described for the synthesis of Intermediate 97, Step a, using 1-(4-bromo-2-isopropylphenyl)ethan-1-one (Intermediate 216) in place of 1-(4-bromo-2-methoxyphenyl)ethan-1-one.

161

Intermediate 217, Step b

Ethyl 5-(4-bromo-2-isopropylphenyl)-1-ethyl-1H-pyrazole-3-carboxylate

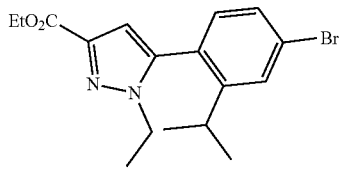 [SMILES: CCOC(=O)c1cc(-c2ccc(Br)cc2C(C)C)n(CC)n1]

The title compound was prepared as described for the synthesis of Intermediate 161, Step b, using ethyl 5-(4-bromo-2-isopropylphenyl)-2,3,5-trioxopentanoate (Intermediate 217, Step a) in place of ethyl 4-(4-bromo-2-(trifluoromethoxy)phenyl)-2,4-dioxobutanoate.

Intermediate 217, Step c

Ethyl 5-(4-bromo-2-isopropylphenyl)-4-chloro-1-ethyl-1H-pyrazole-3-carboxylate

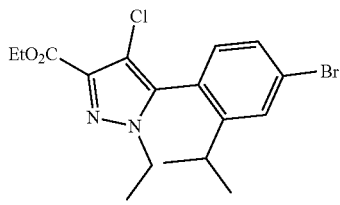 [SMILES: CCOC(=O)c1nn(CC)c(-c2ccc(Br)cc2C(C)C)c1Cl]

The title compound was prepared as described for the synthesis of Intermediate 102, Step c, using ethyl 5-(4-bromo-2-isopropylphenyl)-1-ethyl-1H-pyrazole-3-carboxylate (Intermediate 217, Step b) in place of ethyl 5-(4-bromo-2-(difluoromethoxy)phenyl)-1-ethyl-1H-pyrazole-3-carboxylate.

Intermediate 218

Ethyl (R)-4-chloro-1-ethyl-5-(2-isopropyl-4-((1,1,1-trifluoropropan-2-yl)amino)phenyl)-1H-pyrazole-3-carboxylate

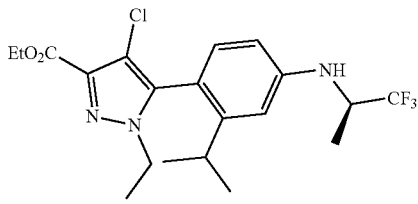 [SMILES: CCOC(=O)c1nn(CC)c(-c2ccc(N[C@H](C)C(F)(F)F)cc2C(C)C)c1Cl]

The title compound was prepared as described for the synthesis of Intermediate 106, using ethyl 5-(4-bromo-2-isopropylphenyl)-4-chloro-1-ethyl-1H-pyrazole-3-carboxylate (Intermediate 217, Step c) in place of ethyl 5-(4-bromo-2-methylphenyl)-4-chloro-1-ethyl-1H-pyrazole-3-carboxylate.

162

Intermediate 219

1-(4-Bromo-2-ethoxyphenyl)ethan-1-one

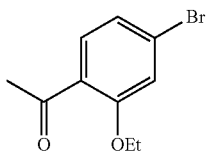

The title compound was prepared as described for the synthesis of Intermediate 96, using iodoethane in place of iodomethane and a reaction time of 1h.

Intermediate 220

Ethyl 5-(4-bromo-2-ethoxyphenyl)-2,3,5-trioxopentanoate

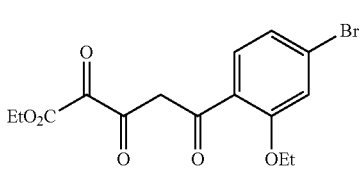 [SMILES: CCOC(=O)C(=O)C(=O)CC(=O)c1ccc(Br)cc1OCC]

The title compound was prepared as described for the synthesis of Intermediate 97, Step a, using 1-(4-bromo-2-ethoxyphenyl)ethan-1-one (Intermediate 219) in place of 1-(4-bromo-2-methoxyphenyl)ethan-1-one.

Intermediate 221

Ethyl 5-(4-bromo-2-ethoxyphenyl)-1-ethyl-1H-pyrazole-3-carboxylate

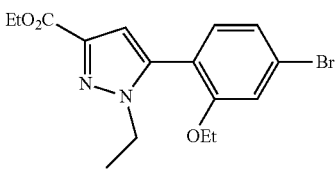 [SMILES: CCOC(=O)c1cc(-c2ccc(Br)cc2OCC)n(CC)n1]

The title compound was prepared as described for the synthesis of Intermediate 161, Step b, using ethyl 5-(4-bromo-2-ethoxyphenyl)-2,3,5-trioxopentanoate (Intermediate 220) in place of ethyl 4-(4-bromo-2-(trifluoromethoxy)phenyl)-2,4-dioxobutanoate.

Intermediate 222

Ethyl 5-(4-bromo-2-ethoxyphenyl)-4-chloro-1-ethyl-1H-pyrazole-3-carboxylate

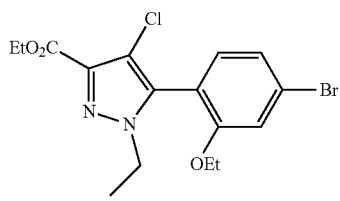 [SMILES: CCOC(=O)c1nn(CC)c(-c2ccc(Br)cc2OCC)c1Cl]

The title compound was prepared as described for the synthesis of Intermediate 102, Step c, using ethyl 5-(4-bromo-2-ethoxyphenyl)-1-ethyl-1H-pyrazole-3-carboxylate (Intermediate 221) in place of ethyl 5-(4-bromo-2-(difluoromethoxy)phenyl)-1-ethyl-1H-pyrazole-3-carboxylate.

Intermediate 223

Ethyl (R)-4-chloro-5-(2-ethoxy-4-((1,1,1-trifluoropropan-2-yl)amino)phenyl)-1-ethyl-1H-pyrazole-3-carboxylate

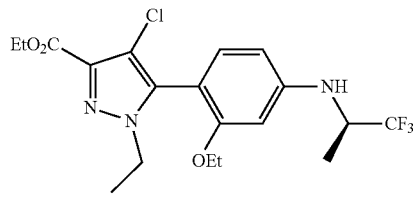 [SMILES: CCOC(=O)c1nn(CC)c(-c2ccc(N[C@H](C)C(F)(F)F)cc2OCC)c1Cl]

The title compound was prepared as described for the synthesis of Intermediate 106, using ethyl 5-(4-bromo-2-ethoxyphenyl)-4-chloro-1-ethyl-1H-pyrazole-3-carboxylate (Intermediate 222) in place of ethyl 5-(4-bromo-2-methoxyphenyl)-4-chloro-1-ethyl-1H-pyrazole-3-carboxylate.

Intermediate 224

4-Bromo-2-ethyl-N-methoxy-N-methylbenzamide

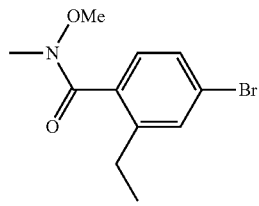

The title compound was prepared as described for the synthesis of Intermediate 107, using 4-bromo-2-ethylbenzoic acid in place of 4-bromo-2-methoxybenzoic acid and DMF as the solvent.

Intermediate 225

1-(4-Bromo-2-ethylphenyl)ethan-1-one

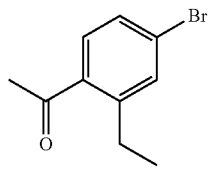

The title compound was prepared as described for the synthesis of Intermediate 108, using methylmagnesium bromide in place of ethylmagnesium chloride and 4-bromo-2-ethyl-N-methoxy-N-methylbenzamide (Intermediate 224) in place of 4-bromo-N,2-dimethoxy-N-methylbenzamide.

Intermediate 226

Ethyl 5-(4-bromo-2-ethylphenyl)-2,3,5-trioxopentanoate

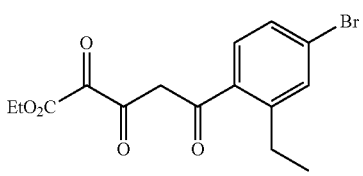 [SMILES: CCOC(=O)C(=O)C(=O)CC(=O)c1ccc(Br)cc1CC]

The title compound was prepared as described for the synthesis of Intermediate 97, Step a, using 1-(4-bromo-2-ethylphenyl)ethan-1-one (Intermediate 225) in place of 1-(4-bromo-2-methoxyphenyl)ethan-1-one.

Intermediate 227

Ethyl 5-(4-bromo-2-ethylphenyl)-1-ethyl-1H-pyrazole-3-carboxylate

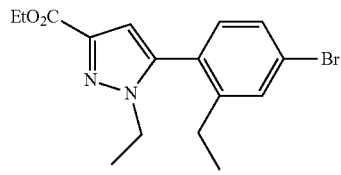 [SMILES: CCOC(=O)c1cc(-c2ccc(Br)cc2CC)n(CC)n1]

The title compound was prepared as described for the synthesis of Intermediate 161, Step b, using ethyl 5-(4-bromo-2-ethylphenyl)-2,3,5-trioxopentanoate (Intermediate 226) in place of ethyl 4-(4-bromo-2-(trifluoromethoxy)phenyl)-2,4-dioxobutanoate.

Intermediate 228

Ethyl 5-(4-bromo-2-ethylphenyl)-4-chloro-1-ethyl-1H-pyrazole-3-carboxylate

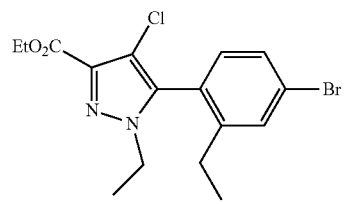 [SMILES: CCOC(=O)c1nn(CC)c(-c2ccc(Br)cc2CC)c1Cl]

The title compound was prepared as described for the synthesis of Intermediate 102, Step c, using ethyl 5-(4-bromo-2-ethylphenyl)-1-ethyl-1H-pyrazole-3-carboxylate (Intermediate 227) in place of ethyl 5-(4-bromo-2-(difluoromethoxy)phenyl)-1-ethyl-1H-pyrazole-3-carboxylate, and the reaction was performed at rt instead of starting at 0° C.

Intermediate 229

Ethyl (R)-4-chloro-1-ethyl-5-(2-ethyl-4-((1,1,1-trifluoropropan-2-yl)amino)phenyl)-1H-pyrazole-3-carboxylate

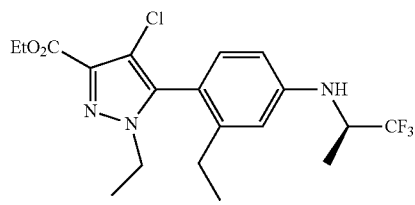 [SMILES: CCOC(=O)c1nn(CC)c(-c2ccc(N[C@H](C)C(F)(F)F)cc2CC)c1Cl]

The title compound was prepared as described for the synthesis of Intermediate 106, using ethyl 5-(4-bromo-2-ethylphenyl)-4-chloro-1-ethyl-1H-pyrazole-3-carboxylate (Intermediate 228) in place of ethyl 5-(4-bromo-2-methoxyphenyl)-4-chloro-1-ethyl-1H-pyrazole-3-carboxylate.

Intermediate 230

1-(4-Bromo-2-isopropoxyphenyl)ethan-1-one

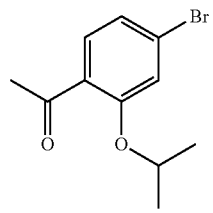

The title compound was prepared as described for the synthesis of Intermediate 96, using 2-iodopropane in place of iodomethane and a reaction time of 1h.

Intermediate 231

Ethyl 5-(4-bromo-2-isopropoxyphenyl)-2,3,5-trioxopentanoate

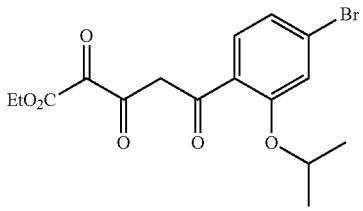 [SMILES: CCOC(=O)C(=O)C(=O)CC(=O)c1ccc(Br)cc1OC(C)C]

The title compound was prepared as described for the synthesis of Intermediate 97, Step a, using 1-(4-bromo-2-isopropoxyphenyl)ethan-1-one (Intermediate 230) in place of 1-(4-bromo-2-methoxyphenyl)ethan-1-one.

Intermediate 232

Ethyl 5-(4-bromo-2-isopropoxyphenyl)-1-ethyl-1H-pyrazole-3-carboxylate

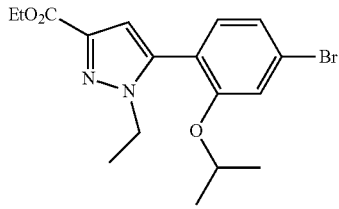 [SMILES: CCOC(=O)c1cc(-c2ccc(Br)cc2OC(C)C)n(CC)n1]

The title compound was prepared as described for the synthesis of Intermediate 161, Step b, using ethyl 5-(4-bromo-2-isopropoxyphenyl)-2,3,5-trioxopentanoate (Intermediate 231) in place of ethyl 4-(4-bromo-2-(trifluoromethoxy)phenyl)-2,4-dioxobutanoate.

Intermediate 233

Ethyl 5-(4-bromo-2-isopropoxyphenyl)-4-chloro-1-ethyl-1H-pyrazole-3-carboxylate

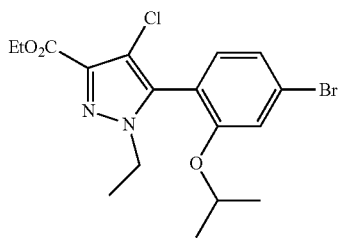 [SMILES: CCOC(=O)c1nn(CC)c(-c2ccc(Br)cc2OC(C)C)c1Cl]

The title compound was prepared as described for the synthesis of Intermediate 102, Step c, using ethyl 5-(4-bromo-2-isopropoxyphenyl)-1-ethyl-1H-pyrazole-3-carboxylate (Intermediate 232) in place of ethyl 5-(4-bromo- 2-(difluoromethoxy)phenyl)-1-ethyl-1H-pyrazole-3-carboxylate, and the reaction was performed at rt instead of starting at 0° C.

Intermediate 234

Ethyl (R)-4-chloro-1-ethyl-5-(2-isopropoxy-4-((1,1,1-trifluoropropan-2-yl)amino)phenyl)-1H-pyrazole-3-carboxylate

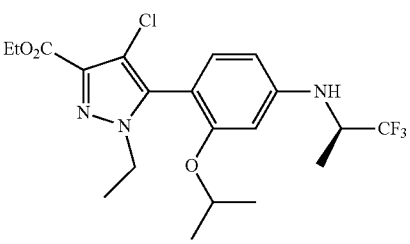 [SMILES: CCOC(=O)c1nn(CC)c(-c2ccc(N[C@H](C)C(F)(F)F)cc2OC(C)C)c1Cl]

The title compound was prepared as described for the synthesis of Intermediate 106, using ethyl 5-(4-bromo-2-isopropoxyphenyl)-4-chloro-1-ethyl-1H-pyrazole-3-carboxylate (Intermediate 233) in place of ethyl 5-(4-bromo-2-methoxyphenyl)-4-chloro-1-ethyl-1H-pyrazole-3-carboxylate.

Intermediate 235

Ethyl 4-chloro-5-(4-((2,2-difluorocyclopropyl)methoxy)-2-methoxyphenyl)-1-ethyl-1H-pyrazole-3-carboxylate

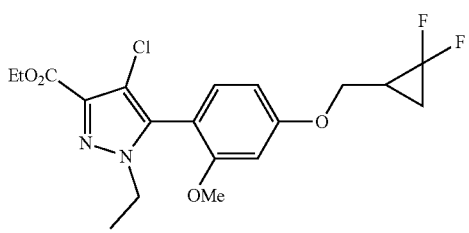 [SMILES: CCOC(=O)c1nn(CC)c(-c2ccc(OCC3CC3(F)F)cc2OC)c1Cl]

A solution of (2,2-difluorocyclopropyl)methanol (225 mg, 2.08 mmol) in toluene (1 mL) was added to a mixture of ethyl 5-(4-bromo-2-methoxyphenyl)-4-chloro-1-ethyl-1H-pyrazole-3-carboxylate (500 mg, 1.29 mmol, Intermediate 97, Step c), K₃PO₄ (570 mg, 2.69 mmol), t-Bu-XPhos (48 mg, 0.11 mmol), and Pd₂(dba)₃ (67 mg, 0.073 mmol) in dry toluene (20 mL). The reactor was evacuated and then backfilled with nitrogen three times and then stirred at 100° C. After 24 h, the mixture was allowed to cool to rt and filtered through a Celite®. The pad was rinsed with EtOAc, and the filtrate and rinse were combined, concentrated, and then purified by silica gel chromatography (5→50% EtOAc/hexanes) to afford the titled compound as a light amber gum.

Intermediate 236

Ethyl 4-chloro-5-(4-((4,4-difluorocyclohexyl)oxy)-2-methoxyphenyl)-1-ethyl-1H-pyrazole-3-carboxylate

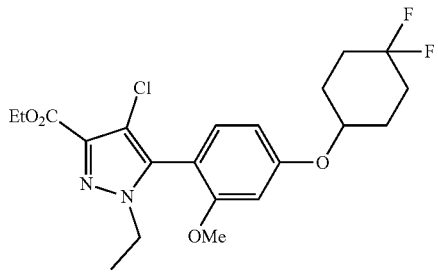 [SMILES: CCOC(=O)c1nn(CC)c(-c2ccc(OC3CCC(F)(F)CC3)cc2OC)c1Cl]

The title compound was prepared as described for the synthesis of Intermediate 235, using 4,4-difluorocyclohexan-1-ol and Cs₂CO₃ in place of (2,2-difluorocyclopropyl)methanol and K₃PO₄.

Intermediate 237

Ethyl 4-chloro-1-ethyl-5-(2-methoxy-4-((1,1,1-trifluoropropan-2-yl)oxy)phenyl)-1H-pyrazole-3-carboxylate

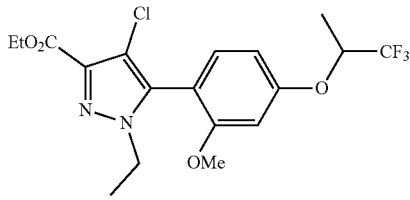 [SMILES: CCOC(=O)c1nn(CC)c(-c2ccc(OC(C)C(F)(F)F)cc2OC)c1Cl]

The title compound was prepared as described for the synthesis of Intermediate 235, using 1,1,1-trifluoropropan-2-ol in place of (2,2-difluorocyclopropyl)methanol.

Intermediate 238

Ethyl 4-chloro-1-ethyl-5-(2-methoxy-4-(3,3,3-trifluoropropoxy)phenyl)-1H-pyrazole-3-carboxylate

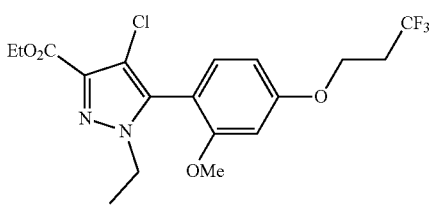 [SMILES: CCOC(=O)c1nn(CC)c(-c2ccc(OCCC(F)(F)F)cc2OC)c1Cl]

The title compound was prepared as described for the synthesis of Intermediate 235, using 3,3,3-trifluoropropan-1-ol in place of (2,2-difluorocyclopropyl)methanol.

Intermediate 239

Ethyl 4-chloro-5-(4-(2,2-difluoropropoxy)-2-methoxyphenyl)-1-ethyl-1H-pyrazole-3-carboxylate

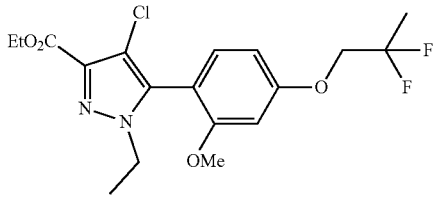 [SMILES: CCOC(=O)c1nn(CC)c(-c2ccc(OCC(C)(F)F)cc2OC)c1Cl]

The title compound was prepared as described for the synthesis of Intermediate 235, using 2,2-difluoropropan-1-ol in place of (2,2-difluorocyclopropyl)methanol.

Intermediate 240

Ethyl 4-chloro-1-ethyl-5-(2-methoxy-4-((1-methylcyclopropyl)methoxy)phenyl)-1H-pyrazole-3-carboxylate

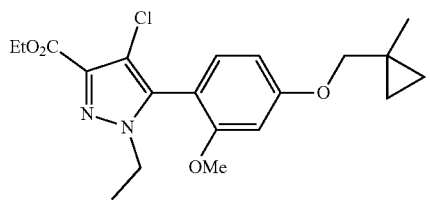 [SMILES: CCOC(=O)c1nn(CC)c(-c2ccc(OCC3(C)CC3)cc2OC)c1Cl]

The title compound was prepared as described for the synthesis of Intermediate 235, using (1-methylcyclopropyl)methanol in place of (2,2-difluorocyclopropyl)methanol.

Intermediate 241

Ethyl 5-(4-bromo-2-methoxyphenyl)-1-ethyl-4-iodo-1H-pyrazole-3-carboxylate

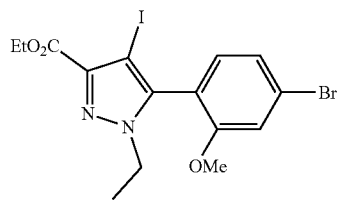 [SMILES: CCOC(=O)c1nn(CC)c(-c2ccc(Br)cc2OC)c1I]

N-Iodosuccinimide (1.91 g, 8.49 mmol) and then CAN (900 mg, 1.64 mmol) were added to a solution of ethyl 5-(4-bromo-2-methoxyphenyl)-1-ethyl-1H-pyrazole-3-carboxylate (2.2 g, 6.2 mmol, Intermediate 97, Step b) in MeCN (190 mL). The mixture was stirred at 50° C. for 4 h, at which time the reaction was judged to be complete. The reaction mixture was concentrated, and the residue was diluted with EtOAc and a saturated aqueous NaHCO₃ solution. The layers were separated, and the aqueous layer was extracted twice with EtOAc. The organic layers were combined, washed with brine, dried with anhydrous MgSO₄, filtered, and then concentrated. The residue was purified by silica gel chromatography (0-5% EtOAc/DCM) to afford the title compound as a pale yellow solid.

Intermediate 242

Ethyl 5-(4-bromo-2-methoxyphenyl)-1-ethyl-4-(trifluoromethyl)-1H-pyrazole-3-carboxylate

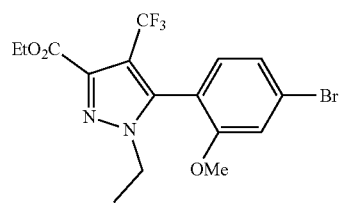 [SMILES: CCOC(=O)c1nn(CC)c(-c2ccc(Br)cc2OC)c1C(F)(F)F]

Methyl 2,2-difluoro-2-(fluorosulfonyl)acetate (0.860 mL, 6.71 mmol) was added to a mixture of ethyl 5-(4-bromo-2-methoxyphenyl)-1-ethyl-4-iodo-1H-pyrazole-3-carboxylate (640 mg, 1.34 mmol, Intermediate 241) and CuI (350 mg, 1.84 mmol) in DMF (25 mL), and the mixture was stirred at 100° C. for 3 h. After this time, the mixture was allowed to cool to rt and filtered through Celite®. The pad was rinsed with EtOAc, and then the filtrate and rinse were combined and concentrated. The residue was purified by silica gel chromatography (100% DCM) to afford the title compound as an amber gum.

Intermediate 243

Ethyl (R)-1-ethyl-5-(2-methoxy-4-((1,1,1-trifluoropropan-2-yl)amino)phenyl)-4-(trifluoromethyl)-1H-pyrazole-3-carboxylate

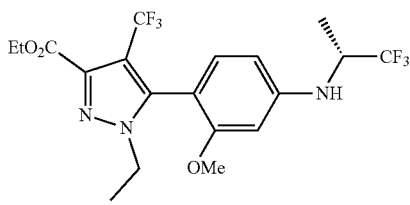 [SMILES: CCOC(=O)c1nn(CC)c(-c2ccc(N[C@H](C)C(F)(F)F)cc2OC)c1C(F)(F)F]

The title compound was prepared as described for the synthesis of Intermediate 106, using ethyl 5-(4-bromo-2-methoxyphenyl)-1-ethyl-4-(trifluoromethyl)-1H-pyrazole-3-carboxylate (Intermediate 242) in place of ethyl 5-(4-bromo-2-methoxyphenyl)-4-chloro-1-ethyl-1H-pyrazole-3-carboxylate (Intermediate 97, Step c).

Intermediate 244

4-Chloro-1-ethyl-5-(2-methoxy-4-(((R)-1,1,1-trifluoropropan-2-yl)amino)phenyl)-N-(((2RS*,5RS*)-5-(methylsulfonyl)tetrahydro-2H-pyran-2-yl)methyl)-1H-pyrazole-3-carboxamide

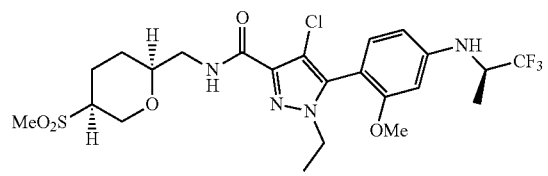 [SMILES: CCn1nc(C(=O)NC[C@@H]2CC[C@H](S(C)(=O)=O)CO2)c(Cl)c1-c1ccc(N[C@H](C)C(F)(F)F)cc1OC]

The title compound was prepared as described for the synthesis of Example 1, using ethyl (R)-4-chloro-1-ethyl-5-(2-methoxy-4-((1,1,1-trifluoropropan-2-yl)amino)phenyl)-1H-pyrazole-3-carboxylate (Intermediate 106) and ((2RS,5RS)-5-(methylsulfonyl)tetrahydro-2H-pyran-2-yl)methanamine hydrochloride (Intermediate 76) in place of ethyl (R*)-4-chloro-1-ethyl-5-(2-methoxy-4-(3,3,3-trifluoro-2-methylpropyl)phenyl)-1H-pyrazole-3-carboxylate and ((1r,4r)-4-(methylsulfonyl)cyclohexyl)methanamine hydrochloride.

Intermediate 245

4-Chloro-5-(2-(difluoromethoxy)-4-(3,3,3-trifluoro-2,2-dimethylpropyl)phenyl)-1-ethyl-N-(((1RS,2SR,4SR)-2-hydroxy-4-(methylsulfonyl)cyclohexyl)methyl)-1H-pyrazole-3-carboxamide

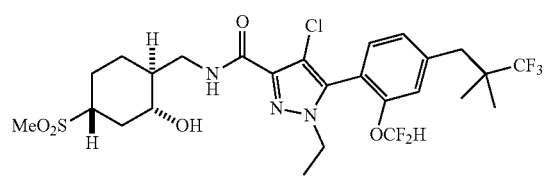

The title compound was prepared as described for the synthesis of Example 1, using ethyl 4-chloro-5-(2-(difluoromethoxy)-4-(3,3,3-trifluoro-2,2-dimethylpropyl)phenyl)-1-ethyl-1H-pyrazole-3-carboxylate (Intermediate 103) and (1RS,2SR,5RS)-2-(aminomethyl)-5-(methylsulfonyl)cyclohexan-1-ol hydrochloride (Intermediate 83) in place of ethyl (R*)-4-chloro-1-ethyl-5-(2-methoxy-4-(3,3,3-trifluoro-2-methylpropyl)phenyl)-1H-pyrazole-3-carboxylate and ((1r,4r)-4-(methylsulfonyl)cyclohexyl)methanamine hydrochloride.

Intermediate 246

4-Chloro-5-(2-(difluoromethoxy)-4-(3,3,3-trifluoro-2,2-dimethylpropyl)phenyl)-N-(((1RS,2RS,4RS)-1,2-dihydroxy-4-(methylsulfonyl)cyclohexyl)methyl)-1-ethyl-1H-pyrazole-3-carboxamide

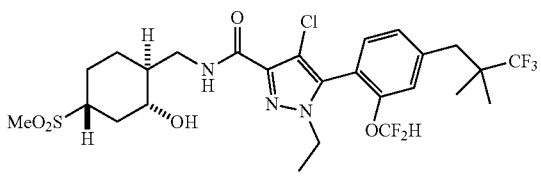

The title compound was prepared as described for the synthesis of Example 1, using ethyl 4-chloro-5-(2-(difluoromethoxy)-4-(3,3,3-trifluoro-2,2-dimethylpropyl)phenyl)-1-ethyl-1H-pyrazole-3-carboxylate (Intermediate 103) and (1RS,2RS,4RS)-1-(aminomethyl)-4-(methylsulfonyl)cyclohexane-1,2-diol hydrochloride (Intermediate 86) in place of ethyl (R*)-4-chloro-1-ethyl-5-(2-methoxy-4-(3,3,3-trifluoro-2-methylpropyl)phenyl)-1H-pyrazole-3-carboxylate and ((1r,4r)-4-(methylsulfonyl)cyclohexyl)methanamine hydrochloride.

Intermediate 247

4-Chloro-5-(2-(difluoromethoxy)-4-(3,3,3-trifluoro-2,2-dimethylpropyl)phenyl)-N-(((1RS,2RS,4SR)-1,2-dihydroxy-4-(methylsulfonyl)cyclohexyl)methyl)-1-ethyl-1H-pyrazole-3-carboxamide

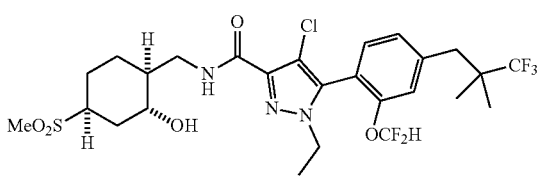

The title compound was prepared as described for the synthesis of Example 1, using ethyl 4-chloro-5-(2-(difluoromethoxy)-4-(3,3,3-trifluoro-2,2-dimethylpropyl)phenyl)-1-ethyl-1H-pyrazole-3-carboxylate (Intermediate 103) and (1RS,2RS,4SR)-1-(aminomethyl)-4-(methylsulfonyl)cyclohexane-1,2-diol hydrochloride (Intermediate 87) in place of ethyl (R*)-4-chloro-1-ethyl-5-(2-methoxy-4-(3,3,3-trifluoro-2-methylpropyl)phenyl)-1H-pyrazole-3-carboxylate and ((1r,4r)-4-(methylsulfonyl)cyclohexyl)methanamine hydrochloride.

Intermediate 248

4-Chloro-5-(2-(difluoromethoxy)-4-(4,4,4-trifluoro-2-hydroxybutan-2-yl)phenyl)-1-ethyl-N-(((1s,4s)-1-hydroxy-4-(methylsulfonyl)cyclohexyl)methyl)-1H-pyrazole-3-carboxamide

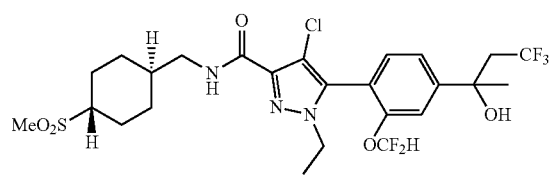

The title compound was prepared as described for the synthesis of Example 2, using ethyl 4-chloro-5-(2-(difluoromethoxy)-4-(4,4,4-trifluoro-2-hydroxybutan-2-yl)phenyl)-1-ethyl-1H-pyrazole-3-carboxylate (Intermediate 256) in place of ethyl 4-chloro-5-(2-(difluoromethoxy)-4-(3,3,3-trifluoro-2,2-dimethylpropyl)phenyl)-1-ethyl-1H-pyrazole-3-carboxylate, (1s,4s)-1-(aminomethyl)-4-(methylsulfonyl)cyclohexan-1-ol hydrochloride (Intermediate 9) in place of ((1r,4r)-4-(methylsulfonyl)cyclohexyl)methanamine hydrochloride, and DCM in place of MeCN as solvent in the amide-bond-forming step.

Intermediate 249

(R)-4-Chloro-5-(2-chloro-4-((1,1,1-trifluoropropan-2-yl)amino)phenyl)-1-ethyl-N-((4-(methylsulfonyl)cyclohexyl)methyl)-1H-pyrazole-3-carboxamide

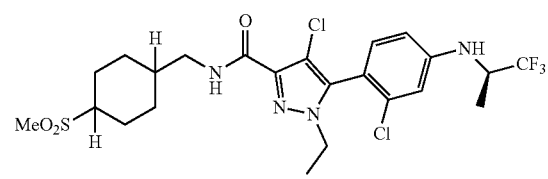 [SMILES: CCn1nc(C(=O)NCC2CCC(S(C)(=O)=O)CC2)c(Cl)c1-c1ccc(N[C@H](C)C(F)(F)F)cc1Cl]

The title compound was prepared as described for the synthesis of Example 1, using ethyl (R)-4-chloro-5-(2-chloro-4-((1,1,1-trifluoropropan-2-yl)amino)phenyl)-1-ethyl-1H-pyrazole-3-carboxylate (Intermediate 194) in place of ethyl (R*)-4-chloro-1-ethyl-5-(2-methoxy-4-(3,3,3-trifluoro-2-methylpropyl)phenyl)-1H-pyrazole-3-carboxylate and (4-(methylsulfonyl)cyclohexyl)methanamine (Intermediate 14) in place of ((1r,4r)-4-(methylsulfonyl)cyclohexyl)methanamine hydrochloride.

Intermediate 250

4-Chloro-5-(2,6-difluoro-4-(3,3,3-trifluoro-2-methylpropyl)phenyl)-1-ethyl-N-(((1s,4s)-1-hydroxy-4-(methylsulfonyl)cyclohexyl)methyl)-1H-pyrazole-3-carboxamide

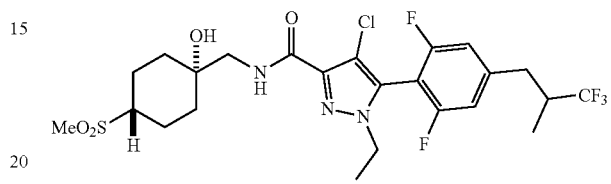

The title compound was prepared as described for the synthesis of Example 1, using ethyl 4-chloro-5-(2,6-difluoro-4-(3,3,3-trifluoro-2-methylpropyl)phenyl)-1-ethyl-1H-pyrazole-3-carboxylate (Intermediate 208) in place of ethyl (R*)-4-chloro-1-ethyl-5-(2-methoxy-4-(3,3,3-trifluoro-2-methylpropyl)phenyl)-1H-pyrazole-3-carboxylate and (1s,4s)-1-(aminomethyl)-4-(methylsulfonyl)cyclohexan-1-ol hydrochloride (Intermediate 9) in place of ((1r,4r)-4-(methylsulfonyl)cyclohexyl)methanamine hydrochloride (Intermediate 13).

Intermediate 251

(R)-4-Chloro-5-(2-ethoxy-4-((1,1,1-trifluoropropan-2-yl)amino)phenyl)-1-ethyl-N-((4-(methylsulfonyl)cyclohexyl)methyl)-1H-pyrazole-3-carboxamide

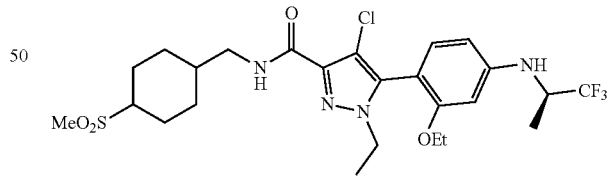

The title compound was prepared as described for the synthesis of Example 1, using ethyl (R)-4-chloro-5-(2-ethoxy-4-((1,1,1-trifluoropropan-2-yl)amino)phenyl)-1-ethyl-1H-pyrazole-3-carboxylate (Intermediate 223) in place of ethyl (R*)-4-chloro-1-ethyl-5-(2-methoxy-4-(3,3,3-trifluoro-2-methylpropyl)phenyl)-1H-pyrazole-3-carboxylate and (4-(methylsulfonyl)cyclohexyl)methanamine (Intermediate 14) in place of ((1r,4r)-4-(methylsulfonyl)cyclohexyl)methanamine hydrochloride.

Intermediate 252

(R)-4-Chloro-1-ethyl-5-(2-isopropoxy-4-((1,1,1-trifluoropropan-2-yl)amino)phenyl)-N-((4-(methyl-sulfonyl)cyclohexyl)methyl)-1H-pyrazole-3-carboxamide

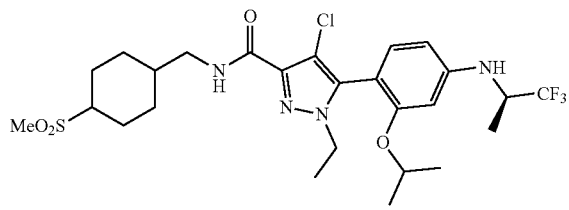 [SMILES: CCn1nc(C(=O)NCC2CCC(S(C)(=O)=O)CC2)c(Cl)c1-c1ccc(N[C@H](C)C(F)(F)F)cc1OC(C)C]

The title compound was prepared as described for the synthesis of Example 1, using ethyl (R)-4-chloro-1-ethyl-5-(2-isopropoxy-4-((1,1,1-trifluoropropan-2-yl)amino)phenyl)-1H-pyrazole-3-carboxylate (Intermediate 234) in place of ethyl (R*)-4-chloro-1-ethyl-5-(2-methoxy-4-(3,3,3-trifluoro-2-methylpropyl)phenyl)-1H-pyrazole-3-carboxylate and (4-(methylsulfonyl)cyclohexyl)methanamine (Intermediate 14) in place of ((1r,4r)-4-(methylsulfonyl)cyclohexyl)methanamine hydrochloride.

Intermediate 253

Ethyl 5-(4-bromo-2-methoxyphenyl)-4-chloro-1-(2-cyanoethyl)-1H-pyrazole-3-carboxylate

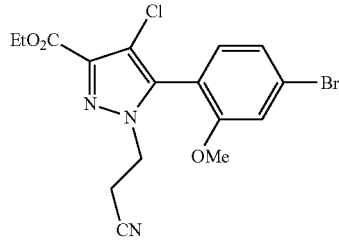 [SMILES: CCOC(=O)c1nn(CCC#N)c(-c2ccc(Br)cc2OC)c1Cl]

The title compound was prepared as described for the synthesis of Intermediate 161, Step c, using ethyl 4-(4-bromo-2-methoxyphenyl)-2,4-dioxobutanoate (Intermediate 97, Step a) and 2-cyanoethylhydrazine in place of 1-(4-bromo-2-(trifluoromethoxy)phenyl)ethan-1-one and ethylhydrazine hydrochloride.

Intermediate 254

Ethyl (R)-4-chloro-1-(2-cyanoethyl)-5-(2-methoxy-4-((1,1,1-trifluoropropan-2-yl)amino)phenyl)-1H-pyrazole-3-carboxylate

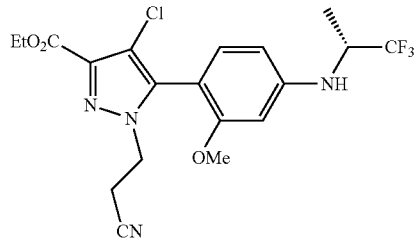 [SMILES: CCOC(=O)c1nn(CCC#N)c(-c2ccc(N[C@H](C)C(F)(F)F)cc2OC)c1Cl]

The title compound was prepared as described for the synthesis of Intermediate 106, using ethyl 5-(4-bromo-2-methoxyphenyl)-4-chloro-1-(2-cyanoethyl)-1H-pyrazole-3-carboxylate (Intermediate 253) in place of ethyl 5-(4-bromo-2-methoxyphenyl)-4-chloro-1-ethyl-1H-pyrazole-3-carboxylate.

Intermediate 255

Ethyl 4-chloro-5-(2-(difluoromethoxy)-4-(4,4,4-trifluoro-1-hydroxybutyl)phenyl)-1-ethyl-1H-pyrazole-3-carboxylate

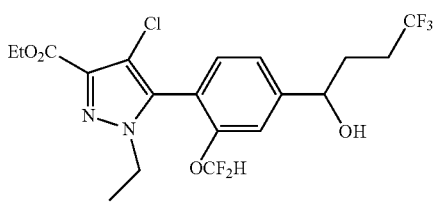

A solution of n-BuLi (2.5 M in hexanes, 0.414 mL, 1.03 mmol) was added to a stirring solution of 2-bromo-1,3,5-triisopropylbenzene (960 mg, 3.4 mmol) in THF (6 mL) at −78° C. After one minute, the solution was removed from the cooling bath and the flask was placed into a rt water bath. A solution of the freshly prepared (2,4,6-triisopropylphenyl)lithium (2.5 mL) was added dropwise to a stirring solution of ethyl 5-(4-bromo-2-(difluoromethoxy)phenyl)-4-chloro-1-ethyl-1H-pyrazole-3-carboxylate (300 mg, 0.71 mmol, Intermediate 102, Step c) and 4,4,4-trifluorobutanal (166 mg, 1.32 mmol) in THF (3 mL) at −78° C. After 30 minutes, EtOAc was added and the mixture allowed to warm to rt. The biphasic mixture was partitioned between saturated aqueous NaCl solution and EtOAc. The layers were separated. The organic layer was dried with anhydrous $Na_2SO_4$, filtered, and then absorbed onto Celite®. Purification by silica gel chromatography (EtOAc/hexanes) afforded the title compound.

Intermediate 256

Ethyl 4-chloro-5-(2-(difluoromethoxy)-4-(4,4,4-trifluoro-2-hydroxybutan-2-yl)phenyl)-1-ethyl-1H-pyrazole-3-carboxylate

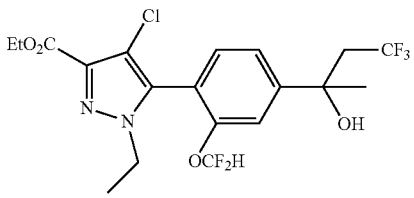

The title compound was prepared as described for the synthesis of Intermediate 255, using 4,4,4-trifluorobutan-2-one in place of 4,4,4-trifluorobutanal.

Intermediate 257

1-Cyano-4-(methylsulfonyl)cyclohexyl benzoate

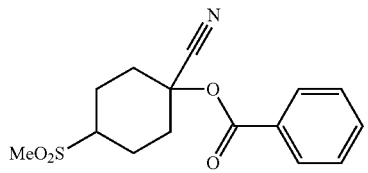 [SMILES: CS(=O)(=O)C1CCC(C#N)(OC(=O)c2ccccc2)CC1]

1,8-Diazabicyclo(5.4.0)undec-7-ene (0.17 mL, 1.1 mmol) was added to a suspension of 4-sulfonylcyclohexanone (2.0 g, 11 mmol, Intermediate 5) and benzoyl cyanide (1.9 g, 14 mmol) in toluene (10 mL), and the mixture was stirred at rt for 15 h. After this time, EtOH (0.2 mL) was added, and the mixture was stirred 30 min before the supernatant was decanted. The remaining insoluble material was filtered, and the solids were washed with toluene (100 mL) and dried by aspiration to afford the title compound as a brown powder.

Intermediate 258 tert-Butyl (((1r,4r)-1-hydroxy-4-(methylsulfonyl)cyclohexyl)methyl)carbamate

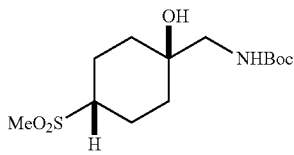 [SMILES: CC(C)(C)OC(=O)NC[C@]1(O)CC[C@H](S(C)(=O)=O)CC1]

1-Cyano-4-(methylsulfonyl)cyclohexyl benzoate (2.95 g, 9.60 mmol, Intermediate 257) was added in portions to a 0° C. solution of LAH in THF (32 mL, 1.0 M, 32 mmol) over 2 min, and the residue in the transfer vessel was washed into the reaction solution with THF (15 mL). The solution was stirred at rt for 5 h, during which time it became heterogeneous. The resulting suspension was diluted with THF (40 mL), cooled to 0° C., and then water (1.1 mL), 15% aqueous NaOH (1.1 mL), and water (3.3 mL) were sequentially added. The mixture was then allowed to warm to rt over 20 min before it was filtered through Celite®. The filtrate was concentrated, and then the residue was diluted with THF (20 mL) and 30% aqueous Rochelle's salt (10 mL). Di-tert-butyl dicarbonate (2.5 mL, 11 mmol) was added, and the mixture was stirred at rt for 60 h. After this time, the solution was then diluted with EtOAc, the layers were separated, and the aqueous layer was extracted with EtOAc. The organic layers were combined, washed with brine, dried with anhydrous MgSO₄, filtered, concentrated, and purified by silica gel chromatography (70-100% EtOAc/hexanes) to afford the title compound as a colorless solid. The title compound was the second-eluting diastereomer.

Intermediate 259

(1r,4r)-1-(Aminomethyl)-4-(methylsulfonyl)cyclohexan-1-ol hydrochloride

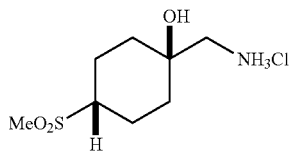

The title compound was prepared as described for the synthesis of Intermediate 35, using tert-butyl (((1r,4r)-1-hydroxy-4-(methylsulfonyl)cyclohexyl)methyl)carbamate (Intermediate 258) in place of tert-butyl (((1s*,4s*)-1-cyano-4-(methylsulfonyl)cyclohexyl)methyl)carbamate.

Intermediate 260

Ethyl 4-chloro-5-(2-(difluoromethoxy)-4-(3,3,3-trifluoropropyl)phenyl)-1-ethyl-1H-pyrazole-3-carboxylate

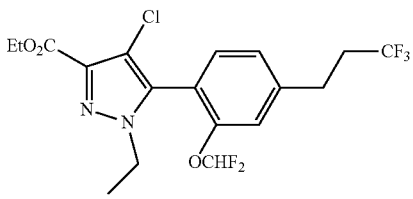 [SMILES: CCOC(=O)c1nn(CC)c(-c2ccc(CCC(F)(F)F)cc2OC(F)F)c1Cl]

The title compound was prepared as described for the synthesis of Intermediate 98, using ethyl 5-(4-bromo-2-(difluoromethoxy)phenyl)-4-chloro-1-ethyl-1H-pyrazole-3-carboxylate (Intermediate 102, Step c) in place of ethyl 5-(4-bromo-2-methoxyphenyl)-4-chloro-1-ethyl-1H-pyrazole-3-carboxylate and 9-(3,3,3-trifluoropropyl)-9-borabicyclo[3.3.1]nonane (Intermediate 95) in place of 9-(3,3,3-trifluoro-2-methylpropyl)-9-borabicyclo[3.3.1]nonane.

Intermediate 261

Ethyl 4-chloro-1-ethyl-5-(2-methoxy-4-(3,3,3-trifluoropropyl)phenyl)-1H-pyrazole-3-carboxylate

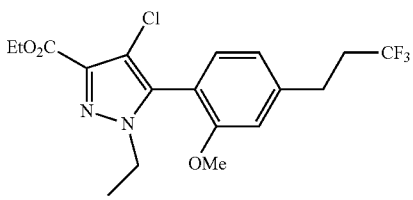 [SMILES: CCOC(=O)c1nn(CC)c(-c2ccc(CCC(F)(F)F)cc2OC)c1Cl]

The title compound was prepared as described for the synthesis of Intermediate 98, using 9-(3,3,3-trifluoropropyl)-9-borabicyclo[3.3.1]nonane (Intermediate 95) in place of 9-(3,3,3-trifluoro-2-methylpropyl)-9-borabicyclo[3.3.1]nonane.

Intermediate 262

Ethyl 1-ethyl-5-(2-methoxy-4-(3,3,3-trifluoropropyl)phenyl)-4-methyl-1H-pyrazole-3-carboxylate

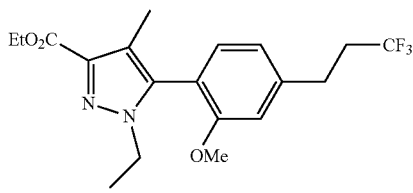 [SMILES: CCOC(=O)c1nn(CC)c(-c2ccc(CCC(F)(F)F)cc2OC)c1C]

The title compound was prepared as described for the synthesis of Intermediate 105, using ethyl 4-chloro-1-ethyl-5-(2-methoxy-4-(3,3,3-trifluoropropyl)phenyl)-1H-pyrazole-3-carboxylate (Intermediate 261) in place of ethyl 4-chloro-5-(2-(difluoromethoxy)-4-((S*)-3,3,3-trifluoro-2-methylpropyl)phenyl)-1-ethyl-1H-pyrazole-3-carboxylate.

Intermediate 263

Ethyl 5-(4-bromo-2-(difluoromethoxy)phenyl)-1-(3-hydroxypropyl)-1H-pyrazole-3-carboxylate

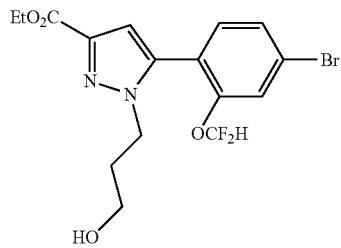

The title compound was prepared as described for the synthesis of Intermediate 102, Step b, using 3-hydrazinylpropan-1-ol hydrochloride in place of ethyl hydrazine oxalate.

Intermediate 264

Ethyl 5-(4-bromo-2-(difluoromethoxy)phenyl)-1-(3-((methylsulfonyl)oxy)propyl)-1H-pyrazole-3-carboxylate

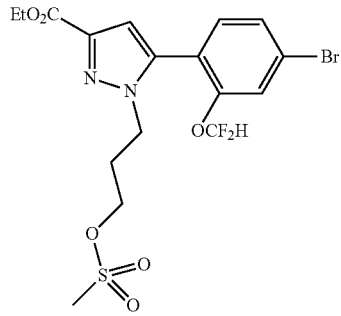

Methanesulfonyl chloride (1.5 g, 13 mmol) was added to a 0° C. mixture of ethyl 5-(4-bromo-2-(difluoromethoxy)phenyl)-1-(3-hydroxypropyl)-1H-pyrazole-3-carboxylate (3.6 g, 8.6 mmol, Intermediate 263) and TEA (1.7 g, 17 mmol) in DCM (50 mL). After 2 h, water was added and the layers were separated. The aqueous layer was extracted with DCM. The organic layers were combined, dried with anhydrous $Na_2SO_4$, filtered, and then concentrated to afford the title compound.

Intermediate 265

Ethyl 5-(4-bromo-2-(difluoromethoxy)phenyl)-1-(3-cyanopropyl)-1H-pyrazole-3-carboxylate

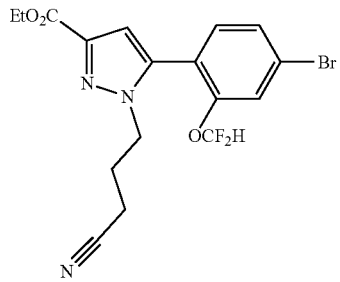

A solution of ethyl 5-(4-bromo-2-(difluoromethoxy)phenyl)-1-(3-((methylsulfonyl)oxy)propyl)-1H-pyrazole-3-carboxylate (4.3 g, 8.6 mmol, Intermediate 264) and KCN (676 mg, 10.4 mmol) in DMSO (50 mL) was stirred at 60° C. After 16 hours, EtOAc and a saturated aqueous $NaHCO_3$ solution were added. The layers was separated and the aqueous layer was extracted with EtOAc. The organic layers were combined, dried with anhydrous $Na_2SO_4$, filtered, and then concentrated. The residue was purified by silica gel chromatography (1:1 petroleum ether/EtOAc) to afford the title compound as a colorless oil.

Intermediate 266

Ethyl 5-(4-bromo-2-(difluoromethoxy)phenyl)-4-chloro-1-(3-cyanopropyl)-1H-pyrazole-3-carboxylate

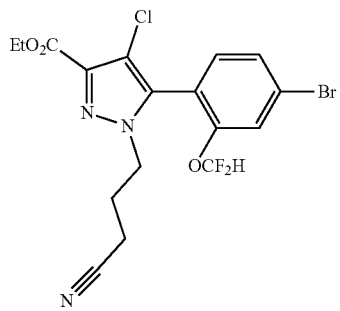

The title compound was prepared as described for the synthesis of Intermediate 102, Step c, using ethyl 5-(4-bromo-2-(difluoromethoxy)phenyl)-1-(3-cyanopropyl)-1H- pyrazole-3-carboxylate (Intermediate 265) in place of ethyl 5-(4-bromo-2-(difluoromethoxy)phenyl)-1-ethyl-1H-pyrazole-3-carboxylate.

Intermediate 267

Ethyl 4-chloro-1-(3-cyanopropyl)-5-(2-(difluoromethoxy)-4-(3,3,3-trifluoro-2,2-dimethylpropyl)phenyl)-1H-pyrazole-3-carboxylate

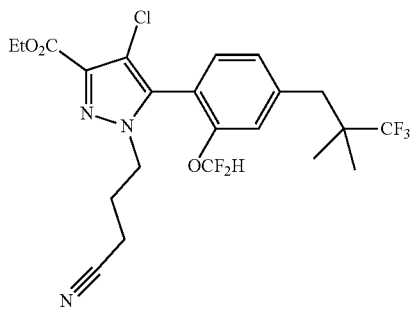

1,2-Dibromoethane (0.066 mL, 0.56 mmol) was added to a stirring suspension of zinc (294 mg, 4.5 mmol) in THF (20 mL). The suspension was warmed to 80° C. After 10 minutes, the flask was allowed to cool to rt, whereupon TMSCl (0.066 mL, 0.52 mmol) was added. A solution of 1,1,1-trifluoro-3-iodo-2,2-dimethylpropane (1.0 g, 4.0 mmol, Intermediate 93) in THF (10 mL) was added dropwise over 40 minutes to the activated zinc solution described above. After 2 h, Pd(t-Bu$_3$P)$_2$ (250 mg, 0.490 mmol) was added followed by a solution of ethyl 5-(4-bromo-2-(difluoromethoxy)phenyl)-4-chloro-1-(3-cyanopropyl)-1H-pyrazole-3-carboxylate (1.6 g, 3.5 mmol, Intermediate 266) in THF (20 mL). The mixture was stirred at 65° C. After 16 h, the mixture was filtered through a pad of silica gel, and the filtrate was concentrated. The residue was purified by preparative HPLC (Phenomenex Synergi Max-RP, 35-75% MeCN/water) to afford the title compound as a white solid after lyophilization.

Intermediate 268

Benzyl ((1RS,2RS,5RS)-2-((4-chloro-5-(2-(difluoromethoxy)-4-(3,3,3-trifluoro-2,2-dimethylpropyl)phenyl)-1-ethyl-1H-pyrazole-3-carboxamido)methyl)-2-hydroxy-5-(methylsulfonyl)cyclohexyl)carbamate

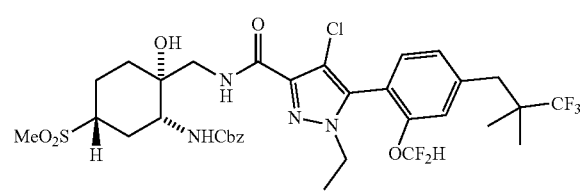

The title compound was prepared as described for the synthesis of Example 1, using 4-chloro-5-(2-(difluoromethoxy)-4-(3,3,3-trifluoro-2,2-dimethylpropyl)phenyl)-1-ethyl-1H-pyrazole-3-carboxylic acid (Example 2, Step a) and benzyl ((1RS,2RS,5RS)-2-(aminomethyl)-2-hydroxy-5-(methylsulfonyl)cyclohexyl)carbamate hydrochloride (Intermediate 64) in place of (R*)-4-chloro-1-ethyl-5-(2-methoxy-4-(3,3,3-trifluoro-2-methylpropyl)phenyl)-1H-pyrazole-3-carboxylic acid and ((1r,4r)-4-(methylsulfonyl)cyclohexyl)methanamine hydrochloride.

Intermediate 269

Benzyl ((1R*,2R*,5R*)-2-((4-chloro-5-(2-(difluoromethoxy)-4-(3,3,3-trifluoro-2,2-dimethylpropyl)phenyl)-1-ethyl-1H-pyrazole-3-carboxamido)methyl)-2-hydroxy-5-(methylsulfonyl)cyclohexyl)carbamate

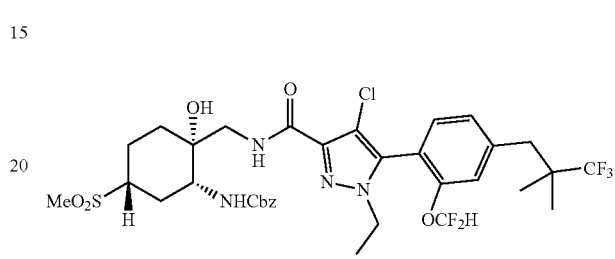

Intermediate 270

Benzyl ((1S*,2S*,5S*)-2-((4-chloro-5-(2-(difluoromethoxy)-4-(3,3,3-trifluoro-2,2-dimethylpropyl)phenyl)-1-ethyl-1H-pyrazole-3-carboxamido)methyl)-2-hydroxy-5-(methylsulfonyl)cyclohexyl)carbamate

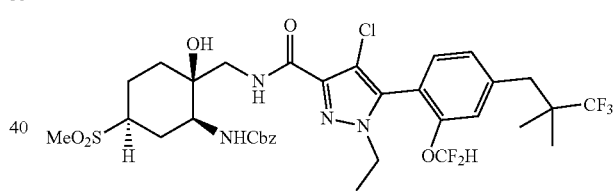

Intermediate 268 was purified by SFC using a chiral stationary phase (Chiralpak IC, 80% CO$_2$, 20% EtOH) to give a pair of enantiomers. The first-eluting enantiomer was Intermediate 269, and the second-eluting enantiomer was Intermediate 270.

Intermediate 271

Benzyl (2RS,5SR)-2-((4-chloro-5-(2-(difluoromethoxy)-4-(3,3,3-trifluoro-2,2-dimethylpropyl)phenyl)-1-ethyl-1H-pyrazole-3-carboxamido)methyl)-5-(methylsulfonyl)piperidine-1-carboxylate

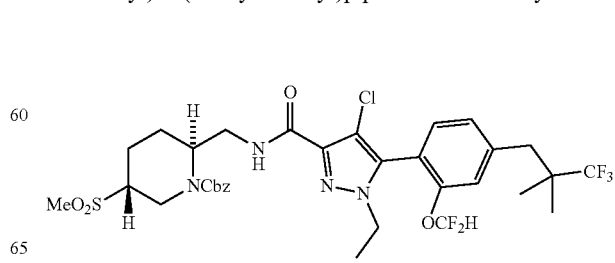

The title compound was prepared as described for the synthesis of Example 1, using 4-chloro-5-(2-(difluoromethoxy)-4-(3,3,3-trifluoro-2,2-dimethylpropyl)phenyl)-1-ethyl-1H-pyrazole-3-carboxylic acid (Example 2, Step a) and benzyl (2RS,5SR)-2-(aminomethyl)-5-(methylsulfonyl)piperidine-1-carboxylate hydrochloride (Intermediate 68) in place of (R*)-4-chloro-1-ethyl-5-(2-methoxy-4-(3,3,3-trifluoro-2-methylpropyl)phenyl)-1H-pyrazole-3-carboxylic acid and ((1r,4r)-4-(methylsulfonyl)cyclohexyl)methanamine hydrochloride.

Intermediate 272

Benzyl (2R*,5S*)-2-((4-chloro-5-(2-(difluoromethoxy)-4-(3,3,3-trifluoro-2,2-dimethylpropyl)phenyl)-1-ethyl-1H-pyrazole-3-carboxamido)methyl)-5-(methylsulfonyl)piperidine-1-carboxylate

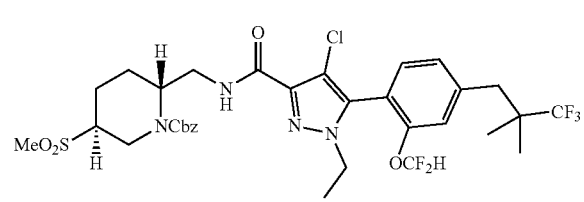

Intermediate 273

Benzyl (2S*,5R*)-2-((4-chloro-5-(2-(difluoromethoxy)-4-(3,3,3-trifluoro-2,2-dimethylpropyl)phenyl)-1-ethyl-1H-pyrazole-3-carboxamido)methyl)-5-(methylsulfonyl)piperidine-1-carboxylate

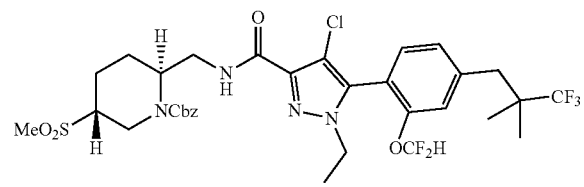

Intermediate 271, Step a was purified by SFC using a chiral stationary phase (Chiralpak IC, 60% CO₂, 40% EtOH) to give a pair of enantiomers. The first-eluting enantiomer was Intermediate 272, and the second-eluting enantiomer was Intermediate 273.

Intermediate 274

Benzyl (2RS,5RS)-2-((4-chloro-5-(2-(difluoromethoxy)-4-(3,3,3-trifluoro-2,2-dimethylpropyl)phenyl)-1-ethyl-1H-pyrazole-3-carboxamido)methyl)-5-(methylsulfonyl)piperidine-1-carboxylate

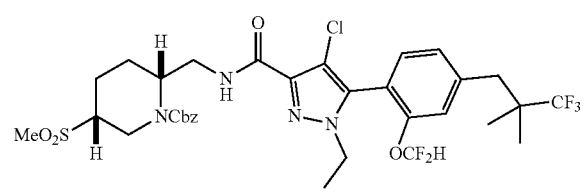

The title compound was prepared as described for the synthesis of Intermediate 271, using benzyl (2RS, 5RS)-2-(((tert-butoxycarbonyl)amino)methyl)-5-(methyl sulfonyl)piperidine-1-carboxylate (Intermediate 67) in place of benzyl (2RS,5SR)-2-(((tert-butoxycarbonyl)amino)methyl)-5-(methylsulfonyl)piperidine-1-carboxylate.

Intermediate 275

Benzyl (2S*,5S*)-2-((4-chloro-5-(2-(difluoromethoxy)-4-(3,3,3-trifluoro-2,2-dimethylpropyl)phenyl)-1-ethyl-1H-pyrazole-3-carboxamido)methyl)-5-(methylsulfonyl)piperidine-1-carboxylate

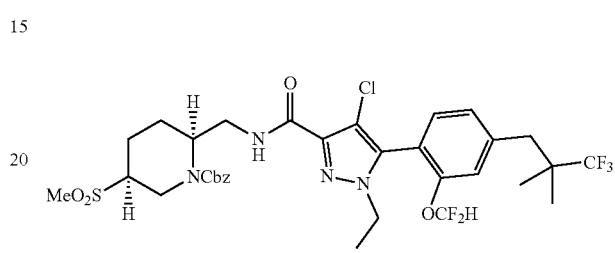

Intermediate 276

Benzyl (2R*,5R*)-2-((4-chloro-5-(2-(difluoromethoxy)-4-(3,3,3-trifluoro-2,2-dimethylpropyl)phenyl)-1-ethyl-1H-pyrazole-3-carboxamido)methyl)-5-(methylsulfonyl)piperidine-1-carboxylate

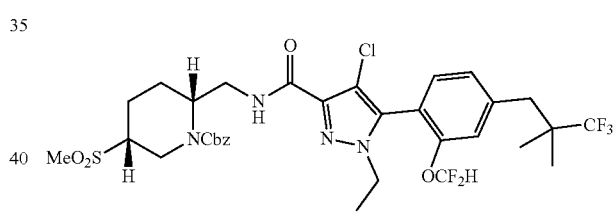

Intermediate 274, Step a was purified by SFC using a chiral stationary phase (Chiralpak IC, 65% CO₂, 35% EtOH) to give a pair of enantiomers. The first-eluting enantiomer was Intermediate 275, and the second-eluting enantiomer was Intermediate 276.

Intermediate 277

Ethyl 4-chloro-5-(2-(difluoromethoxy)-4-(5,5,5-trifluoro-2-hydroxypentan-2-yl)phenyl)-1-ethyl-1H-pyrazole-3-carboxylate

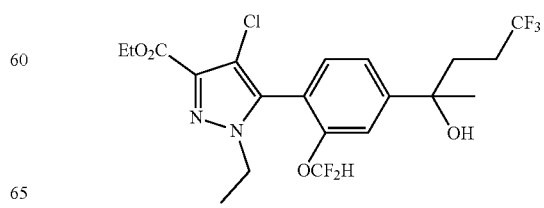

The title compound was prepared as described for the synthesis of Intermediate 255, using 5,5,5-trifluoropentan-2-one in place of 4,4,4-trifluorobutanal.

Intermediate 278

Ethyl 4-chloro-5-(4-(4,4-difluoro-1-hydroxycyclo-hexyl)-2-(difluoromethoxy)phenyl)-1-ethyl-1H-pyrazole-3-carboxylate

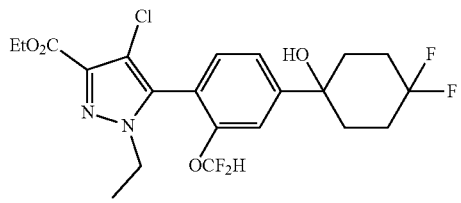

The title compound was prepared as described for the synthesis of Intermediate 255, using 4,4-difluorocyclohexan-1-one in place of 4,4,4-trifluorobutanal.

Intermediate 279

Ethyl 4-chloro-5-(2-(difluoromethoxy)-4-(3,3,3-trifluoro-2,2-dimethylpropanoyl)phenyl)-1-ethyl-1H-pyrazole-3-carboxylate

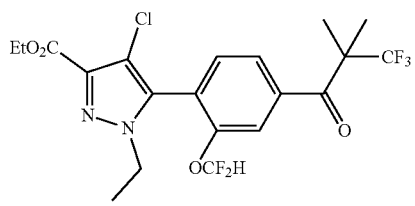

The title compound was prepared as described for the synthesis of Intermediate 255, using 3,3,3-trifluoro-2,2-dimethylpropanoyl chloride in place of 4,4,4-trifluorobutanal.

Intermediate 280

Ethyl 4-chloro-5-(2-(difluoromethoxy)-4-(1-(trifluoromethyl)cyclopropane-1-carbonyl)phenyl)-1-ethyl-1H-pyrazole-3-carboxylate

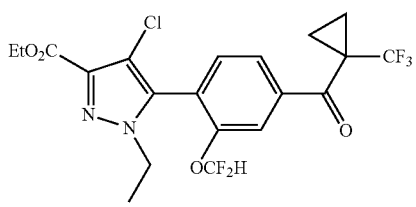

The title compound was prepared as described for the synthesis of Intermediate 255, using 1-(trifluoromethyl) cyclopropane-1-carbonyl chloride in place of 3,3,3-trifluoro-2,2-dimethylpropanoyl chloride.

Intermediate 281

4-Chloro-5-(2-(difluoromethoxy)-4-(1-(trifluoromethyl)cyclopropane-1-carbonyl)phenyl)-1-ethyl-N-(((1s,4s)-1-hydroxy-4-(methylsulfonyl)cyclohexyl)methyl)-1H-pyrazole-3-carboxamide

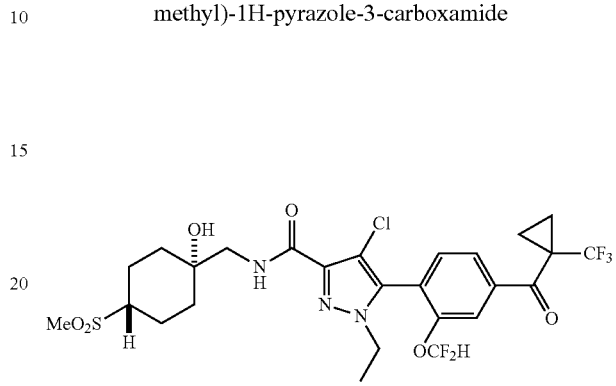

The title compound was prepared as described for the synthesis of Example 2, using ethyl 4-chloro-5-(2-(difluoromethoxy)-4-(1-(trifluoromethyl)cyclopropane-1-carbonyl)phenyl)-1-ethyl-1H-pyrazole-3-carboxylate (Intermediate 280) in place of ethyl 4-chloro-5-(2-(difluoromethoxy)-4-(3,3,3-trifluoro-2,2-dimethylpropyl)phenyl)-1-ethyl-1H-pyrazole-3-carboxylate and (1s,4s)-1-(aminomethyl)-4-(methylsulfonyl)cyclohexan-1-ol hydrochloride (Intermediate 9) in place of ((1r,4r)-4-(methylsulfonyl)cyclohexyl)methanamine hydrochloride, and DCM in place of MeCN as solvent in the amide-bond-forming step.

Intermediate 282

Ethyl 5-(2-(difluoromethoxy)-4-(3,3,3-trifluoro-2,2-dimethylpropyl)phenyl)-1-(2-methoxyethyl)-4-methyl-1H-pyrazole-3-carboxylate

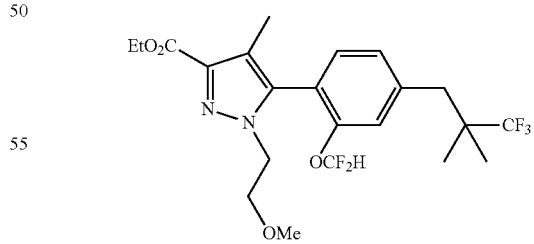

The title compound was prepared as described for the synthesis of Intermediate 105, using ethyl 4-chloro-5-(2-(difluoromethoxy)-4-(3,3,3-trifluoro-2,2-dimethylpropyl)phenyl)-1-(2-methoxyethyl)-1H-pyrazole-3-carboxylate (Intermediate 201) in place of ethyl 4-chloro-5-(2-(difluoromethoxy)-4-((S*)-3,3,3-trifluoro-2-methylpropyl)phenyl)-1-ethyl-1H-pyrazole-3-carboxylate.

Example 1, Step a (R*)-4-Chloro-1-ethyl-5-(2-methoxy-4-(3,3,3-trifluoro-2-methylpropyl)phenyl)-1H-pyrazole-3-carboxylic Acid

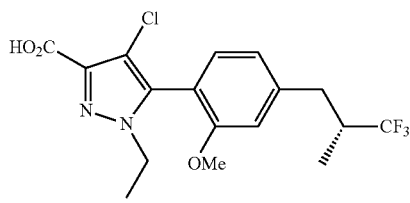 [SMILES: CCn1nc(C(=O)O)c(Cl)c1-c1ccc(C[C@@H](C)C(F)(F)F)cc1OC]

Aqueous NaOH (1.8 mL, 1.8 mmol, 1.0 N) was added to a solution of the ethyl (R*)-4-chloro-1-ethyl-5-(2-methoxy-4-(3,3,3-trifluoro-2-methylpropyl)phenyl)-1H-pyrazole-3-carboxylate (188 mg, 0.449 mmol, Intermediate 99) in 1,4-dioxane (1.8 mL), and the mixture was stirred at 65° C. for 14 h. After this time, the resulting solution was allowed to cool, diluted with EtOAc, and the pH of the mixture was adjusted to pH 4 with 1 N aqueous HCl. The layers were separated, and the aqueous layer was extracted twice with EtOAc. The combined organic layers were dried with anhydrous $MgSO_4$, filtered, and then concentrated to afford the title compound as a colorless solid.

Example 1, Step b

4-Chloro-1-ethyl-5-(2-methoxy-4-((R*)-3,3,3-trifluoro-2-methylpropyl)phenyl)-N-(((1r,4R)-4-(methylsulfonyl)cyclohexyl)methyl)-1H-pyrazole-3-carboxamide

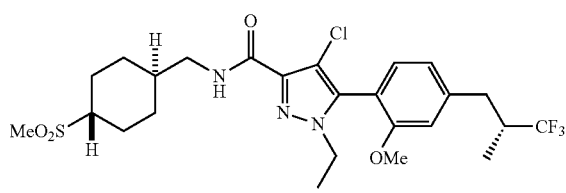 [SMILES: CCn1nc(C(=O)NC[C@H]2CC[C@H](S(C)(=O)=O)CC2)c(Cl)c1-c1ccc(C[C@@H](C)C(F)(F)F)cc1OC]

HATU (72 mg, 0.19 mmol) was added to a suspension of (R*)-4-chloro-1-ethyl-5-(2-methoxy-4-(3,3,3-trifluoro-2-methylpropyl)phenyl)-1H-pyrazole-3-carboxylic acid (74 mg, 0.19 mmol, Example 1, Step a), ((1r,4r)-4-(methylsulfonyl)cyclohexyl)methanamine hydrochloride (43 mg, 0.19 mmol, Intermediate 13), and DIPEA (0.069 mL, 0.40 mmol) in DMF (0.8 mL), and the mixture was stirred at rt for 2 h. The resulting solution was diluted with MeOH, filtered, and then purified by preparative HPLC (XBridge C18, 10→100% MeCN/water, 0.05% TFA) to afford the title compound as a colorless solid. $^1$H NMR (400 MHz, $CDCl_3$) δ 7.19 (dd, J=7.7, 1.7 Hz, 1H), 6.95 (t, J=6.4 Hz, 1H), 6.91 (dt, J=7.7, 1.7 Hz, 1H), 6.83-6.80 (m, 1H), 4.04-3.87 (m, 2H), 3.81 (s, 3H), 3.41-3.28 (m, 2H), 3.22-3.11 (m, 1H), 2.88-2.79 (m, 1H), 2.83 (s, 3H), 2.59-2.43 (m, 2H), 2.33-2.23 (m, 2H), 2.12-2.03 (m, 2H), 1.75-1.60 (m, 1H), 1.64-1.52 (m, 2H), 1.34 (t, J=7.2 Hz, 3H), 1.20-1.07 (m, 2H). 1.10 (d, J=6.4 Hz, 3H). MS (ESI) m/z: [M+H]$^+$ Found 563.8.

Example 2, Step a

4-Chloro-5-(2-(difluoromethoxy)-4-(3,3,3-trifluoro-2,2-dimethylpropyl)phenyl)-1-ethyl-1H-pyrazole-3-carboxylic Acid

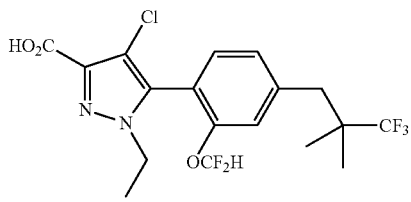

Aqueous NaOH (2.9 mL, 1.8 mmol, 1.0 N) was added to a solution of the ethyl 4-chloro-5-(2-(difluoromethoxy)-4-(3,3,3-trifluoro-2,2-dimethylpropyl)phenyl)-1-ethyl-1H-pyrazole-3-carboxylate (450 mg, 0.960 mmol, Intermediate 103) in THF (3.2 mL), and the mixture was stirred at 60° C. for 1.5 h. After this time, the resulting solution was allowed to cool, diluted with EtOAc, and then the pH of the mixture was adjusted to pH 4 with 1 N aqueous HCl. The layers were separated, and then the aqueous layer was extracted twice with EtOAc. The combined organic layers were dried with anhydrous $MgSO_4$, filtered, and then concentrated to afford the title compound as a colorless solid.

Example 2, Step b

4-Chloro-5-(2-(difluoromethoxy)-4-(3,3,3-trifluoro-2,2-dimethylpropyl)phenyl)-1-ethyl-N-(((1r,4r)-4-(methylsulfonyl)cyclohexyl)methyl)-1H-pyrazole-3-carboxamide

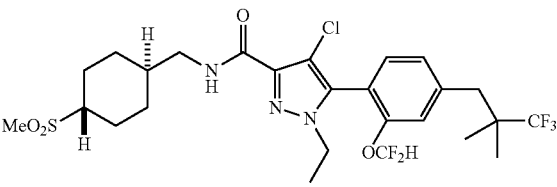

((1r,4r)-4-(Methylsulfonyl)cyclohexyl)methanamine hydrochloride (124 mg, 0.544 mmol, Intermediate 13) and then DIPEA (0.26 mL, 1.5 mmol) were added to a mixture of 4-chloro-5-(2-(difluoromethoxy)-4-(3,3,3-trifluoro-2,2-dimethylpropyl)phenyl)-1-ethyl-1H-pyrazole-3-carboxylic acid (200 mg, 0.454 mmol, Example 2, Step a), HOBt (81 mg, 0.60 mmol), and EDCI (145 mg, 0.758 mmol) in MeCN (1.0 mL) and the reaction was stirred at room temperature for 16 h. After this time, the reaction mixture was diluted with EtOAc and a saturated aqueous $NaHCO_3$ solution, and the layers were mixed and separated. The organic layer was washed with water, dried with anhydrous $MgSO_4$, filtered, and then concentrated. The residue was purified by silica gel chromatography (30→80% EtOAc/hexanes) to afford the title compound as a colorless solid. $^1$H NMR (400 MHz, $CDCl_3$) δ 7.32-7.27 (m, 1H), 7.22-7.15 (dd, J=7.8, 1.6 Hz, 1H), 7.16-7.11 (s, 1H), 6.99-6.91 (t, J=6.3 Hz, 1H), 6.57-6.17 (dd, J=75.2, 70.8 Hz, 1H), 4.06-3.88 (m, 2H), 3.38-3.31 (t, J=6.5 Hz, 2H), 2.90-2.77 (m, 6H), 2.35-2.23 (m, 2H),

Example 3

4-Chloro-1-ethyl-5-(2-methoxy-4-((S*)-3,3,3-trifluoro-2-methylpropyl)phenyl)-N-(((1r,4R)-4-(methylsulfonyl)cyclohexyl)methyl)-1H-pyrazole-3-carboxamide

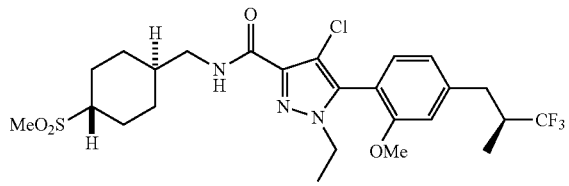 [SMILES: CCn1nc(C(=O)NC[C@H]2CC[C@H](S(C)(=O)=O)CC2)c(Cl)c1-c1ccc(C[C@H](C)C(F)(F)F)cc1OC]

The title compound was prepared as described for the synthesis of Example 1, using ethyl (S*)-4-chloro-1-ethyl-5-(2-methoxy-4-(3,3,3-trifluoro-2-methylpropyl)phenyl)-1H-pyrazole-3-carboxylate (Intermediate 100) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (400 MHz, CDCl$_3$) δ 7.19 (dd, J=7.7, 1.7 Hz, 1H), 6.95 (t, J=6.4 Hz, 1H), 6.91 (dt, J=7.7, 1.7 Hz, 1H), 6.83-6.80 (m, 1H), 4.04-3.87 (m, 2H), 3.81 (s, 3H), 3.41-3.28 (m, 2H), 3.22-3.11 (m, 1H), 2.88-2.79 (m, 1H), 2.83 (s, 3H), 2.59-2.43 (m, 2H), 2.33-2.23 (m, 2H), 2.12-2.03 (m, 2H), 1.75-1.60 (m, 1H), 1.64-1.52 (m, 2H), 1.34 (t, J=7.2 Hz, 3H), 1.20-1.07 (m, 2H). 1.10 (d, J=6.4 Hz, 3H). MS (ESI) m/z: [M+H]$^+$ Found 563.8.

Example 4

5-(2-(difluoromethoxy)-4-((S*)-3,3,3-trifluoro-2-methylpropyl)phenyl)-1-ethyl-N-(((1s,4R)-1-hydroxy-4-(methylsulfonyl)cyclohexyl)methyl)-4-methyl-1H-pyrazole-3-carboxamide

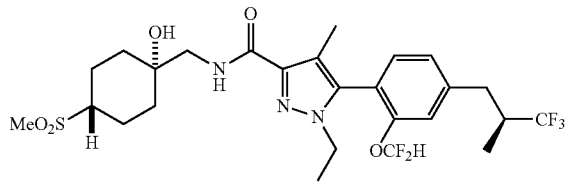

The title compound was prepared as described for the synthesis of Example 1, using ethyl (S*)-5-(2-(difluoromethoxy)-4-(3,3,3-trifluoro-2-methylpropyl)phenyl)-1-ethyl-4-methyl-1H-pyrazole-3-carboxylate (Intermediate 105) and (1s,4s)-1-(aminomethyl)-4-(methyl sulfonyl)cyclohexan-1-ol hydrochloride (Intermediate 9) in place of ethyl (R*)-4-chloro-1-ethyl-5-(2-methoxy-4-(3,3,3-trifluoro-2-methylpropyl)phenyl)-1H-pyrazole-3-carboxylate and ((1r,4r)-4-(methylsulfonyl)cyclohexyl)methanamine hydrochloride. $^1$H NMR (400 MHz, CDCl$_3$) δ 7.54 (t, J=6.3 Hz, 1H), 7.26 (d, J=7.7 Hz, 1H), 7.22 (d, J=8.2 Hz, 1H), 7.18 (s, 1H), 6.59-6.21 (m, 1H), 5.18 (br s, 1H, OH), 4.06-3.89 (m, 2H), 3.51 (d, J=6.3 Hz, 2H), 3.20 (dd, J=13.4, 3.8 Hz, 1H), 2.92-2.82 (m, 1H), 2.88 (s, 3H), 2.64 (dd, J=13.4, 10.1 Hz, 1H), 2.60-2.49 (m, 1H), 2.23-2.14 (m, 2H), 2.16 (s, 3H), 2.09-1.96 (m, 4H), 1.48 (td, J=14.0, 4.3 Hz, 2H), 1.37 (t, J=7.2 Hz, 3H), 1.16 (d, J=6.6 Hz, 3H). MS (ESI) m/z: [M+H]$^+$ Found 596.2.

Example 5

N-(((1RS,2RS,4RS)-2-Amino-1-hydroxy-4-(methylsulfonyl)cyclohexyl)methyl)-4-chloro-5-(2-(difluoromethoxy)-4-(3,3,3-trifluoro-2,2-dimethylpropyl)phenyl)-1-ethyl-1H-pyrazole-3-carboxamide Hydrobromide

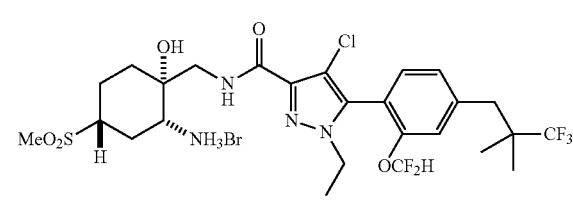

Benzyl ((1RS,2RS, 5RS)-2-((4-chloro-5-(2-(difluoromethoxy)-4-(3,3,3-trifluoro-2,2-dimethylpropyl)phenyl)-1-ethyl-1H-pyrazole-3-carboxamido)methyl)-2-hydroxy-5-(methylsulfonyl)cyclohexyl)carbamate (22 mg, 0.028 mmol, Intermediate 268) was diluted with a solution of HBr in AcOH (1.7 mL, 33% w/w, 9.4 mmol), and the solution was maintained at rt for 30 min. After this time, the solution was concentrated, diluted with MeOH, and then purified by preparative HPLC (XBridge C18, 10→100% MeCN/water, 0.05% TFA) to afford the title compound as a colorless solid. $^1$H NMR (500 MHz, DMSO-d$_6$) δ 8.66 (t, J=6.6 Hz, 1H of one rotamer), 8.61 (t, J=6.6 Hz, 1H of one rotamer), 7.87 (s, 3H), 7.46-7.13 (m, 4H), 5.60 (s, 1H), 4.05-3.91 (m, 2H), 3.59-3.13 (m, 4H), 2.92 (s, 2H), 2.91 (s, 3H), 2.13-2.07 (m, 1H), 1.93-1.86 (m, 1H), 1.84-1.59 (m, 4H), 1.28 (t, J=7.2 Hz, 3H), 1.09 (s, 6H). MS (ESI) m/z: [M+H]$^+$ Found 644.7.

Example 6

N-(((1R*,2R*,4R*)-2-Amino-1-hydroxy-4-(methylsulfonyl)cyclohexyl)methyl)-4-chloro-5-(2-(difluoromethoxy)-4-(3,3,3-trifluoro-2,2-dimethylpropyl)phenyl)-1-ethyl-1H-pyrazole-3-carboxamide Hydrobromide

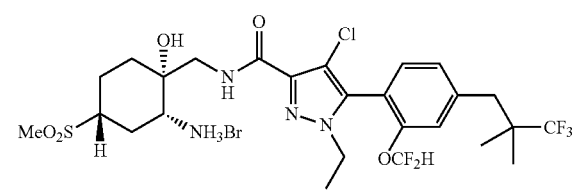

The title compound was prepared as described for the synthesis of Example 5, using benzyl ((1R*,2R*, 5R*)-2-((4-chloro-5-(2-(difluoromethoxy)-4-(3,3,3-trifluoro-2,2-dimethylpropyl)phenyl)-1-ethyl-1H-pyrazole-3-carboxamido)methyl)-2-hydroxy-5-(methylsulfonyl)cyclohexyl)carbamate (Intermediate 269) in place of benzyl ((1RS,2SR, 5SR)-2-((4-chloro-5-(2-(difluoromethoxy)-4-(3,3,3- trifluoro-2,2-dimethylpropyl)phenyl)-1-ethyl-1H-pyrazole-3-carboxamido)methyl)-2-hydroxy-5-(methylsulfonyl)cyclohexyl)carbamate. $^1$H NMR (500 MHz, DMSO-d$_6$) δ 8.66 (t, J=6.6 Hz, 1H of one rotamer), 8.61 (t, J=6.6 Hz, 1H of one rotamer), 7.88 (s, 3H), 7.46-7.13 (m, 4H), 5.61 (s, 1H of one rotamer), 5.60 (s, 1H of one rotamer), 4.04-3.91 (m, 2H), 3.53 (ddd, J=27.8, 14.1, 6.8 Hz, 1H), 3.45-3.14 (m, 3H), 2.92 (s, 2H), 2.91 (s, 3H), 2.14-2.07 (m, 1H), 1.92-1.86 (m, 1H), 1.84-1.75 (m, 2H), 1.75-1.60 (m, 2H), 1.28 (t, J=7.2 Hz, 3H), 1.09 (s, 6H). MS (ESI) m/z: [M+H]$^+$ Found 644.7.

Example 7

N-(((1S*,2S*,4S*)-2-Amino-1-hydroxy-4-(methylsulfonyl)cyclohexyl)methyl)-4-chloro-5-(2-(difluoromethoxy)-4-(3,3,3-trifluoro-2,2-dimethylpropyl)phenyl)-1-ethyl-1H-pyrazole-3-carboxamide hydrobromide

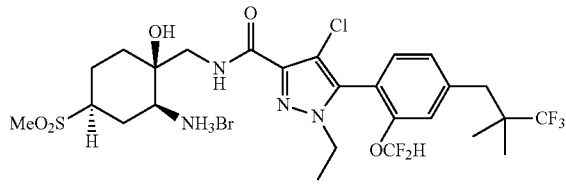

The title compound was prepared as described for the synthesis of Example 5, using benzyl ((1S*,2S*, 5S*)-2-((4-chloro-5-(2-(difluoromethoxy)-4-(3,3,3-trifluoro-2,2-dimethylpropyl)phenyl)-1-ethyl-1H-pyrazole-3-carboxamido)methyl)-2-hydroxy-5-(methylsulfonyl)cyclohexyl)carbamate (Intermediate 270) in place of benzyl ((1RS,2SR, 5SR)-2-((4-chloro-5-(2-(difluoromethoxy)-4-(3,3,3-trifluoro-2,2-dimethylpropyl)phenyl)-1-ethyl-1H-pyrazole-3-carboxamido)methyl)-2-hydroxy-5-(methylsulfonyl)cyclohexyl)carbamate. $^1$H NMR (500 MHz, DMSO-d$_6$) δ 8.66 (t, J=6.6 Hz, 1H of one rotamer), 8.61 (t, J=6.6 Hz, 1H of one rotamer), 7.88 (s, 3H), 7.46-7.13 (m, 4H), 5.61 (s, 1H of one rotamer), 5.59 (s, 1H of one rotamer), 4.04-3.91 (m, 2H), 3.53 (ddd, J=27.8, 14.1, 6.8 Hz, 1H), 3.45-3.14 (m, 3H), 2.92 (s, 2H), 2.91 (s, 3H), 2.14-2.07 (m, 1H), 1.92-1.86 (m, 1H), 1.84-1.75 (m, 2H), 1.75-1.60 (m, 2H), 1.28 (t, J=7.2 Hz, 3H), 1.09 (s, 6H). MS (ESI) m/z: [M+H]$^+$ Found 644.7.

Example 8

4-Chloro-5-(2-(difluoromethoxy)-4-(3,3,3-trifluoro-2,2-dimethylpropyl)phenyl)-1-ethyl-N-(((2RS,5SR)-5-(methylsulfonyl)piperidin-2-yl)methyl)-1H-pyrazole-3-carboxamide Hydrobromide

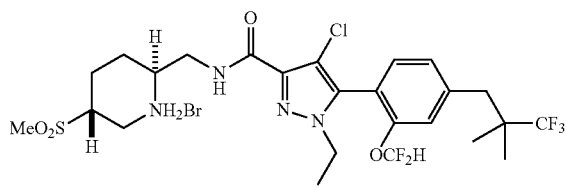

The title compound was prepared as described for the synthesis of Example 5, using benzyl (2RS, 5SR)-2-((4-chloro-5-(2-(difluoromethoxy)-4-(3,3,3-trifluoro-2,2-dimethylpropyl)phenyl)-1-ethyl-1H-pyrazole-3-carboxamido)methyl)-5-(methyl sulfonyl)piperidine-1-carboxylate (Intermediate 271) in place of benzyl ((1RS,2RS,5RS)-2-((4-chloro-5-(2-(difluoromethoxy)-4-(3,3,3-trifluoro-2,2-dimethylpropyl)phenyl)-1-ethyl-1H-pyrazole-3-carboxamido)methyl)-2-hydroxy-5-(methylsulfonyl)cyclohexyl)carbamate. $^1$H NMR (500 MHz, DMSO-d$_6$) δ 9.21 (t, J=11.2 Hz, 1H), 8.76-8.61 (m, 1H), 8.55 (appar q, J=5.8 Hz, 1H), 7.42 (d, J=7.7 Hz, 1H), 7.34-7.30 (m, 2H), 7.45-7.14 (m, 1H), 4.04-3.90 (m, J=7.4 Hz, 2H), 3.68-3.62 (m, 1H), 3.46 (s, 4H), 3.08 (s, 3H), 3.09-3.00 (m, 1H), 2.91 (s, 2H), 2.26-2.19 (m, 1H), 2.06-1.98 (m, 1H), 1.73 (qd, J=12.8, 3.8 Hz, 1H), 1.55 (qt, J=13.1, 4.0 Hz, 1H), 1.28 (t, J=7.2 Hz, 3H), 1.09 (s, 6H). MS (ESI) m/z: [M+H]$^+$ Found 614.7.

Example 9

4-Chloro-5-(2-(difluoromethoxy)-4-(3,3,3-trifluoro-2,2-dimethylpropyl)phenyl)-1-ethyl-N-(((2R*,5S*)-5-(methylsulfonyl)piperidin-2-yl)methyl)-1H-pyrazole-3-carboxamide hydrobromide

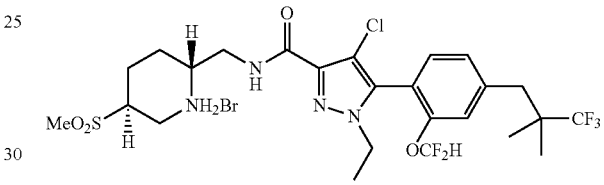

The title compound was prepared as described for the synthesis of Example 5, using benzyl (2R*,5S*)-2-((4-chloro-5-(2-(difluoromethoxy)-4-(3,3,3-trifluoro-2,2-dimethylpropyl)phenyl)-1-ethyl-1H-pyrazole-3-carboxamido)methyl)-5-(methyl sulfonyl)piperidine-1-carboxylate (Intermediate 272) in place of benzyl ((1RS,2RS,5RS)-2-((4-chloro-5-(2-(difluoromethoxy)-4-(3,3,3-trifluoro-2,2-dimethylpropyl)phenyl)-1-ethyl-1H-pyrazole-3-carboxamido)methyl)-2-hydroxy-5-(methylsulfonyl)cyclohexyl)carbamate. $^1$H NMR (500 MHz, DMSO-d$_6$) δ 9.17 (br s, 1H), 8.65 (br s, 1H), 8.55 (q, J=5.9 Hz, 1H), 7.45-7.14 (m, 1H), 7.42 (d, J=7.7 Hz, 1H), 7.34-7.30 (m, 2H), 4.04-3.90 (m, 2H), 3.68-3.61 (m, 1H), 3.58-3.49 (m, 1H), 3.47-3.37 (m, 3H), 3.11-2.98 (m, 1H), 3.08 (s, 3H), 2.91 (s, 2H), 2.26-2.18 (m, 1H), 2.06-1.98 (m, 1H), 1.73 (qd, J=12.9, 6.1 Hz, 1H), 1.61-1.49 (m, 1H), 1.28 (t, J=7.2 Hz, 3H), 1.09 (s, 6H). MS (ESI) m/z: [M+H]$^+$ Found 614.5.

Example 10

4-Chloro-5-(2-(difluoromethoxy)-4-(3,3,3-trifluoro-2,2-dimethylpropyl)phenyl)-1-ethyl-N-(((2S*,5R*)-5-(methylsulfonyl)piperidin-2-yl)methyl)-1H-pyrazole-3-carboxamide hydrobromide

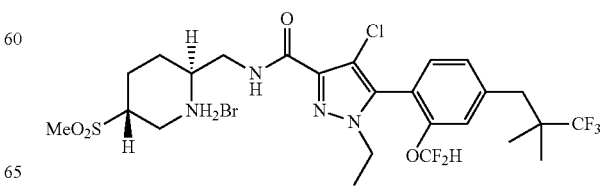

The title compound was prepared as described for the synthesis of Example 5, using benzyl (2S*,5R*)-2-((4-chloro-5-(2-(difluoromethoxy)-4-(3,3,3-trifluoro-2,2-dimethylpropyl)phenyl)-1-ethyl-1H-pyrazole-3-carboxamido)methyl)-5-(methyl sulfonyl)piperidine-1-carboxylate (Intermediate 273) in place of benzyl ((1RS,2RS, 5RS)-2-((4-chloro-5-(2-(difluoromethoxy)-4-(3,3,3-trifluoro-2,2-dimethylpropyl)phenyl)-1-ethyl-1H-pyrazole-3-carboxamido)methyl)-2-hydroxy-5-(methylsulfonyl)cyclohexyl)carbamate. $^1$H NMR (500 MHz, DMSO-$d_6$) δ 9.17 (br s, 1H), 8.62 (br s, 1H), 8.55 (q, J=5.9 Hz, 1H), 7.45-7.14 (m, 1H), 7.42 (d, J=7.7 Hz, 1H), 7.34-7.30 (m, 2H), 4.04-3.90 (m, 2H), 3.68-3.61 (m, 1H), 3.58-3.49 (m, 1H), 3.47-3.37 (m, 3H), 3.11-2.98 (m, 1H), 3.08 (s, 3H), 2.91 (s, 2H), 2.26-2.18 (m, 1H), 2.06-1.98 (m, 1H), 1.73 (qd, J=12.9, 6.1 Hz, 1H), 1.61-1.49 (m, 1H), 1.28 (t, J=7.2 Hz, 3H), 1.09 (s, 6H). MS (ESI) m/z: [M+H]$^+$ Found 614.5.

Example 11

4-Chloro-5-(2-(difluoromethoxy)-4-(3,3,3-trifluoro-2,2-dimethylpropyl)phenyl)-1-ethyl-N-(((2RS,5RS)-5-(methylsulfonyl)piperidin-2-yl)methyl)-1H-pyrazole-3-carboxamide Hydrobromide

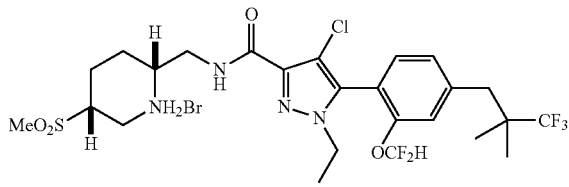

The title compound was prepared as described for the synthesis of Example 5, using benzyl (2RS, 5RS)-2-((4-chloro-5-(2-(difluoromethoxy)-4-(3,3,3-trifluoro-2,2-dimethylpropyl)phenyl)-1-ethyl-1H-pyrazole-3-carboxamido)methyl)-5-(methyl sulfonyl)piperidine-1-carboxylate (Intermediate 274) in place of benzyl ((1RS,2RS, 5RS)-2-((4-chloro-5-(2-(difluoromethoxy)-4-(3,3,3-trifluoro-2,2-dimethylpropyl)phenyl)-1-ethyl-1H-pyrazole-3-carboxamido)methyl)-2-hydroxy-5-(methylsulfonyl)cyclohexyl)carbamate. $^1$H NMR (500 MHz, DMSO-$d_6$) δ 9.39 (s, 1H), 8.53-8.46 (m, 1H), 8.21 (s, 1H), 7.45-7.12 (m, 4H), 4.04-3.89 (m, 2H), 3.68-3.49 (m, 6H), 3.16 (s, 3H), 2.91 (s, 2H), 2.17-2.00 (m, 2H), 1.92-1.79 (m, 2H), 1.28 (t, J=7.2 Hz, 3H), 1.09 (s, 6H). MS (ESI) m/z: [M+H]$^+$ Found 614.7.

Example 12

4-Chloro-5-(2-(difluoromethoxy)-4-(3,3,3-trifluoro-2,2-dimethylpropyl)phenyl)-1-ethyl-N-(((2S*,5S*)-5-(methylsulfonyl)piperidin-2-yl)methyl)-1H-pyrazole-3-carboxamide

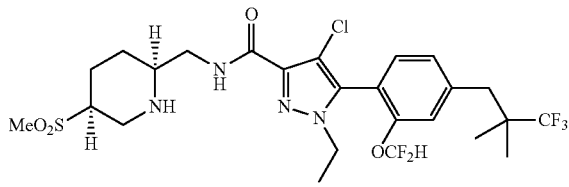

The title compound was prepared as described for the synthesis of Example 5, using benzyl (2S*,5S*)-2-((4-chloro-5-(2-(difluoromethoxy)-4-(3,3,3-trifluoro-2,2-dimethylpropyl)phenyl)-1-ethyl-1H-pyrazole-3-carboxamido)methyl)-5-(methyl sulfonyl)piperidine-1-carboxylate (Intermediate 275) in place of benzyl ((1RS,2RS, 5RS)-2-((4-chloro-5-(2-(difluoromethoxy)-4-(3,3,3-trifluoro-2,2-dimethylpropyl)phenyl)-1-ethyl-1H-pyrazole-3-carboxamido)methyl)-2-hydroxy-5-(methylsulfonyl)cyclohexyl)carbamate. Instead of being purified by preparative HPLC, the crude amine salt was converted to the free base and then purified by silica gel chromatography (0-10% 2 M NH$_3$ in MeOH solution/DCM). $^1$H NMR (500 MHz, CDCl$_3$) δ 7.28 (dd, J=7.8, 5.5 Hz, 1H), 7.25-7.20 (m, 1H), 7.18 (dt, J=7.9, 1.7 Hz, 1H), 7.15-7.12 (m, 1H), 6.37 (dd, J=75.2, 70.8 Hz, 1H), 4.05-3.88 (m, 2H), 3.70-3.58 (m, 2H), 3.35-3.26 (m, 1H), 3.17 (ddd, J=14.2, 4.2, 2.0 Hz, 1H), 3.01-2.90 (m, 2H), 2.98 (s, 3H), 2.87 (s, 2H), 2.47 (dq, J=14.4, 4.5 Hz, 1H), 2.07-1.98 (m, 1H), 1.75-1.64 (m, 3H), 1.38-1.34 (m, 3H), 1.13 (s, 6H). MS (ESI) m/z: [M+H]$^+$ Found 615.1.

Example 13

4-Chloro-5-(2-(difluoromethoxy)-4-(3,3,3-trifluoro-2,2-dimethylpropyl)phenyl)-1-ethyl-N-(((2R*,5R*)-5-(methylsulfonyl)piperidin-2-yl)methyl)-1H-pyrazole-3-carboxamide

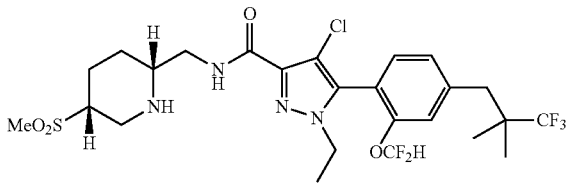

The title compound was prepared as described for the synthesis of Example 5, using benzyl (2R*,5R*)-2-((4-chloro-5-(2-(difluoromethoxy)-4-(3,3,3-trifluoro-2,2-dimethylpropyl)phenyl)-1-ethyl-1H-pyrazole-3-carboxamido)methyl)-5-(methyl sulfonyl)piperidine-1-carboxylate (Intermediate 276) in place of benzyl ((1RS,2RS, 5RS)-2-((4-chloro-5-(2-(difluoromethoxy)-4-(3,3,3-trifluoro-2,2-dimethylpropyl)phenyl)-1-ethyl-1H-pyrazole-3-carboxamido)methyl)-2-hydroxy-5-(methylsulfonyl)cyclohexyl)carbamate. Instead of being purified by preparative HPLC, the crude amine salt was converted to the free base and then purified by silica gel chromatography (0-10% 2 M NH$_3$ in MeOH/DCM). $^1$H NMR (500 MHz, CDCl$_3$) δ 7.29 (dd, J=7.8, 5.5 Hz, 1H), 7.25-7.20 (m, 1H), 7.18 (dt, J=7.9, 1.7 Hz, 1H), 7.15-7.12 (m, 1H), 6.37 (dd, J=75.2, 70.9 Hz, 1H), 4.04-3.89 (m, 2H), 3.70-3.58 (m, 2H), 3.35-3.25 (m, 1H), 3.16 (ddd, J=14.2, 4.1, 2.0 Hz, 1H), 3.00-2.91 (m, 2H), 2.98 (s, 3H), 2.87 (s, 2H), 2.50-2.43 (m, 1H), 2.07-1.98 (m, 1H), 1.74-1.68 (m, 2H), 1.63 (s, 1H), 1.38-1.34 (m, 3H), 1.13 (s, 6H). MS (ESI) m/z: [M+H]$^+$ Found 615.1.

Example 14

4-Chloro-5-(2-(difluoromethoxy)-4-(3,3,3-trifluoro-2,2-dimethylpropyl)phenyl)-1-ethyl-N-(((2RS,5SR)-5-(methylsulfonyl)tetrahydro-2H-pyran-2-yl)methyl)-1H-pyrazole-3-carboxamide

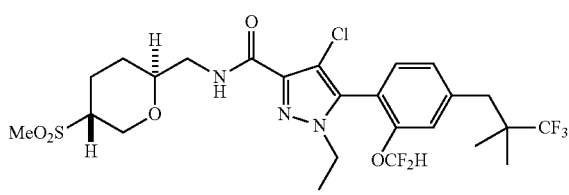

The title compound was prepared as described for the synthesis of Example 1, using 4-chloro-5-(2-(difluoromethoxy)-4-(3,3,3-trifluoro-2,2-dimethylpropyl)phenyl)-1-ethyl-1H-pyrazole-3-carboxylic acid (Example 2, Step a) and ((2RS,5SR)-5-(methylsulfonyl)tetrahydro-2H-pyran-2-yl)methanamine hydrochloride (Intermediate 74) in place of (R*)-4-chloro-1-ethyl-5-(2-methoxy-4-(3,3,3-trifluoro-2-methylpropyl)phenyl)-1H-pyrazole-3-carboxylic acid and ((1r,4r)-4-(methylsulfonyl)cyclohexyl)methanamine hydrochloride. $^1$H NMR (400 MHz, CDCl$_3$) δ 7.29 (d, J=7.8 Hz, 1H), 7.21-7.15 (m, 2H), 7.14 (s, 1H), 6.38 (dd, J=75.1, 70.9 Hz, 1H), 4.45-4.37 (m, 1H), 4.07-3.89 (m, 2H), 3.79-3.70 (m, 1H), 3.66 (t, J=11.2 Hz, 1H), 3.61-3.51 (m, 1H), 3.40-3.29 (m, 1H), 3.21-3.10 (m, 1H), 2.87 (s, 2H), 2.859 (s, 3H of one rotamer), 2.857 (s, 3H of one rotamer), 2.38-2.29 (m, 1H), 1.99-1.84 (m, 2H), 1.57-1.44 (m, 1H), 1.37 (t, J=7.2 Hz, 3H), 1.13 (s, 6H). MS (ESI) m/z: [M+H]$^+$ Found 615.8.

Example 15

4-Chloro-5-(2-(difluoromethoxy)-4-(3,3,3-trifluoro-2,2-dimethylpropyl)phenyl)-1-ethyl-N-(((2R*,5S)-5-(methylsulfonyl)tetrahydro-2H-pyran-2-yl)methyl)-1H-pyrazole-3-carboxamide

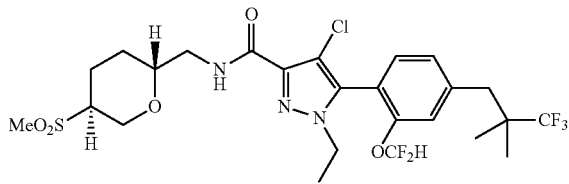

Example 16

4-Chloro-5-(2-(difluoromethoxy)-4-(3,3,3-trifluoro-2,2-dimethylpropyl)phenyl)-1-ethyl-N-(((2S*,5R*)-5-(methylsulfonyl)tetrahydro-2H-pyran-2-yl)methyl)-1H-pyrazole-3-carboxamide

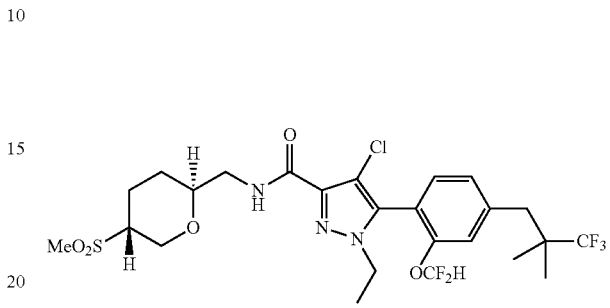

Example 14 was purified by SFC using a chiral stationary phase (Chiralpak IC, 75% CO$_2$, 25% EtOH) to give a pair of enantiomers. The first-eluting enantiomer was Example 15, and the second-eluting enantiomer was Example 16. Example 15: $^1$H NMR (400 MHz, CDCl$_3$) δ 7.29 (d, J=7.8 Hz, 1H), 7.21-7.15 (m, 2H), 7.14 (s, 1H), 6.38 (dd, J=75.1, 70.9 Hz, 1H), 4.45-4.37 (m, 1H), 4.07-3.89 (m, 2H), 3.79-3.70 (m, 1H), 3.66 (t, J=11.2 Hz, 1H), 3.61-3.51 (m, 1H), 3.40-3.29 (m, 1H), 3.21-3.10 (m, 1H), 2.87 (s, 2H), 2.859 (s, 3H of one rotamer), 2.857 (s, 3H of one rotamer), 2.38-2.29 (m, 1H), 1.99-1.84 (m, 2H), 1.57-1.44 (m, 1H), 1.37 (t, J=7.2 Hz, 3H), 1.13 (s, 6H). MS (ESI) m/z: [M+H]$^+$ Found 615.5.
Example 16: $^1$H NMR (400 MHz, CDCl$_3$) δ 7.29 (d, J=7.8 Hz, 1H), 7.21-7.15 (m, 2H), 7.14 (s, 1H), 6.38 (dd, J=75.1, 70.9 Hz, 1H), 4.45-4.37 (m, 1H), 4.07-3.89 (m, 2H), 3.79-3.70 (m, 1H), 3.66 (t, J=11.2 Hz, 1H), 3.61-3.51 (m, 1H), 3.40-3.29 (m, 1H), 3.21-3.10 (m, 1H), 2.87 (s, 2H), 2.859 (s, 3H of one rotamer), 2.857 (s, 3H of one rotamer), 2.38-2.29 (m, 1H), 1.99-1.84 (m, 2H), 1.57-1.44 (m, 1H), 1.37 (t, J=7.2 Hz, 3H), 1.13 (s, 6H). MS (ESI) m/z: [M+H]$^+$ Found 615.5.

Example 17

4-Chloro-1-ethyl-5-(2-methoxy-4-(((R)-1,1,1-trifluoropropan-2-yl)amino)phenyl)-N-(((2R*,5R*)-5-(methylsulfonyl)tetrahydro-2H-pyran-2-yl)methyl)-1H-pyrazole-3-carboxamide

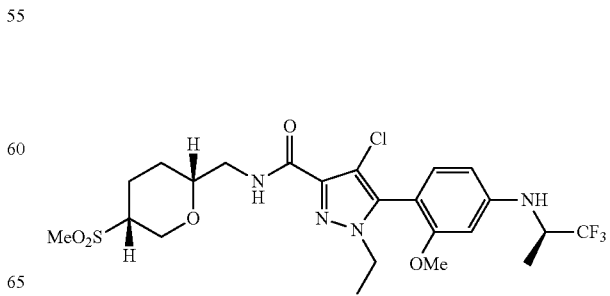

Example 18

4-Chloro-1-ethyl-5-(2-methoxy-4-(((R)-1,1,1-trifluoropropan-2-yl)amino)phenyl)-N-(((2S*,5S*)-5-(methylsulfonyl)tetrahydro-2H-pyran-2-yl)methyl)-1H-pyrazole-3-carboxamide

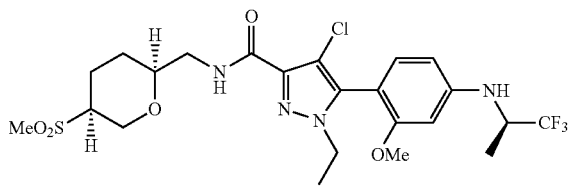 [SMILES: CCn1nc(C(=O)NC[C@@H]2CC[C@H](S(C)(=O)=O)CO2)c(Cl)c1-c1ccc(N[C@H](C)C(F)(F)F)cc1OC]

Intermediate 244 was purified by SFC using a chiral stationary phase (Lux cellulose-4, 60% $CO_2$, 40% MeOH) to give a pair of diastereomers. The first-eluting diastereomers was Example 17, and the second-eluting diastereomers was Example 18. Example 17: $^1$H NMR (500 MHz, CDCl$_3$) δ 7.22-7.16 (m, 1H), 7.08-7.01 (m, 1H), 6.38-6.33 (m, 1H), 6.29-6.25 (m, 1H), 4.63 (appar d, J=13.3 Hz, 1H), 4.13-4.03 (m, 1H), 4.00-3.84 (m, 4H), 3.79-3.70 (m, 1H), 3.762 (s, 3H of one rotamer), 3.755 (s, 3H of one rotamer), 3.69-3.61 (m, 1H), 3.42-3.31 (m, 1H), 3.00 (s, 3H), 2.94-2.88 (m, 1H), 2.59-2.52 (m, 1H), 2.15-2.04 (m, 1H), 1.84-1.73 (m, 1H), 1.73-1.66 (m, 1H), 1.46 (d, J=6.7 Hz, 3H), 1.36-1.30 (m, 3H). MS (ESI) m/z: [M+H]$^+$ Found 567.0. Example 18: $^1$H NMR (500 MHz, CDCl$_3$) δ 7.22-7.16 (m, 1H), 7.07-7.02 (m, 1H), 6.38-6.33 (m, 1H), 6.29-6.25 (m, 1H), 4.63 (d, J=13.4 Hz, 1H), 4.14-4.03 (m, 1H), 4.01-3.84 (m, 4H), 3.79-3.70 (m, 1H), 3.761 (s, 3H of one rotamer), 3.755 (s, 3H of one rotamer), 3.69-3.61 (m, 1H), 3.42-3.32 (m, 1H), 3.00 (s, 3H), 2.93-2.88 (m, 1H), 2.60-2.52 (m, 1H), 2.15-2.05 (m, 1H), 1.84-1.73 (m, 1H), 1.73-1.66 (m, 1H), 1.46 (d, J=6.7 Hz, 3H), 1.35-1.30 (m, 3H). MS (ESI) m/z: [M+H]$^+$ Found 567.2.

Example 19

N-(((1s*,4s*)-1-Amino-4-(methylsulfonyl)cyclohexyl)methyl)-4-chloro-5-(2-(difluoromethoxy)-4-(3,3,3-trifluoro-2,2-dimethylpropyl)phenyl)-1-ethyl-1H-pyrazole-3-carboxamide 2,2,2-trifluoroacetic acid salt

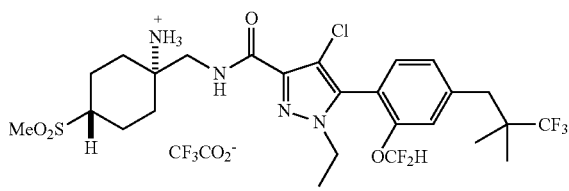

The title compound was prepared as described for the synthesis of Example 1, using ethyl 4-chloro-5-(2-(difluoromethoxy)-4-(3,3,3-trifluoro-2,2-dimethylpropyl)phenyl)-1-ethyl-1H-pyrazole-3-carboxylate (Intermediate 103) and (S)-N-((1s*,4R*)-1-(aminomethyl)-4-(methylsulfonyl)cyclohexyl)-2-methylpropane-2-sulfinamide (Intermediate 81) in place of ethyl (R*)-4-chloro-1-ethyl-5-(2-methoxy-4-(3,3,3-trifluoro-2-methylpropyl)phenyl)-1H-pyrazole-3-carboxylate and ((1r,4r)-4-(methylsulfonyl)cyclohexyl)methanamine hydrochloride. The amide-forming reaction was carried out at 50° C. instead of rt, and the sulfinamide was cleaved under these conditions. $^1$H NMR (500 MHz, CDCl$_3$) δ 7.98 (s, 3H), 7.75 (t, J=6.2 Hz, 1H), 7.27 (d, J=8.1 Hz, 1H), 7.18 (d, J=8.2 Hz, 1H), 7.14 (s, 1H), 6.42 (dd, J=74.2, 71.4 Hz, 1H), 4.06-3.90 (m, 2H), 3.81-3.63 (m, 2H), 3.08-2.99 (m, 1H), 2.92 (s, 3H), 2.87 (s, 2H), 2.43-2.18 (m, 4H), 2.03-1.91 (m, 2H), 1.76 (t, J=12.7 Hz, 2H), 1.31 (t, J=7.2 Hz, 3H), 1.13 (s, 6H). MS (ESI) m/z: [M+H]$^+$ Found 629.2.

Example 20

N-(((1r*,4r*)-1-Amino-4-(methylsulfonyl)cyclohexyl)methyl)-4-chloro-5-(2-(difluoromethoxy)-4-(3,3,3-trifluoro-2,2-dimethylpropyl)phenyl)-1-ethyl-1H-pyrazole-3-carboxamide 2,2,2-trifluoroacetic Acid Salt

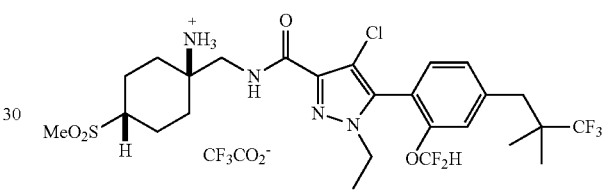

The title compound was prepared as described for the synthesis of Example 19, using benzyl (((1r*,4S*)-1-(((S)-tert-butylsulfinyl)amino)-4-(methylsulfonyl)cyclohexyl)methyl)carbamate (Intermediate 80) instead of benzyl (((1s*,4R*)-1-(((S)-tert-butylsulfinyl)amino)-4-(methylsulfonyl)cyclohexyl)methyl)carbamate. $^1$H NMR (500 MHz, CDCl$_3$) δ 8.32 (s, 3H), 7.72 (t, J=6.2 Hz, 1H), 7.26 (d, J=7.8 Hz, 1H), 7.18 (dd, J=7.9, 1.6 Hz, 1H), 7.13 (s, 1H), 6.40 (dd, J=74.4, 71.1 Hz, 1H), 4.03-3.89 (m, 2H), 3.79 (d, J=6.2 Hz, 2H), 3.09-3.01 (m, 1H), 2.90 (s, 3H), 2.86 (s, 2H), 2.34-2.19 (m, 4H), 1.98-1.79 (m, 4H), 1.32 (t, J=7.2 Hz, 3H), 1.12 (s, 6H). MS (ESI) m/z: [M+H]$^+$ Found 629.2.

Example 21

4-Chloro-5-(2-(difluoromethoxy)-4-(3,3,3-trifluoro-2,2-dimethylpropyl)phenyl)-1-ethyl-N-(((1R*,2S*,4S*)-2-hydroxy-4-(methylsulfonyl)cyclohexyl)methyl)-H-pyrazole-3-carboxamide

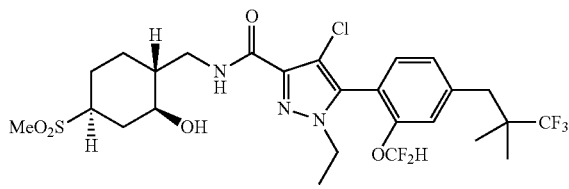

Example 22

4-Chloro-5-(2-(difluoromethoxy)-4-(3,3,3-trifluoro-2,2-dimethylpropyl)phenyl)-1-ethyl-N-(((1S*,2R*,4R*)-2-hydroxy-4-(methylsulfonyl)cyclohexyl)methyl)-1H-pyrazole-3-carboxamide

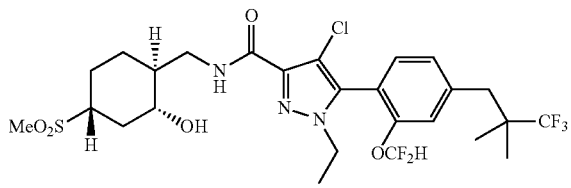

Intermediate 245 was purified by SFC using a chiral stationary phase ((S,S) Whelk-O1, 50% CO$_2$, 50% i-PrOH with 0.3% i-PrNH$_2$) to give a pair of enantiomers. The first-eluting enantiomer was Example 21, and the second-eluting enantiomer was Example 22. The second-eluting enantiomer, Example 22, was purified again by SFC using a chiral stationary phase (Chiralpak AD-H, 80% CO$_2$, 20% i-PrOH with 0.3% i-PrNH$_2$). Example 21: $^1$H NMR (500 MHz, CDCl$_3$) δ 7.29 (dd, J=7.8, 2.5 Hz, 1H), 7.22-7.16 (m, 2H), 7.14 (s, 1H), 6.56-6.22 (m, 1H), 4.73 (dd, J=13.3, 4.2 Hz, 1H), 4.26-4.18 (m, 1H), 4.06-3.90 (m, 2H), 3.45-3.36 (m, 1H), 3.09-3.02 (m, 1H), 2.97-2.89 (m, 1H), 2.88 (s, 2H), 2.83 (s, 3H of one rotamer), 2.83 (s, 3H of one rotamer), 2.50-2.44 (m, 1H), 2.30-2.24 (m, 1H), 1.97-1.91 (m, 1H), 1.73-1.52 (m, 3H), 1.43-1.32 (m, 4H), 1.14 (s, 6H). MS (ESI) m/z: [M+H]$^+$ Found 629.8. Example 22: $^1$H NMR (500 MHz, CDCl$_3$) δ 7.29 (dd, J=7.8, 2.5 Hz, 1H), 7.22-7.16 (m, 2H), 7.14 (s, 1H), 6.56-6.22 (m, 1H), 4.73 (dd, J=13.3, 4.2 Hz, 1H), 4.26-4.18 (m, 1H), 4.06-3.90 (m, 2H), 3.45-3.36 (m, 1H), 3.09-3.02 (m, 1H), 2.97-2.89 (m, 1H), 2.88 (s, 2H), 2.83 (s, 3H of one rotamer), 2.83 (s, 3H of one rotamer), 2.50-2.44 (m, 1H), 2.30-2.24 (m, 1H), 1.97-1.91 (m, 1H), 1.73-1.52 (m, 3H), 1.43-1.32 (m, 4H), 1.14 (s, 6H). MS (ESI) m/z: [M+H]$^+$ Found 629.8.

Example 23

4-Chloro-1-ethyl-5-(2-methoxy-4-(((R)-1,1,1-trifluoropropan-2-yl)amino)phenyl)-N-(((1r,4R)-4-(methylsulfonyl)cyclohexyl)methyl)-1H-pyrazole-3-carboxamide

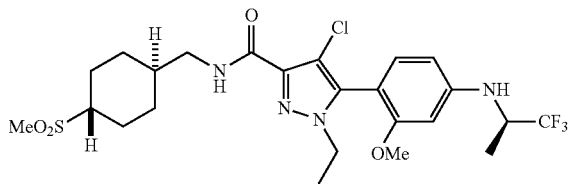 [SMILES: CCn1nc(C(=O)NC[C@H]2CC[C@H](S(C)(=O)=O)CC2)c(Cl)c1-c1ccc(N[C@H](C)C(F)(F)F)cc1OC]

The title compound was prepared as described for the synthesis of Example 1, using ethyl (R)-4-chloro-1-ethyl-5-(2-methoxy-4-((1,1,1-trifluoropropan-2-yl)amino)phenyl)-1H-pyrazole-3-carboxylate (Intermediate 106) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (500 MHz, CDCl$_3$) δ 7.07-7.02 (m, 1H), 6.94 (t, J=6.4 Hz, 1H), 6.38-6.33 (m, 1H), 6.30-6.26 (m, 1H), 4.14-4.04 (m, 1H), 4.01-3.88 (m, 3H), 3.76 (s, 3H of one rotamer), 3.75 (s, 3H of one rotamer), 3.39-3.27 (m, 2H), 2.86-2.78 (m, 1H), 2.82 (s, 3H), 2.31-2.23 (m, 2H), 2.10-2.03 (m, 2H), 1.73-1.62 (m, 1H), 1.62-1.53 (qd, J=12.9, 3.6 Hz, 2H), 1.45 (d, J=6.7 Hz, 3H), 1.33 (t, J=7.2 Hz, 3H), 1.13 (qd, J=13.1, 3.5 Hz, 2H). MS (ESI) m/z: [M+H]$^+$ Found 565.0.

Example 24

4-Chloro-1-ethyl-N-(((1s,4S)-1-hydroxy-4-(methylsulfonyl)cyclohexyl)methyl)-5-(2-methoxy-4-(((R)-1,1,1-trifluoropropan-2-yl)amino)phenyl)-1H-pyrazole-3-carboxamide

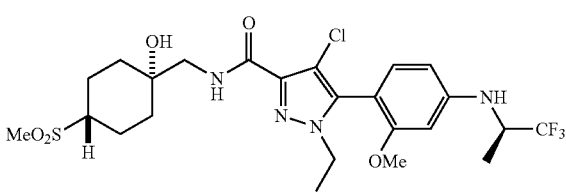 [SMILES: CCn1nc(C(=O)NC[C@]2(O)CC[C@@H](S(C)(=O)=O)CC2)c(Cl)c1-c1ccc(N[C@H](C)C(F)(F)F)cc1OC]

The title compound was prepared as described for the synthesis of Example 1, using ethyl (R)-4-chloro-1-ethyl-5-(2-methoxy-4-((1,1,1-trifluoropropan-2-yl)amino)phenyl)-1H-pyrazole-3-carboxylate (Intermediate 106) and (1s,4s)-1-(aminomethyl)-4-(methylsulfonyl)cyclohexan-1-ol hydrochloride (Intermediate 9) in place of ethyl (R*)-4-chloro-1-ethyl-5-(2-methoxy-4-(3,3,3-trifluoro-2-methylpropyl)phenyl)-1H-pyrazole-3-carboxylate and ((1r,4r)-4-(methylsulfonyl)cyclohexyl)methanamine hydrochloride. $^1$H NMR (500 MHz, CDCl$_3$) δ 7.44 (t, J=6.3 Hz, 1H), 7.06-7.00 (m, 1H), 6.39-6.33 (m, 1H), 6.30-6.26 (m, 1H), 5.22 (br s, 2H), 4.15-4.04 (m, 1H), 4.04-3.89 (m, J=7.1 Hz, 2H), 3.765 (s, 3H of one rotamer), 3.760 (s, 3H of one rotamer), 3.56-3.44 (m, 2H), 2.90-2.79 (m, 1H), 2.85 (s, 3H), 2.18-2.08 (m, 2H), 2.04-1.90 (m, 4H), 1.52-1.41 (m, 5H), 1.33 (t, J=7.2 Hz, 3H). MS (ESI) m/z: [M+H]$^+$ Found 581.2.

Example 25

4-Chloro-1-ethyl-5-(2-methoxy-4-((2,2,2-trifluoroethyl)amino)phenyl)-N-(((1r,4r)-4-(methylsulfonyl)cyclohexyl)methyl)-1H-pyrazole-3-carboxamide

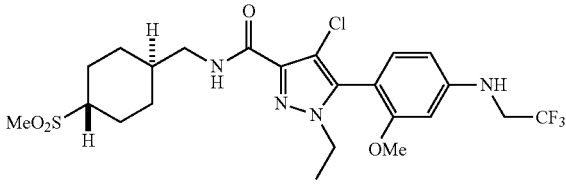 [SMILES: CCn1nc(C(=O)NC[C@H]2CC[C@H](S(C)(=O)=O)CC2)c(Cl)c1-c1ccc(NCC(F)(F)F)cc1OC]

The title compound was prepared as described for the synthesis of Example 23, using 2,2,2-trifluoroethan-1-amine in place of (R)-1,1,1-trifluoropropan-2-amine in the amination step. $^1$H NMR (400 MHz, CDCl$_3$) δ 7.11 (t, J=6.4 Hz, 1H), 7.05 (d, J=8.2 Hz, 1H), 6.39 (dd, J=8.3, 2.2 Hz, 1H), 6.31 (d, J=2.2 Hz, 1H), 4.45 (br s, 1H), 4.03-3.88 (m, J=7.1

Hz, 2H), 3.84 (q, J=8.8 Hz, 2H), 3.77 (s, 3H), 3.43-3.29 (m, 2H), 2.89-2.78 (m, 1H), 2.83 (s, 3H), 2.33-2.23 (m, 2H), 2.10-2.01 (m, 2H), 1.74-1.62 (m, 1H), 1.59 (qd, J=13.1, 3.6 Hz, 2H), 1.33 (t, J=7.2 Hz, 3H), 1.14 (qd, J=13.1, 3.5 Hz, 2H). MS (ESI) m/z: [M+H]$^+$ Found 550.9.

Example 26

1-(tert-Butyl)-4-chloro-5-(2-methoxy-4-(((R)-1,1,1-trifluoropropan-2-yl)amino)phenyl)-N-(((1r,4R)-4-(methylsulfonyl)cyclohexyl)methyl)-1H-pyrazole-3-carboxamide

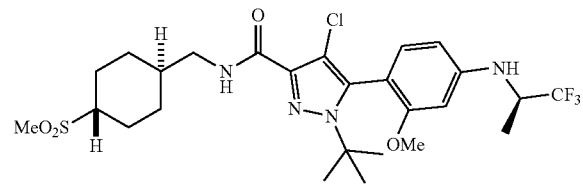 [SMILES: COc1cc(N[C@H](C)C(F)(F)F)ccc1-c1c(Cl)c(C(=O)NC[C@H]2CC[C@H](S(C)(=O)=O)CC2)nn1C(C)(C)C]

The title compound was prepared as described for the synthesis of Example 1, using ethyl (R)-1-(tert-butyl)-4-chloro-5-(2-methoxy-4-((1,1,1-trifluoropropan-2-yl)amino)phenyl)-1H-pyrazole-3-carboxylate (Intermediate 115) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (400 MHz, CDCl$_3$) δ 7.02 (t, J=6.4 Hz, 1H), 6.96-6.90 (m, 1H), 6.35-6.29 (m, 1H), 6.26-6.21 (m, 1H), 4.13-4.02 (m, 1H), 3.73 (s, 3H of one rotamer), 3.72 (s, 3H of one rotamer), 3.40-3.28 (m, 2H), 3.18 (s, 1H), 2.88-2.78 (m, 1H), 2.83 (s, 3H), 2.32-2.23 (m, 2H), 2.11-2.02 (m, 2H), 1.74-1.62 (m, 1H), 1.57 (td, J=12.8, 3.6 Hz, 2H), 1.46 (d, J=6.8 Hz, 3H), 1.45 (s, 9H), 1.13 (qd, J=13.0, 3.5 Hz, 2H). MS (ESI) m/z: [M+H]$^+$ Found 593.3.

Example 27

1-(tert-Butyl)-4-chloro-N-(((1s,4S)-1-hydroxy-4-(methylsulfonyl)cyclohexyl)methyl)-5-(2-methoxy-4-(((R)-1,1,1-trifluoropropan-2-yl)amino)phenyl)-1H-pyrazole-3-carboxamide

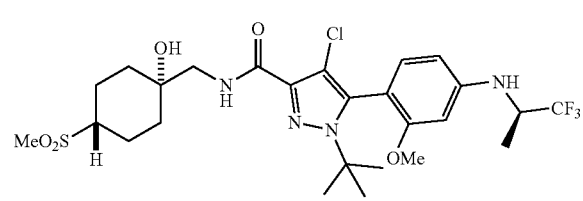 [SMILES: COc1cc(N[C@H](C)C(F)(F)F)ccc1-c1c(Cl)c(C(=O)NC[C@]2(O)CC[C@@H](S(C)(=O)=O)CC2)nn1C(C)(C)C]

The title compound was prepared as described for the synthesis of Example 1, using ethyl (R)-1-(tert-butyl)-4-chloro-5-(2-methoxy-4-((1,1,1-trifluoropropan-2-yl)amino)phenyl)-1H-pyrazole-3-carboxylate (Intermediate 115) and (1s,4s)-1-(aminomethyl)-4-(methylsulfonyl)cyclohexan-1-ol hydrochloride (Intermediate 9) in place of ethyl (R*)-4-chloro-1-ethyl-5-(2-methoxy-4-(3,3,3-trifluoro-2-methylpropyl)phenyl)-1H-pyrazole-3-carboxylate and ((1r,4r)-4-(methylsulfonyl)cyclohexyl)methanamine hydrochloride. $^1$H NMR (400 MHz, CDCl$_3$) δ 7.33 (t, J=6.4 Hz, 1H), 6.96-6.90 (m, 1H), 6.36-6.30 (m, 1H), 6.26-6.22 (m, 1H), 4.14-4.02 (m, 1H), 3.73 (s, 3H of one rotamer), 3.72 (s, 3H of one rotamer), 3.53-3.41 (m, 2H), 3.24 (br s, 2H), 2.87-2.75 (m, 1H), 2.83 (s, 3H), 2.17-2.08 (m, 2H), 2.04-1.90 (m, 4H), 1.50-1.37 (m, 14H). MS (ESI) m/z: [M+H]$^+$ Found 609.2.

Example 28

4-Chloro-1-isobutyl-5-(2-methoxy-4-(((R)-1,1,1-trifluoropropan-2-yl)amino)phenyl)-N-(((1r,4R)-4-(methylsulfonyl)cyclohexyl)methyl)-1H-pyrazole-3-carboxamide

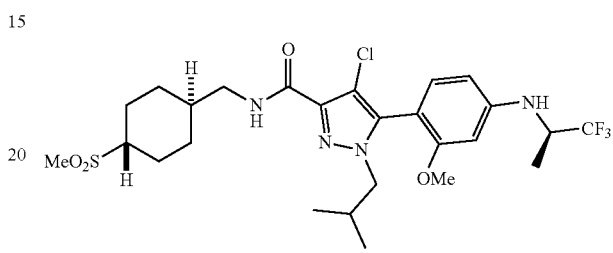

The title compound was prepared as described for the synthesis of Example 1, using ethyl (R)-4-chloro-1-isobutyl-5-(2-methoxy-4-((1,1,1-trifluoropropan-2-yl)amino)phenyl)-1H-pyrazole-3-carboxylate (Intermediate 114) in place of ethyl (R*)-4-chloro-1-ethyl-5-(2-methoxy-4-(3,3,3-trifluoro-2-methylpropyl)phenyl)-1H-pyrazole-3-carboxylate.
$^1$H NMR (400 MHz, CDCl$_3$) δ 7.07 (t, J=6.4 Hz, 1H), 7.03-6.98 (m, 1H), 6.38-6.32 (m, 1H), 6.28-6.25 (m, 1H), 4.14-4.03 (m, 1H), 3.78 (dd, J=13.6, 6.8 Hz, 1H), 3.78 (br s, anilinic NH coincident with excess water), 3.752 (s, 3H of one rotamer), 3.747 (s, 3H of one rotamer), 3.64 (dd, J=13.4, 8.0 Hz, 1H), 3.43-3.27 (m, 2H), 2.88-2.78 (m, 1H), 2.83 (s, 3H), 2.32-2.24 (m, 2H), 2.18-2.08 (m, 1H), 2.10-2.02 (m, 2H), 1.74-1.62 (m, 1H), 1.57 (td, J=12.9, 3.6 Hz, 2H), 1.46 (d, J=6.7 Hz, 3H), 1.13 (qd, J=13.1, 3.5 Hz, 2H), 0.79 (d, J=6.6 Hz, 3H), 0.71 (d, J=6.6 Hz, 3H). MS (ESI) m/z: [M+H]$^+$ Found 593.3.

Example 29

4-Chloro-N-(((1s,4S)-1-hydroxy-4-(methylsulfonyl)cyclohexyl)methyl)-1-isobutyl-5-(2-methoxy-4-(((R)-1,1,1-trifluoropropan-2-yl)amino)phenyl)-1H-pyrazole-3-carboxamide

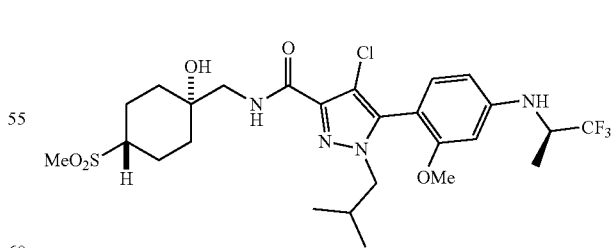

The title compound was prepared as described for the synthesis of Example 1, using ethyl (R)-4-chloro-1-isobutyl-5-(2-methoxy-4-((1,1,1-trifluoropropan-2-yl)amino)phenyl)-1H-pyrazole-3-carboxylate (Intermediate 114) and (1s,4s)-1-(aminomethyl)-4-(methyl sulfonyl)cyclohexan-1-ol hydrochloride (Intermediate 9) in place of ethyl (R*)-4- chloro-1-ethyl-5-(2-methoxy-4-(3,3,3-trifluoro-2-methyl-propyl)phenyl)-1H-pyrazole-3-carboxylate and ((1r,4r)-4-(methylsulfonyl)cyclohexyl)methanamine hydrochloride. $^1$H NMR (400 MHz, CDCl$_3$) δ 7.30 (t, J=6.3 Hz, 1H), 7.03-6.98 (m, 1H), 6.38-6.32 (m, 1H), 6.29-6.25 (m, 1H), 4.14-4.03 (m, 1H), 3.80 (dd, J=13.5, 6.9 Hz, 1H), 3.754 (s, 3H of one rotamer), 3.749 (s, 3H of one rotamer), 3.65 (dd, J=13.4, 8.1 Hz, 1H), 3.51 (dd, J=14.2, 6.4 Hz, 1H), 3.43 (dd, J=14.2, 6.2 Hz, 1H), 3.09 (br s, 2H), 2.86-2.75 (m, 1H), 2.83 (s, 3H), 2.19-2.07 (m, 3H), 2.03-1.90 (m, 4H), 1.46 (d, J=6.4 Hz, 3H), 1.46-1.38 (m, 2H), 0.80 (d, J=6.7 Hz, 3H), 0.71 (d, J=6.6 Hz, 3H). MS (ESI) m/z: [M+H]$^+$ Found 609.2.

Example 30

4-Chloro-5-(2-methoxy-4-(((R)-1,1,1-trifluoropro-pan-2-yl)amino)phenyl)-N-(((1r,4R)-4-(methylsulfo-nyl)cyclohexyl)methyl)-1-propyl-1H-pyrazole-3-carboxamide

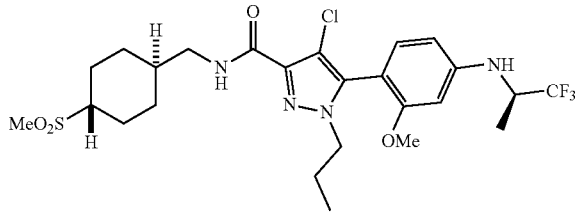 [SMILES: CCCn1nc(C(=O)NC[C@H]2CC[C@H](S(C)(=O)=O)CC2)c(Cl)c1-c1ccc(N[C@H](C)C(F)(F)F)cc1OC]

The title compound was prepared as described for the synthesis of Example 1, using ethyl (R)-4-chloro-5-(2-methoxy-4-((1,1,1-trifluoropropan-2-yl)amino)phenyl)-1-propyl-1H-pyrazole-3-carboxylate (Intermediate 110) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (400 MHz, CDCl$_3$) δ 7.09-7.00 (m, 2H), 6.38-6.33 (m, 1H), 6.29-6.25 (m, 1H), 4.09 (m, 1H), 3.95-3.79 (m, 2H), 3.76 (s, 3H of one rotamer), 3.75 (s, 3H of one rotamer), 3.72 (br s, 1H), 3.42-3.28 (m, 2H), 2.88-2.78 (m, 1H), 2.83 (s, 3H), 2.32-2.24 (m, 2H), 2.10-2.02 (m, 2H), 1.82-1.63 (m, 3H), 1.59 (qd, J=12.9, 3.6 Hz, 2H), 1.46 (d, J=6.7 Hz, 3H), 1.13 (qd, J=13.2, 3.5 Hz, 2H), 0.79 (t, J=7.4 Hz, 3H). MS (ESI) m/z: [M+H]$^+$ Found 579.2.

Example 31

4-Chloro-N-(((1s,4S)-1-hydroxy-4-(methylsulfonyl)cyclohexyl)methyl)-5-(2-methoxy-4-(((R)-1,1,1-trifluoropropan-2-yl)amino)phenyl)-1-propyl-1H-pyrazole-3-carboxamide

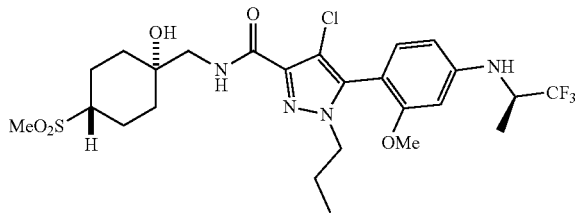 [SMILES: CCCn1nc(C(=O)NC[C@]2(O)CC[C@@H](S(C)(=O)=O)CC2)c(Cl)c1-c1ccc(N[C@H](C)C(F)(F)F)cc1OC]

The title compound was prepared as described for the synthesis of Example 1, using ethyl (R)-4-chloro-5-(2-methoxy-4-((1,1,1-trifluoropropan-2-yl)amino)phenyl)-1-propyl-1H-pyrazole-3-carboxylate (Intermediate 110) and (1s,4s)-1-(aminomethyl)-4-(methylsulfonyl)cyclohexan-1-ol hydrochloride (Intermediate 9) in place of ethyl (R*)-4-chloro-1-ethyl-5-(2-methoxy-4-(3,3,3-trifluoro-2-methylpropyl)phenyl)-1H-pyrazole-3-carboxylate and ((1r,4r)-4-(methylsulfonyl)cyclohexyl)methanamine hydrochloride. $^1$H NMR (400 MHz, CDCl$_3$) δ 7.34 (t, J=6.1 Hz, 1H), 7.06-6.99 (m, 1H), 6.40-6.33 (m, 1H), 6.30-6.25 (m, 1H), 4.14-4.03 (m, 1H), 3.96-3.78 (m, 2H), 3.83 (br s, 2H), 3.76 (s, 3H of one rotamer), 3.75 (s, 3H of one rotamer), 3.55-3.41 (m, 2H), 2.87-2.76 (m, 1H), 2.84 (s, 3H), 2.17-2.08 (m, 2H), 2.03-1.90 (m, 4H), 1.82-1.69 (m, 2H), 1.50-1.38 (m, 2H), 1.46 (d, J=6.8 Hz, 3H), 0.79 (t, J=7.4 Hz, 3H). MS (ESI) m/z: [M+H]$^+$ Found 595.2.

Example 32

4-Chloro-N-(((1s,4S)-1-cyano-4-(methylsulfonyl)cyclohexyl)methyl)-1-ethyl-5-(2-methoxy-4-(((R)-1,1,1-trifluoropropan-2-yl)amino)phenyl)-1H-pyrazole-3-carboxamide

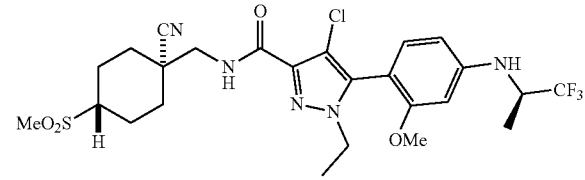 [SMILES: CCn1nc(C(=O)NC[C@]2(C#N)CC[C@@H](S(C)(=O)=O)CC2)c(Cl)c1-c1ccc(N[C@H](C)C(F)(F)F)cc1OC]

The title compound was prepared as described for the synthesis of Example 1, using ethyl (R)-4-chloro-1-ethyl-5-(2-methoxy-4-((1,1,1-trifluoropropan-2-yl)amino)phenyl)-1H-pyrazole-3-carboxylate (Intermediate 106) and (1s*,4s*)-1-(aminomethyl)-4-(methylsulfonyl)cyclohexane-1-carbonitrile hydrochloride (Intermediate 36) in place of ethyl (R*)-4-chloro-1-ethyl-5-(2-methoxy-4-(3,3,3-trifluoro-2-methylpropyl)phenyl)-1H-pyrazole-3-carboxylate and ((1r,4r)-4-(methylsulfonyl)cyclohexyl)methanamine hydrochloride. $^1$H NMR (500 MHz, CDCl$_3$) δ 7.38 (t, J=6.6 Hz, 1H), 7.07-7.01 (m, 1H), 6.39-6.34 (m, 1H), 6.30-6.26 (m, 1H), 4.14-4.05 (m, 1H), 4.04-3.90 (m, 2H), 3.89 (bs s, 1H), 3.77 (s, 3H of one rotamer), 3.77 (s, 3H of one rotamer), 3.73-3.63 (m, 2H), 2.89-2.80 (m, 1H), 2.87 (s, 3H), 2.38-2.31 (m, 2H), 2.30-2.23 (m, 2H), 1.96-1.85 (m, 2H), 1.58 (td, J=13.8, 3.5 Hz, 2H), 1.46 (d, J=6.8 Hz, 3H), 1.34 (t, J=7.1 Hz, 3H). MS (ESI) m/z: [M+H]$^+$ Found 590.2.

Example 33

4-Chloro-N-(((1r,4R)-1-cyano-4-(methylsulfonyl)cyclohexyl)methyl)-1-ethyl-5-(2-methoxy-4-(((R)-1,1,1-trifluoropropan-2-yl)amino)phenyl)-1H-pyrazole-3-carboxamide

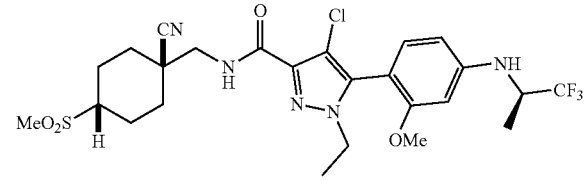 [SMILES: CCn1nc(C(=O)NC[C@]2(C#N)CC[C@H](S(C)(=O)=O)CC2)c(Cl)c1-c1ccc(N[C@H](C)C(F)(F)F)cc1OC]

The title compound was prepared as described for the synthesis of Example 1, using ethyl (R)-4-chloro-1-ethyl-5-(2-methoxy-4-((1,1,1-trifluoropropan-2-yl)amino)phenyl)-1H-pyrazole-3-carboxylate (Intermediate 106) and (1r*,4r*)-1-(aminomethyl)-4-(methylsulfonyl)cyclohexane-1-carbonitrile hydrochloride (Intermediate 35) in place of ethyl (R*)-4-chloro-1-ethyl-5-(2-methoxy-4-(3,3,3-trifluoro-2-methylpropyl)phenyl)-1H-pyrazole-3-carboxylate and ((1r,4r)-4-(methylsulfonyl)cyclohexyl)methanamine hydrochloride. $^1$H NMR (500 MHz, CDCl$_3$) δ 7.31 (t, J=6.9 Hz, 1H), 7.07-7.02 (m, 1H), 6.39-6.34 (m, 1H), 6.30-6.26 (m, 1H), 4.13-4.04 (m, 1H), 4.03-3.89 (m, 2H), 3.79-3.68 (m, 2H), 3.77 (s, 3H of one rotamer), 3.76 (s, 3H of one rotamer), 3.01-2.94 (m, 1H), 2.89 (s, 3H), 2.33 (br s, 1H), 2.27-2.14 (m, 6H), 1.96-1.87 (m, 2H), 1.46 (d, J=6.7 Hz, 3H), 1.34 (t, J=7.2 Hz, 3H). MS (ESI) m/z: [M+H]$^+$ Found 590.0.

Example 34

N-(((1r,4R)-1-carbamoyl-4-(methylsulfonyl)cyclohexyl)methyl)-4-chloro-1-ethyl-5-(2-methoxy-4-(((R)-1,1,1-trifluoropropan-2-yl)amino)phenyl)-1H-pyrazole-3-carboxamide

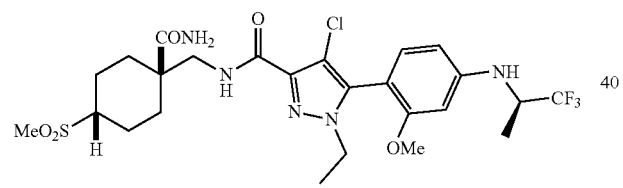

4-Chloro-N-(((1r,4R)-1-cyano-4-(methylsulfonyl)cyclohexyl)methyl)-1-ethyl-5-(2-methoxy-4-(((R)-1,1,1-trifluoropropan-2-yl)amino)phenyl)-1H-pyrazole-3-carboxamide (40 mg, 0.068 mmol, Example 33) was dissolved in H$_2$SO$_4$ (0.60 mL, 11 mmol) and the resulting solution was maintained at rt for 30 min. The reaction solution was then added to 5 g of ice, and the resulting suspension was filtered to afford a colorless solid. This residue was diluted with MeOH, filtered, and then purified by preparative HPLC (XBridge C18, 10→100% MeCN/water, 0.05% TFA) to afford the title compound as a colorless solid. $^1$H NMR (400 MHz, CDCl$_3$) δ 7.30 (t, J=7.0 Hz, 1H), 7.06-7.01 (m, 1H), 6.98 (br s, 1H), 6.38-6.34 (m, 1H), 6.32 (br s, 1H), 6.29-6.26 (m, 1H), 4.14-4.04 (m, 1H), 4.03-3.88 (m, 2H), 3.87-3.73 (m, 2H), 3.766 (s, 3H of one rotamer), 3.759 (s, 3H of one rotamer), 3.25 (br s, 1H), 2.95-2.86 (m, 1H), 2.89 (s, 3H), 2.29-2.19 (m, 2H), 2.13-2.05 (m, 2H), 2.03-1.79 (m, 4H), 1.46 (d, J=6.7 Hz, 3H), 1.32 (t, J=7.2 Hz, 3H). MS (ESI) m/z: [M+H]$^+$ Found 608.0.

Example 35

N-(((1s,4S)-1-carbamoyl-4-(methylsulfonyl)cyclohexyl)methyl)-4-chloro-1-ethyl-5-(2-methoxy-4-(((R)-1,1,1-trifluoropropan-2-yl)amino)phenyl)-1H-pyrazole-3-carboxamide

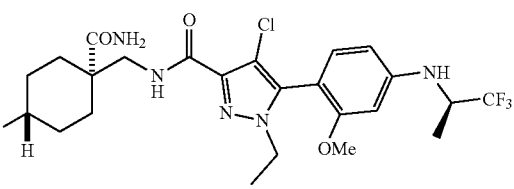

The title compound was prepared as described for the synthesis of Example 34, using 4-chloro-N-(((1s,4S)-1-cyano-4-(methylsulfonyl)cyclohexyl)methyl)-1-ethyl-5-(2-methoxy-4-(((R)-1,1,1-trifluoropropan-2-yl)amino)phenyl)-1H-pyrazole-3-carboxamide (Example 32) in place of 4-chloro-N-(((1r,4R)-1-cyano-4-(methylsulfonyl)cyclohexyl)methyl)-1-ethyl-5-(2-methoxy-4-(((R)-1,1,1-trifluoropropan-2-yl)amino)phenyl)-1H-pyrazole-3-carboxamide. $^1$H NMR (400 MHz, CDCl$_3$) δ 7.19 (t, J=6.5 Hz, 1H), 7.06-7.01 (m, 1H), 6.39-6.33 (m, 1H), 6.29-6.26 (m, 1H), 6.24 (br s, 1H), 5.77 (br s, 1H), 4.14-4.04 (m, 1H), 4.02-3.87 (m, 2H), 3.764 (s, 3H of one rotamer), 3.759 (s, 3H of one rotamer), 3.63-3.51 (m, 2H), 2.90-2.80 (m, 1H), 2.82 (s, 3H), 2.43-2.34 (m, 2H), 2.26-2.18 (m, 2H), 2.05 (br s, 1H), 1.88-1.75 (m, 2H), 1.54-1.43 (m, 2H), 1.46 (d, J=6.7 Hz, 3H), 1.32 (t, J=7.2 Hz, 3H). MS (ESI) m/z: [M+H]$^+$ Found 608.2.

Example 36

4-Chloro-1-ethyl-N-(((1s,4S)-1-hydroxy-4-(methylsulfonyl)cyclohexyl)methyl)-5-(2-methoxy-4-((R)-3,3,3-trifluoro-2-methylpropyl)phenyl)-1H-pyrazole-3-carboxamide

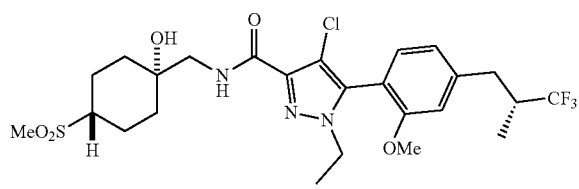 [SMILES: CCn1nc(C(=O)NC[C@]2(O)CC[C@@H](S(C)(=O)=O)CC2)c(Cl)c1-c1ccc(C[C@@H](C)C(F)(F)F)cc1OC]

The title compound was prepared as described for the synthesis of Example 1, using (1s,4s)-1-(aminomethyl)-4-(methylsulfonyl)cyclohexan-1-ol hydrochloride (Intermediate 9) in place of ((1r,4r)-4-(methylsulfonyl)cyclohexyl)methanamine hydrochloride. $^1$H NMR (500 MHz, CDCl$_3$) δ 7.33 (t, J=6.2 Hz, 1H), 7.20-7.16 (m, 1H), 6.94-6.89 (m, 1H), 6.84-6.80 (m, 1H), 4.04-3.88 (m, 2H), 3.81 (s, 3H), 3.54-3.43 (m, 2H), 3.20-3.13 (m, 1H), 3.09, (br s, 1H), 2.85-2.77 (m, 1H), 2.84 (s, 3H), 2.59-2.45 (m, 2H), 2.17-2.09 (m, 2H), 2.03-1.91 (m, 4H), 1.45 (td, J=14.2, 3.7 Hz, 2H), 1.34 (t, J=7.2 Hz, 3H), 1.11 (d, J=6.3 Hz, 3H). MS (ESI) m/z: [M+H]$^+$ Found 580.2.

Example 37

4-Chloro-1-ethyl-N-(((1s,4R)-1-hydroxy-4-(methylsulfonyl)cyclohexyl)methyl)-5-(2-methoxy-4-((S*)-3,3,3-trifluoro-2-methylpropyl)phenyl)-1H-pyrazole-3-carboxamide

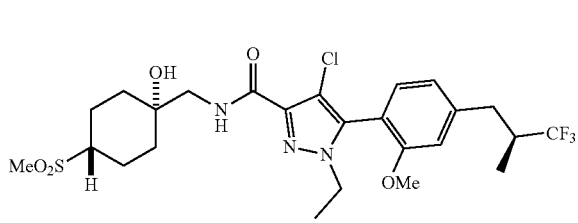 [SMILES: CCn1nc(C(=O)NC[C@]2(O)CC[C@@H](S(C)(=O)=O)CC2)c(Cl)c1-c1ccc(C[C@H](C)C(F)(F)F)cc1OC]

The title compound was prepared as described for the synthesis of Example 1, using ethyl (S*)-4-chloro-1-ethyl-5-(2-methoxy-4-(3,3,3-trifluoro-2-methylpropyl)phenyl)-1H-pyrazole-3-carboxylate (Intermediate 100) and (1s,4s)-1-(aminomethyl)-4-(methylsulfonyl)cyclohexan-1-ol hydrochloride (Intermediate 9) in place of ethyl (R*)-4-chloro-1-ethyl-5-(2-methoxy-4-(3,3,3-trifluoro-2-methylpropyl)phenyl)-1H-pyrazole-3-carboxylate and ((1r,4r)-4-(methylsulfonyl)cyclohexyl)methanamine hydrochloride. $^1$H NMR (500 MHz, CDCl$_3$) δ 7.33 (t, J=6.2 Hz, 1H), 7.20-7.16 (m, 1H), 6.94-6.89 (m, 1H), 6.84-6.80 (m, 1H), 4.04-3.88 (m, 2H), 3.81 (s, 3H), 3.54-3.43 (m, 2H), 3.22, (br s, 1H), 3.20-3.13 (m, 1H), 2.85-2.77 (m, 1H), 2.84 (s, 3H), 2.59-2.45 (m, 2H), 2.17-2.09 (m, 2H), 2.03-1.91 (m, 4H), 1.45 (td, J=14.2, 3.7 Hz, 2H), 1.34 (t, J=7.2 Hz, 3H), 1.11 (d, J=6.3 Hz, 3H). MS (ESI) m/z: [M+H]$^+$ Found 580.2.

Example 38

4-Chloro-1-ethyl-5-(2-methoxy-4-(3,3,3-trifluoropropyl)phenyl)-N-(((1r,4r)-4-(methylsulfonyl)cyclohexyl)methyl)-1H-pyrazole-3-carboxamide

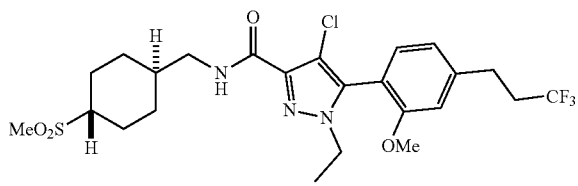 [SMILES: CCn1nc(C(=O)NC[C@H]2CC[C@H](S(C)(=O)=O)CC2)c(Cl)c1-c1ccc(CCC(F)(F)F)cc1OC]

The title compound was prepared as described for the synthesis of Example 1, using ethyl 4-chloro-1-ethyl-5-(2-methoxy-4-(3,3,3-trifluoropropyl)phenyl)-1H-pyrazole-3-carboxylate (Intermediate 261) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (500 MHz, CDCl$_3$) δ 7.19 (d, J=7.7 Hz, 1H), 6.99-6.91 (m, 2H), 6.85 (s, 1H), 4.03-3.87 (m, 2H), 3.81 (s, 3H), 3.40-3.28 (m, 2H), 2.99-2.90 (m, 2H), 2.87-2.78 (m, 1H), 2.83 (s, 3H), 2.53-2.41 (m, 2H), 2.32-2.23 (m, 2H), 2.11-2.03 (m, 2H), 1.75-1.64 (m, 1H), 1.59 (qd, J=13.0, 3.7 Hz, 2H), 1.33 (t, J=7.2 Hz, 3H), 1.14 (qd, J=13.1, 3.6 Hz, 2H). MS (ESI) m/z: [M+H]$^+$ Found 550.2.

Example 39

4-Chloro-1-ethyl-N-(((1s,4s)-1-hydroxy-4-(methylsulfonyl)cyclohexyl)methyl)-5-(2-methoxy-4-(3,3,3-trifluoropropyl)phenyl)-1H-pyrazole-3-carboxamide

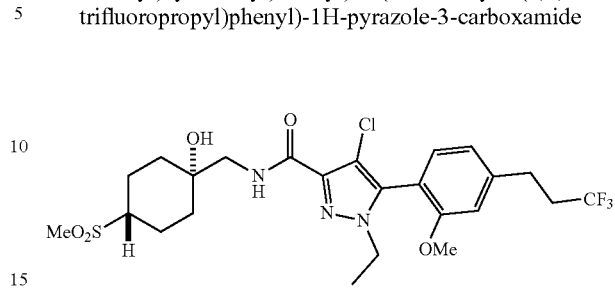

The title compound was prepared as described for the synthesis of Example 1, using ethyl 4-chloro-1-ethyl-5-(2-methoxy-4-(3,3,3-trifluoropropyl)phenyl)-1H-pyrazole-3-carboxylate (Intermediate 261) and (1s,4s)-1-(aminomethyl)-4-(methylsulfonyl)cyclohexan-1-ol hydrochloride (Intermediate 9) in place of ethyl (R*)-4-chloro-1-ethyl-5-(2-methoxy-4-(3,3,3-trifluoro-2-methylpropyl)phenyl)-1H-pyrazole-3-carboxylate and ((1r,4r)-4-(methylsulfonyl)cyclohexyl)methanamine hydrochloride. $^1$H NMR (500 MHz, CDCl$_3$) δ 7.35 (t, J=6.2 Hz, 1H), 7.18 (d, J=7.7 Hz, 1H), 6.94 (d, J=7.5 Hz, 1H), 6.86 (s, 1H), 4.03-3.89 (m, 2H), 3.82 (s, 3H), 3.54 (s, 1H), 3.54-3.43 (m, 2H), 2.98-2.92 (m, 2H), 2.86-2.78 (m, 1H), 2.84 (s, 3H), 2.52-2.41 (m, 2H), 2.17-2.09 (m, 2H), 2.03-1.92 (m, 4H), 1.45 (td, J=14.2, 4.3 Hz, 2H), 1.34 (t, J=7.2 Hz, 3H). MS (ESI) m/z: [M+H]$^+$ Found 566.2.

Example 40

4-Chloro-N-(((1s,4R)-1-hydroxy-4-(methylsulfonyl)cyclohexyl)methyl)-5-(2-methoxy-4-((S*)-3,3,3-trifluoro-2-methylpropyl)phenyl)-1-propyl-1H-pyrazole-3-carboxamide

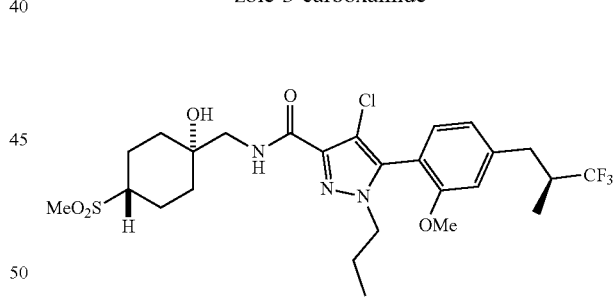

The title compound was prepared as described for the synthesis of Example 1, using ethyl (S*)-4-chloro-5-(2-methoxy-4-(3,3,3-trifluoro-2-methylpropyl)phenyl)-1-propyl-1H-pyrazole-3-carboxylate (Intermediate 113) and (1s,4s)-1-(aminomethyl)-4-(methylsulfonyl)cyclohexan-1-ol hydrochloride (Intermediate 9) in place of ethyl (R*)-4-chloro-1-ethyl-5-(2-methoxy-4-(3,3,3-trifluoro-2-methylpropyl)phenyl)-1H-pyrazole-3-carboxylate and ((1r,4r)-4-(methylsulfonyl)cyclohexyl)methanamine hydrochloride. $^1$H NMR (500 MHz, CDCl$_3$) δ 7.31 (t, J=6.4 Hz, 1H), 7.19-7.15 (m, 1H), 6.93-6.89 (m, 1H), 6.82 (s, 1H), 3.97-3.88 (m, 1H), 3.87-3.80 (m, 1H), 3.81 (s, 3H), 3.48 (qd, J=14.2, 6.3 Hz, 2H), 3.21-3.12 (m, 1H), 2.84 (s, 3H), 2.84-2.77 (m, 1H), 2.77 (br s, 1H), 2.59-2.45 (m, 2H), 2.17-2.09 (m, 2H), 2.03-1.91 (m, 4H), 1.81-1.69 (m, 2H), 1.44 (td, J=14.2, 4.0 Hz, 2H), 1.10 (d, J=6.2 Hz, 3H), 0.78 (t, J=7.4 Hz, 3H). MS (ESI) m/z: [M+H]+ Found 594.2.

Example 41

4-Chloro-5-(2-methoxy-4-((S*)-3,3,3-trifluoro-2-methylpropyl)phenyl)-N-(((1r,4S)-4-(methylsulfonyl)cyclohexyl)methyl)-1-propyl-1H-pyrazole-3-carboxamide

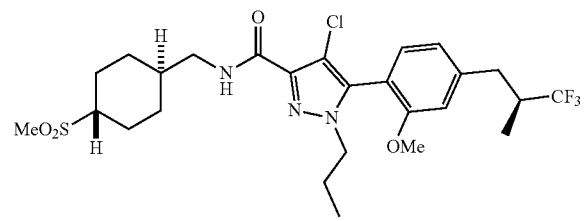 [SMILES: CCCn1nc(C(=O)NC[C@H]2CC[C@H](S(C)(=O)=O)CC2)c(Cl)c1-c1ccc(C[C@H](C)C(F)(F)F)cc1OC]

The title compound was prepared as described for the synthesis of Example 1, using ethyl (S*)-4-chloro-5-(2-methoxy-4-(3,3,3-trifluoro-2-methylpropyl)phenyl)-1-propyl-1H-pyrazole-3-carboxylate (Intermediate 113) in place of ethyl (R*)-4-chloro-1-ethyl-5-(2-methoxy-4-(3,3,3-trifluoro-2-methylpropyl)phenyl)-1H-pyrazole-3-carboxylate.
$^1$H NMR (500 MHz, CDCl$_3$) δ 7.19-7.16 (m, 1H), 6.98 (t, J=6.4 Hz, 1H), 6.92-6.89 (m, 1H), 6.81 (s, 1H), 3.95-3.87 (m, 1H), 3.86-3.79 (m, 1H), 3.81 (s, 3H), 3.41-3.28 (m, 2H), 3.20-3.12 (m, 1H), 2.87-2.78 (m, 1H), 2.83 (s, 3H), 2.58-2.46 (m, 2H), 2.32-2.24 (m, 2H), 2.11-2.03 (m, 2H), 1.81-1.64 (m, 3H), 1.59 (qd, J=13.0, 3.7 Hz, 2H), 1.19-1.07 (m, 5H), 0.78 (t, J=7.4 Hz, 3H). MS (ESI) m/z: [M+H]+ Found 578.2.

Example 42

4-Chloro-N-(((1s,4S)-1-hydroxy-4-(methylsulfonyl)cyclohexyl)methyl)-5-(2-methoxy-4-((R*)-3,3,3-trifluoro-2-methylpropyl)phenyl)-1-propyl-1H-pyrazole-3-carboxamide

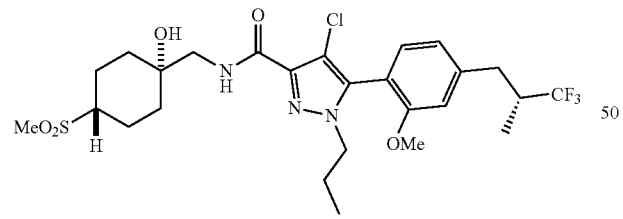

The title compound was prepared as described for the synthesis of Example 1, using ethyl (R*)-4-chloro-5-(2-methoxy-4-(3,3,3-trifluoro-2-methylpropyl)phenyl)-1-propyl-1H-pyrazole-3-carboxylate (Intermediate 112) and (1s,4s)-1-(aminomethyl)-4-(methyl sulfonyl)cyclohexan-1-ol hydrochloride (Intermediate 9) in place of ethyl (R*)-4-chloro-1-ethyl-5-(2-methoxy-4-(3,3,3-trifluoro-2-methylpropyl)phenyl)-1H-pyrazole-3-carboxylate and ((1r,4r)-4-(methylsulfonyl)cyclohexyl)methanamine hydrochloride.
$^1$H NMR (500 MHz, CDCl$_3$) δ 7.29 (t, J=6.4 Hz, 1H), 7.19-7.15 (m, 1H), 6.93-6.89 (m, 1H), 6.82 (s, 1H), 3.97-3.88 (m, 1H), 3.87-3.80 (m, 1H), 3.81 (s, 3H), 3.48 (qd, J=14.2, 6.3 Hz, 2H), 3.21-3.12 (m, 1H), 2.84 (s, 3H), 2.84-2.77 (m, 1H), 2.59-2.45 (m, 2H), 2.30 (br s, 1H), 2.17-2.09 (m, 2H), 2.03-1.91 (m, 4H), 1.81-1.69 (m, 2H), 1.44 (td, J=14.2, 4.0 Hz, 2H), 1.10 (d, J=6.2 Hz, 3H), 0.78 (t, J=7.4 Hz, 3H). MS (ESI) m/z: [M+H]+ Found 594.2.

Example 43

4-Chloro-5-(2-methoxy-4-((R*)-3,3,3-trifluoro-2-methylpropyl)phenyl)-N-(((1r,4R)-4-(methylsulfonyl)cyclohexyl)methyl)-1-propyl-1H-pyrazole-3-carboxamide

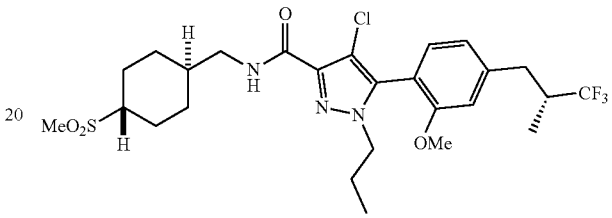

The title compound was prepared as described for the synthesis of Example 1, using ethyl (R*)-4-chloro-5-(2-methoxy-4-(3,3,3-trifluoro-2-methylpropyl)phenyl)-1-propyl-1H-pyrazole-3-carboxylate (Intermediate 112) in place of ethyl (R*)-4-chloro-1-ethyl-5-(2-methoxy-4-(3,3,3-trifluoro-2-methylpropyl)phenyl)-1H-pyrazole-3-carboxylate.
$^1$H NMR (500 MHz, CDCl$_3$) δ 7.19-7.16 (m, 1H), 6.97 (t, J=6.4 Hz, 1H), 6.92-6.89 (m, 1H), 6.81 (s, 1H), 3.95-3.87 (m, 1H), 3.86-3.79 (m, 1H), 3.81 (s, 3H), 3.41-3.28 (m, 2H), 3.20-3.12 (m, 1H), 2.87-2.78 (m, 1H), 2.83 (s, 3H), 2.58-2.46 (m, 2H), 2.32-2.24 (m, 2H), 2.11-2.03 (m, 2H), 1.81-1.64 (m, 3H), 1.59 (qd, J=13.0, 3.7 Hz, 2H), 1.19-1.07 (m, 5H), 0.78 (t, J=7.4 Hz, 3H). MS (ESI) m/z: [M+H]+ Found 578.2.

Example 44

4-Chloro-1-ethyl-5-(2-methoxy-4-(3,3,3-trifluoro-2,2-dimethylpropyl)phenyl)-N-(((1r,4r)-4-(methylsulfonyl)cyclohexyl)methyl)-1H-pyrazole-3-carboxamide

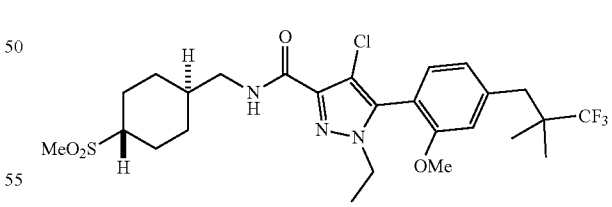

The title compound was prepared as described for the synthesis of Example 1, using ethyl 4-chloro-1-ethyl-5-(2-methoxy-4-(3,3,3-trifluoro-2,2-dimethylpropyl)phenyl)-1H-pyrazole-3-carboxylate (Intermediate 117) in place of ethyl (R*)-4-chloro-1-ethyl-5-(2-methoxy-4-(3,3,3-trifluoro-2-methylpropyl)phenyl)-1H-pyrazole-3-carboxylate.
$^1$H NMR (400 MHz, CDCl$_3$) δ 7.17 (d, J=7.7 Hz, 1H), 7.06 (t, J=6.4 Hz, 1H), 6.92-6.87 (m, 1H), 6.80 (s, 1H), 4.04-3.88 (m, 2H), 3.80 (s, 3H), 3.42-3.30 (m, 2H), 2.88-2.79 (m, 1H), 2.85 (s, 2H), 2.83 (s, 3H), 2.32-2.24 (m, 2H), 2.11-2.03 (m, 2H), 1.75-1.63 (m, 1H), 1.59 (qd, J=13.1, 3.8 Hz, 2H), 1.34 (t, J=7.2 Hz, 3H), 1.21-1.08 (qd, J=13.2, 3.6 Hz, 2H), 1.13 (s, 6H). MS (ESI) m/z: [M+H]+ Found 578.2.

Example 45

4-Chloro-1-ethyl-N-(((1s,4s)-1-hydroxy-4-(methylsulfonyl)cyclohexyl)methyl)-5-(2-methoxy-4-(3,3,3-trifluoro-2,2-dimethylpropyl)phenyl)-1H-pyrazole-3-carboxamide

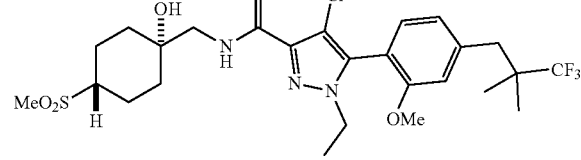

The title compound was prepared as described for the synthesis of Example 1, using ethyl 4-chloro-1-ethyl-5-(2-methoxy-4-(3,3,3-trifluoro-2,2-dimethylpropyl)phenyl)-1H-pyrazole-3-carboxylate (Intermediate 117) and (1s,4s)-1-(aminomethyl)-4-(methyl sulfonyl)cyclohexan-1-ol hydrochloride (Intermediate 9) in place of ethyl (R*)-4-chloro-1-ethyl-5-(2-methoxy-4-(3,3,3-trifluoro-2-methylpropyl)phenyl)-1H-pyrazole-3-carboxylate and ((1r,4r)-4-(methylsulfonyl)cyclohexyl)methanamine hydrochloride. 1H NMR (500 MHz, CDCl3) δ 7.38 (br s, 1H), 7.16 (d, J=7.7 Hz, 1H), 6.90 (dd, J=7.8, 1.5 Hz, 1H), 6.81 (d, J=1.5 Hz, 1H), 4.04-3.88 (m, 2H), 3.81 (s, 3H), 3.62 (br s, 1H), 3.54-3.44 (m, 2H), 2.86-2.78 (m, 1H), 2.852 (s, 2H), 2.845 (s, 3H), 2.17-2.10 (m, 2H), 2.03-1.92 (m, 4H), 1.46 (td, J=14.2, 4.4 Hz, 2H), 1.35 (t, J=6.7 Hz, 3H), 1.13 (s, 6H). MS (ESI) m/z: [M+H]+ Found 594.3.

Example 46

4-Chloro-5-(2-(difluoromethoxy)-4-(3,3,3-trifluoro-2,2-dimethylpropyl)phenyl)-N-(((1R*,2R*,4R*)-1,2-dihydroxy-4-(methylsulfonyl)cyclohexyl)methyl)-1-ethyl-1H-pyrazole-3-carboxamide

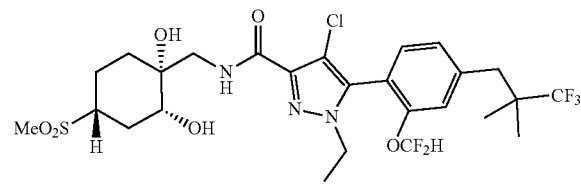

Example 47

4-Chloro-5-(2-(difluoromethoxy)-4-(3,3,3-trifluoro-2,2-dimethylpropyl)phenyl)-N-(((1S*,2S*,4S*)-1,2-dihydroxy-4-(methylsulfonyl)cyclohexyl)methyl)-1-ethyl-1H-pyrazole-3-carboxamide

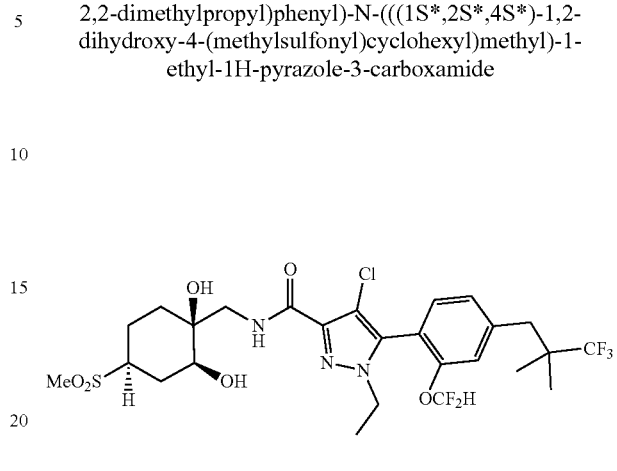

Intermediate 246 was purified by SFC using a chiral stationary phase (Chiralpak AD-H, 80% CO2, 20% i-PrOH) to give a pair of enantiomers. The first-eluting enantiomer was Example 46, and the second-eluting enantiomer was Example 47. Example 46: 1H NMR (500 MHz, CDCl3) δ 7.29 (dd, J=7.8, 1.4 Hz, 1H), 7.26 (t, 1H), 7.20 (dt, J=7.9, 1.6 Hz, 1H), 7.15 (s, 1H), 6.57-6.22 (m, 1H), 4.55 (dd, J=12.1, 5.3 Hz, 1H), 4.06-3.92 (m, 2H), 3.89 (ddd, J=14.2, 8.1, 3.7 Hz, 1H), 3.60 (tt, J=12.3, 5.0 Hz, 1H), 3.07 (dt, J=14.2, 6.1 Hz, 1H), 2.90-2.78 (m, 7H), 2.30-2.24 (m, 1H), 2.11-2.04 (m, 1H), 2.02-1.86 (m, 3H), 1.61-1.50 (m, 1H), 1.38 (appr td, J=7.3, 2.5 Hz, 3H), 1.14 (s, 6H). MS (ESI) m/z: [M+H]+ Found 645.9. Example 47: 1H NMR (500 MHz, CDCl3) δ 7.29 (dd, J=7.8, 1.4 Hz, 1H), 7.26 (t, 1H), 7.20 (dt, J=7.9, 1.6 Hz, 1H), 7.15 (s, 1H), 6.57-6.22 (m, 1H), 4.55 (dd, J=12.1, 5.3 Hz, 1H), 4.06-3.92 (m, 2H), 3.89 (ddd, J=14.2, 8.1, 3.7 Hz, 1H), 3.60 (tt, J=12.3, 5.0 Hz, 1H), 3.07 (dt, J=14.2, 6.1 Hz, 1H), 2.90-2.78 (m, 7H), 2.30-2.24 (m, 1H), 2.11-2.04 (m, 1H), 2.02-1.86 (m, 3H), 1.61-1.50 (m, 1H), 1.38 (appr td, J=7.3, 2.5 Hz, 3H), 1.14 (s, 6H). MS (ESI) m/z: [M+H]+ Found 645.9.

Example 48

4-Chloro-5-(2-(difluoromethoxy)-4-(3,3,3-trifluoro-2,2-dimethylpropyl)phenyl)-N-(((1R*,2R*4S*)-1,2-dihydroxy-4-(methylsulfonyl)cyclohexyl)methyl)-1-ethyl-1H-pyrazole-3-carboxamide

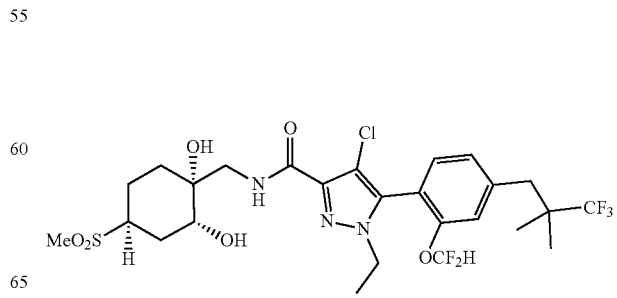

Example 49

4-Chloro-5-(2-(difluoromethoxy)-4-(3,3,3-trifluoro-2,2-dimethylpropyl)phenyl)-N-(((1S*,2S*,4R*)-1,2-dihydroxy-4-(methylsulfonyl)cyclohexyl)methyl)-1-ethyl-1H-pyrazole-3-carboxamide

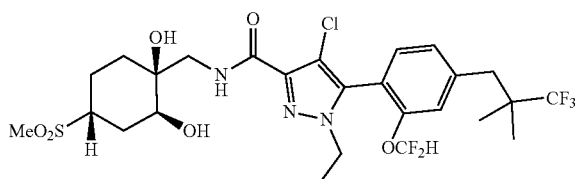

Intermediate 247 was purified by SFC using a chiral stationary phase (Lux cellulose 2, 70% $CO_2$, 70% EtOH) to give a pair of enantiomers. The first-eluting enantiomer was Example 48, and the second-eluting enantiomer was Example 49. Example 48: $^1$H NMR (500 MHz, CDCl$_3$) δ 7.33-7.24 (m, 2H), 7.22-7.17 (m, 1H), 7.15 (d, J=7.2 Hz, 1H), 6.56-6.22 (m, 1H), 4.28 (s, 1H of one rotamer), 4.14 (s, 1H of one rotamer), 4.07-3.90 (m, 3H), 3.74-3.66 (m, 1H), 3.52-3.29 (m, 3H), 2.89 (d, J=14.1 Hz, 5H), 2.33-2.25 (m, 1H), 2.23-2.16 (m, 1H), 2.12-2.02 (m, 1H), 1.99-1.78 (m, 3H), 1.38 (t, J=7.3 Hz, 3H), 1.13 (s, 6H). MS (ESI) m/z: [M+H]$^+$ Found 645.8. Example 49: $^1$H NMR (500 MHz, CDCl$_3$) δ 7.33-7.24 (m, 2H), 7.22-7.17 (m, 1H), 7.15 (d, J=7.2 Hz, 1H), 6.56-6.22 (m, 1H), 4.28 (s, 1H of one rotamer), 4.14 (s, 1H of one rotamer), 4.07-3.90 (m, 3H), 3.74-3.66 (m, 1H), 3.52-3.29 (m, 3H), 2.89 (d, J=14.1 Hz, 5H), 2.33-2.25 (m, 1H), 2.23-2.16 (m, 1H), 2.12-2.02 (m, 1H), 1.99-1.78 (m, 3H), 1.38 (t, J=7.3 Hz, 3H), 1.13 (s, 6H). MS (ESI) m/z: [M+H]$^+$ Found 645.9.

Example 50

4-Chloro-5-(2-(difluoromethoxy)-4-(3,3,3-trifluoro-2,2-dimethylpropyl)phenyl)-1-ethyl-N-(((1r,4r)-4-(N-methylsulfamoyl)cyclohexyl)methyl)-1H-pyrazole-3-carboxamide

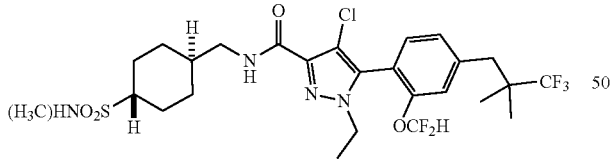

The title compound was prepared as described for the synthesis of Example 1, using ethyl 4-chloro-5-(2-(difluoromethoxy)-4-(3,3,3-trifluoro-2,2-dimethylpropyl)phenyl)-1-ethyl-1H-pyrazole-3-carboxylate (Intermediate 103) and (1 r,4r)-4-(aminomethyl)-N-methylcyclohexane-1-sulfonamide hydrochloride (Intermediate 58) in place of ethyl (R*)-4-chloro-1-ethyl-5-(2-methoxy-4-(3,3,3-trifluoro-2-methylpropyl)phenyl)-1H-pyrazole-3-carboxylate and ((1r,4r)-4-(methylsulfonyl)cyclohexyl)methanamine hydrochloride. $^1$H NMR (500 MHz, CDCl$_3$) δ 7.29 (d, J=7.8 Hz, 1H), 7.18 (dd, J=7.9, 1.6 Hz, 1H), 7.14 (s, 1H), 6.96 (t, J=6.4 Hz, 1H), 6.37 (dd, J=75.2, 70.9 Hz, 1H), 4.05-3.89 (m, 3H), 3.39-3.27 (m, 2H), 2.95-2.88 (m, 1H), 2.87 (s, 2H), 2.83 (s, 3H of one rotamer), 2.82 (s, 3H of one rotamer), 2.28-2.20 (m, 2H), 2.07-2.00 (m, 2H), 1.77-1.55 (m, 3H), 1.36 (t, J=7.3 Hz, 3H), 1.18-1.07 (m, 2H), 1.13 (s, 6H). MS (ESI) m/z: [M+H]$^+$ Found 628.8.

Example 51

4-Chloro-5-(2-(difluoromethoxy)-4-(3,3,3-trifluoro-2,2-dimethylpropyl)phenyl)-1-ethyl-N-(((1r,4r)-4-sulfamoylcyclohexyl)methyl)-1H-pyrazole-3-carboxamide

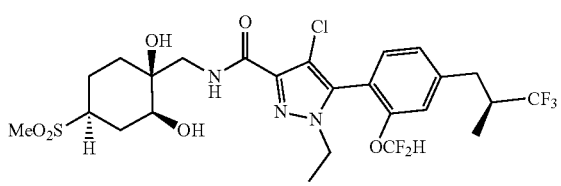

The title compound was prepared as described for the synthesis of Example 1, using ethyl 4-chloro-5-(2-(difluoromethoxy)-4-(3,3,3-trifluoro-2,2-dimethylpropyl)phenyl)-1-ethyl-1H-pyrazole-3-carboxylate (Intermediate 103) and (1r,4r)-4-(aminomethyl)cyclohexane-1-sulfonamide hydrochloride (Intermediate 62) in place of ethyl (R*)-4-chloro-1-ethyl-5-(2-methoxy-4-(3,3,3-trifluoro-2-methylpropyl)phenyl)-1H-pyrazole-3-carboxylate and ((1r,4r)-4-(methylsulfonyl)cyclohexyl)methanamine hydrochloride. $^1$H NMR (500 MHz, CDCl$_3$) δ 7.29 (d, J=7.8 Hz, 1H), 7.18 (dd, J=7.8, 1.6 Hz, 1H), 7.14 (s, 1H), 6.95 (t, J=6.4 Hz, 1H), 6.37 (dd, J=75.2, 70.8 Hz, 1H), 4.36 (s, 2H), 4.05-3.90 (m, 2H), 3.38-3.30 (m, 2H), 2.93 (tt, J=12.3, 3.5 Hz, 1H), 2.87 (s, 2H), 2.36-2.30 (m, 2H), 2.08-2.02 (m, 2H), 1.74-1.52 (m, 3H), 1.36 (t, J=7.2 Hz, 3H), 1.19-1.09 (m, 8H). MS (ESI) m/z: [M+H]$^+$ Found 615.3.

Example 52

4-Chloro-5-(2-(difluoromethoxy)-4-((S*)-3,3,3-trifluoro-2-methylpropyl)phenyl)-N-(((1S*,2S*,4S*)-1,2-dihydroxy-4-(methylsulfonyl)cyclohexyl)methyl)-1-ethyl-1H-pyrazole-3-carboxamide

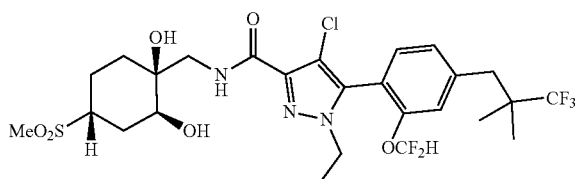

The title compound was prepared as described for the synthesis of Example 1, using ethyl (S*)-4-chloro-5-(2-(difluoromethoxy)-4-(3,3,3-trifluoro-2-methylpropyl)phenyl)-1-ethyl-1H-pyrazole-3-carboxylate (Intermediate 104) and (1S*,2S*,4S*)-1-(aminomethyl)-4-(methylsulfonyl)cyclohexane-1,2-diol hydrochloride (Intermediate 25) in place of ethyl (R*)-4-chloro-1-ethyl-5-(2-methoxy-4-(3,3,3-trifluoro-2-methylpropyl)phenyl)-1H-pyrazole-3-carboxylate and ((1r,4r)-4-(methylsulfonyl)cyclohexyl)methanamine hydrochloride. $^1$H NMR (500 MHz, CDCl$_3$) δ 7.37-7.30 (m, 2H), 7.23 (dd, J=7.8, 1.6 Hz, 1H), 7.17 (s, 1H), 6.60-6.27 (m, 1H), 4.22 (br s, 2H), 4.08-3.93 (m, 2H), 3.93-3.87 (m, 1H), 3.65 (td, J=11.6, 4.7 Hz, 1H), 3.22-3.11 (m, 2H), 2.94-2.82 (m, 4H), 2.63 (dd, J=13.6, 10.1 Hz, 1H), 2.59-2.47 (m, 1H), 2.33-2.27 (m, 1H), 2.11-2.04 (m, 1H), 2.04-1.90 (m, 3H), 1.62-1.51 (m, 1H), 1.39 (appar td, J=7.3, 2.7 Hz, 3H), 1.14 (appar dd, J=6.8, 1.7 Hz, 3H). MS (ESI) m/z: [M+H]$^+$ Found 632.2.

Example 53

4-Chloro-5-(2-(difluoromethoxy)-4-((S*)-3,3,3-trifluoro-2-methylpropyl)phenyl)-N-(((1R*,2R*,4R*)-1,2-dihydroxy-4-(methylsulfonyl)cyclohexyl)methyl)-1-ethyl-1H-pyrazole-3-carboxamide

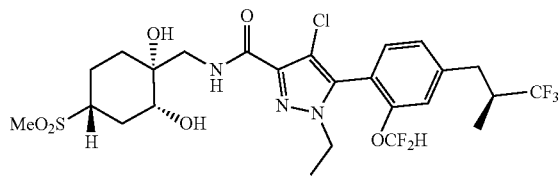

The title compound was prepared as described for the synthesis of Example 1, using ethyl (S*)-4-chloro-5-(2-(difluoromethoxy)-4-(3,3,3-trifluoro-2-methylpropyl)phenyl)-1-ethyl-1H-pyrazole-3-carboxylate (Intermediate 104) and (1R*,2R*,4R*)-1-(Aminomethyl)-4-(methylsulfonyl)cyclohexane-1,2-diol hydrochloride (Intermediate 24) in place of ethyl (R*)-4-chloro-1-ethyl-5-(2-methoxy-4-(3,3,3-trifluoro-2-methylpropyl)phenyl)-1H-pyrazole-3-carboxylate and ((1r,4r)-4-(methylsulfonyl)cyclohexyl)methanamine hydrochloride. $^1$H NMR (500 MHz, CDCl$_3$) δ 7.37-7.33 (m, 1H), 7.32 (d, J=7.8 Hz, 1H), 7.25-7.21 (m, 1H), 7.17 (s, 1H), 6.60-6.27 (m, 1H), 4.50 (br s, 2H), 4.08-3.94 (m, 2H), 3.94-3.87 (m, 1H), 3.66 (td, J=11.6, 4.7 Hz, 1H), 3.21-3.12 (m, 2H), 2.94-2.83 (m, 4H), 2.63 (dd, J=13.6, 10.1 Hz, 1H), 2.58-2.47 (m, 1H), 2.33-2.27 (m, 1H), 2.11-2.05 (m, 1H), 2.04-1.91 (m, 3H), 1.62-1.52 (m, 1H), 1.39 (td, J=7.3, 1.9 Hz, 3H), 1.14 (dd, J=6.8, 2.7 Hz, 3H). MS (ESI) m/z: [M+H]$^+$ Found 632.0.

Example 54

4-Chloro-5-(2-(difluoromethoxy)-4-((S*)-3,3,3-trifluoro-2-methylpropyl)phenyl)-1-ethyl-N-(((1r,4S)-4-sulfamoylcyclohexyl)methyl)-1H-pyrazole-3-carboxamide

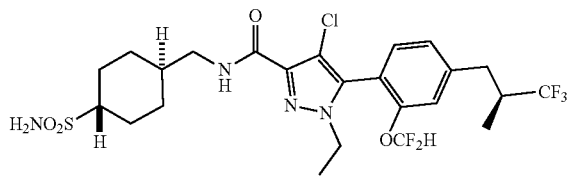

The title compound was prepared as described for the synthesis of Example 1, using ethyl (S*)-4-chloro-5-(2-(difluoromethoxy)-4-(3,3,3-trifluoro-2-methylpropyl)phenyl)-1-ethyl-1H-pyrazole-3-carboxylate (Intermediate 104) and (1r,4r)-4-(aminomethyl)cyclohexane-1-sulfonamide hydrochloride (Intermediate 62) in place of ethyl (R*)-4-chloro-1-ethyl-5-(2-methoxy-4-(3,3,3-trifluoro-2-methylpropyl)phenyl)-1H-pyrazole-3-carboxylate and ((1r,4r)-4-(methylsulfonyl)cyclohexyl)methanamine hydrochloride. $^1$H NMR (500 MHz, CDCl$_3$) δ 7.30 (dd, J=8.0, 1.2 Hz, 1H), 7.20 (d, J=7.9 Hz, 1H), 7.14 (s, 1H), 6.96 (t, J=6.3 Hz, 1H), 6.39 (dd, J=75.2, 70.8 Hz, 1H), 4.47 (s, 2H), 4.05-3.88 (m, 2H), 3.34 (t, J=6.6 Hz, 2H), 3.16 (dd, J=13.4, 3.8 Hz, 1H), 2.93 (tt, J=12.3, 3.6 Hz, 1H), 2.60 (dd, J=13.4, 10.1 Hz, 1H), 2.55-2.43 (m, 1H), 2.37-2.28 (m, 2H), 2.09-2.00 (m, 2H), 1.75-1.52 (m, 3H), 1.36 (t, J=7.2 Hz, 3H), 1.20-1.06 (m, 5H). MS (ESI) m/z: [M+H]$^+$ Found 601.2.

Example 55

4-Chloro-5-(2-(difluoromethoxy)-4-((S*)-3,3,3-trifluoro-2-methylpropyl)phenyl)-1-ethyl-N-(((1r,4S)-4-(methylsulfonyl)cyclohexyl)methyl)-1H-pyrazole-3-carboxamide

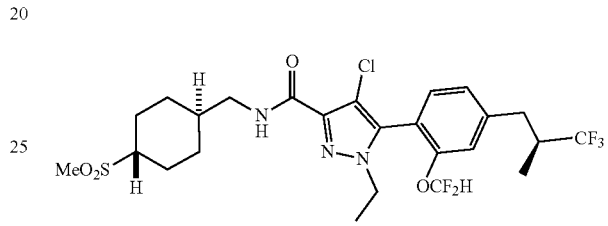

The title compound was prepared as described for the synthesis of Example 1, using ethyl (S*)-4-chloro-5-(2-(difluoromethoxy)-4-(3,3,3-trifluoro-2-methylpropyl)phenyl)-1-ethyl-1H-pyrazole-3-carboxylate (Intermediate 104) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (500 MHz, CDCl$_3$) δ 7.32 (dd, J=7.8, 2.0 Hz, 1H), 7.22 (dt, J=7.9, 1.8 Hz, 1H), 7.16 (s, 1H), 7.07 (t, J=6.2 Hz, 1H), 6.41 (dd, J=75.0, 70.8 Hz, 1H), 4.07-3.91 (m, 2H), 3.42-3.33 (m, 2H), 3.18 (dd, J=13.6, 4.0 Hz, 1H), 2.90-2.82 (m, 1H), 2.85 (s, 3H), 2.62 (dd, J=13.6, 10.2 Hz, 1H), 2.58-2.48 (m, 1H), 2.34-2.27 (m, 2H), 2.12-2.06 (m, 2H), 1.76-1.67 (m, 1H), 1.62 (qd, J=13.0, 3.7 Hz, 2H), 1.38 (t, J=7.2 Hz, 3H), 1.21-1.11 (m, 5H). MS (ESI) m/z: [M+H]$^+$ Found 600.1.

Example 56

4-Chloro-5-(2-(difluoromethoxy)-4-((S*)-3,3,3-trifluoro-2-methylpropyl)phenyl)-1-ethyl-N-(((1s,4R)-1-hydroxy-4-(methylsulfonyl)cyclohexyl)methyl)-1H-pyrazole-3-carboxamide

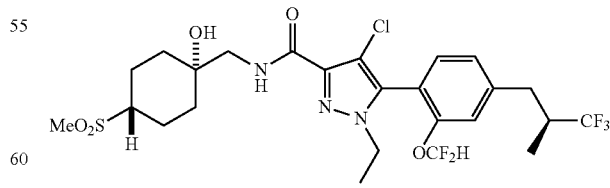

The title compound was prepared as described for the synthesis of Example 1, using ethyl (S*)-4-chloro-5-(2-(difluoromethoxy)-4-(3,3,3-trifluoro-2-methylpropyl)phenyl)-1-ethyl-1H-pyrazole-3-carboxylate (Intermediate 104) and (1s,4s)-1-(aminomethyl)-4-(methyl sulfonyl)cyclohexan-1-ol hydrochloride (Intermediate 9) in place of ethyl (R*)-4-chloro-1-ethyl-5-(2-methoxy-4-(3,3,3-trifluoro-2-methylpropyl)phenyl)-1H-pyrazole-3-carboxylate and ((1r,4r)-4-(methylsulfonyl)cyclohexyl)methanamine hydrochloride. ¹H NMR (500 MHz, CDCl₃) δ 7.36 (t, J=6.3 Hz, 1H), 7.31 (dd, J=7.8, 1.9 Hz, 1H), 7.22 (dt, J=7.9, 1.8 Hz, 1H), 7.17 (s, 1H), 6.42 (dd, J=74.9, 70.8 Hz, 1H), 4.50 (s, 1H), 4.07-3.92 (m, 2H), 3.51 (d, J=6.3 Hz, 2H), 3.18 (dd, J=13.6, 4.0 Hz, 1H), 2.88-2.80 (m, 1H), 2.86 (s, 3H), 2.62 (dd, J=13.6, 10.2 Hz, 1H), 2.58-2.47 (m, 1H), 2.18-2.11 (m, 2H), 2.04-1.94 (m, 4H), 1.48 (td, J=14.1, 4.5 Hz, 2H), 1.38 (t, J=7.2 Hz, 3H), 1.13 (dd, J=6.9, 2.2 Hz, 3H). MS (ESI) m/z: [M+H]⁺ Found 616.2.

Example 57

5-(2-(Difluoromethoxy)-4-((S*)-3,3,3-trifluoro-2-methylpropyl)phenyl)-N-(((1S*,2S*,4S*)-1,2-dihydroxy-4-(methylsulfonyl)cyclohexyl)methyl)-1-ethyl-4-methyl-1H-pyrazole-3-carboxamide

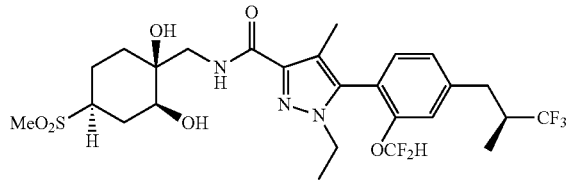

The title compound was prepared as described for the synthesis of Example 1, using ethyl (S*)-5-(2-(difluoromethoxy)-4-(3,3,3-trifluoro-2-methylpropyl)phenyl)-1-ethyl-4-methyl-1H-pyrazole-3-carboxylate (Intermediate 105) and (1S*,2S*,4S*)-1-(aminomethyl)-4-(methyl sulfonyl)cyclohexane-1,2-diol hydrochloride (Intermediate 25) in place of ethyl (R*)-4-chloro-1-ethyl-5-(2-methoxy-4-(3,3,3-trifluoro-2-methylpropyl)phenyl)-1H-pyrazole-3-carboxylate and ((1r,4r)-4-(methyl sulfonyl)cyclohexyl)methanamine hydrochloride. ¹H NMR (500 MHz, CDCl₃) δ 7.47-7.41 (m, 1H), 7.23 (dd, J=7.8, 1.7 Hz, 1H), 7.20 (d, J=7.9 Hz, 1H), 7.16 (d, J=3.2 Hz, 1H), 6.56-6.22 (m, 1H), 4.25 (br s, 2H), 4.03-3.83 (m, 3H), 3.64 (ddd, J=15.5, 11.5, 4.6 Hz, 1H), 3.21-3.10 (m, 2H), 2.94-2.82 (m, 4H), 2.62 (dd, J=13.6, 10.1 Hz, 1H), 2.58-2.47 (m, 1H), 2.34-2.27 (m, 1H), 2.14 (s, 3H), 2.11-2.05 (m, 1H), 2.04-1.91 (m, 3H), 1.58 (qd, J=14.5, 14.0, 4.7 Hz, 1H), 1.35 (td, J=7.2, 3.1 Hz, 3H), 1.14 (d, J=6.8 Hz, 3H). MS (ESI) m/z: [M+H]⁺ Found 612.3.

Example 58

5-(2-(difluoromethoxy)-4-((S*)-3,3,3-trifluoro-2-methylpropyl)phenyl)-N-(((1R*,2R*,4R*)-1,2-dihydroxy-4-(methylsulfonyl)cyclohexyl)methyl)-1-ethyl-4-methyl-1H-pyrazole-3-carboxamide The title compound was prepared as described for the synthesis of Example 1, using ethyl (S*)-5-(2-(difluoromethoxy)-4-(3,3,3-trifluoro-2-methylpropyl)phenyl)-1-ethyl-4-methyl-1H-pyrazole-3-carboxylate (Intermediate 105) and (1S*,2S*,4S*)-1-(aminomethyl)-4-(methyl sulfonyl)cyclohexane-1,2-diol hydrochloride (Intermediate 25) in place of ethyl (R*)-4-chloro-1-ethyl-5-(2-methoxy-4-(3,3,3-trifluoro-2-methylpropyl)phenyl)-1H-pyrazole-3-carboxylate and ((1r,4r)-4-(methyl sulfonyl)cyclohexyl)methanamine hydrochloride. ¹H NMR (400 MHz, CDCl₃) δ 7.33-7.26 (m, 1H), 7.14 (d, J=7.8 Hz, 1H), 7.12-7.08 (m, 1H), 7.06 (s, 1H), 6.50-6.08 (m, 1H), 3.94-3.73 (m, 3H), 3.53 (td, J=11.8, 4.6 Hz, 1H), 3.08 (dd, J=13.4, 4.0 Hz, 1H), 3.04 (br s, 2H), 3.04-2.98 (m, 1H), 2.84-2.70 (m, 4H), 2.52 (dd, J=13.4, 10.1 Hz, 1H), 2.48-2.36 (m, 1H), 2.24-2.16 (m, 1H), 2.05 (s, 3H), 2.03-1.94 (m, 1H), 1.94-1.79 (m, 3H), 1.54-1.42 (m, 1H), 1.26 (appar td, J=7.3, 1.9 Hz, 3H), 1.04 (appar dd, J=6.7, 1.1 Hz, 3H). MS (ESI) m/z: [M+H]⁺ Found 612.3.

Example 59

5-(2-(difluoromethoxy)-4-((S*)-3,3,3-trifluoro-2-methylpropyl)phenyl)-1-ethyl-4-methyl-N-(((1r,4S)-4-sulfamoylcyclohexyl)methyl)-1H-pyrazole-3-carboxamide

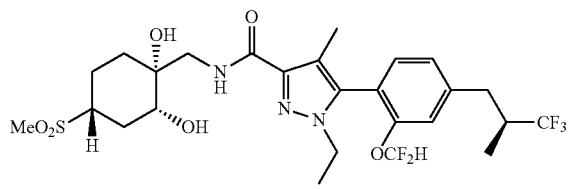

The title compound was prepared as described for the synthesis of Example 1, using ethyl (S*)-5-(2-(difluoromethoxy)-4-(3,3,3-trifluoro-2-methylpropyl)phenyl)-1-ethyl-4-methyl-1H-pyrazole-3-carboxylate (Intermediate 105) and (1r,4r)-4-(aminomethyl)cyclohexane-1-sulfonamide hydrochloride (Intermediate 62) in place of ethyl (R*)-4-chloro-1-ethyl-5-(2-methoxy-4-(3,3,3-trifluoro-2-methylpropyl)phenyl)-1H-pyrazole-3-carboxylate and ((1r,4r)-4-(methylsulfonyl)cyclohexyl)methanamine hydrochloride. ¹H NMR (400 MHz, CDCl₃) δ 7.14 (d, J=7.7 Hz, 1H), 7.08 (d, J=8.2 Hz, 1H), 7.06-6.99 (m, 2H), 6.26 (dd, J=74.4, 71.8 Hz, 1H), 4.30 (s, 2H), 3.93-3.75 (m, 2H), 3.24 (t, J=6.6 Hz, 2H), 3.08 (dd, J=13.4, 3.7 Hz, 1H), 2.86 (tt, J=12.3, 3.4 Hz, 1H), 2.51 (dd, J=13.4, 10.2 Hz, 1H), 2.47-2.36 (m, 1H), 2.29-2.21 (m, 2H), 2.06 (s, 3H), 2.02-1.94 (m, 2H), 1.66-1.45 (m, 3H), 1.25 (t, J=7.2 Hz, 3H), 1.12-0.99 (m, 5H). MS (ESI) m/z: [M+H]⁺ Found 581.2.

Example 60

4-Chloro-5-(2-(difluoromethoxy)-4-((S*)-3,3,3-trifluoro-2-methylpropyl)phenyl)-1-ethyl-N-(((1s,4R)-1-hydroxy-4-sulfamoylcyclohexyl)methyl)-1H-pyrazole-3-carboxamide

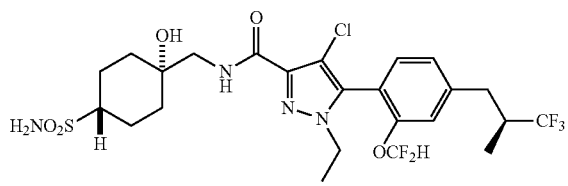

The title compound was prepared as described for the synthesis of Example 1, using ethyl (S*)-4-chloro-5-(2-(difluoromethoxy)-4-(3,3,3-trifluoro-2-methylpropyl)phenyl)-1-ethyl-1H-pyrazole-3-carboxylate (Intermediate 104) and (1s,4s)-4-(aminomethyl)-4-hydroxycyclohexane-1-sulfonamide hydrochloride (Intermediate 46) in place of ethyl (R*)-4-chloro-1-ethyl-5-(2-methoxy-4-(3,3,3-trifluoro-2-methylpropyl)phenyl)-1H-pyrazole-3-carboxylate and ((1r,4r)-4-(methylsulfonyl)cyclohexyl)methanamine hydrochloride. $^1$H NMR (500 MHz, CDCl$_3$) δ 7.35 (t, J=6.3 Hz, 1H), 7.30 (dd, J=7.8, 1.9 Hz, 1H), 7.20 (dt, J=7.9, 1.7 Hz, 1H), 7.15 (s, 1H), 6.41 (dd, J=74.9, 70.9 Hz, 1H), 4.71 (s, 2H), 4.05-3.90 (m, 2H), 3.48 (d, J=6.3 Hz, 2H), 3.17 (dd, J=13.6, 4.0 Hz, 1H), 3.05 (br s, 1H), 2.95 (tt, J=12.4, 3.6 Hz, 1H), 2.60 (dd, J=13.6, 10.2 Hz, 1H), 2.56-2.46 (m, 1H), 2.18-2.11 (m, 2H), 2.03-1.92 (m, 4H), 1.46 (td, J=14.2, 4.3 Hz, 2H), 1.36 (t, J=7.2 Hz, 3H), 1.12 (dd, J=6.9, 2.1 Hz, 3H). MS (ESI) m/z: [M+H]$^+$ Found 617.2.

Example 61

5-(2-(difluoromethoxy)-4-((S*)-3,3,3-trifluoro-2-methylpropyl)phenyl)-1-ethyl-N-(((1s,4R)-1-hydroxy-4-sulfamoylcyclohexyl)methyl)-4-methyl-1H-pyrazole-3-carboxamide

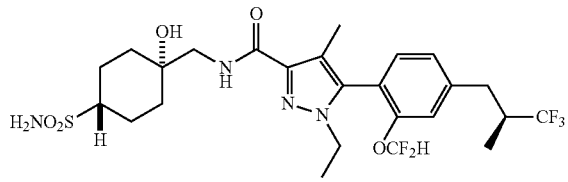

The title compound was prepared as described for the synthesis of Example 1, using ethyl (S*)-5-(2-(difluoromethoxy)-4-(3,3,3-trifluoro-2-methylpropyl)phenyl)-1-ethyl-4-methyl-1H-pyrazole-3-carboxylate (Intermediate 105) and (1s,4s)-4-(aminomethyl)-4-hydroxycyclohexane-1-sulfonamide hydrochloride (Intermediate 46) in place of ethyl (R*)-4-chloro-1-ethyl-5-(2-methoxy-4-(3,3,3-trifluoro-2-methylpropyl)phenyl)-1H-pyrazole-3-carboxylate and ((1r,4r)-4-(methylsulfonyl)cyclohexyl)methanamine hydrochloride. $^1$H NMR (500 MHz, CDCl$_3$) δ 7.40 (t, J=6.3 Hz, 1H), 7.21 (d, J=7.7 Hz, 1H), 7.17 (d, J=7.9 Hz, 1H), 7.14 (s, 1H), 6.35 (dd, J=74.1, 71.8 Hz, 1H), 4.57 (s, 2H), 4.00-3.85 (m, 2H), 3.45 (d, J=6.3 Hz, 2H), 3.16 (dd, J=13.5, 3.9 Hz, 1H), 2.95 (tt, J=12.2, 3.5 Hz, 1H), 2.58 (d, J=13.5 Hz, 1H), 2.52 (br s, 2H), 2.18-2.11 (m, 2H), 2.13 (s, 3H), 2.04-1.93 (m, 4H), 1.43 (td, J=13.9, 4.1 Hz, 2H), 1.33 (t, J=7.2 Hz, 3H), 1.11 (d, J=6.5 Hz, 3H). MS (ESI) m/z: [M+H]$^+$ Found 597.3.

Example 62

4-Chloro-5-(2-(difluoromethoxy)-4-(3,3,3-trifluoro-2,2-dimethylpropyl)phenyl)-1-ethyl-N-(((1s,4s)-1-hydroxy-4-sulfamoylcyclohexyl)methyl)-1H-pyrazole-3-carboxamide

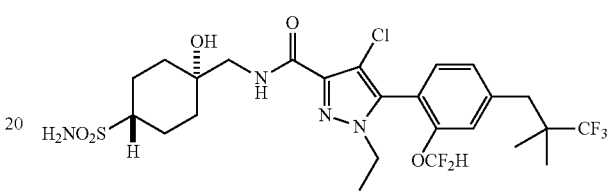

The title compound was prepared as described for the synthesis of Example 1, using ethyl 4-chloro-5-(2-(difluoromethoxy)-4-(3,3,3-trifluoro-2,2-dimethylpropyl)phenyl)-1-ethyl-1H-pyrazole-3-carboxylate (Intermediate 103) and (1 s,4s)-4-(aminomethyl)-4-hydroxycyclohexane-1-sulfonamide hydrochloride (Intermediate 46) in place of ethyl (R*)-4-chloro-1-ethyl-5-(2-methoxy-4-(3,3,3-trifluoro-2-methylpropyl)phenyl)-1H-pyrazole-3-carboxylate and ((1r,4r)-4-(methylsulfonyl)cyclohexyl)methanamine hydrochloride. $^1$H NMR (500 MHz, CDCl$_3$) δ 7.33 (t, J=6.3 Hz, 1H), 7.28 (d, J=7.8 Hz, 1H), 7.19 (dd, J=7.9, 1.6 Hz, 1H), 7.15 (s, 1H), 6.39 (dd, J=74.9, 70.9 Hz, 1H), 4.57 (s, 2H), 4.06-3.91 (m, 2H), 3.49 (d, J=6.3 Hz, 2H), 2.99-2.91 (m, 1H), 2.87 (s, 2H), 2.80 (br s, 1H), 2.20-2.11 (m, 2H), 2.04-1.91 (m, 4H), 1.46 (td, J=14.3, 4.4 Hz, 2H), 1.37 (t, J=7.2 Hz, 3H), 1.13 (s, 6H). MS (ESI) m/z: [M+H]$^+$ Found 631.2.

Example 63

N-(((2S*,5R*)-1-(2-(Aminooxy)-2-oxoethyl)-5-(methylsulfonyl)piperidin-2-yl)methyl)-4-chloro-5-(2-(difluoromethoxy)-4-(3,3,3-trifluoro-2,2-dimethylpropyl)phenyl)-1-ethyl-1H-pyrazole-3-carboxamide Trifluoroacetic Acid Salt

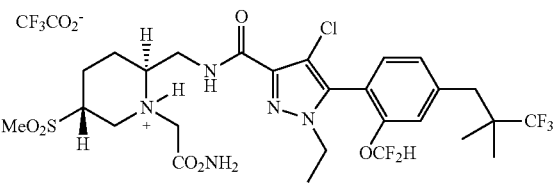

Potassium carbonate (6 mg, 0.04 mmol) and KI (4 mg, 0.02 mmol) were added to a solution of 4-chloro-5-(2-(difluoromethoxy)-4-(3,3,3-trifluoro-2,2-dimethylpropyl)phenyl)-1-ethyl-N-(((2S*, 5R*)-5-(methylsulfonyl)piperidin-2-yl)methyl)-1H-pyrazole-3-carboxamide hydrobromide (15 mg, 0.022 mmol, Example 10) and 2-bromoacetamide (3.3 mg, 0.024 mmol) in MeCN (0.2 mL), and the reaction mixture was stirred at 50° C. for 14 h. After this time, additional 2-bromoacetamide (1.5 mg, 0.011 mmol) and K$_2$CO$_3$ (3 mg, 0.02 mmol) were added, and stirring was continued at 50° C. for another 24 h. After this time, the reaction mixture was allowed to cool, diluted with MeCN, filtered, and then purified by preparative HPLC (XBridge C18, 30→100% MeCN/water, 0.05% TFA) to afford the title compound as a colorless solid. $^1$H NMR (400 MHz, DMSO-d$_6$) δ 8.36 (br s, 1H), 7.87 (br s, 1H), 7.64 (br s, 1H), 7.41-7.02 (m, 4H), 4.17 (br s, 1H), 3.98-3.82 (m, 2H), 3.81-3.07 (m, 8H), 2.98 (s, 3H), 2.84 (s, 2H), 2.18-2.09 (m, 1H), 2.05-1.95 (m, 1H), 1.75-1.54 (m, 2H), 1.21 (t, J=7.2 Hz, 3H), 1.02 (s, 6H). MS (ESI) m/z: [M+H]$^+$ Found 672.3.

Example 64

N-(((2R*,5S*)-1-(2-(Aminooxy)-2-oxoethyl)-5-(methylsulfonyl)piperidin-2-yl)methyl)-4-chloro-5-(2-(difluoromethoxy)-4-(3,3,3-trifluoro-2,2-dimethylpropyl)phenyl)-1-ethyl-1H-pyrazole-3-carboxamide Trifluoroacetic Acid Salt

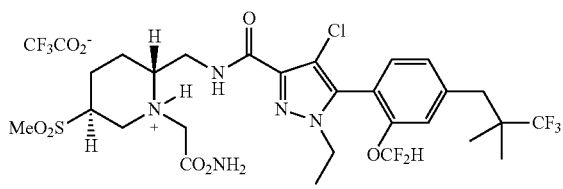

The title compound was prepared as described for the synthesis of Example 63, using 4-chloro-5-(2-(difluoromethoxy)-4-(3,3,3-trifluoro-2,2-dimethylpropyl)phenyl)-1-ethyl-N-(((2R*,5S*)-5-(methylsulfonyl)piperidin-2-yl)methyl)-1H-pyrazole-3-carboxamide hydrobromide (Example 9) in place of 4-chloro-5-(2-(difluoromethoxy)-4-(3,3,3-trifluoro-2,2-dimethylpropyl)phenyl)-1-ethyl-N-(((2S*,5R*)-5-(methylsulfonyl)piperidin-2-yl)methyl)-1H-pyrazole-3-carboxamide hydrobromide. $^1$H NMR (400 MHz, DMSO-d$_6$) δ 8.36 (br s, 1H), 7.87 (br s, 1H), 7.64 (br s, 1H), 7.41-7.02 (m, 4H), 4.17 (br s, 1H), 3.98-3.82 (m, 2H), 3.81-3.07 (m, 8H), 2.98 (s, 3H), 2.84 (s, 2H), 2.18-2.09 (m, 1H), 2.05-1.95 (m, 1H), 1.75-1.54 (m, 2H), 1.21 (t, J=7.2 Hz, 3H), 1.02 (s, 6H). MS (ESI) m/z: [M+H]$^+$ Found 672.3.

Example 65

N-(((2S*,5R*)-1-Acetyl-5-(methylsulfonyl)piperidin-2-yl)methyl)-4-chloro-5-(2-(difluoromethoxy)-4-(3,3,3-trifluoro-2,2-dimethylpropyl)phenyl)-1-ethyl-1H-pyrazole-3-carboxamide

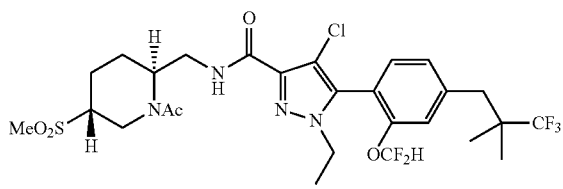

Acetic anhydride (3.5 μL, 0.037 mmol) was added to a solution of 4-chloro-5-(2-(difluoromethoxy)-4-(3,3,3-trifluoro-2,2-dimethylpropyl)phenyl)-1-ethyl-N-(((2S*, 5R*)-5-(methylsulfonyl)piperidin-2-yl)methyl)-1H-pyrazole-3-carboxamide hydrobromide (13 mg, 0.019 mmol, Example 10) and DIPEA (8.0 μL, 0.047 mmol) in THF (0.2 mL), and the resulting solution was stirred at rt for 2 h. After this time, the resulting mixture was concentrated with a stream of nitrogen and then purified by silica gel chromatography (50-100% acetone/hexanes) to afford the title compound as a colorless solid. $^1$H NMR (500 MHz, CDCl$_3$, two rotamers) δ 7.29 (d, J=7.8 Hz, 1H of both rotamers), 7.22 (s, 1H one rotamer), 7.18 (d, J=7.8 Hz, 1H of both rotamers), 7.15-7.13 (m, 1H of both rotamers), 7.04-6.96 (m, 1H of one rotamer), 6.54-6.22 (m, 1H of both rotamers), 5.33-5.19 (m, 1H of one rotamer), 4.88-4.77 (m, 1H of one rotamer), 4.45-4.35 (m, 1H of one rotamer), 4.35-4.22 (m, 1H of one rotamer), 4.05-3.88 (m, 2H of both rotamers), 3.87-3.69 (m, 1H of both rotamers and 1H of one rotamer), 3.69-3.49 (m, 1H of both rotamers), 3.34-3.19 (m, 1H of one rotamer), 3.17-2.82 (m, 6H of both rotamers), 2.53-2.04 (m, 6H of both rotamers), 1.69-1.60 (m, 1H of both rotamers), 1.36 (t, J=7.2 Hz, 3H of both rotamers), 1.13 (s, 6H of both rotamers). MS (ESI) m/z: [M+H]$^+$ Found 657.1.

Example 66

N-(((2R*,5S*)-1-Acetyl-5-(methylsulfonyl)piperidin-2-yl)methyl)-4-chloro-5-(2-(difluoromethoxy)-4-(3,3,3-trifluoro-2,2-dimethylpropyl)phenyl)-1-ethyl-1H-pyrazole-3-carboxamide

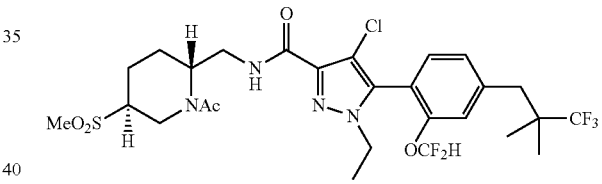

The title compound was prepared as described for the synthesis of Example 65, using 4-chloro-5-(2-(difluoromethoxy)-4-(3,3,3-trifluoro-2,2-dimethylpropyl)phenyl)-1-ethyl-N-(((2R*,5S*)-5-(methylsulfonyl)piperidin-2-yl)methyl)-1H-pyrazole-3-carboxamide hydrobromide (Example 9) in place of 4-chloro-5-(2-(difluoromethoxy)-4-(3,3,3-trifluoro-2,2-dimethylpropyl)phenyl)-1-ethyl-N-(((2S*,5R*)-5-(methylsulfonyl)piperidin-2-yl)methyl)-1H-pyrazole-3-carboxamide hydrobromide. $^1$H NMR (500 MHz, CDCl$_3$, two rotamers) δ 7.29 (d, J=7.8 Hz, 1H of both rotamers), 7.22 (s, 1H one rotamer), 7.18 (d, J=7.8 Hz, 1H of both rotamers), 7.15-7.13 (m, 1H of both rotamers), 7.04-6.96 (m, 1H of one rotamer), 6.54-6.22 (m, 1H of both rotamers), 5.33-5.19 (m, 1H of one rotamer), 4.88-4.77 (m, 1H of one rotamer), 4.45-4.35 (m, 1H of one rotamer), 4.35-4.22 (m, 1H of one rotamer), 4.05-3.88 (m, 2H of both rotamers), 3.87-3.69 (m, 1H of both rotamers and 1H of one rotamer), 3.69-3.49 (m, 1H of both rotamers), 3.34-3.19 (m, 1H of one rotamer), 3.17-2.82 (m, 6H of both rotamers), 2.53-2.04 (m, 6H of both rotamers), 1.69-1.60 (m, 1H of both rotamers), 1.36 (t, J=7.2 Hz, 3H of both rotamers), 1.13 (s, 6H of both rotamers). MS (ESI) m/z: [M+H]$^+$ Found 657.3.

Example 67

4-Chloro-5-(2-(difluoromethoxy)-4-(3,3,3-trifluoro-2,2-dimethylpropyl)phenyl)-1-ethyl-N-(((1r,4r)-4-(N-formylsulfamoyl)cyclohexyl)methyl)-1H-pyrazole-3-carboxamide

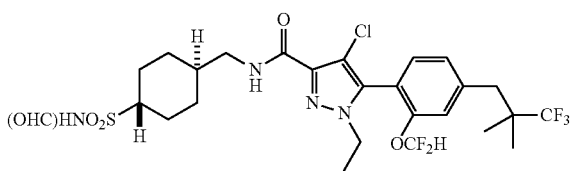

A solution of NaOMe in MeOH (0.010 mL, 25% w/w, 0.043 mmol) and then ethyl formate (0.015 mL, 0.18 mmol) were added to a solution of 4-chloro-5-(2-(difluoromethoxy)-4-(3,3,3-trifluoro-2,2-dimethylpropyl)phenyl)-1-ethyl-N-(((1 r,4r)-4-sulfamoylcyclohexyl)methyl)-1H-pyrazole-3-carboxamide (22 mg, 0.036 mmol, Example 51) in MeOH (0.15 mL), and the resulting solution was maintained at 45° C. for 2.5 h. After this time, additional NaOMe in MeOH (0.010 mL, 25% w/w, 0.043 mmol) was added, and the solution was maintained at 45° C. for an additional 15 h. After this time, additional NaOMe in MeOH (0.010 mL, 25% w/w, 0.043 mmol) was added, and the solution was maintained at 45° C. for an additional 6 h. After this time, the solution was allowed to cool, and a drop of TFA was added to make it acidic according to bromocresol green indicator. The resulting solution was diluted with MeOH, filtered, and then purified by preparative HPLC (XBridge C18, 30→100% MeCN/water, 0.05% TFA) to afford the title compound as a colorless solid. $^1$H NMR (500 MHz, CDCl$_3$) δ 8.53 (s, 1H), 8.15 (br s, 1H), 7.28 (d, J=7.8 Hz, 1H), 7.18 (dd, J=7.9, 1.6 Hz, 1H), 7.14 (s, 1H), 7.02 (t, J=6.4 Hz, 1H), 6.37 (dd, J=75.1, 70.9 Hz, 1H), 4.07-3.88 (m, 2H), 3.41-3.29 (m, 2H), 3.11 (appr t, J=12.3 Hz, 1H), 2.87 (s, 2H), 2.35-2.26 (m, 2H), 2.13-2.02 (m, 2H), 1.75-1.53 (m, 3H), 1.36 (t, J=7.2 Hz, 3H), 1.13 (s, 8H). MS (ESI) m/z: [M+H]$^+$ Found 643.2.

Example 68

N-(((1r,4r)-4-(N-Acetylsulfamoyl)cyclohexyl)methyl)-4-chloro-5-(2-(difluoromethoxy)-4-(3,3,3-trifluoro-2,2-dimethylpropyl)phenyl)-1-ethyl-1H-pyrazole-3-carboxamide

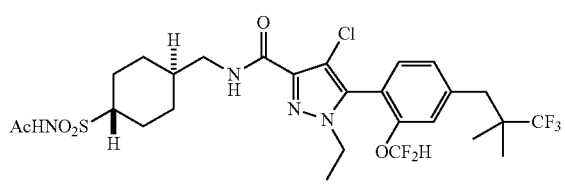

Acetic anhydride (0.051 mL, 0.54 mmol) and then ZnCl$_2$ (1 mg, 0.005 mmol) were added to a solution of 4-chloro-5-(2-(difluoromethoxy)-4-(3,3,3-trifluoro-2,2-dimethylpropyl)phenyl)-1-ethyl-N-(((1r,4r)-4-sulfamoylcyclohexyl)methyl)-1H-pyrazole-3-carboxamide (33 mg, 0.054 mmol, Example 51) in DCM (0.05 mL), and resulting the solution was maintained at rt for 14 h. After this time, an additional portion of Ac$_2$O (0.1 mL, 1 mmol) was added, and the solution was maintained at 80° C. for 4 h. The solution was then allowed to cool, diluted with MeOH, filtered, and purified by preparative HPLC (XBridge C18, 30→100% MeCN/water, 0.05% TFA) to afford the title compound as a colorless solid. $^1$H NMR (500 MHz, CDCl$_3$) δ 8.17 (s, 1H), 7.29 (d, J=7.9 Hz, 1H), 7.18 (dd, J=7.9, 1.6 Hz, 1H), 7.14 (s, 1H), 7.03 (t, J=6.3 Hz, 1H), 6.38 (dd, J=75.1, 70.9 Hz, 1H), 4.05-3.90 (m, 2H), 3.51 (tt, J=12.4, 3.6 Hz, 1H), 3.34 (t, J=6.5 Hz, 2H), 2.87 (s, 2H), 2.30-2.22 (m, 2H), 2.18 (s, 3H), 2.05 (dd, J=14.1, 3.7 Hz, 2H), 1.75-1.61 (m, 3H), 1.37 (t, J=7.2 Hz, 3H), 1.20-1.09 (m, 8H). MS (ESI) m/z: [M+H]$^+$ Found 656.8.

Example 69

N-(((1r,4r)-4-(N-Carbamoylsulfamoyl)cyclohexyl)methyl)-4-chloro-5-(2-(difluoromethoxy)-4-(3,3,3-trifluoro-2,2-dimethylpropyl)phenyl)-1-ethyl-1H-pyrazole-3-carboxamide

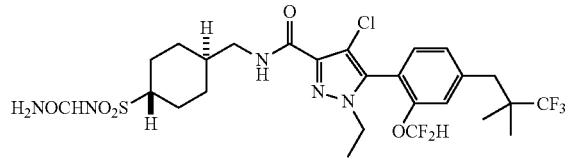

4-Methoxybenzyl isocyanate (0.0080 mL, 0.054 mmol) was added to a mixture of 4-chloro-5-(2-(difluoromethoxy)-4-(3,3,3-trifluoro-2,2-dimethylpropyl)phenyl)-1-ethyl-N-(((1 r,4r)-4-sulfamoylcyclohexyl)methyl)-1H-pyrazole-3-carboxamide (30 mg, 0.049 mmol, Example 51) and K$_2$CO$_3$ (14 mg, 0.10 mmol) in acetone (0.25 mL), and the resulting mixture was stirred at 65° C. for 2 h. After this time, additional 4-methoxybenzyl isocyanate (0.0050 mL, 0.034 mmol) was added, and stirring was continued at 65° C. for 65 h. The reaction mixture was then allowed to cool, neutralized with drops of AcOH, and concentrated. The concentrate was diluted with 0.5 TFA (0.50 mL, 6.5 mmol) and stirred at 65° C. for 2 h. After this time, the solution was concentrated, diluted with MeOH, filtered, and then purified by preparative HPLC (XBridge C18, 30→100% MeCN/water, 0.05% TFA) to afford the title compound as a colorless solid. $^1$H NMR (400 MHz, CDCl$_3$) δ 7.50 (br s, 1H), 7.28 (d, J=7.9 Hz, 1H), 7.18 (dd, J=7.9, 1.6 Hz, 1H), 7.14 (s, 1H), 7.02 (t, J=6.5 Hz, 1H), 6.37 (dd, J=75.1, 70.9 Hz, 1H), 5.89 (br s, 2H), 4.06-3.89 (m, 2H), 3.34 (t, J=6.6 Hz, 2H), 3.19 (tt, J=12.2, 3.5 Hz, 1H), 2.87 (s, 2H), 2.34-2.27 (m, 2H), 2.12-2.03 (m, 2H), 1.84-1.58 (m, 3H), 1.36 (t, J=7.2 Hz, 3H), 1.21-1.08 (m, 2H), 1.13 (s, 6H). MS (ESI) m/z: [M+H]$^+$ Found 657.8.

Example 70

4-Chloro-5-(2-(difluoromethoxy)-4-(3,3,3-trifluoro-2,2-dimethylpropyl)phenyl)-1-ethyl-N-(((r,4r)-4-(N-propionylsulfamoyl)cyclohexyl)methyl)-1H-pyrazole-3-carboxamide

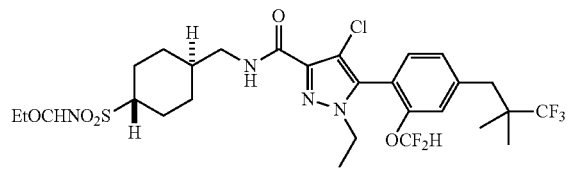

The title compound was prepared as described for the synthesis of Example 68, using propionic anhydride in place of acetic anhydride. $^1$H NMR (500 MHz, CDCl$_3$) δ 8.13 (s, 1H), 7.29 (d, J=7.8 Hz, 1H), 7.19 (dd, J=7.8, 1.6 Hz, 1H), 7.14 (s, 1H), 7.07 (t, J=6.4 Hz, 1H), 6.38 (dd, J=75.0, 70.9 Hz, 1H), 3.98 (ddt, J=26.0, 13.8, 7.0 Hz, 2H), 3.54 (tt, J=12.4, 3.5 Hz, 1H), 3.34 (t, J=6.5 Hz, 2H), 2.87 (s, 2H), 2.40 (q, J=7.4 Hz, 2H), 2.29-2.20 (m, 2H), 2.08-2.00 (m, 2H), 1.74-1.61 (m, 3H), 1.37 (t, J=7.2 Hz, 3H), 1.21-1.10 (m, 11H). MS (ESI) m/z: [M+H]$^+$ Found 670.9.

Example 71

4-Chloro-5-(2-(difluoromethoxy)-4-(3,3,3-trifluoro-2,2-dimethylpropyl)phenyl)-1-ethyl-N-(((1r,4r)-4-(N-(methylcarbamoyl)sulfamoyl)cyclohexyl)methyl)-1H-pyrazole-3-carboxamide

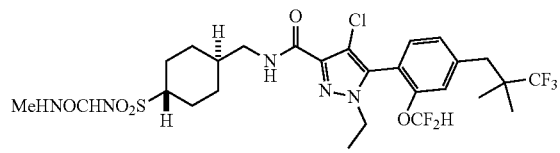

(Methylimino)(oxo)methane (0.0060 mL, 0.098 mmol) was added to a mixture of 4-chloro-5-(2-(difluoromethoxy)-4-(3,3,3-trifluoro-2,2-dimethylpropyl)phenyl)-1-ethyl-N-(((1 r,4r)-4-sulfamoylcyclohexyl)methyl)-1H-pyrazole-3-carboxamide (30 mg, 0.049 mmol, Example 51) and K$_2$CO$_3$ (14 mg, 0.10 mmol) in acetone (0.25 mL), and the resulting mixture was stirred at 65° C. for 1 h. After this time, the reaction mixture was allowed to cool, diluted with MeOH, filtered, and then purified by preparative HPLC (XBridge C18, 30→100% MeCN/water, 0.05% TFA) to afford the title compound as a colorless solid. $^1$H NMR (400 MHz, CDCl$_3$) δ 7.41 (br s, 1H), 7.29 (d, J=7.9 Hz, 1H), 7.18 (dd, J=7.9, 1.4 Hz, 1H), 7.14 (s, 1H), 7.01 (t, J=6.1 Hz, 1H), 6.55-6.49 (m, 1H), 6.38 (dd, J=70.9, 75.2 Hz, 1H), 4.06-3.89 (m, 2H), 3.34 (appar t, J=6.6 Hz, 2H), 3.18 (tt, J=12.4, 3.5 Hz, 1H), 2.87 (s, 2H), 2.85 (s, 3H of one rotamer), 2.84 (s, 3H of one rotamer), 2.33-2.23 (m, 2H), 2.11-2.01 (m, 2H), 1.74-1.57 (m, 3H), 1.36 (t, J=7.2 Hz, 3H), 1.20-1.07 (m, 2H), 1.13 (s, 6H). MS (ESI) m/z: [M+H]$^+$ Found 671.8.

Example 72

4-Chloro-1-ethyl-5-(4-isobutyl-2-methoxyphenyl)-N-(((1r,4r)-4-(methylsulfonyl)cyclohexyl)methyl)-1H-pyrazole-3-carboxamide

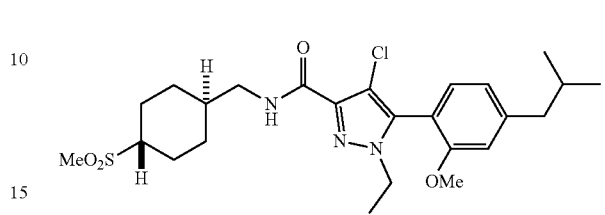

The title compound was prepared as described for the synthesis of Example 1, using ethyl 4-chloro-1-ethyl-5-(4-isobutyl-2-methoxyphenyl)-1H-pyrazole-3-carboxylate (Intermediate 134) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (500 MHz, CDCl$_3$) δ 7.15-7.09 (m, 1H), 6.97 (t, J=6.7 Hz, 1H), 6.87 (d, J=7.3 Hz, 1H), 6.79 (s, 1H), 4.03-3.88 (m, 2H), 3.83-3.76 (m, 3H), 3.40-3.28 (m, 2H), 2.88-2.78 (m, 4H), 2.54 (d, J=7.1 Hz, 2H), 2.28 (d, J=12.6 Hz, 2H), 2.07 (d, J=13.0 Hz, 2H), 1.99-1.88 (m, 1H), 1.73-1.64 (m, 1H, coincident with water), 1.64-1.52 (m, 2H), 1.37-1.28 (m, 3H), 1.19-1.07 (m, 2H), 0.99-0.92 (m, 6H); MS (ESI) m/z: [M+H]$^+$ Found 510.0.

Example 73

4-Chloro-1-ethyl-N-(((1s,4s)-1-hydroxy-4-(methylsulfonyl)cyclohexyl)methyl)-5-(4-isobutyl-2-methoxyphenyl)-1H-pyrazole-3-carboxamide

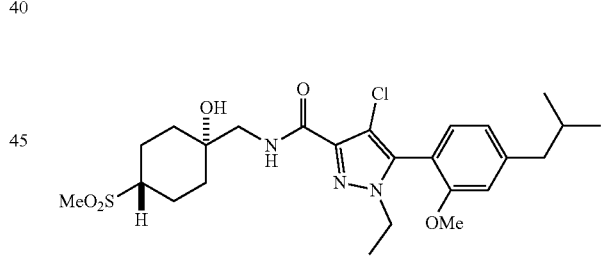

The title compound was prepared as described for the synthesis of Example 1, using ethyl 4-chloro-1-ethyl-5-(4-isobutyl-2-methoxyphenyl)-1H-pyrazole-3-carboxylate (Intermediate 134) in place of ethyl (R*)-4-chloro-1-ethyl-5-(2-methoxy-4-(3,3,3-trifluoro-2-methylpropyl)phenyl)-1H-pyrazole-3-carboxylate and (1 s,4s)-1-(aminomethyl)-4-(methylsulfonyl)cyclohexan-1-ol hydrochloride Intermediate 9) in place of ((1r,4r)-4-(methylsulfonyl)cyclohexyl)methanamine hydrochloride. $^1$H NMR (500 MHz, CDCl$_3$) δ 7.30-7.25 (m, 1H), 7.13 (d, J=7.7 Hz, 1H), 6.89-6.86 (m, 1H), 6.80 (d, J=1.4 Hz, 1H), 4.04-3.89 (m, 2H), 3.80 (s, 3H), 3.52-3.42 (m, 2H), 2.86-2.75 (m, 4H), 2.54 (d, J=7.2 Hz, 2H), 2.17-2.09 (m, 2H), 2.02-1.89 (m, 6H coincident with water), 1.47-1.38 (m, 2H), 1.36-1.31 (m, 3H), 0.99-0.93 (m, 6H); MS (ESI) m/z: [M+H]$^+$ Found 526.0.

Example 74

4-Chloro-1-ethyl-5-(4-isopentyl-2-methoxyphenyl)-N-(((1r,4r)-4-(methylsulfonyl)cyclohexyl)methyl)-1H-pyrazole-3-carboxamide

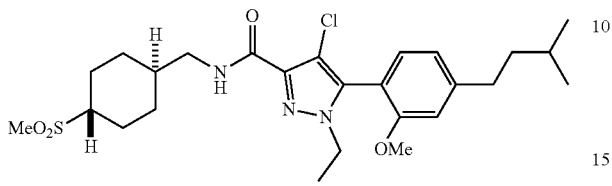

The title compound was prepared as described for the synthesis of Example 1, using ethyl 4-chloro-1-ethyl-5-(4-isopentyl-2-methoxyphenyl)-1H-pyrazole-3-carboxylate (Intermediate 135) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (500 MHz, CDCl$_3$) δ 7.15-7.11 (m, 1H), 6.96-6.87 (m, 2H), 6.84-6.81 (m, 1H), 4.02-3.88 (m, 2H), 3.82-3.77 (m, 3H), 3.40-3.27 (m, 2H), 2.86-2.79 (m, 4H), 2.70-2.64 (m, 2H), 2.27 (d, J=12.2 Hz, 2H), 2.07 (d, J=12.8 Hz, 2H), 1.72-1.53 (m, 6H, coincident with water), 1.36-1.30 (m, 3H), 1.18-1.09 (m, 2H), 0.99-0.93 (m, 6H); MS (ESI) m/z: [M+H]$^+$ Found 524.3.

Example 75

4-Chloro-1-ethyl-N-(((1s,4s)-1-hydroxy-4-(methylsulfonyl)cyclohexyl)methyl)-5-(4-isopentyl-2-methoxyphenyl)-1H-pyrazole-3-carboxamide

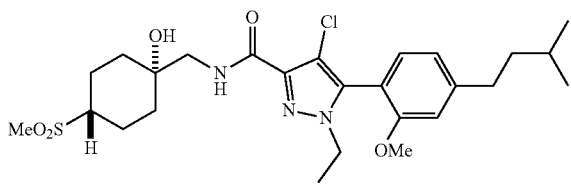 [SMILES: CCn1nc(C(=O)NC[C@]2(O)CC[C@@H](S(C)(=O)=O)CC2)c(Cl)c1-c1ccc(CCC(C)C)cc1OC]

The title compound was prepared as described for the synthesis of Example 1, using ethyl 4-chloro-1-ethyl-5-(4-isopentyl-2-methoxyphenyl)-1H-pyrazole-3-carboxylate (Intermediate 135) in place of ethyl (R*)-4-chloro-1-ethyl-5-(2-methoxy-4-(3,3,3-trifluoro-2-methylpropyl)phenyl)-1H-pyrazole-3-carboxylate and (1 s,4s)-1-(aminomethyl)-4-(methylsulfonyl)cyclohexan-1-ol hydrochloride Intermediate 9) in place of ((1r,4r)-4-(methylsulfonyl)cyclohexyl)methanamine hydrochloride. $^1$H NMR (500 MHz, CDCl$_3$) δ 7.26-7.22 (m, 1H), 7.13 (d, J=7.7 Hz, 1H), 6.93-6.89 (m, 1H), 6.85-6.82 (m, 1H), 4.06-3.86 (m, 2H), 3.80 (s, 3H), 3.53-3.38 (m, 2H), 3.22 (s, 1H), 2.85-2.74 (m, 4H), 2.73-2.63 (m, 2H), 2.19-2.08 (m, 2H), 2.06-1.92 (m, 4H), 1.71-1.61 (m, 1H), 1.61-1.52 (m, 2H coincident with water), 1.48-1.38 (m, 2H), 1.38-1.30 (m, 3H), 1.00-0.95 (m, 6H); MS (ESI) m/z: [M+H]$^+$ Found 540.3.

Example 76

4-Chloro-5-(2-(difluoromethoxy)-4-(4,4,4-trifluorobutyl)phenyl)-1-ethyl-N-(((1r,4r)-4-(methylsulfonyl)cyclohexyl)methyl)-1H-pyrazole-3-carboxamide

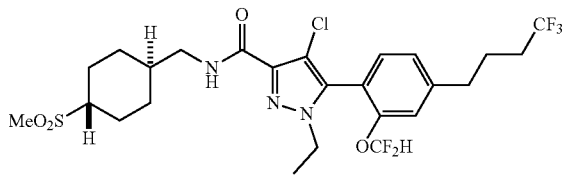

The title compound was prepared as described for the synthesis of Example 2, using ethyl 4-chloro-5-(2-(difluoromethoxy)-4-(4,4,4-trifluorobutyl)phenyl)-1-ethyl-1H-pyrazole-3-carboxylate (Intermediate 136) in place of ethyl 4-chloro-5-(2-(difluoromethoxy)-4-(3,3,3-trifluoro-2,2-dimethylpropyl)phenyl)-1-ethyl-1H-pyrazole-3-carboxylate and DCM in place of MeCN as solvent in the amide-bond-forming step. $^1$H NMR (500 MHz, CDCl$_3$) δ 7.31-7.27 (m, 1H), 7.23-7.17 (m, 1H), 7.16-7.12 (s, 1H), 6.98-6.92 (m, 1H), 6.54-6.22 (m, 1H), 4.06-3.89 (m, 2H), 3.39-3.30 (m, 2H), 2.89-2.74 (m, 6H), 2.33-2.24 (m, 2H), 2.23-2.11 (m, 2H), 2.11-2.05 (m, 2H), 2.01-1.92 (m, 2H), 1.75-1.65 (m, 1H), 1.65-1.56 (m, 2H), 1.39-1.34 (t, J=7.2 Hz, 3H), 1.20-1.09 (m, 2H); MS (ESI) m/z: [M+H]$^+$ Found 600.2.

Example 77

4-Chloro-5-(2-(difluoromethoxy)-4-(4,4,4-trifluorobutyl)phenyl)-1-ethyl-N-(((1s,4s)-1-hydroxy-4-(methylsulfonyl)cyclohexyl)methyl)-1H-pyrazole-3-carboxamide

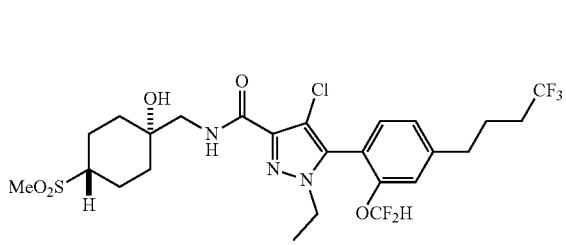

The title compound was prepared as described for the synthesis of Example 2, using ethyl 4-chloro-5-(2-(difluoromethoxy)-4-(4,4,4-trifluorobutyl)phenyl)-1-ethyl-1H-pyrazole-3-carboxylate (Intermediate 137) in place of ethyl 4-chloro-5-(2-(difluoromethoxy)-4-(3,3,3-trifluoro-2,2-dimethylpropyl)phenyl)-1-ethyl-1H-pyrazole-3-carboxylate, (1s,4s)-1-(aminomethyl)-4-(methylsulfonyl)cyclohexan-1-ol hydrochloride (Intermediate 9) in place of ((1r,4r)-4-(methylsulfonyl)cyclohexyl)methanamine hydrochloride, and DCM in place of MeCN as solvent in the amide-bond-forming step. $^1$H NMR (500 MHz, CDCl$_3$) δ 7.30-7.22 (m, 2H), 7.22-7.19 (m, 1H), 7.15 (s, 1H), 6.55-6.24 (m, 1H), 4.06-3.90 (m, 2H), 3.47 (d, J=6.3 Hz, 2H), 3.08 (s, 1H), 2.83 (s, 3H), 2.82-2.77 (m, 3H), 2.23-2.09 (m, 4H), 2.04-1.93 (m, 6H), 1.49-1.40 (m, 2H), 1.40-1.34 (m, 3H); MS (ESI) m/z: [M+H]$^+$ Found 616.0.

Example 78

5-(2-(Difluoromethoxy)-4-(4,4,4-trifluorobutyl)phenyl)-1-ethyl-4-methyl-N-(((1r,4r)-4-(methylsulfonyl)cyclohexyl)methyl)-1H-pyrazole-3-carboxamide

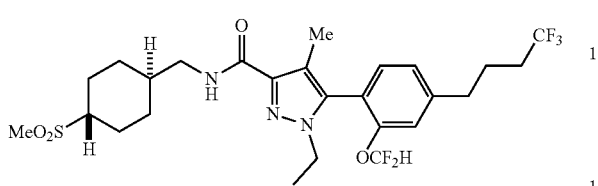

A microwave tube was charged with 4-chloro-5-(2-(difluoromethoxy)-4-(4,4,4-trifluorobutyl)phenyl)-1-ethyl-N-(((1r,4r)-4-(methyl sulfonyl)cyclohexyl)methyl)-1H-pyrazole-3-carboxamide (119 mg, 0.198 mmol, Example 76), $K_2CO_3$ (110 mg, 0.796 mmol), RuPhos G1 (9 mg, 0.01 mmol), and RuPhos (5 mg, 0.01 mmol) and then the tube was sparged with a stream of nitrogen gas. Dioxane (1.2 mL, degassed by bubbling nitrogen gas for 15 minutes) was added followed by trimethylboroxine (0.055 mL, 0.39 mmol). The tube was capped and warmed to 110° C. in a metal heating block. After 3 h, the tube was allowed to cool to rt. EtOAc was added and the mixture was filtered through a pad of Celite®, rinsing with EtOAc. The filtrate was absorbed onto Celite® and then purified by silica gel chromatography (hexanes-EtOAc) to provide the title compound as a clear colorless oil. The oil was dissolved in a minimal amount of MeCN-water, frozen in a dry ice-acetone bath, and then lyophilized to provide the title compound as a colorless powder. $^1$H NMR (400 MHz, $CDCl_3$) δ 7.22-7.11 (m, 3H), 7.09-7.02 (m, 1H), 6.56-6.12 (m, 1H), 4.02-3.81 (m, 2H), 3.37-3.25 (m, 2H), 2.89-2.74 (m, 6H), 2.32-2.25 (m, 2H), 2.22-2.05 (m, 7H), 2.02-1.92 (m, 2H), 1.75-1.53 (m, 3H coincident with water), 1.37-1.30 (m, 3H), 1.21-1.06 (m, 2H); MS (ESI) m/z: $[M+H]^+$ Found 580.2.

Example 79

5-(2-(Difluoromethoxy)-4-(4,4,4-trifluorobutyl)phenyl)-1-ethyl-N-(((1s,4s)-1-hydroxy-4-(methylsulfonyl)cyclohexyl)methyl)-4-methyl-1H-pyrazole-3-carboxamide

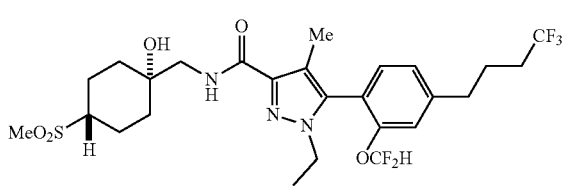

The title compound was prepared as described for the synthesis of Example 78, using 4-chloro-5-(2-(difluoromethoxy)-4-(4,4,4-trifluorobutyl)phenyl)-1-ethyl-N-(((1s,4s)-1-hydroxy-4-(methylsulfonyl)cyclohexyl)methyl)-1H-pyrazole-3-carboxamide (Example 77) in place of 4-chloro-5-(2-(difluoromethoxy)-4-(4,4,4-trifluorobutyl)phenyl)-1-ethyl-N-(((1 r,4r)-4-(methylsulfonyl)cyclohexyl)methyl)-1H-pyrazole-3-carboxamide. $^1$H NMR (400 MHz, $CDCl_3$) δ 7.35-7.29 (m, 1H), 7.22-7.11 (m, 3H), 6.55-6.15 (m, 1H), 4.02-3.83 (m, 2H), 3.59 (s, 1H), 3.44 (d, J=6.3 Hz, 2H), 2.83 (s, 3H), 2.82-2.75 (m, 3H), 2.24-2.09 (m, 7H), 2.06-1.91 (m, 6H), 1.47-1.30 (m, 5H); MS (ESI) m/z: $[M+H]^+$ Found 596.1.

Example 80

4-Chloro-1-ethyl-5-(2-methoxy-4-(4,4,4-trifluorobutyl)phenyl)-N-(((1r,4r)-4-(methylsulfonyl)cyclohexyl)methyl)-1H-pyrazole-3-carboxamide

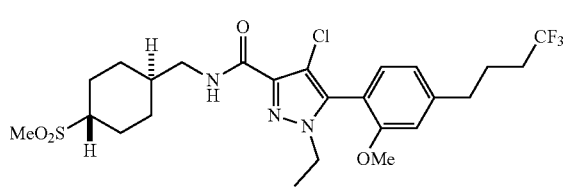

The title compound was prepared as describe for the synthesis of Example 2, using ethyl 4-chloro-1-ethyl-5-(2-methoxy-4-(4,4,4-trifluorobutyl)phenyl)-1H-pyrazole-3-carboxylate (Intermediate 137) in place of ethyl 4-chloro-5-(2-(difluoromethoxy)-4-(3,3,3-trifluoro-2,2-dimethylpropyl)phenyl)-1-ethyl-1H-pyrazole-3-carboxylate and using DCM in place of MeCN as solvent in the amide-bond-forming step. $^1$H NMR (500 MHz, $CDCl_3$) δ 7.17 (d, J=7.7 Hz, 1H), 6.97-6.92 (m, 1H), 6.91 (dd, J=7.7, 1.5 Hz, 1H), 6.83 (d, J=1.4 Hz, 1H), 4.03-3.88 (m, 2H), 3.81 (s, 3H), 3.40-3.28 (m, 2H), 2.87-2.79 (m, 4H), 2.79-2.74 (m, 2H), 2.31-2.25 (m, 2H), 2.22-2.11 (m, 2H), 2.11-2.05 (m, 2H), 2.00-1.93 (m, 2H), 1.74-1.64 (m, 1H), 1.64-1.54 (m, 2H coincident with water), 1.36-1.31 (m, 3H), 1.19-1.09 (m, 2H); MS (ESI) m/z: $[M+H]^+$ Found 564.2.

Example 81

4-Chloro-1-ethyl-N-(((1s,4s)-1-hydroxy-4-(methylsulfonyl)cyclohexyl)methyl)-5-(2-methoxy-4-(4,4,4-trifluorobutyl)phenyl)-1H-pyrazole-3-carboxamide

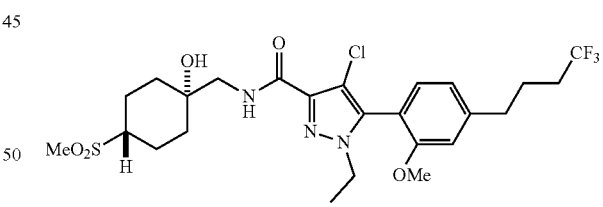

The title compound was prepared as describe for the synthesis of Example 2, using ethyl 4-chloro-1-ethyl-5-(2-methoxy-4-(4,4,4-trifluorobutyl)phenyl)-1H-pyrazole-3-carboxylate (Intermediate 137) in place of ethyl 4-chloro-5-(2-(difluoromethoxy)-4-(3,3,3-trifluoro-2,2-dimethylpropyl)phenyl)-1-ethyl-1H-pyrazole-3-carboxylate, (1s,4s)-1-(aminomethyl)-4-(methylsulfonyl)cyclohexan-1-ol hydrochloride (Intermediate 9) in place of ((1r,4r)-4-(methylsulfonyl)cyclohexyl)methanamine hydrochloride, and DCM in place of MeCN as solvent in the amide-bond-forming step. $^1$H NMR (500 MHz, $CDCl_3$) δ 7.26-7.21 (m, 1H coincident with residual $CHCl_3$), 7.17 (d, J=7.7 Hz, 1H), 6.91 (dd, J=7.7, 1.5 Hz, 1H), 6.83 (d, J=1.5 Hz, 1H), 4.04-3.89 (m, 2H), 3.81 (s, 3H), 3.53-3.40 (m, 2H), 3.19 (s, 1H), 2.83 (s, 3H), 2.81-2.74 (m, 3H), 2.22-2.09 (m, 4H), 2.03-1.93 (m, 6H), 1.47-1.38 (m, 2H), 1.34 (t, J=7.3 Hz, 3H); MS (ESI) m/z: [M+H]⁺ Found 580.2.

Example 82

1-Ethyl-5-(2-methoxy-4-(4,4,4-trifluorobutyl)phenyl)-4-methyl-N-(((1r,4r)-4-(methylsulfonyl)cyclohexyl)methyl)-1H-pyrazole-3-carboxamide

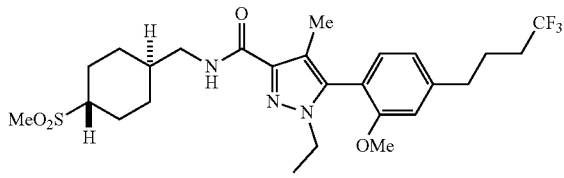 [SMILES: CCn1nc(C(=O)NC[C@H]2CC[C@H](S(C)(=O)=O)CC2)c(C)c1-c1ccc(CCCC(F)(F)F)cc1OC]

The title compound was prepared as described for the synthesis of Example 2, using ethyl 1-ethyl-5-(2-methoxy-4-(4,4,4-trifluorobutyl)phenyl)-4-methyl-1H-pyrazole-3-carboxylate (Intermediate 138) in place of ethyl 4-chloro-5-(2-(difluoromethoxy)-4-(3,3,3-trifluoro-2,2-dimethylpropyl)phenyl)-1-ethyl-1H-pyrazole-3-carboxylate and DCM in place of MeCN as solvent in the amide-bond-forming step. ¹H NMR (500 MHz, CDCl₃) δ 7.09-7.03 (m, 2H), 6.89-6.86 (m, 1H), 6.81 (d, J=1.5 Hz, 1H), 3.99-3.84 (m, 2H), 3.79 (s, 3H), 3.37-3.25 (m, 2H), 2.87-2.79 (m, 4H), 2.79-2.73 (m, 2H), 2.31-2.25 (m, 2H), 2.22-2.12 (m, 5H), 2.12-2.06 (m, 2H), 2.01-1.93 (m, 2H), 1.72-1.64 (m, 1H), 1.64-1.54 (m, 2H coincident with water), 1.34-1.30 (m, 3H), 1.18-1.07 (m, 2H); MS (ESI) m/z: [M+H]⁺ Found 544.2.

Example 83

1-Ethyl-N-(((1s,4s)-1-hydroxy-4-(methylsulfonyl)cyclohexyl)methyl)-5-(2-methoxy-4-(4,4,4-trifluorobutyl)phenyl)-4-methyl-1H-pyrazole-3-carboxamide

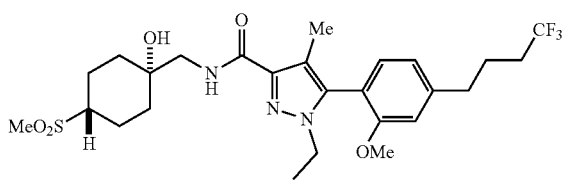 [SMILES: CCn1nc(C(=O)NC[C@]2(O)CC[C@@H](S(C)(=O)=O)CC2)c(C)c1-c1ccc(CCCC(F)(F)F)cc1OC]

The title compound was prepared as described for the synthesis of Example 2, using ethyl 1-ethyl-5-(2-methoxy-4-(4,4,4-trifluorobutyl)phenyl)-4-methyl-1H-pyrazole-3-carboxylate (Intermediate 138) in place of ethyl 4-chloro-5-(2-(difluoromethoxy)-4-(3,3,3-trifluoro-2,2-dimethylpropyl)phenyl)-1-ethyl-1H-pyrazole-3-carboxylate, (1s,4s)-1-(aminomethyl)-4-(methylsulfonyl)cyclohexan-1-ol hydrochloride (Intermediate 9) in place of ((1r,4r)-4-(methylsulfonyl)cyclohexyl)methanamine hydrochloride, and DCM in place of MeCN as solvent in the amide-bond-forming step. ¹H NMR (500 MHz, CDCl₃) δ 7.35-7.30 (m, 1H), 7.07 (d, J=7.6 Hz, 1H), 6.88 (dd, J=7.6, 1.5 Hz, 1H), 6.81 (d, J=1.6 Hz, 1H), 3.98-3.84 (m, 2H), 3.79 (s, 3H), 3.71 (s, 1H), 3.48-3.38 (m, 2H), 2.82 (s, 3H), 2.80-2.73 (m, 3H), 2.21-2.09 (m, 7H), 2.04-1.92 (m, 6H), 1.44-1.35 (m, 2H), 1.34-1.29 (m, 3H); MS (ESI) m/z: [M+H]⁺ Found 560.1.

Example 84

4-Chloro-1-ethyl-5-(2-methoxy-4-(3,3,3-trifluoro-2-(trifluoromethyl)propyl)phenyl)-N-(((1r,4r)-4-(methylsulfonyl)cyclohexyl)methyl)-1H-pyrazole-3-carboxamide

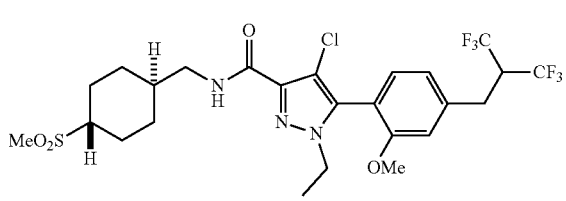 [SMILES: CCn1nc(C(=O)NC[C@H]2CC[C@H](S(C)(=O)=O)CC2)c(Cl)c1-c1ccc(CC(C(F)(F)F)C(F)(F)F)cc1OC]

A suspension of Rieke® zinc in THF (1.0 mL, 0.05 g/mL, 0.76 mmol) was added dropwise to a 0-5° C. stirring solution of 2-(bromomethyl)-1,1,1,3,3,3-hexafluoropropane (0.11 mL, 0.76 mmol) in THF (1.5 mL). After 1 h, a solution of 5-(4-bromo-2-methoxyphenyl)-4-chloro-1-ethyl-N-(((1r,4r)-4-(methylsulfonyl)cyclohexyl)methyl)-1H-pyrazole-3-carboxamide (100 mg, 0.188 mmol, Intermediate 146) in THF (0.5 mL) followed by Pd(t-Bu₃P)₂ (11 mg, 0.022 mmol) was added. The reaction tube was sealed and removed from the cooling bath and then placed into a pre-warmed 60° C. metal heating block. After 18 h, the mixture was allowed to cool to rt and then EtOAc was added. The mixture was filtered through Celite®. The filtrate was concentrated and then purified by preparative HPLC (MeCN/water containing 0.05% TFA) to provide the title compound as a colorless solid. ¹H NMR (500 MHz, CDCl₃) δ 7.22 (d, J=7.7 Hz, 1H), 7.00-6.94 (m, 2H), 6.86 (d, J=1.5 Hz, 1H), 4.03-3.88 (m, 2H), 3.82 (s, 3H), 3.41-3.22 (m, 3H), 3.22-3.16 (m, 2H), 2.88-2.78 (m, 4H), 2.33-2.24 (m, 2H), 2.12-2.04 (m, 2H), 1.73-1.64 (m, 1H), 1.64-1.54 (m, 2H), 1.36-1.31 (m, 3H), 1.19-1.08 (m, 2H); MS (ESI) m/z: [M+H]⁺ Found 618.2.

Example 85

4-Chloro-1-ethyl-N-(((1s,4s)-1-hydroxy-4-(methylsulfonyl)cyclohexyl)methyl)-5-(2-methoxy-4-(3,3,3-trifluoro-2-(trifluoromethyl)propyl)phenyl)-1H-pyrazole-3-carboxamide

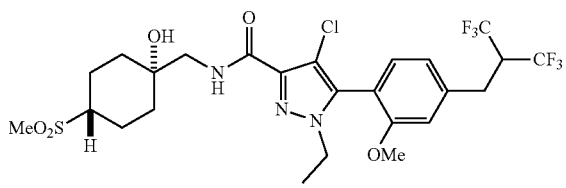 [SMILES: CCn1nc(C(=O)NC[C@]2(O)CC[C@@H](S(C)(=O)=O)CC2)c(Cl)c1-c1ccc(CC(C(F)(F)F)C(F)(F)F)cc1OC]

The title compound was prepared as described for the synthesis of Example 84, using 5-(4-bromo-2-methoxyphenyl)-4-chloro-1-ethyl-N-(((1s,4s)-1-hydroxy-4-(methylsulfonyl)cyclohexyl)methyl)-1H-pyrazole-3-carboxamide (Intermediate 147) in place of 5-(4-bromo-2-methoxyphenyl)-4-chloro-1-ethyl-N-(((1r,4r)-4-(methylsulfonyl)cyclohexyl)methyl)-1H-pyrazole-3-carboxamide. $^1$H NMR (500 MHz, CDCl$_3$) δ 7.27-7.23 (m, 1H), 7.21 (d, J=7.7 Hz, 1H), 6.97 (dd, J=7.7, 1.5 Hz, 1H), 6.86 (d, J=1.5 Hz, 1H), 4.02-3.88 (m, 2H), 3.81 (s, 3H), 3.52-3.42 (m, 2H), 3.33-3.21 (m, 1H), 3.19-3.14 (m, 2H), 2.86-2.75 (m, 4H), 2.17-1.91 (m, 7H), 1.47-1.39 (m, 2H), 1.38-1.31 (m, 3H); MS (ESI) m/z: [M+H]$_+$ Found 634.0.

Example 86

4-Chloro-5-(2-(difluoromethoxy)-4-(3,3,3-trifluoro-2-(trifluoromethyl)propyl)phenyl)-1-ethyl-N-(((1r,4r)-4-(methylsulfonyl)cyclohexyl)methyl)-1H-pyrazole-3-carboxamide

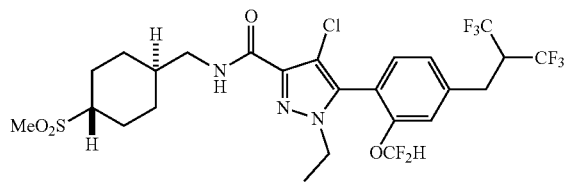

2-(Bromomethyl)-1,1,1,3,3,3-hexafluoropropane (0.7 mL, 4.9 mmol) was added to a stirring suspension of Rieke® zinc in THF (5.8 mL, 0.05 g/mL, 4.4 mmol) at 0° C. The mixture was allowed to stir at 0-5° C. for 1 h then removed from the cooling bath. After 5 min, a solution of 5-(4-bromo-2-(difluoromethoxy)phenyl)-4-chloro-1-ethyl-N-(((1 r,4r)-4-(methyl sulfonyl)cyclohexyl)methyl)-1H-pyrazole-3-carboxamide (431 mg, 0.758 mmol, Intermediate 148) in THF was added, followed by Pd(t-Bu$_3$P)$_2$ (92 mg, 0.18 mmol). The mixture was warmed to 55° C. After 1 h, the reaction was allowed to cool to rt and EtOAc was added. The mixture was filtered through a pad of Celite® and the filtrate was absorbed onto Celite®. Purification by silica gel chromatography provided the title compound as a colorless solid. $^1$H NMR (400 MHz, DMSO-d$_6$) δ 8.23 (t, J=6.1 Hz, 1H), 7.49-7.05 (m, 4H), 4.71-4.53 (m, 1H), 4.01-3.85 (m, 2H), 3.14-3.07 (m, 2H), 3.05-2.95 (m, 1H), 2.90 (s, 3H), 2.11 (d, J=12.2 Hz, 2H), 1.86 (d, J=12.7 Hz, 2H), 1.55 (s, 1H), 1.43-1.30 (m, 2H), 1.28-1.22 (m, 3H), 1.09-0.96 (m, 2H), 3.31-3.26 (m, 2H); MS (ESI) m/z: [M+H]$^+$ Found 654.2.

Example 87

5-(2-(Difluoromethoxy)-4-(3,3,3-trifluoro-2-(trifluoromethyl)propyl)phenyl)-1-ethyl-4-methyl-N-(((1r,4r)-4-(methylsulfonyl)cyclohexyl)methyl)-1H-pyrazole-3-carboxamide

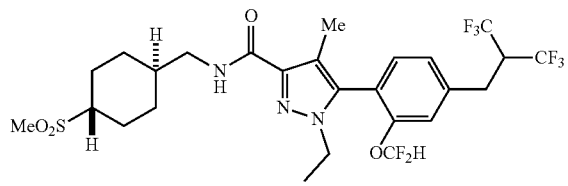

The title compound was prepared as described for the synthesis of Example 78, using 4-chloro-5-(2-(difluoromethoxy)-4-(3,3,3-trifluoro-2-(trifluoromethyl)propyl)phenyl)-1-ethyl-N-(((1 r,4r)-4-(methylsulfonyl)cyclohexyl)methyl)-1H-pyrazole-3-carboxamide (Example 86) in place of 4-chloro-5-(2-(difluoromethoxy)-4-(4,4,4-trifluorobutyl)phenyl)-1-ethyl-N-(((1 r,4r)-4-(methylsulfonyl)cyclohexyl)methyl)-1H-pyrazole-3-carboxamide. $^1$H NMR (400 MHz, CDCl$_3$) δ 7.25-7.17 (m, 3H), 7.09-7.01 (m, 1H), 6.53-6.13 (m, 1H), 4.00-3.83 (m, 2H), 3.38-3.17 (m, 5H), 2.91-2.78 (m, 4H), 2.36-2.22 (m, 2H), 2.15 (s, 3H), 2.13-2.05 (m, 2H), 1.76-1.52 (m, 3H coincident with water), 1.37-1.27 (m, 3H), 1.22-1.05 (m, 2H); MS (ESI) m/z: [M+H]$^+$ Found 634.1.

Example 88

4-Chloro-5-(2-cyano-4-(3,3,3-trifluoro-2,2-dimethylpropyl)phenyl)-1-ethyl-N-(((1s,4s)-1-hydroxy-4-(methylsulfonyl)cyclohexyl)methyl)-1H-pyrazole-3-carboxamide

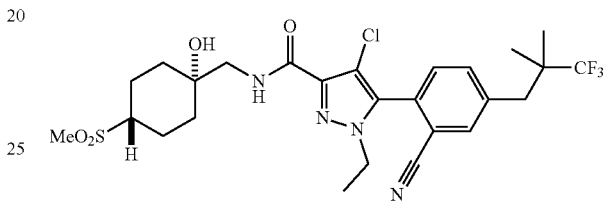

A mixture containing 5-(2-cyano-4-(3,3,3-trifluoro-2,2-dimethylpropyl)phenyl)-1-ethyl-N-(((1s,4s)-1-hydroxy-4-(methylsulfonyl)cyclohexyl)methyl)-1H-pyrazole-3-carboxamide (65 mg, 0.12 mmol, Intermediate 149) and NCS (22 mg) in DMF (2 mL) was stirred. After 18 h, additional NCS (32 mg) was added and the mixture was warmed to 55° C. After 5 h, the mixture was partitioned between water and EtOAc. The layers were separated. The aqueous layer was extracted with EtOAc. The organic layers were combined, dried over anhydrous Na$_2$SO$_4$, filtered, and the filtrate was absorbed onto Celite®. Purification by silica gel chromatography (hexanes-EtOAc) provided the tile compound after lyophilization. $^1$H NMR (400 MHz, CDCl$_3$) δ 7.66 (d, J=1.8 Hz, 1H), 7.59-7.56 (m, 1H), 7.41 (d, J=7.9 Hz, 1H), 7.26-7.21 (m, 1H), 4.16-3.95 (m, 2H), 3.54-3.42 (m, 2H), 2.94 (s, 1H), 2.91 (s, 2H), 2.87-2.76 (m, 4H), 2.19-2.09 (m, 2H), 2.06-1.91 (m, 4H), 1.51-1.37 (m, 5H), 1.15 (s, 6H); MS (ESI) m/z: [M+H]$^+$ Found 589.0.

Example 89

4-Chloro-5-(2-(difluoromethoxy)-4-(4,4,4-trifluoro-2,2-dimethylbutyl)phenyl)-1-ethyl-N-(((1r,4r)-4-(methylsulfonyl)cyclohexyl)methyl)-1H-pyrazole-3-carboxamide

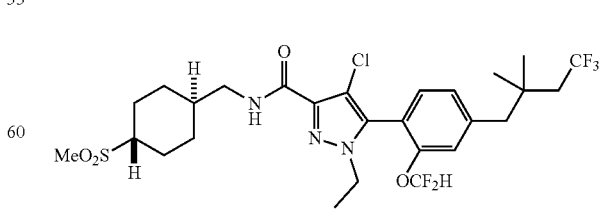

The title compound was prepared as described for the synthesis of Example 2, using ethyl 4-chloro-5-(2-(difluoromethoxy)-4-(4,4,4-trifluoro-2,2-dimethylbutyl)phenyl)-1- ethyl-1H-pyrazole-3-carboxylate (Intermediate 141) in place of ethyl 4-chloro-5-(2-(difluoromethoxy)-4-(3,3,3-trifluoro-2,2-dimethylpropyl)phenyl)-1-ethyl-1H-pyrazole-3-carboxylate and DCM in place of MeCN as solvent in the amide-bond-forming step. $^1$H NMR (400 MHz, CDCl$_3$) δ 7.30-7.24 (m, 1H coincident with residual chloroform), 7.18-7.13 (m, 1H), 7.11 (s, 1H), 6.98-6.91 (m, 1H), 6.57-6.17 (m, 1H), 4.08-3.88 (m, 2H), 3.39-3.31 (m, 2H), 2.89-2.78 (m, 4H), 2.74 (s, 2H), 2.33-2.24 (m, 2H), 2.15-2.01 (m, 4H), 1.76-1.55 (m, 3H coincident with water), 1.36 (t, J=7.2 Hz, 3H), 1.21-1.07 (m, 8H); MS (ESI) m/z: [M+H]$^+$ Found 628.0.

Example 90

4-Chloro-5-(2-(difluoromethoxy)-4-(4,4,4-trifluoro-2,2-dimethylbutyl)phenyl)-1-ethyl-N-(((1s,4s)-1-hydroxy-4-(methylsulfonyl)cyclohexyl)methyl)-1H-pyrazole-3-carboxamide

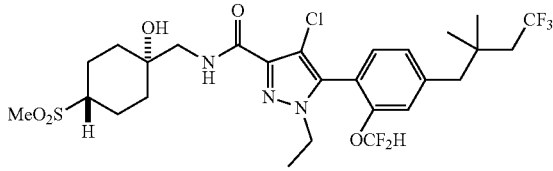

The title compound was prepared as described for the synthesis of Example 2, using ethyl 4-chloro-5-(2-(difluoromethoxy)-4-(4,4,4-trifluoro-2,2-dimethylbutyl)phenyl)-1-ethyl-1H-pyrazole-3-carboxylate (Intermediate 141) in place of ethyl 4-chloro-5-(2-(difluoromethoxy)-4-(3,3,3-trifluoro-2,2-dimethylpropyl)phenyl)-1-ethyl-1H-pyrazole-3-carboxylate, (1s,4s)-1-(aminomethyl)-4-(methylsulfonyl)cyclohexan-1-ol hydrochloride (Intermediate 9) in place of ((1r,4r)-4-(methylsulfonyl)cyclohexyl)methanamine hydrochloride, and DCM in place of MeCN as solvent in the amide-bond-forming step. $^1$H NMR (400 MHz, CDCl$_3$) δ 7.30-7.22 (m, 2H coincident with residual chloroform), 7.18-7.14 (m, 1H), 7.12 (s, 1H), 6.59-6.17 (m, 1H), 4.08-3.88 (m, 2H), 3.47 (d, J=6.3 Hz, 2H), 3.06 (s, 1H), 2.86-2.76 (m, 4H), 2.74 (s, 2H), 2.18-1.92 (m, 8H), 1.50-1.35 (m, 5H), 1.11 (s, 6H); MS (ESI) m/z: [M+H]$^+$ Found 644.1.

Example 91

4-Chloro-5-(2-(difluoromethoxy)-4-(3,3,3-trifluoro-2,2-dimethylpropyl)phenyl)-1-ethyl-N-(((1s*,4s*)-1-(hydroxymethyl)-4-(methylsulfonyl)cyclohexyl)methyl)-1H-pyrazole-3-carboxamide The title compound was prepared as described for the synthesis of Example 2, using (1s*,4s*)-(1-(aminomethyl)-4-(methylsulfonyl)cyclohexyl)methanol hydrochloride (Intermediate 121) in place of ((1r,4r)-4-(methylsulfonyl)cyclohexyl)methanamine hydrochloride and DCM in place of MeCN as solvent. $^1$H NMR (500 MHz, CDCl$_3$) δ 7.29 (d, J=7.8 Hz, 1H), 7.21-7.13 (m, 3H), 6.39 (dd, J=75.0, 70.9 Hz, 1H), 4.08-3.91 (m, 3H), 3.51 (d, J=7.4 Hz, 2H), 3.29 (d, J=7.0 Hz, 2H), 2.88 (s, 2H), 2.86-2.78 (m, 4H), 2.15-2.03 (m, 4H), 1.80-1.67 (m, 2H), 1.37 (t, J=7.3 Hz, 3H), 1.24-1.16 (m, 2H), 1.13 (s, 6H); MS (ESI) m/z: [M+H]$^+$ Found 644.1.

Example 92

4-Chloro-1-ethyl-N-(((1s*,4s*)-1-(hydroxymethyl)-4-(methylsulfonyl)cyclohexyl)methyl)-5-(2-methoxy-4-(3,3,3-trifluoro-2-methylpropyl)phenyl)-1H-pyrazole-3-carboxamide

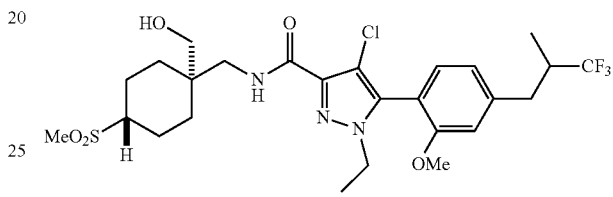

The title compound was prepared as described for the synthesis of Example 1, using ethyl 4-chloro-1-ethyl-5-(2-methoxy-4-(3,3,3-trifluoro-2-methylpropyl)phenyl)-1H-pyrazole-3-carboxylate (Intermediate 98) in place of ethyl (R*)-4-chloro-1-ethyl-5-(2-methoxy-4-(3,3,3-trifluoro-2-methylpropyl)phenyl)-1H-pyrazole-3-carboxylate and (1s*,4s*)-(1-(aminomethyl)-4-(methylsulfonyl)cyclohexyl)methanol (Intermediate 121, free base) in place of ((1r,4r)-4-(methylsulfonyl)cyclohexyl)methanamine hydrochloride. $^1$H NMR (500 MHz, CDCl$_3$) δ 7.19 (dd, J=7.7, 2.2 Hz, 1H), 7.15-7.07 (m, 1H), 6.96-6.87 (m, 1H), 6.82 (s, 1H), 4.22-4.12 (m, 1H), 4.04-3.89 (m, 2H), 3.82 (s, 3H), 3.60-3.47 (m, 2H), 3.33-3.22 (m, 2H), 3.22-3.11 (m, 1H), 2.88 (s, 3H), 2.61-2.46 (m, 2H), 2.21-1.76 (m, 6H), 1.40-1.31 (m, 3H), 1.30-1.17 (m, 3H), 1.11 (d, J=6.2 Hz, 3H); MS (ESI) m/z: [M+H]$^+$ Found 594.2.

Example 93

4-Chloro-1-ethyl-N-(((1s*,4S*)-1-(hydroxymethyl)-4-(methylsulfonyl)cyclohexyl)methyl)-5-(2-methoxy-4-(((R)-1,1,1-trifluoropropan-2-yl)amino)phenyl)-1H-pyrazole-3-carboxamide

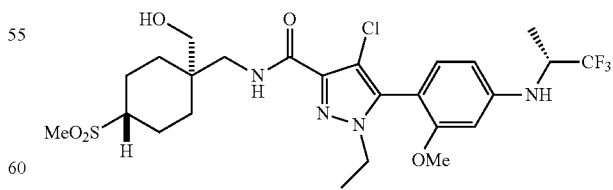

The title compound was prepared as described for the synthesis of Example 2, using ethyl (R)-4-chloro-1-ethyl-5-(2-methoxy-4-((1,1,1-trifluoropropan-2-yl)amino)phenyl)-1H-pyrazole-3-carboxylate (Intermediate 106) in place of ethyl 4-chloro-5-(2-(difluoromethoxy)-4-(3,3,3-trifluoro-2, 2-dimethylpropyl)phenyl)-1-ethyl-1H-pyrazole-3-carboxylate, (1s*,4s*)-(1-(aminomethyl)-4-(methyl sulfonyl)cyclohexyl)methanol hydrochloride (Intermediate 121) in place of ((1r,4r)-4-(methylsulfonyl)cyclohexyl)methanamine hydrochloride, and DCM in place of MeCN as solvent in the amide-bond-forming step. $^1$H NMR (500 MHz, DMSO-d$_6$) δ 8.06-8.01 (m, 1H), 6.96 (d, J=8.3 Hz, 1H), 6.54-6.51 (m, 1H), 6.49-6.43 (m, 2H), 4.55-4.46 (m, 1H), 3.94-3.84 (m, 2H), 3.72 (s, 3H), 3.37 (s, 2H), 3.19-3.10 (m, 2H), 3.04-2.97 (m, 1H), 2.90 (s, 3H), 1.92-1.86 (m, 2H), 1.73-1.67 (m, 2H), 1.54-1.45 (m, 2H), 1.33 (d, J=6.6 Hz, 3H), 1.26-1.18 (m, 5H); MS (ESI) m/z: [M+H]$^+$ Found 595.1.

Example 94

Ethyl (1s*,4S*)-1-((4-chloro-1-ethyl-5-(2-methoxy-4-(((R)-1,1,1-trifluoropropan-2-yl)amino)phenyl)-1H-pyrazole-3-carboxamido)methyl)-4-(methylsulfonyl)cyclohexane-1-carboxylate

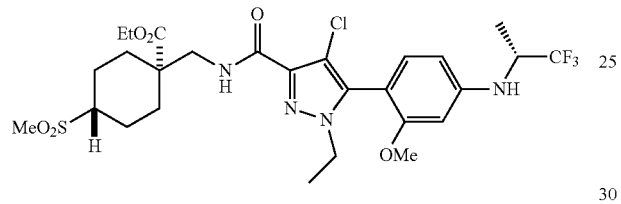

The title compound was prepared as described for the synthesis of Example 1, using ethyl (R)-4-chloro-1-ethyl-5-(2-methoxy-4-((1,1,1-trifluoropropan-2-yl)amino)phenyl)-1H-pyrazole-3-carboxylate (Intermediate 106) in place of ethyl (R*)-4-chloro-1-ethyl-5-(2-methoxy-4-(3,3,3-trifluoro-2-methylpropyl)phenyl)-1H-pyrazole-3-carboxylate and ethyl (1s*,4s*)-1-(aminomethyl)-4-(methylsulfonyl)cyclohexane-1-carboxylate (Intermediate 124) in place of ((1r,4r)-4-(methylsulfonyl)cyclohexyl)methanamine hydrochloride. $^1$H NMR (400 MHz, CDCl$_3$) δ 7.12-7.07 (m, 1H), 7.06-7.01 (m, 1H), 6.39-6.33 (m, 1H), 6.29-6.25 (m, 1H), 4.29-4.22 (m, 2H), 4.12-4.05 (m, 1H), 4.00-3.89 (m, 2H), 3.76 (d, J=2.5 Hz, 3H), 1.48-1.44 (m, 3H), 3.62-3.51 (m, 2H), 2.88-2.79 (m, 4H), 2.50-2.43 (m, 2H), 2.22-2.15 (m, 2H), 1.77-1.64 (m, 2H), 1.44-1.35 (m, 2H), 1.35-1.30 (m, 6H); MS (ESI) m/z: [M+H]$^+$ Found 637.2.

Example 95

Ethyl (1r*,4R*)-1-((4-chloro-1-ethyl-5-(2-methoxy-4-(((R)-1,1,1-trifluoropropan-2-yl)amino)phenyl)-1H-pyrazole-3-carboxamido)methyl)-4-(methylsulfonyl)cyclohexane-1-carboxylate

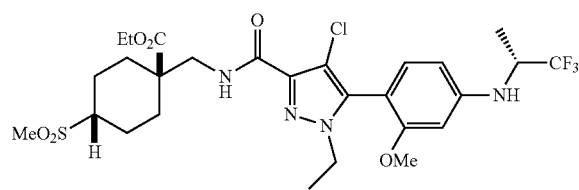 [SMILES: CCOC(=O)[C@]1(CNC(=O)c2nn(CC)c(-c3ccc(N[C@H](C)C(F)(F)F)cc3OC)c2Cl)CC[C@@H](S(C)(=O)=O)CC1]

The title compound was prepared as described for the synthesis of Example 1, using ethyl (R)-4-chloro-1-ethyl-5-(2-methoxy-4-((1,1,1-trifluoropropan-2-yl)amino)phenyl)-1H-pyrazole-3-carboxylate (Intermediate 106) in place of (R*)-4-chloro-1-ethyl-5-(2-methoxy-4-(3,3,3-trifluoro-2-methylpropyl)phenyl)-1H-pyrazole-3-carboxylic acid and ethyl (1r*,4r*)-1-(aminomethyl)-4-(methylsulfonyl)cyclohexane-1-carboxylate (Intermediate 125) in place of ((1r,4r)-4-(methylsulfonyl)cyclohexyl)methanamine hydrochloride. $^1$H NMR (500 MHz, CDCl$_3$) δ 7.39 (t, J=6.6 Hz, 1H), 7.06-7.02 (m, 1H), 6.38-6.34 (m, 1H), 6.27 (dd, J=4.8, 2.2 Hz, 1H), 4.25-4.20 (m, 2H), 4.12-4.05 (m, 1H), 4.01-3.88 (m, 2H), 3.83-3.74 (m, 5H), 2.87 (s, 3H), 2.86-2.80 (m, 1H), 2.23-2.17 (m, 2H), 2.06-1.91 (m, 4H), 1.88-1.81 (m, 2H), 1.46 (d, J=6.7 Hz, 3H), 1.35-1.30 (m, 6H); MS (ESI) m/z: [M+H]$^+$ Found 637.2.

Example 96

(1r*,4R*)-1-((4-Chloro-1-ethyl-5-(2-methoxy-4-(((R)-1,1,1-trifluoropropan-2-yl)amino)phenyl)-1H-pyrazole-3-carboxamido)methyl)-4-(methylsulfonyl)cyclohexane-1-carboxylic Acid

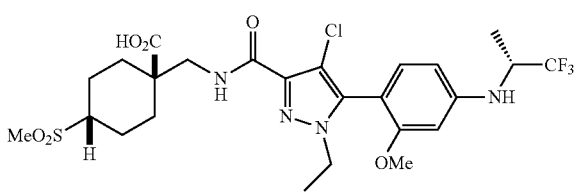 [SMILES: CCn1nc(C(=O)NC[C@]2(C(=O)O)CC[C@H](S(C)(=O)=O)CC2)c(Cl)c1-c1ccc(N[C@H](C)C(F)(F)F)cc1OC]

A mixture containing ethyl (1r*,4R*)-1-((4-chloro-1-ethyl-5-(2-methoxy-4-(((R)-1,1,1-trifluoropropan-2-yl)amino)phenyl)-1H-pyrazole-3-carboxamido)methyl)-4-(methylsulfonyl)cyclohexane-1-carboxylate (28 mg, 0.44 mmol, Example 95), 1.0 M aqueous NaOH solution (0.22 mL), and dioxane (0.5 mL) was stirred at rt. After 3 h, water was added followed by 1 M aqueous HCl solution until pH 3-4 was reached. The reaction mixture was then extracted with EtOAc, dried with anhydrous Na$_2$SO$_4$, filtered, and concentrated to furnish the title compound after lyophilization. $^1$H NMR (500 MHz, DMSO-d$_6$) δ 12.71 (s, 1H), 7.62-7.53 (m, 1H), 6.96 (d, J=8.3 Hz, 1H), 6.54-6.51 (m, 1H), 6.48-6.43 (m, 2H), 4.55-4.45 (m, 1H), 3.96-3.81 (m, 2H), 3.71 (s, 3H), 3.63-3.51 (m, 2H), 3.15-3.04 (m, 1H), 2.94 (s, 3H), 1.98-1.90 (m, 2H), 1.88-1.66 (m, 6H), 1.33 (d, J=6.6 Hz, 3H), 1.24-1.20 (m, 3H); MS (ESI) m/z: [M+H]$^+$ Found 609.0.

Example 97

(1s*,4S*)-1-((4-Chloro-1-ethyl-5-(2-methoxy-4-(((R)-1,1,1-trifluoropropan-2-yl)amino)phenyl)-1H-pyrazole-3-carboxamido)methyl)-4-(methylsulfonyl)cyclohexane-1-carboxylic Acid

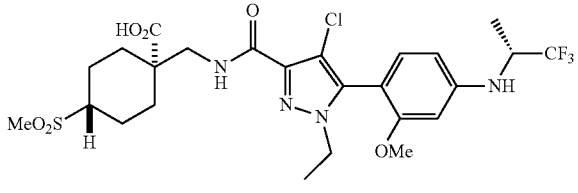 [SMILES: CCn1nc(C(=O)NC[C@]2(C(=O)O)CC[C@@H](S(C)(=O)=O)CC2)c(Cl)c1-c1ccc(N[C@H](C)C(F)(F)F)cc1OC]

The title compound was prepared as described for the synthesis of Example 96, using ethyl (1s*,4S*)-1-((4-chloro-1-ethyl-5-(2-methoxy-4-(((R)-1,1,1-trifluoropropan-2-yl)amino)phenyl)-1H-pyrazole-3-carboxamido)methyl)-4-(methylsulfonyl)cyclohexane-1-carboxylate (Example 94) in place ethyl (1r*,4R*)-1-((4-chloro-1-ethyl-5-(2-methoxy-4-(((R)-1,1,1-trifluoropropan-2-yl)amino)phenyl)-1H-pyrazole-3-carboxamido)methyl)-4-(methyl sulfonyl)cyclohexane-1-carboxylate. $^1$H NMR (500 MHz, DMSO-$d_6$) δ 12.59 (s, 1H), 7.90-7.85 (m, 1H), 6.95 (d, J=8.3 Hz, 1H), 6.54-6.51 (m, 1H), 6.48-6.43 (m, 2H), 4.55-4.44 (m, 1H), 3.96-3.83 (m, 2H), 3.72 (s, 3H), 3.42-3.31 (m, 2H), 3.12-3.02 (m, 1H), 2.89 (s, 3H), 2.17 (d, J=12.9 Hz, 2H), 2.04-1.97 (m, 2H), 1.47-1.36 (m, 2H), 1.35-1.26 (m, 5H), 1.26-1.22 (m, 3H); MS (ESI) m/z: [M+H]$^+$ Found 609.2.

Example 98

4-Chloro-5-(2-(difluoromethoxy)-4-(4,4,4-trifluoro-1-hydroxybutyl)phenyl)-1-ethyl-N-(((1s,4s)-1-hydroxy-4-(methylsulfonyl)cyclohexyl)methyl)-1H-pyrazole-3-carboxamide

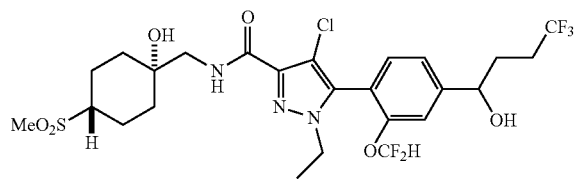

The title compound was prepared as described for the synthesis of Example 2, using ethyl 4-chloro-5-(2-(difluoromethoxy)-4-(4,4,4-trifluoro-1-hydroxybutyl)phenyl)-1-ethyl-1H-pyrazole-3-carboxylate (Intermediate 255) in place of ethyl 4-chloro-5-(2-(difluoromethoxy)-4-(3,3,3-trifluoro-2,2-dimethylpropyl)phenyl)-1-ethyl-1H-pyrazole-3-carboxylate, (1s,4s)-1-(aminomethyl)-4-(methylsulfonyl)cyclohexan-1-ol hydrochloride (Intermediate 9) in place of ((1r,4r)-4-(methylsulfonyl)cyclohexyl)methanamine hydrochloride, and DCM in place of MeCN as solvent in the amide-bond-forming step. $^1$H NMR (500 MHz, CDCl$_3$) δ 7.41-7.33 (m, 3H), 7.30-7.27 (m, 1H), 6.60-6.28 (m, 1H), 4.91-4.86 (m, 1H), 4.07-3.90 (m, 2H), 3.48 (d, J=6.3 Hz, 2H), 2.87-2.76 (m, 4H), 2.42-1.91 (m, 12H), 1.49-1.40 (m, 2H), 1.40-1.34 (m, 3H); MS (ESI) m/z: [M+H]$^+$ Found 632.1.

Example 99

4-Chloro-5-(2-(difluoromethoxy)-4-((S*)-4,4,4-trifluoro-2-hydroxybutan-2-yl)phenyl)-1-ethyl-N-(((1s,4R)-1-hydroxy-4-(methylsulfonyl)cyclohexyl)methyl)-1H-pyrazole-3-carboxamide

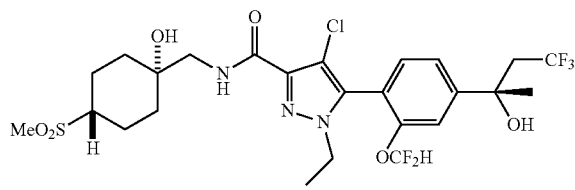

Example 100

4-Chloro-5-(2-(difluoromethoxy)-4-((R*)-4,4,4-trifluoro-2-hydroxybutan-2-yl)phenyl)-1-ethyl-N-(((1s,4S)-1-hydroxy-4-(methylsulfonyl)cyclohexyl)methyl)-1H-pyrazole-3-carboxamide

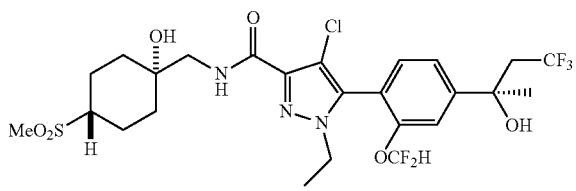

Intermediate 248 was purified by SFC using a chiral stationary phase (CYANO, 75% CO$_2$, 25% MeOH, 0.3% i-PrNH$_2$) to afford two isomers. The first-eluting isomer was Example 99: $^1$H NMR (400 MHz, CDCl$_3$) δ 7.57-7.32 (m, 3H), 7.26-7.20 (m, 1H), 6.65-6.22 (m, 1H), 4.09-3.88 (m, 2H), 3.47 (d, J=6.3 Hz, 2H), 3.02 (s, 1H), 2.88-2.62 (m, 6H), 2.32 (s, 1H), 2.19-2.09 (m, 2H), 2.06-1.91 (m, 4H), 1.78 (s, 3H), 1.50-1.33 (m, 5H); MS (ESI) m/z: [M+H]$^+$ Found 632.2. The second-eluting isomer was Example 100: $^1$H NMR (400 MHz, CDCl$_3$) δ 7.57-7.33 (m, 3H), 7.25-7.21 (m, 1H), 6.65-6.22 (m, 1H), 4.08-3.89 (m, 2H), 3.47 (d, J=6.3 Hz, 2H), 3.02 (s, 1H), 2.89-2.60 (m, 6H), 2.31 (s, 1H), 2.20-2.07 (m, 2H), 2.06-1.91 (m, 4H), 1.78 (s, 3H), 1.50-1.32 (m, 5H); MS (ESI) m/z: [M+H]$^+$ Found 632.2.

Example 101

4-Chloro-5-(2-(difluoromethoxy)-4-(5,5,5-trifluoro-2-hydroxypentan-2-yl)phenyl)-1-ethyl-N-(((1s,4s)-1-hydroxy-4-(methylsulfonyl)cyclohexyl)methyl)-1H-pyrazole-3-carboxamide

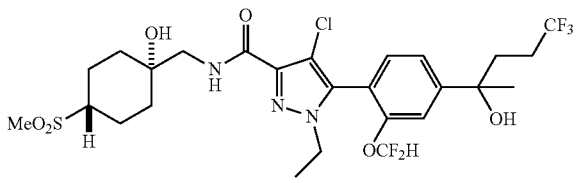

The title compound was prepared as described for the synthesis of Example 2, using ethyl 4-chloro-5-(2-(difluoromethoxy)-4-(5,5,5-trifluoro-2-hydroxypentan-2-yl)phenyl)-1-ethyl-1H-pyrazole-3-carboxylate (Intermediate 277) in place of ethyl 4-chloro-5-(2-(difluoromethoxy)-4-(3,3,3-trifluoro-2,2-dimethylpropyl)phenyl)-1-ethyl-1H-pyrazole-3-carboxylate, (1s,4s)-1-(aminomethyl)-4-(methyl sulfonyl)cyclohexan-1-ol hydrochloride (Intermediate 9) in place of ((1r,4r)-4-(methylsulfonyl)cyclohexyl)methanamine hydrochloride, and DCM in place of MeCN as solvent in the amide-bond-forming step. $^1$H NMR (400 MHz, CDCl$_3$) δ 7.50-7.32 (m, 3H), 7.26-7.21 (m, 1H), 6.64-6.23 (m, 1H), 4.07-3.88 (m, 2H), 3.47 (d, J=6.3 Hz, 2H), 3.05 (d, J=1.7 Hz, 1H), 2.90-2.73 (m, 4H), 2.38-2.21 (m, 1H), 2.18-1.89 (m, 9H), 1.81 (d, J=3.1 Hz, 1H), 1.67 (d, J=2.7 Hz, 3H), 1.49-1.34 (m, 5H); MS (ESI) m/z: [M+H]$^+$ Found 646.0.

Example 102

4-Chloro-5-(2-(difluoromethoxy)-4-((S*)-5,5,5-trifluoro-2-hydroxypentan-2-yl)phenyl)-1-ethyl-N-(((1s,4R)-1-hydroxy-4-(methylsulfonyl)cyclohexyl)methyl)-1H-pyrazole-3-carboxamide

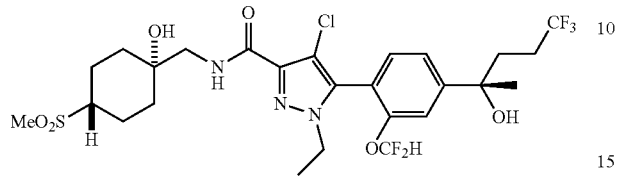

Example 103

4-Chloro-5-(2-(difluoromethoxy)-4-((R*)-5-trifluoro-2-hydroxypentan-2-yl)phenyl)-1-ethyl-N-(((1s,4S)-1-hydroxy-4-(methylsulfonyl)cyclohexyl)methyl)-1H-pyrazole-3-carboxamide

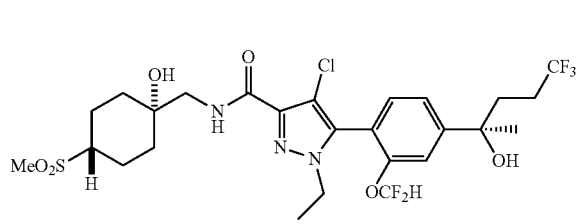

Example 101 was purified by SFC using a chiral stationary phase (Chiralcel OD-H, 85% CO$_2$, 15% EtOH) to afford two isomers. The first-eluting isomer was Example 102: $^1$H NMR (400 MHz, CDCl$_3$) δ 7.50-7.32 (m, 3H), 7.26-7.21 (m, 1H), 6.64-6.24 (m, 1H), 4.09-3.89 (m, 2H), 3.47 (d, J=6.3 Hz, 2H), 3.05 (s, 1H), 2.88-2.74 (m, 4H), 2.42-2.20 (m, 1H), 2.20-1.87 (m, 9H), 1.80 (d, J=3.9 Hz, 1H), 1.70-1.65 (m, 3H), 1.49-1.36 (m, 5H); MS (ESI) m/z: [M+H]$^+$ Found 646.2. The second-eluting isomer was Example 103: $^1$H NMR (500 MHz, CDCl$_3$) δ 7.49-7.33 (m, 3H), 7.26-7.20 (m, 1H), 6.59-6.27 (m, 1H), 4.09-3.89 (m, 2H), 3.47 (d, J=6.3 Hz, 2H), 3.06 (d, J=2.2 Hz, 1H), 2.90-2.73 (m, 4H), 2.37-2.20 (m, 1H), 2.18-1.89 (m, 9H), 1.81 (d, J=5.3 Hz, 1H), 1.67 (d, J=3.3 Hz, 3H), 1.49-1.35 (m, 5H); MS (ESI) m/z: [M+H]$^+$ Found 646.2.

Example 104

4-Chloro-5-(4-(4,4-difluoro-1-hydroxycyclohexyl)-2-(difluoromethoxy)phenyl)-1-ethyl-N-(((1s,4s)-1-hydroxy-4-(methylsulfonyl)cyclohexyl)methyl)-1H-pyrazole-3-carboxamide

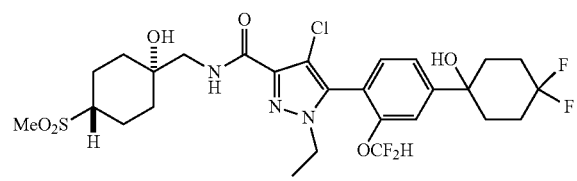

The title compound was prepared as described for the synthesis of Example 2, using ethyl 4-chloro-5-(4-(4,4-difluoro-1-hydroxycyclohexyl)-2-(difluoromethoxy)phenyl)-1-ethyl-1H-pyrazole-3-carboxylate (Intermediate 278) in place of ethyl 4-chloro-5-(2-(difluoromethoxy)-4-(3,3,3-trifluoro-2,2-dimethylpropyl)phenyl)-1-ethyl-1H-pyrazole-3-carboxylate, (1s,4s)-1-(aminomethyl)-4-(methylsulfonyl)cyclohexan-1-ol hydrochloride (Intermediate 9) in place of ((1r,4r)-4-(methylsulfonyl)cyclohexyl)methanamine hydrochloride, and DCM in place of MeCN as solvent in the amide-bond-forming step. $^1$H NMR (400 MHz, CDCl$_3$) δ 7.51 (s, 1H), 7.49-7.44 (m, 1H), 7.34 (d, J=8.0 Hz, 1H), 7.26-7.20 (m, 1H), 6.62-6.22 (m, 1H), 4.10-3.87 (m, 2H), 3.47 (d, J=6.3 Hz, 2H), 3.03 (s, 1H), 2.88-2.75 (m, 4H), 2.42-1.88 (m, 14H), 1.71 (s, 1H), 1.50-1.34 (m, 5H); MS (ESI) m/z: [M+H]$^+$ Found 640.0.

Example 105

4-Chloro-5-(2-(difluoromethoxy)-4-(3,3,3-trifluoro-2,2-dimethylpropanoyl)phenyl)-1-ethyl-N-(((1s,4s)-1-hydroxy-4-(methylsulfonyl)cyclohexyl)methyl)-1H-pyrazole-3-carboxamide

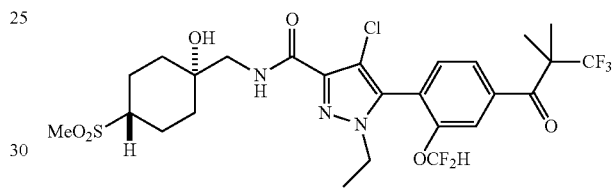

The title compound was prepared as described for the synthesis of Example 2, using ethyl 4-chloro-5-(2-(difluoromethoxy)-4-(3,3,3-trifluoro-2,2-dimethylpropanoyl)phenyl)-1-ethyl-1H-pyrazole-3-carboxylate (Intermediate 279) in place of ethyl 4-chloro-5-(2-(difluoromethoxy)-4-(3,3,3-trifluoro-2,2-dimethylpropyl)phenyl)-1-ethyl-1H-pyrazole-3-carboxylate, (1s,4s)-1-(aminomethyl)-4-(methylsulfonyl)cyclohexan-1-ol hydrochloride (Intermediate 9) in place of ((1r,4r)-4-(methylsulfonyl)cyclohexyl)methanamine hydrochloride, and DCM in place of MeCN as solvent in the amide-bond-forming step. $^1$H NMR (500 MHz, CDCl$_3$) δ 7.66-7.63 (m, 1H), 7.60 (s, 1H), 7.43 (d, J=8.0 Hz, 1H), 7.26-7.21 (m, 1H), 6.45 (dd, J=74.1, 70.5 Hz, 1H), 4.08-3.91 (m, 2H), 3.47 (d, J=6.4 Hz, 2H), 2.94 (s, 1H), 2.85-2.77 (m, 4H), 2.17-2.10 (m, 2H), 2.04-1.93 (m, 4H), 1.63-1.59 (m, 6H), 1.49-1.41 (m, 2H), 1.38 (t, J=7.3 Hz, 3H); MS (ESI) m/z: [M+H]$^+$ Found 644.1.

Example 106

4-Chloro-5-(2-(difluoromethoxy)-4-(3,3,3-trifluoro-1-hydroxy-2,2-dimethylpropyl)phenyl)-1-ethyl-N-(((1s,4s)-1-hydroxy-4-(methylsulfonyl)cyclohexyl)methyl)-1H-pyrazole-3-carboxamide

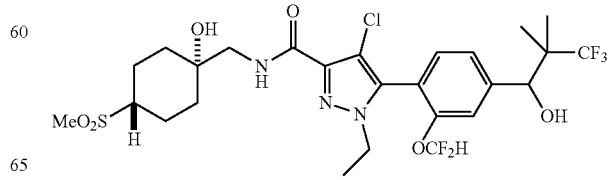

Sodium borohydride (30 mg, 0.79 mmol) was added to a stirring solution of 4-chloro-5-(2-(difluoromethoxy)-4-(3,3,3-trifluoro-2,2-dimethylpropanoyl)phenyl)-1-ethyl-N-(((1s,4s)-1-hydroxy-4-(methylsulfonyl)cyclohexyl)methyl)-1H-pyrazole-3-carboxamide (90 mg, 0.14 mmol, Example 105) in methanol (2 mL). After 10 minutes, water and EtOAc were added. The biphasic mixture was separated. The organic layer was dried with anhydrous Na$_2$SO$_4$, filtered, and purified by preparative HPLC to afford the title compound as a colorless solid after lyophilization. $^1$H NMR (500 MHz, CDCl$_3$) δ 7.40-7.31 (m, 3H), 6.57-6.24 (m, 1H), 5.00 (d, J=1.9 Hz, 1H), 4.08-3.89 (m, 2H), 3.48 (d, J=6.3 Hz, 2H), 2.88-2.75 (m, 4H), 2.13 (d, J=11.1 Hz, 2H), 2.04-1.93 (m, 5H coincident with water), 1.49-1.40 (m, 2H), 1.40-1.34 (m, 3H), 1.26 (d, J=4.4 Hz, 3H), 1.03 (s, 3H); MS (ESI) m/z: [M+H]$^+$ Found 646.0.

Example 107

4-Chloro-5-(2-(difluoromethoxy)-4-((S*)-3,3,3-trifluoro-1-hydroxy-2,2-dimethylpropyl)phenyl)-1-ethyl-N-(((1s,4R)-1-hydroxy-4-(methylsulfonyl)cyclohexyl)methyl)-1H-pyrazole-3-carboxamide

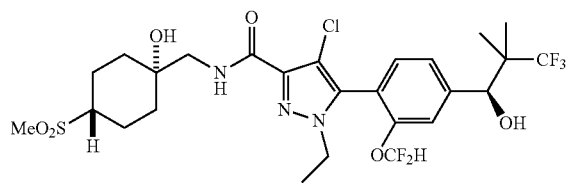

Example 108

4-Chloro-5-(2-(difluoromethoxy)-4-((R*)-3,3,3-trifluoro-1-hydroxy-2,2-dimethylpropyl)phenyl)-1-ethyl-N-(((1s,4S)-1-hydroxy-4-(methylsulfonyl)cyclohexyl)methyl)-1H-pyrazole-3-carboxamide

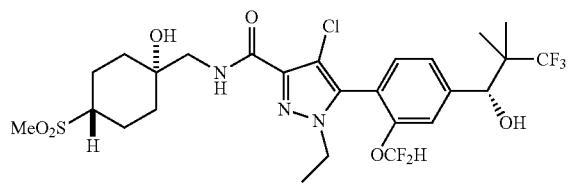

Example 106 was purified by SFC using a chiral stationary phase (Lux cellulose, 65% CO$_2$, 35% EtOH, 0.3% iPrNH$_2$) to afford two isomers. The first-eluting isomer was Example 107: $^1$H NMR (400 MHz, CDCl$_3$) δ 7.41-7.30 (m, 3H), 7.26-7.21 (m, 1H), 6.61-6.20 (m, 1H), 4.99 (s, 1H), 4.11-3.88 (m, 2H), 3.47 (d, J=6.3 Hz, 2H), 3.01 (s, 1H), 2.87-2.75 (m, 4H), 2.30 (s, 1H), 2.14 (d, J=10.6 Hz, 2H), 1.98 (d, J=12.1 Hz, 4H), 1.49-1.40 (m, 2H), 1.39-1.34 (m, 3H), 1.31-1.22 (m, 3H), 1.04 (s, 3H); MS (ESI) m/z: [M+H]$^+$ Found 646.0. The second-eluting isomer was Example 108: $^1$H NMR (400 MHz, CDCl$_3$) δ 7.40-7.30 (m, 3H), 7.25-7.20 (m, 1H), 6.61-6.22 (m, 1H), 5.00 (s, 1H), 4.08-3.88 (m, 2H), 3.47 (d, J=6.3 Hz, 2H), 3.06 (s, 1H), 2.87-2.75 (m, 4H), 2.31 (s, 1H), 2.14 (d, J=11.0 Hz, 2H), 1.98 (d, J=11.9 Hz, 4H), 1.48-1.30 (m, 5H), 1.30-1.23 (m, 3H), 1.04 (s, 3H); MS (ESI) m/z: [M+H]$^+$ Found 646.0.

Example 109

4-Chloro-5-(2-(difluoromethoxy)-4-(hydroxy(1-(trifluoromethyl)cyclopropyl)methyl)phenyl)-1-ethyl-N-(((1s,4s)-1-hydroxy-4-(methylsulfonyl)cyclohexyl)methyl)-1H-pyrazole-3-carboxamide

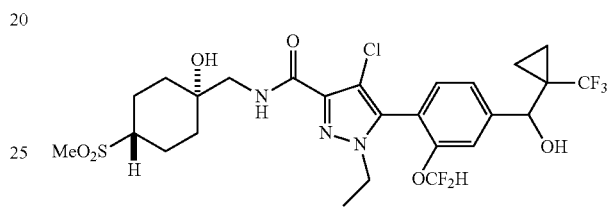

The title compound was prepared as described for the synthesis of Example 106, using 4-chloro-5-(2-(difluoromethoxy)-4-(1-(trifluoromethyl)cyclopropane-1-carbonyl)phenyl)-1-ethyl-N-(((1s,4s)-1-hydroxy-4-(methylsulfonyl)cyclohexyl)methyl)-1H-pyrazole-3-carboxamide (Intermediate 281) in place of 4-chloro-5-(2-(difluoromethoxy)-4-(3,3,3-trifluoro-2,2-dimethylpropanoyl)phenyl)-1-ethyl-N-(((1s,4s)-1-hydroxy-4-(methylsulfonyl)cyclohexyl)methyl)-1H-pyrazole-3-carboxamide. $^1$H NMR (400 MHz, CDCl$_3$) δ 7.41-7.30 (m, 3H), 7.22 (d, J=6.3 Hz, 1H), 6.63-6.21 (m, 1H), 5.25-5.19 (m, 1H), 4.07-3.88 (m, 2H), 3.48 (d, J=6.3 Hz, 2H), 3.03 (s, 1H), 2.81 (s, 4H), 2.35 (d, J=3.5 Hz, 1H), 2.14 (d, J=11.3 Hz, 2H), 2.06-1.90 (m, 4H), 1.50-1.39 (m, 2H), 1.39-1.33 (m, 3H), 1.15-0.99 (m, 3H), 0.66-0.58 (m, 1H); MS (ESI) m/z: [M+H]$^+$ Found 644.1.

Example 110

4-Chloro-5-(2-(difluoromethoxy)-4-((S*)-hydroxy(1-(trifluoromethyl)cyclopropyl)methyl)phenyl)-1-ethyl-N-(((1s,4R)-1-hydroxy-4-(methylsulfonyl)cyclohexyl)methyl)-1H-pyrazole-3-carboxamide

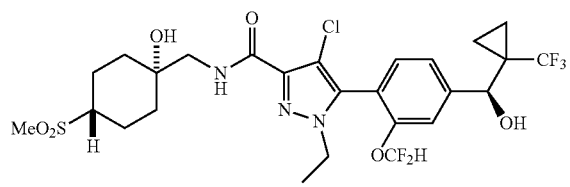

Example 111

4-Chloro-5-(2-(difluoromethoxy)-4-((R*)-hydroxy(1-(trifluoromethyl)cyclopropyl)methyl)phenyl)-1-ethyl-N-(((1s,4S)-1-hydroxy-4-(methylsulfonyl)cyclohexyl)methyl)-1H-pyrazole-3-carboxamide

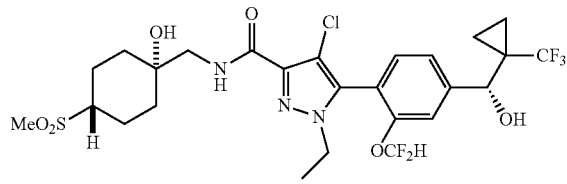

Example 109 was purified by SFC using a chiral stationary phase (Lux cellulose, 70% CO₂, 30% EtOH) to afford to isomers. The first-eluting isomer was Example 110: $^1$H NMR (400 MHz, CDCl₃) δ 7.40-7.30 (m, 3H), 7.26-7.21 (m, 1H), 6.62-6.22 (m, 1H), 5.22 (d, J=4.9 Hz, 1H), 4.09-3.87 (m, 2H), 3.47 (d, J=6.3 Hz, 2H), 2.88-2.75 (m, 4H), 2.21-2.07 (m, 2H), 2.07-1.91 (m, 4H), 1.51-1.40 (m, 2H), 1.40-1.31 (m, 3H), 1.15-0.98 (m, 3H), 0.68-0.57 (m, 1H); MS (ESI) m/z: [M+H]⁺ Found 644.3. The second-eluting isomer was Example 111: $^1$H NMR (400 MHz, CDCl₃) δ 7.39-7.30 (m, 3H), 7.25-7.22 (m, 1H), 6.61-6.22 (m, 1H), 5.22 (d, J=4.9 Hz, 1H), 4.07-3.87 (m, 2H), 3.47 (d, J=6.3 Hz, 2H), 2.89-2.74 (m, 4H), 2.19-2.09 (m, 2H), 2.05-1.91 (m, 4H), 1.51-1.38 (m, 2H), 1.38-1.31 (m, 3H), 1.14-0.98 (m, 3H), 0.69-0.57 (m, 1H); MS (ESI) m/z: [M+H]⁺ Found 644.3.

Example 112

4-Chloro-5-(2-(difluoromethoxy)-4-((1s*,4s*)-1-hydroxy-4-(trifluoromethyl)cyclohexyl)phenyl)-1-ethyl-N-(((1s,4S)-1-hydroxy-4-(methylsulfonyl)cyclohexyl)methyl)-1H-pyrazole-3-carboxamide

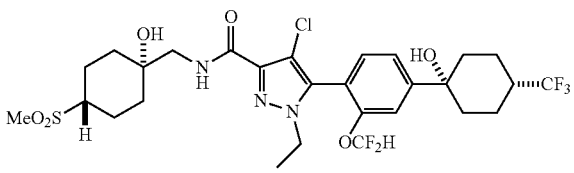

The title compound was prepared as described for the synthesis of Example 2, using ethyl 4-chloro-5-(2-(difluoromethoxy)-4-((1s*,4s*)-1-hydroxy-4-(trifluoromethyl)cyclohexyl)phenyl)-1-ethyl-1H-pyrazole-3-carboxylate (Intermediate 144) in place of ethyl 4-chloro-5-(2-(difluoromethoxy)-4-(3,3,3-trifluoro-2,2-dimethylpropyl)phenyl)-1-ethyl-1H-pyrazole-3-carboxylate, (1s,4s)-1-(aminomethyl)-4-(methylsulfonyl)cyclohexan-1-ol hydrochloride (Intermediate 9) in place of ((1r,4r)-4-(methylsulfonyl)cyclohexyl)methanamine hydrochloride, and DCM in place of MeCN as solvent in the amide-bond-forming step. $^1$H NMR (400 MHz, CDCl₃) δ 7.50 (s, 1H), 7.48-7.44 (m, 1H), 7.33 (d, J=8.0 Hz, 1H), 7.26-7.20 (m, 1H), 6.61-6.22 (m, 1H), 4.08-3.88 (m, 2H), 3.48 (d, J=6.3 Hz, 2H), 3.03 (s, 1H), 2.86-2.74 (m, 4H), 2.21-2.08 (m, 3H), 2.06-1.82 (m, 12H), 1.72 (s, 1H), 1.49-1.33 (m, 5H); MS (ESI) m/z: [M+H]⁺ Found 672.1.

Example 113

4-Chloro-5-(2-(difluoromethoxy)-4-((1r*,4r*)-1-hydroxy-4-(trifluoromethyl)cyclohexyl)phenyl)-1-ethyl-N-(((1s,4s)-1-hydroxy-4-(methylsulfonyl)cyclohexyl)methyl)-1H-pyrazole-3-carboxamide

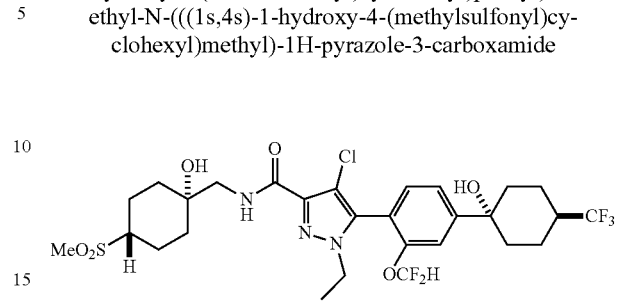

The title compound was prepared as described for the synthesis of Example 2, using ethyl 4-chloro-5-(2-(difluoromethoxy)-4-((1r*,4r*)-1-hydroxy-4-(trifluoromethyl)cyclohexyl)phenyl)-1-ethyl-1H-pyrazole-3-carboxylate (Intermediate 145) in place of ethyl 4-chloro-5-(2-(difluoromethoxy)-4-(3,3,3-trifluoro-2,2-dimethylpropyl)phenyl)-1-ethyl-1H-pyrazole-3-carboxylate, (1s,4s)-1-(aminomethyl)-4-(methylsulfonyl)cyclohexan-1-ol hydrochloride (Intermediate 9) in place of ((1r,4r)-4-(methylsulfonyl)cyclohexyl)methanamine hydrochloride, and DCM in place of MeCN as solvent in the amide-bond-forming step. $^1$H NMR (400 MHz, CDCl₃) δ 7.51-7.45 (m, 2H), 7.36 (d, J=8.0 Hz, 1H), 7.26-7.22 (m, 1H), 6.62-6.20 (m, 1H), 4.08-3.88 (m, 2H), 3.47 (d, J=6.3 Hz, 2H), 3.06 (s, 1H), 2.87-2.75 (m, 4H), 2.42-2.26 (m, 3H), 2.17-1.91 (m, 8H), 1.83-1.71 (m, 5H), 1.49-1.35 (m, 5H); MS (ESI) m/z: [M+H]⁺ Found 672.0.

Example 114

4-Chloro-5-(2-(difluoromethoxy)-4-((1s*,4s*)-1-hydroxy-4-(trifluoromethyl)cyclohexyl)phenyl)-1-ethyl-N-(((1r,4r)-4-(methylsulfonyl)cyclohexyl)methyl)-1H-pyrazole-3-carboxamide

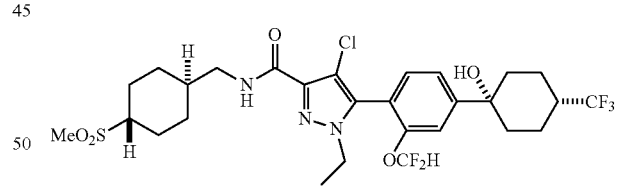

The title compound was prepared as described for the synthesis of Example 2, using ethyl 4-chloro-5-(2-(difluoromethoxy)-4-((1s*,4s*)-1-hydroxy-4-(trifluoromethyl)cyclohexyl)phenyl)-1-ethyl-1H-pyrazole-3-carboxylate (Intermediate 144) in place of ethyl 4-chloro-5-(2-(difluoromethoxy)-4-(3,3,3-trifluoro-2,2-dimethylpropyl)phenyl)-1-ethyl-1H-pyrazole-3-carboxylate and DCM in place of MeCN as solvent in the amide-bond-forming step. $^1$H NMR (400 MHz, CDCl₃) δ 7.50 (s, 1H), 7.48-7.43 (m, 1H), 7.35-7.32 (m, 1H), 6.99-6.91 (m, 1H), 6.41 (dd, J=75.3, 70.9 Hz, 1H), 4.08-3.87 (m, 2H), 3.39-3.29 (m, 2H), 2.89-2.76 (m, 4H), 2.34-2.23 (m, 2H), 2.23-2.03 (m, 3H), 2.02-1.81 (m, 8H), 1.75-1.55 (m, 4H), 1.41-1.32 (m, 3H), 1.22-1.07 (m, 2H); MS (ESI) m/z: [M+H]⁺ Found 656.1.

Example 115

4-Chloro-5-(2-(difluoromethoxy)-4-((1r*,4r*)-1-hydroxy-4-(trifluoromethyl)cyclohexyl)phenyl)-1-ethyl-N-(((1r,4r)-4-(methylsulfonyl)cyclohexyl)methyl)-1H-pyrazole-3-carboxamide

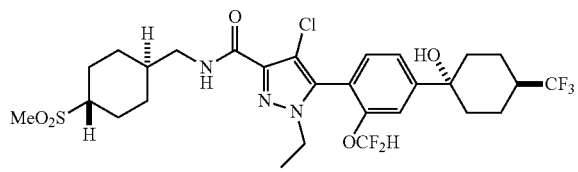

The title compound was prepared as described for the synthesis of Example 2, using ethyl 4-chloro-5-(2-(difluoromethoxy)-4-((r*,4r*)-1-hydroxy-4-(trifluoromethyl)cyclohexyl)phenyl)-1-ethyl-1H-pyrazole-3-carboxylate (Intermediate 145) in place of ethyl 4-chloro-5-(2-(difluoromethoxy)-4-(3,3,3-trifluoro-2,2-dimethylpropyl)phenyl)-1-ethyl-1H-pyrazole-3-carboxylate and DCM in place of MeCN as solvent in the amide-bond-forming step. $^1$H NMR (400 MHz, CDCl$_3$) δ 7.51-7.45 (m, 2H), 7.36 (d, J=7.9 Hz, 1H), 6.98-6.92 (m, 1H), 6.60-6.20 (m, 1H), 4.08-3.88 (m, 2H), 3.39-3.30 (m, 2H), 2.89-2.77 (m, 4H), 2.42-2.24 (m, 5H), 2.16-2.03 (m, 4H), 1.85-1.56 (m, 8H), 1.41-1.33 (m, 3H), 1.21-1.08 (m, 2H); MS (ESI) m/z: [M+H]$^+$ Found 656.1.

Example 116

4-Chloro-5-(2-(difluoromethoxy)-4-(1,1,1,3,3,3-hexafluoro-2-hydroxypropan-2-yl)phenyl)-1-ethyl-N-(((1r,4r)-4-(methylsulfonyl)cyclohexyl)methyl)-1H-pyrazole-3-carboxamide

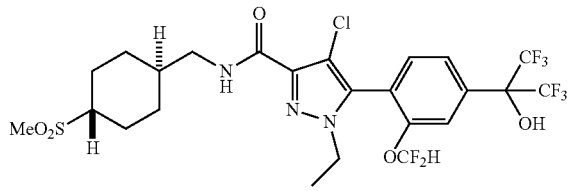

The title compound was prepared as described for the synthesis of Example 2, using ethyl 4-chloro-5-(2-(difluoromethoxy)-4-(1,1,1,3,3,3-hexafluoro-2-hydroxypropan-2-yl)phenyl)-1-ethyl-1H-pyrazole-3-carboxylate (Intermediate 143) in place of ethyl 4-chloro-5-(2-(difluoromethoxy)-4-(3,3,3-trifluoro-2,2-dimethylpropyl)phenyl)-1-ethyl-1H-pyrazole-3-carboxylate and DCM in place of MeCN as solvent in the amide-bond-forming step. $^1$H NMR (400 MHz, CDCl$_3$) δ 7.77-7.68 (m, 2H), 7.48-7.42 (m, 1H), 7.01-6.93 (m, 1H), 6.43 (dd, J=74.6, 70.5 Hz, 1H), 4.24 (s, 1H), 4.10-3.87 (m, 2H), 3.35 (t, J=6.5 Hz, 2H), 2.92-2.75 (m, 4H), 2.35-2.23 (m, 2H), 2.14-2.02 (m, 2H), 1.77-1.53 (m, 3H coincident with water), 1.43-1.36 (m, 3H), 1.23-1.08 (m, 2H); MS (ESI) m/z: [M+H]$^+$ Found 656.1.

Example 117

4-Chloro-5-(2-(difluoromethoxy)-4-(1,1,1,3,3,3-hexafluoro-2-hydroxypropan-2-yl)phenyl)-1-ethyl-N-(((1s,4s)-1-hydroxy-4-(methylsulfonyl)cyclohexyl)methyl)-1H-pyrazole-3-carboxamide

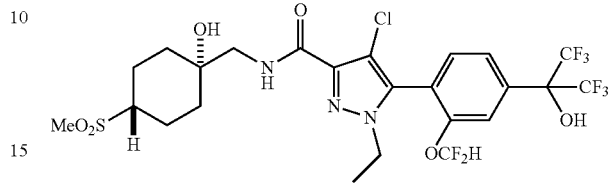

The title compound was prepared as described for the synthesis of Example 1, using ethyl 4-chloro-5-(2-(difluoromethoxy)-4-(1,1,1,3,3,3-hexafluoro-2-hydroxypropan-2-yl)phenyl)-1-ethyl-1H-pyrazole-3-carboxylate (Intermediate 143) in place of ethyl (R*)-4-chloro-1-ethyl-5-(2-methoxy-4-(3,3,3-trifluoro-2-methylpropyl)phenyl)-1H-pyrazole-3-carboxylate and (1s,4s)-1-(aminomethyl)-4-(methylsulfonyl)cyclohexan-1-ol hydrochloride (Intermediate 9) in place of ((1r,4r)-4-(methylsulfonyl)cyclohexyl)methanamine hydrochloride. $^1$H NMR (400 MHz, CDCl$_3$) δ 7.77-7.70 (m, 2H), 7.49-7.44 (m, 1H), 7.26-7.22 (m, 1H), 6.45 (dd, J=74.4, 70.5 Hz, 1H), 4.20-3.89 (m, 3H), 3.49 (d, J=6.3 Hz, 2H), 3.03 (s, 1H), 2.89-2.75 (m, 4H), 2.21-2.08 (m, 2H), 2.07-1.92 (m, 4H), 1.51-1.36 (m, 5H); MS (ESI) m/z: [M+H]$^+$ Found 672.0.

Example 118

Ethyl (1s*,4s*)-1-((4-chloro-5-(2-(difluoromethoxy)-4-(3,3,3-trifluoro-2,2-dimethylpropyl)phenyl)-1-ethyl-1H-pyrazole-3-carboxamido)methyl)-4-(methylsulfonyl)cyclohexane-1-carboxylate

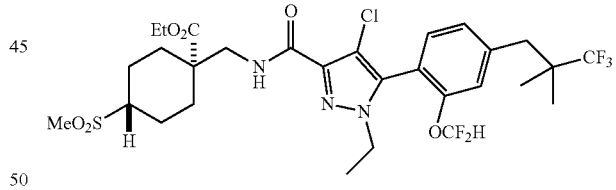

The title compound was prepared as described for the synthesis of Example 1, using ethyl 4-chloro-5-(2-(difluoromethoxy)-4-(3,3,3-trifluoro-2,2-dimethylpropyl)phenyl)-1-ethyl-1H-pyrazole-3-carboxylate (Intermediate 103) in place of ethyl (R*)-4-chloro-1-ethyl-5-(2-methoxy-4-(3,3,3-trifluoro-2-methylpropyl)phenyl)-1H-pyrazole-3-carboxylate and ethyl (1s*,4s*)-1-(aminomethyl)-4-(methylsulfonyl)cyclohexane-1-carboxylate (Intermediate 124) in place of ((1r,4r)-4-(methylsulfonyl)cyclohexyl)methanamine hydrochloride. $^1$H NMR (500 MHz, CDCl$_3$) δ 7.28 (d, J=7.8 Hz, 1H), 7.18 (dd, J=7.8, 1.6 Hz, 1H), 7.14 (s, 1H), 7.07 (t, J=6.4 Hz, 1H), 6.38 (dd, J=75.1, 70.9 Hz, 1H), 4.26 (q, J=7.1 Hz, 2H), 4.06-3.89 (m, 2H), 3.57 (d, J=6.5 Hz, 2H), 2.91-2.79 (m, 6H), 2.51-2.44 (m, 2H), 2.24-2.15 (m, 2H), 1.78-1.65 (m, 2H), 1.45-1.30 (m, 8H), 1.13 (s, 6H). MS (ESI) m/z: [M+H]$^+$ Found 686.2.

Example 119

(1s*,4s*)-1-((4-Chloro-5-(2-(difluoromethoxy)-4-(3,3,3-trifluoro-2,2-dimethylpropyl)phenyl)-1-ethyl-1H-pyrazole-3-carboxamido)methyl)-4-(methylsulfonyl)cyclohexane-1-carboxylic Acid

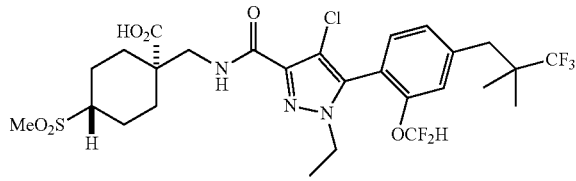

Aqueous NaOH (0.62 mL, 1.0 M, 0.62 mmol) was added to a solution of (1s*,4s*)-1-((4-chloro-5-(2-(difluoromethoxy)-4-(3,3,3-trifluoro-2,2-dimethylpropyl)phenyl)-1-ethyl-1H-pyrazole-3-carboxamido)methyl)-4-(methylsulfonyl)cyclohexane-1-carboxylate (83.9 mg, 0.122 mmol, Example 118) in 1,4-dioxane (1.3 mL) and the mixture was stirred at rt overnight. After this time, 1 N HCl was added to the reaction to acidify the mixture to pH 2. Ethyl acetate was added, the layers were separated, and the aqueous layer was extracted with EtOAc. The combined organic layers were dried with anhydrous magnesium sulfate, filtered, and concentrated to dryness to provide the title compound without further purification. $^1$H NMR (500 MHz, CDCl$_3$) δ 7.36-7.31 (m, 1H), 7.29-7.27 (m, 1H), 7.18 (dd, J=7.9, 1.6 Hz, 1H), 7.14 (s, 1H), 6.53-6.23 (m, 1H), 4.04-3.90 (m, 2H), 3.81 (d, J=6.7 Hz, 2H), 2.91-2.81 (m, 6H), 2.22 (d, J=12.6 Hz, 2H), 2.09 (d, J=13.7 Hz, 2H), 2.06-1.95 (m, 2H), 1.95-1.86 (m, 2H), 1.36-1.32 (m, 3H), 1.13 (s, 6H). MS (ESI) m/z: [M+H]$^+$ Found 657.8.

Example 120

Ethyl (1r*,4r*)-1-((4-chloro-5-(2-(difluoromethoxy)-4-(3,3,3-trifluoro-2,2-dimethylpropyl)phenyl)-1-ethyl-1H-pyrazole-3-carboxamido)methyl)-4-(methylsulfonyl)cyclohexane-1-carboxylate

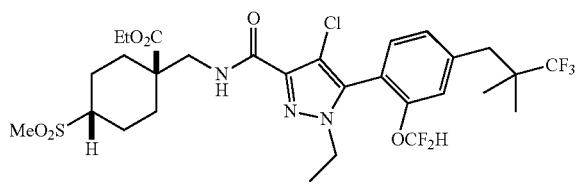

The title compound was prepared as described for the synthesis of Example 118, using ethyl (1r*,4r*)-1-(aminomethyl)-4-(methylsulfonyl)cyclohexane-1-carboxylate (Intermediate 125) in place of ethyl (1s*,4s*)-1-(aminomethyl)-4-(methylsulfonyl)cyclohexane-1-carboxylate. $^1$H NMR (500 MHz, CDCl$_3$) δ 7.28 (d, J=7.8 Hz, 1H), 7.18 (dd, J=7.8, 1.6 Hz, 1H), 7.14 (s, 1H), 7.07 (t, J=6.4 Hz, 1H), 6.38 (dd, J=75.1, 70.9 Hz, 1H), 4.26 (q, J=7.1 Hz, 2H), 4.06-3.89 (m, 2H), 3.57 (d, J=6.5 Hz, 2H), 2.91-2.79 (m, 6H), 2.48 (dt, J=14.1, 3.2 Hz, 2H), 2.24-2.15 (m, 2H), 1.78-1.65 (m, 2H), 1.45-1.30 (m, 8H), 1.13 (s, 6H). MS (ESI) m/z: [M+H]$^+$ Found 686.2.

Example 121

(1r*,4r*)-1-((4-Chloro-5-(2-(difluoromethoxy)-4-(3,3,3-trifluoro-2,2-dimethylpropyl)phenyl)-1-ethyl-1H-pyrazole-3-carboxamido)methyl)-4-(methylsulfonyl)cyclohexane-1-carboxylic Acid

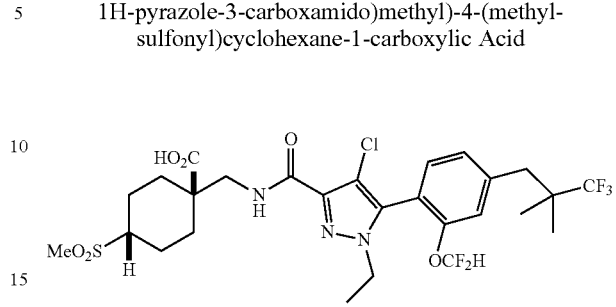

The title compound was prepared as described for the synthesis of Example 119, using ethyl (1r*,4r*)-1-((4-chloro-5-(2-(difluoromethoxy)-4-(3,3,3-trifluoro-2,2-dimethylpropyl)phenyl)-1-ethyl-1H-pyrazole-3-carboxamido)methyl)-4-(methylsulfonyl)cyclohexane-1-carboxylate (Example 120) in place of (1s*,4s*)-1-((4-chloro-5-(2-(difluoromethoxy)-4-(3,3,3-trifluoro-2,2-dimethylpropyl)phenyl)-1-ethyl-1H-pyrazole-3-carboxamido)methyl)-4-(methylsulfonyl)cyclohexane-1-carboxylate. $^1$H NMR (500 MHz, CDCl$_3$) δ 7.36-7.24 (m, 2H), 7.24-7.16 (m, 1H), 7.14 (s, 1H), 6.39 (dd, J=74.9, 70.9 Hz, 1H), 4.05-3.90 (m, 2H), 3.69-3.60 (m, 2H), 2.93-2.75 (m, 6H), 2.49 (d, J=13.5 Hz, 2H), 2.27-2.17 (m, 2H), 1.85-1.72 (m, 2H), 1.50-1.39 (m, 2H), 1.34 (t, J=7.2 Hz, 3H), 1.13 (s, 6H). MS (ESI) m/z: [M+H]$^+$ Found 658.2.

Example 122

4-Cyano-1-ethyl-N-(((1s,4s)-1-hydroxy-4-(methylsulfonyl)cyclohexyl)methyl)-5-(2-methoxy-4-(3,3,3-trifluoro-2-methylpropyl)phenyl)-1H-pyrazole-3-carboxamide

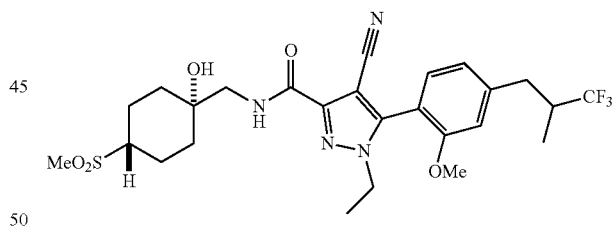

The title compound was prepared as described for the synthesis of Example 1, using ethyl 4-cyano-1-ethyl-5-(2-methoxy-4-(3,3,3-trifluoro-2-methylpropyl)phenyl)-1H-pyrazole-3-carboxylate (Intermediate 152) in place of ethyl (R*)-4-chloro-1-ethyl-5-(2-methoxy-4-(3,3,3-trifluoro-2-methylpropyl)phenyl)-1H-pyrazole-3-carboxylate and (1s,4s)-1-(aminomethyl)-4-(methylsulfonyl)cyclohexan-1-ol hydrochloride (Intermediate 9) in place of ((1r,4r)-4-(methylsulfonyl)cyclohexyl)methanamine hydrochloride. $^1$H NMR (400 MHz, CDCl$_3$) δ 7.24 (d, J=7.7 Hz, 1H), 7.21-7.15 (m, 1H), 6.93 (dd, J=7.8, 1.4 Hz, 1H), 6.84 (s, 1H), 4.01 (q, J=7.0 Hz, 2H), 3.85 (s, 3H), 3.49 (d, J=6.3 Hz, 2H), 3.16 (d, J=11.6 Hz, 1H), 2.83-2.76 (m, 4H), 2.60-2.43 (m, 2H), 2.13 (d, J=10.9 Hz, 2H), 2.05-1.91 (m, 4H), 1.52-1.37 (m, 5H), 1.10 (d, J=6.3 Hz, 3H). MS (ESI) m/z: [M+H]$^+$ Found 571.2.

Example 123

4-Cyano-1-ethyl-5-(2-methoxy-4-(3,3,3-trifluoro-2-methylpropyl)phenyl)-N-(((1r,4r)-4-(methylsulfonyl)cyclohexyl)methyl)-1H-pyrazole-3-carboxamide

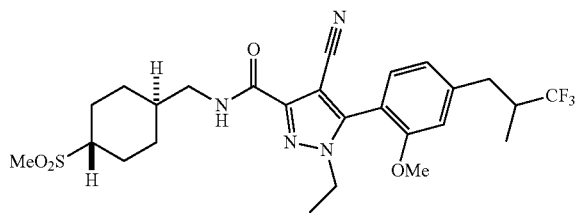 [SMILES: CCn1nc(C(=O)NC[C@H]2CC[C@H](S(C)(=O)=O)CC2)c(C#N)c1-c1ccc(CC(C)C(F)(F)F)cc1OC]

The title compound was prepared as described for the synthesis of Example 1, using ethyl 4-cyano-1-ethyl-5-(2-methoxy-4-(3,3,3-trifluoro-2-methylpropyl)phenyl)-1H-pyrazole-3-carboxylate (Intermediate 152) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (400 MHz, CDCl$_3$) δ 7.24 (d, J=7.7 Hz, 1H), 6.93 (dd, J=7.7, 1.5 Hz, 1H), 6.89 (t, J=6.3 Hz, 1H), 6.83 (d, J=1.5 Hz, 1H), 4.00 (q, J=7.0 Hz, 2H), 3.85 (s, 3H), 3.42-3.33 (m, 2H), 3.20-3.13 (m, 1H), 2.89-2.79 (m, 4H), 2.59-2.45 (m, 2H), 2.33-2.25 (m, 2H), 2.13-2.03 (m, 2H), 1.66-1.54 (m, 1H), 1.77-1.66 (m, 2H), 1.40 (t, J=7.2 Hz, 3H), 1.21-1.05 (m, 5H). MS (ESI) m/z: [M+H]$^+$ Found 555.3.

Example 124

4-Cyano-1-ethyl-N-(((1s,4s)-1-hydroxy-4-(methylsulfonyl)cyclohexyl)methyl)-5-(2-methoxy-4-(3,3,3-trifluoropropyl)phenyl)-1H-pyrazole-3-carboxamide

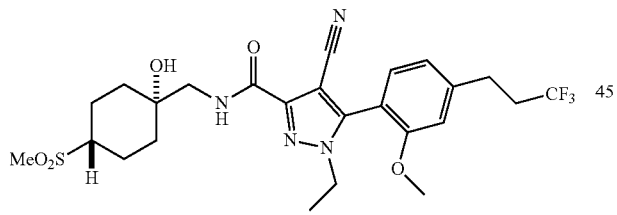

The title compound was prepared as described for the synthesis of Example 1, using ethyl 4-cyano-1-ethyl-5-(2-methoxy-4-(3,3,3-trifluoropropyl)phenyl)-1H-pyrazole-3-carboxylate (Intermediate 153) in place of ethyl (R*)-4-chloro-1-ethyl-5-(2-methoxy-4-(3,3,3-trifluoro-2-methylpropyl)phenyl)-1H-pyrazole-3-carboxylate and (1s,4s)-1-(aminomethyl)-4-(methylsulfonyl)cyclohexan-1-ol hydrochloride (Intermediate 9) in place of ((1r,4r)-4-(methylsulfonyl)cyclohexyl)methanamine hydrochloride. $^1$H NMR (500 MHz, CDCl$_3$) δ 7.26-7.23 (m, 1H), 7.18 (t, J=6.2 Hz, 1H), 6.95 (dd, J=7.7, 1.5 Hz, 1H), 6.87 (d, J=1.5 Hz, 1H), 4.01 (q, J=7.1 Hz, 2H), 3.85 (s, 3H), 3.49 (d, J=6.3 Hz, 2H), 2.98-2.91 (m, 2H), 2.84 (s, 3H), 2.82-2.77 (m, 1H), 2.51-2.40 (m, 2H), 2.17-2.10 (m, 2H), 2.04-1.92 (m, 4H), 1.50-1.42 (m, 2H), 1.40 (t, J=7.2 Hz, 3H). MS (ESI) m/z: [M+H]$^+$ Found 556.9.

Example 125

4-Cyano-1-ethyl-5-(2-methoxy-4-(3,3,3-trifluoropropyl)phenyl)-N-(((1r,4r)-4-(methylsulfonyl)cyclohexyl)methyl)-1H-pyrazole-3-carboxamide

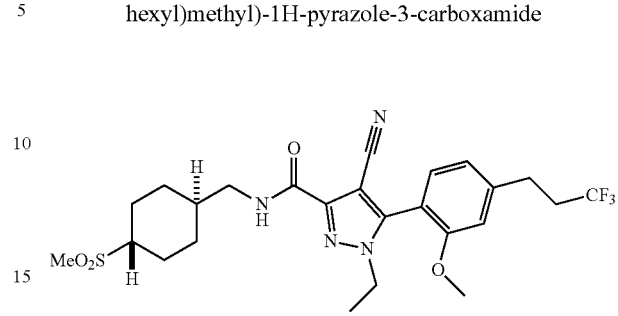

The title compound was prepared as described for the synthesis of Example 1, using ethyl 4-cyano-1-ethyl-5-(2-methoxy-4-(3,3,3-trifluoropropyl)phenyl)-1H-pyrazole-3-carboxylate (Intermediate 153) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (500 MHz, CDCl$_3$) δ 7.25-7.23 (m, 1H), 6.95 (dd, J=7.8, 1.5 Hz, 1H), 6.90-6.86 (m, 2H), 4.00 (q, J=7.1 Hz, 2H), 3.85 (s, 3H), 3.36 (t, J=6.6 Hz, 2H), 2.98-2.92 (m, 2H), 2.87-2.80 (m, 4H), 2.52-2.39 (m, 2H), 2.29 (d, J=12.4 Hz, 2H), 2.07 (d, J=12.8 Hz, 2H), 1.75-1.65 (m, 1H), 1.65-1.57 (m, 2H), 1.40 (t, J=7.3 Hz, 3H), 1.14 (qd, J=13.1, 3.3 Hz, 2H). MS (ESI) m/z: [M+H]$^+$ Found 540.9.

Example 126

4-Cyano-1-ethyl-N-(((1s,4s)-1-hydroxy-4-(methylsulfonyl)cyclohexyl)methyl)-5-(2-methoxy-4-(3,3,3-trifluoro-2,2-dimethylpropyl)phenyl)-1H-pyrazole-3-carboxamide

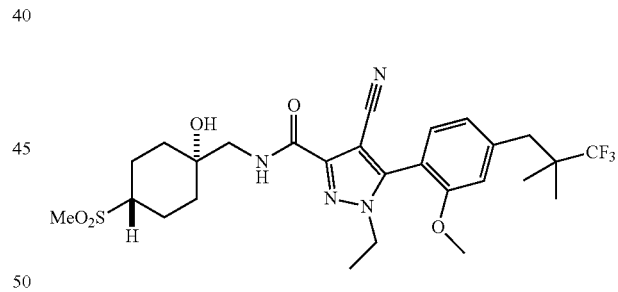

The title compound was prepared as described for the synthesis of Example 1, using ethyl 4-cyano-1-ethyl-5-(2-methoxy-4-(3,3,3-trifluoro-2,2-dimethylpropyl)phenyl)-1H-pyrazole-3-carboxylate (Intermediate 154) in place of ethyl (R*)-4-chloro-1-ethyl-5-(2-methoxy-4-(3,3,3-trifluoro-2-methylpropyl)phenyl)-1H-pyrazole-3-carboxylate and (1s,4s)-1-(aminomethyl)-4-(methylsulfonyl)cyclohexan-1-ol hydrochloride (Intermediate 9) in place of ((1r,4r)-4-(methylsulfonyl)cyclohexyl)methanamine hydrochloride. $^1$H NMR (500 MHz, CDCl$_3$) δ 7.23 (d, J=7.7 Hz, 1H), 7.18 (t, J=6.2 Hz, 1H), 6.92 (dd, J=7.8, 1.5 Hz, 1H), 6.82 (d, J=1.5 Hz, 1H), 4.01 (q, J=7.2 Hz, 2H), 3.84 (s, 3H), 3.49 (d, J=6.3 Hz, 2H), 2.86-2.80 (m, 6H), 2.70 (s, 1H), 2.14 (d, J=10.9 Hz, 2H), 2.03-1.93 (m, 4H), 1.50-1.43 (m, 2H), 1.41 (t, J=7.2 Hz, 3H), 1.13 (s, 6H). MS (ESI) m/z: [M+H]$^+$ Found 585.3.

Example 127

4-Cyano-1-ethyl-5-(2-methoxy-4-(3,3,3-trifluoro-2,2-dimethylpropyl)phenyl)-N-(((1r,4r)-4-(methylsulfonyl)cyclohexyl)methyl)-1H-pyrazole-3-carboxamide

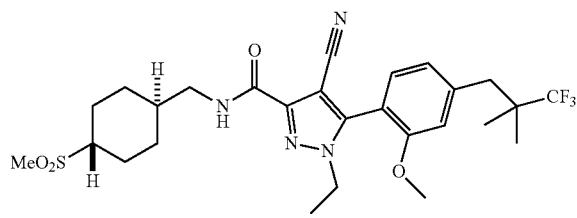 [SMILES: CCn1nc(C(=O)NC[C@H]2CC[C@H](S(C)(=O)=O)CC2)c(C#N)c1-c1ccc(CC(C)(C)C(F)(F)F)cc1OC]

The title compound was prepared as described for the synthesis of Example 1, using ethyl 4-cyano-1-ethyl-5-(2-methoxy-4-(3,3,3-trifluoro-2,2-dimethylpropyl)phenyl)-1H-pyrazole-3-carboxylate (Intermediate 154) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (500 MHz, CDCl$_3$) δ 7.23 (d, J=7.7 Hz, 1H), 6.91 (dd, J=7.7, 1.5 Hz, 1H), 6.88 (t, J=6.4 Hz, 1H), 6.82 (d, J=1.5 Hz, 1H), 4.04-3.97 (m, 2H), 3.84 (s, 3H), 3.36 (t, J=6.6 Hz, 2H), 2.87-2.79 (m, 6H), 2.29 (d, J=12.6 Hz, 2H), 2.07 (d, J=13.0 Hz, 2H), 1.74-1.66 (m, 1H), 1.65-1.56 (m, 2H), 1.41 (t, J=7.2 Hz, 3H), 1.19-1.09 (m, 8H). MS (ESI) m/z: [M+H]$^+$ Found 569.2.

Example 128

N-((1-Amino-4-(methylsulfonyl)cyclohexyl)methyl)-4-chloro-1-ethyl-5-(2-methoxy-4-(3,3,3-trifluoro-2-methylpropyl)phenyl)-1H-pyrazole-3-carboxamide

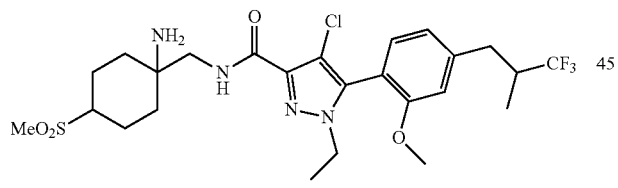

The title compound was prepared as described for the synthesis of Example 1, using ethyl 4-chloro-1-ethyl-5-(2-methoxy-4-(3,3,3-trifluoro-2-methylpropyl)phenyl)-1H-pyrazole-3-carboxylate (Intermediate 98) in place of ethyl (R*)-4-chloro-1-ethyl-5-(2-methoxy-4-(3,3,3-trifluoro-2-methylpropyl)phenyl)-1H-pyrazole-3-carboxylate and 1-(aminomethyl)-4-(methylsulfonyl)cyclohexan-1-amine (Intermediate 150, Step d) in place of ((1r,4r)-4-(methylsulfonyl)cyclohexyl)methanamine hydrochloride. $^1$H NMR (500 MHz, CD$_3$OD) δ 7.11 (dd, J=7.7, 1.3 Hz, 1H), 6.96 (s, 1H), 6.92-6.88 (m, 1H), 3.96-3.82 (m, 2H), 3.73 (s, 3H), 3.48-3.37 (m, 2H), 3.08 (dd, J=13.1, 3.6 Hz, 1H), 2.98-2.89 (m, 1H), 2.84 (s, 3H), 2.64-2.48 (m, 2H), 2.06-1.98 (m, 2H), 1.88-1.73 (m, 4H), 1.40-1.31 (m, 2H), 1.22 (t, J=7.2 Hz, 3H), 0.99 (d, J=6.6 Hz, 3H). MS (ESI) m/z: [M+H]$^+$ Found 579.2.

Example 129

4-Chloro-1-(2-cyanoethyl)-5-(2-methoxy-4-(((R)-1,1,1-trifluoropropan-2-yl)amino)phenyl)-N-(((1r,4R)-4-(methylsulfonyl)cyclohexyl)methyl)-1H-pyrazole-3-carboxamide

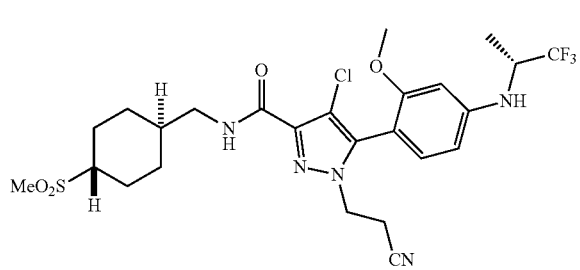 [SMILES: COc1cc(N[C@H](C)C(F)(F)F)ccc1-c1c(Cl)c(C(=O)NC[C@H]2CC[C@H](S(C)(=O)=O)CC2)nn1CCC#N]

The title compound was prepared as described for the synthesis of Example 1, using ethyl (R)-4-chloro-1-(2-cyanoethyl)-5-(2-methoxy-4-((1,1,1-trifluoropropan-2-yl)amino)phenyl)-1H-pyrazole-3-carboxylate (Intermediate 254) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (400 MHz, CD$_3$OD) δ 7.06-7.02 (m, 1H), 6.51-6.42 (m, 2H), 4.35-4.26 (m, 1H), 4.24-4.12 (m, 2H), 3.78 (d, J=1.2 Hz, 3H), 3.29-3.24 (m, 2H), 3.07-2.91 (m, 3H), 2.89 (s, 3H), 2.24 (d, J=12.4 Hz, 2H), 2.02 (d, J=12.4 Hz, 2H), 1.73-1.61 (m, 1H), 1.60-1.48 (m, 2H), 1.40 (d, J=6.7 Hz, 3H), 1.22-1.09 (m, 2H). MS (ESI) m/z: [M+H]$^+$ Found 590.2.

Example 130

1,4-Diethyl-5-(2-methoxy-4-(((R)-1,1,1-trifluoropropan-2-yl)amino)phenyl)-N-(((r,4R)-4-(methylsulfonyl)cyclohexyl)methyl)-1H-pyrazole-3-carboxamide

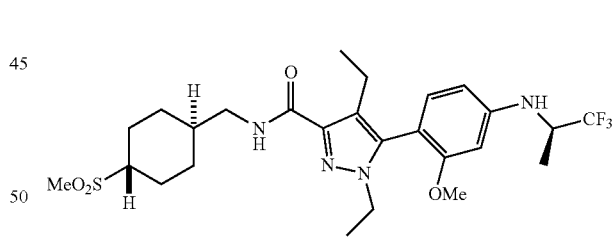

The title compound was prepared as described for the synthesis of Example 1 using ethyl (R)-1,4-diethyl-5-(2-methoxy-4-((1,1,1-trifluoropropan-2-yl)amino)phenyl)-1H-pyrazole-3-carboxylate (Intermediate 170) in place of (R*)-4-chloro-1-ethyl-5-(2-methoxy-4-(3,3,3-trifluoro-2-methylpropyl)phenyl)-1H-pyrazole-3-carboxylic acid. $^1$H NMR (500 MHz, CDCl$_3$) δ 7.10-7.06 (m, 1H), 6.95 (dd, J=8.2, 3.8 Hz, 1H), 6.35-6.31 (m, 1H), 6.28-6.25 (m, 1H), 4.13-4.04 (m, 1H), 3.94-3.79 (m, 3H), 3.77-3.71 (m, 3H), 3.38-3.25 (m, 2H), 2.89-2.77 (m, 4H), 2.63-2.52 (m, 2H), 2.32-2.23 (m, 2H), 2.14-2.03 (m, 2H), 1.71-1.56 (m, 3H), 1.46 (d, J=6.8 Hz, 3H), 1.30 (t, J=7.3 Hz, 3H), 1.19-1.08 (m, 2H), 1.05 (t, J=7.4 Hz, 3H). MS (ESI) m/z: [M+H]$^+$ Found 559.3.

Example 131

1-Ethyl-4-isopropyl-5-(2-methoxy-4-(((R)-1,1,1-trifluoropropan-2-yl)amino)phenyl)-N-(((1r,4R)-4-(methylsulfonyl)cyclohexyl)methyl)-1H-pyrazole-3-carboxamide

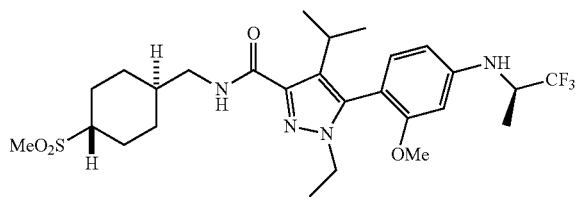 [SMILES: CCn1nc(C(=O)NC[C@H]2CC[C@H](S(C)(=O)=O)CC2)c(C(C)C)c1-c1ccc(N[C@H](C)C(F)(F)F)cc1OC]

The title compound was prepared as described for the synthesis of Example 1 using ethyl (R)-1-ethyl-4-isopropyl-5-(2-methoxy-4-((1,1,1-trifluoropropan-2-yl)amino)phenyl)-1H-pyrazole-3-carboxylate (Intermediate 173) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (400 MHz, CDCl$_3$) δ 7.14 (t, J=6.2 Hz, 1H), 6.94 (dd, J=8.2, 3.1 Hz, 1H), 6.32 (dt, J=8.2, 2.4 Hz, 1H), 6.28-6.23 (m, 1H), 4.16-4.02 (m, 1H), 3.89-3.76 (m, 3H), 3.76-3.70 (m, 3H), 3.38-3.22 (m, 3H), 2.89-2.76 (m, 4H), 2.34-2.22 (m, 2H), 2.15-2.03 (m, 2H), 1.74-1.51 (m, 3H), 1.46 (d, J=6.8 Hz, 3H), 1.28 (t, J=7.2 Hz, 3H), 1.16 (d, J=7.0 Hz, 3H), 1.15-1.05 (m, 5H). MS (ESI) m/z: [M+H]$^+$ Found 573.3.

Example 132

4-Chloro-5-(2-(difluoromethoxy)-4-(3,3,3-trifluoro-2,2-dimethylpropyl)phenyl)-1-ethyl-N-(((1s,4s)-1-hydroxy-4-(methylsulfonyl)cyclohexyl)methyl)-1H-pyrazole-3-carboxamide

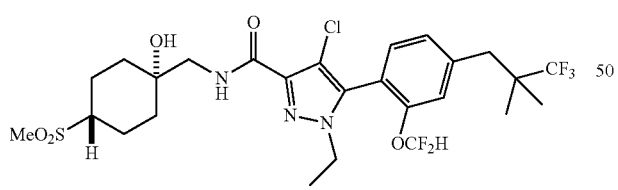

The title compound was prepared as described for the synthesis of Example 2, using (1s,4s)-1-(aminomethyl)-4-(methylsulfonyl)cyclohexan-1-ol hydrochloride (Intermediate 9) in place of ((1r,4r)-4-(methylsulfonyl)cyclohexyl)methanamine hydrochloride. $^1$H NMR (500 MHz, CDCl$_3$) δ 7.30-7.27 (m, 1H), 7.25-7.22 (m, 1H), 7.20-7.17 (m, 1H), 7.14 (s, 1H), 6.54-6.22 (m, 1H), 4.06-3.90 (m, 2H), 3.47 (d, J=6.3 Hz, 2H), 3.05 (s, 1H), 2.87 (s, 2H), 2.85-2.75 (m, 4H), 2.17-2.09 (m, 2H), 2.04-1.93 (m, 4H), 1.49-1.39 (m, 2H), 1.37 (t, J=7.2 Hz, 3H), 1.13 (s, 6H). MS (ESI) m/z: [M+H]$^+$ Found 629.9.

Example 133

4-Chloro-5-(2-(difluoromethoxy)-4-(3,3,3-trifluoro-2,2-dimethylpropyl)phenyl)-1-ethyl-N-(((1r,4r)-4-(ethylsulfonyl)cyclohexyl)methyl)-1H-pyrazole-3-carboxamide

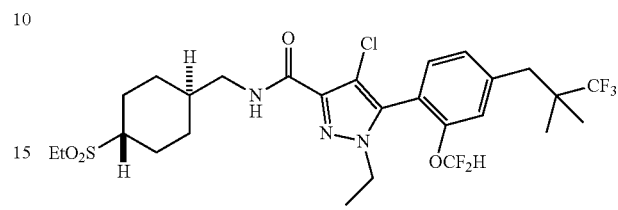

The title compound was prepared as described for the synthesis of Example 2, using ((1r,4r)-4-(ethyl sulfonyl)cyclohexyl)methanamine hydrochloride (Intermediate 40) in place of ((1r,4r)-4-(Methylsulfonyl)cyclohexyl)methanamine hydrochloride. $^1$H NMR (400 MHz, CDCl$_3$) δ 7.30-7.27 (m, 1H), 7.20-7.16 (m, 1H), 7.14 (s, 1H), 6.97-6.91 (m, 1H), 6.56-6.17 (m, 1H), 4.04-3.90 (m, 2H), 3.35 (t, J=6.6 Hz, 2H), 3.00-2.91 (m, 2H), 2.91-2.82 (m, 3H), 2.27-2.18 (m, 2H), 2.12-2.03 (m, 2H), 1.72-1.50 (m, 3H), 1.43-1.33 (m, 6H), 1.20-1.07 (m, 8H). MS (ESI) m/z: [M+H]$^+$ Found 628.2.

Example 134

4-Chloro-N-(((1s*,4s*)-1-cyano-4-(methylsulfonyl)cyclohexyl)methyl)-5-(2-(difluoromethoxy)-4-(3,3,3-trifluoro-2,2-dimethylpropyl)phenyl)-1-ethyl-1H-pyrazole-3-carboxamide

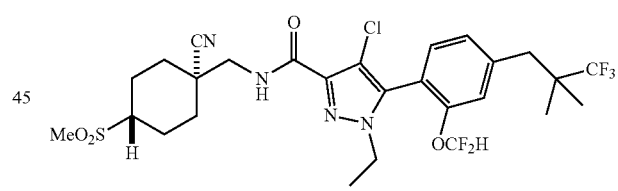

The title compound was prepared as described for the synthesis of Example 1, using (1s*,4s*)-1-(aminomethyl)-4-(methylsulfonyl)cyclohexane-1-carbonitrile hydrochloride (Intermediate 35) in place of ((1r,4r)-4-(methylsulfonyl)cyclohexyl)methanamine hydrochloride and 4-chloro-5-(2-(difluoromethoxy)-4-(3,3,3-trifluoro-2,2-dimethylpropyl)phenyl)-1-ethyl-1H-pyrazole-3-carboxylic acid (Example 2, Step a) in place of (R*)-4-chloro-1-ethyl-5-(2-methoxy-4-(3,3,3-trifluoro-2-methylpropyl)phenyl)-1H-pyrazole-3-carboxylic acid. $^1$H NMR (500 MHz, CDCl$_3$) δ 7.31-7.27 (m, 2H), 7.19 (dd, J=7.9, 1.5 Hz, 1H), 7.16-7.14 (m, 1H), 6.55-6.23 (m, 1H), 4.07-3.91 (m, 2H), 3.68 (d, J=7.0 Hz, 2H), 2.91-2.78 (m, 6H), 2.40-2.32 (m, 2H), 2.32-2.25 (m, 2H), 1.97-1.86 (m, 2H), 1.63-1.55 (m, 2H), 1.38 (t, J=7.3 Hz, 3H), 1.13 (s, 6H). MS (ESI) m/z: [M+H]$^+$ Found 638.9.

Example 135

4-Chloro-5-(2-(difluoromethoxy)-4-((R*)-3,3,3-trifluoro-2-methylpropyl)phenyl)-1-ethyl-N-(((1r,4R)-4-(methylsulfonyl)cyclohexyl)methyl)-1H-pyrazole-3-carboxamide

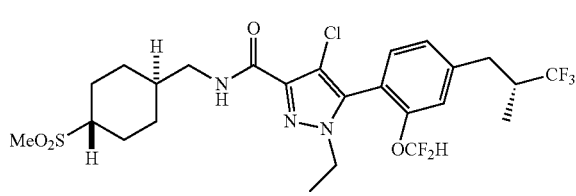

The title compound was prepared as described for the synthesis of Example 2, using ethyl (R*)-4-chloro-5-(2-(difluoromethoxy)-4-(3,3,3-trifluoro-2-methylpropyl)phenyl)-1-ethyl-1H-pyrazole-3-carboxylate (Intermediate 116) in place of ethyl 4-chloro-5-(2-(difluoromethoxy)-4-(3,3,3-trifluoro-2,2-dimethylpropyl)phenyl)-1-ethyl-1H-pyrazole-3-carboxylate. $^1$H NMR (400 MHz, CDCl$_3$) δ 7.33-7.28 (m, 1H), 7.23-7.17 (m, 1H), 7.14 (s, 1H), 6.98-6.91 (m, 1H), 6.59-6.18 (m, 1H), 4.07-3.87 (m, 2H), 3.35 (t, J=6.5 Hz, 2H), 3.21-3.12 (m, 1H), 2.90-2.77 (m, 4H), 2.66-2.42 (m, 2H), 2.33-2.23 (m, 2H), 2.13-2.02 (m, 2H), 1.77-1.54 (m, 3H), 1.36 (t, J=7.3 Hz, 3H), 1.21-1.07 (m, 5H). MS (ESI) m/z: [M+H]$^+$ Found 600.2.

Example 136

4-Chloro-5-(2-(difluoromethoxy)-4-((R*)-3,3,3-trifluoro-2-methylpropyl)phenyl)-1-ethyl-N-(((1s,4S)-1-hydroxy-4-(methylsulfonyl)cyclohexyl)methyl)-1H-pyrazole-3-carboxamide

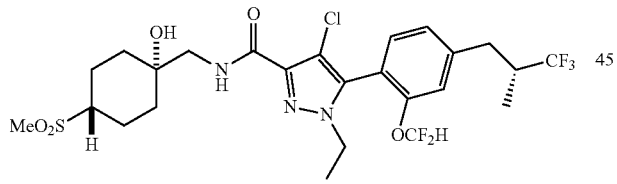

The title compound was prepared as described for the synthesis of Example 2, using (1s,4s)-1-(aminomethyl)-4-(methylsulfonyl)cyclohexan-1-ol hydrochloride (Intermediate 9) in place of ((1r,4r)-4-(methylsulfonyl)cyclohexyl)methanamine hydrochloride and ethyl (R*)-4-chloro-5-(2-(difluoromethoxy)-4-(3,3,3-trifluoro-2-methylpropyl)phenyl)-1-ethyl-1H-pyrazole-3-carboxylate (Intermediate 116) in place of ethyl 4-chloro-5-(2-(difluoromethoxy)-4-(3,3,3-trifluoro-2,2-dimethylpropyl)phenyl)-1-ethyl-1H-pyrazole-3-carboxylate. $^1$H NMR (400 MHz, CDCl$_3$) δ 7.32-7.28 (m, 1H), 7.24-7.18 (m, 2H), 7.15 (s, 1H), 6.58-6.20 (m, 1H), 4.06-3.89 (m, 2H), 3.47 (d, J=6.4 Hz, 2H), 3.21-3.13 (m, 1H), 3.01 (s, 1H), 2.83 (s, 3H), 2.82-2.75 (m, 1H), 2.64-2.47 (m, 2H), 2.17-2.09 (m, 2H), 2.04-1.92 (m, 4H), 1.50-1.33 (m, 5H), 1.14-1.10 (m, 3H). MS (ESI) m/z: [M+H]$^+$ Found 616.2.

Example 137

4-Chloro-5-(2-(difluoromethoxy)-4-((R*)-3,3,3-trifluoro-2-methylpropyl)phenyl)-N-(((1R*,2R*,4R*)-1,2-dihydroxy-4-(methylsulfonyl)cyclohexyl)methyl)-1-ethyl-1H-pyrazole-3-carboxamide

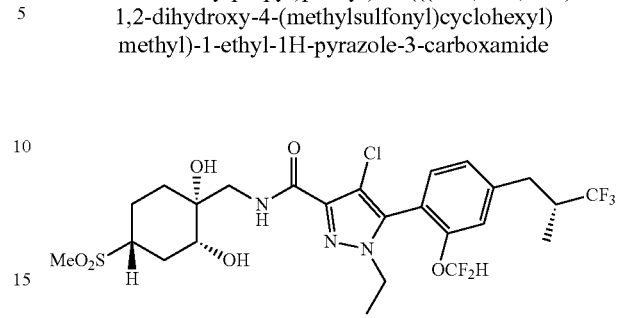

The title compound was prepared as described for the synthesis of Example 1, using (1R*,2R*,4R*)-1-(aminomethyl)-4-(methylsulfonyl)cyclohexane-1,2-diol hydrochloride (Intermediate 24) in place of ((1r,4r)-4-(methylsulfonyl)cyclohexyl)methanamine hydrochloride and ethyl (R*)-4-chloro-5-(2-(difluoromethoxy)-4-(3,3,3-trifluoro-2-methylpropyl)phenyl)-1-ethyl-1H-pyrazole-3-carboxylate (Intermediate 116) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (400 MHz, CDCl$_3$) δ 7.33-7.27 (m, 2H), 7.24-7.19 (m, 1H), 7.15 (s, 1H), 6.63-6.21 (m, 1H), 4.08-3.84 (m, 3H), 3.68-3.58 (m, 1H), 3.48 (br s, 2 OH plus excess water), 3.21-3.06 (m, 2H), 2.92-2.77 (m, 4H), 2.66-2.44 (m, 2H), 2.33-2.22 (m, 1H), 2.14-2.03 (m, 1H), 2.03-1.86 (m, 3H), 1.63-1.47 (m, 1H), 1.41-1.33 (m, 3H), 1.16-1.08 (m, 3H). MS (ESI) m/z: [M+H]$^+$ Found 632.2.

Example 138

4-Chloro-5-(2-(difluoromethoxy)-4-((R*)-3,3,3-trifluoro-2-methylpropyl)phenyl)-N-(((1S*,2S*,4S*)-1,2-dihydroxy-4-(methylsulfonyl)cyclohexyl)methyl)-1-ethyl-1H-pyrazole-3-carboxamide

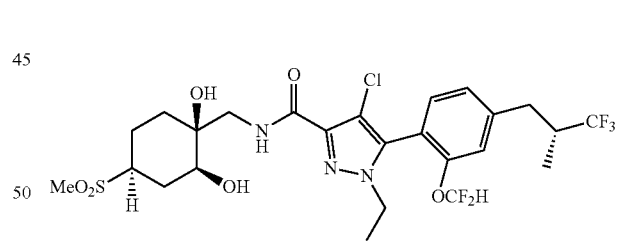

The title compound was prepared as described for the synthesis of Example 2, using (1S*,2S*,4S*)-1-(aminomethyl)-4-(methylsulfonyl)cyclohexane-1,2-diol hydrochloride (Intermediate 25) in place of ((1r,4r)-4-(methylsulfonyl)cyclohexyl)methanamine hydrochloride and ethyl (R*)-4-chloro-5-(2-(difluoromethoxy)-4-(3,3,3-trifluoro-2-methylpropyl)phenyl)-1-ethyl-1H-pyrazole-3-carboxylate (Intermediate 116) in place of ethyl 4-chloro-5-(2-(difluoromethoxy)-4-(3,3,3-trifluoro-2,2-dimethylpropyl)phenyl)-1-ethyl-1H-pyrazole-3-carboxylate. $^1$H NMR (500 MHz, CDCl$_3$) δ 7.33-7.28 (m, 1H), 7.25-7.19 (m, 2H), 7.15 (s, 1H), 6.59-6.24 (m, 1H), 4.08-3.85 (m, 3H), 3.66-3.56 (m, 1H), 3.20-3.13 (m, 1H), 3.12-3.03 (m, 1H), 2.92-2.77 (m, 4H), 2.65-2.57 (m, 1H), 2.57-2.45 (m, 1H), 2.32-2.23 (m, 1H), 2.13-2.03 (m, 1H), 2.03-1.86 (m, 3H), 1.61-1.48 (m, 1H), 1.41-1.34 (m, 3H), 1.16-1.08 (m, 3H). MS (ESI) m/z: [M+H]+ Found 632.2.

Example 139

4-Chloro-5-(2-(difluoromethoxy)-4-((R*)-3,3,3-trifluoro-2-methylpropyl)phenyl)-1-ethyl-N-(((1r,4R)-4-sulfamoylcyclohexyl)methyl)-1H-pyrazole-3-carboxamide

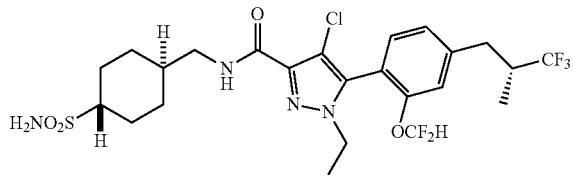

The title compound was prepared as described for the synthesis of Example 1, using (1r,4r)-4-(aminomethyl)cyclohexane-1-sulfonamide hydrochloride (Intermediate 62) in place of ((1r,4r)-4-(methyl sulfonyl)cyclohexyl)methanamine hydrochloride and ethyl (R*)-4-chloro-5-(2-(difluoromethoxy)-4-(3,3,3-trifluoro-2-methylpropyl)phenyl)-1-ethyl-1H-pyrazole-3-carboxylate (Intermediate 116) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (400 MHz, CDCl$_3$) δ 7.30 (dd, J=7.8, 1.6 Hz, 1H), 7.23-7.17 (m, 1H), 7.14 (s, 1H), 6.95 (t, J=6.4 Hz, 1H), 6.38 (dd, J=75.2, 70.8 Hz, 1H), 4.37 (s, 2H), 4.07-3.88 (m, 2H), 3.34 (t, J=6.5 Hz, 2H), 3.17 (dd, J=13.5, 3.8 Hz, 1H), 2.93 (tt, J=12.2, 3.5 Hz, 1H), 2.65-2.42 (m, 2H), 2.39-2.28 (m, 2H), 2.10-2.00 (m, 2H), 1.77-1.56 (m, 3H), 1.36 (t, J=7.3 Hz, 3H), 1.20-1.06 (m, 5H). MS (ESI) m/z: [M+H]+ Found 601.3.

Example 140

5-(2-(Difluoromethoxy)-4-((R*)-3,3,3-trifluoro-2-methylpropyl)phenyl)-N-(((1R*,2R*,4R*)-1,2-dihydroxy-4-(methylsulfonyl)cyclohexyl)methyl)-1-ethyl-4-methyl-1H-pyrazole-3-carboxamide

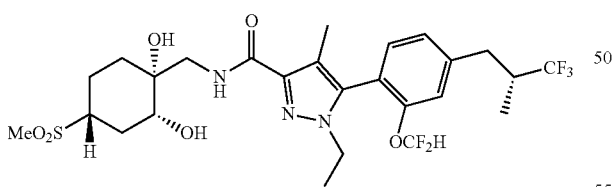

The title compound was prepared as described for the synthesis of Example 1 using (1R*,2R*,4R*)-1-(aminomethyl)-4-(methylsulfonyl)cyclohexane-1,2-diol hydrochloride (Intermediate 24) in place of ((1r,4r)-4-(methylsulfonyl)cyclohexyl)methanamine hydrochloride and ethyl (R*)-5-(2-(difluoromethoxy)-4-(3,3,3-trifluoro-2-methylpropyl)phenyl)-1-ethyl-4-methyl-1H-pyrazole-3-carboxylate (Intermediate 180) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (400 MHz, CDCl$_3$) δ 7.35-7.28 (m, 1H), 7.23-7.15 (m, 2H), 7.13 (s, 1H), 6.37 (ddd, J=74.1, 71.9, 17.4 Hz, 1H), 4.85 (dd, J=9.5, 5.1 Hz, 1H), 4.02-3.80 (m, 3H), 3.65-3.52 (m, 1H), 3.16 (dd, J=13.4, 3.8 Hz, 1H), 3.05 (ddd, J=14.2, 5.8, 3.1 Hz, 1H), 2.92-2.77 (m, 5H), 2.64-2.55 (m, 1H), 2.56-2.45 (m, 1H), 2.31-2.23 (m, 1H), 2.14 (s, 3H), 2.11-2.02 (m, 1H), 2.03-1.85 (m, 3H), 1.63-1.49 (m, 1H), 1.34 (td, J=7.2, 2.7 Hz, 3H), 1.12 (d, J=6.7 Hz, 3H). MS (ESI) m/z: [M+H]+ Found 612.3.

Example 141

5-(2-(Difluoromethoxy)-4-((R*)-3,3,3-trifluoro-2-methylpropyl)phenyl)-N-(((1S*,2S*,4S*)-1,2-dihydroxy-4-(methylsulfonyl)cyclohexyl)methyl)-1-ethyl-4-methyl-1H-pyrazole-3-carboxamide

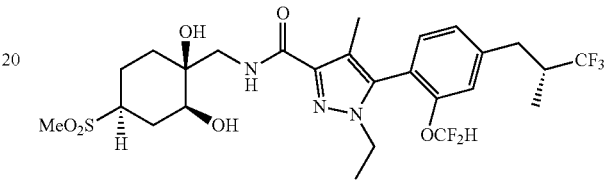

The title compound was prepared as described for the synthesis of Example 1, using (1S*,2S*,4S*)-1-(aminomethyl)-4-(methylsulfonyl)cyclohexane-1,2-diol hydrochloride (Intermediate 25) in place of ((1r,4r)-4-(methylsulfonyl)cyclohexyl)methanamine hydrochloride and ethyl (R*)-5-(2-(difluoromethoxy)-4-(3,3,3-trifluoro-2-methylpropyl)phenyl)-1-ethyl-4-methyl-1H-pyrazole-3-carboxylate (Intermediate 180) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (400 MHz, CDCl$_3$) δ 7.41-7.34 (m, 1H), 7.24-7.16 (m, 2H), 7.14 (s, 1H), 6.59-6.15 (m, 1H), 4.03-3.79 (m, 3H), 3.66-3.55 (m, 1H), 3.34 (s, 2 OH plus water), 3.20-3.13 (m, 1H), 3.13-3.04 (m, 1H), 2.92-2.77 (m, 4H), 2.66-2.56 (m, 1H), 2.56-2.44 (m, 1H), 2.33-2.23 (m, 1H), 2.17-2.02 (m, 4H), 2.02-1.86 (m, 3H), 1.64-1.48 (m, 1H), 1.38-1.29 (m, 3H), 1.16-1.08 (m, 3H). MS (ESI) m/z: [M+H]+ Found 612.2.

Example 142

5-(2-(Difluoromethoxy)-4-((R)-3,3,3-trifluoro-2-methylpropyl)phenyl)-1-ethyl-N-(((1s,4S)-1-hydroxy-4-(methylsulfonyl)cyclohexyl)methyl)-4-methyl-1H-pyrazole-3-carboxamide

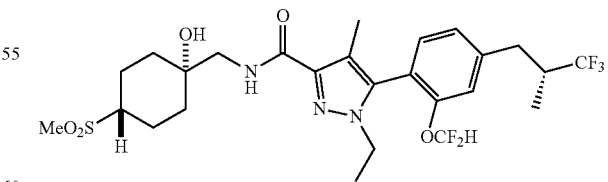

The title compound was prepared as described for the synthesis of Example 1, using (1s,4s)-1-(aminomethyl)-4-(methylsulfonyl)cyclohexan-1-ol hydrochloride (Intermediate 9) in place of ((1r,4r)-4-(methylsulfonyl)cyclohexyl)methanamine hydrochloride and ethyl (R*)-5-(2-(difluoromethoxy)-4-(3,3,3-trifluoro-2-methylpropyl)

phenyl)-1-ethyl-4-methyl-1H-pyrazole-3-carboxylate (Intermediate 180) in place of ethyl (R*)-4-chloro-1-ethyl-5-(2-methoxy-4-(3,3,3-trifluoro-2-methylpropyl)phenyl)-1H-pyrazole-3-carboxylate. ¹H NMR (400 MHz, CDCl₃) δ 7.44-7.34 (m, 1H), 7.24-7.10 (m, 3H), 6.55-6.14 (m, 1H), 4.02-3.83 (m, 2H), 3.45 (d, J=6.3 Hz, 2H), 3.21-3.12 (m, 2H), 2.87-2.74 (m, 4H), 2.64-2.42 (m, 2H), 2.19-2.08 (m, 5H), 2.05-1.91 (m, 4H), 1.48-1.36 (m, 2H), 1.33 (t, J=7.2 Hz, 3H), 1.15-1.08 (m, 3H). MS (ESI) m/z: [M+H]⁺ Found 596.3.

Example 143

5-(2-(Difluoromethoxy)-4-(3,3,3-trifluoro-2,2-dimethylpropyl)phenyl)-1-ethyl-N-(((1s,4s)-1-hydroxy-4-(methylsulfonyl)cyclohexyl)methyl)-4-methyl-1H-pyrazole-3-carboxamide

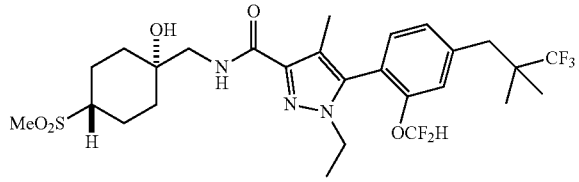

The title compound was prepared as described for the synthesis of Example 2, using ethyl 5-(2-(difluoromethoxy)-4-(3,3,3-trifluoro-2,2-dimethylpropyl)phenyl)-1-ethyl-4-methyl-1H-pyrazole-3-carboxylate (Intermediate 181) in place of ethyl 4-chloro-5-(2-(difluoromethoxy)-4-(3,3,3-trifluoro-2,2-dimethylpropyl)phenyl)-1-ethyl-1H-pyrazole-3-carboxylate and (1s,4s)-1-(aminomethyl)-4-(methylsulfonyl)cyclohexan-1-ol hydrochloride (Intermediate 9) in place of ((1r,4r)-4-(Methylsulfonyl)cyclohexyl)methanamine hydrochloride. ¹H NMR (400 MHz, CDCl₃) δ 7.36-7.30 (m, 1H), 7.23-7.09 (m, 3H), 6.54-6.12 (m, 1H), 4.01-3.83 (m, 2H), 3.57 (s, 1H), 3.44 (d, J=6.3 Hz, 2H), 2.86 (s, 2H), 2.85-2.74 (m, 4H), 2.19-2.09 (m, 5H), 2.06-1.92 (m, 4H), 1.46-1.29 (m, 5H), 1.13 (s, 6H). MS (ESI) m/z: [M+H]⁺ Found 610.3.

Example 144

4-Chloro-5-(2-(difluoromethoxy)-4-(3,3,3-trifluoro-2,2-dimethylpropyl)phenyl)-1-(2-hydroxy-2-methylpropyl)-N-(((1s,4s)-1-hydroxy-4-(methylsulfonyl)cyclohexyl)methyl)-1H-pyrazole-3-carboxamide

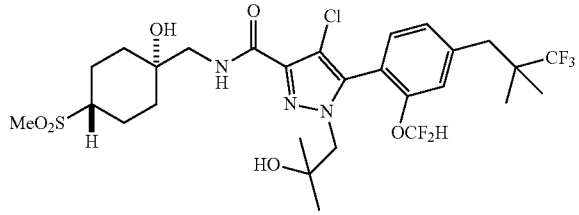

The title compound was prepared as described for the synthesis of Example 2, using ethyl 4-chloro-5-(2-(difluoromethoxy)-4-(3,3,3-trifluoro-2,2-dimethylpropyl)phenyl)-1-(2-hydroxy-2-methylpropyl)-1H-pyrazole-3-carboxylate (Intermediate 176) in place of ethyl 4-chloro-5-(2-(difluoromethoxy)-4-(3,3,3-trifluoro-2,2-dimethylpropyl)phenyl)-1-ethyl-1H-pyrazole-3-carboxylate and (1s,4s)-1-(aminomethyl)-4-(methylsulfonyl)cyclohexan-1-ol hydrochloride (Intermediate 9) in place of ((1r,4r)-4-(methylsulfonyl)cyclohexyl)methanamine hydrochloride. ¹H NMR (400 MHz, CDCl₃) δ 7.35-7.32 (m, 1H), 7.26-7.16 (m, 3H), 6.64-6.25 (m, 1H), 4.08-4.02 (m, 1H), 3.93-3.86 (m, 1H), 3.59-3.44 (m, 2H), 2.92 (s, 2H), 2.90-2.80 (m, 4H), 2.23-2.13 (m, 2H), 2.09-1.95 (m, 4H), 1.54-1.42 (m, 2H), 1.22-1.13 (m, 9H), 1.03 (s, 3H). MS (ESI) m/z: [M+H]⁺ Found 674.2.

Example 145

4-Chloro-5-(2-(difluoromethoxy)-4-(3,3,3-trifluoro-2,2-dimethylpropyl)phenyl)-1-(2-hydroxy-2-methylpropyl)-N-(((1r,4r)-4-(methylsulfonyl)cyclohexyl)methyl)-1H-pyrazole-3-carboxamide

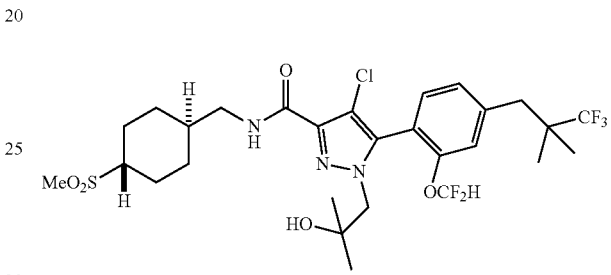

The title compound was prepared as described for the synthesis of Example 2, using ethyl 4-chloro-5-(2-(difluoromethoxy)-4-(3,3,3-trifluoro-2,2-dimethylpropyl)phenyl)-1-(2-hydroxy-2-methylpropyl)-1H-pyrazole-3-carboxylate (Intermediate 176) in place of ethyl 4-chloro-5-(2-(difluoromethoxy)-4-(3,3,3-trifluoro-2,2-dimethylpropyl)phenyl)-1-ethyl-1H-pyrazole-3-carboxylate. ¹H NMR (400 MHz, CDCl₃) δ 7.31-7.27 (m, 1H), 7.21-7.16 (m, 1H), 7.14 (s, 1H), 6.87-6.78 (m, 1H), 6.60-6.19 (m, 1H), 4.03-3.96 (m, 1H), 3.88-3.79 (m, 1H), 3.42-3.27 (m, 2H), 2.90-2.76 (m, 6H), 2.34-2.24 (m, 2H), 2.11-2.02 (m, 2H), 1.75-1.65 (m, 1H), 1.65-1.57 (m, 2H), 1.20-1.05 (m, 11H), 0.97 (s, 3H). MS (ESI) m/z: [M+H]⁺ Found 658.3.

Example 146

5-(2-(Difluoromethoxy)-4-(3,3,3-trifluoro-2,2-dimethylpropyl)phenyl)-1-(2-hydroxy-2-methylpropyl)-N-(((1s,4s)-1-hydroxy-4-(methylsulfonyl)cyclohexyl)methyl)-4-methyl-1H-pyrazole-3-carboxamide

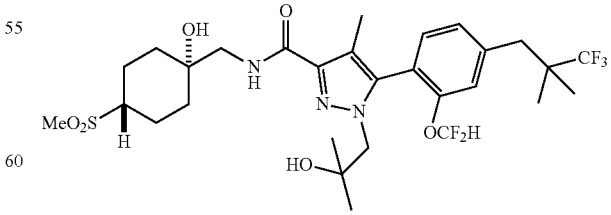

The title compound was prepared as described for the synthesis of Example 2, using ethyl 5-(2-(difluoromethoxy)-4-(3,3,3-trifluoro-2,2-dimethylpropyl)phenyl)-1-(2-hydroxy-2-methylpropyl)-4-methyl-1H-pyrazole-3-carboxylate (Intermediate 182) in place of ethyl 4-chloro-5-(2-(difluoromethoxy)-4-(3,3,3-trifluoro-2,2-dimethylpropyl)phenyl)-1-ethyl-1H-pyrazole-3-carboxylate and (1s,4s)-1-(aminomethyl)-4-(methyl sulfonyl)cyclohexan-1-ol hydrochloride (Intermediate 9) in place of ((1r,4r)-4-(methylsulfonyl)cyclohexyl)methanamine hydrochloride. $^1$H NMR (400 MHz, CDCl$_3$) δ 7.20-7.11 (m, 4H), 6.56-6.16 (m, 1H), 3.99-3.72 (m, 3H), 3.53-3.35 (m, 3H), 2.87 (s, 2H), 2.85-2.74 (m, 4H), 2.21-2.09 (m, 5H), 2.05-1.91 (m, 4H), 1.48-1.33 (m, 2H), 1.18-1.08 (m, 9H), 0.95 (s, 3H). MS (ESI) m/z: [M+H]$^+$ Found 654.3.

Example 147

5-(2-(Difluoromethoxy)-4-(3,3,3-trifluoro-2,2-dimethylpropyl)phenyl)-1-(2-hydroxy-2-methylpropyl)-4-methyl-N-(((1r,4r)-4-(methylsulfonyl)cyclohexyl)methyl)-1H-pyrazole-3-carboxamide

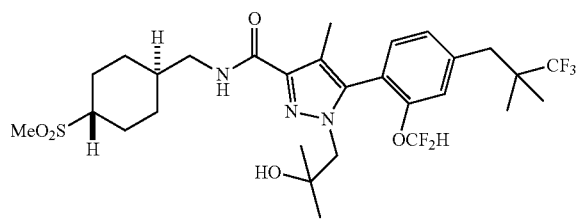

The title compound was prepared as described for the synthesis of Example 2, using ethyl 5-(2-(difluoromethoxy)-4-(3,3,3-trifluoro-2,2-dimethylpropyl)phenyl)-1-(2-hydroxy-2-methylpropyl)-4-methyl-1H-pyrazole-3-carboxylate (Intermediate 182) in place of ethyl 4-chloro-5-(2-(difluoromethoxy)-4-(3,3,3-trifluoro-2,2-dimethylpropyl)phenyl)-1-ethyl-1H-pyrazole-3-carboxylate. $^1$H NMR (400 MHz, CDCl$_3$) δ 7.22-7.11 (m, 3H), 6.93-6.83 (m, 1H), 6.56-6.13 (m, 1H), 4.10 (s, 1H), 3.98-3.72 (m, 2H), 3.37-3.26 (m, 2H), 2.87 (s, 2H), 2.84-2.78 (m, 4H), 2.32-2.24 (m, 2H), 2.18 (s, 3H), 2.11-2.02 (m, 2H), 1.74-1.56 (m, 3H), 1.19-1.06 (m, 11H), 0.94 (s, 3H). MS (ESI) m/z: [M+H]$^+$ Found 638.3.

Example 148

4-Chloro-5-(2-(difluoromethoxy)-4-(3,3,3-trifluoro-2,2-dimethylpropyl)phenyl)-1-(2-methoxyethyl)-N-(((1r,4r)-4-(methylsulfonyl)cyclohexyl)methyl)-1H-pyrazole-3-carboxamide

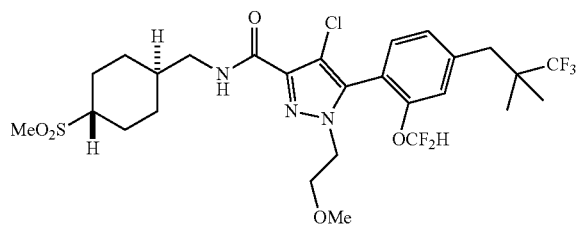

The title compound was prepared as described for the synthesis of Example 1, using ethyl 4-chloro-5-(2-(difluoromethoxy)-4-(3,3,3-trifluoro-2,2-dimethylpropyl)phenyl)-1-(2-methoxyethyl)-1H-pyrazole-3-carboxylate (Intermediate 201) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (400 MHz, CDCl$_3$) δ 7.36-7.31 (m, 1H), 7.21-7.16 (m, 1H), 7.13 (s, 1H), 7.01 (t, J=6.3 Hz, 1H), 6.58-6.18 (m, 1H), 4.17-4.05 (m, 2H), 3.82-3.71 (m, 1H), 3.67-3.57 (m, 1H), 3.43-3.29 (m, 2H), 3.20 (s, 3H), 2.92-2.79 (m, 6H), 2.34-2.23 (m, 2H), 2.12-2.03 (m, 2H), 1.77-1.51 (m, 3H), 1.23-1.06 (m, 8H). MS (ESI) m/z: [M+H]$^+$ Found 643.9.

Example 149

4-Chloro-5-(2-(difluoromethoxy)-4-(3,3,3-trifluoro-2,2-dimethylpropyl)phenyl)-N-(((1s,4s)-1-hydroxy-4-(methylsulfonyl)cyclohexyl)methyl)-1-(2-methoxyethyl)-1H-pyrazole-3-carboxamide

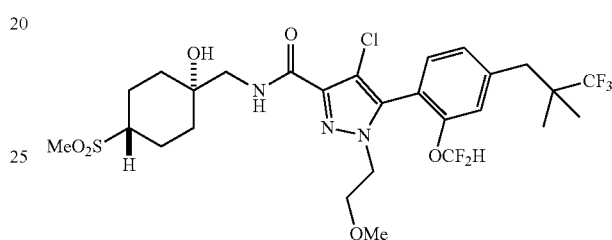

The title compound was prepared as described for the synthesis of Example 1, using (1s,4s)-1-(aminomethyl)-4-(methylsulfonyl)cyclohexan-1-ol hydrochloride (Intermediate 9) in place of ((1r,4r)-4-(methylsulfonyl)cyclohexyl)methanamine hydrochloride and ethyl 4-chloro-5-(2-(difluoromethoxy)-4-(3,3,3-trifluoro-2,2-dimethylpropyl)phenyl)-1-(2-methoxyethyl)-1H-pyrazole-3-carboxylate (Intermediate 201) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (500 MHz, CDCl$_3$) δ 7.35-7.31 (m, 1H), 7.31-7.27 (m, 1H), 7.21-7.16 (m, 1H), 7.13 (s, 1H), 6.56-6.22 (m, 1H), 4.18-4.05 (m, 2H), 3.80-3.72 (m, 1H), 3.65-3.57 (m, 1H), 3.55-3.41 (m, 2H), 3.20 (s, 3H), 2.87 (s, 2H), 2.86-2.76 (m, 4H), 2.18-2.08 (m, 2H), 2.04-1.91 (m, 4H), 1.50-1.39 (m, 2H), 1.13 (s, 6H). MS (ESI) m/z: [M+H]$^+$ Found 659.9.

Example 150

5-(2-(Difluoromethoxy)-4-(3,3,3-trifluoro-2,2-dimethylpropyl)phenyl)-N-(((1s,4s)-1-hydroxy-4-(methylsulfonyl)cyclohexyl)methyl)-1-(2-methoxyethyl)-4-methyl-1H-pyrazole-3-carboxamide

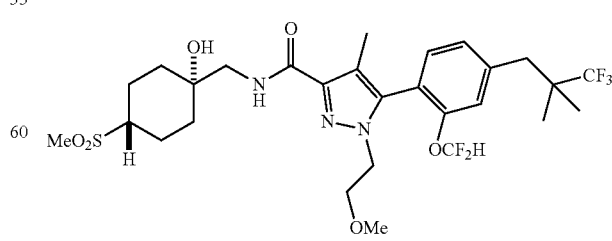

The title compound was prepared as described for the synthesis of Example 2, using ethyl 5-(2-(difluoromethoxy)-

4-(3,3,3-trifluoro-2,2-dimethylpropyl)phenyl)-1-(2-methoxyethyl)-4-methyl-1H-pyrazole-3-carboxylate (Intermediate 282) in place of ethyl 4-chloro-5-(2-(difluoromethoxy)-4-(3,3,3-trifluoro-2,2-dimethylpropyl)phenyl)-1-ethyl-1H-pyrazole-3-carboxylate and (1s,4s)-1-(aminomethyl)-4-(methylsulfonyl)cyclohexan-1-ol hydrochloride (Intermediate 9) in place of ((1r,4r)-4-(methylsulfonyl)cyclohexyl)methanamine hydrochloride. $^1$H NMR (400 MHz, CDCl$_3$) δ 7.32 (t, J=6.4 Hz, 1H), 7.25-7.22 (m, 1H), 7.17-7.13 (m, 1H), 7.12 (s, 1H), 6.53-6.11 (m, 1H), 4.13-4.01 (m, 2H), 3.76-3.69 (m, 1H), 3.66-3.58 (m, 1H), 3.52 (s, 1H), 3.43 (d, J=6.3 Hz, 2H), 3.20 (s, 3H), 2.86 (s, 2H), 2.84-2.74 (m, 4H), 2.18-2.08 (m, 5H), 2.05-1.92 (m, 4H), 1.47-1.35 (m, 2H), 1.12 (s, 6H). MS (ESI) m/z: [M+H]$^+$ Found 639.9.

Example 151

4-Chloro-5-(2-(difluoromethoxy)-4-((R)-3,3,3-trifluoro-2-methylpropyl)phenyl)-1-methyl-N-(((1r,4R)-4-(methylsulfonyl)cyclohexyl)methyl)-1H-pyrazole-3-carboxamide

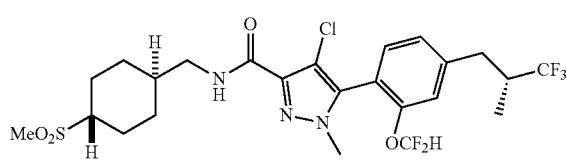

The title compound was prepared as described for the synthesis of Example 1, using ethyl (R*)-4-chloro-5-(2-(difluoromethoxy)-4-(3,3,3-trifluoro-2-methylpropyl)phenyl)-1-methyl-1H-pyrazole-3-carboxylate (Intermediate 184) in place of ethyl (R*)-4-chloro-1-ethyl-5-(2-methoxy-4-(3,3,3-trifluoro-2-methylpropyl)phenyl)-1H-pyrazole-3-carboxylate (Intermediate 99). $^1$H NMR (400 MHz, CDCl$_3$) δ 7.34-7.30 (m, 1H), 7.23-7.18 (m, 1H), 7.15 (s, 1H), 7.00 (t, J=6.4 Hz, 1H), 6.59-6.20 (m, 1H), 3.73 (s, 3H), 3.36 (t, J=6.5 Hz, 2H), 3.21-3.13 (m, 1H), 2.89-2.78 (m, 4H), 2.64-2.56 (m, 1H), 2.56-2.44 (m, 1H), 2.33-2.24 (m, 2H), 2.12-2.02 (m, 2H), 1.75-1.53 (m, 3H), 1.21-1.07 (m, 5H). MS (ESI) m/z: [M+H]$^+$ Found 586.2.

Example 152

4-Chloro-5-(2-(difluoromethoxy)-4-((R*)-3,3,3-trifluoro-2-methylpropyl)phenyl)-N-(((1s,4S)-1-hydroxy-4-(methylsulfonyl)cyclohexyl)methyl)-1-methyl-1H-pyrazole-3-carboxamide

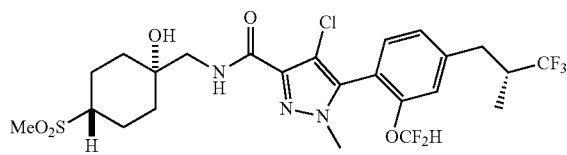

The title compound was prepared as described for the synthesis of Example 1, using (1s,4s)-1-(aminomethyl)-4-(methylsulfonyl)cyclohexan-1-ol hydrochloride (Intermediate 9) in place of ((1r,4r)-4-(methylsulfonyl)cyclohexyl)methanamine hydrochloride and ethyl (R)-4-chloro-5-(2-(difluoromethoxy)-4-(3,3,3-trifluoro-2-methylpropyl)phenyl)-1-methyl-1H-pyrazole-3-carboxylate (Intermediate 184) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (400 MHz, CDCl$_3$) δ 7.35-7.27 (m, 2H), 7.23-7.18 (m, 1H), 7.15 (s, 1H), 6.61-6.20 (m, 1H), 3.74 (s, 3H), 3.48 (d, J=6.3 Hz, 2H), 3.21-3.13 (m, 1H), 3.05 (br s, OH plus water), 2.88-2.76 (m, 4H), 2.65-2.56 (m, 1H), 2.57-2.43 (m, 1H), 2.19-2.08 (m, 2H), 2.05-1.89 (m, 4H), 1.51-1.38 (m, 2H), 1.17-1.07 (m, 3H). MS (ESI) m/z: [M+H]$^+$ Found 602.2.

Example 153

4-Chloro-5-(2-(difluoromethoxy)-4-(3,3,3-trifluoro-2,2-dimethylpropyl)phenyl)-N-(((1S*,2S*,4S*)-1,2-dihydroxy-4-(methylsulfonyl)cyclohexyl)methyl)-1-methyl-1H-pyrazole-3-carboxamide

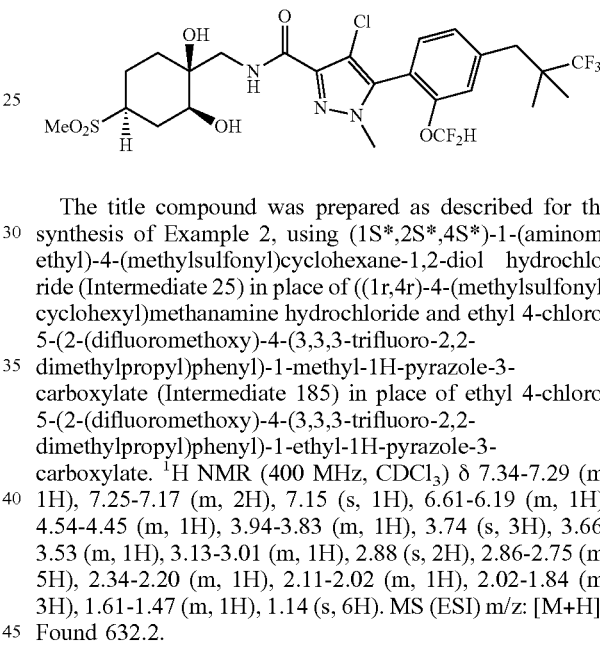

The title compound was prepared as described for the synthesis of Example 2, using (1S*,2S*,4S*)-1-(aminomethyl)-4-(methylsulfonyl)cyclohexane-1,2-diol hydrochloride (Intermediate 25) in place of ((1r,4r)-4-(methylsulfonyl)cyclohexyl)methanamine hydrochloride and ethyl 4-chloro-5-(2-(difluoromethoxy)-4-(3,3,3-trifluoro-2,2-dimethylpropyl)phenyl)-1-methyl-1H-pyrazole-3-carboxylate (Intermediate 185) in place of ethyl 4-chloro-5-(2-(difluoromethoxy)-4-(3,3,3-trifluoro-2,2-dimethylpropyl)phenyl)-1-ethyl-1H-pyrazole-3-carboxylate. $^1$H NMR (400 MHz, CDCl$_3$) δ 7.34-7.29 (m, 1H), 7.25-7.17 (m, 2H), 7.15 (s, 1H), 6.61-6.19 (m, 1H), 4.54-4.45 (m, 1H), 3.94-3.83 (m, 1H), 3.74 (s, 3H), 3.66-3.53 (m, 1H), 3.13-3.01 (m, 1H), 2.88 (s, 2H), 2.86-2.75 (m, 5H), 2.34-2.20 (m, 1H), 2.11-2.02 (m, 1H), 2.02-1.84 (m, 3H), 1.61-1.47 (m, 1H), 1.14 (s, 6H). MS (ESI) m/z: [M+H]$^+$ Found 632.2.

Example 154

4-Chloro-5-(2-(difluoromethoxy)-4-(3,3,3-trifluoro-2,2-dimethylpropyl)phenyl)-N-(((1s,4s)-1-hydroxy-4-(methylsulfonyl)cyclohexyl)methyl)-1-methyl-1H-pyrazole-3-carboxamide

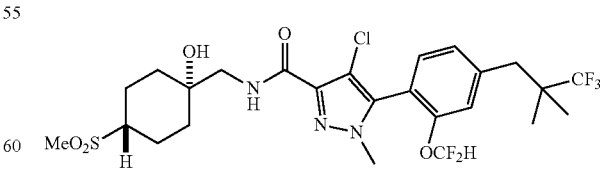

The title compound was prepared as described for the synthesis of Example 2, using (1s,4s)-1-(aminomethyl)-4-(methylsulfonyl)cyclohexan-1-ol hydrochloride (Intermediate 9) in place of ((1r,4r)-4-(methylsulfonyl)cyclohexyl)methanamine hydrochloride and ethyl 4-chloro-5-(2-

(difluoromethoxy)-4-(3,3,3-trifluoro-2,2-dimethylpropyl) phenyl)-1-methyl-1H-pyrazole-3-carboxylate (Intermediate 185) in place of ethyl 4-chloro-5-(2-(difluoromethoxy)-4-(3,3,3-trifluoro-2,2-dimethylpropyl)phenyl)-1-ethyl-1H-pyrazole-3-carboxylate. $^1$H NMR (500 MHz, CDCl$_3$) δ 7.33-7.29 (m, 1H), 7.24-7.18 (m, 2H), 7.15 (s, 1H), 6.54-6.23 (m, 1H), 3.74 (s, 3H), 3.47 (d, J=6.3 Hz, 2H), 2.93 (s, 1H), 2.88 (s, 2H), 2.83 (s, 3H), 2.82-2.76 (m, 1H), 2.18-2.09 (m, 2H), 2.03-1.92 (m, 4H), 1.49-1.37 (m, 2H), 1.13 (s, 6H). MS (ESI) m/z: [M+H]$^+$ Found 616.2.

Example 155

4-Chloro-5-(2-(difluoromethoxy)-4-(3,3,3-trifluoro-2,2-dimethylpropyl)phenyl)-1-methyl-N-(((1r,4r)-4-(methylsulfonyl)cyclohexyl)methyl)-1H-pyrazole-3-carboxamide

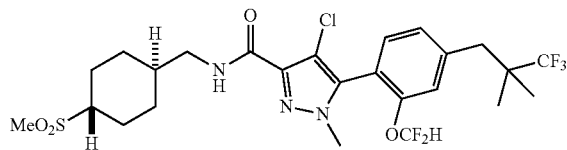

The title compound was prepared as described for the synthesis of Example 2, using ethyl 4-chloro-5-(2-(difluoromethoxy)-4-(3,3,3-trifluoro-2,2-dimethylpropyl)phenyl)-1-methyl-1H-pyrazole-3-carboxylate (Intermediate 185) in place of ethyl 4-chloro-5-(2-(difluoromethoxy)-4-(3,3,3-trifluoro-2,2-dimethylpropyl)phenyl)-1-ethyl-1H-pyrazole-3-carboxylate. $^1$H NMR (500 MHz, CDCl$_3$) δ 7.33-7.29 (m, 1H), 7.20-7.17 (m, 1H), 7.14 (s, 1H), 6.95-6.89 (m, 1H), 6.53-6.21 (m, 1H), 3.73 (s, 3H), 3.34 (t, J=6.6 Hz, 2H), 2.92-2.77 (m, 7H), 2.33-2.23 (m, 2H), 2.12-2.03 (m, 2H), 1.72-1.55 (m, 2H), 1.21-1.08 (m, 8H). MS (ESI) m/z: [M+H]$^+$ Found 600.2.

Example 156

4-Chloro-5-(2-(difluoromethoxy)-4-(3,3,3-trifluoro-2,2-dimethylpropyl)phenyl)-N-(((1r,4r)-4-(ethylsulfonyl)cyclohexyl)methyl)-1-methyl-1H-pyrazole-3-carboxamide

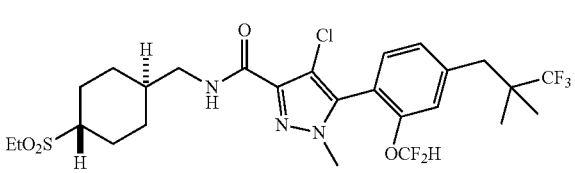

The title compound was prepared as described for the synthesis of Example 2, using ((1r,4r)-4-(ethyl sulfonyl) cyclohexyl)methanamine hydrochloride (Intermediate 40) in place of ((1r,4r)-4-(methyl sulfonyl)cyclohexyl)methanamine hydrochloride and ethyl 4-chloro-5-(2-(difluoromethoxy)-4-(3,3,3-trifluoro-2,2-dimethylpropyl)phenyl)-1-methyl-1H-pyrazole-3-carboxylate (Intermediate 185) in place of ethyl 4-chloro-5-(2-(difluoromethoxy)-4-(3,3,3-trifluoro-2,2-dimethylpropyl)phenyl)-1-ethyl-1H-pyrazole-3-carboxylate. $^1$H NMR (400 MHz, CDCl$_3$) δ 7.34-7.29 (m, 1H), 7.21-7.16 (m, 1H), 7.14 (s, 1H), 6.96-6.88 (m, 1H), 6.58-6.16 (m, 1H), 3.73 (s, 3H), 3.34 (t, J=6.5 Hz, 2H), 3.00-2.91 (m, 2H), 2.91-2.80 (m, 3H), 2.28-2.17 (m, 2H), 2.12-2.01 (m, 2H), 1.74-1.57 (m, 3H), 1.39 (t, J=7.5 Hz, 3H), 1.20-1.06 (m, 8H). MS (ESI) m/z: [M+H]$^+$ Found 614.2.

Example 157

5-(2-(Difluoromethoxy)-4-(3,3,3-trifluoro-2,2-dimethylpropyl)phenyl)-N-(((1s,4s)-1-hydroxy-4-(methylsulfonyl)cyclohexyl)methyl)-1,4-dimethyl-1H-pyrazole-3-carboxamide

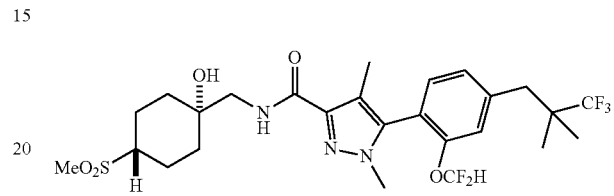

The title compound was prepared as described for the synthesis of Intermediate 105, using 4-chloro-5-(2-(difluoromethoxy)-4-(3,3,3-trifluoro-2,2-dimethylpropyl)phenyl)-N-(((1s,4s)-1-hydroxy-4-(methylsulfonyl)cyclohexyl) methyl)-1-methyl-1H-pyrazole-3-carboxamide (Example 154) in place of ethyl 4-chloro-5-(2-(difluoromethoxy)-4-((S*)-3,3,3-trifluoro-2-methylpropyl)phenyl)-1-ethyl-1H-pyrazole-3-carboxylate. $^1$H NMR (400 MHz, CDCl$_3$) δ 7.28-7.22 (m, 1H), 7.18-7.06 (m, 3H), 6.49-6.08 (m, 1H), 3.63 (s, 3H), 3.38 (d, J=6.4 Hz, 2H), 2.82 (s, 2H), 2.80-2.69 (m, 4H), 2.14-2.03 (m, 5H), 2.00-1.88 (m, 4H), 1.41-1.30 (m, 2H), 1.08 (s, 6H). MS (ESI) m/z: [M+H]$^+$ Found 596.2.

Example 158

4-Chloro-5-(2-(difluoromethoxy)-4-(4,4,4-trifluorobutyl)phenyl)-N-(((1s,4s)-1-hydroxy-4-(methylsulfonyl)cyclohexyl)methyl)-1-methyl-1H-pyrazole-3-carboxamide

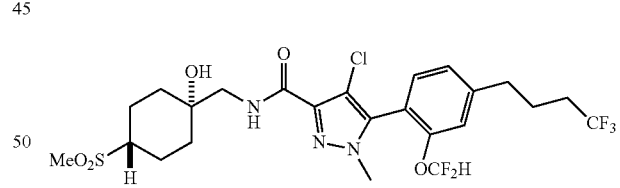

The title compound was prepared as described for the synthesis of Example 2, using (1s,4s)-1-(aminomethyl)-4-(methylsulfonyl)cyclohexan-1-ol hydrochloride (Intermediate 9) in place of ((1r,4r)-4-(methylsulfonyl)cyclohexyl) methanamine hydrochloride and ethyl 4-chloro-5-(2-(difluoromethoxy)-4-(4,4,4-trifluorobutyl)phenyl)-1-methyl-1H-pyrazole-3-carboxylate (Intermediate 186) in place of ethyl 4-chloro-5-(2-(difluoromethoxy)-4-(3,3,3-trifluoro-2,2-dimethylpropyl)phenyl)-1-ethyl-1H-pyrazole-3-carboxylate. $^1$H NMR (400 MHz, CDCl$_3$) δ 7.34-7.28 (m, 1H), 7.24-7.13 (m, 3H), 6.61-6.19 (m, 1H), 3.74 (s, 3H), 3.51-3.43 (m, 2H), 2.95 (s, 1H), 2.87-2.74 (m, 6H), 2.25-2.08 (m, 4H), 2.04-1.91 (m, 6H), 1.50-1.38 (m, 2H). MS (ESI) m/z: [M+H]$^+$ Found 602.2.

Example 159

4-Chloro-5-(2-(difluoromethoxy)-4-(4,4,4-trifluorobutyl)phenyl)-N-(((1S*,2S*,4S*)-1,2-dihydroxy-4-(methylsulfonyl)cyclohexyl)methyl)-1-methyl-1H-pyrazole-3-carboxamide

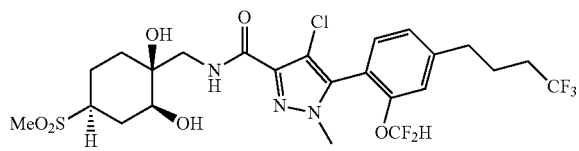

The title compound was prepared as described for the synthesis of Example 2, using (1S*,2S*,4S*)-1-(aminomethyl)-4-(methylsulfonyl)cyclohexane-1,2-diol hydrochloride (Intermediate 25) in place of (((1r,4r)-4-(methylsulfonyl)cyclohexyl)methanamine hydrochloride and ethyl 4-chloro-5-(2-(difluoromethoxy)-4-(4,4,4-trifluorobutyl)phenyl)-1-methyl-1H-pyrazole-3-carboxylate (Intermediate 186) in place of ethyl 4-chloro-5-(2-(difluoromethoxy)-4-(3,3,3-trifluoro-2,2-dimethylpropyl)phenyl)-1-ethyl-1H-pyrazole-3-carboxylate. $^1$H NMR (400 MHz, CDCl$_3$) δ 7.34-7.28 (m, 1H), 7.25-7.19 (m, 2H), 7.15 (s, 1H), 6.64-6.20 (m, 1H), 4.55-4.47 (m, 1H), 3.94-3.85 (m, 1H), 3.78-3.71 (m, 3H), 3.64-3.53 (m, 1H), 3.10-3.00 (m, 1H), 2.90-2.75 (m, 7H), 2.31-2.22 (m, 1H), 2.22-2.10 (m, 2H), 2.10-2.02 (m, 1H), 2.02-1.86 (m, 5H), 1.62-1.46 (m, 1H). MS (ESI) m/z: [M+H]$^+$ Found 618.1.

Example 160

4-Chloro-5-(2-(difluoromethoxy)-4-(4,4,4-trifluorobutyl)phenyl)-N-(((1R*,2R*,4R*)-1,2-dihydroxy-4-(methylsulfonyl)cyclohexyl)methyl)-1-methyl-1H-pyrazole-3-carboxamide

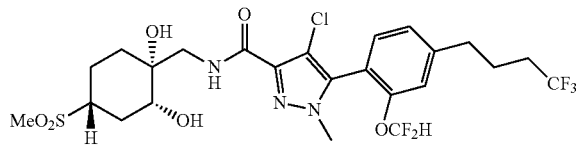

The title compound was prepared as described for the synthesis of Example 2, using (1R*,2R*,4R*)-1-(aminomethyl)-4-(methylsulfonyl)cyclohexane-1,2-diol hydrochloride (Intermediate 24) in place of (((1r,4r)-4-(methylsulfonyl)cyclohexyl)methanamine hydrochloride and ethyl 4-chloro-5-(2-(difluoromethoxy)-4-(4,4,4-trifluorobutyl)phenyl)-1-methyl-1H-pyrazole-3-carboxylate (Intermediate 186) in place of ethyl 4-chloro-5-(2-(difluoromethoxy)-4-(3,3,3-trifluoro-2,2-dimethylpropyl)phenyl)-1-ethyl-1H-pyrazole-3-carboxylate. $^1$H NMR (400 MHz, CDCl$_3$) δ 7.34-7.28 (m, 1H), 7.25-7.19 (m, 2H), 7.17-7.13 (m, 1H), 6.63-6.20 (m, 1H), 4.54-4.47 (m, 1H), 3.94-3.84 (m, 1H), 3.77-3.71 (m, 3H), 3.64-3.53 (m, 1H), 3.10-3.01 (m, 1H), 2.89-2.76 (m, 7H), 2.31-2.22 (m, 1H), 2.23-2.11 (m, 2H), 2.11-2.03 (m, 1H), 2.03-1.85 (m, 5H), 1.61-1.47 (m, 1H). MS (ESI) m/z: [M+H]$^+$ Found 618.2.

Example 161

5-(2-(Difluoromethoxy)-4-(4,4,4-trifluorobutyl)phenyl)-N-(((1s,4s)-1-hydroxy-4-(methylsulfonyl)cyclohexyl)methyl)-1,4-dimethyl-1H-pyrazole-3-carboxamide

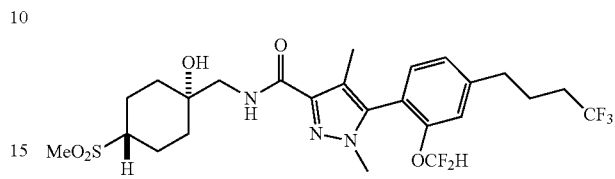

The title compound was prepared as described for the synthesis of Example 2, using (1s,4s)-1-(aminomethyl)-4-(methylsulfonyl)cyclohexan-1-ol hydrochloride (Intermediate 9) in place of ((1 r,4r)-4-(methylsulfonyl)cyclohexyl)methanamine hydrochloride and ethyl 5-(2-(difluoromethoxy)-4-(4,4,4-trifluorobutyl)phenyl)-1,4-dimethyl-1H-pyrazole-3-carboxylate (Intermediate 187) in place of ethyl 4-chloro-5-(2-(difluoromethoxy)-4-(3,3,3-trifluoro-2,2-dimethylpropyl)phenyl)-1-ethyl-1H-pyrazole-3-carboxylate. $^1$H NMR (400 MHz, CDCl$_3$) δ 7.33-7.28 (m, 1H), 7.24-7.10 (m, 3H), 6.56-6.13 (m, 1H), 3.67 (s, 3H), 3.49 (s, 1H), 3.43 (d, J=6.3 Hz, 2H), 2.87-2.73 (m, 6H), 2.24-2.08 (m, 7H), 2.04-1.90 (m, 6H), 1.47-1.33 (m, 2H). MS (ESI) m/z: [M+H]$^+$ Found 582.2.

Example 162

4-Chloro-1-ethyl-N-(((1r,4r)-4-(methylsulfonyl)cyclohexyl)methyl)-5-(4-(3,3,3-trifluoro-2,2-dimethylpropyl)-2-(trifluoromethyl)phenyl)-1H-pyrazole-3-carboxamide

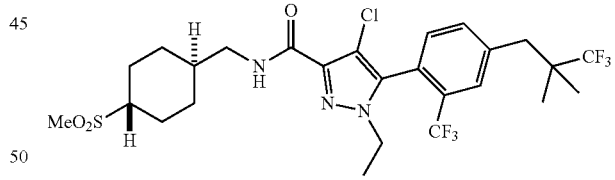

The title compound was prepared as described for the synthesis of Example 2, using ethyl 5-(2-(difluoromethoxy)-4-(4,4,4-trifluorobutyl)phenyl)-1,4-dimethyl-1H-pyrazole-3-carboxylate (Intermediate 187) in place of ethyl 4-chloro-5-(2-(difluoromethoxy)-4-(3,3,3-trifluoro-2,2-dimethylpropyl)phenyl)-1-ethyl-1H-pyrazole-3-carboxylate. $^1$H NMR (500 MHz, CDCl$_3$) δ 7.66-7.62 (m, 1H), 7.53-7.48 (m, 1H), 7.30-7.27 (m, 1H), 6.98-6.90 (m, 1H), 3.95-3.86 (m, 1H), 3.83-3.73 (m, 1H), 3.35 (t, J=6.5 Hz, 2H), 2.93 (s, 2H), 2.88-2.79 (m, 4H), 2.34-2.25 (m, 2H), 2.13-2.05 (m, 2H), 1.75-1.66 (m, 1H), 1.66-1.55 (m, 2H), 1.35 (t, J=7.3 Hz, 3H), 1.20-1.09 (m, 8H). MS (ESI) m/z: [M+H]$^+$ Found 615.9.

Example 163

4-Chloro-1-ethyl-N-(((1s,4s)-1-hydroxy-4-(methylsulfonyl)cyclohexyl)methyl)-5-(4-(3,3,3-trifluoro-2,2-dimethylpropyl)-2-(trifluoromethyl)phenyl)-1H-pyrazole-3-carboxamide

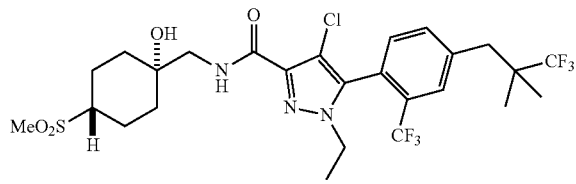 [SMILES: CCn1nc(C(=O)NC[C@]2(O)CC[C@@H](S(C)(=O)=O)CC2)c(Cl)c1-c1ccc(CC(C)(C)C(F)(F)F)cc1Cl]

The title compound was prepared as described for the synthesis of Example 2, using (1s,4s)-1-(aminomethyl)-4-(methylsulfonyl)cyclohexan-1-ol hydrochloride (Intermediate 9) in place of ((1r,4r)-4-(methylsulfonyl)cyclohexyl)methanamine hydrochloride and ethyl 5-(2-(difluoromethoxy)-4-(4,4,4-trifluorobutyl)phenyl)-1,4-dimethyl-1H-pyrazole-3-carboxylate (Intermediate 187) in place of ethyl 4-chloro-5-(2-(difluoromethoxy)-4-(3,3,3-trifluoro-2,2-dimethylpropyl)phenyl)-1-ethyl-1H-pyrazole-3-carboxylate. $^1$H NMR (500 MHz, CDCl$_3$) δ 7.66-7.63 (m, 1H), 7.53-7.48 (m, 1H), 7.29-7.27 (m, 1H), 7.25-7.21 (m, 1H), 3.96-3.86 (m, 1H), 3.84-3.75 (m, 1H), 3.52-3.42 (m, 2H), 3.02 (s, 1H), 2.94 (s, 2H), 2.86-2.76 (m, 4H), 2.18-2.09 (m, 2H), 2.03-1.93 (m, 4H), 1.50-1.39 (m, 2H), 1.36 (t, J=7.3 Hz, 3H), 1.17-1.11 (s, 6H). MS (ESI) m/z: [M+H]$^+$ Found 631.9.

Example 164

4-Chloro-5-(2-chloro-4-(3,3,3-trifluoro-2,2-dimethylpropyl)phenyl)-1-ethyl-N-(((1s,4s)-1-hydroxy-4-(methylsulfonyl)cyclohexyl)methyl)-1H-pyrazole-3-carboxamide

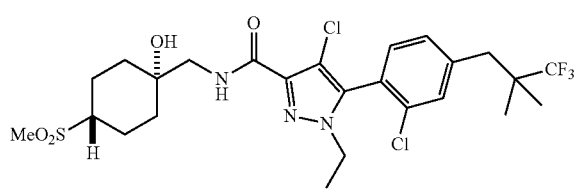

The title compound was prepared as described for the synthesis of Example 2, using (1s,4s)-1-(aminomethyl)-4-(methylsulfonyl)cyclohexan-1-ol hydrochloride (Intermediate 9) in place of ((1r,4r)-4-(methylsulfonyl)cyclohexyl)methanamine hydrochloride and ethyl 4-chloro-5-(2-chloro-4-(3,3,3-trifluoro-2,2-dimethylpropyl)phenyl)-1-ethyl-1H-pyrazole-3-carboxylate (Intermediate 189) in place of ethyl 4-chloro-5-(2-(difluoromethoxy)-4-(3,3,3-trifluoro-2,2-dimethylpropyl)phenyl)-1-ethyl-1H-pyrazole-3-carboxylate. $^1$H NMR (500 MHz, CDCl$_3$) δ 7.40-7.36 (m, 1H), 7.31-7.27 (m, 1H), 7.25-7.20 (m, 2H), 4.08-3.88 (m, 2H), 3.49 (d, J=6.3 Hz, 2H), 2.90-2.74 (m, 6H), 2.20-2.08 (m, 2H), 2.05-1.91 (m, 4H), 1.52-1.39 (m, 2H), 1.35 (t, J=7.2 Hz, 3H), 1.13 (s, 6H). MS (ESI) m/z: [M+H]$^+$ Found 597.8.

Example 165

4-Chloro-5-(2-chloro-4-(3,3,3-trifluoro-2,2-dimethylpropyl)phenyl)-1-ethyl-N-(((1r,4r)-4-(methylsulfonyl)cyclohexyl)methyl)-1H-pyrazole-3-carboxamide

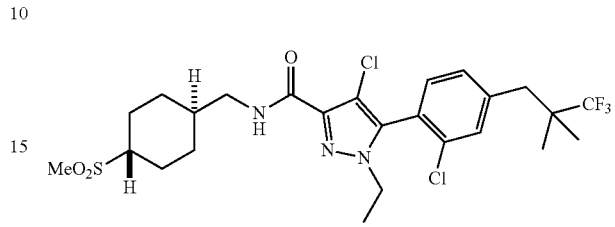

The title compound was prepared as described for the synthesis of Example 1, using ethyl 4-chloro-5-(2-chloro-4-(3,3,3-trifluoro-2,2-dimethylpropyl)phenyl)-1-ethyl-1H-pyrazole-3-carboxylate (Intermediate 189) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (400 MHz, CDCl$_3$) δ 7.40-7.36 (m, 1H), 7.25-7.20 (m, 2H), 7.10-7.03 (m, 1H), 4.08-3.87 (m, 2H), 3.42-3.32 (m, 2H), 2.91-2.79 (m, 6H), 2.34-2.23 (m, 2H), 2.13-2.03 (m, 2H), 1.77-1.53 (m, 3H), 1.35 (t, J=7.3 Hz, 3H), 1.13 (s, 8H). MS (ESI) m/z: [M+H]$^+$ Found 581.8

Example 166

4-Chloro-5-(2-chloro-4-(3,3,3-trifluoro-2,2-dimethylpropyl)phenyl)-N-(((1s*,4s*)-1-cyano-4-(methylsulfonyl)cyclohexyl)methyl)-1-ethyl-1H-pyrazole-3-carboxamide

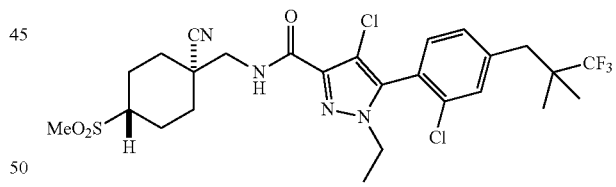

The title compound was prepared as described for the synthesis of Example 1, using ethyl 4-chloro-5-(2-chloro-4-(3,3,3-trifluoro-2,2-dimethylpropyl)phenyl)-1-ethyl-1H-pyrazole-3-carboxylate (Intermediate 189) in place of ethyl (R*)-4-chloro-1-ethyl-5-(2-methoxy-4-(3,3,3-trifluoro-2-methylpropyl)phenyl)-1H-pyrazole-3-carboxylate and (1s*,4s*)-1-(aminomethyl)-4-(methylsulfonyl)cyclohexane-1-carbonitrile hydrochloride (Intermediate 35) in place of ((1r,4r)-4-(methylsulfonyl)cyclohexyl)methanamine hydrochloride. $^1$H NMR (500 MHz, CDCl$_3$) δ 7.39-7.37 (m, 1H), 7.31-7.27 (m, 1H), 7.25-7.21 (m, 2H), 4.05-3.91 (m, 2H), 3.68 (d, J=6.9 Hz, 2H), 2.90-2.78 (m, 6H), 2.40-2.32 (m, 2H), 2.32-2.25 (m, 2H), 1.97-1.86 (m, 2H), 1.62-1.54 (m, 2H), 1.36 (t, J=7.2 Hz, 3H), 1.14 (s, 6H). MS (ESI) m/z: [M+H]$^+$ Found 606.8.

Example 167

4-Chloro-1-ethyl-N-(((1s,4s)-1-hydroxy-4-(methylsulfonyl)cyclohexyl)methyl)-5-(4-(3,3,3-trifluoro-2,2-dimethylpropyl)phenyl)-1H-pyrazole-3-carboxamide

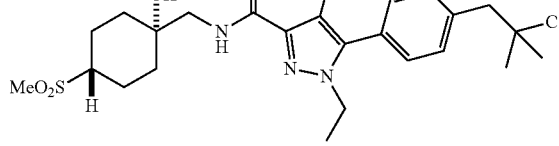

The title compound was prepared as described for the synthesis of Example 1, using ethyl 4-chloro-1-ethyl-5-(4-(3,3,3-trifluoro-2,2-dimethylpropyl)phenyl)-1H-pyrazole-3-carboxylate (Intermediate 190) in place of ethyl (R*)-4-chloro-1-ethyl-5-(2-methoxy-4-(3,3,3-trifluoro-2-methylpropyl)phenyl)-1H-pyrazole-3-carboxylate and (1s,4s)-1-(aminomethyl)-4-(methylsulfonyl)cyclohexan-1-ol hydrochloride (Intermediate 9) in place of ((1r,4r)-4-(methylsulfonyl)cyclohexyl)methanamine hydrochloride. $^1$H NMR (500 MHz, CDCl$_3$) δ 7.35-7.30 (m, 4H), 7.29-7.26 (m, 1H), 4.14-4.08 (m, 2H), 3.48 (d, J=6.3 Hz, 2H), 2.88-2.77 (m, 6H), 2.26 (br s, 1H), 2.17-2.10 (m, 2H), 2.03-1.92 (m, 4H), 1.48-1.36 (m, 5H), 1.11 (s, 6H). MS (ESI) m/z: [M+H]$^+$ Found 563.9.

Example 168

4-Chloro-1-ethyl-N-(((1r,4r)-4-(methylsulfonyl)cyclohexyl)methyl)-5-(4-(3,3,3-trifluoro-2,2-dimethylpropyl)phenyl)-1H-pyrazole-3-carboxamide

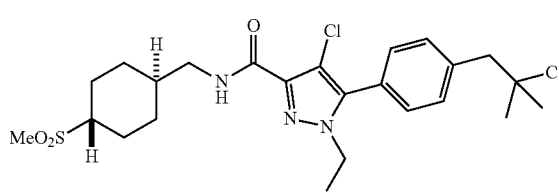

The title compound was prepared as described for the synthesis of Example 1, using ethyl 4-chloro-1-ethyl-5-(4-(3,3,3-trifluoro-2,2-dimethylpropyl)phenyl)-1H-pyrazole-3-carboxylate (Intermediate 190) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (500 MHz, CDCl$_3$) δ 7.33-7.31 (m, 4H), 7.05-7.01 (m, 1H), 4.14-4.07 (m, 2H), 3.36 (t, J=6.6 Hz, 2H), 2.89-2.79 (m, 6H), 2.33-2.24 (m, 2H), 2.11-2.03 (m, 2H), 1.76-1.65 (m, 1H), 1.65-1.54 (m, 2H), 1.38 (t, J=7.2 Hz, 3H), 1.20-1.08 (m, 8H). MS (ESI) m/z: [M+H]$^+$ Found 548.0.

Example 169

4-Chloro-N-(((1s*,4s*)-1-cyano-4-(methylsulfonyl)cyclohexyl)methyl)-1-ethyl-5-(4-(3,3,3-trifluoro-2,2-dimethylpropyl)phenyl)-1H-pyrazole-3-carboxamide

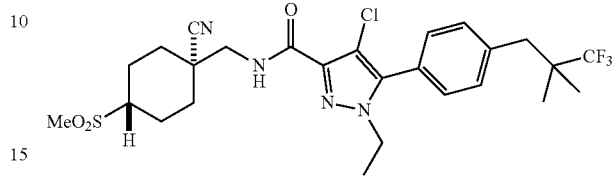

The title compound was prepared as described for the synthesis of Example 1, using ethyl 4-chloro-1-ethyl-5-(4-(3,3,3-trifluoro-2,2-dimethylpropyl)phenyl)-1H-pyrazole-3-carboxylate (Intermediate 190) in place of ethyl (R*)-4-chloro-1-ethyl-5-(2-methoxy-4-(3,3,3-trifluoro-2-methylpropyl)phenyl)-1H-pyrazole-3-carboxylate and (1s*,4s*)-1-(aminomethyl)-4-(methylsulfonyl)cyclohexane-1-carbonitrile hydrochloride (Intermediate 35) in place of ((1r,4r)-4-(methylsulfonyl)cyclohexyl)methanamine hydrochloride. $^1$H NMR (400 MHz, CDCl$_3$) δ 7.34-7.27 (m, 5H), 4.15-4.08 (m, 2H), 3.68 (d, J=6.9 Hz, 2H), 2.90-2.78 (m, 6H), 2.41-2.23 (m, 4H), 1.91 (qd, J=13.5, 3.3 Hz, 2H), 1.65-1.52 (m, 2), 1.39 (t, J=7.2 Hz, 3H), 1.11 (s, 6H). MS (ESI) m/z: [M+H]$^+$ Found 572.9.

Example 170

4-Chloro-1-ethyl-N-(((1s,4s)-1-hydroxy-4-(methylsulfonyl)cyclohexyl)methyl)-5-(2-(trifluoromethyl)-4-(3,3,3-trifluoropropyl)phenyl)-1H-pyrazole-3-carboxamide

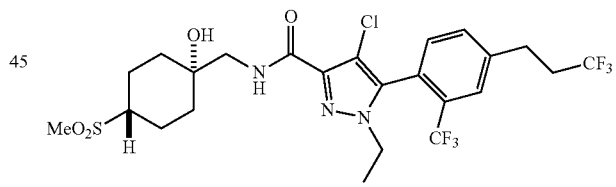

The title compound was prepared as described for the synthesis of Example 1, using ethyl 4-chloro-1-ethyl-5-(2-(trifluoromethyl)-4-(3,3,3-trifluoropropyl)phenyl)-1H-pyrazole-3-carboxylate (Intermediate 191) in place of ethyl (R*)-4-chloro-1-ethyl-5-(2-methoxy-4-(3,3,3-trifluoro-2-methylpropyl)phenyl)-1H-pyrazole-3-carboxylate (Intermediate 99) and (1s,4s)-1-(aminomethyl)-4-(methylsulfonyl)cyclohexan-1-ol hydrochloride (Intermediate 9) in place of ((1r,4r)-4-(methylsulfonyl)cyclohexyl)methanamine hydrochloride. $^1$H NMR (500 MHz, DMSO-d$_6$) δ 7.96 (s, 1H), 7.87 (t, J=6.3 Hz, 1H), 7.84-7.79 (m, 1H), 7.59-7.52 (m, 1H), 4.61 (s, 1H), 3.95-3.84 (m, 1H), 3.84-3.72 (m, 1H), 3.28-3.23 (m, 2H), 3.09-2.95 (m, 3H), 2.89 (s, 3H), 2.82-2.68 (m, 2H), 1.93-1.81 (m, 2H), 1.81-1.64 (m, 4H), 1.45-1.32 (m, 2H), 1.26 (t, J=7.2 Hz, 3H). MS (ESI) m/z: [M+H]$^+$ Found 603.3.

Example 171

4-Chloro-1-ethyl-N-(((1r,4r)-4-(methylsulfonyl)cyclohexyl)methyl)-5-(2-(trifluoromethyl)-4-(3,3,3-trifluoropropyl)phenyl)-1H-pyrazole-3-carboxamide

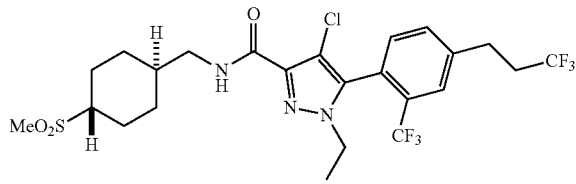 [SMILES: CCn1nc(C(=O)NC[C@H]2CC[C@H](S(C)(=O)=O)CC2)c(Cl)c1-c1ccc(CCC(F)(F)F)cc1C(F)(F)F]

The title compound was prepared as described for the synthesis of Example 1, using ethyl 4-chloro-1-ethyl-5-(2-(trifluoromethyl)-4-(3,3,3-trifluoropropyl)phenyl)-1H-pyrazole-3-carboxylate (Intermediate 191) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (500 MHz, CDCl$_3$) δ 7.69 (s, 1H), 7.55 (d, J=8.0 Hz, 1H), 7.30 (d, J=7.9 Hz, 1H), 6.98-6.89 (m, 1H), 3.90 (dt, J=14.6, 7.3 Hz, 1H), 3.78 (dt, J=13.8, 7.2 Hz, 1H), 3.35 (t, J=6.6 Hz, 2H), 3.09-3.00 (m, 2H), 2.89-2.77 (m, 4H), 2.58-2.44 (m, 2H), 2.32-2.24 (m, 2H), 2.12-2.05 (m, 2H), 1.75-1.65 (m, 1H), 1.67-1.56 (m, 2H), 1.34 (t, J=7.3 Hz, 3H), 1.21-1.07 (m, 2H). MS (ESI) m/z: [M+H]$^+$ Found 588.1.

Example 172

4-Chloro-1-ethyl-N-(((1r,4R)-4-(methylsulfonyl)cyclohexyl)methyl)-5-(2-(trifluoromethyl)-4-(((R)-1,1,1-trifluoropropan-2-yl)amino)phenyl)-1H-pyrazole-3-carboxamide

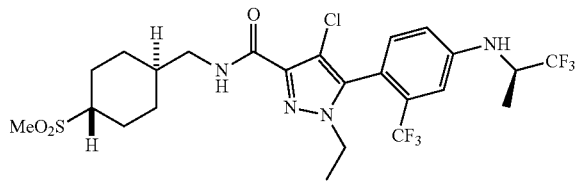 [SMILES: CCn1nc(C(=O)NC[C@H]2CC[C@H](S(C)(=O)=O)CC2)c(Cl)c1-c1ccc(N[C@H](C)C(F)(F)F)cc1C(F)(F)F]

The title compound was prepared as described for the synthesis of Example 1, using ethyl (R)-4-chloro-1-ethyl-5-(2-(trifluoromethyl)-4-((1,1,1-trifluoropropan-2-yl)amino)phenyl)-1H-pyrazole-3-carboxylate (Intermediate 192) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (400 MHz, CDCl$_3$) δ 7.15-7.09 (m, 1H), 7.07-7.04 (m, 1H), 6.97-6.86 (m, 2H), 4.18-4.07 (m, 2H), 3.90 (dt, J=14.5, 7.3 Hz, 1H), 3.86-3.76 (m, 1H), 3.34 (t, J=6.6 Hz, 2H), 2.88-2.77 (m, 4H), 2.33-2.23 (m, 2H), 2.13-2.03 (m, 2H), 1.76-1.56 (m, 3H), 1.49 (d, J=6.0 Hz, 3H), 1.38-1.29 (m, 3H), 1.21-1.07 (m, 2H). MS (ESI) m/z: [M+H]$^+$ Found 603.2

Example 173

4-Chloro-5-(2-chloro-4-(3,3,3-trifluoropropyl)phenyl)-1-ethyl-N-(((1s,4s)-1-hydroxy-4-(methylsulfonyl)cyclohexyl)methyl)-1H-pyrazole-3-carboxamide

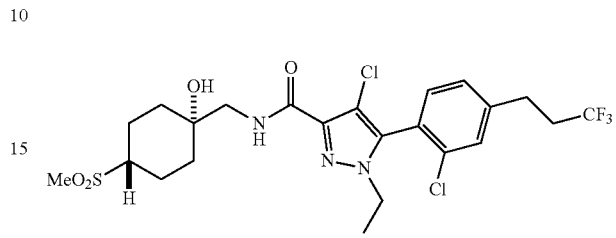

The title compound was prepared as described for the synthesis of Example 1, using ethyl 4-chloro-5-(2-chloro-4-(3,3,3-trifluoropropyl)phenyl)-1-ethyl-1H-pyrazole-3-carboxylate (Intermediate 193) in place of ethyl (R*)-4-chloro-1-ethyl-5-(2-methoxy-4-(3,3,3-trifluoro-2-methylpropyl)phenyl)-1H-pyrazole-3-carboxylate and (1s,4s)-1-(aminomethyl)-4-(methylsulfonyl)cyclohexan-1-ol hydrochloride (Intermediate 9) in place of ((1r,4r)-4-(methylsulfonyl)cyclohexyl)methanamine hydrochloride. $^1$H NMR (400 MHz, CDCl$_3$) δ 7.42 (s, 1H), 7.29-7.21 (m, 3H), 4.07-3.87 (m, 2H), 3.47 (d, J=6.5 Hz, 2H), 3.08 (s, 1H), 3.00-2.90 (m, 2H), 2.87-2.74 (m, 4H), 2.55-2.39 (m, 2H), 2.18-2.08 (m, 2H), 2.04-1.91 (m, 4H), 1.51-1.38 (m, 2H), 1.34 (t, J=7.3 Hz, 3H). MS (ESI) m/z: [M+H]$^+$ Found 570.1.

Example 174

4-Chloro-5-(2-chloro-4-(3,3,3-trifluoropropyl)phenyl)-1-ethyl-N-(((1r,4r)-4-(methylsulfonyl)cyclohexyl)methyl)-1H-pyrazole-3-carboxamide

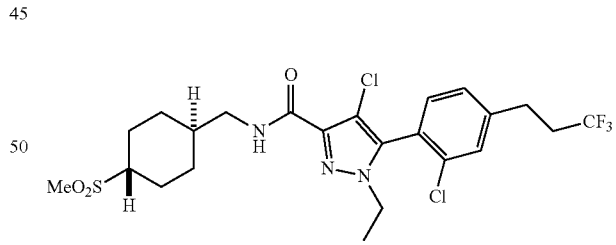

The title compound was prepared as described for the synthesis of Example 1, using ethyl 4-chloro-5-(2-chloro-4-(3,3,3-trifluoropropyl)phenyl)-1-ethyl-1H-pyrazole-3-carboxylate (Intermediate 193) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (500 MHz, CDCl$_3$) δ 7.42 (s, 1H), 7.29-7.24 (m, 2H), 6.94 (t, J=6.3 Hz, 1H), 4.02-3.85 (m, 2H), 3.35 (td, J=6.6, 2.3 Hz, 2H), 2.99-2.91 (m, 2H), 2.88-2.81 (m, 4H), 2.53-2.41 (m, 2H), 2.33-2.24 (m, 2H), 2.12-2.05 (m, 2H), 1.75-1.65 (m, 1H), 1.65-1.54 (m, 2H), 1.34 (t, J=7.3 Hz, 3H), 1.20-1.09 (m, 2H). MS (ESI) m/z: [M+H]$^+$ Found 554.1

Example 175

4-Chloro-5-(2-chloro-4-(((R)-1,1,1-trifluoropropan-2-yl)amino)phenyl)-1-ethyl-N-(((1s,4S)-4-(methylsulfonyl)cyclohexyl)methyl)-1H-pyrazole-3-carboxamide

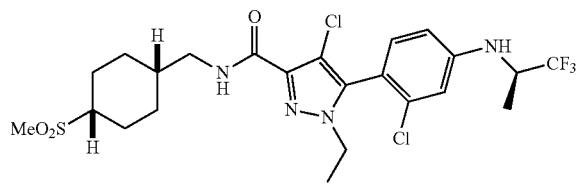 [SMILES: CCn1nc(C(=O)NC[C@H]2CC[C@@H](S(C)(=O)=O)CC2)c(Cl)c1-c1ccc(N[C@H](C)C(F)(F)F)cc1Cl]

Example 176

4-Chloro-5-(2-chloro-4-(((R)-1,1,1-trifluoropropan-2-yl)amino)phenyl)-1-ethyl-N-(((1r,4R)-4-(methylsulfonyl)cyclohexyl)methyl)-1H-pyrazole-3-carboxamide

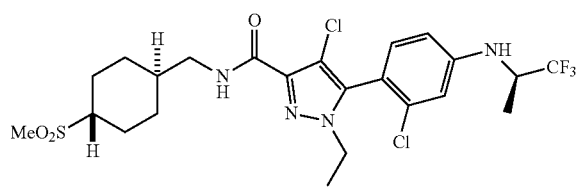 [SMILES: CCn1nc(C(=O)NC[C@H]2CC[C@H](S(C)(=O)=O)CC2)c(Cl)c1-c1ccc(N[C@H](C)C(F)(F)F)cc1Cl]

Intermediate 249 was purified by SFC using a chiral stationary phase (Chiralpak IC, 60% $CO_2$, 40% MeOH) to give a pair of diastereomers. The first-eluting diastereomer was Example 175, and the second-eluting diastereomer was Example 176. Example 175: $^1$H NMR (400 MHz, $CDCl_3$) δ 7.12-7.06 (m, 1H), 6.97-6.90 (m, 1H), 6.83-6.80 (m, 1H), 6.69-6.63 (m, 1H), 4.11-3.87 (m, 4H), 3.39-3.30 (m, 2H), 2.85-2.80 (m, 1H), 2.82 (s, 3H), 2.34-2.23 (m, 2H), 2.14-2.02 (m, 2H), 1.76-1.57 (m, 3H), 1.46 (d, J=6.6 Hz, 3H), 1.34 (t, 3H), 1.22-1.06 (m, 2H). MS (ESI) m/z: $[M+H]^+$ Found 569.2. Example 176: $^1$H NMR (400 MHz, $CDCl_3$) δ 7.12-7.06 (m, 1H), 6.96-6.91 (m, 1H), 6.82 (d, J=2.3 Hz, 1H), 6.69-6.62 (m, 1H), 4.12-3.88 (m, 4H), 3.40-3.28 (m, 2H), 2.88-2.78 (m, 4H), 2.33-2.23 (m, 2H), 2.13-2.02 (m, 2H), 1.75-1.52 (m, 3H), 1.46 (d, J=6.6 Hz, 3H), 1.34 (t, J=7.3 Hz, 3H), 1.20-1.07 (m, 2H). MS (ESI) m/z: $[M+H]^+$ Found 569.1.

Example 177

4-Chloro-1-ethyl-5-(2-fluoro-4-(3,3,3-trifluoro-2,2-dimethylpropyl)phenyl)-N-(((1r,4r)-4-(methylsulfonyl)cyclohexyl)methyl)-1H-pyrazole-3-carboxamide

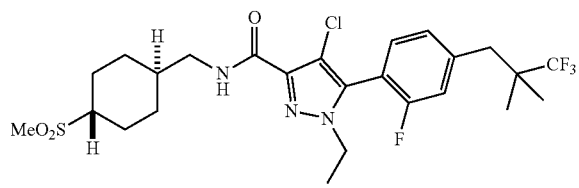

The title compound was prepared as described for the synthesis of Example 1, using ethyl 4-chloro-1-ethyl-5-(2-fluoro-4-(3,3,3-trifluoro-2,2-dimethylpropyl)phenyl)-1H-pyrazole-3-carboxylate (Intermediate 195) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (500 MHz, $CDCl_3$) δ 7.29 (t, J=7.6 Hz, 1H), 7.11 (dd, J=7.9, 1.6 Hz, 1H), 7.08-7.03 (m, 1H), 6.97 (t, J=6.5 Hz, 1H), 4.09-3.97 (m, 2H), 3.35 (t, J=6.4 Hz, 2H), 2.89-2.79 (m, 6H), 2.33-2.25 (m, 2H), 2.12-2.04 (m, 2H), 1.75-1.65 (m, 1H), 1.65-1.53 (m, 2H), 1.38 (t, J=7.2 Hz, 3H), 1.20-1.08 (m, 8H). MS (ESI) m/z: $[M+H]^+$ Found 565.9.

Example 178

4-Chloro-1-ethyl-5-(2-fluoro-4-(3,3,3-trifluoro-2,2-dimethylpropyl)phenyl)-N-(((1s,4s)-1-hydroxy-4-(methylsulfonyl)cyclohexyl)methyl)-1H-pyrazole-3-carboxamide

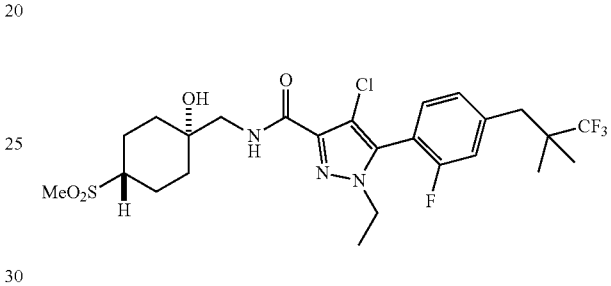

The title compound was prepared as described for the synthesis of Example 1, using ethyl 4-chloro-1-ethyl-5-(2-fluoro-4-(3,3,3-trifluoro-2,2-dimethylpropyl)phenyl)-1H-pyrazole-3-carboxylate (Intermediate 195) in place of ethyl (R*)-4-chloro-1-ethyl-5-(2-methoxy-4-(3,3,3-trifluoro-2-methylpropyl)phenyl)-1H-pyrazole-3-carboxylate and (1s,4s)-1-(aminomethyl)-4-(methylsulfonyl)cyclohexan-1-ol hydrochloride (Intermediate 9) in place of ((1r,4r)-4-(methylsulfonyl)cyclohexyl)methanamine hydrochloride. $^1$H NMR (500 MHz, $CDCl_3$) δ 7.31-7.27 (m, 2H), 7.12 (dd, J=7.8, 1.6 Hz, 1H), 7.09-7.04 (m, 1H), 4.10-3.97 (m, 2H), 3.48 (d, J=6.3 Hz, 2H), 2.90-2.77 (m, 6H), 2.64 (bs, 1H), 2.18-2.10 (m, 2H), 2.04-1.92 (m, 4H), 1.50-1.35 (m, 5H), 1.13 (s, 6H). MS (ESI) m/z: $[M+H]^+$ Found 581.8.

Example 179

4-Chloro-1-ethyl-5-(2-fluoro-4-(3,3,3-trifluoropropyl)phenyl)-N-(((1r,4r)-4-(methylsulfonyl)cyclohexyl)methyl)-1H-pyrazole-3-carboxamide

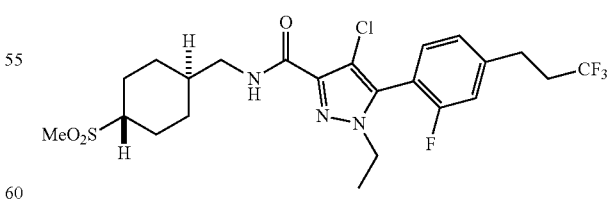

The title compound was prepared as described for the synthesis of Example 1, using ethyl 4-chloro-1-ethyl-5-(2-fluoro-4-(3,3,3-trifluoropropyl)phenyl)-1H-pyrazole-3-carboxylate (Intermediate 196) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (500 MHz, CDCl$_3$) δ 7.31 (t, J=7.6 Hz, 1H), 7.16 (dd, J=7.9, 1.5 Hz, 1H), 7.12-7.07 (m, 1H), 6.93 (t, J=6.2 Hz, 1H), 4.09-3.93 (m, 2H), 3.35 (t, J=6.2 Hz, 2H), 3.03-2.92 (m, 2H), 2.89-2.77 (m, 4H), 2.54-2.40 (m, 2H), 2.34-2.23 (m, 2H), 2.13-2.02 (m, 2H), 1.74-1.64 (m, 1H), 1.65-1.56 (m, 2H), 1.37 (t, J=7.3 Hz, 3H), 1.21-1.07 (m, 2H). MS (ESI) m/z: [M+H]$^+$ Found 538.2.

Example 180

4-Chloro-1-ethyl-5-(2-fluoro-4-(3,3,3-trifluoropropyl)phenyl)-N-(((1s,4s)-1-hydroxy-4-(methylsulfonyl)cyclohexyl)methyl)-1H-pyrazole-3-carboxamide

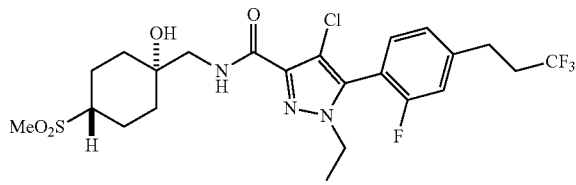 [SMILES: CCn1nc(C(=O)NC[C@]2(O)CC[C@@H](S(C)(=O)=O)CC2)c(Cl)c1-c1ccc(CCC(F)(F)F)cc1F]

The title compound was prepared as described for the synthesis of Example 1, using ethyl 4-chloro-1-ethyl-5-(2-fluoro-4-(3,3,3-trifluoropropyl)phenyl)-1H-pyrazole-3-carboxylate (Intermediate 196) in place of ethyl (R*)-4-chloro-1-ethyl-5-(2-methoxy-4-(3,3,3-trifluoro-2-methylpropyl)phenyl)-1H-pyrazole-3-carboxylate and (1s,4s)-1-(Aminomethyl)-4-(methylsulfonyl)cyclohexan-1-ol hydrochloride (Intermediate 9) in place of ((1r,4r)-4-(methylsulfonyl)cyclohexyl)methanamine hydrochloride. $^1$H NMR (400 MHz, CDCl$_3$) δ 7.31 (t, J=7.6 Hz, 1H), 7.25-7.19 (m, 1H), 7.18-7.14 (m, 1H), 7.13-7.07 (m, 1H), 4.09-3.96 (m, 2H), 3.47 (d, J=6.4 Hz, 2H), 3.03-2.93 (m, 3H), 2.86-2.74 (m, 4H), 2.55-2.41 (m, 2H), 2.19-2.08 (m, 2H), 2.04-1.90 (m, 4H), 1.50-1.34 (m, 5H). MS (ESI) m/z: [M+H]$^+$ Found 554.1.

Example 181

4-Chloro-1-ethyl-5-(2-fluoro-4-(((R)-1,1,1-trifluoropropan-2-yl)amino)phenyl)-N-(((1r,4R)-4-(methylsulfonyl)cyclohexyl)methyl)-1H-pyrazole-3-carboxamide

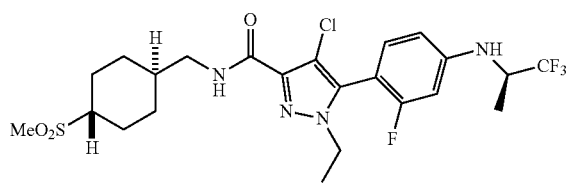 [SMILES: CCn1nc(C(=O)NC[C@H]2CC[C@H](S(C)(=O)=O)CC2)c(Cl)c1-c1ccc(N[C@H](C)C(F)(F)F)cc1F]

The title compound was prepared as described for the synthesis of Example 1, ethyl (R)-4-chloro-1-ethyl-5-(2-fluoro-4-((1,1,1-trifluoropropan-2-yl)amino)phenyl)-1H-pyrazole-3-carboxylate (Intermediate 197) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (400 MHz, CDCl$_3$) δ 7.13 (t, J=8.2 Hz, 1H), 6.99-6.88 (m, 1H), 6.55 (dd, J=8.5, 2.3 Hz, 1H), 6.49 (dd, J=11.9, 2.3 Hz, 1H), 4.10-3.96 (m, 4H), 3.40-3.28 (m, 2H), 2.89-2.76 (m, 4H), 2.34-2.21 (m, 2H), 2.14-2.04 (m, 2H), 1.77-1.56 (m, 3H), 1.46 (d, J=6.1 Hz, 3H), 1.37 (t, J=7.2 Hz, 3H), 1.22-1.06 (m, 2H). MS (ESI) m/z: [M+H]$^+$ Found 553.2.

Example 182

4-Chloro-1-ethyl-5-(2-methyl-4-(3,3,3-trifluoro-2,2-dimethylpropyl)phenyl)-N-(((1r,4r)-4-(methylsulfonyl)cyclohexyl)methyl)-1H-pyrazole-3-carboxamide

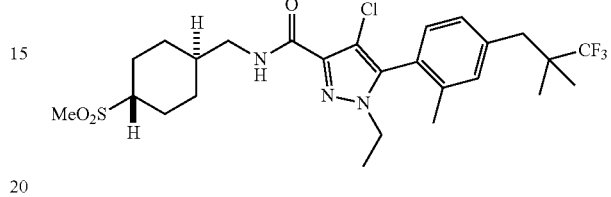

The title compound was prepared as described for the synthesis of Example 1, using ethyl 4-chloro-1-ethyl-5-(2-methyl-4-(3,3,3-trifluoro-2,2-dimethylpropyl)phenyl)-1H-pyrazole-3-carboxylate (Intermediate 198) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (500 MHz, CDCl$_3$) δ 7.15 (s, 1H), 7.13-7.08 (m, 2H), 7.01 (t, J=6.3 Hz, 1H), 4.02-3.83 (m, 2H), 3.36 (t, J=6.6 Hz, 2H), 2.90-2.79 (m, 6H), 2.33-2.25 (m, 2H), 2.15 (s, 3H), 2.12-2.04 (m, 2H), 1.76-1.66 (m, 1H), 1.66-1.55 (m, 2H), 1.31 (t, J=7.3 Hz, 3H), 1.20-1.07 (m, 8H). MS (ESI) m/z: [M+H]$^+$ Found 561.9.

Example 183

4-Chloro-1-ethyl-N-(((1s,4s)-1-hydroxy-4-(methylsulfonyl)cyclohexyl)methyl)-5-(2-methyl-4-(3,3,3-trifluoro-2,2-dimethylpropyl)phenyl)-1H-pyrazole-3-carboxamide

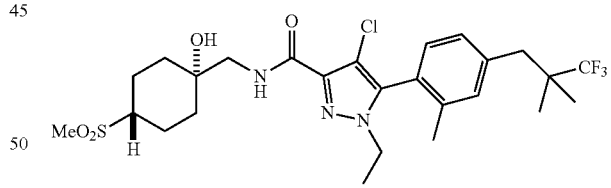

The title compound was prepared as described for the synthesis of Example 1, using ethyl 4-chloro-1-ethyl-5-(2-methyl-4-(3,3,3-trifluoro-2,2-dimethylpropyl)phenyl)-1H-pyrazole-3-carboxylate (Intermediate 198) in place of ethyl (R*)-4-chloro-1-ethyl-5-(2-methoxy-4-(3,3,3-trifluoro-2-methylpropyl)phenyl)-1H-pyrazole-3-carboxylate and (1s,4s)-1-(aminomethyl)-4-(methylsulfonyl)cyclohexan-1-ol hydrochloride (Intermediate 9) in place of ((1r,4r)-4-(methylsulfonyl)cyclohexyl)methanamine hydrochloride. $^1$H NMR (500 MHz, CDCl$_3$) δ 7.30 (t, J=6.2 Hz, 1H), 7.15 (s, 1H), 7.14-7.08 (m, 2H), 4.01-3.85 (m, 2H), 3.54-3.45 (m, 2H), 2.87-2.78 (m, 7H), 2.28-2.09 (m, 5H), 2.04-1.92 (m, 4H), 1.50-1.40 (m, 2H), 1.31 (t, J=7.3 Hz, 3H), 1.11 (s, 6H). MS (ESI) m/z: [M+H]$^+$ Found 577.9.

Example 184

4-Chloro-1-ethyl-5-(2-methyl-4-(((R)-1,1,1-trifluoropropan-2-yl)amino)phenyl)-N-(((1r,4R)-4-(methylsulfonyl)cyclohexyl)methyl)-1H-pyrazole-3-carboxamide

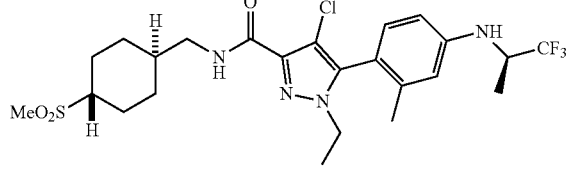

The title compound was prepared as described for the synthesis of Example 1, using ethyl (R)-4-chloro-1-ethyl-5-(2-methyl-4-((1,1,1-trifluoropropan-2-yl)amino)phenyl)-1H-pyrazole-3-carboxylate (Intermediate 199) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (400 MHz, CDCl$_3$) δ 7.02-6.94 (m, 2H), 6.63-6.55 (m, 2H), 4.14-4.02 (m, 1H), 4.02-3.84 (m, 2H), 3.37-3.33 (m, 2H), 2.83 (s, 3H), 2.84-2.81 (m, 1H), 2.33-2.24 (m, 2H), 2.12-2.04 (m, 5H), 1.75-1.52 (m, 3H), 1.44 (d, J=6.7 Hz, 3H), 1.32-1.27 (m, 3H), 1.21-1.07 (m, 2H). MS (ESI) m/z: [M+H]$^+$ Found 549.2.

Example 185

4-Chloro-5-(2-methoxy-4-(3,3,3-trifluoro-2,2-dimethylpropyl)phenyl)-1-(2-methoxyethyl)-N-(((1r,4r)-4-(methylsulfonyl)cyclohexyl)methyl)-1H-pyrazole-3-carboxamide

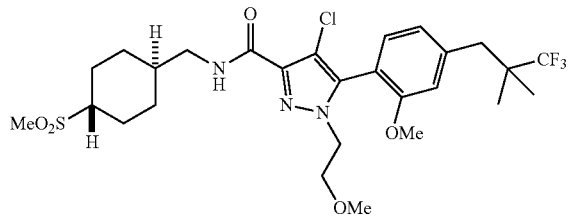 [SMILES: COCCn1nc(C(=O)NC[C@H]2CC[C@H](S(C)(=O)=O)CC2)c(Cl)c1-c1ccc(CC(C)(C)C(F)(F)F)cc1OC]

The title compound was prepared as described for the synthesis of Example 1, using 4-chloro-5-(2-methoxy-4-(3,3,3-trifluoro-2,2-dimethylpropyl)phenyl)-1-(2-methoxyethyl)-1H-pyrazole-3-carboxylate (Intermediate 178) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (400 MHz, CDCl$_3$) δ 7.21 (d, J=7.7 Hz, 1H), 7.09-6.99 (m, 1H), 6.90 (dd, J=7.7, 1.4 Hz, 1H), 6.82-6.78 (m, 1H), 4.11 (t, J=5.9 Hz, 2H), 3.80 (s, 3H), 3.77-3.69 (m, 1H), 3.64-3.57 (m, 1H), 3.43-3.28 (m, 2H), 3.21 (s, 3H), 2.89-2.78 (m, 6H), 2.35-2.23 (m, 2H), 2.14-2.02 (m, 2H), 1.76-1.53 (m, 3H), 1.21-1.07 (m, 8H). MS (ESI) m/z: [M+H]$^+$ Found 608.2.

Example 186

4-Chloro-N-(((1s,4s)-1-hydroxy-4-(methylsulfonyl)cyclohexyl)methyl)-5-(2-methoxy-4-(3,3,3-trifluoro-2,2-dimethylpropyl)phenyl)-1-(2-methoxyethyl)-1H-pyrazole-3-carboxamide

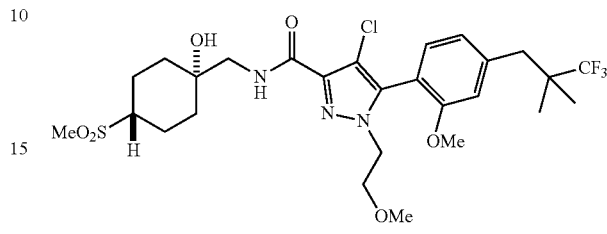

The title compound was prepared as described for the synthesis of Example 1, using (1s,4s)-1-(aminomethyl)-4-(methylsulfonyl)cyclohexan-1-ol hydrochloride (Intermediate 9) in place of ((1r,4r)-4-(methylsulfonyl)cyclohexyl)methanamine hydrochloride and 4-chloro-5-(2-methoxy-4-(3,3,3-trifluoro-2,2-dimethylpropyl)phenyl)-1-(2-methoxyethyl)-1H-pyrazole-3-carboxylate (Intermediate 178) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (400 MHz, CDCl$_3$) δ 7.36-7.30 (m, 1H), 7.21 (d, J=7.7 Hz, 1H), 6.90 (dd, J=7.7, 1.4 Hz, 1H), 6.82-6.78 (m, 1H), 4.12 (t, J=5.9 Hz, 2H), 3.81 (s, 3H), 3.79-3.69 (m, 1H), 3.66-3.57 (m, 1H), 3.56-3.41 (m, 2H), 3.21 (s, 3H), 2.88-2.76 (m, 6H), 2.19-2.08 (m, 2H), 2.05-1.91 (m, 4H), 1.51-1.38 (m, 2H), 1.13 (s, 6H). MS (ESI) m/z: [M+H]$^+$ Found 624.1.

Example 187

4-Chloro-5-(2-methoxy-4-(((R)-1,1,1-trifluoropropan-2-yl)amino)phenyl)-1-(2-methoxyethyl)-N-(((1r,4R)-4-(methylsulfonyl)cyclohexyl)methyl)-1H-pyrazole-3-carboxamide

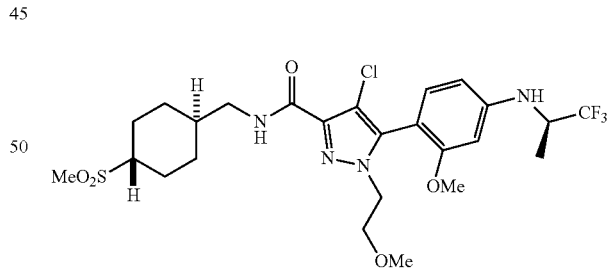

The title compound was prepared as described for the synthesis of Example 1, using ethyl (R)-4-chloro-5-(2-methoxy-4-((1,1,1-trifluoropropan-2-yl)amino)phenyl)-1-(2-methoxyethyl)-1H-pyrazole-3-carboxylate (Intermediate 202) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (500 MHz, CDCl$_3$) δ 7.08 (dd, J=8.3, 5.2 Hz, 1H), 6.99 (t, J=6.3 Hz, 1H), 6.39-6.33 (m, 1H), 6.29-6.24 (m, 1H), 4.16-4.04 (m, 3H), 3.80-3.75 (m, 3H), 3.75-3.68 (m, 1H), 3.65-3.57 (m, 1H), 3.42-3.26 (m, 2H), 3.26-3.20 (m, 3H), 2.88-2.78 (m, 4H), 2.33-2.24 (m, 3H), 2.11-2.03 (m, 2H), 1.73-1.63 (m, 1H), 1.64-1.53 (m, 2H), 1.45 (d, J=6.7 Hz, 3H), 1.20-1.07 (m, 2H). MS (ESI) m/z: [M+H]+ Found 595.0.

Example 188

4-Chloro-1-ethyl-N-(((1s,4s)-1-hydroxy-4-(methylsulfonyl)cyclohexyl)methyl)-5-(2-(trifluoromethoxy)-4-(3,3,3-trifluoropropyl)phenyl)-1H-pyrazole-3-carboxamide

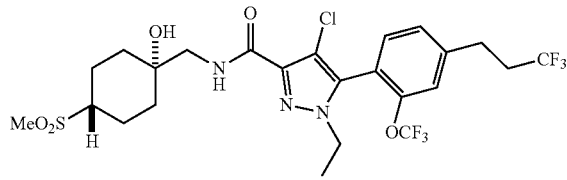 [SMILES: CCn1nc(C(=O)NC[C@]2(O)CC[C@@H](S(C)(=O)=O)CC2)c(Cl)c1-c1ccc(CCC(F)(F)F)cc1OC(F)(F)F]

The title compound was prepared as described for the synthesis of Example 1, using (1s,4s)-1-(aminomethyl)-4-(methylsulfonyl)cyclohexan-1-ol hydrochloride (Intermediate 9) in place of ((1r,4r)-4-(methylsulfonyl)cyclohexyl)methanamine hydrochloride and ethyl 4-chloro-1-ethyl-5-(2-(trifluoromethoxy)-4-(3,3,3-trifluoropropyl)phenyl)-1H-pyrazole-3-carboxylate (Intermediate 203) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (400 MHz, CDCl$_3$) δ 7.37-7.21 (m, 4H), 4.04-3.89 (m, 2H), 3.47 (d, J=6.7 Hz, 2H), 3.05-2.96 (m, 3H), 2.87-2.74 (m, 4H), 2.56-2.40 (m, 2H), 2.19-2.08 (m, 2H), 2.05-1.91 (m, 4H), 1.50-1.33 (m, 5H). MS (ESI) m/z: [M+H]+ Found 620.1.

Example 189

4-Chloro-1-ethyl-N-(((1r,4r)-4-(methylsulfonyl)cyclohexyl)methyl)-5-(2-(trifluoromethoxy)-4-(3,3,3-trifluoropropyl)phenyl)-1H-pyrazole-3-carboxamide

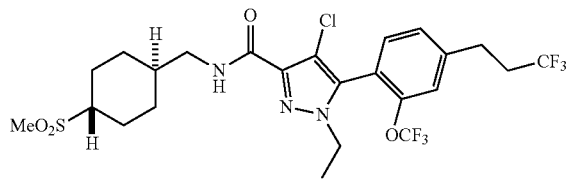 [SMILES: CCn1nc(C(=O)NC[C@H]2CC[C@H](S(C)(=O)=O)CC2)c(Cl)c1-c1ccc(CCC(F)(F)F)cc1OC(F)(F)F]

The title compound was prepared as described for the synthesis of Example 1, using ethyl 4-chloro-1-ethyl-5-(2-(trifluoromethoxy)-4-(3,3,3-trifluoropropyl)phenyl)-1H-pyrazole-3-carboxylate (Intermediate 203) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (500 MHz, CDCl$_3$) δ 7.36-7.27 (m, 3H), 6.98-6.91 (m, 1H), 4.05-3.86 (m, 2H), 3.35 (t, J=6.6 Hz, 2H), 3.00 (dd, J=9.8, 6.8 Hz, 2H), 2.90-2.77 (m, 4H), 2.55-2.40 (m, 2H), 2.34-2.23 (m, 2H), 2.13-2.05 (m, 2H), 1.77-1.65 (m, 1H), 1.65-1.56 (m, 2H), 1.37 (t, J=7.3 Hz, 3H), 1.20-1.09 (m, 2H). MS (ESI) m/z: [M+H]+ Found 604.2.

Example 190

4-Chloro-1-ethyl-N-(((1r,4R)-4-(methylsulfonyl)cyclohexyl)methyl)-5-(2-(trifluoromethoxy)-4-(((R)-1,1,1-trifluoropropan-2-yl)amino)phenyl)-1H-pyrazole-3-carboxamide

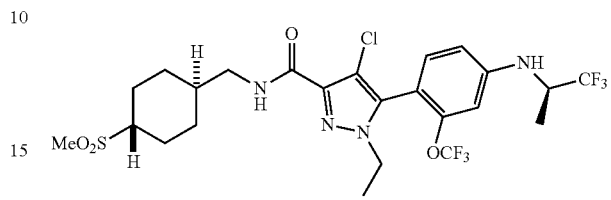

The title compound was prepared as described for the synthesis of Example 1, using ethyl (R)-4-chloro-1-ethyl-5-(2-(trifluoromethoxy)-4-((1,1,1-trifluoropropan-2-yl)amino)phenyl)-1H-pyrazole-3-carboxylate (Intermediate 204) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (400 MHz, CDCl$_3$) δ 7.16 (dd, J=8.4, 5.3 Hz, 1H), 6.97-6.91 (m, 1H), 6.73-6.64 (m, 2H), 4.13-4.02 (m, 2H), 4.02-3.89 (m, 2H), 3.34 (t, J=6.6 Hz, 2H), 2.89-2.78 (m, 4H), 2.33-2.23 (m, 2H), 2.12-2.04 (m, 2H), 1.76-1.56 (m, 3H), 1.48 (d, J=6.0 Hz, 3H), 1.36 (t, J=7.3 Hz, 3H), 1.21-1.08 (m, 2H). MS (ESI) m/z: [M+H]+ Found 619.2.

Example 191

4-Chloro-1-ethyl-N-(((1s,4s)-1-hydroxy-4-(methylsulfonyl)cyclohexyl)methyl)-5-(4-(3,3,3-trifluoro-2-methylpropyl)-2-(trifluoromethoxy)phenyl)-1H-pyrazole-3-carboxamide

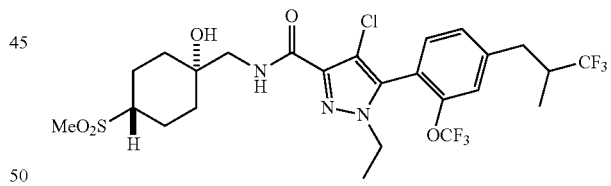

The title compound was prepared as described for the synthesis of Example 1, using (1s,4s)-1-(aminomethyl)-4-(methylsulfonyl)cyclohexan-1-ol hydrochloride (Intermediate 9) in place of ((1r,4r)-4-(methylsulfonyl)cyclohexyl)methanamine hydrochloride and ethyl 4-chloro-1-ethyl-5-(4-(3,3,3-trifluoro-2-methylpropyl)-2-(trifluoromethoxy)phenyl)-1H-pyrazole-3-carboxylate (Intermediate 205) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (400 MHz, CDCl$_3$) δ 7.36-7.21 (m, 4H), 4.06-3.87 (m, 2H), 3.47 (d, J=6.3 Hz, 2H), 3.18 (dd, J=13.7, 4.2 Hz, 1H), 2.99 (s, 1H), 2.87-2.75 (m, 4H), 2.69-2.58 (m, 1H), 2.58-2.43 (m, 1H), 2.19-2.09 (m, 2H), 2.04-1.91 (m, 4H), 1.48-1.34 (m, 5H), 1.12 (dd, J=6.8, 2.0 Hz, 3H). MS (ESI) m/z: [M+H]+ Found 634.2.

Example 192

4-Chloro-1-ethyl-N-(((1s,4s)-1-hydroxy-4-(methylsulfonyl)cyclohexyl)methyl)-5-(2-(methoxy-d3)-4-(3,3,3-trifluoro-2,2-dimethylpropyl)phenyl)-1H-pyrazole-3-carboxamide

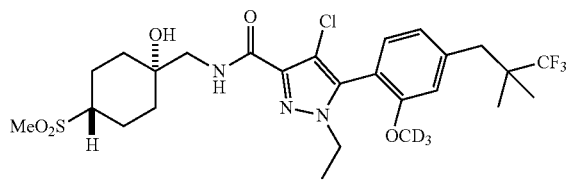

The title compound was prepared as described for the synthesis of Example 1, using (1s,4s)-1-(aminomethyl)-4-(methylsulfonyl)cyclohexan-1-ol hydrochloride (Intermediate 9) in place of ((1r,4r)-4-(methylsulfonyl)cyclohexyl)methanamine hydrochloride and ethyl 4-chloro-1-ethyl-5-(2-(methoxy-d$_3$)-4-(3,3,3-trifluoro-2,2-dimethylpropyl)phenyl)-1H-pyrazole-3-carboxylate (Intermediate 119) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (500 MHz, CDCl$_3$) δ 7.25-7.22 (m, 1H), 7.17 (d, J=7.7 Hz, 1H), 6.90 (dd, J=7.7, 1.5 Hz, 1H), 6.80 (d, J=1.4 Hz, 1H), 4.03-3.89 (m, 2H), 3.52-3.42 (m, 2H), 3.17 (s, 1H), 2.87-2.76 (m, 6H), 2.17-2.10 (m, 2H), 2.03-1.93 (m, 4H), 1.47-1.38 (m, 2H), 1.35 (t, J=7.3 Hz, 3H), 1.13 (s, 6H). MS (ESI) m/z: [M+H]$^+$ Found 596.9.

Example 193

4-Chloro-1-ethyl-5-(2-(methoxy-d3)-4-(3,3,3-trifluoro-2,2-dimethylpropyl)phenyl)-N-(((1r,4r)-4-(methylsulfonyl)cyclohexyl)methyl)-1H-pyrazole-3-carboxamide

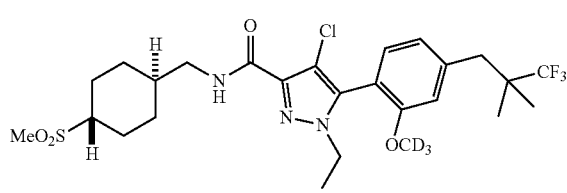

The title compound was prepared as described for the synthesis of Example 1, using ethyl 4-chloro-1-ethyl-5-(2-(methoxy-d$_3$)-4-(3,3,3-trifluoro-2,2-dimethylpropyl)phenyl)-1H-pyrazole-3-carboxylate (Intermediate 119) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (500 MHz, CDCl$_3$) δ 7.17 (d, J=7.7 Hz, 1H), 7.11-7.04 (m, 1H), 6.89 (dd, J=7.7, 1.5 Hz, 1H), 6.80 (d, J=1.4 Hz, 1H), 4.02-3.89 (m, 2H), 3.41-3.31 (m, 2H), 2.90-2.79 (m, 6H), 2.33-2.24 (m, 2H), 2.12-2.02 (m, 2H), 1.75-1.64 (m, 1H), 1.59 (qd, J=13.0, 3.6 Hz, 2H), 1.34 (t, J=7.3 Hz, 3H), 1.21-1.09 (m, 8H). MS (ESI) m/z: [M+H]$^+$ Found 580.9.

Example 194

4-Chloro-1-ethyl-N-(((1r,4R)-4-(methylsulfonyl)cyclohexyl)methyl)-5-(4-(((R)-1,1,1-trifluoropropan-2-yl)amino)phenyl)-1H-pyrazole-3-carboxamide

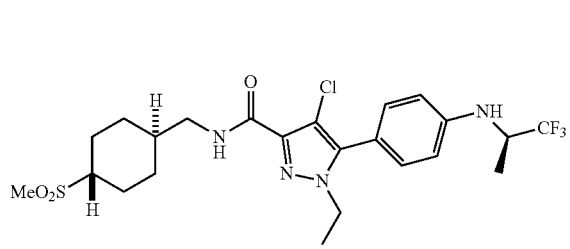 [SMILES: CCn1nc(C(=O)NC[C@H]2CC[C@H](S(C)(=O)=O)CC2)c(Cl)c1-c1ccc(N[C@H](C)C(F)(F)F)cc1]

The title compound was prepared as described for the synthesis of Example 1, using ethyl (R)-4-chloro-1-ethyl-5-(4-((1,1,1-trifluoropropan-2-yl)amino)phenyl)-1H-pyrazole-3-carboxylate (Intermediate 206) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (400 MHz, CDCl$_3$) δ 7.20 (d, J=8.7 Hz, 2H), 7.05-6.95 (m, 1H), 6.77 (d, J=8.7 Hz, 2H), 4.14-4.04 (m, 3H), 3.35 (t, J=6.6 Hz, 2H), 2.89-2.78 (m, 5H), 2.34-2.23 (m, 2H), 2.11-2.01 (m, 2H), 1.76-1.65 (m, 1H), 1.65-1.52 (m, 2H), 1.45 (d, J=6.8 Hz, 3H), 1.37 (t, J=7.2 Hz, 3H), 1.21-1.07 (m, 2H). MS (ESI) m/z: [M+H]$^+$ Found 534.9.

Example 195

4-Chloro-1-ethyl-N-(((1s,4S)-1-hydroxy-4-(methylsulfonyl)cyclohexyl)methyl)-5-(4-(((R)-1,1,1-trifluoropropan-2-yl)amino)phenyl)-1H-pyrazole-3-carboxamide

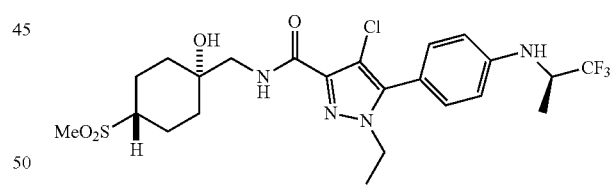

The title compound was prepared as described for the synthesis of Example 1, using (1s,4s)-1-(aminomethyl)-4-(methylsulfonyl)cyclohexan-1-ol hydrochloride (Intermediate 9) in place of ((1r,4r)-4-(methylsulfonyl)cyclohexyl)methanamine hydrochloride and ethyl (R)-4-chloro-1-ethyl-5-(4-((1,1,1-trifluoropropan-2-yl)amino)phenyl)-1H-pyrazole-3-carboxylate (Intermediate 206) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (400 MHz, CDCl$_3$) δ 7.25-7.17 (m, 3H), 6.77 (d, J=8.7 Hz, 2H), 4.09 (q, J=7.3 Hz, 3H), 3.87 (d, J=8.9 Hz, 1H), 3.46 (d, J=6.3 Hz, 2H), 3.11 (s, 1H), 2.83 (s, 3H), 2.82-2.75 (m, 1H), 2.18-2.09 (m, 2H), 2.06-1.90 (m, 4H), 1.49-1.34 (m, 8H). MS (ESI) m/z: [M+H]$^+$ Found 550.9.

Example 196

4-Chloro-5-(2,6-difluoro-4-(((R)-1,1,1-trifluoropropan-2-yl)amino)phenyl)-1-ethyl-N-(((1r,4R)-4-(methylsulfonyl)cyclohexyl)methyl)-1H-pyrazole-3-carboxamide

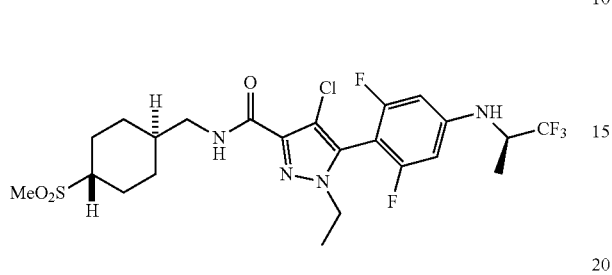

The title compound was prepared as described for the synthesis of Example 1, using ethyl (R)-4-chloro-5-(2,6-difluoro-4-((1,1,1-trifluoropropan-2-yl)amino)phenyl)-1-ethyl-1H-pyrazole-3-carboxylate (Intermediate 207) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (400 MHz, CDCl$_3$) δ 6.95-6.89 (m, 1H), 6.32 (dd, J=9.7, 2.0 Hz, 2H), 4.18-4.09 (m, 1H), 4.07-3.95 (m, 3H), 3.34 (t, J=6.5 Hz, 2H), 2.90-2.77 (m, 4H), 2.33-2.23 (m, 2H), 2.13-2.02 (m, 2H), 1.75-1.56 (m, 3H), 1.47 (d, J=6.7 Hz, 3H), 1.38 (t, J=7.3 Hz, 3H), 1.20-1.07 (m, 2H). MS (ESI) m/z: [M+H]$^+$ Found 571.0.

Example 197

4-Chloro-5-(2,6-difluoro-4-(3,3,3-trifluoro-2-methylpropyl)phenyl)-1-ethyl-N-(((1r,4r)-4-(methylsulfonyl)cyclohexyl)methyl)-1H-pyrazole-3-carboxamide

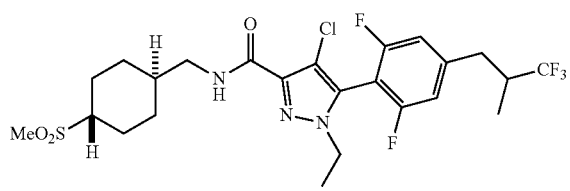 [SMILES: CCn1nc(C(=O)NC[C@H]2CC[C@H](S(C)(=O)=O)CC2)c(Cl)c1-c1c(F)cc(CC(C)C(F)(F)F)cc1F]

The title compound was prepared as described for the synthesis of Example 1, using ethyl 4-chloro-5-(2,6-difluoro-4-(3,3,3-trifluoro-2-methylpropyl)phenyl)-1-ethyl-1H-pyrazole-3-carboxylate (Intermediate 208) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (400 MHz, CDCl$_3$) δ 7.03 (t, J=6.3 Hz, 1H), 6.96-6.89 (m, 2H), 4.01 (q, J=7.3 Hz, 2H), 3.36 (t, J=6.6 Hz, 2H), 3.14 (dd, J=13.4, 3.8 Hz, 1H), 2.90-2.78 (m, 4H), 2.64-2.44 (m, 2H), 2.34-2.23 (m, 2H), 2.13-2.01 (m, 2H), 1.76-1.51 (m, 3H), 1.39 (t, J=7.3 Hz, 3H), 1.22-1.06 (m, 5H). MS (ESI) m/z: [M+H]$^+$ Found 570.2.

Example 198

4-Chloro-5-(2,6-difluoro-4-((S*)-3,3,3-trifluoro-2-methylpropyl)phenyl)-1-ethyl-N-(((1s,4R)-1-hydroxy-4-(methylsulfonyl)cyclohexyl)methyl)-1H-pyrazole-3-carboxamide

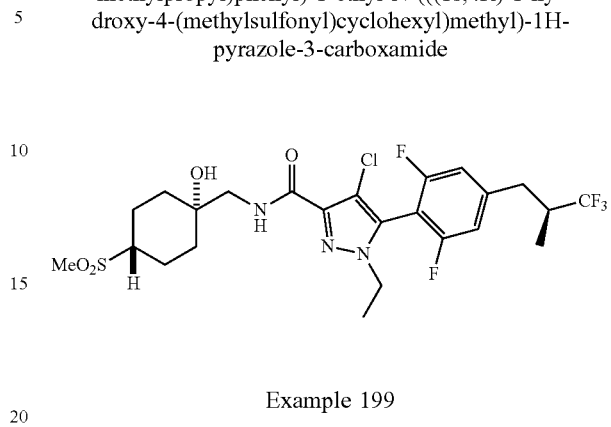

Example 199

4-Chloro-5-(2,6-difluoro-4-((R*)-3,3,3-trifluoro-2-methylpropyl)phenyl)-1-ethyl-N-(((1s,4S)-1-hydroxy-4-(methylsulfonyl)cyclohexyl)methyl)-1H-pyrazole-3-carboxamide

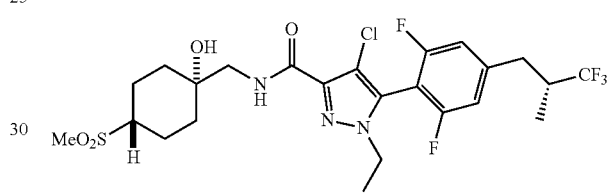

Intermediate 250 was purified by SFC using a chiral stationary phase (Lux amylose 2, 60% CO$_2$, 40% i-PrOH) to give a pair of enantiomers. The first-eluting enantiomer was Example 199, and the second-eluting enantiomer was Example 198. Example 198: $^1$H NMR (500 MHz, CDCl$_3$) δ 7.24 (t, J=6.2 Hz, 1H), 6.96-6.89 (m, 2H), 4.01 (q, J=7.2 Hz, 2H), 3.47 (d, J=6.3 Hz, 2H), 3.14 (dd, J=13.6, 4.0 Hz, 1H), 3.02 (s, 1H), 2.87-2.75 (m, 4H), 2.65-2.46 (m, 2H), 2.19-2.08 (m, 2H), 2.06-1.92 (m, 4H), 1.49-1.37 (m, 5H), 1.13 (d, J=6.7 Hz, 3H). MS (ESI) m/z: [M+H]$^+$ Found 586.2
Example 199: $^1$H NMR (500 MHz, CDCl$_3$) δ 7.24 (t, J=6.2 Hz, 1H), 6.95-6.90 (m, 2H), 4.01 (q, J=7.3 Hz, 2H), 3.47 (d, J=6.4 Hz, 2H), 3.14 (dd, J=13.6, 4.0 Hz, 1H), 3.01 (s, 1H), 2.88-2.75 (m, 4H), 2.65-2.45 (m, 2H), 2.18-2.08 (m, 2H), 2.05-1.92 (m, 4H), 1.51-1.36 (m, 5H), 1.13 (d, J=6.8 Hz, 3H). MS (ESI) m/z: [M+H]$^+$ Found 586.1.

Example 200

4-Chloro-1-(2-hydroxyethyl)-5-(2-methoxy-4-(3,3,3-trifluoro-2-methylpropyl)phenyl)-N-(((1r,4r)-4-(methylsulfonyl)cyclohexyl)methyl)-1H-pyrazole-3-carboxamide

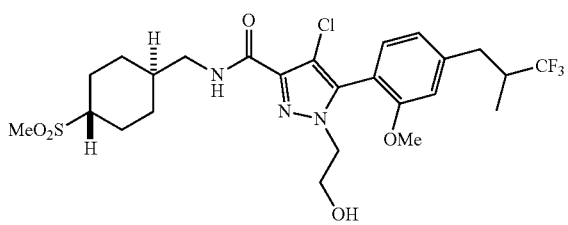 [SMILES: COc1cc(CC(C)C(F)(F)F)ccc1-c1c(Cl)c(C(=O)NC[C@H]2CC[C@H](S(C)(=O)=O)CC2)nn1CCO]

The title compound was prepared as described for the synthesis of Example 1, using ethyl 4-chloro-1-(2-hydroxyethyl)-5-(2-methoxy-4-(3,3,3-trifluoro-2-methylpropyl)phenyl)-1H-pyrazole-3-carboxylate (Intermediate 209) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (500 MHz, CDCl$_3$) δ 7.21 (dd, J=7.7, 1.5 Hz, 1H), 6.95-6.86 (m, 2H), 6.82 (s, 1H), 4.11-3.90 (m, 4H), 3.82 (s, 3H), 3.36 (dt, J=14.5, 6.8 Hz, 2H), 3.19-3.13 (m, 1H), 2.89-2.77 (m, 4H), 2.59-2.45 (m, 2H), 2.32-2.24 (m, 2H), 2.12-2.02 (m, 2H), 1.73-1.64 (m, 1H), 1.64-1.55 (m, 2H), 1.19-1.12 (m, 2H), 1.10 (d, J=6.3 Hz, 3H). MS (ESI) m/z: [M+H]$^+$ Found 580.2.

Example 201

4-Chloro-1-(2-hydroxyethyl)-5-(2-methoxy-4-(((R)-1,1,1-trifluoropropan-2-yl)amino)phenyl)-N-(((r,4R)-4-(methylsulfonyl)cyclohexyl)methyl)-1H-pyrazole-3-carboxamide

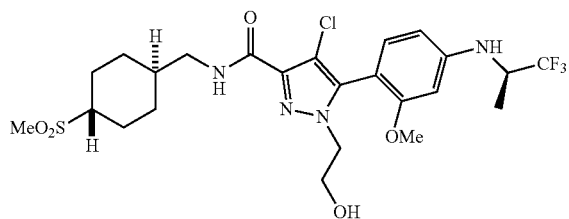 [SMILES: COc1cc(N[C@H](C)C(F)(F)F)ccc1-c1c(Cl)c(C(=O)NC[C@H]2CC[C@H](S(C)(=O)=O)CC2)nn1CCO]

The title compound was prepared as described for the synthesis of Example 1, using ethyl (R)-4-chloro-1-(2-hydroxyethyl)-5-(2-methoxy-4-((1,1,1-trifluoropropan-2-yl)amino)phenyl)-1H-pyrazole-3-carboxylate (Intermediate 210) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (500 MHz, CDCl$_3$) δ 7.06 (dd, J=8.2, 4.3 Hz, 1H), 6.98-6.90 (m, 1H), 6.41-6.33 (m, 1H), 6.30-6.24 (m, 1H), 4.15-3.88 (m, 5H), 3.80-3.74 (m, 3H), 3.43-3.29 (m, 2H), 2.88-2.78 (m, 4H), 2.33-2.24 (m, 2H), 2.11-2.02 (m, 2H), 1.73-1.65 (m, 1H), 1.64-1.53 (m, 2H), 1.46 (d, J=6.7 Hz, 3H), 1.20-1.08 (m, 2H). MS (ESI) m/z: [M+H]$^+$ Found 581.1.

Example 202

4-Chloro-1-(2-hydroxy-2-methylpropyl)-5-(2-methoxy-4-(((R)-1,1,1-trifluoropropan-2-yl)amino)phenyl)-N-(((r,4R)-4-(methylsulfonyl)cyclohexyl)methyl)-1H-pyrazole-3-carboxamide

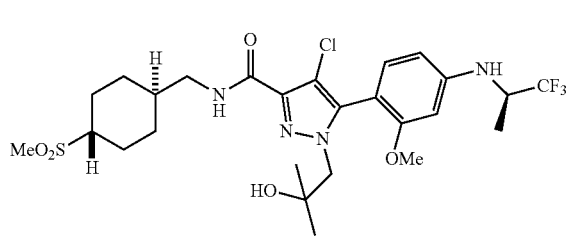 [SMILES: COc1cc(N[C@H](C)C(F)(F)F)ccc1-c1c(Cl)c(C(=O)NC[C@H]2CC[C@H](S(C)(=O)=O)CC2)nn1CC(C)(C)O]

The title compound was prepared as described for the synthesis of Example 1, using ethyl (R)-4-chloro-1-(2-hydroxy-2-methylpropyl)-5-(2-methoxy-4-((1,1,1-trifluoropropan-2-yl)amino)phenyl)-1H-pyrazole-3-carboxylate (Intermediate 212) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (500 MHz, CDCl$_3$) δ 7.06-7.00 (m, 1H), 6.80 (t, J=6.5 Hz, 1H), 6.39-6.33 (m, 1H), 6.29-6.24 (m, 1H), 4.12-4.03 (m, 1H), 3.98-3.89 (m, 2H), 3.85-3.79 (m, 2H), 3.79-3.72 (m, 3H), 3.40-3.26 (m, 2H), 2.88-2.76 (m, 4H), 2.33-2.22 (m, 2H), 2.09-2.00 (m, 2H), 1.72-1.63 (m, 1H), 1.63-1.56 (m, 2H), 1.46 (d, J=6.7 Hz, 3H), 1.18-1.05 (m, 5H), 0.94 (s, 3H). MS (ESI) m/z: [M+H]$^+$ Found 609.3.

Example 203

1-Ethyl-4-fluoro-5-(2-methoxy-4-(((R)-1,1,1-trifluoropropan-2-yl)amino)phenyl)-N-(((1r,4R)-4-(methylsulfonyl)cyclohexyl)methyl)-1H-pyrazole-3-carboxamide

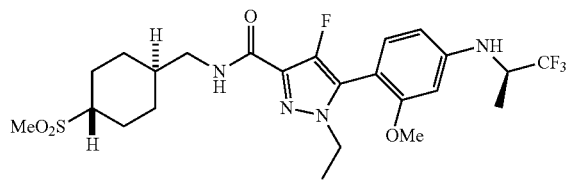 [SMILES: CCn1nc(C(=O)NC[C@H]2CC[C@H](S(C)(=O)=O)CC2)c(F)c1-c1ccc(N[C@H](C)C(F)(F)F)cc1OC]

The title compound was prepared as described for the synthesis of Example 1, using ethyl (R)-1-ethyl-4-fluoro-5-(2-methoxy-4-((1,1,1-trifluoropropan-2-yl)amino)phenyl)-1H-pyrazole-3-carboxylate (Intermediate 214) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (500 MHz, CDCl$_3$) δ 7.06-7.02 (m, 1H), 6.90-6.81 (m, 1H), 6.34 (dd, J=8.3, 2.2 Hz, 1H), 6.27 (d, J=2.2 Hz, 1H), 4.12-4.04 (m, 1H), 3.93 (q, J=7.2 Hz, 2H), 3.77 (s, 3H), 3.35 (t, J=6.6 Hz, 2H), 2.87-2.71 (m, 9H), 2.32-2.24 (m, 2H), 2.10-2.02 (m, 2H), 1.71-1.64 (m, 1H), 1.64-1.53 (m, 2H), 1.45 (d, J=6.8 Hz, 3H), 1.33 (t, J=7.3 Hz, 3H), 1.19-1.07 (m, 2H). MS (ESI) m/z: [M+H]$^+$ Found 549.0

Example 204

4-Chloro-1-ethyl-5-(2-isopropyl-4-(((R)-1,1,1-trifluoropropan-2-yl)amino)phenyl)-N-(((1r,4R)-4-(methylsulfonyl)cyclohexyl)methyl)-1H-pyrazole-3-carboxamide

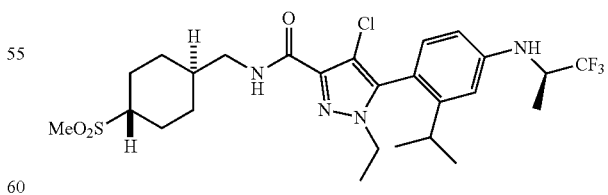

The title compound was prepared as described for the synthesis of Example 1, using ethyl (R)-4-chloro-1-ethyl-5-(2-isopropyl-4-((1,1,1-trifluoropropan-2-yl)amino)phenyl)-1H-pyrazole-3-carboxylate (Intermediate 218) in place of ethyl (R*)-4-chloro-1-ethyl-5-(2-methoxy-4-(3,3,3-trifluoro-2-methylpropyl)phenyl)-1H-pyrazole-3-carboxylate.

¹H NMR (500 MHz, CDCl₃) δ 6.98-6.91 (m, 2H), 6.69-6.66 (m, 1H), 6.61-6.56 (m, 1H), 4.14-4.03 (m, 1H), 3.98-3.81 (m, 3H), 3.35 (td, J=6.6, 2.3 Hz, 2H), 2.89-2.78 (m, 4H), 2.61-2.51 (m, 1H), 2.33-2.23 (m, 2H), 2.13-2.06 (m, 2H), 1.76-1.65 (m, 1H), 1.65-1.57 (m, 2H), 1.46 (d, J=6.8 Hz, 3H), 1.33 (t, J=7.2 Hz, 3H), 1.21-1.07 (m, 8H). MS (ESI) m/z: [M+H]⁺ Found 577.2.

Example 205

4-Chloro-5-(2-ethoxy-4-(((R)-1,1,1-trifluoropropan-2-yl)amino)phenyl)-1-ethyl-N-(((1r,4R)-4-(methylsulfonyl)cyclohexyl)methyl)-1H-pyrazole-3-carboxamide

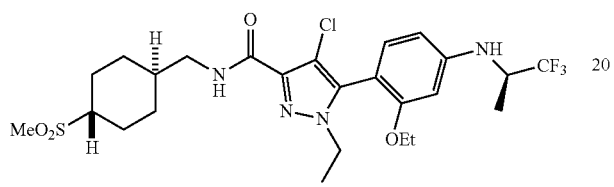

Intermediate 251 was purified by SFC using a chiral stationary phase (CHIRALPAK IC, 60% CO₂, 40% MeOH) to give the title compound as the second-eluting isomer. ¹H NMR (500 MHz, CDCl₃) δ 7.03 (dd, J=8.3, 5.7 Hz, 1H), 6.96 (t, J=6.4 Hz, 1H), 6.38-6.32 (m, 1H), 6.29-6.25 (m, 1H), 4.13-3.89 (m, 6H), 3.34 (t, J=6.6 Hz, 2H), 2.88-2.78 (m, 4H), 2.32-2.23 (m, 2H), 2.12-2.03 (m, 2H), 1.73-1.63 (m, 1H), 1.58 (qd, J=12.9, 3.6 Hz, 2H), 1.45 (d, J=6.7 Hz, 3H), 1.37-1.24 (m, 6H), 1.19-1.07 (m, 2H). MS (ESI) m/z: [M+H]⁺ Found 579.0.

Example 206

4-Chloro-1-ethyl-5-(2-ethyl-4-(((R)-1,1,1-trifluoropropan-2-yl)amino)phenyl)-N-(((1r,4R)-4-(methylsulfonyl)cyclohexyl)methyl)-1H-pyrazole-3-carboxamide

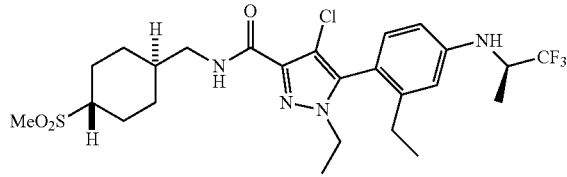 [SMILES: CCc1cc(N[C@H](C)C(F)(F)F)ccc1-c1c(Cl)c(C(=O)NC[C@H]2CC[C@H](S(C)(=O)=O)CC2)nn1CC]

The title compound was prepared as described for the synthesis of Example 1, using ethyl (R)-4-chloro-1-ethyl-5-(2-ethyl-4-((1,1,1-trifluoropropan-2-yl)amino)phenyl)-1H-pyrazole-3-carboxylate (Intermediate 229) in place of ethyl (R*)-4-chloro-1-ethyl-5-(2-methoxy-4-(3,3,3-trifluoro-2-methylpropyl)phenyl)-1H-pyrazole-3-carboxylate. ¹H NMR (400 MHz, CDCl₃) δ 7.04-6.93 (m, 2H), 6.64 (t, J=2.6 Hz, 1H), 6.62-6.55 (m, 1H), 4.14-4.03 (m, 1H), 4.00-3.81 (m, 2H), 3.35 (t, J=6.5 Hz, 2H), 2.88-2.77 (m, 4H), 2.40-2.25 (m, 4H), 2.12-2.04 (m, 3H), 1.75-1.66 (m, 1H), 1.65-1.52 (m, 2H), 1.45 (d, J=6.8 Hz, 3H), 1.32 (t, J=7.2 Hz, 3H), 1.21-1.10 (m, 2H), 1.10-1.04 (m, 3H). MS (ESI) m/z: [M+H]⁺ Found 563.2.

Example 207

4-Chloro-1-ethyl-5-(2-isopropoxy-4-(((R)-1,1,1-trifluoropropan-2-yl)amino)phenyl)-N-(((1r,4R)-4-(methylsulfonyl)cyclohexyl)methyl)-1H-pyrazole-3-carboxamide

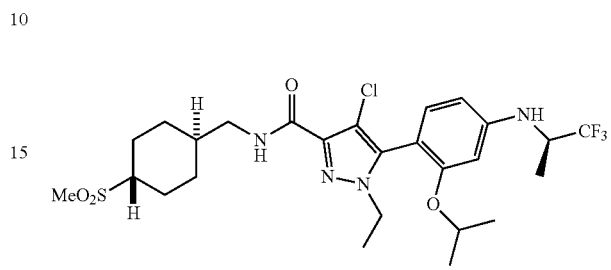

Intermediate 252 was purified by SFC using a chiral stationary phase (CHIRALPAK IC, 60% CO₂, 40% MeOH) to give the title compound as the second-eluting isomer. ¹H NMR (400 MHz, CDCl₃) δ 7.03 (dd, J=8.3, 4.3 Hz, 1H), 6.95 (t, J=6.4 Hz, 1H), 6.39-6.31 (m, 1H), 6.28 (t, J=2.7 Hz, 1H), 4.41 (dq, J=11.9, 5.9 Hz, 1H), 4.12-3.91 (m, 3H), 3.84 (d, J=8.9 Hz, 1H), 3.34 (td, J=6.6, 2.4 Hz, 2H), 2.89-2.77 (m, 4H), 2.33-2.23 (m, 2H), 2.13-2.03 (m, 2H), 1.76-1.65 (m, 1H), 1.65-1.52 (m, 2H), 1.45 (d, J=6.7 Hz, 3H), 1.36-1.29 (m, 3H), 1.26 (dd, J=6.1, 1.5 Hz, 3H), 1.19-1.08 (m, 5H). MS (ESI) m/z: [M+H]⁺ Found 593.2.

Example 208

4-Chloro-1-ethyl-5-(2-methoxy-4-(3-(trifluoromethyl)azetidin-1-yl)phenyl)-N-(((1r,4r)-4-(methylsulfonyl)cyclohexyl)methyl)-1H-pyrazole-3-carboxamide

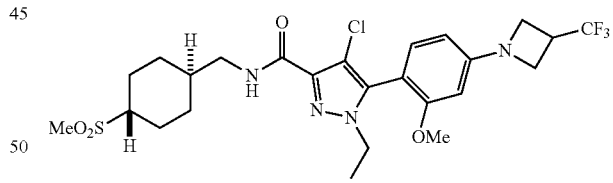

The title compound was prepared as described for the synthesis of Intermediate 106, using 5-(4-bromo-2-methoxyphenyl)-4-chloro-1-ethyl-N-(((1r,4r)-4-(methylsulfonyl)cyclohexyl)methyl)-1H-pyrazole-3-carboxamide (Intermediate 146) in place of ethyl 5-(4-bromo-2-methoxyphenyl)-4-chloro-1-ethyl-1H-pyrazole-3-carboxylate and 3-(trifluoromethyl)azetidine hydrochloride in place of R-1,1,1-trifluoro-2-propylamine. ¹H NMR (400 MHz, CDCl₃) δ 7.07 (d, J=8.2 Hz, 1H), 7.04-6.97 (m, 1H), 6.13 (dd, J=8.2, 2.1 Hz, 1H), 6.01 (d, J=2.0 Hz, 1H), 4.14 (t, J=8.2 Hz, 2H), 4.09-4.01 (m, 2H), 4.01-3.88 (m, 2H), 3.77 (s, 3H), 3.51-3.28 (m, 3H), 2.89-2.77 (m, 4H), 2.34-2.22 (m, 2H), 2.13-2.01 (m, 2H), 1.76-1.51 (m, 3H), 1.32 (t, J=7.2 Hz, 3H), 1.21-1.06 (m, 2H). MS (ESI) m/z: [M+H]⁺ Found 577.2.

Example 209

4-Chloro-5-(4-((2,2-difluorocyclopropyl)methoxy)-2-methoxyphenyl)-1-ethyl-N-(((1r,4r)-4-(methylsulfonyl)cyclohexyl)methyl)-1H-pyrazole-3-carboxamide

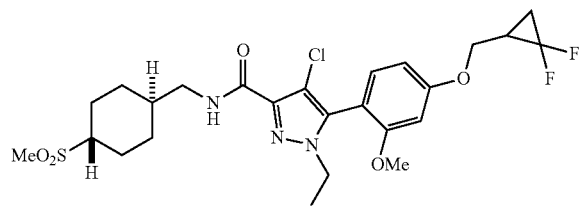 [SMILES: CCn1nc(C(=O)NC[C@H]2CC[C@H](S(C)(=O)=O)CC2)c(Cl)c1-c1ccc(OCC2CC2(F)F)cc1OC]

The title compound was prepared as described for the synthesis of Example 1, using ethyl 4-chloro-5-(4-((2,2-difluorocyclopropyl)methoxy)-2-methoxyphenyl)-1-ethyl-1H-pyrazole-3-carboxylate (Intermediate 235) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (500 MHz, CDCl$_3$) δ 7.20-7.10 (m, 1H), 6.94 (t, J=6.3 Hz, 1H), 6.64-6.54 (m, 2H), 4.19-4.05 (m, 2H), 4.04-3.86 (m, 2H), 3.79 (s, 3H), 3.43-3.23 (m, 2H), 2.81 (s, 3H), 2.28 (d, J=11.8 Hz, 2H), 2.19-1.99 (m, 3H), 1.77-1.52 (m, 6H), 1.37-1.27 (m, 3H), 1.12-1.14 (m, 2H).

Example 210

4-Chloro-5-(4-(((S*)-2,2-difluorocyclopropyl)methoxy)-2-methoxyphenyl)-1-ethyl-N-(((1r,4R)-4-(methylsulfonyl)cyclohexyl)methyl)-1H-pyrazole-3-carboxamide

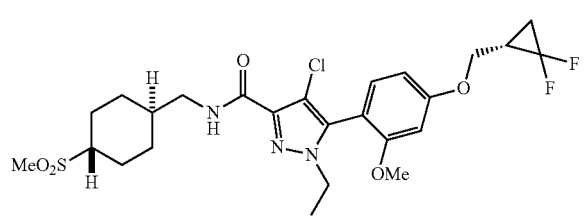 [SMILES: CCn1nc(C(=O)NC[C@H]2CC[C@H](S(C)(=O)=O)CC2)c(Cl)c1-c1ccc(OC[C@@H]2CC2(F)F)cc1OC]

Example 211

4-Chloro-5-(4-(((R*)-2,2-difluorocyclopropyl)methoxy)-2-methoxyphenyl)-1-ethyl-N-(((1r,4R)-4-(methylsulfonyl)cyclohexyl)methyl)-1H-pyrazole-3-carboxamide

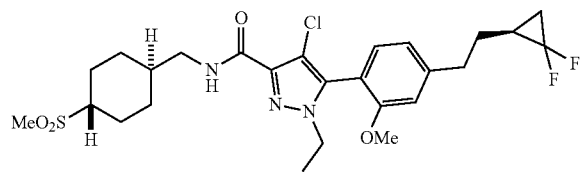 [SMILES: CCn1nc(C(=O)NC[C@H]2CC[C@H](S(C)(=O)=O)CC2)c(Cl)c1-c1ccc(CC[C@H]2CC2(F)F)cc1OC]

Example 209 was purified by SFC using a chiral stationary phase (CHIRALCEL OD-H, 85% CO$_2$, 15% MeOH) to give a pair of enantiomers. The first-eluting enantiomer was Example 210, and the second-eluting enantiomer was Example 211. Example 210: MS (ESI) m/z: [M+H]$^+$ Found 560.2. Example 211: MS (ESI) m/z: [M+H]$^+$ Found 560.2.

Example 212

4-Chloro-1-ethyl-5-(2-methoxy-4-((1,1,1-trifluoropropan-2-yl)oxy)phenyl)-N-(((1r,4r)-4-(methylsulfonyl)cyclohexyl)methyl)-1H-pyrazole-3-carboxamide The title compound was prepared as described for the synthesis of Example 1, using ethyl 4-chloro-1-ethyl-5-(2-methoxy-4-((1,1,1-trifluoropropan-2-yl)oxy)phenyl)-1H-pyrazole-3-carboxylate (Intermediate 237) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (400 MHz, CDCl$_3$) δ 7.18 (d, J=8.3 Hz, 1H), 6.94 (t, J=6.2 Hz, 1H), 6.68-6.53 (m, 2H), 4.80-4.67 (m, 1H), 4.04-3.86 (m, 2H), 3.82-3.75 (m, 3H), 3.41-3.26 (m, 2H), 2.82 (s, 3H), 2.28 (d, J=10.7 Hz, 2H), 2.07 (d, J=11.1 Hz, 2H), 1.74-1.52 (m, 4H), 1.51-1.40 (m, 3H), 1.37-1.28 (m, 3H), 1.22-1.05 (m, 2H). MS (ESI) m/z: [M+H]$^+$ Found 565.9.

Example 213

4-Chloro-1-ethyl-5-(2-methoxy-4-(3,3,3-trifluoropropoxy)phenyl)-N-(((1r,4r)-4-(methylsulfonyl)cyclohexyl)methyl)-1H-pyrazole-3-carboxamide The title compound was prepared as described for the synthesis of Example 1, using ethyl 4-chloro-1-ethyl-5-(2-methoxy-4-(3,3,3-trifluoropropoxy)phenyl)-1H-pyrazole-3-carboxylate (Intermediate 238) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (500 MHz, CDCl$_3$) δ 7.17 (d, J=8.2 Hz, 1H), 6.95 (t, J=6.3 Hz, 1H), 6.67-6.47 (m, 2H), 4.26 (t, J=6.5 Hz, 2H), 4.08-3.85 (m, 2H), 3.79 (s, 3H), 3.43-3.20 (m, 2H), 2.82 (s, 3H), 2.74-2.59 (m, 2H), 2.27 (d, J=11.0 Hz, 2H), 2.07 (d, J=11.1 Hz, 2H), 1.81-1.51 (m, 4H), 1.33 (t, J=7.2 Hz, 3H), 1.22-1.04 (m, 2H). MS (ESI) m/z: [M+H]$^+$ Found 565.9.

Example 214

4-Chloro-5-(4-(2,2-difluoropropoxy)-2-methoxyphenyl)-1-ethyl-N-(((1r,4r)-4-(methylsulfonyl)cyclohexyl)methyl)-1H-pyrazole-3-carboxamide

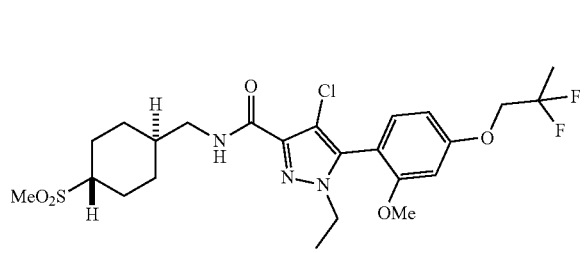 [SMILES: CCn1nc(C(=O)NC[C@H]2CC[C@H](S(C)(=O)=O)CC2)c(Cl)c1-c1ccc(OCC(C)(F)F)cc1OC]

The title compound was prepared as described for the synthesis of Example 1, using ethyl 4-chloro-5-(4-(2,2-difluoropropoxy)-2-methoxyphenyl)-1-ethyl-1H-pyrazole-3-carboxylate (Intermediate 239) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (500 MHz, CD$_3$OD) δ 7.18 (d, J=8.4 Hz, 1H), 6.80-6.70 (m, 2H), 4.27 (t, J=11.7 Hz, 2H), 3.96 (bs, 1H), 3.81 (s, 3H), 3.25 (d, J=6.0 Hz, 2H), 3.01 (m, 2H), 2.89 (s, 3H), 2.24 (d, J=10.9 Hz, 2H), 2.02 (d, J=11.1 Hz, 2H), 1.78 (t, J=18.9 Hz, 3H), 1.71-1.46 (m, 4H), 1.30 (t, J=6.6 Hz, 3H), 1.22-1.09 (m, 2H). MS (ESI) m/z: [M+H]$^+$ Found 547.9.

Example 215

4-Chloro-1-ethyl-5-(2-methoxy-4-((1-methylcyclopropyl)methoxy)phenyl)-N-(((1r,4r)-4-(methylsulfonyl)cyclohexyl)methyl)-1H-pyrazole-3-carboxamide

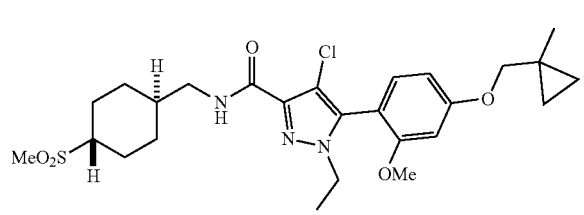 [SMILES: CCn1nc(C(=O)NC[C@H]2CC[C@H](S(C)(=O)=O)CC2)c(Cl)c1-c1ccc(OCC2(C)CC2)cc1OC]

The title compound was prepared as described for the synthesis of Example 1, using ethyl 4-chloro-1-ethyl-5-(2-methoxy-4-((1-methylcyclopropyl)methoxy)phenyl)-1H-pyrazole-3-carboxylate (Intermediate 240) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (400 MHz, CDCl$_3$) δ 7.13 (d, J=8.4 Hz, 1H), 6.94 (t, J=6.2 Hz, 1H), 6.66-6.38 (m, 2H), 4.09-3.85 (m, 2H), 3.78 (s, 5H), 3.49-3.29 (m, 2H), 2.91-2.73 (m, 4H), 2.28 (d, J=11.3 Hz, 2H), 2.07 (d, J=11.2 Hz, 2H), 1.74-1.48 (m, 3H), 1.32 (t, J=7.2 Hz, 3H), 1.26 (s, 3H), 1.20-1.05 (m, 2H), 0.62-0.55 (m, 2H), 0.51-0.43 (m, 2H). MS (ESI) m/z: [M+H]$^+$ Found 538.2.

Example 216

4-Chloro-1-ethyl-5-(4-((1,1,1,3,33-hexafluoropropan-2-yl)amino)-2-methoxyphenyl)-N-(((1r,4r)-4-(methylsulfonyl)cyclohexyl)methyl)-1H-pyrazole-3-carboxamide

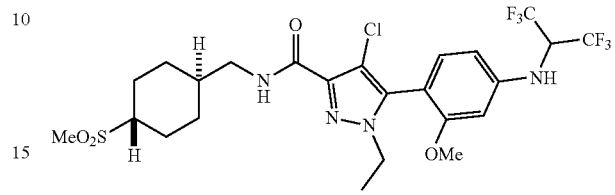

The title compound was prepared as described for the synthesis of Intermediate 106, using 5-(4-bromo-2-methoxyphenyl)-4-chloro-1-ethyl-N-(((1r,4r)-4-(methylsulfonyl)cyclohexyl)methyl)-1H-pyrazole-3-carboxamide (Intermediate 146) and 1,1,1,3,3,3-hexafluoropropan-2-amine in place of ethyl 5-(4-bromo-2-methoxyphenyl)-4-chloro-1-ethyl-1H-pyrazole-3-carboxylate (Intermediate 97, Step c) and (R)-1,1,1-trifluoro-2-propylamine. $^1$H NMR (400 MHz, CD$_3$OD) δ 7.03 (d, J=8.3 Hz, 1H), 6.67 (d, J=2.1 Hz, 1H), 6.60 (dd, J=8.4, 2.1 Hz, 1H), 5.61-5.42 (m, 1H), 4.10-3.88 (m, 3H), 3.78 (s, 3H), 3.26 (d, J=6.5 Hz, 2H), 3.13-2.95 (m, 2H), 2.89 (s, 3H), 2.24 (d, J=11.1 Hz, 2H), 2.02 (d, J=11.2 Hz, 2H), 1.76-1.42 (m, 3H), 1.39-1.26 (m, 3H), 1.24-1.05 (m, 2H). MS (ESI) m/z: [M+H]$^+$ Found 619.2.

Example 217

1-Ethyl-N-(((1s,4S)-1-hydroxy-4-(methylsulfonyl)cyclohexyl)methyl)-5-(2-methoxy-4-(((R)-1,1,1-trifluoropropan-2-yl)amino)phenyl)-4-(trifluoromethyl)-1H-pyrazole-3-carboxamide

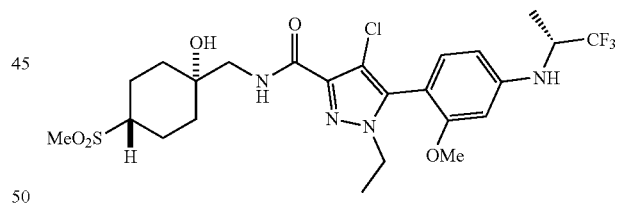

The title compound was prepared as described for the synthesis of Example 1, using ethyl (R)-1-ethyl-5-(2-methoxy-4-((1,1,1-trifluoropropan-2-yl)amino)phenyl)-4-(trifluoromethyl)-1H-pyrazole-3-carboxylate (Intermediate 243) and (1 s,4s)-1-(aminomethyl)-4-(methylsulfonyl)cyclohexan-1-ol hydrochloride (Intermediate 9) in place of ethyl (R*)-4-chloro-1-ethyl-5-(2-methoxy-4-(3,3,3-trifluoro-2-methylpropyl)phenyl)-1H-pyrazole-3-carboxylate and ((1r,4r)-4-(methylsulfonyl)cyclohexyl)methanamine hydrochloride. $^1$H NMR (500 MHz, CD$_3$OD) δ 6.93 (dd, J=8.3, 4.8 Hz, 1H), 6.46 (s, 1H), 6.41 (d, J=8.3 Hz, 1H), 4.34-4.23 (m, 1H), 4.03-3.86 (m, 2H), 3.74 (d, J=2.1 Hz, 3H), 3.44-3.35 (m, 2H), 3.09-2.96 (m, 1H), 2.90 (s, 3H), 2.09-1.81 (m, 6H), 1.61-1.47 (m, 2H), 1.40 (d, J=6.8 Hz, 3H), 1.31 (dt, J=7.2, 1.7 Hz, 3H). MS (ESI) m/z: [M+H]$^+$ Found 615.2.

Example 218

1-Ethyl-5-(2-methoxy-4-(((R)-1,1,1-trifluoropropan-2-yl)amino)phenyl)-N-(((1r,4R)-4-(methylsulfonyl)cyclohexyl)methyl)-4-(trifluoromethyl)-1H-pyrazole-3-carboxamide

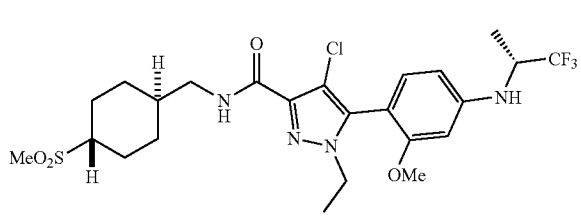 [SMILES: CCn1nc(C(=O)NC[C@H]2CC[C@H](S(C)(=O)=O)CC2)c(Cl)c1-c1ccc(N[C@H](C)C(F)(F)F)cc1OC]

The title compound was prepared as described for the synthesis of Example 1, ethyl (R)-1-ethyl-5-(2-methoxy-4-((1,1,1-trifluoropropan-2-yl)amino)phenyl)-4-(trifluoromethyl)-1H-pyrazole-3-carboxylate (Intermediate 243) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (500 MHz, CDCl$_3$) δ 7.08 (br s, 1H), 6.96 (t, J=7.7 Hz, 1H), 6.39-6.21 (m, 2H), 5.08 (br s, 1H), 4.14-4.02 (m, 1H), 3.99-3.82 (m, 2H), 3.73 (s, 3H), 3.43-3.26 (m, 2H), 2.83 (appar s, 4H), 2.27 (d, J=12.6 Hz, 2H) 2.05 (d, J=13.3 Hz, 2H), 1.51-1.75 (m, 3H), 1.45 (d, J=6.6 Hz, 3H), 1.32 (t, J=6.9 Hz, 3H), 1.13 (m, 2H). MS (ESI) m/z: [M+H]$^+$ Found 599.2.

Example 219

4-Chloro-5-(4-((4,4-difluorocyclohexyl)oxy)-2-methoxyphenyl)-1-ethyl-N-(((1r,4r)-4-(methylsulfonyl)cyclohexyl)methyl)-1H-pyrazole-3-carboxamide

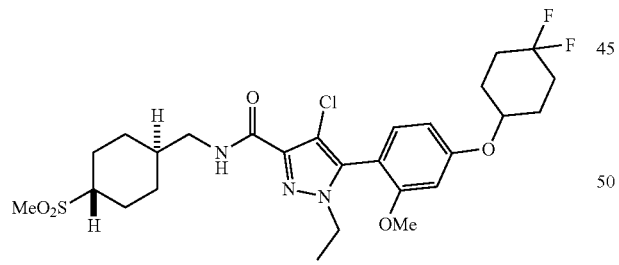

The title compound was prepared as described for the synthesis of Example 1, using ethyl 4-chloro-5-(4-((4,4-difluorocyclohexyl)oxy)-2-methoxyphenyl)-1-ethyl-1H-pyrazole-3-carboxylate (Intermediate 236) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (400 MHz, CDCl$_3$) δ 7.14 (d, J=8.3 Hz, 1H), 6.94 (t, J=6.3 Hz, 1H), 6.63-6.54 (m, 2H), 4.57 (br s, 1H), 4.05-3.85 (m, 2H), 3.70-3.80 (m, 4H), 3.41-3.25 (m, 2H), 2.80-2.84 (m, 4H), 2.34-1.88 (m, 8H), 1.77-1.49 (m, 8H), 1.34 (t, J=7.2 Hz, 3H), 1.23-1.04 (m, 2H). MS (ESI) m/z: [M+H]$^+$ Found=587.9.

Example 220

4-Chloro-1-ethyl-N-(((1r,4R)-1-hydroxy-4-(methylsulfonyl)cyclohexyl)methyl)-5-(2-methoxy-4-(((R)-1,1,1-trifluoropropan-2-yl)amino)phenyl)-1H-pyrazole-3-carboxamide

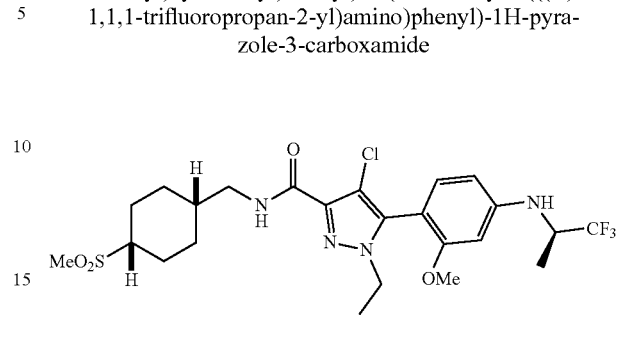

The title compound was prepared as described for the synthesis of Example 1, using ethyl (R)-4-chloro-1-ethyl-5-(2-methoxy-4-((1,1,1-trifluoropropan-2-yl)amino)phenyl)-1H-pyrazole-3-carboxylate (Intermediate 106) and (1r,4r)-1-(aminomethyl)-4-(methyl sulfonyl)cyclohexan-1-ol hydrochloride (Intermediate 259) in place of ethyl (R*)-4-chloro-1-ethyl-5-(2-methoxy-4-(3,3,3-trifluoro-2-methylpropyl)phenyl)-1H-pyrazole-3-carboxylate and ((1r,4r)-4-(methylsulfonyl)cyclohexyl)methanamine hydrochloride. $^1$H NMR (400 MHz, CDCl$_3$) δ 7.42 (t, J=6.1 Hz, 1H), 7.06-7.01 (m, 1H), 6.39-6.34 (m, 1H), 6.30-6.26 (m, 1H), 4.32 (br s, 2H), 4.14-4.04 (m, 1H), 4.04-3.89 (m, 2H), 3.77 (s, 3H of one rotamer), 3.76 (s, 3H of one rotamer), 3.66-3.55 (m, 2H), 2.95 (tt, J=10.8, 4.2 Hz, 1H), 2.89 (s, 3H), 2.27-2.18 (m, 2H), 2.12-2.03 (m, 2H), 1.89-1.77 (m, 2H), 1.62 (td, J=12.8, 4.1 Hz, 2H), 1.46 (d, J=6.7 Hz, 3H), 1.34 (t, J=7.2 Hz, 3H). MS (ESI) m/z: [M+H]$^+$ Found 581.2.

Example 221

4-Chloro-5-(2-(difluoromethoxy)-4-(3,3,3-trifluoropropyl)phenyl)-1-ethyl-N-(((1s,4s)-1-hydroxy-4-(methylsulfonyl)cyclohexyl)methyl)-1H-pyrazole-3-carboxamide

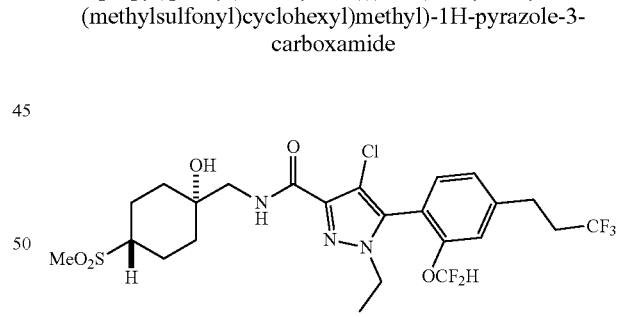

The title compound was prepared as described for the synthesis of Example 1, using ethyl 4-chloro-5-(2-(difluoromethoxy)-4-(3,3,3-trifluoropropyl)phenyl)-1-ethyl-1H-pyrazole-3-carboxylate (Intermediate 260) and (1s,4s)-1-(aminomethyl)-4-(methylsulfonyl)cyclohexan-1-ol hydrochloride (Intermediate 9) in place of ethyl (R*)-4-chloro-1-ethyl-5-(2-methoxy-4-(3,3,3-trifluoro-2-methylpropyl)phenyl)-1H-pyrazole-3-carboxylate and ((1r,4r)-4-(methylsulfonyl)cyclohexyl)methanamine hydrochloride. $^1$H NMR (500 MHz, CDCl$_3$) δ 7.36-7.29 (m, 2H), 7.26-7.21 (m, 1H), 7.18 (s, 1H), 6.43 (dd, J=74.9, 71.0 Hz, 1H), 4.06-3.88 (m, 2H), 3.48 (d, J=6.3 Hz, 2H), 3.36 (s, 1H), 3.03-2.94 (m, 2H), 2.89-2.77 (m, 4H), 2.56-2.41 (m, 2H), 2.15-2.06 (m, 2H), 2.04-1.93 (m, 4H), 1.51-1.41 (m, 2H), 1.35 (t, J=7.3 Hz, 3H). MS (ESI) m/z: [M+H]⁺ Found 602.2.

Example 222

4-Chloro-5-(2-(difluoromethoxy)-4-(3,3,3-trifluoropropyl)phenyl)-1-ethyl-N-(((1r,4r)-4-(methylsulfonyl)cyclohexyl)methyl)-1H-pyrazole-3-carboxamide

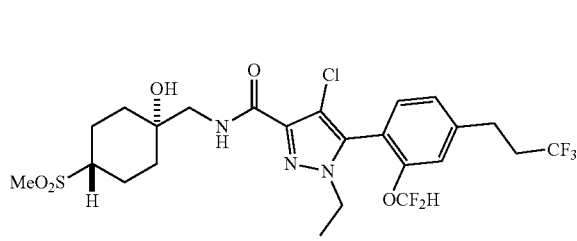

The title compound was prepared as described for the synthesis of Example 1, using ethyl 4-chloro-5-(2-(difluoromethoxy)-4-(3,3,3-trifluoropropyl)phenyl)-1-ethyl-1H-pyrazole-3-carboxylate (Intermediate 260) in place of ethyl (R*)-4-chloro-1-ethyl-5-(2-methoxy-4-(3,3,3-trifluoro-2-methylpropyl)phenyl)-1H-pyrazole-3-carboxylate. ¹H NMR (500 MHz, CDCl₃) δ 7.32-7.29 (m, 1H), 7.23 (dd, J=1.5, 7.8 Hz, 1H), 7.18 (s, 1H), 6.99 (t, J=6.4 Hz, 1H), 6.59-6.26 (m, 1H), 4.04-3.92 (m, 2H), 3.34 (t, J=6.6 Hz, 2H), 3.01-2.96 (m, 2H), 2.84-2.82 (m, 3H), 2.53-2.43 (m, 2H), 2.31-2.25 (m, 2H), 2.10-2.04 (m, 2H), 1.73-1.66 (m, 1H), 1.64-1.53 (m, 2H), 1.36 (t, J=7.3 Hz, 3H), 1.19-1.13 (m, 2H). MS (ESI) m/z: [M+H]⁺ Found 586.2.

Example 223

5-(2-(Difluoromethoxy)-4-(3,3,3-trifluoropropyl)phenyl)-1-ethyl-N-(((1s,4s)-1-hydroxy-4-(methylsulfonyl)cyclohexyl)methyl)-4-methyl-1H-pyrazole-3-carboxamide

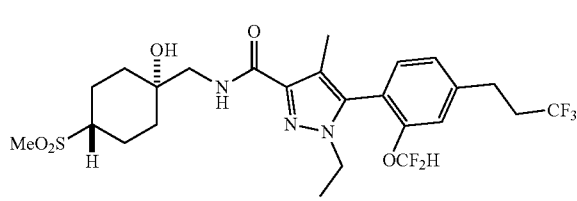

The title compound was prepared as described for the synthesis of Example 78, using 4-chloro-5-(2-(difluoromethoxy)-4-(3,3,3-trifluoropropyl)phenyl)-1-ethyl-N-(((1s,4s)-1-hydroxy-4-(methyl sulfonyl)cyclohexyl)methyl)-1H-pyrazole-3-carboxamide (Example 221) in place of 4-chloro-5-(2-(difluoromethoxy)-4-(4,4,4-trifluorobutyl)phenyl)-1-ethyl-N-(((1 r,4r)-4-(methylsulfonyl)cyclohexyl)methyl)-1H-pyrazole-3-carboxamide. ¹H NMR (500 MHz, CDCl₃) δ 7.39 (t, J=6.3 Hz, 1H), 7.29 (s, 1H), 7.22-7.20 (m, 1H), 7.17 (s, 1H), 6.54-6.21 (m, 1H), 3.97-3.86 (m, 2H), 3.77 (s, 1H), 3.45 (d, J=6.3 Hz, 2H), 3.00-2.95 (m, 2H), 2.83 (s, 3H), 2.53-2.45 (m, 2H), 2.15-2.10 (m, 4H), 2.04-1.96 (m, 4H), 1.47-1.40 (m, 2H), 1.34-1.26 (m, 3H). MS (ESI) m/z: [M+H]⁺ Found 582.2.

Example 224

5-(2-(Difluoromethoxy)-4-(3,3,3-trifluoropropyl)phenyl)-1-ethyl-4-methyl-N-(((1r,4r)-4-(methylsulfonyl)cyclohexyl)methyl)-1H-pyrazole-3-carboxamide

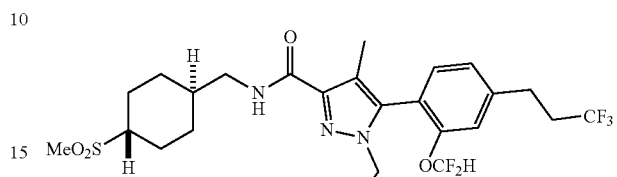

The title compound was prepared as described for the synthesis of Example 78, using 4-chloro-5-(2-(difluoromethoxy)-4-(3,3,3-trifluoropropyl)phenyl)-1-ethyl-N-(((1r,4r)-4-(methylsulfonyl)cyclohexyl)methyl)-1H-pyrazole-3-carboxamide (Example 222) in place of 4-chloro-5-(2-(difluoromethoxy)-4-(4,4,4-trifluorobutyl)phenyl)-1-ethyl-N-(((1 r,4r)-4-(methylsulfonyl)cyclohexyl)methyl)-1H-pyrazole-3-carboxamide. ¹H NMR (500 MHz, CDCl₃) δ 7.29 (s, 1H), 7.23-7.20 (m, 1H), 7.16 (s, 1H), 7.09 (t, J=6.4 Hz, 1H), 6.52-6.20 (m, 1H), 3.97-3.86 (m, 2H), 3.35-3.30 (m, 2H), 2.99-2.95 (m, 2H), 2.84-2.81 (m, 3H), 2.53-2.45 (m, 2H), 2.31-2.26 (m, 2H), 2.15 (s, 3H), 2.11-2.04 (m, 2H), 1.71-1.55 (m, 3H), 1.33 (t, J=7.3 Hz, 3H), 1.18-1.12 (m, 2H). MS (ESI) m/z: [M+H]⁺ Found 566.2.

Example 225

1-Ethyl-N-(((1s,4s)-1-hydroxy-4-(methylsulfonyl)cyclohexyl)methyl)-5-(2-methoxy-4-(3,3,3-trifluoropropyl)phenyl)-4-methyl-1H-pyrazole-3-carboxamide

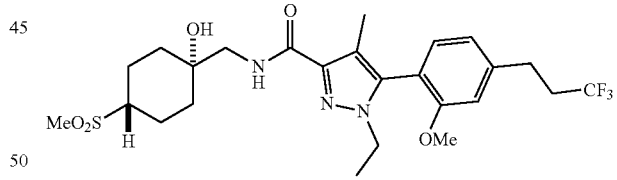

The title compound was prepared as described for the synthesis of Example 1, using ethyl 1-ethyl-5-(2-methoxy-4-(3,3,3-trifluoropropyl)phenyl)-4-methyl-1H-pyrazole-3-carboxylate (Intermediate 262) and (1s,4s)-1-(aminomethyl)-4-(methyl sulfonyl)cyclohexan-1-ol hydrochloride (Intermediate 9) in place of ethyl (R*)-4-chloro-1-ethyl-5-(2-methoxy-4-(3,3,3-trifluoro-2-methylpropyl)phenyl)-1H-pyrazole-3-carboxylate and ((1r,4r)-4-(methylsulfonyl)cyclohexyl)methanamine hydrochloride. ¹H NMR (500 MHz, CDCl₃) δ 7.36 (t, J=6.3 Hz, 1H), 7.09 (d, J=7.7 Hz, 1H), 6.90 (dd, J=7.7, 1.6 Hz, 1H), 6.84 (d, J=1.5 Hz, 1H), 3.99-3.83 (m, 2H), 3.80 (s, 3H), 3.50-3.37 (m, 2H), 2.98-2.91 (m, 2H), 2.86-2.75 (m, 4H), 2.53-2.41 (m, 2H), 2.13 (s, 5H), 2.05-1.93 (m, 5H), 1.46-1.35 (m, 2H), 1.31 (t, J=7.2 Hz, 3H). MS (ESI) m/z: [M+H]⁺ Found 546.0.

Example 226

1-Ethyl-5-(2-methoxy-4-(3,3,3-trifluoropropyl)phenyl)-4-methyl-N-(((1r,4r)-4-(methylsulfonyl)cyclohexyl)methyl)-1H-pyrazole-3-carboxamide

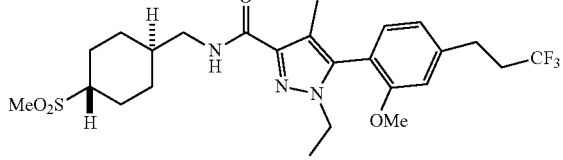

The title compound was prepared as described for the synthesis of Example 1, using ethyl 1-ethyl-5-(2-methoxy-4-(3,3,3-trifluoropropyl)phenyl)-4-methyl-1H-pyrazole-3-carboxylate (Intermediate 262) in place of ethyl (R*)-4-chloro-1-ethyl-5-(2-methoxy-4-(3,3,3-trifluoro-2-methylpropyl)phenyl)-1H-pyrazole-3-carboxylate. $^1$H NMR (500 MHz, CDCl$_3$) δ 7.11-7.03 (m, 2H), 6.90 (dd, J=7.7, 1.5 Hz, 1H), 6.83 (d, J=1.6 Hz, 1H), 3.98-3.83 (m, 2H), 3.80 (s, 3H), 3.37-3.25 (m, 2H), 2.98-2.90 (m, 2H), 2.87-2.78 (m, 4H), 2.53-2.41 (m, 2H), 2.32-2.24 (m, 2H), 2.15 (s, 3H), 2.12-2.05 (m, 2H), 1.73-1.52 (m, 3H), 1.31 (t, J=7.2 Hz, 3H), 1.19-1.07 (m, 2H). MS (ESI) m/z: [M+H]$^+$ Found 530.0.

Example 227

1-Ethyl-5-(2-methoxy-4-(3,3,3-trifluoro-2,2-dimethylpropyl)phenyl)-4-methyl-N-(((1r,4r)-4-(methylsulfonyl)cyclohexyl)methyl)-1H-pyrazole-3-carboxamide

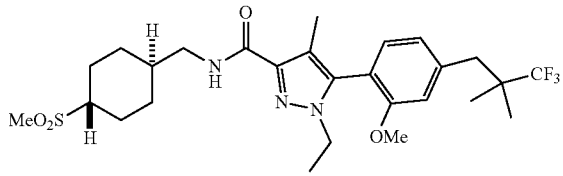 [SMILES: CCn1nc(C(=O)NC[C@H]2CC[C@H](S(C)(=O)=O)CC2)c(C)c1-c1ccc(CC(C)(C)C(F)(F)F)cc1OC]

The title compound was prepared as described for the synthesis of Example 78, using 4-chloro-1-ethyl-5-(2-methoxy-4-(3,3,3-trifluoro-2,2-dimethylpropyl)phenyl)-N-(((1r,4r)-4-(methylsulfonyl)cyclohexyl)methyl)-1H-pyrazole-3-carboxamide (Example 44) in place of 4-chloro-5-(2-(difluoromethoxy)-4-(4,4,4-trifluorobutyl)phenyl)-1-ethyl-N-(((1 r,4r)-4-(methylsulfonyl)cyclohexyl)methyl)-1H-pyrazole-3-carboxamide. $^1$H NMR (500 MHz, CDCl$_3$) δ 7.12-7.05 (m, 2H), 6.86 (dd, J=7.7, 1.5 Hz, 1H), 6.79 (d, J=1.5 Hz, 1H), 3.99-3.84 (m, 2H), 3.79 (s, 3H), 3.37-3.26 (m, 2H), 2.88-2.78 (m, 6H), 2.32-2.24 (m, 2H), 2.16 (s, 3H), 2.12-2.05 (m, 2H), 1.70-1.53 (m, 3H), 1.32 (t, J=7.2 Hz, 3H), 1.16-1.10 (m, 8H). MS (ESI) m/z: [M+H]$^+$ Found 558.0.

Example 228

1-Ethyl-5-(2-methoxy-4-(((R)-1,1,1-trifluoropropan-2-yl)amino)phenyl)-4-methyl-N-(((1r,4R)-4-(methylsulfonyl)cyclohexyl)methyl)-1H-pyrazole-3-carboxamide

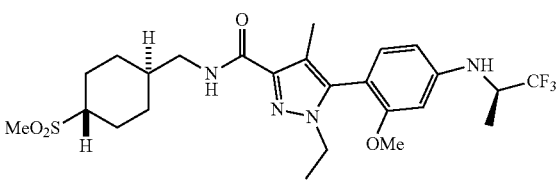 [SMILES: CCn1nc(C(=O)NC[C@H]2CC[C@H](S(C)(=O)=O)CC2)c(C)c1-c1ccc(N[C@H](C)C(F)(F)F)cc1OC]

The title compound was prepared as described for the synthesis of Example 78, using 4-chloro-1-ethyl-5-(2-methoxy-4-(((R)-1,1,1-trifluoropropan-2-yl)amino)phenyl)-N-(((1 r,4R)-4-(methylsulfonyl)cyclohexyl)methyl)-1H-pyrazole-3-carboxamide (Example 23) in place of 4-chloro-5-(2-(difluoromethoxy)-4-(4,4,4-trifluorobutyl)phenyl)-1-ethyl-N-(((1 r,4r)-4-(methylsulfonyl)cyclohexyl)methyl)-1H-pyrazole-3-carboxamide. $^1$H NMR (500 MHz, CDCl$_3$) δ 7.09 (t, J=6.4 Hz, 1H), 6.94 (dd, J=8.2, 2.5 Hz, 1H), 6.36-6.32 (m, 1H), 6.28 (t, J=2.3 Hz, 1H), 4.15-4.04 (m, 1H), 3.99-3.84 (m, 3H), 3.76-3.73 (m, 3H), 3.37-3.24 (m, 2H), 2.82 (s, 3H), 2.31-2.23 (m, 2H), 2.14 (s, 3H), 2.11-2.03 (m, 3H), 1.72-1.52 (m, 3H), 1.46 (d, J=6.7 Hz, 3H), 1.31 (t, J=7.2 Hz, 3H), 1.17-1.07 (m, 2H). MS (ESI) m/z: [M+H]$^+$ Found 545.0.

Example 229

4-Chloro-1-(3-cyanopropyl)-5-(2-(difluoromethoxy)-4-(3,3,3-trifluoro-2,2-dimethylpropyl)phenyl)-N-(((1s,4s)-1-hydroxy-4-(methylsulfonyl)cyclohexyl)methyl)-1H-pyrazole-3-carboxamide

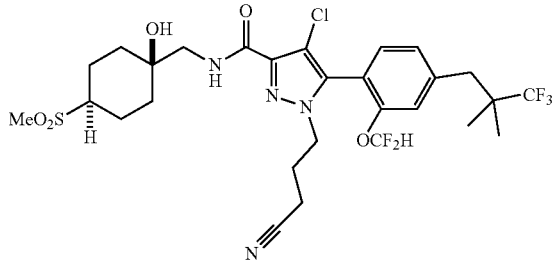

The title compound was prepared as described for the synthesis of Example 1, using ethyl 4-chloro-1-(3-cyanopropyl)-5-(2-(difluoromethoxy)-4-(3,3,3-trifluoro-2,2-dimethylpropyl)phenyl)-1H-pyrazole-3-carboxylate (Intermediate 267) in place of ethyl (R*)-4-chloro-1-ethyl-5-(2-methoxy-4-(3,3,3-trifluoro-2-methylpropyl)phenyl)-1H-pyrazole-3-carboxylate and (1s,4s)-1-(aminomethyl)-4-(methylsulfonyl)cyclohexan-1-ol hydrochloride (Intermediate 9) in place of (((1r,4r)-4-(methylsulfonyl)cyclohexyl)methanamine hydrochloride. $^1$H NMR (400 MHz, DMSO-d$_6$) 7.96-7.90 (m, 1H), 7.50-7.08 (m, 4H), 4.62 (s, 1H), 4.10-3.93 (m, 2H), 3.28-3.22 (m, 2H), 3.05-2.95 (m, 1H), 2.93-2.87 (m, 5H), 2.49-2.42 (m, 2H), 2.09-1.94 (m, 2H), 1.91-1.81 (m, 2H), 1.80-1.64 (m, 4H), 1.45-1.33 (m, 2H), 1.08 (s, 6H); MS (ESI) m/z: [M+H]$^+$ Found 669.1.

In Vitro Biological Data

ThermoFluor® Assay

ThermoFluor® is a fluorescence based assay that estimates ligand binding affinities by measuring the effect of a ligand on protein thermal stability (Pantoliano, M. W., Petrella, E. C., Kwasnoski, J. D., Lobanov, V. S., Myslik, J., Graf, E., Carver, T., Asel, E., Springer, B. A., Lane, P., and Salemme, F. R. (2001) High-density miniaturized thermal shift assays as a general strategy for drug discovery. *J Biomol Screen* 6, 429-40, and Matulis, D., Kranz, J. K., Salemme, F. R., and Todd, M. J. (2005) Thermodynamic stability of carbonic anhydrase: measurements of binding affinity and stoichiometry using ThermoFluor. *Biochemistry* 44, 5258-66). This approach is applicable to a wide variety of systems, and rigorous in theoretical interpretation through quantitation of equilibrium binding constants ($K_D$).

In a ThermoFluor® experiment where protein stability is monitored as the temperature is steadily increased, an equilibrium binding ligand causes the midpoint of an unfolding transition ($T_m$) to occur at a higher temperature. The shift in the melting point described as a $\Delta T_m$ is proportional to the concentration and affinity of the ligand. The compound potency may be compared as a rank order of either $\Delta T_m$ values at a single compound concentration or in terms of $K_D$ values, estimated from concentration response curves.

RORγt ThermoFluor® Assay Construct

For the RORγt construct used in the ThermoFluor® assay, numbering for the nucleotide sequences was based on the reference sequence for human RORγt, transcript variant 2, NCBI Accession: NM_001001523.1 (SEQ ID NO:1). Nucleotides 850-1635 (SEQ ID NO:2) coding for the wild type human RORγt ligand binding domain (RORγt LBD) were cloned into the pHIS1 vector, a modified pET *E. coli* expression vector (Accelagen, San Diego), containing an in-frame N-terminal His-tag and a TurboTEV protease cleavage site (ENLYFQG, SEQ ID NO:3) upstream of the cloned insert sequence. The amino acid sequence for the RORγt construct used in the Thermofluor® assay is shown as SEQ ID NO:4.

ThermoFluor® experiments were carried out using instruments owned by Janssen Research and Development, L.L.C. through its acquisition of 3-Dimensional Pharmaceuticals, Inc. 1,8-ANS (Invitrogen) was used as a fluorescent dye. Protein and compound solutions are dispensed into black 384-well polypropylene PCR microplates (Abgene) and overlayed with silicone oil (1 μL, Fluka, type DC 200) to prevent evaporation.

Bar-coded assay plates are robotically loaded onto a thermostatically controlled PCR-type thermal block and then heated at a typical ramp-rate of 1° C./min for all experiments. Fluorescence was measured by continuous illumination with UV light (Hamamatsu LC6) supplied via fiber optic and filtered through a band-pass filter (380-400 nm; >6 OD cutoff). Fluorescence emission of the entire 384-well plate was detected by measuring light intensity using a CCD camera (Sensys, Roper Scientific) filtered to detect 500±25 nm, resulting in simultaneous and independent readings of all 384 wells. Images were collected at each temperature, and the sum of the pixel intensity in a given area of the assay plate was recorded versus temperature. Reference wells contained RORγt without compounds, and the assay conditions were as follows:

0.065 mg/mL RORγt
60 μM 1,8-ANS
100 mM Hepes, pH 7.0
10 mM NaCl
2.5 mM GSH
0.002% Tween-20

Project compounds were arranged in a pre-dosed mother plate (Greiner Bio-one) wherein compounds are serially diluted in 100% DMSO by 1:2 from a high concentration of 10 mM over 12 columns within a series (column 12 is a reference well containing DMSO, no compound). The compounds were robotically dispensed directly into assay plates (1×=46 nL) using a Hummingbird capillary liquid handling instrument (Digilab). Following compound dispense, protein and dye in buffer was added to achieve the final assay volume of 3 μL, followed by 1 μL of silicone oil.

The binding affinity was estimated as described previously (Matulis, D., Kranz, J. K., Salemme, F. R., and Todd, M. J. (2005) Thermodynamic stability of carbonic anhydrase: measurements of binding affinity and stoichiometry using ThermoFluor®. *Biochemistry* 44, 5258-66) using the following thermodynamic parameters of protein unfolding:

Reference RORγt $T_m$: 47.8° C.
$\Delta H_{(Tm)}$=115 kcal/mol
$\Delta C_{p(Tm)}$=3 kcal/mol Cell Based Biological Data RORγt (Full-Length Human) Reporter Assay:

Two similar reporter assay protocols, shown below, have been used to test the functional activity of RORγt modulatory compounds on transcriptional activation driven by full-length human RORγt. Both provide similar data and can be used interchangeably.

Conditions A

Cells used in this assay were transiently co-transfected with three different plasmids, one expressing the GAL4-DNA binding domain (DBD)-RORγt fusion protein under control of a CMV promoter (NH2-Gal4-DBD:RORC-COOH in pCMV-BD, Stratagene #211342), and two reporter plasmids—the firefly luciferase reporter under control of a GAL4 promoter (pFR-Luc 2×GAL4) and *Renilla* luciferase reporter under control of CMV promoter (pRL-CMV, Promega # E2261). The full-length coding sequence was used for human RORγt, i.e., nucleotides 142-1635 of human RORγt, transcript variant 2, NCBI Accession: NM_001001523.1 (SEQ ID NO: 1). HEK293T cells were plated at 35,000 per well in 96-well plate in medium of DMEM with 10% FBS. After 18-22 hours incubation, the transfection was carried out by using a PEI solution with 170.5 ng total DNA/well (50 ng pCMV-BD-ROR plus 20 ng of pFR-Luc reporter and 0.5 ng of pRL-CMV reporter plus 100 ng Carrier DNA (Clontech #630440) for each well). 4-6 hours after transfection, cells were treated with compounds for overnight in the medium with final concentration of FBS 1.3% and DMSO 0.1%. After overnight (16 to 20 hours) incubation, media were removed and cells were lysed with 50 L Glo Lysis Buffer (Promega) for 10-15 minutes followed by 10 minute incubation with 50 μL Dual Glo reagent (Promega) at room temperature. Firefly luciferase luminescence was measured using a BMG Pherastar plate reader. To each well, 50 μL Stop and Glo reagent was added and incubated for 10 minutes at room temperature. *Renilla* luminescence was measured using a BMG Pherastar plate reader. To calculate the effect of compounds on RORγt activity, firefly values were normalized against values of DMSO only and values of reference compound at saturating concentration, then further normalized against *Renilla* signals. IC50s were generated by plotting final *Renilla* normalized data against compound concentration and percent inhibition was calculated against DMSO control.

Conditions B

Cells used in this assay were transiently co-transfected with three different plasmids, one expressing the GAL4-DNA binding domain (DBD)-RORγt fusion protein under control of a CMV promoter (NH$_2$-Gal4-DBD:RORC-COOH in pCMV-BD, Stratagene #211342), and two reporter plasmids—the firefly luciferase reporter under control of a GAL4 promoter (pFR-Luc 2×GAL4) and *Renilla* luciferase reporter under control of CMV promoter (pRL-CMV, Promega # E2261). The full-length coding sequence was used for human RORγt, i.e., nucleotides 142-1635 of human RORγt, transcript variant 2, NCBI Accession: NM_001001523.1 (SEQ ID NO: 1). HEK293T cells were plated at 8750 cells per well in 384-well plate in medium of DMEM with 10% FBS. After 18-22 hours incubation, the transfection was carried out by using a PEI solution with 42.6 ng total DNA/well (12.5 ng pCMV-BD-ROR plus 5 ng of pFR-Luc reporter and 0.125 ng of pRL-CMV reporter plus 25 ng Carrier DNA (Clontech #630440) for each well). 4-6 hours after transfection, cells were treated with compounds for overnight in the medium with final concentration of FBS 1.3% and DMSO 0.1%. After overnight (16 to 20 hours) incubation, media were removed and cells were lysed with 20 L Glo Lysis Buffer (Promega) for 10-15 minutes followed by 10 minute incubation with 20 µL Dual Glo reagent (Promega) at room temperature. Firefly luciferase luminescence was measured using a BMG Pherastar plate reader. To each well, 20 µL Stop and Glo reagent was added and incubated for 10 minutes at room temperature. *Renilla* luminescence was measured using a BMG Pherastar plate reader. To calculate the effect of compounds on RORγt activity, firefly values were normalized against values of DMSO only and values of reference compound at saturating concentration, then further normalized against *Renilla* signals. IC50s were generated by plotting final *Renilla* normalized data against compound concentration and percent inhibition was calculated against DMSO control.

Human Th17 Assay

The human Th17 assay tests the effect of RORγt modulatory compounds on IL-17 production by CD4 T cells under conditions which favor Th17 differentiation. Total CD4$^+$ T cells were isolated from the peripheral blood mononuclear cells (PBMC) of healthy donors using a CD4$^+$ T cell isolation kit II, following the manufacturer's instructions (Miltenyi Biotec). Cells were resuspended in a medium of RPMI-1640 supplemented with 10% fetal bovine serum, penicillin, streptomycin, glutamate, and β-mercaptoethanol and were added to 96-well plates at 1.5×10$^5$ per 100 µL per well. 50 µL of compound at titrated concentrations in DMSO were added into each well at final DMSO concentration at 0.2%. Cells were incubated for 1 hour, then 50 µL of Th17 cell differentiation medium was added to each well. The final concentrations of antibodies and cytokines (R&D Systems) in differentiation medium were: 3×10$^6$/mL anti-CD3/CD28 beads (prepared using human T cell activation/expansion kit, Miltenyi Biotec), 10 µg/mL anti-IL4, 10 µg/mL anti-IFNγ, 10 ng/mL IL1β, 10 ng/mL IL23, 50 ng/mL IL6, 3 ng/mL TGFβ and 20 U/mL IL2. Cells were cultured at 37° C. and 5% CO$_2$ for 3 days. Supernatants were collected and the accumulated IL-17 in culture was measured by using MULTI-SPOT® Cytokine Plate following manufacture's instruction (Meso Scale Discovery). The plate was read using Sector Imager 6000, and IL-17 concentration was extrapolated from the standard curve. The IC50s were determined by GraphPad.

TABLE 1

| Example # | ThermoFluor ® Assay, Kd (µM) | RORγt (FL) Reporter Assay A or B, IC$_{50}$ (µM) | RORγt (FL) Reporter Assay A or B, % inhibition @ 6 µM | Human Th17 Assay, IC$_{50}$ (µM) |
|---|---|---|---|---|
| 1 | 0.00060 | 0.0060 | 99**** | ND |
| 2 | 0.00016 | 0.0044 | 94******* | ND |
| 3 | 0.00063 | 0.0090 | 98**** | 0.015 |
| 4 | 0.0020 | 0.027 | 98***** | ND |
| 5 | 0.0017 | 0.12 | 103* | ND |
| 6 | 0.0024 | 0.029 | 117* | ND |
| 7 | 0.0021 | 0.068 | 103*** | ND |
| 8 | 0.00073 | 0.013 | 92* | ND |
| 9 | 0.0016 | 0.0091 | 104*** | ND |
| 10 | 0.0026 | 0.025 | 103* | ND |
| 11 | 0.035 | 0.19 | 100* | ND |
| 12 | 0.074 | 0.091 | 92* | ND |
| 13 | 0.11 | 0.19 | 90* | ND |
| 14 | 0.00014 | 0.0016 | 99******* | ND |
| 15 | 0.00013 | 0.0054 | 113**** | ND |
| 16 | 0.00019 | 0.0048 | 105**** | ND |
| 17 | 1.3 | 2.2 | 67 | ND |
| 18 | 0.24 | 0.83 | 102 | ND |
| 19 | 0.0022 | 0.10 | 122* | 0.014 |
| 20 | 0.095 | >3 | 15* | ND |
| 21 | 0.00037 | 0.0036 | 103***** | ND |
| 22 | 0.00044 | 0.0042 | 100*** | ND |
| 23 | 0.0046 | 0.028 | 104** | 0.038 |
| 24 | 0.021 | 0.052 | 104** | ND |
| 25 | 0.031 | 0.12 | 105 | ND |
| 26 | 0.0039 | 0.029 | 108 | ND |
| 27 | 0.0074 | 0.060 | 105 | ND |
| 28 | 0.0025 | 0.023 | 103** | ND |
| 29 | 0.0083 | 0.061 | 108 | ND |
| 30 | 0.0021 | 0.027 | 104** | ND |
| 31 | 0.0072 | 0.041 | 105 | ND |
| 32 | 0.0076 | 0.053 | 96** | 0.062 |
| 33 | 0.45 | 1.1 | 88 | ND |
| 34 | 3.0 | >6 | 6 | ND |
| 35 | 0.034 | 0.73 | 102 | ND |
| 36 | 0.0010 | 0.012 | 101** | ND |
| 37 | 0.0020 | 0.017 | 97*** | ND |
| 38 | 0.0033 | 0.012 | 84**** | ND |
| 39 | 0.010 | 0.038 | 85 | ND |
| 40 | 0.00071 | 0.013 | 99** | ND |
| 41 | 0.00028 | 0.0080 | 98*** | ND |
| 42 | 0.00042 | 0.0090 | 101** | ND |
| 43 | 0.00021 | 0.0070 | 99**** | ND |
| 44 | 0.00033 | 0.0060 | 96**** | 0.0052 |
| 45 | 0.00057 | 0.0080 | 88** | ND |
| 46 | 0.00042 | 0.0050 | 92**** | 0.013 |
| 47 | 0.00037 | 0.0017 | 103** | ND |
| 48 | 0.031 | 0.061 | 95** | ND |
| 49 | 0.026 | 0.061 | 96** | ND |
| 50 | 0.00010 | 0.0030 | 89***** | ND |
| 51 | 0.00025 | 0.0046 | 113*** | ND |
| 52 | 0.0035 | 0.026 | 103* | ND |
| 53 | 0.0016 | 0.0063 | 99*** | 0.013 |
| 54 | 0.00069 | 0.0098 | 102***** | ND |
| 55 | 0.00035 | 0.010 | 94******** | ND |
| 56 | 0.0010 | 0.0087 | 94******** | ND |
| 57 | 0.0057 | 0.035 | 95* | ND |
| 58 | 0.0026 | 0.0097 | 100* | 0.019 |
| 59 | 0.0012 | 0.019 | 93***** | ND |
| 60 | 0.0019 | 0.038 | 114* | ND |
| 61 | 0.0065 | 0.068 | 130*** | ND |
| 62 | 0.00078 | 0.012 | 120* | 0.036 |
| 63 | 0.0010 | 0.0080 | 109* | ND |
| 64 | 0.0032 | 0.051 | 119* | ND |
| 65 | 0.0057 | 0.018 | 106* | ND |
| 66 | 0.037 | 0.38 | 89* | ND |
| 67 | 0.000039 | 0.056 | 118* | ND |
| 68 | 0.00070 | 0.039 | 97* | ND |
| 69 | 0.00029 | 0.051 | 100* | ND |
| 70 | 0.00072 | 0.023 | 103* | ND |
| 71 | 0.00023 | 0.013 | 114* | ND |
| 72 | 0.00029 | 0.010 | 67** | ND |
| 73 | 0.00063 | 0.011 | 61** | ND |
| 74 | 0.00033 | 0.038 | 50**** | ND |

TABLE 1-continued

| Example # | ThermoFluor ® Assay, Kd (μM) | RORγt (FL) Reporter Assay A or B, IC$_{50}$ (μM) | RORγt (FL) Reporter Assay A or B, % inhibition @ 6 μM | Human Th17 Assay, IC$_{50}$ (μM) |
|---|---|---|---|---|
| 75 | 0.00088 | 0.025 | 62** | ND |
| 76 | 0.00028 | 0.0021 | 103******* | ND |
| 77 | 0.0012 | 0.0056 | 96** | ND |
| 78 | 0.00059 | 0.012 | 93******** | ND |
| 79 | 0.0020 | 0.0087 | 99**** | 0.058 |
| 80 | 0.0023 | 0.0060 | 89** | ND |
| 81 | 0.0051 | 0.013 | 89** | ND |
| 82 | 0.0041 | 0.014 | 87**** | ND |
| 83 | 0.011 | 0.033 | 87**** | ND |
| 84 | 0.00070 | 0.010 | 87**** | ND |
| 85 | 0.00043 | 0.0026 | 103**** | 0.0093 |
| 86 | 0.00017 | 0.0056 | 103**** | ND |
| 87 | 0.00014 | 0.0030 | 100********* | ND |
| 88 | 0.015 | 0.13 | 88* | ND |
| 89 | 0.00024 | 0.0054 | 98***** | ND |
| 90 | 0.00051 | 0.0096 | 91***** | ND |
| 91 | 0.00024 | 0.0037 | 99*** | ND |
| 92 | 0.039 | 0.066 | 87**** | 0.27 |
| 93 | 0.011 | 0.030 | 96** | ND |
| 94 | 0.00022 | 0.0060 | 101 | ND |
| 95 | 0.11 | 0.38 | 76** | ND |
| 96 | 25 | >6 | −10 | ND |
| 97 | 0.18 | 0.73 | 94 | ND |
| 98 | 0.31 | 0.071 | 89* | ND |
| 99 | 0.23 | 2.6 | −21* | ND |
| 100 | 0.069 | 0.22 | 49* | ND |
| 101 | 0.033 | 0.099 | 115* | ND |
| 102 | 0.12 | 0.36 | 85* | ND |
| 103 | 0.02 | 0.052 | 107* | ND |
| 104 | 0.047 | 0.22 | 98* | ND |
| 105 | 0.0033 | 0.013 | 28* | ND |
| 106 | 0.0099 | 0.024 | 115*** | ND |
| 107 | 0.0053 | 0.019 | 104* | ND |
| 108 | 0.017 | 0.26 | 92* | ND |
| 109 | 0.015 | 0.060 | 88* | ND |
| 110 | 0.028 | 0.17 | 75*** | ND |
| 111 | 0.031 | 0.23 | 95*** | ND |
| 112 | 3.0 | >1 | 44*** | ND |
| 113 | 0.12 | 0.061 | 88* | ND |
| 114 | 0.98 | 0.41 | 82** | ND |
| 115 | 0.032 | 0.016 | 89* | ND |
| 116 | 0.00015 | 0.0034 | 106* | ND |
| 117 | 0.00027 | 0.0042 | 102* | ND |
| 118 | ND | 0.0024 | 103** | ND |
| 119 | 1.5 | >6 | 14 | ND |
| 120 | 0.010 | 0.028 | 92******* | ND |
| 121 | 0.043 | 0.83 | 106 | ND |
| 122 | 0.027 | 0.15 | 104 | ND |
| 123 | 0.0096 | 0.035 | 85** | ND |
| 124 | 0.17 | 0.77 | 83 | ND |
| 125 | 0.044 | 0.23 | 85 | ND |
| 126 | 0.012 | 0.084 | 101 | ND |
| 127 | 0.0037 | 0.020 | 94**** | ND |
| 128 | 0.14 | 0.85 | 63** | ND |
| 129 | 0.072 | 0.81 | 102 | 2.3 |
| 130 | 0.0099 | 0.061 | 100** | ND |
| 131 | 0.033 | 0.14 | 100** | ND |
| 132 | 0.00045 | 0.0081 | 99** | 0.0060 |
| 133 | 0.00020 | 0.0046 | 107******* | ND |
| 134 | 0.00020 | 0.0013 | 102***** | ND |
| 135 | 0.00046 | 0.011 | 83***** | ND |
| 136 | 0.0011 | 0.0036 | 89***** | ND |
| 137 | 0.0020 | 0.0048 | 102* | ND |
| 138 | 0.0037 | 0.012 | 101*** | ND |
| 139 | 0.00058 | 0.0027 | 122*** | ND |
| 140 | 0.0024 | 0.015 | 109* | ND |
| 141 | 0.0058 | 0.085 | 84* | ND |
| 142 | 0.0023 | 0.011 | 87***** | ND |
| 143 | 0.00037 | 0.0073 | 101******* | 0.010 |
| 144 | 0.011 | 0.031 | 112 | ND |
| 145 | 0.0025 | 0.013 | 105** | ND |
| 146 | 0.015 | 0.015 | 106* | ND |
| 147 | 0.0031 | 0.018 | 108* | ND |
| 148 | 0.00016 | 0.0020 | 91**** | ND |
| 149 | 0.00083 | 0.0060 | 99** | ND |
| 150 | 0.0019 | 0.013 | 95** | ND |
| 151 | 0.0016 | 0.023 | 92*** | ND |
| 152 | 0.0079 | 0.037 | 72***** | ND |
| 153 | 0.0090 | 0.049 | 85* | ND |
| 154 | 0.00079 | 0.0045 | 91**** | ND |
| 155 | 0.00033 | 0.0042 | 105******* | ND |
| 156 | 0.0015 | 0.020 | 89***** | ND |
| 157 | 0.00080 | 0.013 | 101****** | ND |
| 158 | 0.016 | 0.0034 | 111* | ND |
| 159 | 0.041 | 0.039 | 73* | ND |
| 160 | 0.039 | 0.027 | 96* | ND |
| 161 | 0.032 | 0.0078 | 81* | 0.20 |
| 162 | 0.00048 | 0.0059 | 72******* | ND |
| 163 | 0.00063 | 0.0033 | 78******* | ND |
| 164 | 0.00050 | 0.0066 | 78******* | ND |
| 165 | 0.00045 | 0.0080 | 52********* | 0.013 |
| 166 | 0.00071 | 0.00092 | 88********* | ND |
| 167 | 0.0086 | 0.024 | 83**** | ND |
| 168 | 0.0040 | 0.018 | 71******* | ND |
| 169 | 0.0034 | 0.041 | 85******** | ND |
| 170 | 0.028 | >2 | 5** | ND |
| 171 | 0.014 | 0.44 | 24** | ND |
| 172 | 0.0038 | 0.028 | 100** | ND |
| 173 | 0.012 | 0.028 | 36**** | ND |
| 174 | 0.0059 | 0.038 | 40**** | ND |
| 175 | 0.23 | 0.51 | 88** | ND |
| 176 | 0.0038 | 0.018 | 102**** | ND |
| 177 | 0.0022 | 0.0072 | 77******* | ND |
| 178 | 0.0024 | 0.030 | 89**** | ND |
| 179 | 0.015 | 0.069 | 52** | ND |
| 180 | 0.046 | 0.066 | 41** | ND |
| 181 | 0.0070 | 0.045 | 101** | ND |
| 182 | 0.0010 | 0.019 | 81******* | ND |
| 183 | 0.0030 | 0.0039 | 70******* | ND |
| 184 | 0.013 | 0.052 | 101** | ND |
| 185 | 0.0024 | 0.030 | 92** | ND |
| 186 | 0.0077 | 0.034 | 96 | ND |
| 187 | 0.018 | 0.11 | 104 | 0.054 |
| 188 | 0.011 | >2 | 34** | ND |
| 189 | 0.0048 | >2 | 47** | ND |
| 190 | 0.0012 | 0.021 | 104** | ND |
| 191 | 0.0015 | 0.022 | 69**** | 0.063 |
| 192 | 0.00043 | 0.0070 | 96** | ND |
| 193 | 0.00028 | 0.0070 | 93**** | ND |
| 194 | 0.029 | 0.12 | 93** | ND |
| 195 | 0.052 | 0.30 | 96 | ND |
| 196 | 0.0054 | 0.020 | 101** | ND |
| 197 | 0.0020 | 0.021 | 70**** | ND |
| 198 | 0.016 | 0.079 | 69*** | ND |
| 199 | 0.014 | 0.058 | 75** | ND |
| 200 | 0.013 | 0.078 | 96** | ND |
| 201 | 0.20 | 1.6 | 82 | 2.8 |
| 202 | 0.18 | 0.85 | 93 | ND |
| 203 | 0.017 | 0.13 | 105 | 0.039 |
| 204 | 0.013 | 0.053 | 102** | ND |
| 205 | 0.0054 | 0.029 | 104** | ND |
| 206 | 0.0070 | 0.031 | 100** | ND |
| 207 | 0.010 | 0.040 | 101 | ND |
| 208 | 0.040 | 0.15 | 87** | ND |
| 209 | 0.034 | 0.076 | 82** | ND |
| 210 | 0.024 | 0.087 | 77** | ND |
| 211 | 0.026 | 0.11 | 66** | ND |
| 212 | 0.0074 | 0.033 | 81** | ND |
| 213 | 0.034 | 0.077 | 77** | ND |
| 214 | 0.039 | 0.084 | 79** | ND |
| 215 | 0.0066 | 0.056 | 80** | ND |
| 216 | 0.00097 | 0.028 | 107** | ND |
| 217 | 0.017 | 0.013 | 104*** | ND |
| 218 | 0.0063 | 0.061 | 105 | ND |
| 219 | 0.0099 | 0.030 | 98**** | ND |

TABLE 1-continued

| Example # | ThermoFluor® Assay, Kd (µM) | RORγt (FL) Reporter Assay A or B, IC$_{50}$ (µM) | RORγt (FL) Reporter Assay A or B, % inhibition @ 6 µM | Human Th17 Assay, IC$_{50}$ (µM) |
|---|---|---|---|---|
| 220 | 0.43 | 1.1 | 90 | ND |
| 221 | 0.0025 | 0.0093 | 90* | ND |
| 222 | 0.00075 | 0.0062 | 101* | 0.011 |
| 223 | 0.010 | 0.0023 | 68***** | ND |
| 224 | 0.0024 | 0.00044 | 95******** | ND |
| 225 | 0.026 | 0.093 | 76** | ND |
| 226 | 0.012 | 0.038 | 71**** | ND |
| 227 | 0.0011 | 0.0090 | 92**** | 0.014 |
| 228 | 0.012 | 0.029 | 99 | ND |
| 229 | 0.0031 | 0.0090 | 78* | ND |

ND: value not determined.
*% inhibition is shown at 3 µM compound concentration,
**% inhibition is shown at 2 µM compound concentration,
***% inhibition is shown at 1 µM compound concentration,
****% inhibition is shown at 0.67 µM compound concentration,
*****% inhibition is shown at 0.33 µM compound concentration,
******% inhibition is shown at 0.3 µM compound concentration,
*******% inhibition is shown at 0.22 µM compound concentration,
********% inhibition is shown at 0.11 µM compound concentration,
*********% inhibition is shown at 0.07 µM compound concentration

We claim:

1. A compound of Formula I

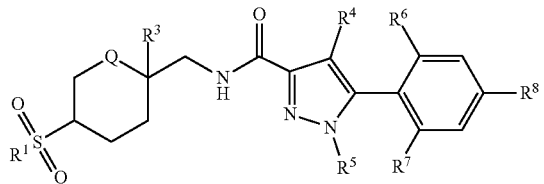

Formula I wherein $R^1$ is —$C_{(1-4)}$alkyl, —$NH_2$, —$NHC_{(1-4)}$alkyl, —NHC(O)H, —NHC(O)$NH_2$, —NHC(O)NH$C_{(1-4)}$alkyl, —NHC(O)$C_{(1-4)}$alkyl, or —N($C_{(1-4)}$alkyl)$_2$;

Q is NC(O)$C_{(1-3)}$alkyl, NCH$_2$C(O)$C_{(1-3)}$alkyl, NCH$_2$CO$_2$NH$_2$, NH, O, or CHR$^2$;

$R^2$ is —H, —$NH_2$, —OH, —CN, or —C(O)$NH_2$;

$R^3$ is —H, —OH, —CN, —$NH_2$, —CONH$_2$, —CO$_2$H, —CO$_2$C$_{(1-4)}$alkyl, —CH$_2$OH, —CH$_2$NH$_2$, —CH$_2$CN, —NHC$_{(1-4)}$alkyl, or —CONHC$_{(1-4)}$alkyl;

$R^4$ is —Cl, —$C_{(1-4)}$alkyl, —F, —CN, —C(O)NH$_2$,

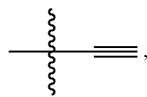

or —H; wherein said —$C_{(1-4)}$alkyl is optionally substituted with up to six fluorine atoms;

$R^5$ is —$C_{(1-4)}$alkyl, wherein said —$C_{(1-4)}$alkyl is optionally substituted with —CN, —OH, —OCH$_3$, —OCF$_3$, or up to six fluorine atoms;

$R^6$ is H, —Cl, —F, —$C_{(1-3)}$alkyl, —OC$_{(1-3)}$alkyl, —OCD$_3$, or —CN, wherein said —$C_{(1-3)}$alkyl and said —OC$_{(1-3)}$alkyl are optionally substituted with up to three fluorine atoms;

$R^7$ is H, —F, —OCH$_3$, —CH$_3$, —CF$_3$, —OCF$_3$, or —Cl;

$R^8$ is

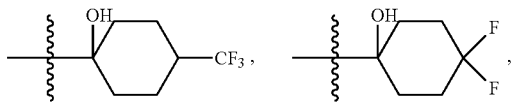

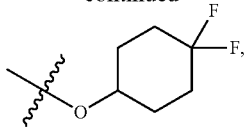

—$C_{(1-6)}$alkyl, —OC$_{(1-6)}$alkyl, or —NA$^1$A$^2$; wherein said —$C_{(1-6)}$alkyl is optionally substituted with —OH, or oxo, and the —$C_{(1-6)}$alkyl may additionally be substituted with up to six fluorine atoms or —$C_{(3-6)}$cycloalkyl, wherein said cycloalkyl is optionally substituted with —CF$_3$, —CH$_3$, or up to four fluorine atoms, and said —OC$_{(1-6)}$alkyl is optionally substituted with up to three fluorine atoms, and the —OC$_{(1-6)}$alkyl may additionally be substituted with —$C_{(3-6)}$cycloalkyl, wherein said cycloalkyl is optionally substituted with —CF$_3$, —CH$_3$, or up to four fluorine atoms;

A$^1$ is —$C_{(1-3)}$alkyl, wherein said —$C_{(1-3)}$alkyl is optionally substituted with up to six fluorine atoms;

A$^2$ is —H, or —$C_{(1-3)}$alkyl, wherein said —$C_{(1-3)}$alkyl is optionally substituted with up to six fluorine atoms; or A$^1$ and A$^2$ are taken together with their attached nitrogen to form

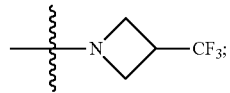 [SMILES: *N1CC(C(F)(F)F)C1]

and pharmaceutically acceptable salts thereof.

2. The compound of claim 1 wherein $R^1$ is —$C_{(1-3)}$alkyl, —$NH_2$, —NHC$_{(1-2)}$alkyl, —NHC(O)H, —NHC(O)$NH_2$, —NHC(O)NHC$_{(1-2)}$alkyl, NHC(O)C$_{(1-3)}$alkyl, or —N(CH$_3$)$_2$;

Q is NC(O)CH$_3$, NCH$_2$C(O)CH$_3$, NCH$_2$CO$_2$NH$_2$, NH, O, or CHR$^2$;

$R^2$ is —H, —$NH_2$, or —OH;

$R^3$ is —H, —OH, —CN, —$NH_2$, —CONH$_2$, —CO$_2$H, —CO$_2$CH$_2$CH$_3$, or —CH$_2$OH;

$R^4$ is —Cl, —$C_{(1-4)}$alkyl, —F, —CN, —CF$_3$, —C(O)NH$_2$,

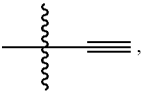

or —H;

$R^5$ is —$C_{(1-4)}$alkyl, wherein said —$C_{(1-4)}$alkyl is optionally substituted with —CN, —OH, —OCH$_3$, or —OCF$_3$;

$R^7$ is H, —F, —OCH$_3$, —CH$_3$, —CF$_3$, or —OCF$_3$;
$R^8$ is

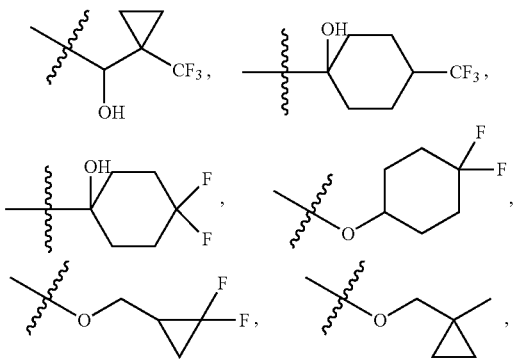

—C$_{(1-6)}$alkyl, —OC$_{(1-6)}$alkyl, or —NA$^1$A$^2$; wherein said —C$_{(1-6)}$alkyl is optionally substituted with —OH or oxo, and the —C$_{(1-6)}$alkyl may additionally be substituted with up to six fluorine atoms, and said —OC$_{(1-6)}$alkyl is optionally substituted with up to three fluorine atoms;
and pharmaceutically acceptable salts thereof.

3. The compound of claim 2 wherein
$R^1$ is —C$_{(1-3)}$alkyl, —NH$_2$, —NHC$_{(1-2)}$alkyl, —NHC(O)H, —NHC(O)NH$_2$, —NHC(O)NHC$_{(1-2)}$alkyl, or NHC(O)C$_{(1-3)}$alkyl;
$R^4$ is —Cl, —C$_{(1-4)}$alkyl, —F, —CN, —CF$_3$, —C(O)NH$_2$, or

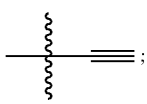

$R^5$ is —C$_{(1-4)}$alkyl, wherein said —C$_{(1-4)}$alkyl is optionally substituted with —CN, —OH, or —OCH$_3$;
$R^7$ is H, —F, —OCH$_3$, or —CH$_3$;
$A^2$ is —H, —CH$_3$, —CF$_3$ or $A^1$ and $A^2$ are taken together with their attached nitrogen to form

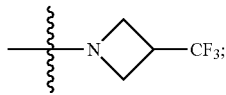 [SMILES: *N1CC(C(F)(F)F)C1]

and pharmaceutically acceptable salts thereof.

4. The compound of claim 3 wherein
$R^1$ is —C$_{(1-2)}$alkyl, —NH$_2$, —NHC$_{(1-2)}$alkyl, —NHC(O)H, —NHC(O)NH$_2$, —NHC(O)NHC$_{(1-2)}$alkyl, or —NHC(O)C$_{(1-2)}$alkyl;
$R^4$ is —Cl, —C$_{(1-4)}$alkyl, —F, —CN, or —CF$_3$;
$R^7$ is H, —F, or —OCH$_3$;
$R^8$ is

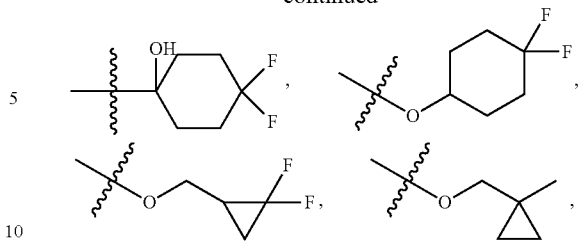

—C$_{(3-6)}$alkyl, —OC$_{(1-3)}$alkyl, or —NA$^1$A$^2$; wherein said —C$_{(3-6)}$alkyl is optionally substituted with —OH or oxo, and the —C$_{(3-6)}$alkyl may additionally be substituted with up to six fluorine atoms, and said —OC$_{(1-3)}$alkyl is optionally substituted with up to three fluorine atoms;
$A^2$ is —H, —CH$_3$, or $A^1$ and $A^2$ are taken together with their attached nitrogen to form

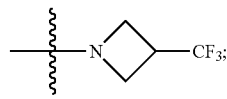

and pharmaceutically acceptable salts thereof.

5. The compound of claim 4 wherein
$R^1$ is —C$_{(1-2)}$alkyl, —NH$_2$, —NHCH$_3$, —NHC(O)H, —NHC(O)NH$_2$, —NHC(O)NHCH$_3$, or —NHC(O)C$_{(1-2)}$alkyl;
$R^4$ is —Cl, —C$_{(1-3)}$alkyl, —F, —CN, or —CF$_3$;
$R^7$ is H, or —F;
$A^1$ is —C$_{(2-3)}$alkyl, wherein said —C$_{(2-3)}$alkyl is optionally substituted with up to six fluorine atoms;
$A^2$ is H, or $A^1$ and $A^2$ are taken together with their attached nitrogen to form

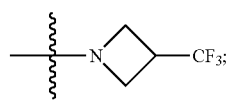 [SMILES: *N1CC(C(F)(F)F)C1]

and pharmaceutically acceptable salts thereof.

6. The compound of claim 5 selected from the group consisting of:

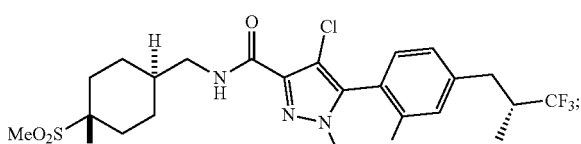

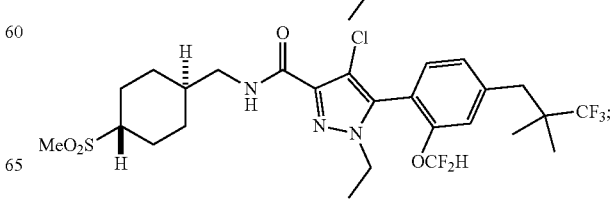

319
-continued
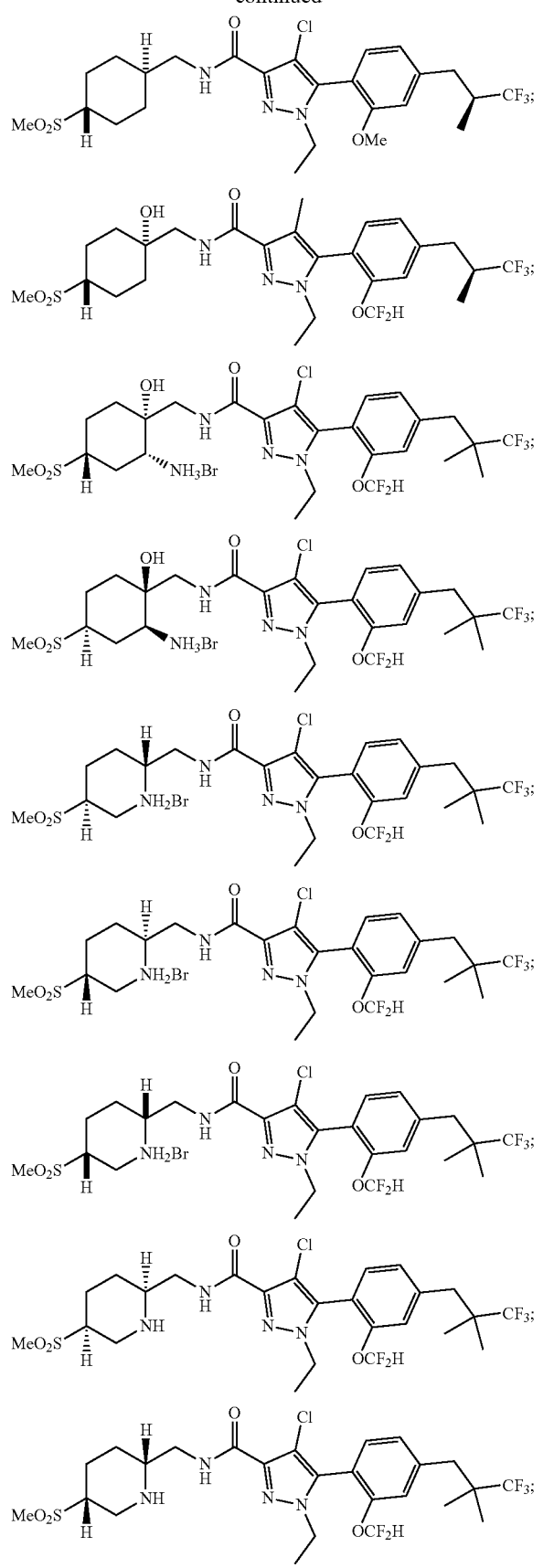
320
-continued
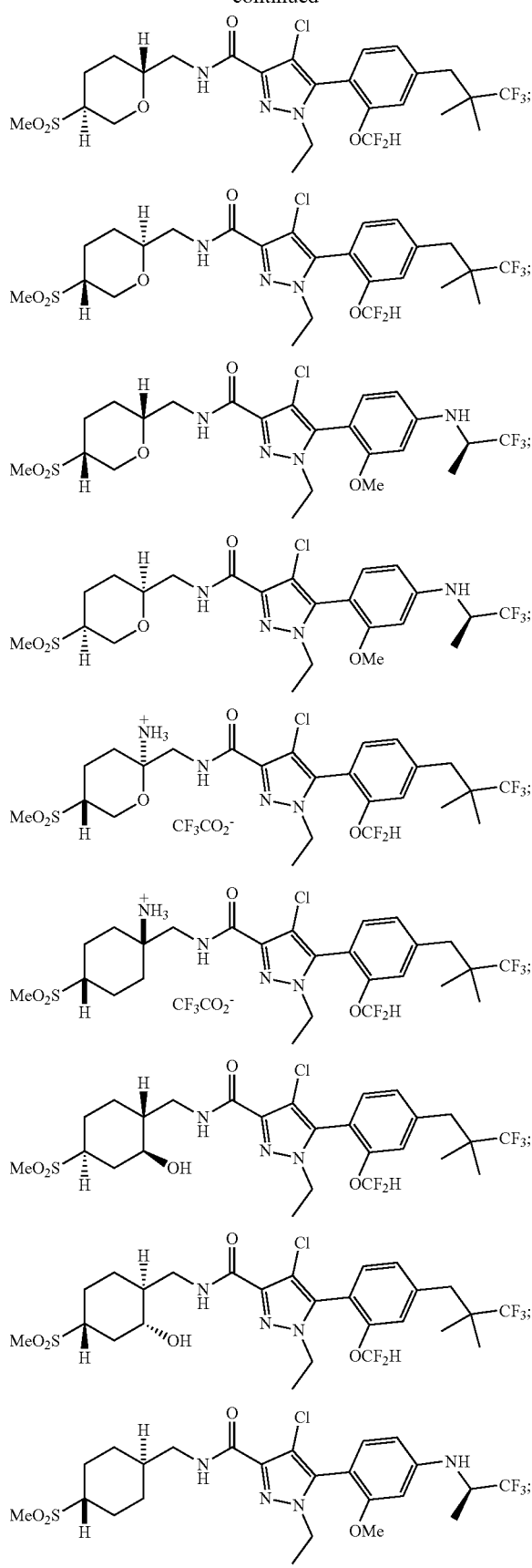

-continued
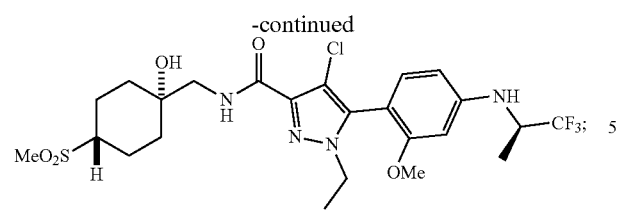
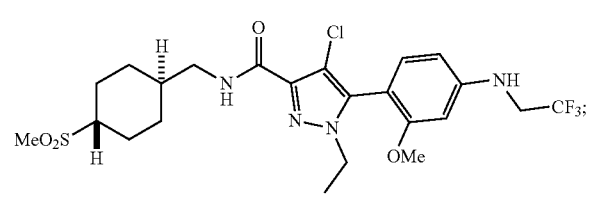
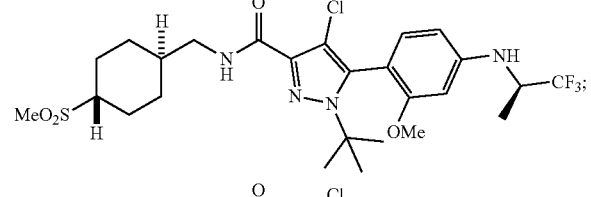
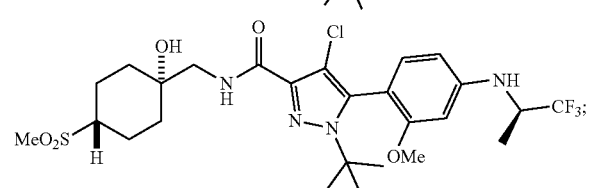
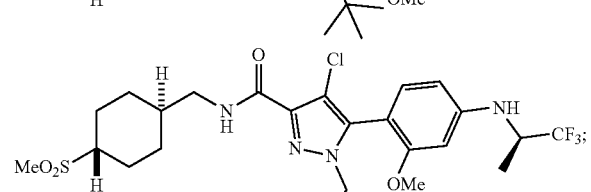
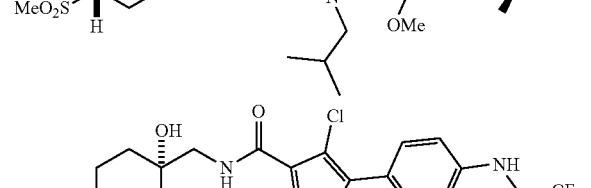
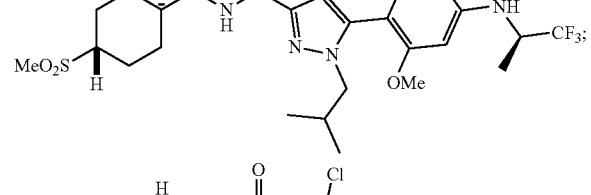
-continued
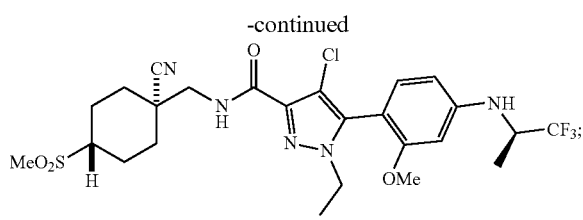
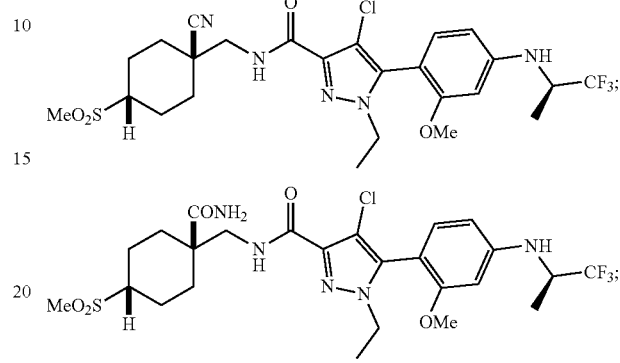
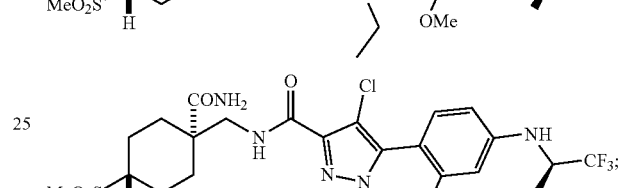
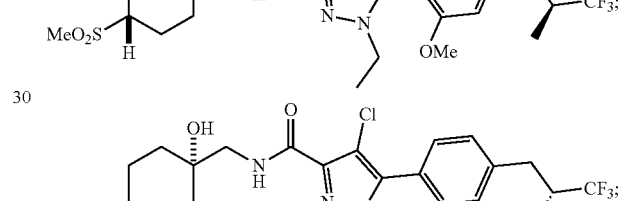
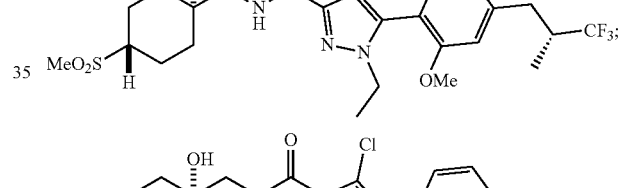
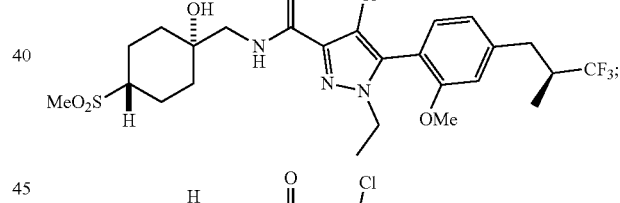
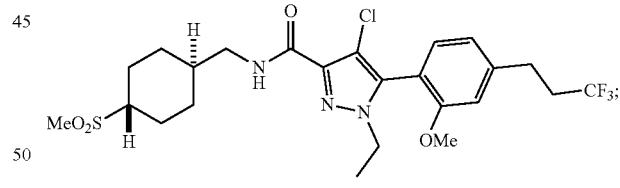

323
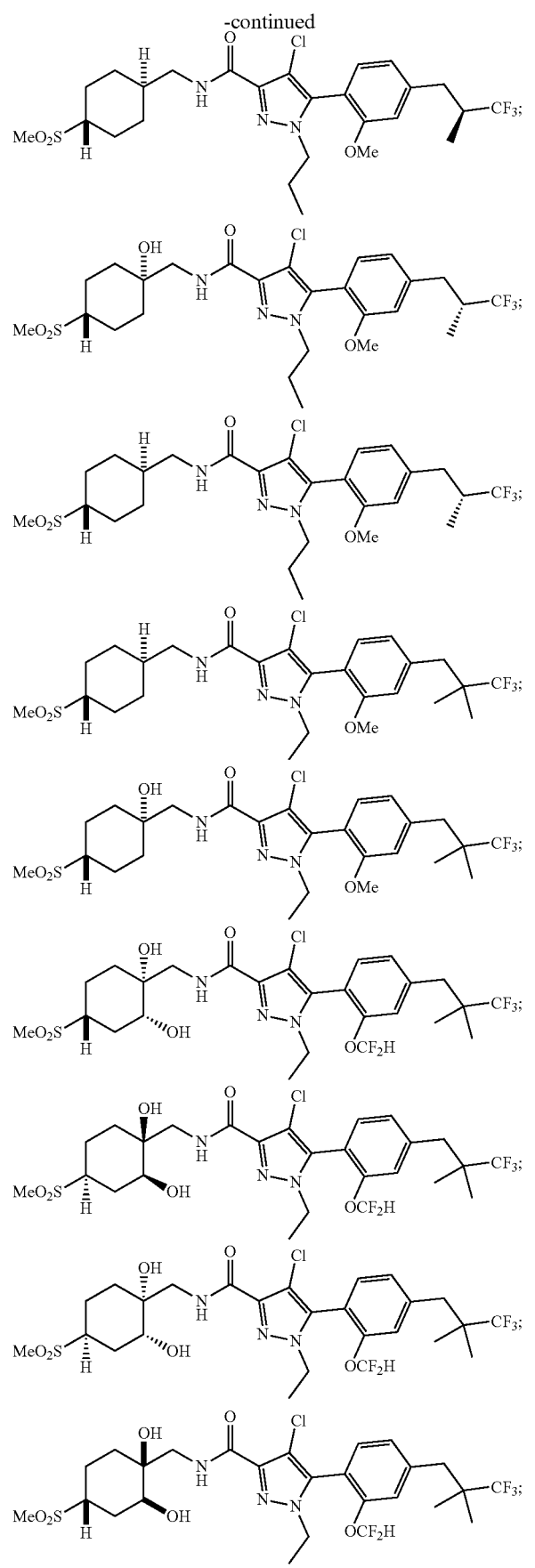
324
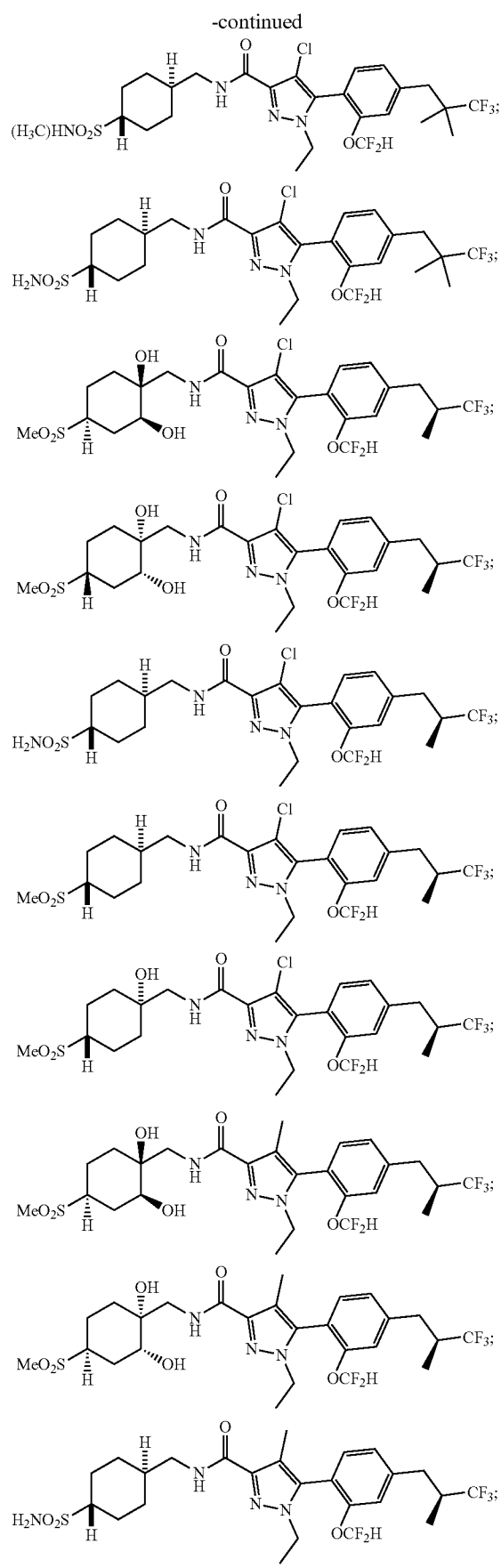

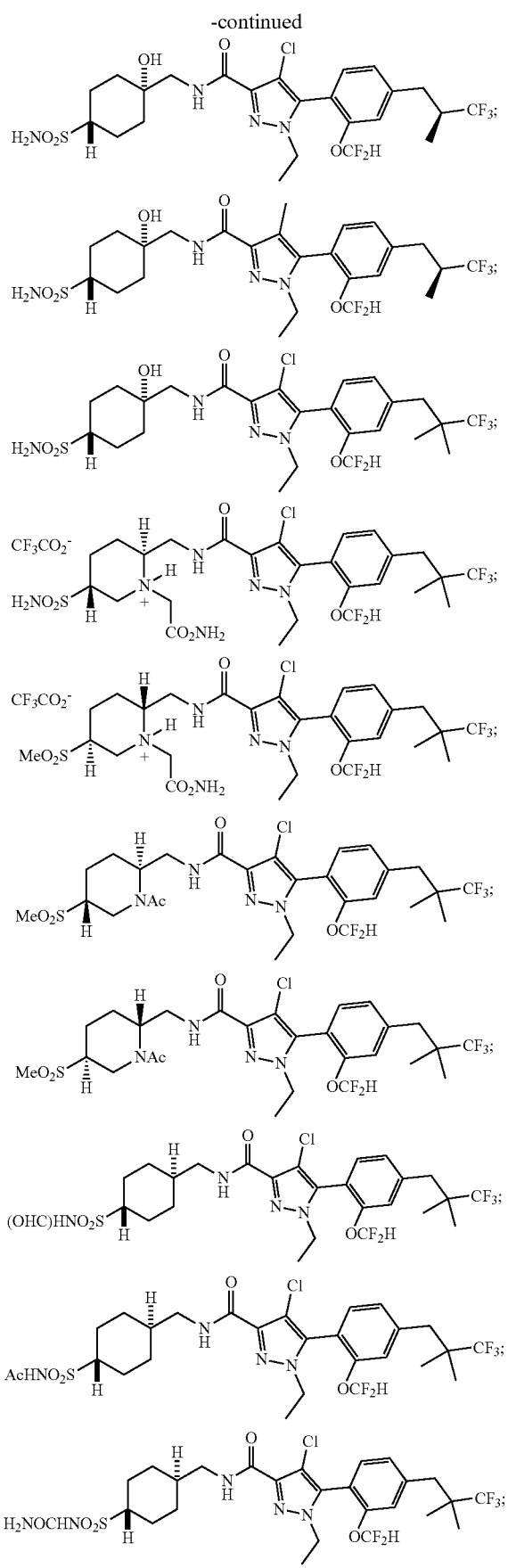
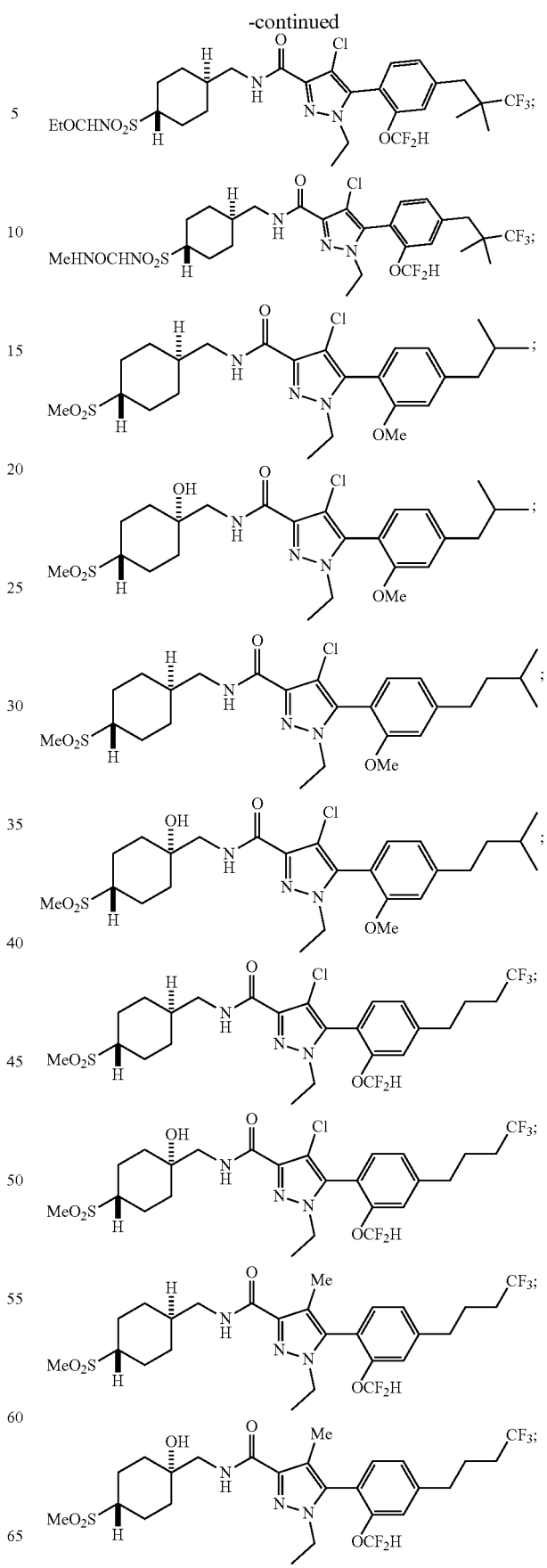

327
-continued
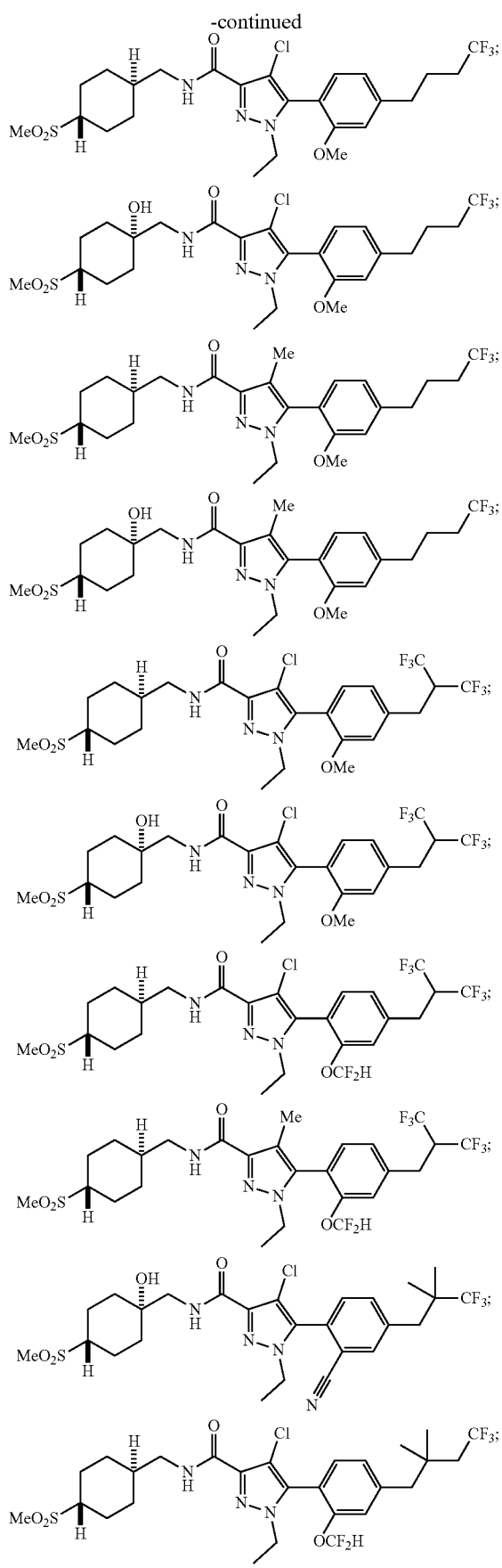
328
-continued
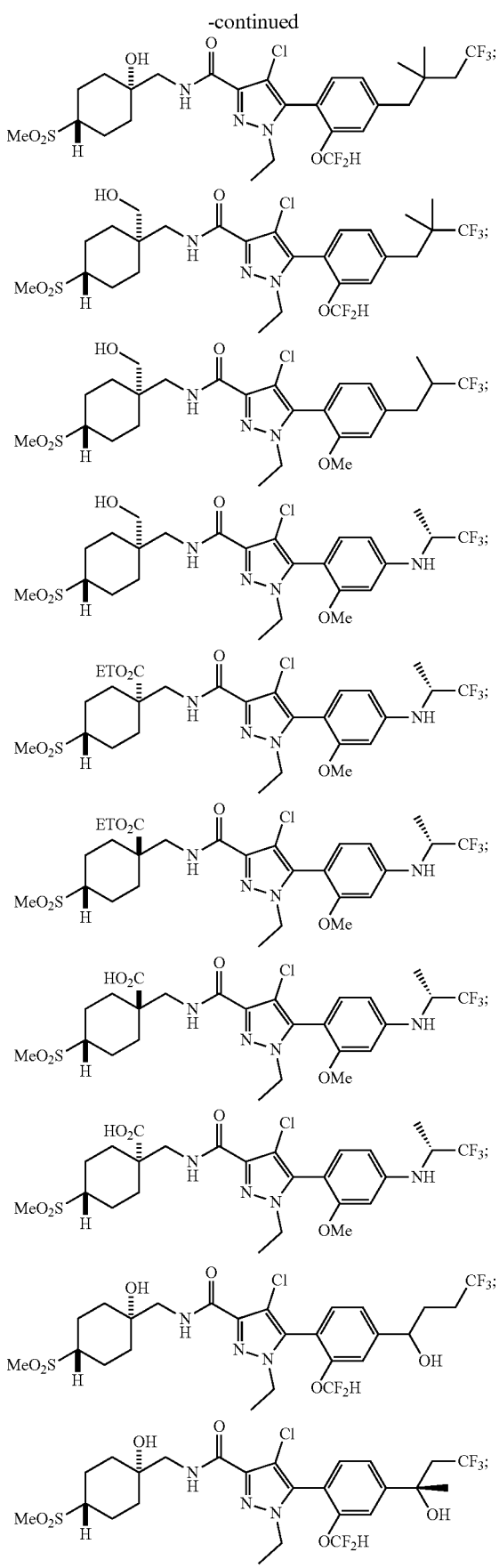

329
-continued
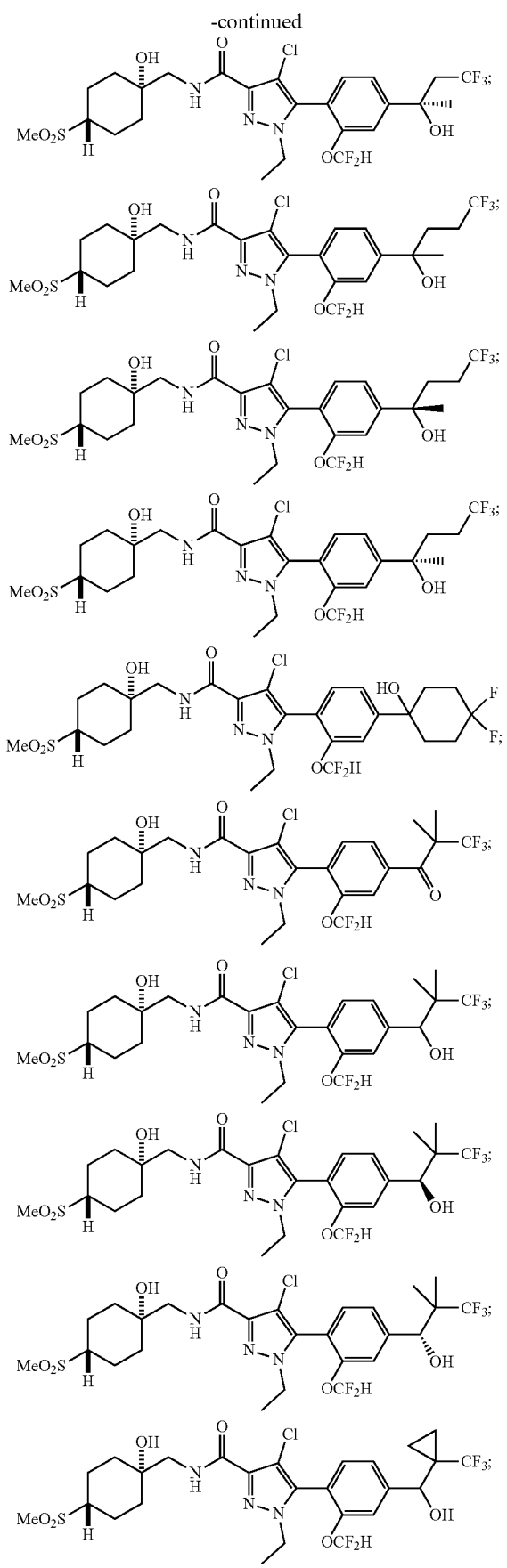
330
-continued
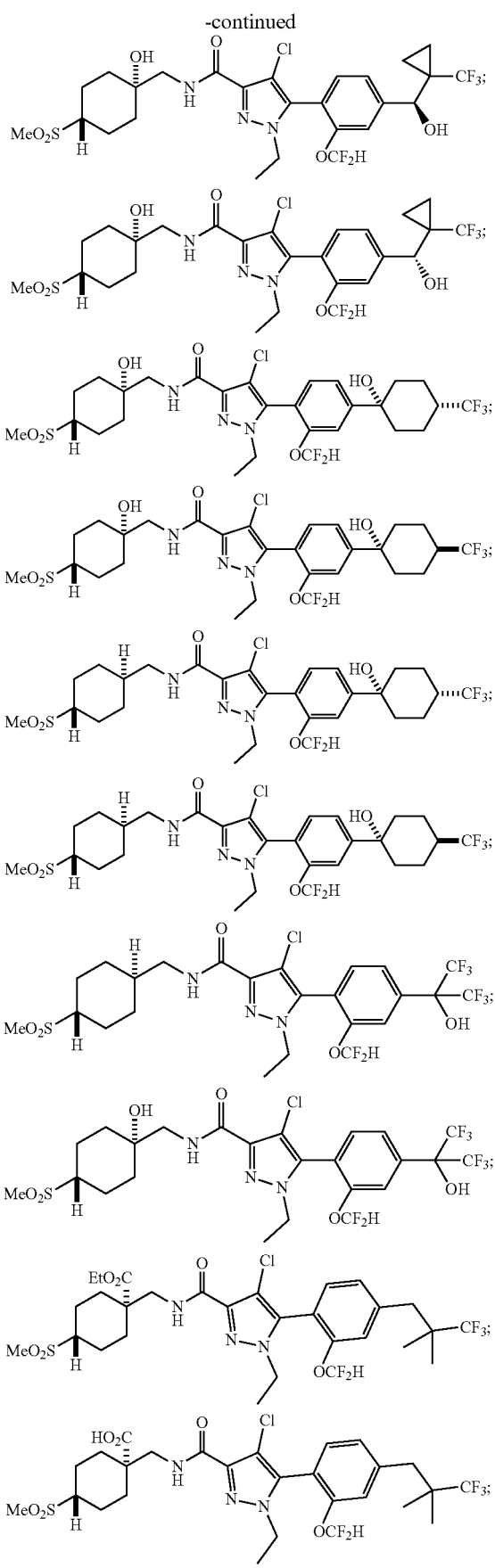

331
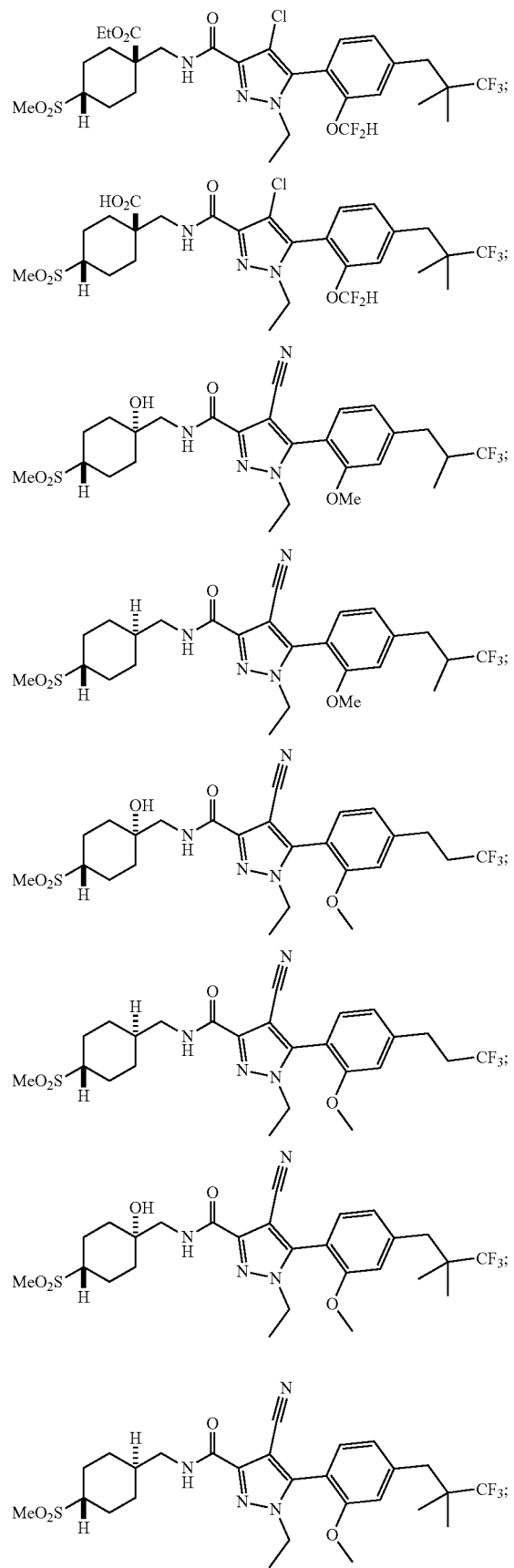
332
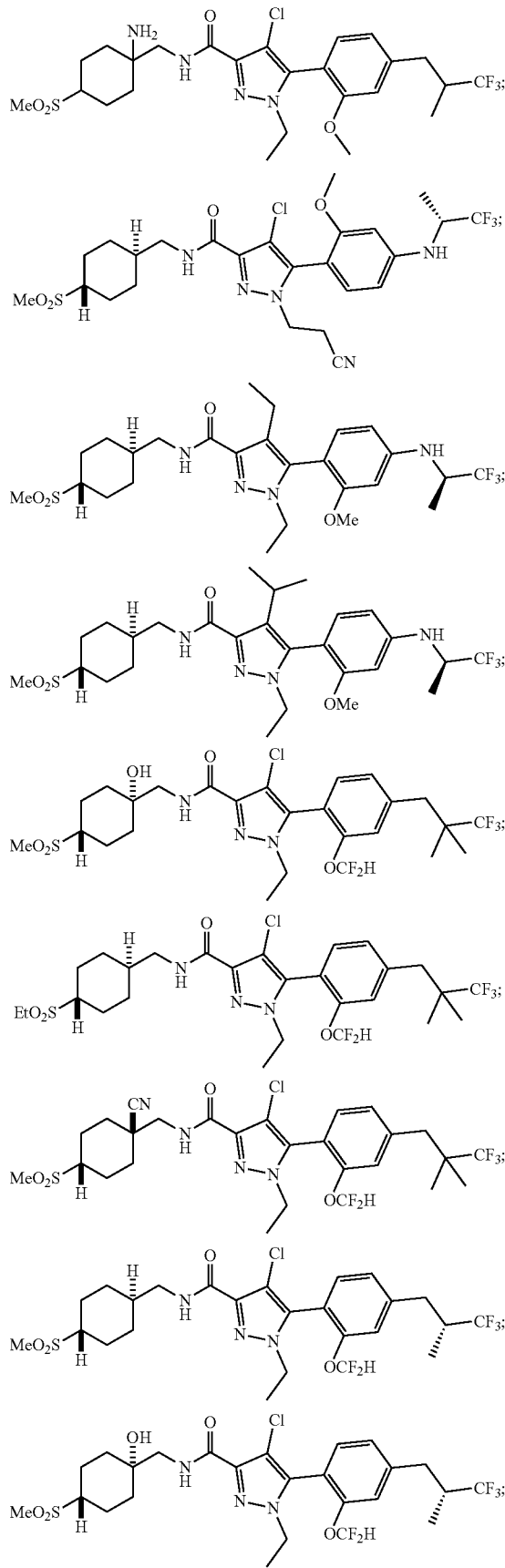

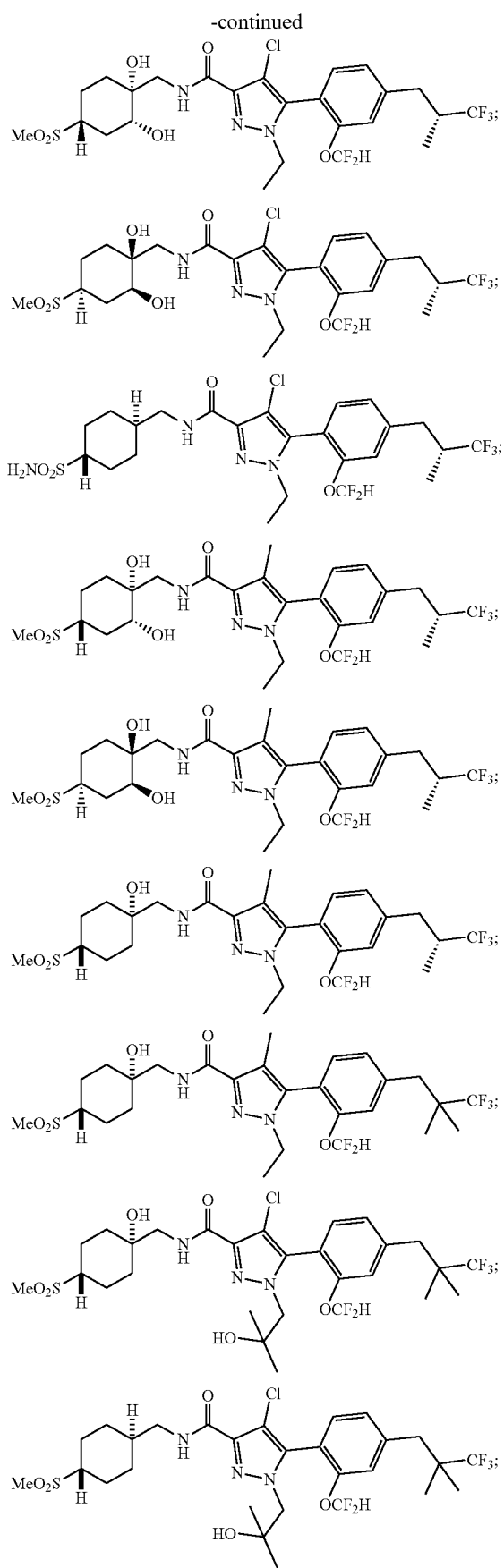
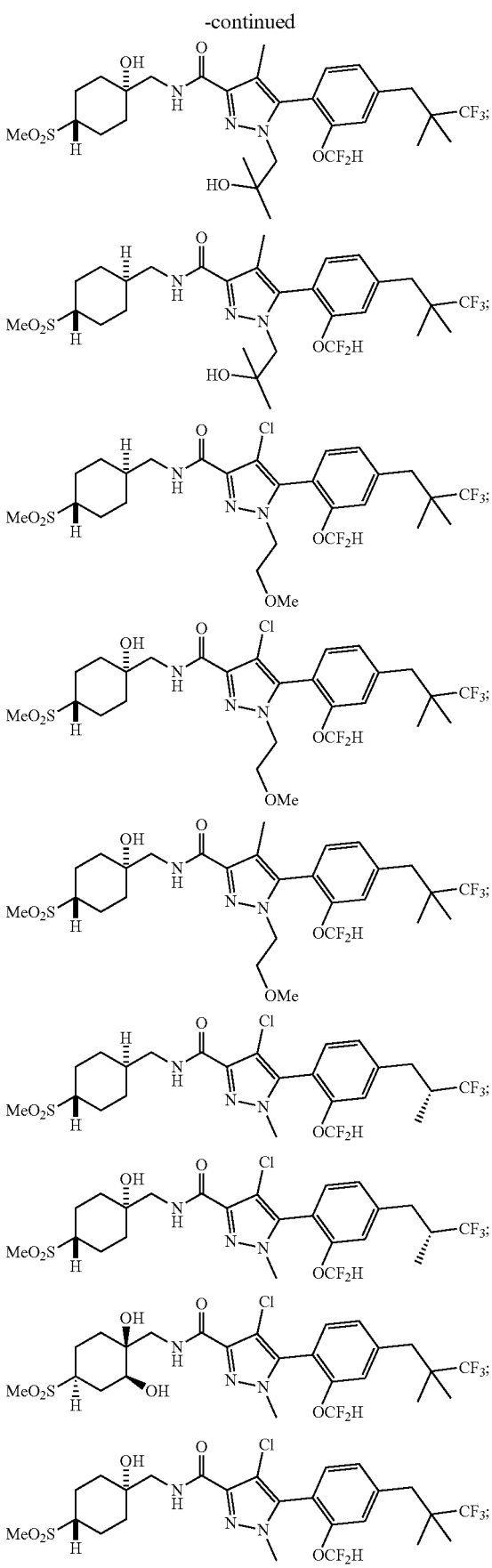

335
-continued
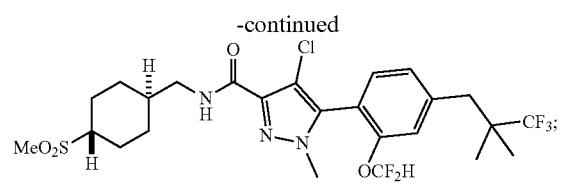
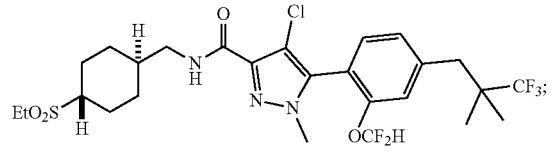
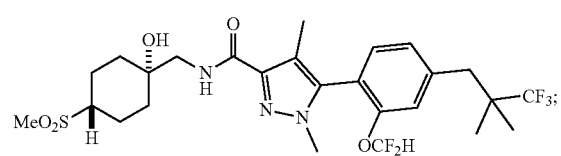
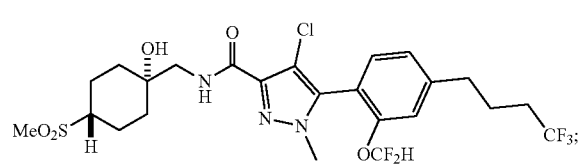
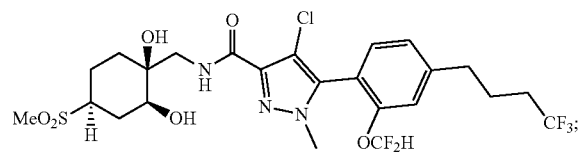
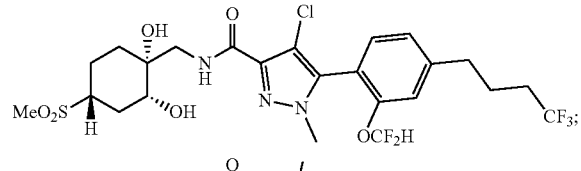
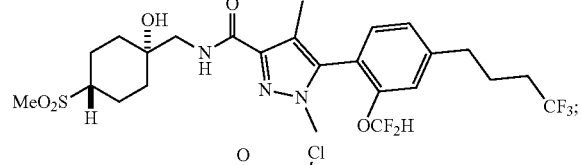
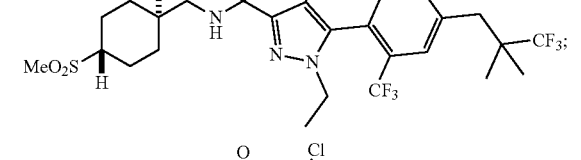
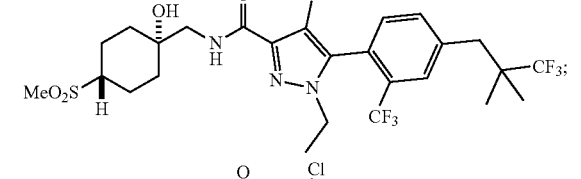
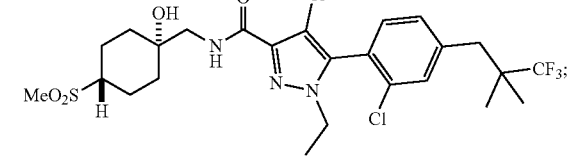
336
-continued
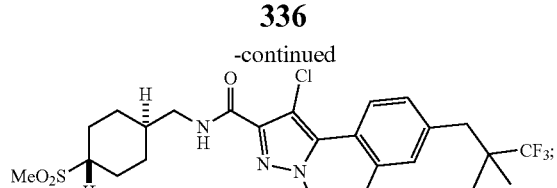
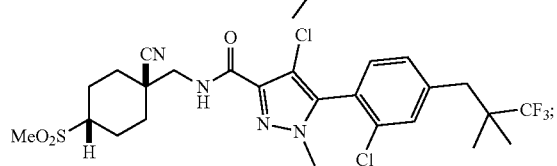
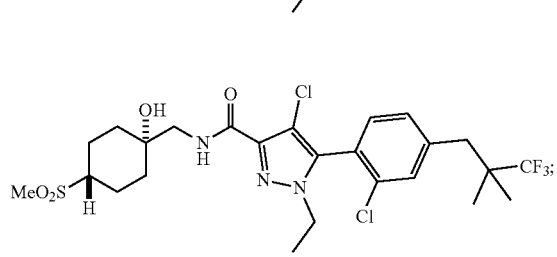
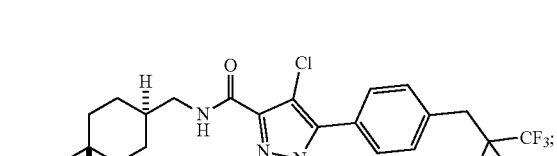
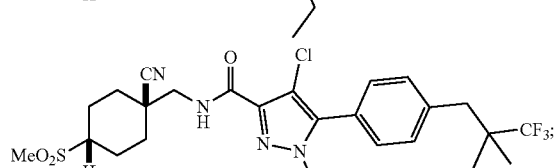
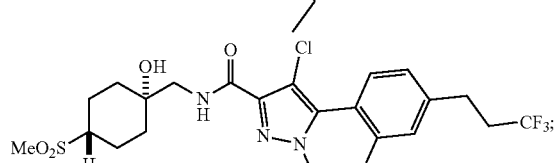
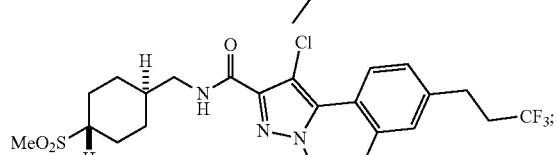
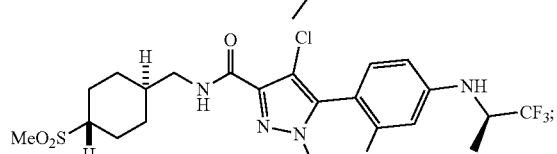
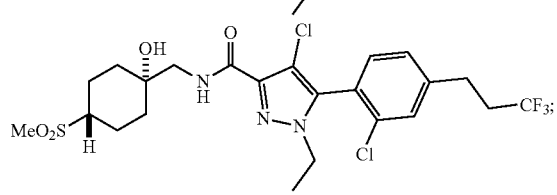

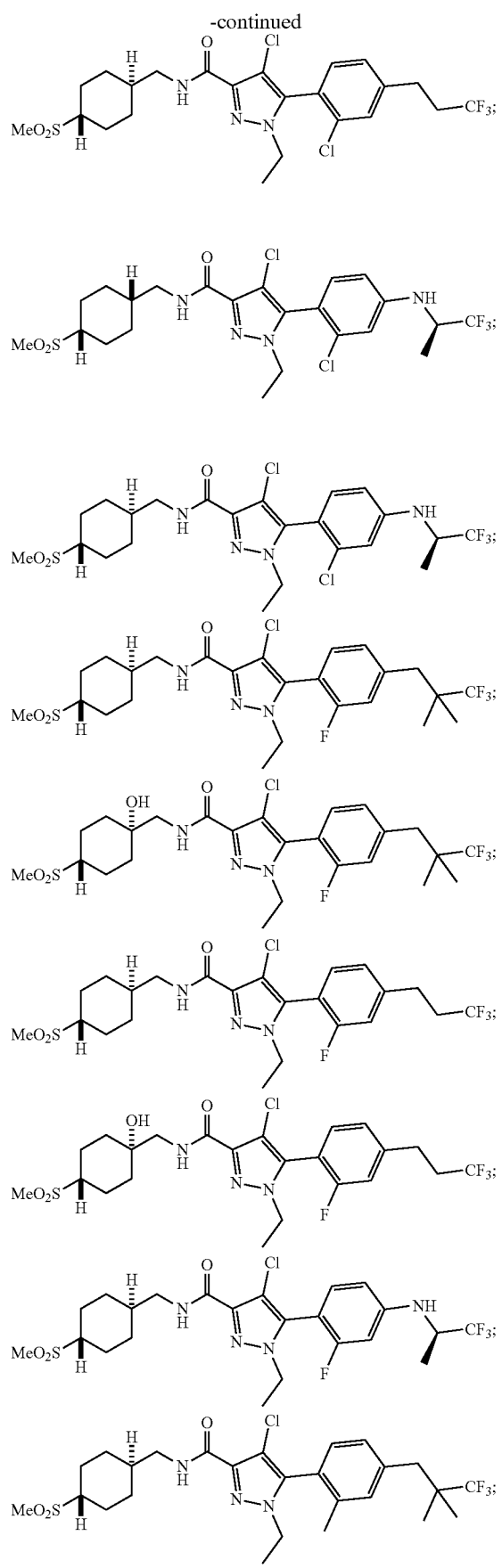
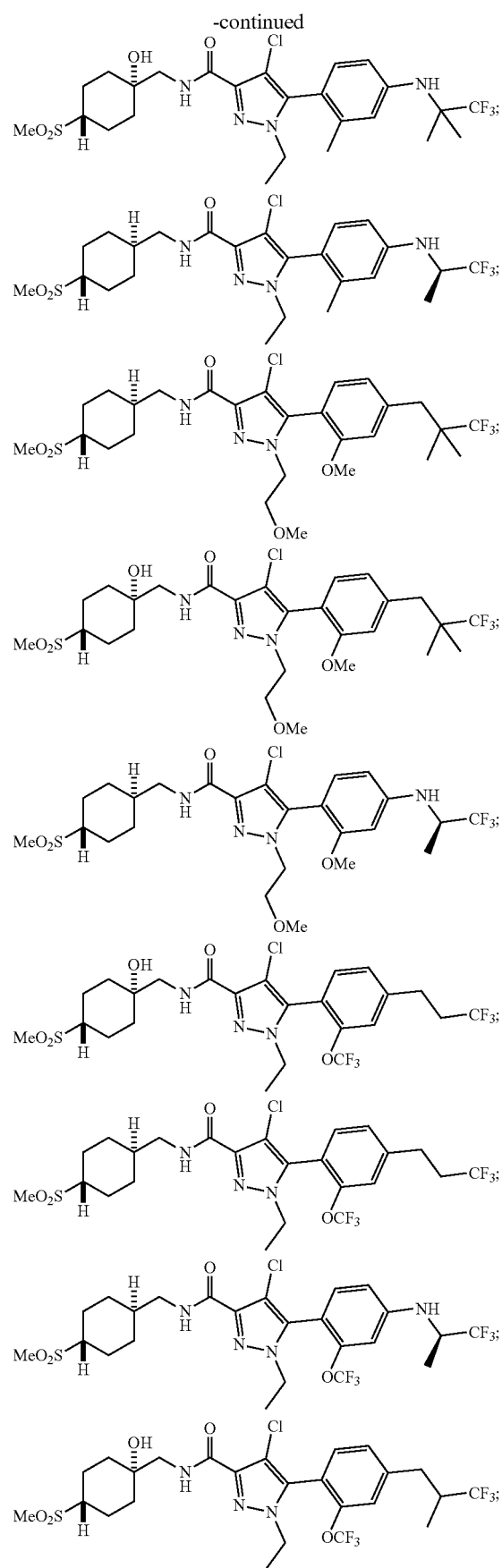

339
-continued
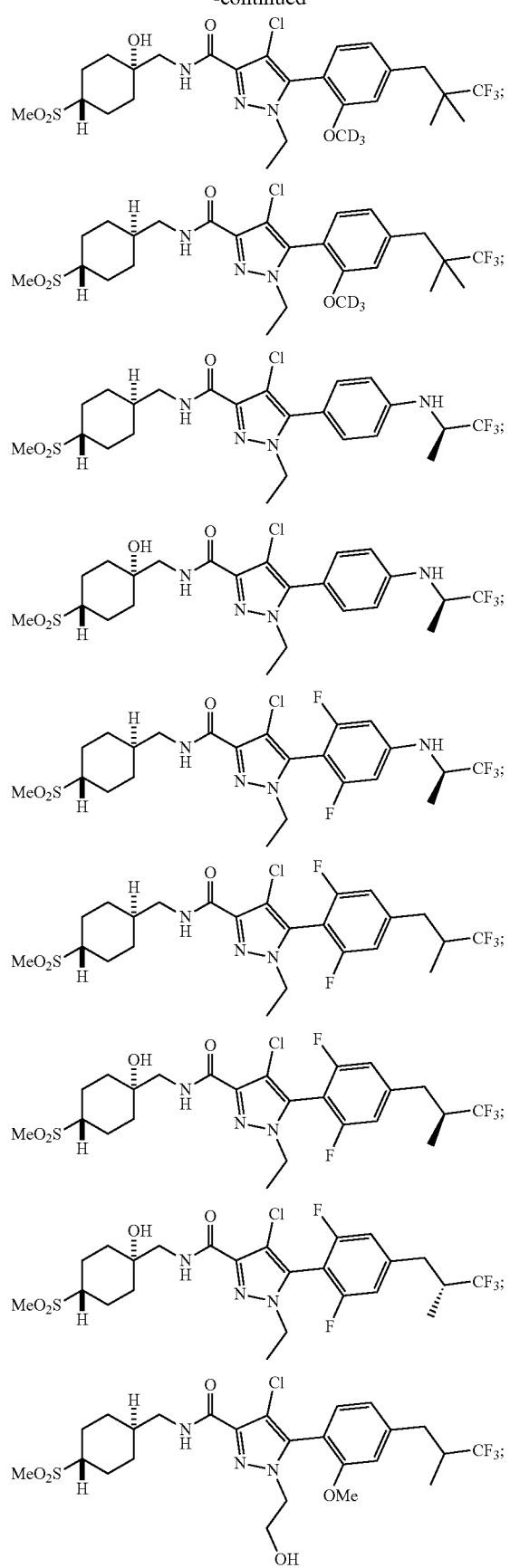
340
-continued
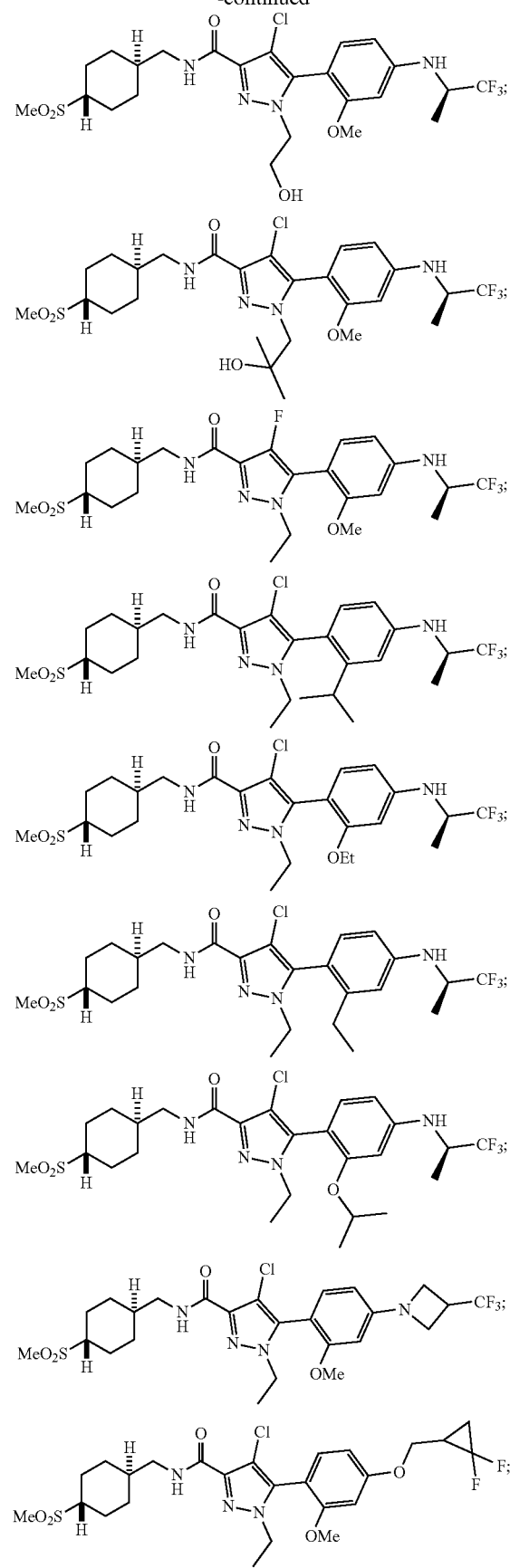

-continued
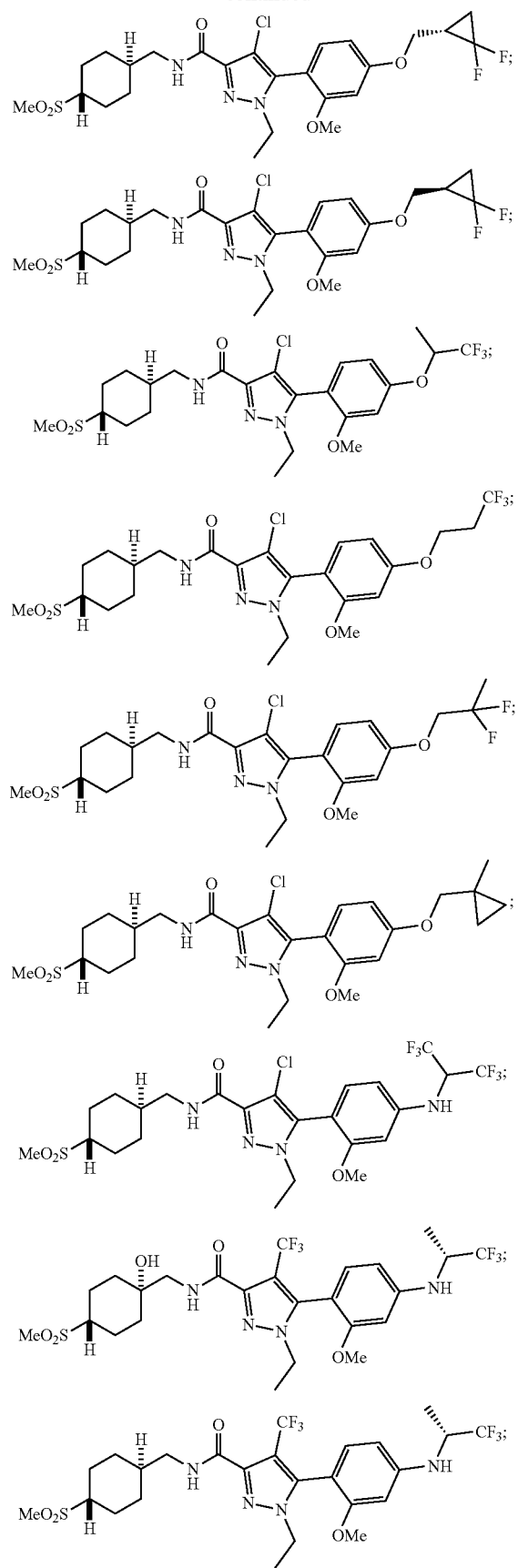
-continued
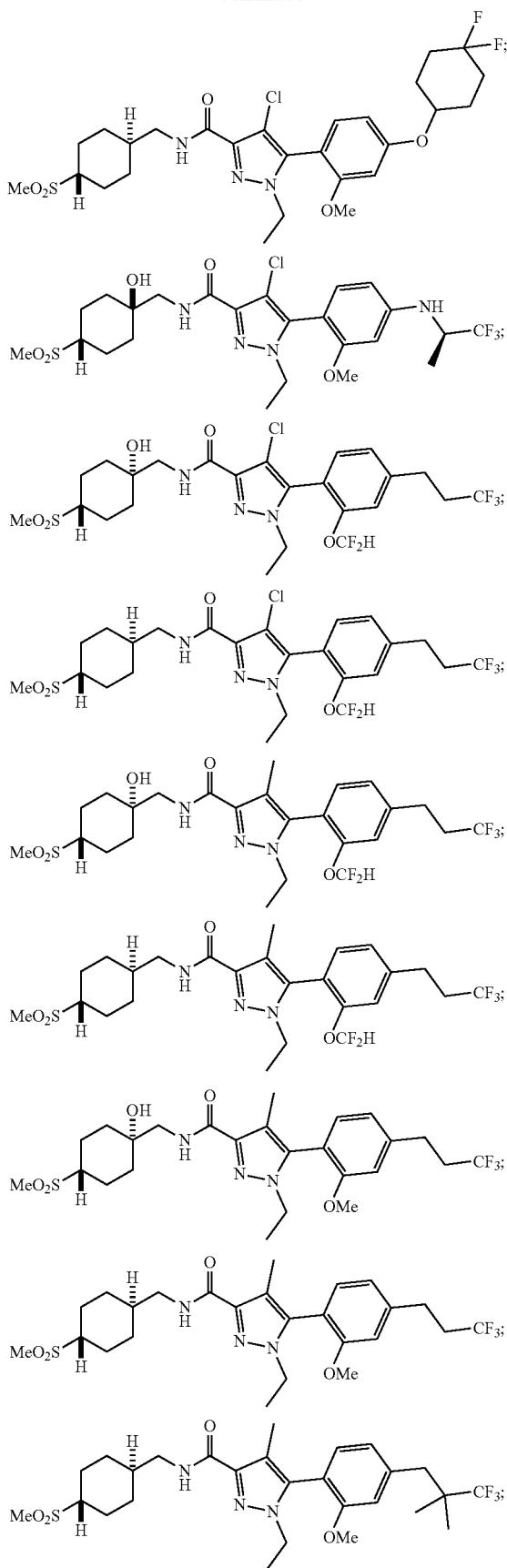

-continued

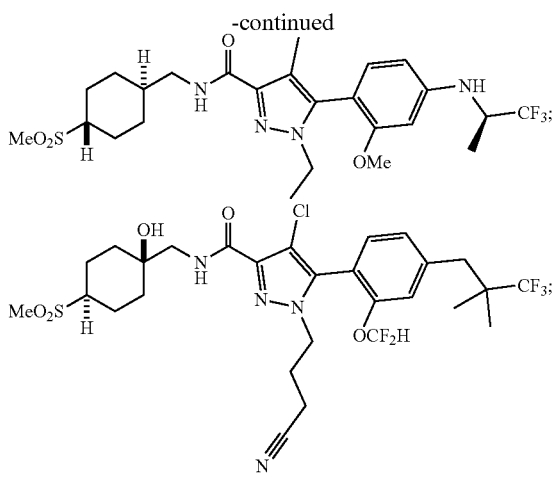

and pharmaceutically acceptable salts thereof.

7. A pharmaceutical composition, comprising a compound of claim 1 and a pharmaceutically acceptable carrier.

8. A pharmaceutical composition made by mixing a compound of claim 1 and a pharmaceutically acceptable carrier.

9. A process for making a pharmaceutical composition comprising mixing a compound of claim 1 and a pharmaceutically acceptable carrier.

10. A method for treating or ameliorating a RORγt mediated inflammatory syndrome, disorder or disease comprising administering to a subject in need thereof an effective amount of a compound of claim 1.

11. The method of claim 10, wherein the disease is selected from the group consisting of: inflammatory bowel diseases, rheumatoid arthritis, psoriasis, chronic obstructive pulmonary disorder, psoriatic arthritis, ankylosing spondylitis, neutrophilic asthma, steroid resistant asthma, multiple sclerosis, and systemic lupus erythematosus.

12. The method of claim 10, wherein the disease is selected from the group consisting of: depression and metabolic syndrome.

13. The method of claim 11, wherein the disease is psoriasis.

14. The method of claim 11, wherein the disease is rheumatoid arthritis.

15. The method of claim 11, wherein the inflammatory bowel disease is ulcerative colitis.

16. The method of claim 11, wherein the inflammatory bowel disease is Crohn's disease.

17. The method of claim 11, wherein the disease is multiple sclerosis.

18. The method of claim 11, wherein the disease is neutrophilic asthma.

19. The method of claim 11, wherein the disease is steroid resistant asthma.

20. The method of claim 11, wherein the disease is psoriatic arthritis.

21. The method of claim 11, wherein the disease is ankylosing spondylitis.

22. The method of claim 11, wherein the disease is systemic lupus erythematosus.

23. The method of claim 11, wherein the disease is chronic obstructive pulmonary disorder.

24. The method of claim 12, wherein the disease is depression.

25. The method of claim 12, wherein the disease is metabolic syndrome.

26. A method of treating or ameliorating a syndrome, disorder or disease, in a subject in need thereof comprising administering to the subject an effective amount of a compound of claim 1 or composition or medicament thereof in a combination therapy with one or more anti-inflammatory agents, or immunosuppressive agents, wherein said syndrome, disorder or disease is selected from the group consisting of: rheumatoid arthritis and psoriasis.

27. A method of treating or ameliorating a syndrome, disorder or disease, in a subject in need thereof comprising administering to the subject an effective amount of a compound of claim 1 or composition or medicament thereof in a combination therapy with one or more anti-inflammatory agents, or immunosuppressive agents, wherein said syndrome, disorder or disease is selected from the group consisting of: psoriatic arthritis and psoriasis.

28. A method of inhibiting production of interleukin-17, comprising administering to a subject in need thereof an effective amount of a compound of claim 1.

* * * * *

SEQUENCE LISTING

<160> NUMBER OF SEQ ID NOS: 4

<210> SEQ ID NO 1
<211> LENGTH: 3054
<212> TYPE: DNA
<213> ORGANISM: Homo sapiens

<400> SEQUENCE: 1

```
agagagctag gtgcagagct tcaggctgag gcgctgctga gagggcctcg ccccgcctct     60
gccgccagct gcaccccact cctggaccac ccctgctga gaaggacagg gagccaaggc    120
cggcagagcc aaggctcagt catgagaaca caaattgaag tgatcccttg caaaatctgt    180
ggggacaagt cgtctgggat ccactacggg gttatcacct gtgaggggtg caagggcttc    240
ttccgccgga gccagcgctg taacgcggcc tactcctgca cccgtcagca gaactgcccc    300
atcgaccgca ccagccgaaa ccgatgccag cactgccgcc tgcagaaatg cctggcgctg    360
ggcatgtccc gagatgctgt caagttcggc cgcatgtcca agaagcagag ggacagcctg    420
catgcagaag tgcagaaaca gctgcagcag cggcaacagc agcaacagga accagtggtc    480
aagacccctc cagcagggc ccaaggagca gatacccctca cctacacctt ggggctccca    540
gacgggcagc tgccctggg ctcctcgcct gacctgcctg aggcttctgc ctgtccccct    600
ggcctcctga agcctcagg ctctgggccc tcatattcca acaacttggc caaggcaggg    660
ctcaatgggg cctcatgcca ccttgaatac agccctgagc ggggcaaggc tgagggcaga    720
gagagcttct atagcacagg cagccagctg acccctgacc gatgtggact tcgttttgag    780
gaacacaggc atcctgggct tggggaactg ggacagggcc cagacagcta cggcagcccc    840
agtttccgca gcacaccgga ggcacctat gcctccctga cagagataga gcacctggtg    900
cagagcgtct gcaagtccta cagggagaca tgccagctgc ggctggagga cctgctgcgg    960
cagcgctcca acatcttctc ccgggaggaa gtgactggca ccagaggaa gtccatgtgg   1020
gagatgtggg aacggtgtgc ccaccacctc accgaggcca ttcagtacgt ggtggagttc   1080
gccaagagc tctcaggctt tatggagctc tgccagaatg accagattgt gcttctcaaa   1140
gcaggagcaa tggaagtggt gctggttagg atgtgccggg cctacaatgc tgacaaccgc   1200
acggtctttt tgaaggcaa atacggtggc atggagctgt tccgagcctt gggctgcagc   1260
gagctcatca gctccatctt tgacttctcc cactccctaa gtgccttgca cttttccgag   1320
gatgagattg ccctctacac agcccttgtt ctcatcaatg cccatcggcc aggctccaa   1380
```

```
gagaaaagga aagtagaaca gctgcagtac aatctggagc tggcctttca tcatcatctc  1440
tgcaagactc atcgccaaag catcctggca aagctgccac ccaaggggaa gcttcggagc  1500
ctgtgtagcc agcatgtgga aaggctgcag atcttccagc acctccaccc catcgtggtc  1560
caagccgctt tccctccact ctacaaggag ctcttcagca ctgaaaccga gtcacctgtg  1620
gggctgtcca agtgacctgg aagagggact ccttgcctct ccctatggcc tgctggccca  1680
cctccctgga ccccgttcca ccctcaccct tttcctttcc catgaaccct ggagggtggt  1740
ccccaccagc tctttggaag tgagcagatg ctgcggctgg ctttctgtca gcaggccggc  1800
ctggcagtgg gacaatcgcc agagggtggg gctggcagaa caccatctcc agcctcagct  1860
ttgacctgtc tcatttccca tattccttca cacccagctt ctggaaggca tggggtggct  1920
gggatttaag gacttctggg ggaccaagac atcctcaaga aaacaggggc atccagggct  1980
ccctggatga atagaatgca attcattcag aagctcagaa gctaagaata agcctttgaa  2040
atacctcatt gcatttccct tgggcttcg gcttggggag atggatcaag ctcagagact   2100
ggcagtgaga gcccagaagg acctgtataa aatgaatctg gagctttaca ttttctgcct  2160
ctgccttcct cccagctcag caaggaagta tttgggcacc ctacccttta cctggggtct  2220
aaccaaaaat ggatgggatg aggatgagag gctggagata attgttttat gggatttggg  2280
tgtgggacta gggtacaatg aaggccaaga gcatctcaga catagagtta aaactcaaac  2340
ctcttatgtg cactttaaag atagacttta ggggctggca caaatctgat cagagacaca  2400
tatccataca caggtgaaac acatacagac tcaacagcaa tcatgcagtt ccagagacac  2460
atgaacctga cacaatctct cttatccttg aggccacagc ttggaggagc ctagaggcct  2520
caggggaaag tcccaatcct gagggaccct cccaaacatt tccatggtgc tccagtccac  2580
tgatcttggg tctggggtga tccaaatacc accccagctc cagctgtctt ctaccactag  2640
aagacccaag agaagcagaa gtcgctcgca ctggtcagtc ggaaggcaag atcagatcct  2700
ggaggacttt cctggcctgc ccgccagccc tgctcttgtt gtggagaagg aagcagatgt  2760
gatcacatca ccccgtcatt gggcaccgct gactccagca tggaggacac cagggagcag  2820
ggcctgggcc tgtttcccca gctgtgatct tgcccagaac ctctcttggc ttcataaaca  2880
gctgtgaacc ctcccctgag ggattaacag caatgatggg cagtcgtgga gttgggggg   2940
ttggggggtgg gattgtgtcc tctaagggga cgggttcatc tgagtaaaca taaaccccaa  3000
cttgtgccat tctttataaa atgattttaa aggcaaaaaa aaaaaaaaaa aaaa         3054
```

<210> SEQ ID NO 2
<211> LENGTH: 786
<212> TYPE: DNA
<213> ORGANISM: Homo sapiens

<400> SEQUENCE: 2

```
agcacaccgg aggcacccta tgcctccctg acagagatag agcacctggt gcagagcgtc   60
tgcaagtcct acagggagac atgccagctg cggctggagg acctgctgcg gcagcgctcc  120
aacatcttct cccgggagga agtgactggc taccagagga agtccatgtg ggagatgtgg  180
gaacggtgtg cccaccacct caccgaggcc attcagtacg tggtggagtt cgccaagagg  240
ctctcaggct ttatggagct ctgccagaat gaccagattg tgcttctcaa agcaggagca  300
atggaagtgt gctggttag gatgtgccgg gcctacaatg ctgacaaccg cacggtcttt  360
tttgaaggca aatacggtgg catggagctg ttccgagcct tgggctgcag cgagctcatc  420
```

```
agctccatct tgacttctc ccactcccta agtgccttgc acttttccga ggatgagatt    480
gccctctaca cagccttgt tctcatcaat gcccatcggc cagggctcca agagaaaagg    540
aaagtagaac agctgcagta caatctggag ctggcctttc atcatcatct ctgcaagact    600
catcgccaaa gcatcctggc aaagctgcca cccaagggga agcttcggag cctgtgtagc    660
cagcatgtgg aaaggctgca gatcttccag cacctccacc ccatcgtggt ccaagccgct    720
ttccctccac tctacaagga gctcttcagc actgaaaccg agtcacctgt ggggctgtcc    780
aagtga                                                              786
```

<210> SEQ ID NO 3
<211> LENGTH: 7
<212> TYPE: PRT
<213> ORGANISM: Artificial Sequence
<220> FEATURE:
<223> OTHER INFORMATION: TurboTEV protease cleavage site

<400> SEQUENCE: 3

Glu Asn Leu Tyr Phe Gln Gly
1               5

<210> SEQ ID NO 4
<211> LENGTH: 283
<212> TYPE: PRT
<213> ORGANISM: Artificial Sequence
<220> FEATURE:
<223> OTHER INFORMATION: Construct used in the Thermofluor assay

<400> SEQUENCE: 4

Met Ala His His His His His His Ala Gly Gly Ala Glu Asn Leu Tyr
1               5                   10                  15

Phe Gln Gly Ala Met Asp Ser Thr Pro Glu Ala Pro Tyr Ala Ser Leu
                20                  25                  30

Thr Glu Ile Glu His Leu Val Gln Ser Val Cys Lys Ser Tyr Arg Glu
            35                  40                  45

Thr Cys Gln Leu Arg Leu Glu Asp Leu Leu Arg Gln Arg Ser Asn Ile
        50                  55                  60

Phe Ser Arg Glu Glu Val Thr Gly Tyr Gln Arg Lys Ser Met Trp Glu
65                  70                  75                  80

Met Trp Glu Arg Cys Ala His His Leu Thr Glu Ala Ile Gln Tyr Val
                85                  90                  95

Val Glu Phe Ala Lys Arg Leu Ser Gly Phe Met Glu Leu Cys Gln Asn
            100                 105                 110

Asp Gln Ile Val Leu Leu Lys Ala Gly Ala Met Glu Val Val Leu Val
        115                 120                 125

Arg Met Cys Arg Ala Tyr Asn Ala Asp Asn Arg Thr Val Phe Phe Glu
    130                 135                 140

Gly Lys Tyr Gly Gly Met Glu Leu Phe Arg Ala Leu Gly Cys Ser Glu
145                 150                 155                 160

Leu Ile Ser Ser Ile Phe Asp Phe Ser His Ser Leu Ser Ala Leu His
                165                 170                 175

Phe Ser Glu Asp Glu Ile Ala Leu Tyr Thr Ala Leu Val Leu Ile Asn
            180                 185                 190

Ala His Arg Pro Gly Leu Gln Glu Lys Arg Lys Val Glu Gln Leu Gln
        195                 200                 205

Tyr Asn Leu Glu Leu Ala Phe His His Leu Cys Lys Thr His Arg
    210                 215                 220

```
Gln Ser Ile Leu Ala Lys Leu Pro Pro Lys Gly Lys Leu Arg Ser Leu
225                 230             235                 240

Cys Ser Gln His Val Glu Arg Leu Gln Ile Phe Gln His Leu His Pro
                245             250             255

Ile Val Val Gln Ala Ala Phe Pro Pro Leu Tyr Lys Glu Leu Phe Ser
                260             265             270

Thr Glu Thr Glu Ser Pro Val Gly Leu Ser Lys
    275             280
```